(12) United States Patent
Lloyd et al.

(10) Patent No.: US 7,582,654 B2
(45) Date of Patent: Sep. 1, 2009

(54) HETEROCYCLO INHIBITORS OF POTASSIUM CHANNEL FUNCTION

(75) Inventors: John Lloyd, Yardley, PA (US); Yoon T. Jeon, Belle Meade, NJ (US); Heather Finlay, Skillman, NJ (US); Lin Yan, East Brunswick, NJ (US); Michael F. Gross, Durham, NC (US); Serge Beaudoin, Morrisville, NC (US)

(73) Assignees: Bristol-Myers Squibb Company, Princeton, NJ (US); Icagen, Inc., Durham, NC (US)

( * ) Notice: Subject to any disclaimer, the term of this patent is extended or adjusted under 35 U.S.C. 154(b) by 620 days.

(21) Appl. No.: 11/186,991

(22) Filed: Jul. 21, 2005

(65) Prior Publication Data

US 2006/0014792 A1 Jan. 19, 2006

Related U.S. Application Data

(62) Division of application No. 10/417,355, filed on Apr. 16, 2003, now Pat. No. 7,005,436.

(60) Provisional application No. 60/374,279, filed on Apr. 19, 2002.

(51) Int. Cl.
*C07D 401/02* (2006.01)
*A61K 31/445* (2006.01)
(52) U.S. Cl. ...................... 514/326; 546/207
(58) Field of Classification Search ................ 546/207; 514/326
See application file for complete search history.

(56) References Cited

U.S. PATENT DOCUMENTS

| | | | |
|---|---|---|---|
| 3,097,209 A | 7/1963 | Janssen | |
| 5,612,359 A | 3/1997 | Murugesan | |
| 5,631,282 A | 5/1997 | Goetz | |
| 5,670,504 A | 9/1997 | Bochis et al. | |
| 5,679,705 A | 10/1997 | Baker et al. | |
| 5,696,156 A | 12/1997 | Baker et al. | |
| 6,043,265 A | 3/2000 | Murugesan et al. | |
| 6,071,953 A | 6/2000 | Lang et al. | |
| 6,303,637 B1 | 10/2001 | Bao et al. | |
| 6,350,760 B1 * | 2/2002 | Bakshi et al. | 514/323 |
| 6,559,153 B2 * | 5/2003 | Becker et al. | 514/266.22 |
| 6,660,742 B2 | 12/2003 | Lee | |

FOREIGN PATENT DOCUMENTS

| | | |
|---|---|---|
| EP | 0857724 | 8/1998 |
| EP | 0861836 | 12/2004 |
| WO | WO98/04521 | 2/1998 |
| WO | WO 00/01389 | 1/2000 |
| WO | WO 03/088908 | 10/2003 |

OTHER PUBLICATIONS

Dorwald F. A. Side Reactions in Organic Synthesis, 2005, Wiley: VCH, Weinheim p. IX of Preface.*
McManus, J. M. et al., J. Medicinal Chem., vol. 8, No. 6, pp. 766-776 (1965).
Chandy and Gutman, "Voltage-gated potassium channel genes" in Handbook of Receptors and Channels—Ligand and Voltage-gated Ion Channels, ed. R.A. North, 1995.
Doupnik et al., Curr. Opin. Neurobiol. 5:268, 1995.
Chandy et al., J. Exp. Med. 160, 369, 1984.
Price et al., Proc. Natl, Acad, Sci. USA, 86, 10171, 1989.
Leonard et al., Proc. Natl. Acad. Sci, USA, 89, 10094, 1992.
Lin et al., J. exp. Med, 177, 637, 1993.
Singh B.N., Vaughan Williams E.M. "A Third Class of Anti-Arrhythmic Action: Effects On Atrial And Ventricular Intracellular Potentials And Other Pharmacological Actions On Cardiac Muscle, of MJ 1999 and AH 3747" Br. J. Pharmacol 1970; 39:675-689.
Singh B.N., Vaughan Williams E.M, "The Effect of Amiodarone, A New Anti-Anginal Drug, On Cardiac Muscle", Br J. Pharmacol 1970; 39:657-667.
Decoursey et al., Nature, 307, 465, 1984.
Sanguinetti and Jurkiewicz, Two Components Of Cardiac Delayed Rectifier K+ Current: Differential Sensitivity To Block By Class III Antiarrhythmic Agents, J Gen Physiol 1990, 96:195-215.
Balser J.R. Bennett, P.B., Hondeghem, L.M. and Roden, D.M. Suppression Of Time-Dependent Outward Current in Guinea Pig Ventricular Myocytes: Actions Of Quinidine And Amiodarone. Circ. Res. 1991, 69:519-529.
Nademanee, K. "The Amiodarone Odessey" .J.Am. Coll. Cardiol. 1992;20:1063-1065.
Roden, D.M. "Current Status of Class III Antiarrhythmic Drug Therapy", Am J. Cardiol, 1993; 72:44B-49B.
Hondeghem, L.M. "Development of Class III Antiarrhythmic Agents". J.Cadiovasc.Cardiol. 20 (Suppl.2):S17-S22 (1992).
Wang et al., 1993, Circ Res 73:1061-1076.
Fedida et al., 1993, Circ Res 73:210-216.
Snyders et al., 1993, J Gen Physiol 101:513-543.
Swanson et al., (1990), Neuron 4:929-939.

(Continued)

*Primary Examiner*—Rita J Desai
(74) *Attorney, Agent, or Firm*—Terence J. Bogie

(57) ABSTRACT

Novel heterocyclo compounds useful as inhibitors of potassium channel function (especially inhibitors of the $K_v1$ subfamily of voltage gated $K^+$ channels, especially inhibitors $K_v1.5$ which has been linked to the ultra-rapidly activating delayed rectifier $K^+$ current $I_{Kur}$), methods of using such compounds in the prevention and treatment of arrhythmia and $I_{Kur}$-associated conditions, and pharmaceutical compositions containing such compounds.

4 Claims, No Drawings

OTHER PUBLICATIONS

Vaughn Williams, E.M. "Classification Of Antiarrhythmic Drugs" In Symposium on Cardiac Arrhythmias, edited by: E. Sandoe, E. Flensted-Jensen, K. Olesen; Sweden, Astra, Sodertalje, pp. 449-472, 1970.

Br. J. Pharmacol. May 1995;115(2):267-74.

Grissmer S, et al., Mol Pharmacol Jun. 1994;45(6):1227-34.

Petersen KR, and Nerbonne JM, Pflugers Arch Feb. 1999;437(3):381-92.

Bowlby MR, and Levitan IB, J Neurophysiol Jun. 1995;73(6):2221-9.

Kalman K, et al., J Biol Chem Mar. 6, 1998;273(10):5851-7.

Cochran et al., "Regionally selective alterations in local cerebral glucose utilization evoked by charybdotoxin, a blocker of central voltage-activated K+-channels," Eur J Neurosci. Nov. 2001;14(9):1455-63.

Coleman et al., "Subunit composition of Kv1 channels in human CNS," J Neurochem. Aug. 1999;73(2):849-58.

Davies et al., "Kv channel subunit expression in rat pulmonary arteries," Lung. 2001;179(3):147-61. Epub Feb. 4, 2002.

Frey et al., "Blocking of cloned and native delayed rectifier K channels from visceral smooth muscles by phencyclidine," Neurogastroenterol Motil. Dec. 2000;12(6):509-16.

Hanson et al., "UK-78,282, a novel piperidine compound that potently blocks the Kv1.3 voltage-gated potassium channel and inhibits human T cell activation," British Journal of Pharmacology (1999), 126, 1707-1716.

Hatton et al., "Functional and molecular expression of a voltage-dependent K(+) channel (Kv1.1) in interstitial cells of Cajal," J Physiol. Jun. 1, 2001;533 (Pt 2):315-27.

Koh et al., "Contribution of delayed rectifier potassium currents to the electrical activity of murine colonic smooth muscle," J Physiol. Mar. 1, 1999; 515 (Pt 2):475-87.

Kourrich et al., "Kaliotoxin, a Kv1.1 and Kv1.3 channel blocker, improves associative learning in rats," Behav Brain Res. Apr. 8, 2001;120(1):35-46.

Lopantsev et al., "Hyperexcitability of CA3 pyramidal cells in mice lacking the potassium channel subunit Kv1.1," Epilepsia. Dec. 2003;44(12):1506-12.

MacDonald et al., "Members of the Kv1 and Kv2 voltage-dependent K(+) channel families regulate insulin secretion," Mol Endocrinol. Aug. 2001;15(8):1423-35.

MacDonald et al., "Voltage-dependent K(+) channels in pancreatic beta cells: role, regulation and potential as therapeutic targets," Diabetologia. Aug. 2003;46(8):1046-62. Epub Jun. 27, 2003.

Pozeg et al., "In vivo gene transfer of the O2-sensitive potassium channel Kv1.5 reduces pulmonary hypertension and restores hypoxic pulmonary vasoconstriction in chronically hypoxic rats," Circulation. Apr. 22, 2003;107(15):2037-44. Epub Apr. 14, 2003.

Rho et al., "Developmental seizure susceptibility of kv1.1 potassium channel knockout mice," Dev Neurosci. Nov. 1999;21(3-5):320-7.

Shah et al., "Immunosuppressive effects of a Kv1.3 inhibitor," Cellular Immunology 221, (2003), 100-106.

Vianna-Jorge et al., "Shaker-type Kv1 channel blockers increase the peristaltic activity of guinea-pig ileum by stimulating acetylcholine and tachykinins release by the enteric nervous system," Br J Pharmacol. Jan. 2003; 138(1):57-62.

Wickenden, "Potassium channels as anti-epileptic drug targets," Neuropharmacology. Dec. 2002;43(7):1055-60.

Wulff et al., "Potassium channels as therapeutic targets for autoimmune disorders," Current Opinion in Drug Discovery & Development 2003 6(5):640-647.

Xu et al., "The voltage-gated potassium channel Kv1.3 regulates peripheral insulin sensitivity," Proc Natl Acad Sci U S A. Mar. 2, 2004;101(9):3112-7. Epub Feb. 23, 2004 (epublished Feb. 23, 2004).

* cited by examiner

HETEROCYCLO INHIBITORS OF POTASSIUM CHANNEL FUNCTION

This application is a Divisional Application of prior application Ser. No. 10/417,355 filed on Apr. 16, 2003 now U.S. Pat. No. 7,005,436, which claims priority to U.S. Provisional Application Ser. No. 60/374,279, filed Apr. 19, 2002, the entirety of which is incorporated herein by reference.

FIELD OF THE INVENTION

The present invention provides for heterocyclyl compounds useful as inhibitors of potassium channel function (especially inhibitors of the $K_v1$ subfamily of voltage gated $K^+$ channels, more especially inhibitors $K_v1.5$ which has been linked to the ultra-rapidly activating delayed rectifier $K^+$ current $I_{Kur}$) and to pharmaceutical compositions containing such compounds. The present invention further provides for methods of using such compounds in the treatment of arrhythmia, $I_{Kur}$-associated disorders, and other disorders mediated by ion channel function.

BACKGROUND OF THE INVENTION

The importance of potassium channels was first recognized approximately fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels that exhibit functional, pharmacological and tissue distribution characteristics have been cloned. These cloned potassium channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostatis, and resting membrane potential.

Potassium channels are expressed in eukaryotic and procaryotic cells and are elements in the control of electrical and non-electrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., $K_v1$, $K_v2$, $K_v3$, $K_v4$). Subtypes within these subclasses have been characterized as to their putative function, pharmacology and distribution in cells and tissues (Chandy and Gutman, "Voltage-gated potassium channel genes" in Handbook of Receptors and Channels—Ligand and Voltage-gated Ion Channels, ed. R. A. North, 1995; Doupnik et al., Curr. Opin. Neurobiol. 5:268, 1995). For example, the $K_v1$ class of potassium channels is further subdivided depending on the molecular sequence of the channel, for example $K_v1.1$, $K_v1.2$, $K_v1.3$, $K_v1.4$, $K_v1.5$, $K_v1.6$, and $K_v1.7$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., J. Exp. Med. 160, 369, 1984; Decoursey et al., Nature, 307, 465, 1984). However, the $K^+$ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., Proc. Natl, Acad. Sci. USA, 86, 10171, 1989) showed that charybdotoxin would block $K_v1.3$ in human T-cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., Proc. Natl, Acad. Sci, USA, 89, 10094, 1992). Margatoxin, on the other hand, blocks only Kv1.3 in T-cells, and has immunosuppressant activity on both in in vitro and in vivo models. (Lin et al., J. exp. Med, 177, 637, 1993). The therapeutic utility of this compound, however, is limited by its potent toxicity. Recently, a class of compounds has been reported that may be an attractive alternative to the above mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) and atrial flutter are the most common cardiac arrhythmias in clinical practice and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class of Anti-Arrhythmic Action: Effects On Atrial And Ventricular Intracellular Potentials And Other Pharmacological Actions On Cardiac Muscle, of MJ 1999 and AH 3747" Br. J. Pharmacol 1970; 39:675-689. and Singh B. N., Vaughan Williams E. M, "The Effect of Amiodarone, A New Anti-Anginal Drug, On Cardiac Muscle", Br J. Pharmacol 1970; 39:657-667), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". J. Am. Coll. Cardiol. 1992; 20:1063-1065.) Drugs of this class are expected to be effective in preventing ventricular fibrillation. Selective class HI agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$, respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{K1}$) $K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{KS}$ (slowly activating and deactivating) (Sanguinetti and Jurkiewicz, Two Components Of Cardiac Delayed Rectifier $K^+$ Current: Differential Sensitivity To Block By Class III Antiarrhythmic Agents, J Gen Physiol 1990, 96:195-215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl]monochloride, predominantly, if not exclusively, block $I_{Kr}$. Although, amiodarone is a blocker of $I_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. Circ. Res. 1991, 69:519-529), it also blocks $I_{Na}$ and $I_{Ca}$, effects thyroid function, is as a nonspecific adrenergic blocker, and acts as an inhibitor of the enzyme phospholipase (Nademanee, K. "The Amiodarone Odessey" .J.Am. Coll. Cardiol. 1992; 20: 1063-1065). Therefore its method of treating arrhythmia is uncertain. Most Class III agents that are known to be in development predominantly block $I_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block $I_{kr}$, the rapidly activating component of $I_K$ found both in the human atrium and ventricle.

Since these $I_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", Am J. Cardiol, 1993; 72:44B-49B). This exaggerated effect at slow heart rates has been termed "reverse frequency-dependence", and is in contrast to frequency-independent or frequency-dependent actions (Hondeghem, L. M. "Development of Class III Antiarrhythmic Agents". J.Cadiovasc.Cardiol. 20 (Suppl.2): S17-S22).

The slowly activating component of the delayed rectifier ($I_{ks}$) potentially overcomes some of the limitations of $I_{kr}$ blockers associated with ventricular arrhythmias. Because of its slow activation kinetics however, the role of $I_{ks}$ in atrial repolarization may be limited due to the relatively short APD of the atrium. Consequently, although $I_{ks}$ blockers may provide distinct advantage in the case of ventricular arrhythmias, their ability to affect SVT is considered to be minimal.

The ultra-rapidly activating delayed rectifier $K^+$ current ($I_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv1.5, would overcome the short coming of other compounds by prolonging refractoriness by retarding repolarization in the human atrium without causing the delays in ventricular reporlarization that underlie arrhythmogenic after depolarizations and acquired long QT syndrome observed during treatment with current Class III drugs.

In intact human atrial myocytes an ultra-rapidly activating delayed rectifier $K^+$ current $I_{kur}$ which is also known as the sustained outward current, $I_{sus}$ or $I_{so}$, has been identified and this current has properties and kinetics identical to those expressed by the human $K^+$ channel clone (hKv1.5, HK2) when isolated from human heart and stably expressed in human (HEK-293) cell lines (Wang et al., 1993, Circ Res 73:1061-1076; Fedida et al., 1993, Circ Res 73:210-216; Snyders et al., 1993, J Gen Physiol 101:513-543) and originally cloned from rat brain (Swanson et al., 10, Neuron 4:929-939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs: In: Cardiac Arrhythmias, edited by: E. Sandoe, E. Flensted-Jensen, K. Olesen; Sweden, Astra, Sodertalje, pp 449-472, 1981) which cause a selective inhibition of the maximum velocity of the upstroke of the action potential ($V_{max}$) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

SUMMARY OF THE INVENTION

The present invention provides heterocylyl compounds of the following formula I, including enantiomers, diastereomers, and salts thereof, useful as inhibitors of potassium channel function (especially inhibitors of the $K_v1$ subfamily of voltage gated $K^+$ channels, more especially inhibitors of $K_v1.5$ which has been linked to the ultra-rapidly activating delayed rectifier $K^+$ current, $I_{Kur}$) for the treatment of disorders such as arrhythmia and $I_{Kur}$-associated disorders:

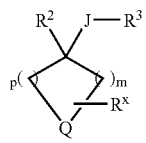

I including enantiomers, diastereomers and salts thereof wherein m and p are independently 0, 1, 2 or 3 provided that the sum of m and p is at least 2;

Q is NR', O, S, S(O) or S(O)$_2$;

$R^1$ is

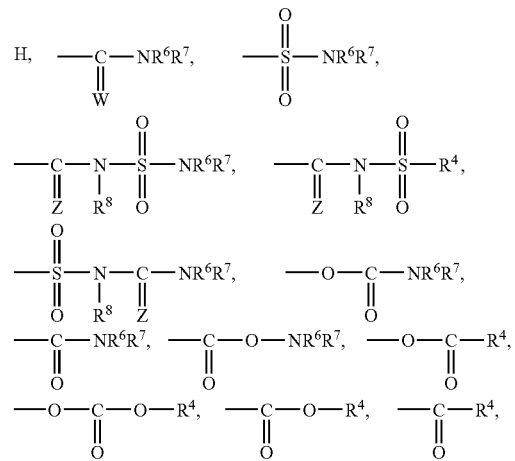

—C(=NR$^{8b}$)R$^{8c}$, —SO$_2$R$^{8c}$, —OC(O)CCl$_3$, —C(=S)R$^{8c}$, optionally substituted aryl, optionally substituted heteroaryl, optionally substituted heterocyclo, perfluoroalkyl, cyano, hydroxy, optionally substituted alkoxy, optionally substituted aryloxy, optionally substituted heteroaryloxy, optionally substituted alkyl, optionally substituted cycloalkyl, optionally subsituted alkenyl, or optionally subsituted alkynyl;

$R^2$ is heteroaryl, (heteroaryl)alkyl, aryl, (aryl)alkyl, heterocyclo, (heterocyclojalkyl, alkyl or cycloalkyl, any of which may be optionally independently substituted with one or more groups $T^1$, $T^2$ or $T^3$;

J is a bond, $C_{1-4}$ alkylene optionally independently substituted with one or more groups $T^{1a}$, $T^{2a}$ or $T^{3a}$, or $C_{1-4}$ alkenylene optionally independently substituted with one or more groups $T^{1a}$, $T^{2a}$ or $T^{3a}$;

$R^3$ is

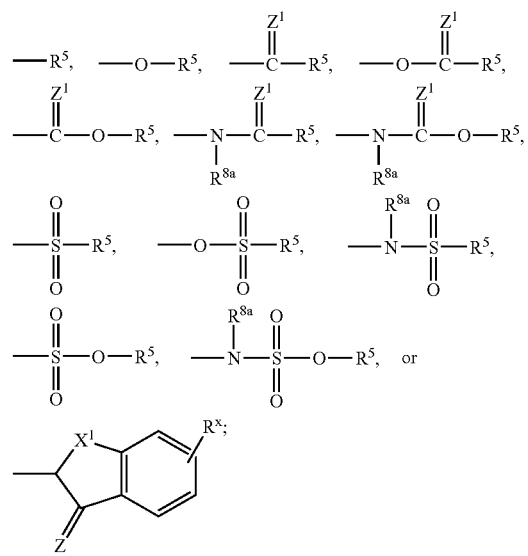

$R^4$ is H, alkyl, haloalkyl, alkenyl, alkynyl, cycloalkyl, heterocyclo, aryl, (aryl)alkyl or heteroaryl any of which may be optionally independently substituted with one or more groups $T^{1b}$, $T^{2b}$ or $T^{3b}$;

$R^5$ is
(a) —$NR^{6a}R^{7a}$, cyano or
(b) heteroaryl, (heteroaryl)alkyl, aryl, (aryl)alkyl, alkyl, cycloalkyl, (cycloalkyl)alkyl, heterocyclo, (heterocyclo)alkyl, or alkyl any of which may be optionally independently substituted with one or more groups $T^{1c}$, $T^{2c}$ or $T^{3c}$;

$R^6$, $R^{6a}$, $R^7$, $R^{7a}$, $R^8$, $R^{8a1}$, $R^{82a}$, and $R^{8a3}$ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, (cyano)alkyl, (alkenyl)alkyl, (alkynyl)alkyl, cycloalkyl, (cycloalkyl)alkyl, aryl, (aryl)alkyl, heteroaryl, (heteroaryl)alkyl, heterocyclo, (heterocyclo)alkyl, —C(O)$R^9$, —$CO_2R^9$, —C(O)—$NR^9R^{10}$, or —$NR^9R^{10}$ any of which may be optionally independently substituted with one or more groups $T^{1d}$, $T^{2d}$ or $T^{3d}$;

or $R^6$ and $R^7$, or $R^{6a}$ and $R^{7a}$ together with the nitrogen atom to which they are attached may combine to form a 4 to 8 membered heterocyclo ring optionally independently substituted with one or more groups $T^{1d}$, $T^{2d}$ or $T^{3d}$;

or one of $R^6$ or $R^7$, may combine with one of $R^8$, $R^{8a}$ or $R^9$ to form a saturated or unsaturated 5 to 8 membered ring optionally independently substituted with one or more groups $T^{1d}$, $T^{2d}$ or $T^{3d}$.

or one of $R^{6a}$ or $R^{7a}$, may combine with $R^{8a1}$ to form a saturated or unsaturated 5 to 8 membered ring optionally independently substituted with one or more groups $T^{1d}$, $T^{2d}$ or $T^{3d}$ $R^{8b}$ is H, alkyl, aryl, cyano, nitro, acyl or —$SO_2$(alkyl) were the alkyl and aryl groups may be optionally independently substituted with one or more groups $T^{1d}$, $T^{2d}$ or $T^{3d}$;

$R^{8c}$ is H, alkyl, cycloalkyl, alkenyl, alkynyl, aryl, arylalkyl, heterocylco, heteroaryl, alkoxy or aryloxy any of which may be optionally independently substituted with one or more groups $T^{1d}$, $T^{2d}$ or $T^{3d}$;

$R^{8d}$ is $R^4$, $COR^4$, $CO_2R^4$, $SO_2R^4$, $CONR^6R^7$, or $SO_2NR^6R^7$;

$R^9$ and $R^{10}$ are independently H, alkyl, hydroxy, alkoxy, aryloxy, heterocyclooxy, heteroaryloxy, (hydroxy)alkyl, (alkoxy)alkyl, (aryloxy)alkyl, (heterocylooxy)alkyl, (heteroaryloxy)alkyl, cycloalkyl, (cycloalkyl)alkyl, aryl, (aryl)alkyl, heteroaryl, (heteroaryl)alkyl, heterocyclo, or (heterocyclo)alkyl any of which may be optionally independently substituted with one or more groups $T^{1f}$, $T^{2f}$ or $T^{3f}$ or $R^9$ and $R^{10}$ together with the nitrogen atom to which they are attached may combine to form a saturated or unsaturated ring which may be optionally independently substituted with one or more groups $T^{1f}$, $T^{2f}$ or $T^{3f}$;

W is =$NR^{8a1}$, =N—$CO_2R^{8a1}$, =N—$COR^{8a1}$, =N—CN, =N—$SO_2R^{8a1}$, or

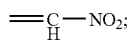

$X^1$ is O, S, $NR^{8a2}$ or $CH_2$;

Z, $Z^1$ and $Z^2$ are independently =O, =S, =$NR^{8a3}$ or =N—CN;

$R^X$ is one or more optional substituents, attached to any available ring carbon atom, independently selected from $T^{1g}$, $T^{2g}$ or $T^{3g}$;

$T^{1-1g}$, $T^{2-2}g$, and $T^{3-3g}$ are each independently (1) hydrogen or $T^6$, where $T^6$ is
  (i) alkyl, (hydroxy)alkyl, (alkoxy)alkyl, alkenyl, alkynyl, cycloalkyl, (cycloalkyl)alkyl, cycloalkenyl, (cyclokenyl)alkyl, aryl, (aryl)alkyl, heterocyclo, (heterocylco)alkyl, heteroaryl, or (heteroaryl)alkyl;
  (ii) a group (i) which is itself substituted by one or more of the same or different groups (i); or
  (iii) a group (i) or (ii) which is independently substituted by one or more (preferably 1 to 3) of the following groups (2) to (13) of the definition of $T^{1-1g}$, $T^{2-2g}$ and $T^{3-3g}$, (2) —OH or —$OT^6$,
(3) —SH or —$ST^6$,
(4) —C(O)$_t$H, —C(O)$_tT^6$, or —O—C(O)$T^6$, where t is 1 or 2;
(5) —$SO_3H$, —S(O)$_tT^6$, or S(O)$_tN(T^9)T^6$,
(6) halo,
(7) cyano,
(8) nitro,
(9) -$T^4$-$NT^7T^8$,
(10) -T-N($T^9$)-$T^5$-$NT^7T^8$,
(11) -$T^4$-N($T^{10}$)-$T^5$-$T^6$,
(12) -$T^4$-N($T^{10}$)-$T^5$-H,
(13) oxo, $T^4$ and $T^5$ are each independently
(1) a single bond,
(2) -$T^{11}$-S(O)$_t$-$T^{12}$-,
(3) -$T^{11}$-C(O)-$T^{12}$-,
(4) -$T^{11}$-C(S)-$T^{12}$-,
(5) -$T^{11}$-O-$T^{12}$-,
(6) -$T^{11}$-S-$T^{12}$-,
(7) -$T^{11}$-O—C(O)-$T^{12}$-,
(8) -$T^{11}$-C(O)—O-$T^{12}$-,
(9) -$T^{11}$-C(=NT )-$T^{12}$, or
(10) -$T^{11}$-C(O)—C(O)-$T^{12}$-, $T^7$, $T^8$, $T^9$, $T^{9a}$ and $T^{10}$
(1) are each independently hydrogen or a group provided in the definition of $T^6$, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1g}$, $T^{2-2g}$ and $T^{3-3g}$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^{1-1g}$, $T^{2-2g}$ and $T^{3-3g}$, or
(4) $T^7$ and $T^8$ or $T^9$ and $T^{10}$ together with the nitrogen atom to which they are attached may combine to form a group —N=$CT^{13}$ $T^{14}$ where $T^{13}$ and $T^{14}$ are each independently H or a group provided in the definition of $T^6$; and $T^{11}$ and $T^{12}$ are each independently
(1) a single bond,
(2) alkylene,
(3) alkenylene, or
(4) alkynylene.

The present invention provides novel methods for the prevention and treatment of arrhythmia and $I_{Kur}$-associated disorders employing one or more compounds of the formula I, enantiomers, diastereomers or pharmaceutically acceptable salts thereof. In particular the present invention provides a novel method for the selective prevention and treatment of supraventricular arrhythmias.

Preferred compounds within the scope of formula I include compounds and salts thereof wherein one or more, and especially all of Q, $R^2$, J and $R^3$ are selected from the following definitions:

Q is $NR^1$ or O;

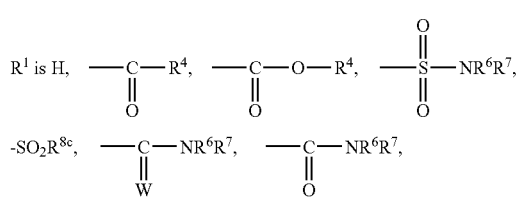

—C(=S)$R^{8c}$, —C(=$NR^{8b}$)$R^{8c}$ or heteroaryl;

$R^2$ is aryl, (aryl)alkyl or heteroaryl any of which may be optionally independently substituted with one or more $T^1$, $T^2$ $T^3$;

J is a bond or methylene; and

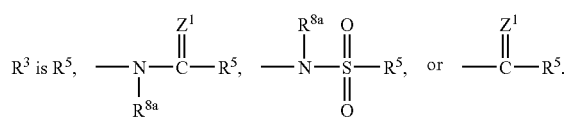

More preferred compounds within the scope of formula I include compounds and salts thereof wherein one or more, and especially all of Q, $R^2$, J and $R^3$ are selected from the following definitions:

Q is $NR^1$;

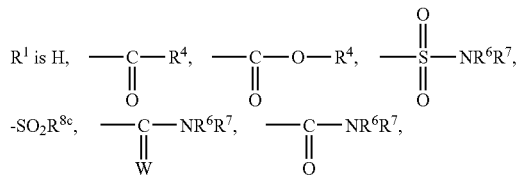

—C(=S)$R^{8c}$, or heteroaryl;

$R^2$ is aryl, (aryl)alkyl or heteroaryl (especially where aryl is phenyl and heteroaryl is thiophenyl) any of which may be optionally independently substituted with one or more $T^1$, $T^2T^3$;

J is a bond or methylene;

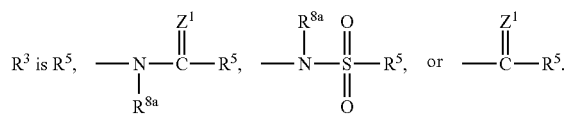

$R^4$ is alkyl, alkenyl, alkynyl, cycloalkyl, heterocyclo, aryl, (aryl)alkyl, heteroaryl or (heteroaryl)alkyl any of which may be optionally independently substituted with one or more $T^{1b}$, $T^{2b}$ $T^{3b}$;

$R^5$ is (a) —$NR^{6a}R^{7a}$ or (b) aryl, (aryl)alkyl, heteroaryl, (heteroaryl)alkyl, heterocyclo or (heterocyclo)alkyl any of which may be optionally independently substituted with one or more $T^{1c}$, $T^{2c}$ $T^{3c}$;

$R^6$, $R^{6a}$, $R^7$ and $R^{7a}$ are independently H, alkyl, alkenyl, alkynyl, aryl, (aryl)alkyl, (alkoxy)alkyl, cycloalkyl, (cycloalkyl)alkyl, (hydroxy)alkyl, heteroaryl, (heteroaryl)alkyl, heterocyclo, (heterocyclo)alkyl, (aryloxy)alkyl, —C(O)$R^9$, —$CO_2R^9$, or —C(O)—$NR^9R^{10}$ any of which may be optionally independently substituted with one or more $T^{1d}$, $T^{2d}$ $T^{3d}$;

or $R^6$ and $R^7$, or $R^{6a}$ and $R^{7a}$ together with the nitrogen atom to which they are attached combine to form an optionally substituted 4 to 8 membered heterocyclo ring (e.g.,

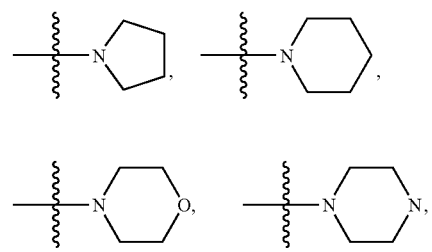

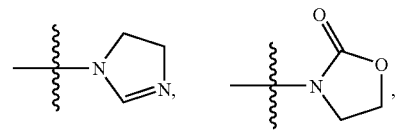

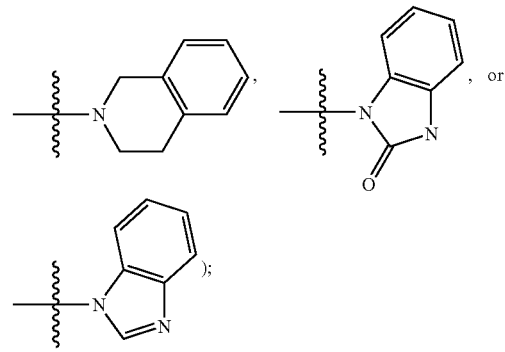

);

$R^{8a}$ is H, alkyl, or (aryl)alkyl;

$R^{8c}$ is (a) alkyl, aryl, heteroaryl any of which may be optionally independently substituted with one or more $T^{1d}$, $T^{2d}$ $T^{3d}$; or (b) —$NR^9R^{10}$;

W is =N—CN;

$Z^1$ is =O or =N—CN; and $T^1$, $T^{1b}$, $T^{1c}$, $T^{1d}$, $T^2$, $T^{2b}$, $T^{2c}$, $T^{2d}$, $T^3$, $T^{3b}$, $T^{3c}$ and $T^{3d}$ are independently halo, cyano, alkyl, aryl, (aryl)alkyl, heteroaryl, (heteroaryl)alkyl, haloalkyl, —OH, —$OT^6$, —C(O)$_tT^6$, —$SO_2T^6$, -$T^4NT^7T^8$, or -$T^4N(T^{10})T^5$-$T^6$.

Preferred compounds generally have the structure

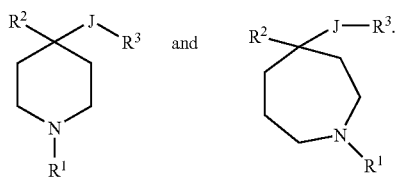

and

Preferred -JR³ moeities include:

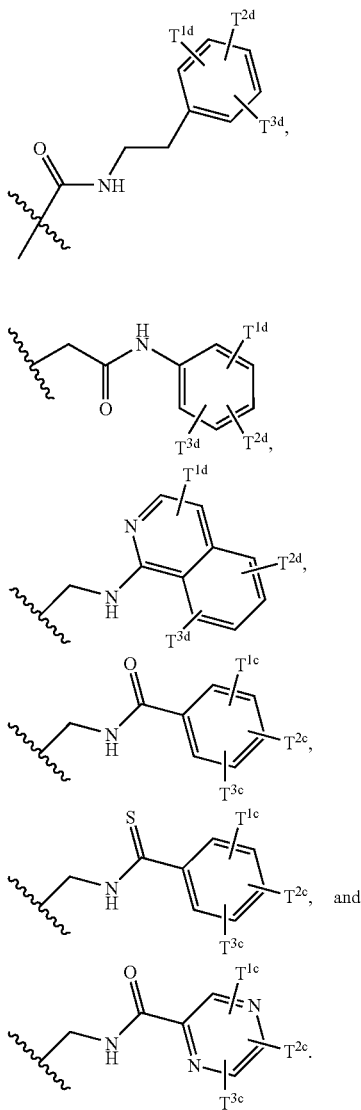

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ or —$S(O)_tN(T^9)T^6$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T_4$-$N(T^9)$-$T^5$-$T^6$, —$S(O)_tT^6$ or —$S(O)_tN(T^9)T^6$.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ r —$S(O)_tN(T^9)T^6$.

The term "alkylene" refers to a straight chain bridge of 1 to 4 carbon atoms connected by single bonds (e.g., —$(CH_2)_x$— wherein x is 1 to 5), which may be substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ or —$S(O)_tN(T^9)T^6$.

The term "alkenylene" refers to a straight chain bridge of 2 to 5 carbon atoms having one or two double bonds that is connected by single bonds and may be substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, -$S(O)T6$ or —$S(O)_tN(T^9)T^6$. Exemplary alkenylene groups are —CH═CH—CH═CH—, —$CH_2$—CH═CH—, —$CH_2$—CH═CH—$CH_2$—, —$C(CH_3)_2$CH═CH— and —$CH(C_2H_5)$—CH═CH—.

The term "alkynylene" refers to a straight chain bridge of 2 to 5 carbon atoms that has a triple bond therein, is connected by single bonds, and may be substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ or —$S(O)_tN(T^9)T^6$. Exemplary alkynylene groups are —C≡C—, —$CH_2$—C≡C—, —$CH(CH_3)$—C≡C— and —C≡C—$CH(C_2H_5)CH_2$—.

The terms "ar" or "aryl" refer to aromatic homocyclic (i.e., hydrocarbon) mono-, bi- or tricyclic ring-containing groups preferably having 6 to 14 members such as phenyl, naphthyl and biphenyl, as well as such rings fused to a cycloalkyl, cycloalkenyl, heterocyclo, or heteroaryl ring. Examples include:

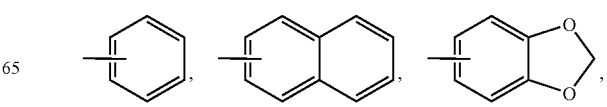

-continued

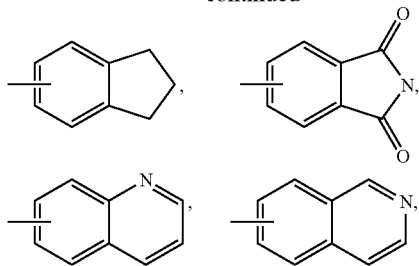

and the like.

The term "substituted aryl" refers to aryl groups substituted with one or more groups listed in the definition of $T^{1-1g}$, $T^{2-2g}$ and $T^{3-3g}$, preferably selected cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ or —$S(O)_tN(T^9)T^6$.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons forming the ring, and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

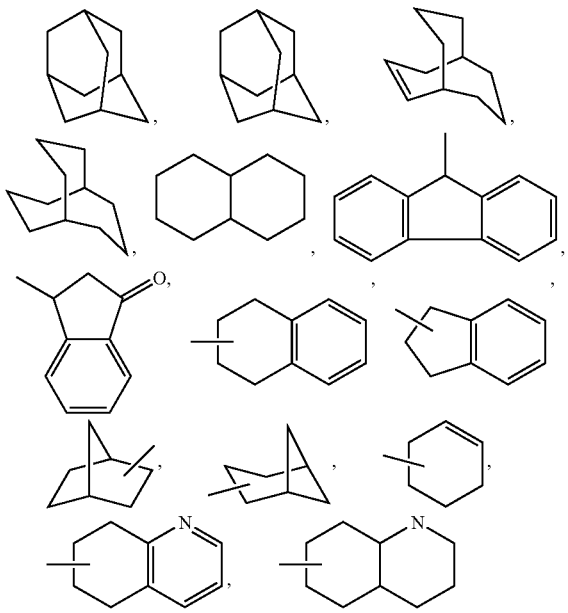

and the like. The terms "substituted cycloalkyl" refers to cycloalkyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, —$S(O)_tT^6$ or —$S(O)_tN(T^9)T^6$.

The terms "halogen" and "halo" refer to fluorine, chlorine, bromine and iodine.

The terms "heterocycle", "heterocyclic", "heterocyclyl", "heterocyclic group" or "heterocyclo" refer to fully saturated or partially or unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be substituted or quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

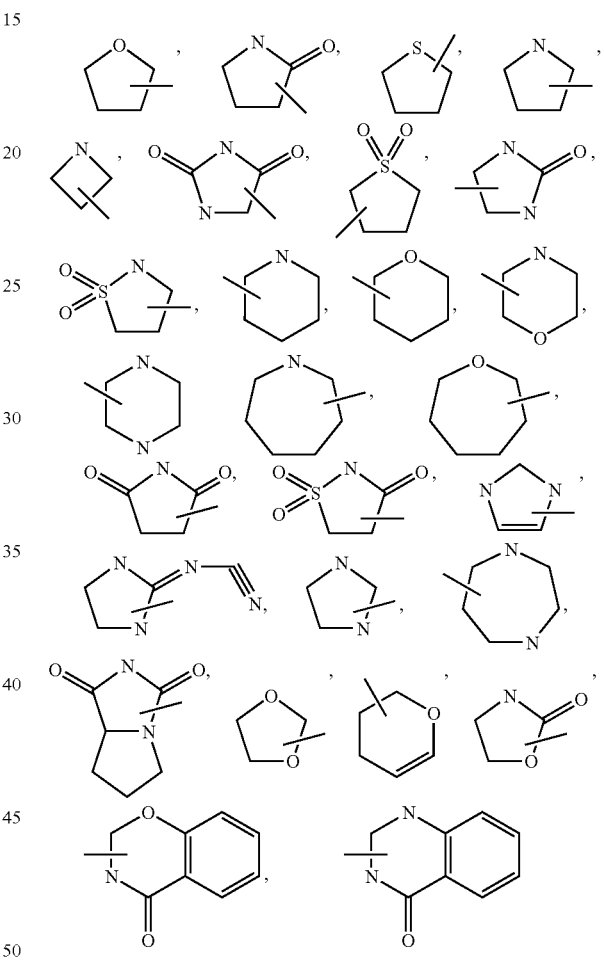

and the like.

The terms "substituted heterocycle", "substituted heterocyclic", "substituted heterocyclic group" and "substituted heterocyclo" refer to heterocycle, heterocyclic and heterocyclo groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, -$T^4$-$NT^7T^8$, -$T^4$-$N(T^9)$-$T^5$-$T^6$, $S(O)_tT^6$ or —$S(O)_tN(T^9)T^6$.

The term "heteroaryl" as used herein alone or as part of another group refers to a 5-6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the description of $T^1$, $T^2$ and $T^3$. Also an available nitrogen or sulfur atom in the heteroaryl ring can be oxidized. Examples of heteroaryl rings include

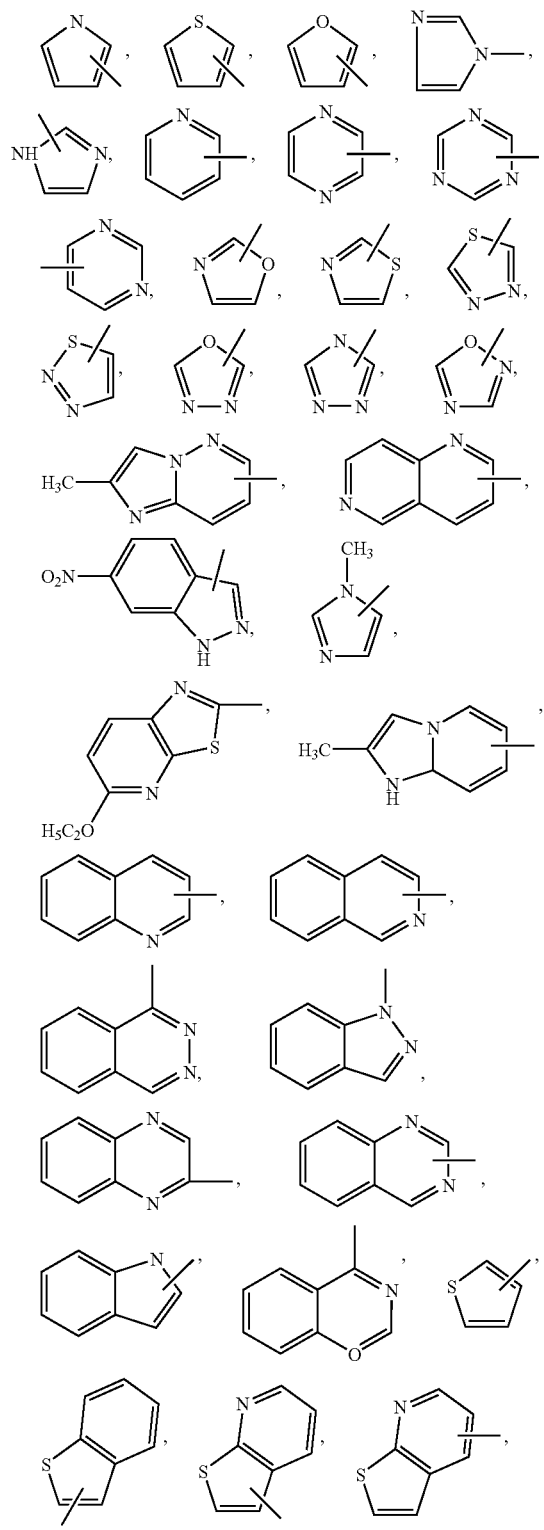

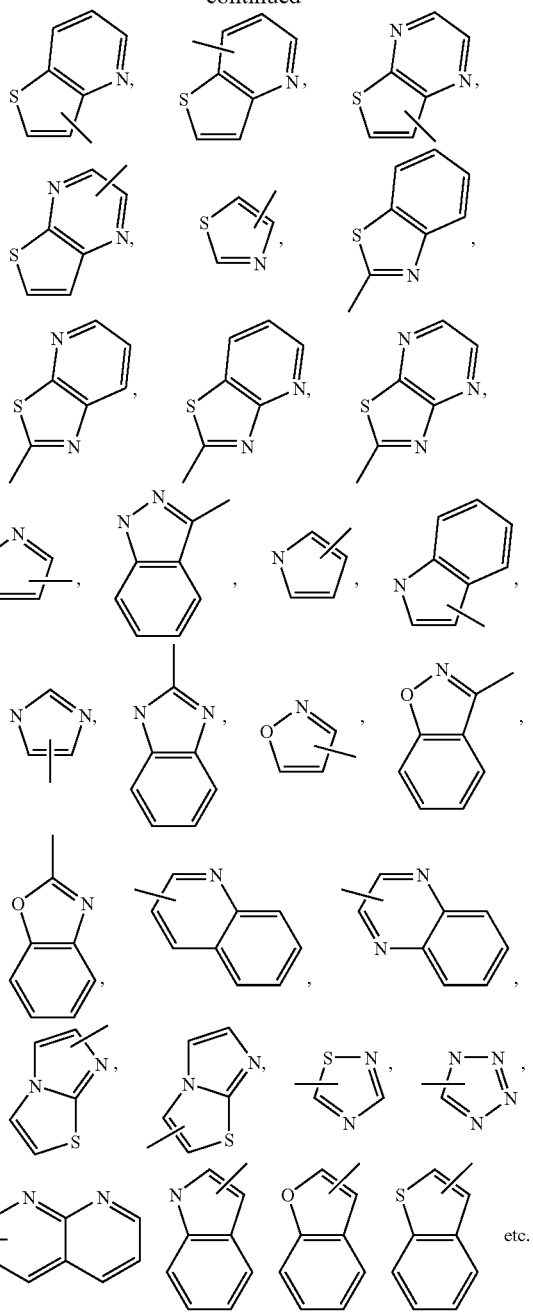

etc.

Throughout the specification, groups and substituents thereof may be chosen to provide stable moieties and compounds.

The compounds of the present invention form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of the present invention which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of the present invention which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the present invention, and salts thereof, may exist in their tautomeric form, all such tautomeric forms are contemplated herein as part of the present invention.

All stereoisomers of the present compounds, such as those which may exist due to asymmetric carbons on the various R and Z substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IWPAC 1974 Recommendations.

The terms "including", "such as", "for example" and the like are intended to refer to exemplary embodiments and not to limit the scope of the present invention.

Schemes

Compounds of the formula I may be prepared using the sequence of steps outlined below.

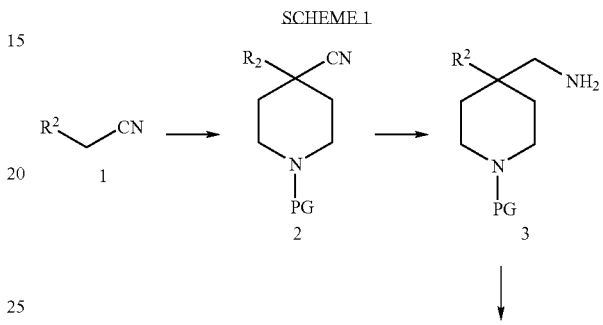

Compounds of the forumula I may be prepared using the sequence of steps outlined in scheme 1. Specifically, compounds of the formula I where $R^2$ is heteroaryl or substituted heteroaryl and $R^5$ is aryl, substituted aryl, heteroaryl or substituted heteroaryl may be prepared using Scheme 1. Heteroaryl acetonitrile 1 is deprotonated and alkylated to form the N-protected piperidine ring 2. Reduction of nitrile 2 generates primary amine 3. The amine is subsequently acylated with Heterocyle2 acyl chloride, deprotected and the resulting amine is taken onto final product carbamates, sulfonamides, sulfenyl ureas and cyanoguanidines.

Compounds of formula I where $R^3$ is $$\underset{\phantom{x}}{\overset{Z^1}{\|}}\!\!-\!\!R^5,$$

$Z^1$ is O and $R^5$ is —$NR^{6a}R^{7a}$ may be prepared as described in Scheme 2.

SCHEME 2

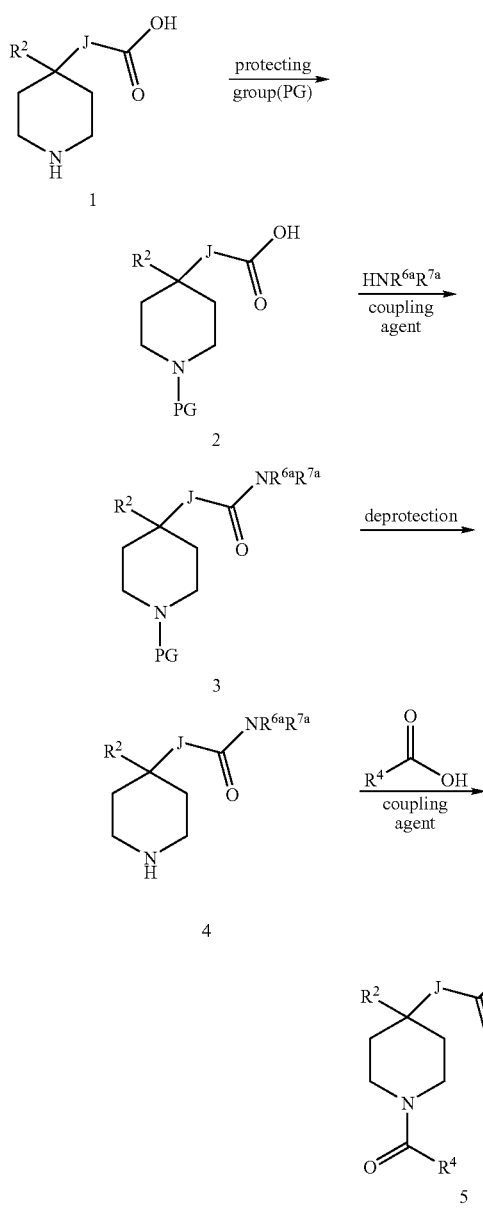

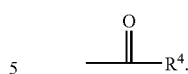

In addition to carboxylic acids or acid chlorides, one skilled in the art will recognize that the piperidine nitrogen atom of compound 4 may be made to react with a number of other readily available raw materials to provide compounds of formula I. For example, compound 4 may be made to react with sulfonyl chlorides (e.g.; $R^{8c}SO_2Cl$) in the presence of an acid scavenger to provide compounds of formula I where Q is $NR^1$ and $R^1$ is

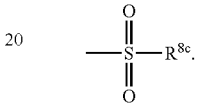

Compound 4 may made to react with isocyanates (e.g.; $R^7R^6NCO$) to provide compounds of formula I where Q is $NR^1$ and $R^1$ is

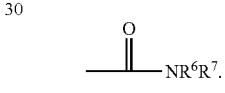

Compound 4 may be made to react with chloroformates (e.g.; $R^4OCOCl$) in the presence of an acid scavenger to provide compounds of formula I where Q is $NR^1$ and $R^1$ is

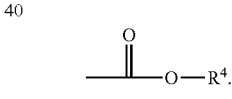

Compound 4 may be made to react with certain heteroaryl groups (e.g; heteroaryl-X where X is a leaving group such as a halogen atom) in the presence of an acid scavenger to provide compound 5 where Q is $NR^1$ and $R^1$ is heteroaryl. This reaction is may be performed in an organic solvent such a tetrahydrofuran or acetonitrile at elevated temperatures. Alternatively, this reaction may be performed in the presence of a palladium catalyst to provide compound 5 where Q is $NR^1$ and $R^1$ is heteroaryl.

Protection of the nitrogen atom of compound 1 gives compound 2. One skilled in the art will recognize a variety of nitrogen protecting groups that are known in the literature. In this example, suitable nitrogen protecting groups include the benzyl (Bn), N-tert-butoxycarbonyl (Boc) and carbobenzyloxy (CBz) groups. The carboxylic acid moiety of compound 2 may be coupled with an amine $HNR^{6a}R^{7a}$ using a variety of coupling procedures known in the literature to provide carboxamide compound 3. The nitrogen atom of compound 3 may be deprotected and made to react with a carboxylic acid (e.g.; $R^4CO_2H$; shown in Scheme 1) in the presence of a coupling agent or an acid chloride (e.g.; $R^4COCl$) in the presence of an acid scavenger such as triethylamine or polystyrene-diisoproplyethylamine resin to give compound 5 where Q is $NR^1$ and $R^1$ is Additional compounds of formula I where $R^3$ is

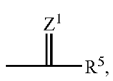

$Z^1$ is O and $R^5$ is $-NR^{6a}R^{7a}$ may be prepared using as described in Scheme 3 and Scheme 4.

SCHEME 3

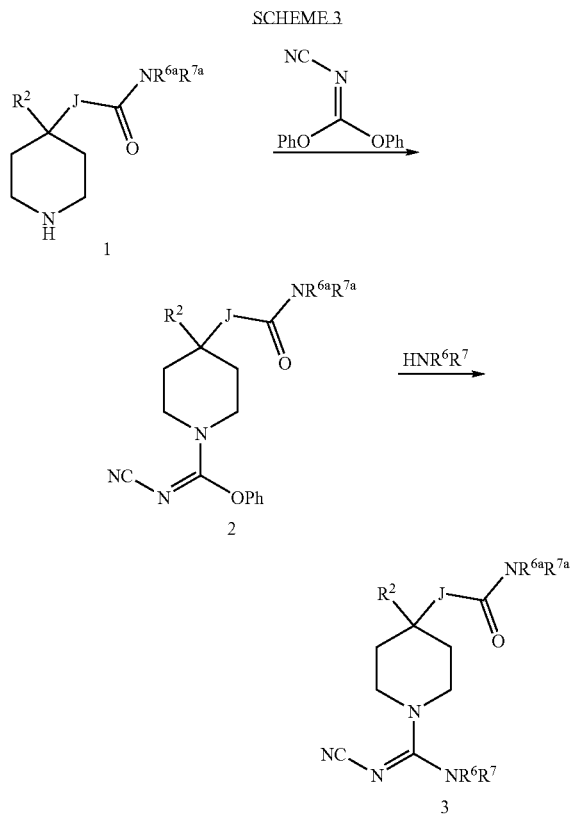

Referring to Scheme 2, compound 1 may be made to react with diphenyl N-cyanocarbonimidate in a solvent such as tetrahydrofuran, acetonitrile or isopropanol to provide compound 2. Typically this reaction is conducted at elevated temperatures. Compound 2 may be made to react with an amine HNR⁶R⁷ to provide cyano guanidine compound 3 where Q is NR¹ and R¹ is

and W is N—CN.

SCHEME 4

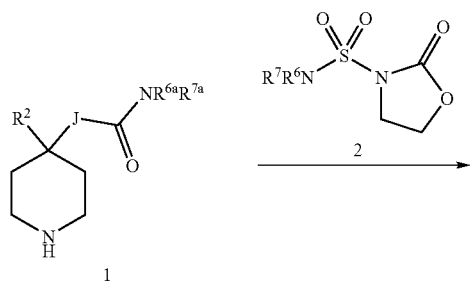

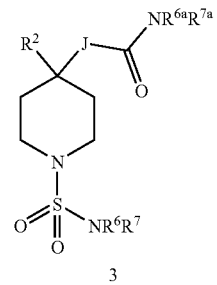

Referring to Scheme 3, compound 1 may be made to react with compound 2 to provide sulfenyl urea compound 3 where Q is NR¹ and R¹ is

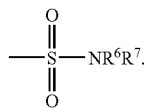

Compound 2 may be prepared by reacting 2-chloroethanol with chlorosulfonyl isocyanate followed by an amine HNR⁶R⁷ in the presence of an acid scavenger such as triethylamine in an organic solvent such as dichloromethane. One skilled in the art will recognize certain sulfenyl ureas may be prepared from commercially available raw materials. For example, compound 1 may be made to react with dimethylsulfamoyl chloride in a solvent such as tetrahydrofuran or dichloromethane in the presence of an acid scavenger such as triethylamine or polystyrene-diisopropylethylamine resin to provide compound 3 where Q is NR¹ and R¹ is

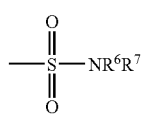

and R⁶ and R⁷ are each methyl. Compound 1 may be made to react with sulfamide in a solvent such as 1,4-dioxane at elevated temperature to provide compound 3 where Q is NR¹ and R¹ is

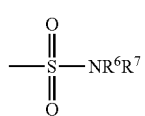

and R⁶ and R⁷ are each hydrogen.

Compounds of formula I where J is C₁-alkylene (e.g.; CH₂), R³ is

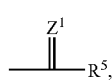

Z¹ is O and R⁵ is —NR⁶ᵃR⁷ᵃ may be prepared using as described in Scheme 5.

SCHEME 5

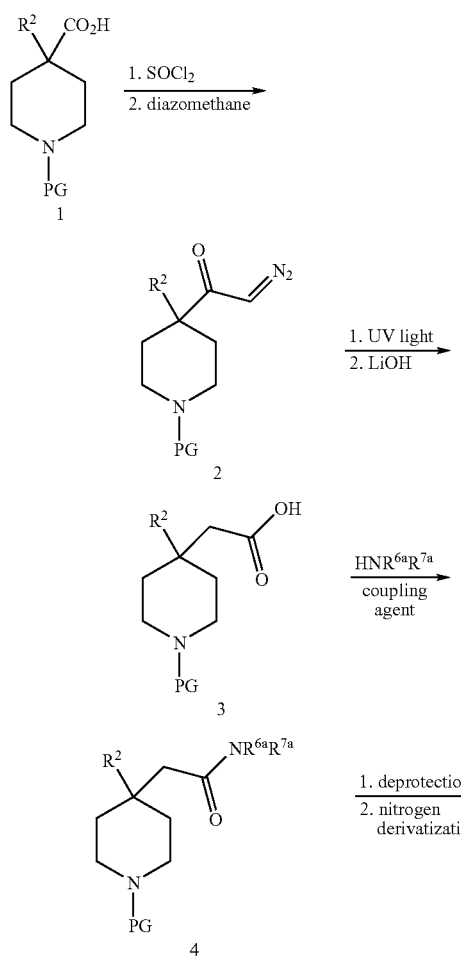

The carboxylic acid compound 1 may be treated with thionyl chloride to convert the carboxylic acid to the acid chloride that is made to react with diazomethane in a solvent such as ethyl ether to produce a diazo intermediate compound 2. Compound 2 may be irradiated under ultra-violet light (λ=365 nM) in a solvent such as methanol to provide an ester that may be hydrolyzed to the carboxylic acid compound 3 by treatment with aqueous lithium hydroxide. The carboxylic acid moiety of compound 3 may be coupled with an amine $HNR^{6a}R^{7a}$ using a variety of coupling procedures known in the literature to provide carboxamide compound 4. The nitrogen atom of compound 3 may be deprotected and the nitrogen atom further derivatized (see Schemes 1-3) to provide compounds of formula I.

Compounds of formula I where J is a bond, $R^3$ is

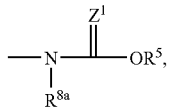

$Z^1$ is O, $R^5$ is —$NR^{6a}R^{7a}$ and $R^{8a}$ is hydrogen may be prepared using as described in Scheme 6.

SCHEME 6

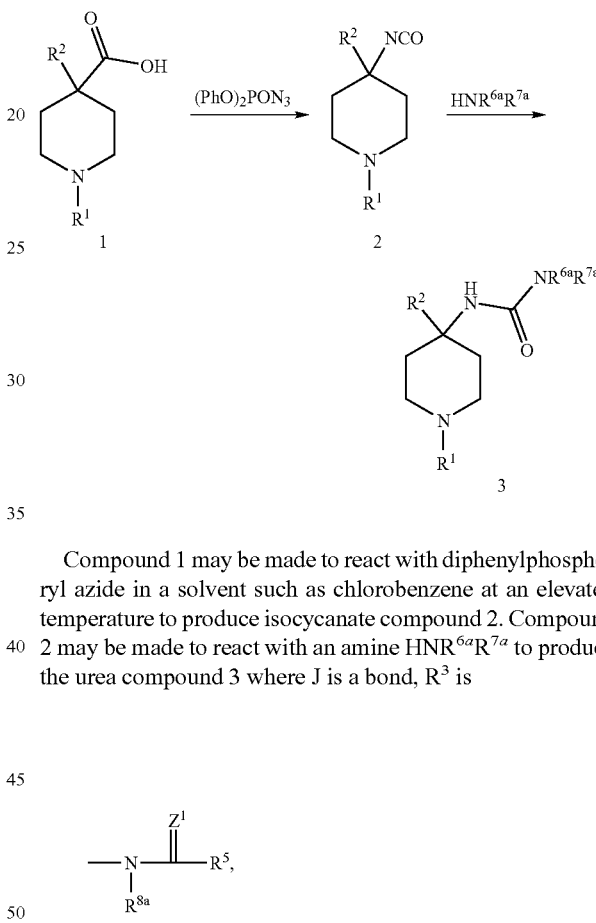

Compound 1 may be made to react with diphenylphosphoryl azide in a solvent such as chlorobenzene at an elevated temperature to produce isocycanate compound 2. Compound 2 may be made to react with an amine $HNR^{6a}R^{7a}$ to produce the urea compound 3 where J is a bond, $R^3$ is $Z^1$ is O, $R^5$ is —$NR^{6a}R^{7a}$ and $R^{8a}$ is hydrogen.

Compounds of formula I where J is a bond, $R^3$ is $Z^1$ is O and $R^{8a}$ is hydrogen may be prepared using as described in Scheme 7.

SCHEME 7

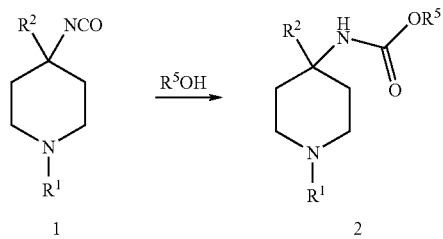

Isocyanate compound 1 may be made to react with an alcohol $R^5OH$ in a solvent such as chlorobenzene or terahydrofuran to provide compound 2 where J is a bond, $R^3$ is

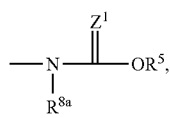

$Z^1$ is O and $R^{8a}$ is hydrogen.

Compounds of formula I where J is a bond, $R^3$ is

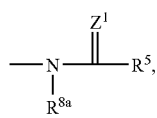

$Z^1$ is O, $R^5$ is not $NR^{6a}R^{7a}$ and $R^{8a}$ is hydrogen may be prepared using as described in Scheme 8.

SCHEME 8

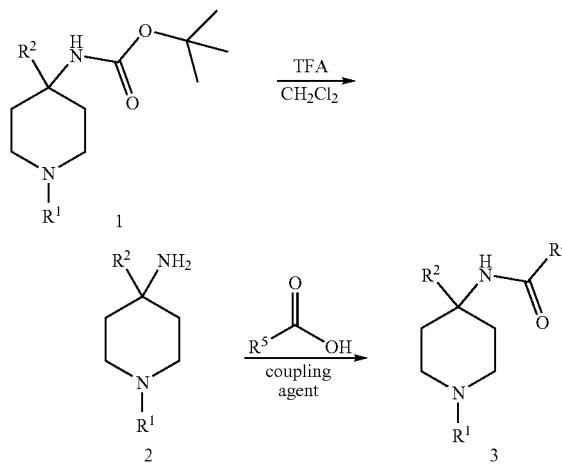

Compound 1 (see Scheme 6; $R^5$ is tert-butyl) may be deprotected by treatment with trifluoroacetic acid in a solvent such as dichloromethane to provide amine compound 2. The amino group of compound 2 may be made to react with a carboxylic acid (e.g.; $R^5CO_2H$; shown in Scheme 7) in the presence of a coupling agent or an acid chloride (e.g.; $R^5COCl$) in the presence of an acid scavenger such as triethylamine or polystyrene-diisoproplyethylamine resin to give compound 3 where J is a bond, $R^3$ is

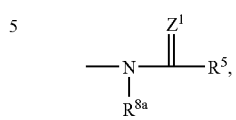

$Z^1$ is O, $R^5$ is not $NR^{6a}R^{7a}$ and $R^{8a}$ is hydrogen. In addition to carboxylic acids or acid chlorides, one skilled in the art will recognize that compound 2 may be made to react with a number of other readily available raw materials to provide compounds of formula I. For example, compound 2 may be made to react with sulfonyl chlorides (e.g.; $R^5SO_2Cl$) in the presence of an acid scavenger to provide compounds of formula I where J is a bond and $R^3$ is

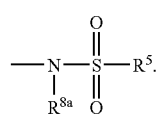

Compounds of formula I where $R^3$ is R., $R^5$ is $NR^{6a}R^7$ and $R^{6a}$ is heteroaryl may be prepared as described in Scheme 9.

SCHEME 9

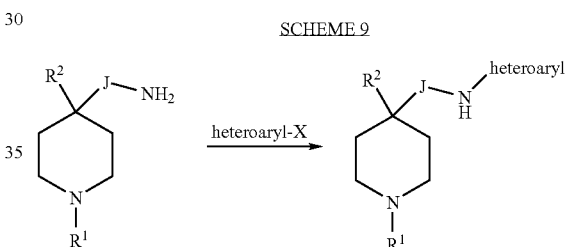

Amine compound 1 may be made to react with a substituted aryl or heteroaryl compound where X is a halogen atom, triflate or similar leaving group to provide compound 2. This reaction may be conducted in an organic solvent such a tetrahydrofuran or acetonitrile at an elevated temperature. Alternatively, this reaction may be performed in the presence of a palladium catalyst to provide compound 2 where $R^3$ is $R^5$, $R^5$ is $NR^{6a}R^{7a}$ and $R^{6a}$ is heteroaryl.

Compounds of formula I where $R^3$ is $R^5$ and $R^5$ is heteroaryl may be prepared as described in Scheme 10 and Scheme 11.

SCHEME 10

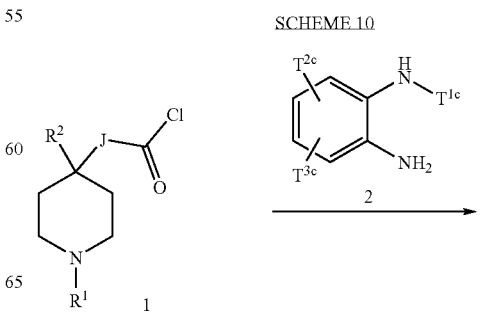

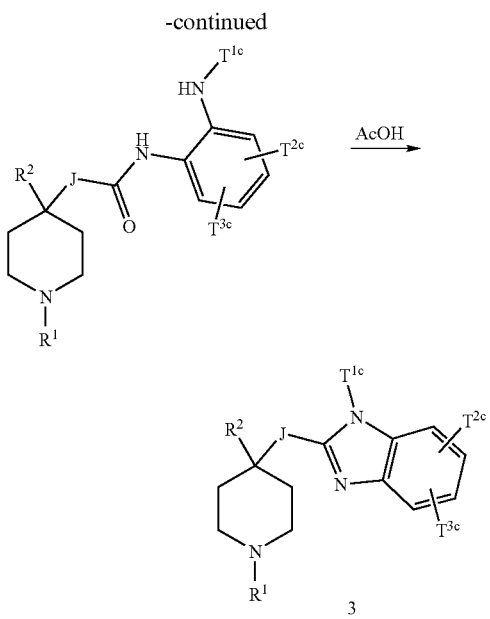

Referring to Scheme 9, acid chloride compound 1 may be made to react compound 2 in an organic solvent such as dichlormethane to provide carboxamide compound 3. Cyclization of compound 2 in the presence of an acid such as acetic acid at elevated temperature provides compound 3 where $R^3$ is $R^5$ and $R^5$ is heteroaryl (e.g.; benzimidazole). One skilled in the art will recognize that carboxylic acids or acid chlorides may be converted to a wide variety of heteroaryl groups. For example, compound 1 may be made to react with a 2-amino phenol to provide compounds of formula I where $R^3$ is $R^5$ and $R^5$ is heteroaryl (e.g.; benzoxazole). Compound 1 may be made to react with a 2-amino benzenethiol to provide compounds of formula I where $R^3$ is $R^5$ and $R^5$ is heteroaryl (e.g.; benzthiazole). Compound 1 may be made to react with an N-hydroxyamidine to provide compounds of formula 3 where $R^3$ is $R^5$ and $R^5$ is heteroaryl (e.g.; oxadiazole).

SCHEME 11

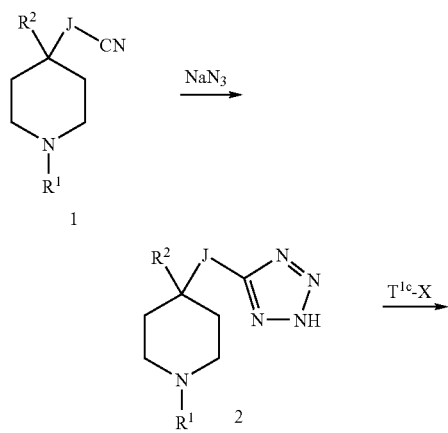

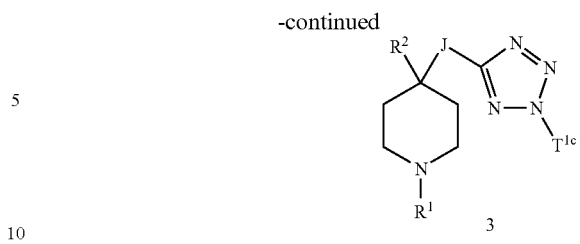

Referring to Scheme 10, cyano compound 1 may be made to react with sodium azide in a solvent such as methyl sulfoxide at elevated temperatures to provide tetrazole compound 2. Compound 2 may be made to react with $T^{1c}$-X where X is a leaving group such as a halogen atom or triflate to provide compound 3 where $R^3$ is $R^5$ and $R^5$ is heteroaryl (e.g.; tetrazole).

Compounds of formula I where $R^2$ is alkyl, cycloalkyl or (aryl)alkyl may be prepared as described in Scheme 12.

SCHEME 12

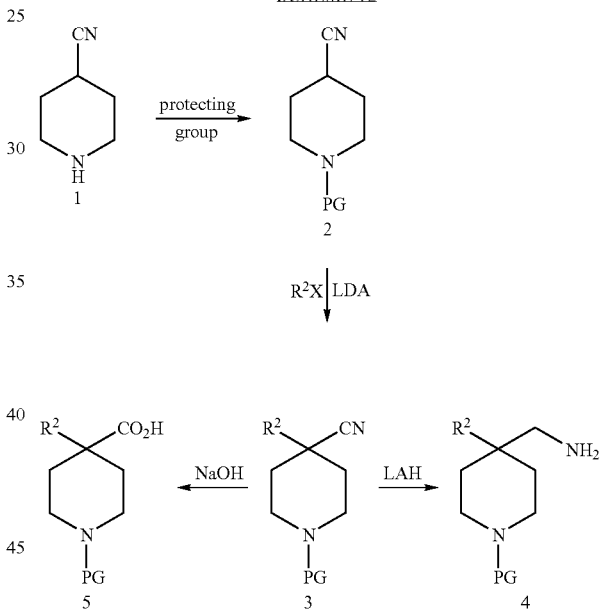

Protection of the nitrogen atom of compound 1 provides compound 2. Deprotonation of compound 2 with a base such as lithium diisopropylamide in an organic solvent such as tetrahydrofuran a low temperature followed by reaction with a benzyl halide, for example, provides compound 3 where $R^2$ is (aryl)alkyl. One skilled in the art will recognize that aldehydes and ketone may also be made to react with compound 2 after deprotoation with lithium diisopropylamide. The cyano group of compound 3 may be reduced with lithium aluminum hydride in a solvent such as tetrahydrofuran to provide amino compound 4. Alternatively, the cyano group of compound 3 may be hydrolyzed with aqueous sodium hydroxide to provide carboxylic acid compound 5. Compounds of formula I may be prepared from compounds 4 and 5 as described previously.

SCHEME 13

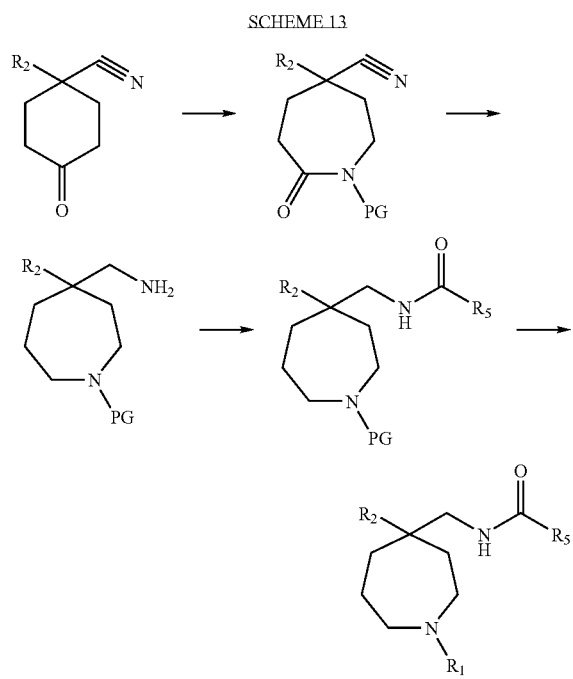

Compounds of the formula 1 where p=3, m=2, Q=NR1, R2=aryl may be prepared as described in Scheme 13. The lactam was prepared from intermediate cyclohexanone which was synthesized as described in Journal of Medicinal Chemistry, 1998, 821. The lactam nitrogen was protected using standard protecting group methodology and the lactam carbonyl group and the nitrile group were reduced either simultaneously or subsequently. The primary amine was acylated, the protecting group was removed and the azapene was further functionalized to the sulfinyl urea, the carbamate, the amide or alkylated directly.

SCHEME 14

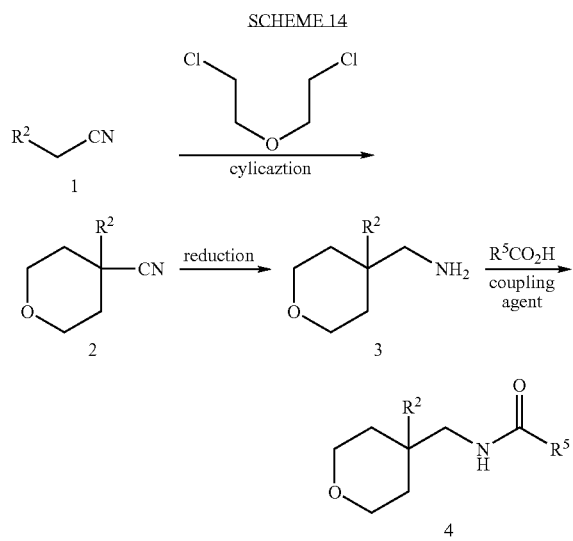

Compounds of formula I where Q is O, $R^3$ is $$-N\underset{R^{8a}}{\overset{Z^1}{-}}R^5,$$

$Z^1$ is O, and $R^{8a}$ is hydrogen may be prepared as described in Scheme 14. Compound 1 may be made to react with bis(2-chloroethyl)ether under phase-transfer catalysis conditions to provide the cyclized product compound 2. The nitrile group of compound 2 may be reduced using various methods, including treatment with lithium aluminum hydride or hydrogenation in the presence of platinum (IV) oxide, to provide the amine compound 3. The amino group of compound 3 may be made to react with a carboxylic acid (e.g.; $R^5CO_2H$) in the presence of a coupling agent in an organic solvent such as tetrahydrofuran to provide the acylated product compound 4.

Additional compounds within the scope of the present invention can be prepared from the compounds obtained by the above described methods through conversion of the substituent groups to other functionality by the usual methods of chemical synthesis, as illustrated in the following examples.

Compounds of formula I that contain chiral centers may be obtained in non-racemic form by non-racemic synthesis or resolution by methods well known to those skilled in the art. Compounds that are non-racemic are designated as "chiral" in the examples.

In the examples described below it may be necessary to protect reactive functionality such as hydroxy, amino, thio or carboxy groups, where these are desired in the final product, to avoid their unwanted participation in reactions. The introduction and removal of protecting groups are well known to those skilled in the art, for example see (Green, T. W. in "Protective Groups in Organic Synthesis", John Wiley and Sons, 1991).

Utility

Compounds within the scope of the present invention inhibit the $K_v1$ subfamily of voltage-gated $K^+$ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma, chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are useful to treat a variety of disorders including resistance by transplantation of organs or tissue, graft-versus-host diseases brought about by medulla ossium transplantation, rheumatoid arthritis, systemnic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, Lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of $K_v1.5$ compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The Kv1.5 gene is known to be expressed in stomach tissue, intestinal/colon tissue, the pulmonary artery, and pancreatic beta cells. Thus, administration of an $I_{Kur}$ blocker could provide useful treatment for disorders such as: reflux esauphagitis, functional dispepsia, constipation, asthma, and diabetes. Additionally, Kv1.5 is known to be expressed in the anterior pituitary. Thus, administration of an $I_{Kur}$ blocker could stimulate growth hormone secretion. $I_{Kur}$ inhibitors can additionally be useful in cell poliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the present invention. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the present invention or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inibitors (i.e., COX-1 and/or COX-2 inhibitors) such as aspirin, indomethacin, ibuprofen, piroxicam, naproxen, celebrex, vioxx and NSAIDs; antiplatelet agents such as GPIIb/IIIa blockers (e.g., abciximab, eptifibatide and tirofiban), $P2Y_{12}$ antagonists (e.g., clopidogrel, ticlopidine and CS-747), thromboxane receptor antagonists (e.g., ifetroban), aspirin, and PDE-III inhibitors (e.g., dipyridamole) with or without aspirin; diruetics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors, thromin inibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., questran); antipoliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e,. glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an $I_{Kur}$ inhibitor are well known in the art and are described in references such as *J. Gen. Physiol.* April; 101(4):513-43, and *Br. J. Pharmacol.* 1995 May; 115(2):267-74.

Assays to determine the degree of activity of a compound as an inhibitor of other members of the $K_v 1$ subfamily are also well known in the art. For example, inhibition of $K_v 1.1$, $K_v 1.2$ and $K_v 1.3$ can be measured using procedures described by Grissmer S, et al., *Mol Pharnacol* June 1994; 45(6):1227-34. Inhibition of Kv1.4 can be measured using procedures described by Petersen K R, and Nerbonne J M, *Pflugers Arch* February 1999; 437(3):381-92. Inhibition of Kv1.6 can be measured using procedures described by Bowlby M R, and Levitan I B, *J Neurophysiol* June 1995; 73(6):2221-9. And inhibition of Kv1.7 can be measured using procedures described by Kalman K, et al., *J Biol Chem* Mar. 6, 1998; 273(10):5851-7.

Compounds within the scope of the present invention demonstrate activity in $K_v 1$ assays such as the ones described above.

All documents cited in the present specification are incorporated herein by reference in their entirety.

The following examples and preparations describe the manner and process of making and using the invention and are illustrative rather than limiting. It is to be understood that there may be other embodiments which fall within the spirit and scope of the invention as defined by the claims appended hereto.

EXAMPLES

Example 1

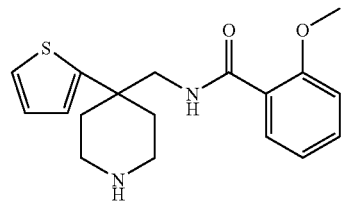

2-Methoxy-N-(4-thiophen-2-yl-piperidin-4-ylmethyl)-benzamide

Synthesis

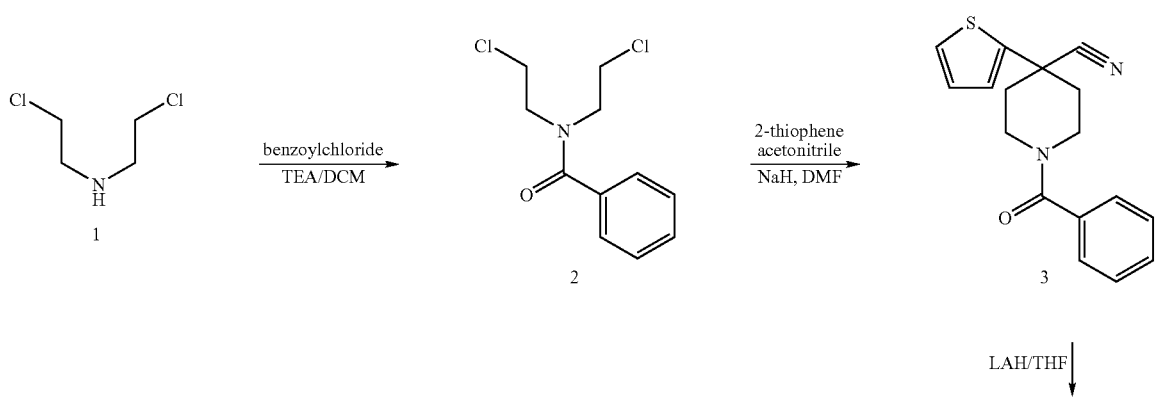

LAH/THF

-continued

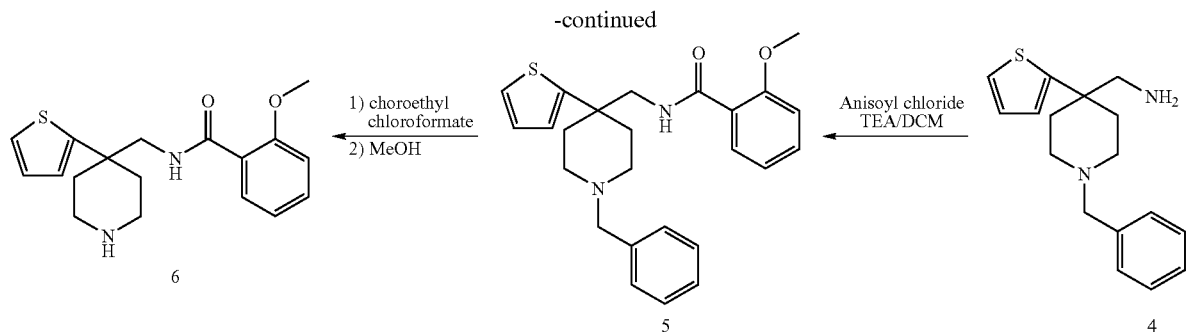

Compound 1: Compound 1 is commercially available.

Compound 2: Compound 1 (20 g, 0.11 mol) was suspended in 200 mL dichloromethane. Benzoylchloride (17 mL, 0.14 mol) was added. At 0° C. TEA (42 mL, 0.30mol) in dichloromethane (10 mL) was added slowly to the reaction mixture. The reaction mixture was stirred at room temperature for 14 h, diluted with Ethyl acetate (500 mL), washed with saturated NaHCO$_3$ (2×250 mL), 1N HCl (2×250 mL), dried over MgSO$_4$, filtered and concentrated. The residue was purified by silica gel chromotography using Hexanes/Ethyl acetate (4/1, 1/1) as eluent to give an orange oil compound 2, 25.85 g (94% yield).

Compound 3: NaH (6.0 g, 0.25 mol) was suspended in DMF (100 mL). At 0° C. 2-thiopheneacetonitrile (7.5 g, 0.061 mol) was added followed by the addition of compound 2 (12 g, 0.048 mol) in 100 mL DMF. The reaction was stirred at 0° C. for 0.5 h and then at ambient temperature for 14 h. The reaction mixture was poured into ice and extracted with Ethyl acetate (250 mL). The aqueous layer was extracted with Ethyl acetate (2×250 mL). The organic layers were combined and washed with 10% LiCl (2×200 mL), dried over MgSO$_4$, filtered and concentrated. The residue was purified by silica gel flash chromatography eluted with 2/1 and 1/1 Hexane:Ethyl acetate yielding 9.14 g (64% isolated yield) of compound 3 as a dark brown solid. HPLC Rt 2.87 min, Purity 100%, YMC S5 column 4.6×50 mm, 4 min gradient 0 to 100% MeOH (90% in water, 0.2% PPA) UV detection at 220 nm. LCMS Rt 1.47 min, [M+1] 297.22 Phenomenex S5 column 4.6×30 mm, 2 min gradient 0 to 100% MeOH (90% in water, 0.1% TFA) UV detection at 220 nm. NMR H (CDCl$_3$) 1.74-2.32 ppm, 4H, m; 3.22-3.43 ppm, 2H, m; 3.78-3.84 ppm, 1H, broadpeak; 4.79 ppm, 1H, broad peak; 6.94 ppm, 1H, dd, J=5.0 Hz and 3.6 Hz; 7.08 ppm, 1H, dd, J=3.3 Hz and 1.1 Hz; 7.24 ppm, 1H, dd, J=5.0 Hz and 1.1 Hz; 7.34-7.42 ppm, 5H, m.

Compound 4: To a solution of compound 3 (2.1 g, 7.2 mmol) in THF (40 mL) was added LAH (20 mL, 20 mmol, 1.0M solution in THF). The reaction mixture was heated to reflux for 1 h then allowed to cool to ambient temperature. The solution was cooled to 0° C. and quenched with water (5.3 mL), 1N NaOH (3.4 mL) and water (5.3 mL). The quenched reaction mixture was stirred at ambient temperature for 0.5 h. The slurry was filtered through a celite pad and the filtrate was concentrated. The residue was diluted with EtOAc (200 mL), washed with saturated NaHCO$_3$ (2×100 mL), dried over MgSO$_4$, filtered and concentrated to give a brown oil compound 4 sufficiently pure to be taken on to the next step. HPLC Rt 0.20 min and 0.59 min, Purity 100%, YMC S5 column 4.6×50 mm, 4 min gradient 0 to 100% MeOH (90% in water, 0.2% PPA) UV detection at 220 nm. LCMS Rt 0.73 min, [M+1] 287.39 Phenomenex S5 column 4.6×30 mm, 2min gradient 0 to 100% MeOH (90% in water, 0.1% TFA) UV detection at 220 nm. NMR H (CDCl$_3$) 1.85 ppm, 2H, m; 2.05-2.08 ppm, 2H, m; 2.22-2.27 ppm, 2H, m; 2.67 ppm, 1H, s; 2.69 ppm, 2H, m; 3.44 ppm, 2H, s; 6.77-6.78 ppm, 1H, m; 6.94 ppm, 1H, dd, J=5.0 Hz and 3.3 Hz; 7.17-7.30ppm, 6H, m.

Compound 5: Compound 4 was dissolved in dichloromethane (30 mL) and ortho-anisoyl chloride (1.11 mL, 7.4 mmol) was added followed by the addition of TEA (2.3 mL, 16 mmol). The reaction was stirred at ambient temperature for 14 h, diluted with dichloromethane (200 mL), washed with saturated NaHCO$_3$, dried over MgSO$_4$, filtered and concentrated. The product amide compound 5 was eluted with 2:1 and 1:1 hexane:ethylacetate as a white foam (2.19g, 77% yield for two steps). HPLC Rt 2.50 min, Purity 100%, YMC S5 column 4.6×50 mm, 4 min gradient 0 to 100% MeOH (90% in water, 0.2% PPA) UV detection at 220 nm. LCMS Rt 1.36 min, [M+1] 421.27 Phenomenex S5 column 4.6×30 mm, 2 min gradient 0 to 100% MeOH (90% in water, 0.1% TFA) UV detection at 220 nm. NMR H (CD$_3$OD) 1.98-2.00 ppm, 2H, m; 2.15-2.18 ppm, 2H, m; 2.44 ppm, 2H, m; 2.74-2.76 ppm, 2H, m; 3.53 ppm, 2H, s; 3.65 ppm, 2H, s; 3.77 ppm, 3H, s; 7.02-7.09 ppm, 4H, m; 7.25-7.31 ppm, 5H, m; 7.39-7.40 ppm, 1H, m; 7.45-7.48ppm, 1H, m; 7.93-7.95 ppm, 1H, m.

Compound 6: Compound 5 (2.2 g, 5.2 mmol) was dissolved in dichloroethane (40 mL) and TEA (3.6 mL, 26 mmol) was added. At 0° C. chloroethyl chloroformate (1.11 mL, 10 mmol) in dichloroethane (20 mL) was added. The reaction mixture was stirred at ambient temperature for 1 h, then another 1.11 mL chloroethyl chloroformate in dichloroethane (20 mL) was added. The reaction was stopped till no starting material left according to LC-MS. The reaction mixture was concentrated and dried on oil pump for 0.5 h. MeOH (40 mL) was added to the residue and was heated to reflux for 4 h. The reaction mixture was concentrated and the residue was purified by a silica gel pad eluted with 1:1 EtOAc:Hexane and then 1:1 MeOH:DCM yielding a pale yellow solid 2-methoxy-N-(4-thiophen-2-yl-piperidin-4-ylmethyl)-benzamide 6 (1.63 g, 95% yield). HPLC Rt 2.09 min, Purity 100%, YMC S5 column 4.6×50 mm, 4 min gradient 0 to 100% MeOH (90% in water, 0.2% PPA) UV detection at 220 nm. LCMS Rt 1.20 min, [M+1] 331.41 Phenomenex S5 column 4.6×30 mm, 2 min gradient 0 to 100% MeOH (90% in water, 0.1% TFA) UV detection at 220 nm. NMR H (CDCl$_3$) 2.01-2.04 ppm, 2H, m; 2.14-2.18 ppm, 2H, m; 2.92-2.94 ppm, 2H, m; 3.16 ppm, 2H, m; 3.64 ppm, 2H, s; 3.67 ppm, 3H, s; 6.82-6.86 ppm, 2H, m; 6.96-7.00 ppm, 2H, m; 7.23-7.25 ppm, 1H, m; 7.32-7.37 ppm, 1H, m; 8.09-8.11 ppm, 1H, m.

Example 2

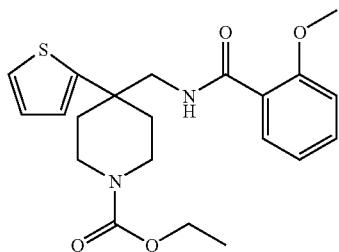

4-[(2-Methoxy-benzoylamino)-methyl]-4-thiophen-2-yl-piperidine-1-carboxylic acid ethyl ester Synthesis

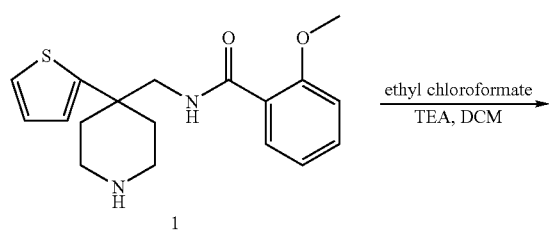

Compound 1: Compound 1 was prepared using methodology described in Example 1.

Compound 2: Compound 1 (14 mg, 0.043 mmol) was dissolved in dichloromethane (0.20 mL). At ambient temperature TEA (12 uL, 0.086 mmol) was added followed by the addition of ethyl chloroformate (4.90 mg, 0.045 mmol) in dichloromethane (0.10 mL). The reaction mixture was stirred for 2.5 h and then concentrated. 4-[(2-Methoxy-benzoylamino)-methyl]-4-thiophen-2-yl-piperidine-1-carboxylic acid ethyl ester 2 (13.7 mg, 79% yield) was isolated by Prep-HPLC as a colorless oil. HPLC Rt 3.43 min, Purity 100%, YMC S5 column 4.6×50 mm, 4 min gradient 0 to 100% MeOH (90% in water, 0.2% PPA) UV detection at 220 nm. LCMS Rt 1.78 min, [M+1] 403.17 YMC S5 column 4.6×30 mm, 2 min gradient 0 to 100% MeOH (90% in water, 0.1% TFA) UV detection at 220 nm. NMR H (CDCl$_3$) 1.18 ppm, 3H, t, J=7.1 Hz; 1.81-1.84 ppm, 2H, m; 2.00-2.04 ppm, 2H, m; 3.18-3.25 ppm, 2H, m; 3.67 ppm, 3H, s; 3.73-3.77 ppm, 4H, m; 4.05 ppm, 2H, q, J=7.1 Hz; 6.83-6.88 ppm, 2H, m; 6.98-7.02 ppm, 2H, m; 7.25 ppm, 1H, dd, J=5.0 Hz and 0.76 Hz; 7.34-7.39 ppm, 1H, m; 7.83 ppm, 1H, m; 8.10 ppm, 1H, dd, J=7.8 Hz and 1.7 Hz.

Example 3

Example 3 was prepared using methodology described in Example 2.

| Example | Structure | Name | [M + 1] |
|---|---|---|---|
| 3 | 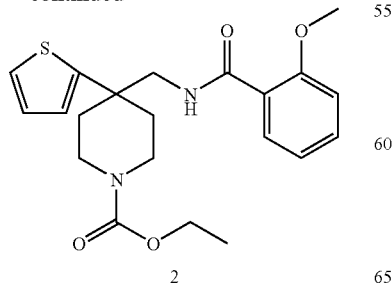 | 4-[(2-Methoxy-benzoylamino)-methyl]-4-thiophen-2-yl-piperidine-1-carboxylic acid tert-butyl ester | 430 |

Example 4

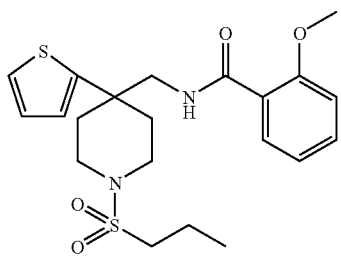

2-Methoxy-N-[1-(propane-1-sulfonyl)-4-thiophen-2-yl-piperidin-4-ylmethyl]-benzamide Synthesis

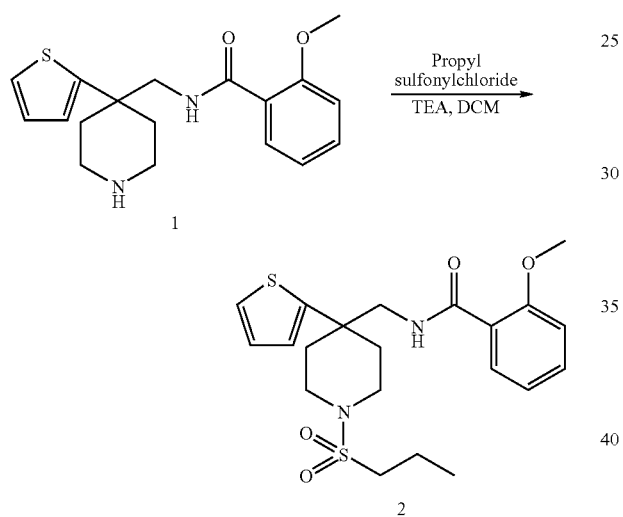

Compound 1: Compound 1 was prepared using methodology described in Example 1.

Compound 3: Compound 1 (14 mg, 0.043 mmol) was dissolved in dichloromethane (0.20 mL). At ambient temperature TEA (12 uL, 0.086 mmol) was added followed by the addition of propyl sulfonylchloride (6.4 mg, 0.045 mmol) in dichloromethane (0.10 mL). The reaction mixture was stirred for 1 h and then concentrated. 2-Methoxy-N-[1-(propane-1-sulfonyl)-4-thiophen-2-yl-piperidin-4-ylmethyl]-benzamide (14.5 mg, 77% yield) was isolated by Prep-HPLC as a colorless oil. HPLC Rt 3.21 min, Purity 100%, YMC S5 column 4.6×50 mm, 4 min gradient 0 to 100% MeOH (90% in water, 0.2% PPA) UV detection at 220 nm. LCMS Rt 1.67 min, [M+1] 437.15 YMC S5 column 4.6×30 mm, 2 min gradient 0 to 100% MeOH (90% in water, 0.1% TFA) UV detection at 220 nm. NMR H (CDCl$_3$) 0.97 ppm, 3H, t, J=7.5 Hz; 1.73-1.79 ppm, 2H, m; 1.92-1.98 ppm, 2H, m; 2.09-2.14 ppm, 2H m; 2.78-2.82 ppm, 2H, m; 3.19-3.25 ppm, 2H, m; 3.40-3.45 ppm, 2H, m; 3.66 ppm, 3H, s; 3.71 ppm, 2H, d, J=6.2 Hz; 6.84-6.88 ppm, 2H, m; 6.99-7.03 ppm, 2H, m; 7.27 ppm, 1H, dd, J=5.0 Hz and 0.74 Hz; 7.37-7.41 ppm, 1H, m; 7.98 ppm, 1H, m; 8.07 ppm, 1H, dd, J=7.8 Hz and 1.8 Hz.

Examples 5 and 6

Examples 5 and 6 were synthesized using methodology described in Example 4.

| Example | Structure | Name | [M + 1] |
|---|---|---|---|
| 5 | 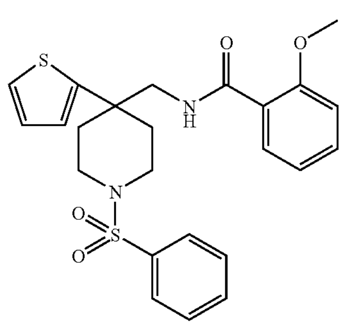 | N-(1-Benzenesulfonyl-4-thiophen-2-yl-piperidin-4-ylmethyl)-2-methoxy-benzamide | 470 |

-continued

| Example | Structure | Name | [M + 1] |
|---|---|---|---|
| 6 | 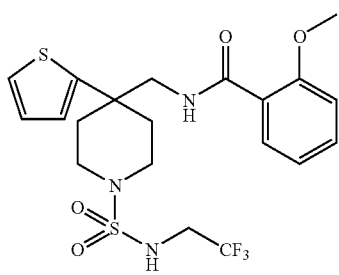 | N-[1-(4-Fluoro-benzenesulfonyl)-4-thiophen-2-yl-piperidin-4-ylmethyl]-2-methoxy-benzamide | 488 |

Example 7

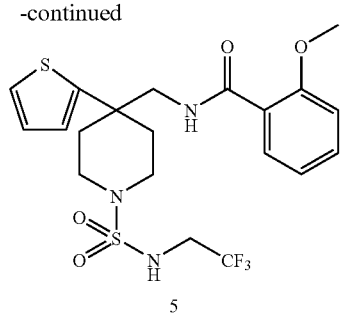

2-Methoxy-N-[4-thiophen-2-yl-1-(2,2,2-trifluoro-ethylsulfamoyl)-piperidin-4-ylmethyl]-benzamide

Synthesis

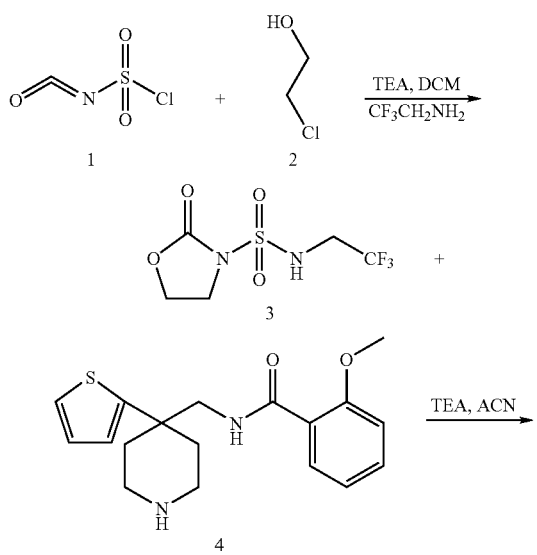

Compound 1: Compound 1 is commercially available.

Compound 2: Compound 2 is commercially available.

Compound 3: Compound 1 (26 mg, 0.18 mmol) was dissolved in dichloromethane (0.50 mL). At 0° C. compound 2 (15 mg, 0.18 mmol) in dichloromethane (0.50 mL) was added and the reaction mixture was stirred for 1 h. Trifluoroethylamine (18 mg, 0.18 mmol) in dichloromethane (0.50 mL) was added followed by the addition of TEA (75 uL, 0.54 mmol). The reaction mixture was stirred at ambient temperature for 2 h and then at 35° C. for 14 h. The reaction was diluted with dichloromethane (20 mL), washed with 1N HCl (10 mL), dried over $MgSO_4$, filtered and concentrated to yield compound 3 sufficient pure to be taken to the next step.

Compound 4: Compound 4 was prepared using methodology described in Example 1.

Title Compound: Compound 4 (20 mg, 0.060 mmol) and TEA (130 uL, 0.94 mmol) were dissolved into acetonitrile (1.0 mL). To this mixture compound 3 was added and the reaction mixture was heated at 95° C. for 14 h. The reaction was concentrated and the residue was purified by PrepHPLC yielding 2-methoxy-N-[4-thiophen-2-yl-1-(2,2,2-trifluoro-ethylsulfamoyl)-piperidin-4-ylmethyl]-benzamide (17.2 mg, 58% yield) as a clear oil. HPLC Rt 3.25 min, Purity 100%, YMC S5 column 4.6×50 mm, 4 min gradient 0 to 100% MeOH (90% in water, 0.2% PPA) UV detection at 220 nm. LCMS Rt 1.66 min, [M+1] 492.14 YMC S5 column 4.6×30 mm, 2 min gradient 0 to 100% MeOH (90% in water, 0.1% TFA) UV detection at 220 nm. NMR H ($CDCl_3$) 1.94-1.96 ppm, 2H, m; 2.01-2.12 ppm, 2H, m; 3.11-3.13 pm, 2H, m; 3.43 ppm, 2H, m; 3.56-3.59 ppm, 2H, m; 3.64 ppm, 2H, s; 3.66 ppm, 3H, s; 4.95 ppm, 1H, t, J=5.7 Hz; 6.85-6.86 ppm, 2H, m; 6.99-7.00 ppm, 2H, m; 7.25-7.26 ppm, 1H, m; 7.35-7.36 ppm, 1H, m; 7.75-7.78 ppm, 1H, m; 8.12 ppm, 1H, dd, J=6.2 Hz and 1.3 Hz.

Examples 8 to 14

Examples 8 to 14 were prepared using methodology described in Example 7.

| Example | Structure | Name | [M + 1] |
|---|---|---|---|
| 8 | 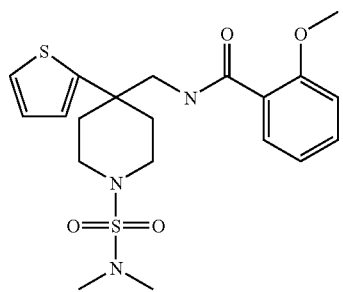 | N-(1-Dimethylsulfamoyl-4-thiophen-2-yl-piperidin-4-ylmethyl)-2-methoxy-benzamide | 437 |
| 9 | 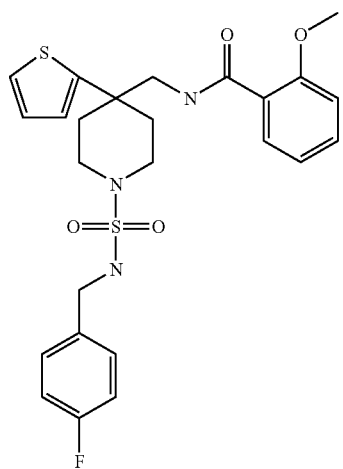 | N-[1-(4-Fluoro-benzylsulfamoyl)-4-thiophen-2-yl-piperidin-4-ylmethyl]-2-methoxy-benzamide | 517 |
| 10 | 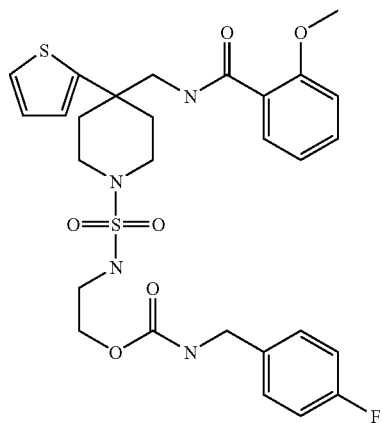 | (4-Fluoro-benzyl)-carbamic acid 2-{4-[(2-methoxy-benzoylamino)-methyl]-4-thiophen-2-yl-piperidine-1-sulfonylamino}-ethyl ester | 604 |

-continued

| Example | Structure | Name | [M + 1] |
|---|---|---|---|
| 11 | 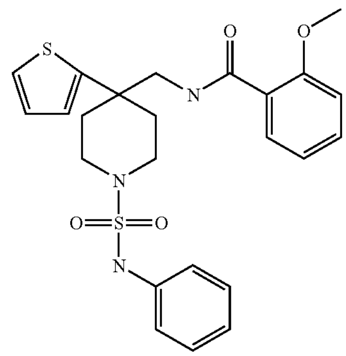 | 2-Methoxy-N-(1-phenylsulfamoyl-4-thiophen-2-yl-piperidin-4-ylmethyl)-benzamide | 485 |
| 12 | 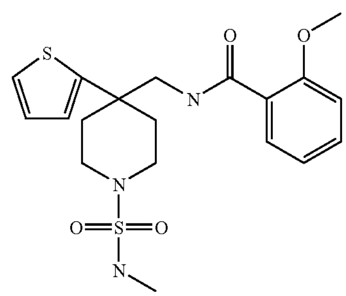 | 2-Methoxy-N-(1-methylsulfamoyl-4-thiophen-2-yl-piperidin-4-ylmethyl)-benzamide | 423 |
| 13 | 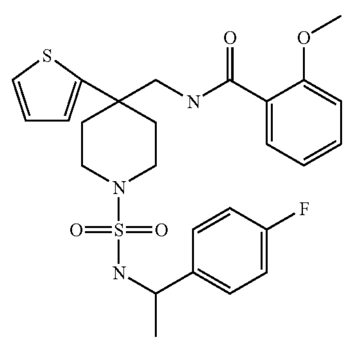 | N-{1-[1-(4-Fluoro-phenyl)-ethylsulfamoyl]-4-thiophen-2-yl-piperidin-4-ylmethylp}-2-methoxy-benzamide | |
| 14 | 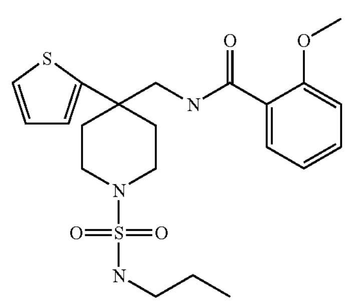 | 2-Methoxy-N-(1-propylsulfamoyl-4-thiophen-2-yl-piperidin-4-ylmethyl)-benzamide | |

Example 15

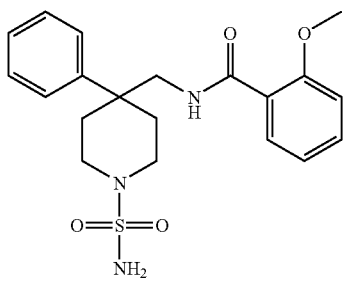

2-Methoxy-N-(4-phenyl-1-sulfamoyl-piperidin-4-ylmethyl)-benzamide

Synthesis

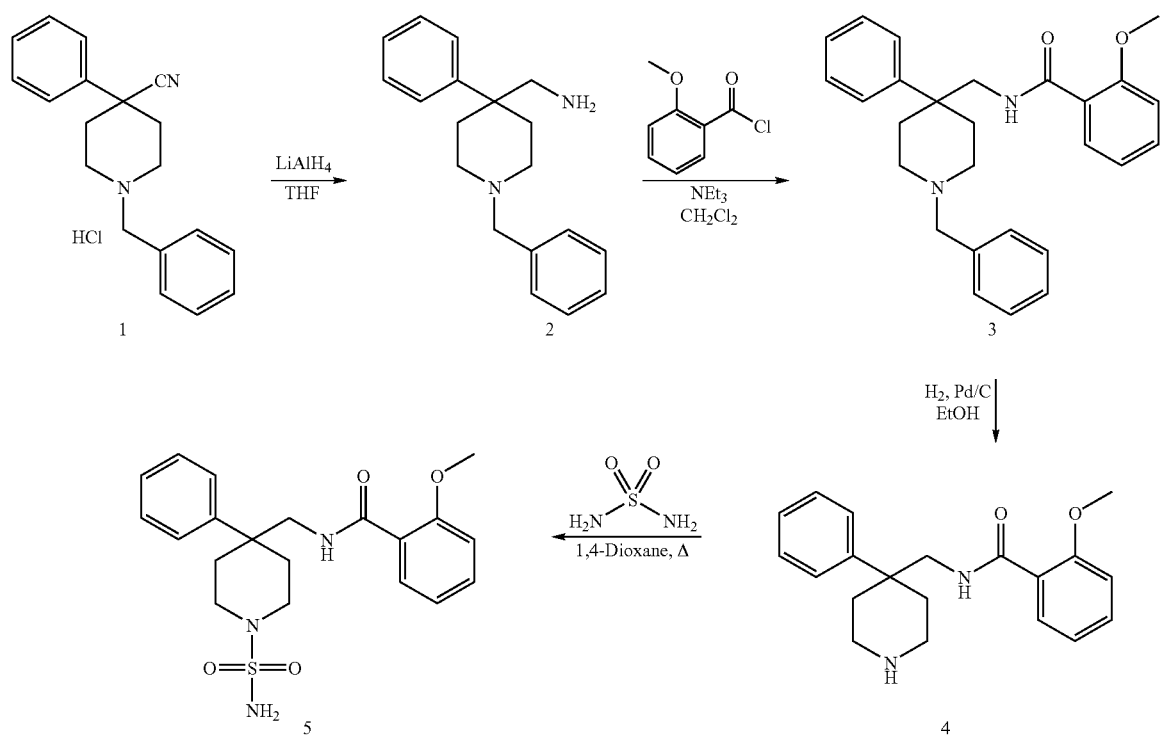

Compound 1: Compound 1 is commercially available.

Compound 2: To 1-N-benzyl-4-phenyl-4-cyanopiperidine.HCl (10.0 g, 31.97 mmol) was added 220 mL of THF and the reaction flask was cooled to 0C. Lithium aluminum hydride (4.85 g, 127.86 mmol) was added slowly and the reaction mixed 12 h at room temperature. The reaction was quenched by the addition of 5 ML of water, 15 mL of 15% aqueous solution of sodium hydroxide followed by 5 mL of water. The organic fraction was dried over anhydrous sodium sulfate, filtered and the filtrate was concentrated to give compound 2 that was used without further purification. LCMS Rt 1.70 min, [M+1] 281.0.

Compound 3: To a solution of 1-N-benzyl-4-phenyl-4-aminomethylpiperidine (4.0 g, 14.26 mmol) and triethylamine (3.0 g, 21.39 mmol) in 18 mL of dichloromethane was added o-anisoyl chloride (425 μL, 2.85 mmol) at 0° C. The reaction was stirred for 12 h and quenched with (100 mL) of 1 M hydrochloric acid. Dichloromethane (100 mL) was also added and the aqueous layer was washed with dichloromethane (50 mL portions, 2×). The organic fractions were combined and washed with 1 N sodium hydroxide (50 mL portions, 2×) followed by brine (100 mL). The organics were dried over anhydrous sodium sulfate and concentrated. 4.54 g (77% yield) of compound 3 was obtained. LCMS Rt 1.41 min, [M+1] 415.1.

Compound 4: To a solution of N-(1-benzyl-4-phenyl-piperidin-4-ylmethyl)-benzamide (4.54 g, 10.95 mmol) in ethanol (100 mL) was added 10% palladium/carbon (1.40 g). The reaction mixture was stirred in a hydrogen atmosphere (50 psi) for 78 h. After filtration, the filtrate was concentrated and purified using column chromatography o silica gel using 9:1:0.1 chloroform:methanol:ammonium hydroxide as the eluent to give a yellow oil. After lyophilization 2.7 g (76% yield) of compound 4 as a white/yellow powdery solid was obtained. LCMS Rt 1.43 min, [M+1] 325.3.

Title Compound: To compound 4 (50 mg, 0.154 mmol) in 1,4-dioxane (1.7 mL) was added sulfamide (148 mg, 1.54 mmol) and then stirred at 100° C. overnight. The solution was cooled to room temperature and the solvent was concentrated under reduced pressure. The crude material was diluted with dichloromethane (10 mL) and washed with water (10 mL) (2×), brine (10 mL) (1×) and dried over $Na_2SO_4$, filtered and concentrated under reduced pressure to give a white solid. The crude was purified using preparative HPLC and lyophilized to give 54 mg (87% yield) of 2-methoxy-N-(4-phenyl-1-sulfamoyl-piperidin-4-ylmethyl)-benzamide. $^1$H NMR (CDCl₃, rt): δ ppm) 2.11-2.19 (2H, m), 2.22-2.25 (2H, m), 3.24-3.26 (2H, m), 3.35-3.38 (2H, m), 3.57 (3H, s), 3.67 (2H, d, J=6 Hz), 4.43 (2H, s), 6.86 (1 H, d, J=8.3 Hz), 7.05 (1H, t, J=7.5 Hz), 7.30-7.45 (6H, m), 7.63 (1H, s), 8.16 (1H, d, J=7.5). LCMS Rt 1.50 min, [M+1] 404.2.

Example 16

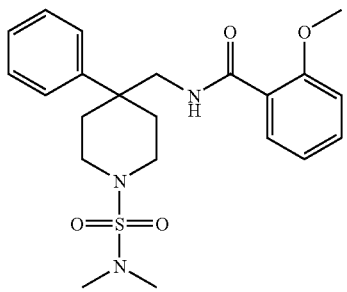

N-(1-Dimethylsulfamoyl-4-phenyl-piperidin-4-ylmethyl)-2-methoxy-benzamide

Synthesis

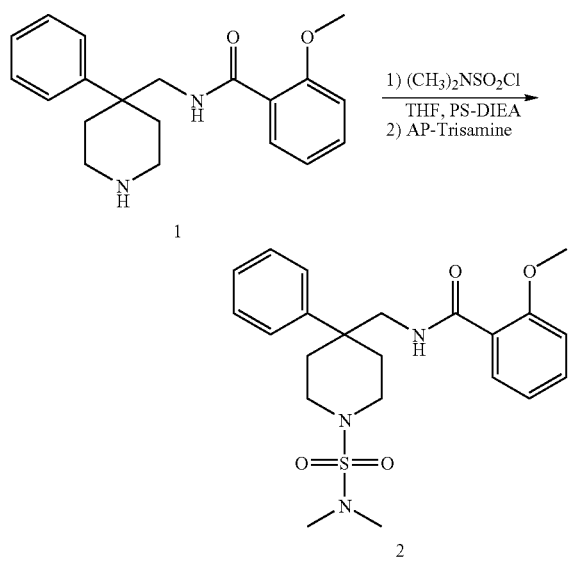

Compound 1: Compound 1 was prepared as described in Example 15.

Title Compound: To compound 1 (35 mg, 0.108 mmol) in tetrahydrofuran (1.5 mL) was added polystrene-diisopropylethylamine resin (394 mg, 1.4 mmol) and dimethylsulfamoyl chloride (35 μL, 0.324 mmol). The reaction was mixed overnight at room temperature. Excess dimethylsulfamoyl chloride (35 μL, 0.324 mmol) was added to the reaction to drive it to completion. To the reaction was added AP-Trisamine (232 mg, 0.972 mmol) and the reaction mixed for 6 hr at room temperature. After filtration, the solvent was concentrated under reduced pressure. The crude material was purified using the preparative HPLC and lyophilized to give N-(1-dimethylsulfamoyl-4-phenyl-piperidin-4-ylmethyl)-2-methoxy-benzamide 34.5 mg (73% yield). ¹H NMR (CDCl₃, rt): δ ppm) 1.94-1.99 (2H, m), 2.01-2.67 (2H, m), 2.79 (6H, s), 3.16-3.24 (2H, m), 3.42-3.5 (2H, m), 3.58 (3H, s), 3.74 (2H, d, J=6.3 Hz), 6.86 (1H, d, J=8.1 Hz), 7.05 (1H, t, J=7.5 Hz), 7.29-7.46 (6H, m), 7.59 (1H, s), 8.18 (1H, dd, J=1.7, 7.8 Hz). LCMS Rt 1.36 min, [M+1] 432.3.

Example 17

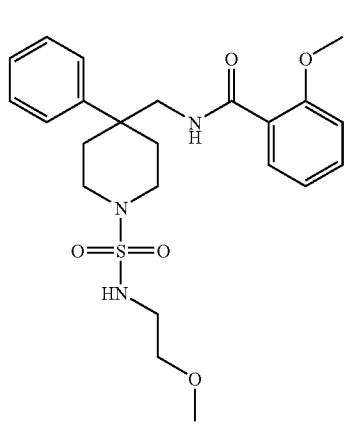

2-Methoxy-N-[1-(2-methoxy-ethylsulfamoyl)-4-phenyl-piperidin-4-ylmethyl]-benzamide Synthesis

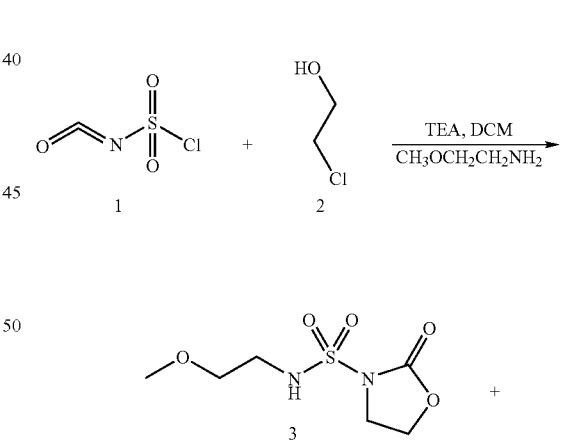

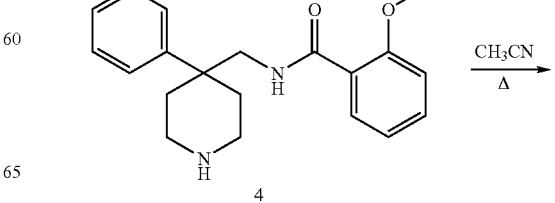

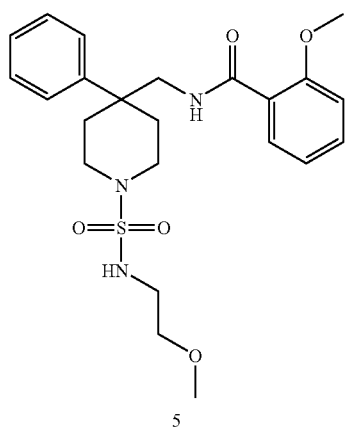

Compound 1: Compound 1 is commercially available.
Compound 2: Compound 2 is commercially available.
Compound 3: Compound 3 was prepared using methodology described in Example 7 using 2-methoxy-ethylamine instead of 2,2,2-trifluoro-ethylamine.
Compound 4: Compound 4 was as described in Example 15.

Title Compound: 2-Methoxy-N-[1-(2-methoxy-ethylsulfamoyl)-4-phenyl-piperidin-4-ylmethyl]-benzamide was prepared using methodology described in Example 7. $^1$H NMR (CDCl$_3$, rt): δ ppm) 1.95-2.03 (2H, m), 2.2-2.29 (2H, m), 3.12-3.22 (4H, m), 3.30 (3H, s), 3.41-3.48 (4H, m), 3.58 (3H, s), 3.73 (2H, d, J=4.55(1H, t, J=5.8, 11.7 Hz), 6.86 (1H, d, J=8.2 Hz), 7.04 (1H, dt, J=0.9, 7.5 Hz), 7.28-7.45 (6H, m), 7.59 (1H, t, J=5.7, 8.65 Hz), 8.17 (1H, dd, J=2.0, 7.85 Hz). LCMS Rt 1.36 min, [M+1] 462.

Examples 18 to 22

Examples 18 to 22 were prepared using methodology described in Example 17.

| Example | Structure | Name | M + H |
|---|---|---|---|
| 18 | 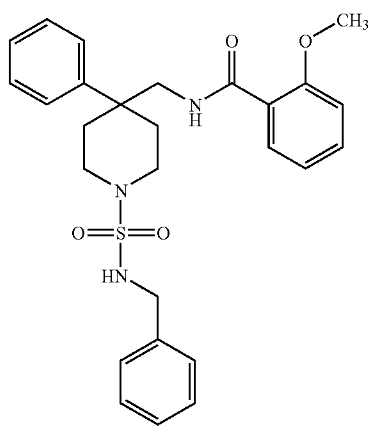 | N-(1-Benzylsulfamoyl-4-phenyl-piperidin-4-ylmethyl)-2-methoxy-benzamide | 495 |
| 19 | 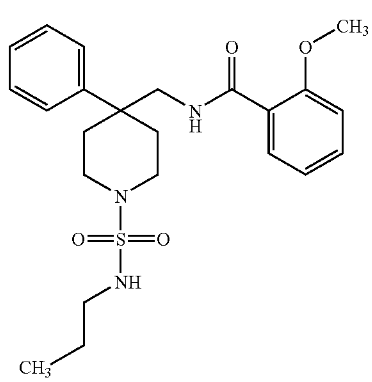 | 2-Methoxy-N-(4-phenyl-1-propylsulfamoyl-piperidin-4-ylmethyl)-benzamide | 447 |

| Example | Structure | Name | M + H |
|---------|-----------|------|-------|
| 20 | 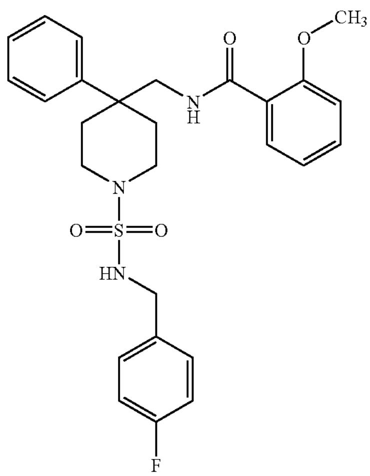 | N-[1-(4-Fluoro-benzylsulfamoyl)-4-phenyl-piperidin-4-ylmethyl]-2-methoxy-benzamide | 513 |
| 21 | 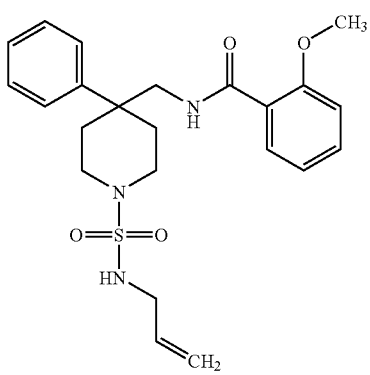 | N-(1-Allylsulfamoyl-4-phenyl-piperidin-4-ylmethyl)-2-methoxy-benzamide | 445 |
| 22 | 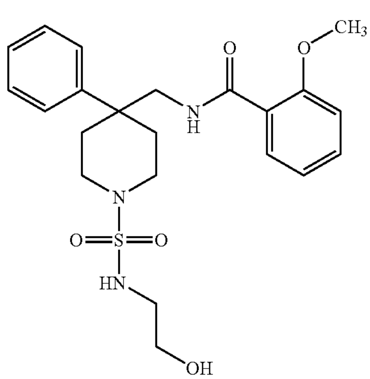 | N-[1-(2-Hydroxy-ethylsulfamoyl)-4-phenyl-piperidin-4-ylmethyl]-2-methoxy-benzamide | 449 |

Example 23

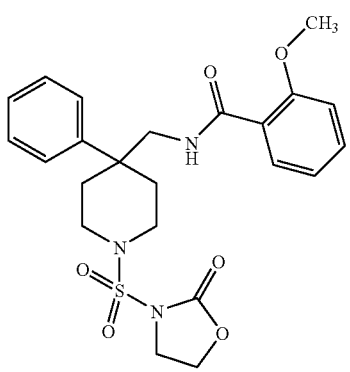

2-Methoxy-N-[1-(2-oxo-oxazolidine-3-sulfonyl)-4-phenyl-piperidin-4-ylmethyl]-benzamide Synthesis

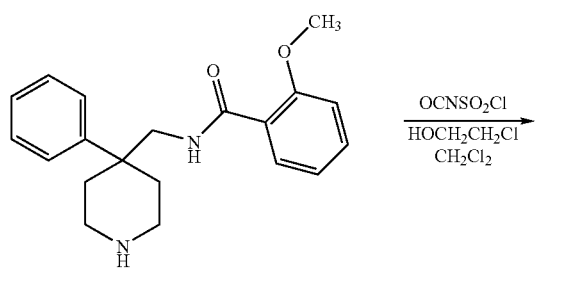

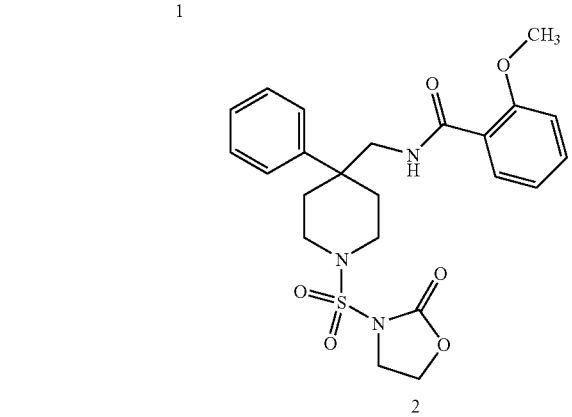

Compound 1: Compound 1 was prepared as described in Example 15.

Title Compound: A solution of chlorosulfonyl isocyanate (0.12 mL; 1.4 mmol) in dichloromethane (20 mL) was cooled to 0° C. and treated with 2-chloroethanol (0.094 mL; 1.3 mmol. After 2 h a solution of compound 1 (0.42 g; 1.3 mmol) and triethylamine (0.72 mL; 5.2 mmol) in dichloromethane (15 mL) was added dropwise. When the addition was complete the cooling bath was removed and the reaction mixture was allowed to stir at room temperature for 24 h. 20% aqueous hydrochloric acid was added and the organic layer was separated, washed with saturated aqueous sodium chloride, dried (anhydrous sodium sulfate), filtered and concentrated. The residue was purified by column chromatography on silica gel using 9:1 ethyl acetate:hexane as the eluent to give 0.3 g of 2-methoxy-N-[1-(2-oxo-oxazolidine-3-sulfonyl)-4-phenyl-piperidin-4-ylmethyl]-benzamide as a white solid. LCMS m/z=475 (M+H)$^+$

Example 24

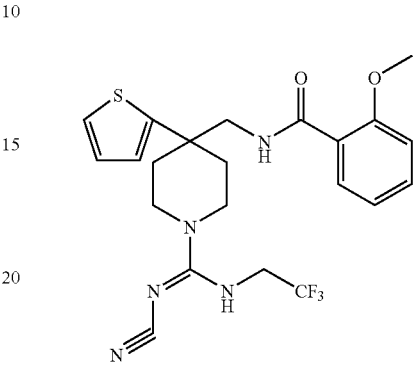

Synthesis

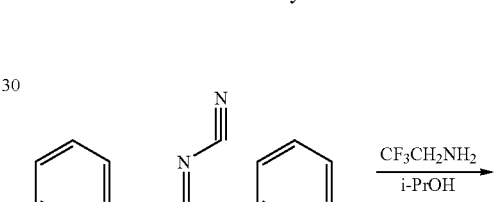

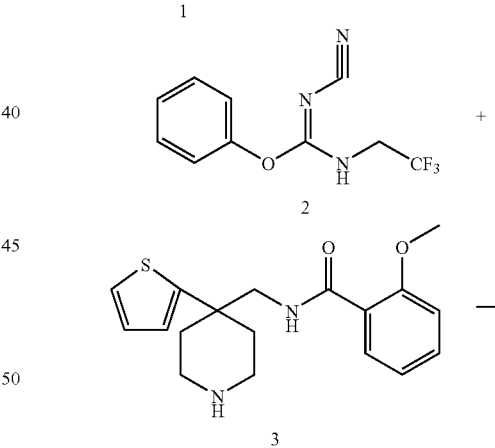

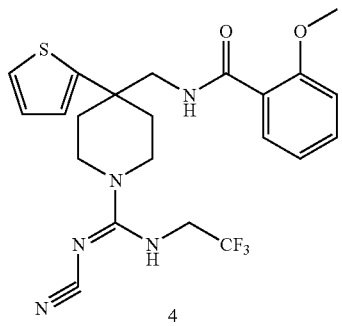

Compound 1: Compound 1 is commercially available.

Compound 2: Trifluroethylamine (6.6 mg, 0.067 mmol) and compound 1 (16 mg, 0.067 mmol) were added into iPrOH (1.0 mL). The reaction mixture was heated at 95° C. for 6 h.

Compound 3: Compound 3 was prepared as described in Example 1.

Title Compound: Compound 3 (20 mg, 0.060 mmol) in acetonitrile (0.50 mL) was added to compound 2 in iPrOH. The reaction was heated at 95° C. for 14 h and concentrated. The residue was purified through Prep HPLC to yield the title compound (4.4 mg, 15% yield) as a clear oil. HPLC Rt 3.13 min, Purity 91%, YMC S5 column 4.6×50 mm, 4 min gradient 0 to 100% MeOH (90% in water, 0.2% PPA) UV detection at 220 nm. LCMS Rt 1.62 min, [M+1] 480.18 YMC S5 column 4.6×30 mm, 2 min gradient 0 to 100% MeOH (90% in water, 0.1% TFA) UV detection at 220 nm. NMR H (CDCl$_3$) 1.91-1.99 ppm, 2H, m; 2.12-2.16 ppm, 2H, m; 3.40-3.47 ppm, 2H, m; 3.65-3.68 ppm, 5H, m; 3.77-3.83 ppm, 2H, m; 3.94-3.97 ppm, 2H, m; 5.32 ppm, 1H, m; 6.85-6.87 ppm, 2H, m; 6.98-7.02 ppm, 2H, m; 7.27 ppm, 1H, dd, J=5.0 Hz and 0.8 Hz; 7.35-7.40 ppm, 1H, m; 7.82 ppm, 1H, m; 8.06-8.09 ppm, 1H, m.

Example 25

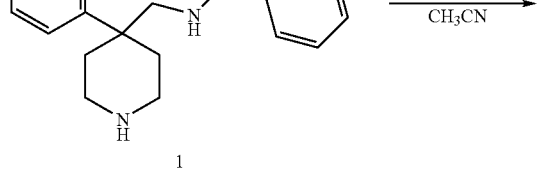

Scheme

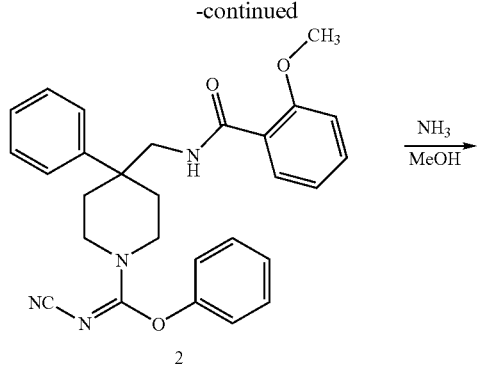

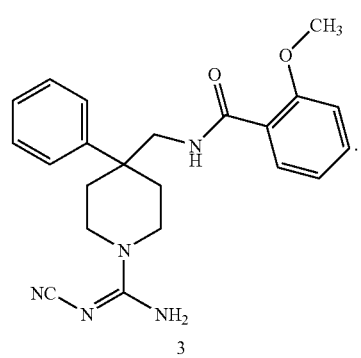

Compound 1: Compound 1 was prepared as described in Example 15.

Compound 2: A solution of compound 1 (0.63 g; 1.9 mmol) in anhydrous acetonitrile (20 mL) was treated with diphenyl N-cyanocarbonimidate (0.95 g; 4.0 mmol) and the reaction mixture was heated to 85° C. After 19 h the acetonitrile was removed by evaporation and the residue was portioned between ethyl acetate and saturated aqueous sodium bicarbonate. The organic layer was separated, washed with saturated aqueous sodium chloride, dried (anhydrous sodium sulfate), filtered and concentrated. Column chromatography on silica gel using 7:3 ethyl acetate:hexane as the eluent gave 0.89 g of compound 2 as a white solid. LCMS m/z=470 (M+H)$^+$ Title Compound: Compound 3 (0.1 g; 0.2 mmol) was treated with 7 N ammonia in methanol (1.5 mL) and heated to 45° C. in a sealed tube for 1 h. The methanol and ammonia was removed by evaporation and the residue was portioned between ethyl acetate and 1 N sodium hydroxide. The organic layer was separated, washed with saturated aqueous sodium chloride, dried (anhydrous sodium sulfate), filtered and concentrated. The crude product was purified by recrystallization from ethyl acetate to give 0.064 g of the title compound as white crystals. LCMS m/z=392 (M+H)$^+$ Examples 26 to 58

Examples 26 to 58 were prepared using methology described in Example 24 and Example 25.

| Example | Structure | Name | [M + 1] |
|---|---|---|---|
| 26 | 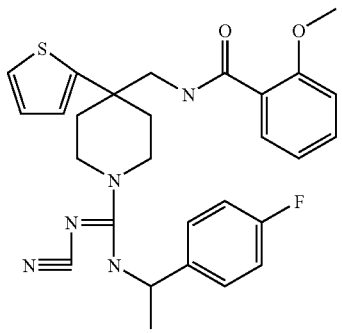 | | 519 |
| 27 | 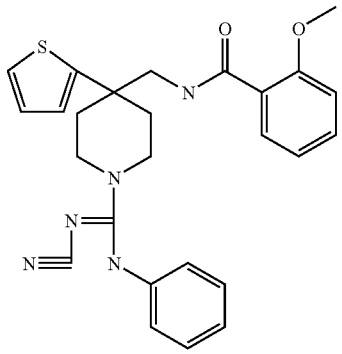 | | 473 |
| 28 | 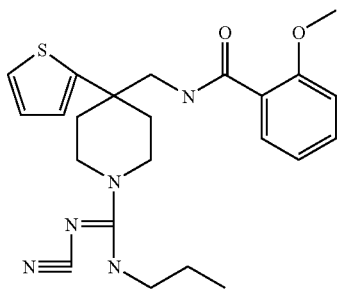 | | 439 |
| 29 | 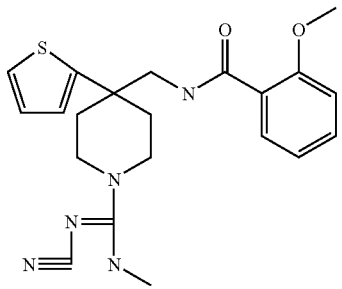 | | 411 |

-continued
| Example | Structure | Name | [M + 1] |
|---|---|---|---|
| 30 | 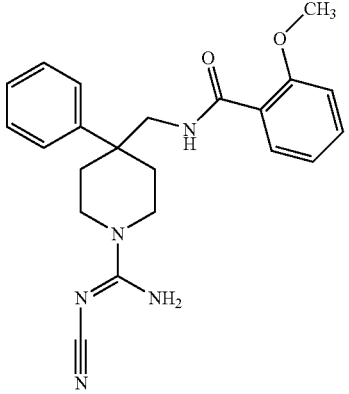 | | 392 |
| 31 | 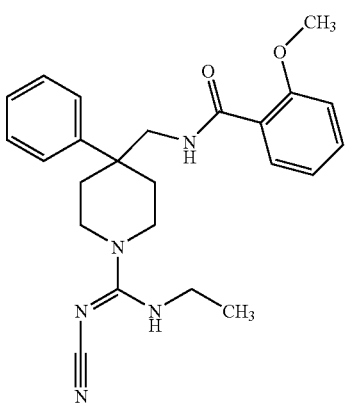 | | 421 |
| 32 | 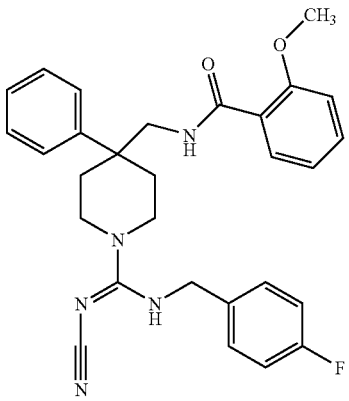 | | 501 |
| 33 | 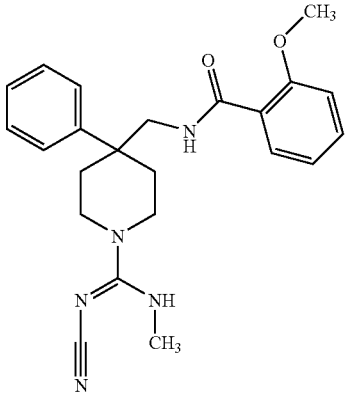 | | 407 |

-continued
| Example | Structure | Name | [M + 1] |
|---------|-----------|------|---------|
| 34 | 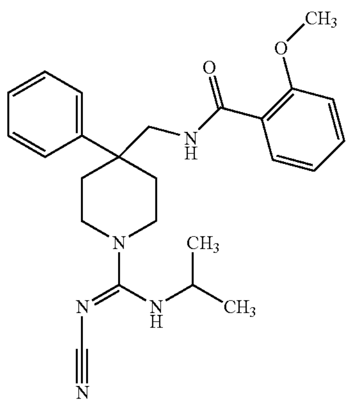 | | 435 |
| 35 | 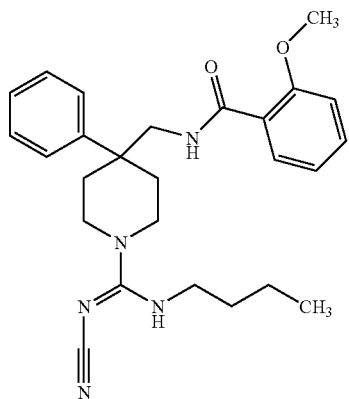 | | 449 |
| 36 | 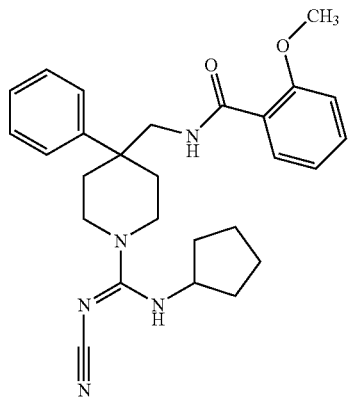 | | 461 |

-continued
| Example | Structure | Name | [M + 1] |
|---|---|---|---|
| 37 | 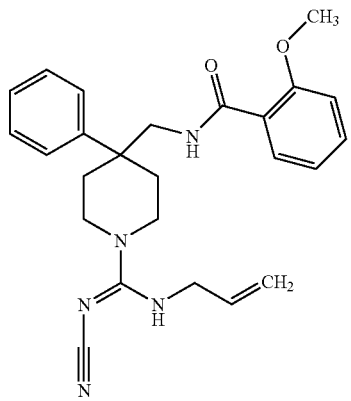 | | 433 |
| 38 | 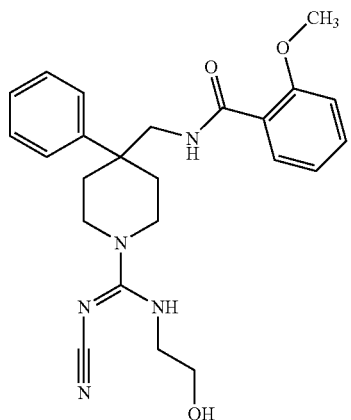 | | 437 |
| 39 | 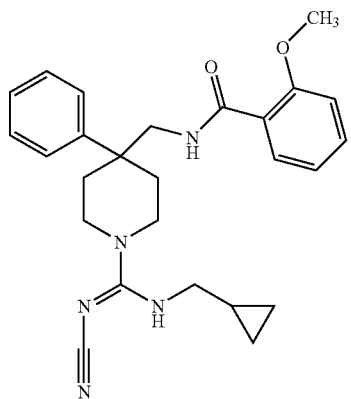 | | 447 |

-continued
| Example | Structure | Name | [M + 1] |
|---|---|---|---|
| 40 | 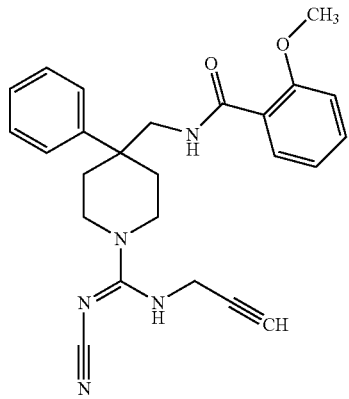 | | 431 |
| 41 | 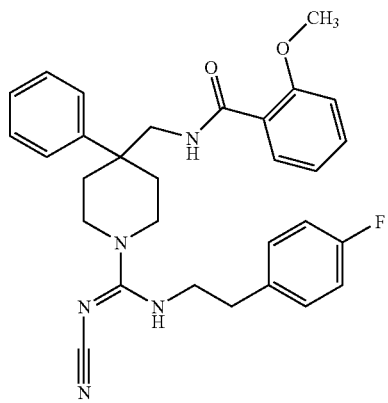 | | 515 |
| 42 | 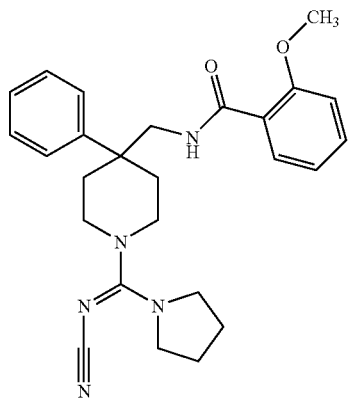 | | 447 |

-continued
| Example | Structure | Name | [M + 1] |
|---------|-----------|------|---------|
| 43 | 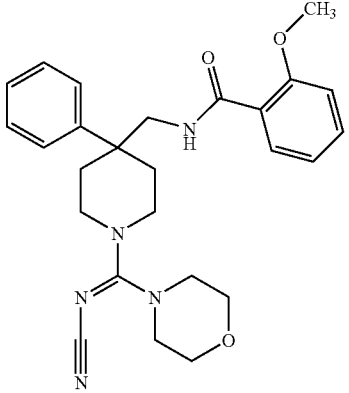 | | 463 |
| 44 | 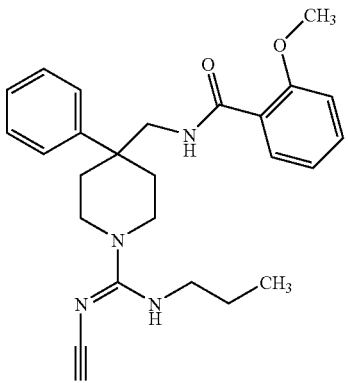 | | 435 |
| 45 | 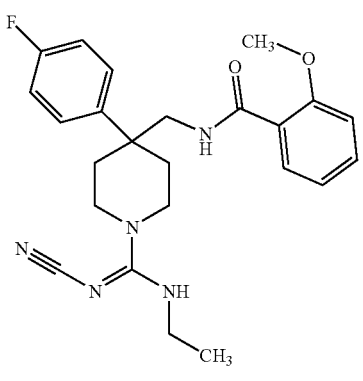 | | 439 |
| 46 | 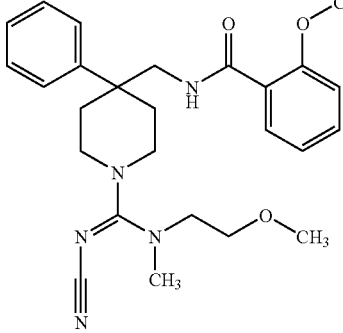 | | 465 |

-continued
| Example | Structure | Name | [M + 1] |
|---|---|---|---|
| 47 | 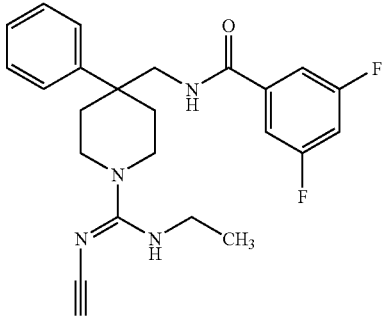 | | 426 |
| 48 | 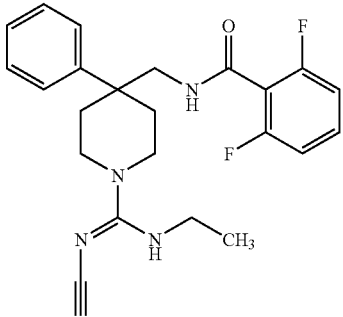 | | 426 |
| 49 | 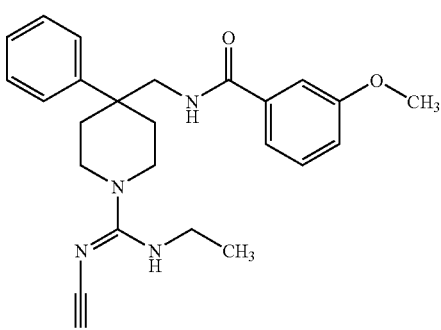 | | 421 |
| 50 | 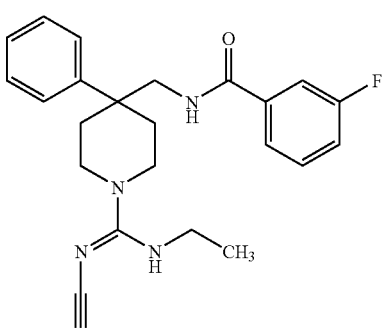 | | 408 |

-continued
| Example | Structure | Name | [M + 1] |
|---|---|---|---|
| 51 | 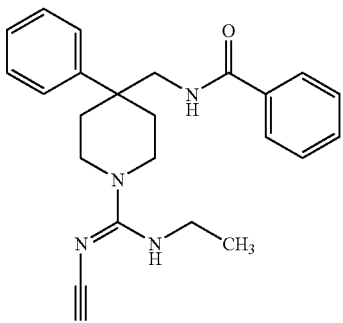 | | 391 |
| 52 | 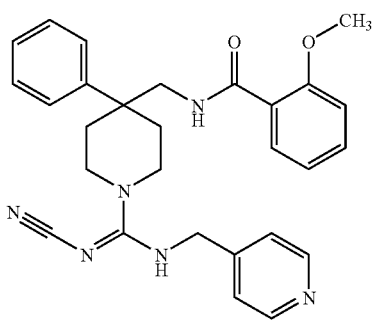 | | 484 |
| 53 | 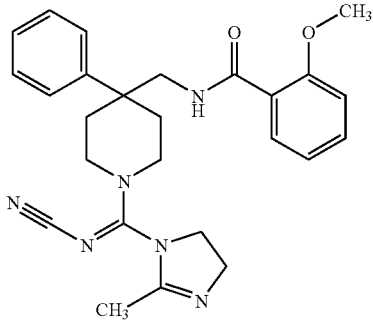 | | 460 |
| 54 | 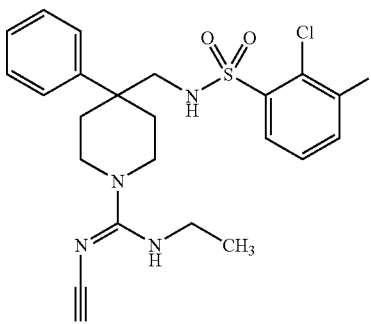 | | 495 |

-continued
| Example | Structure | Name | [M + 1] |
|---|---|---|---|
| 55 | 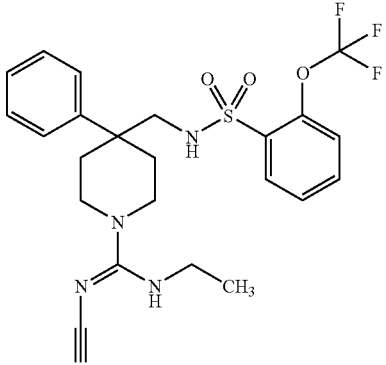 | | 511 |
| 56 | 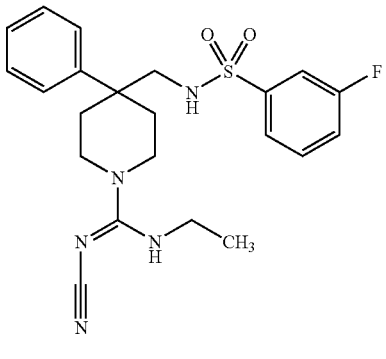 | | 445 |
| 57 | 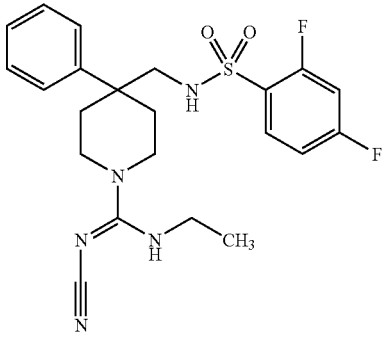 | | 463 |
| 58 | 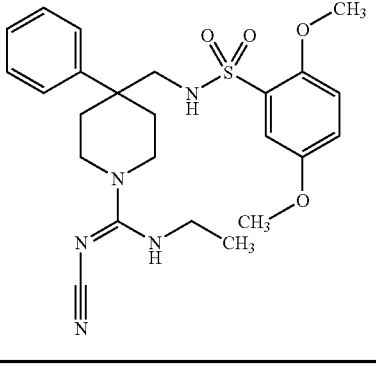 | | 487 |

59

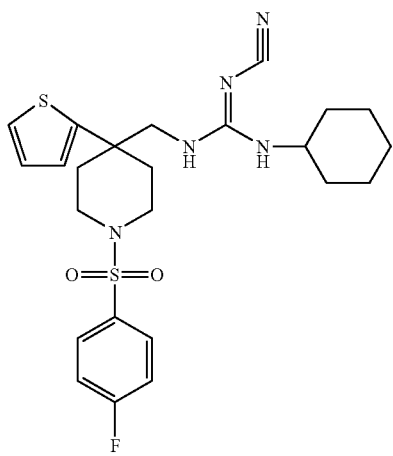

Synthesis

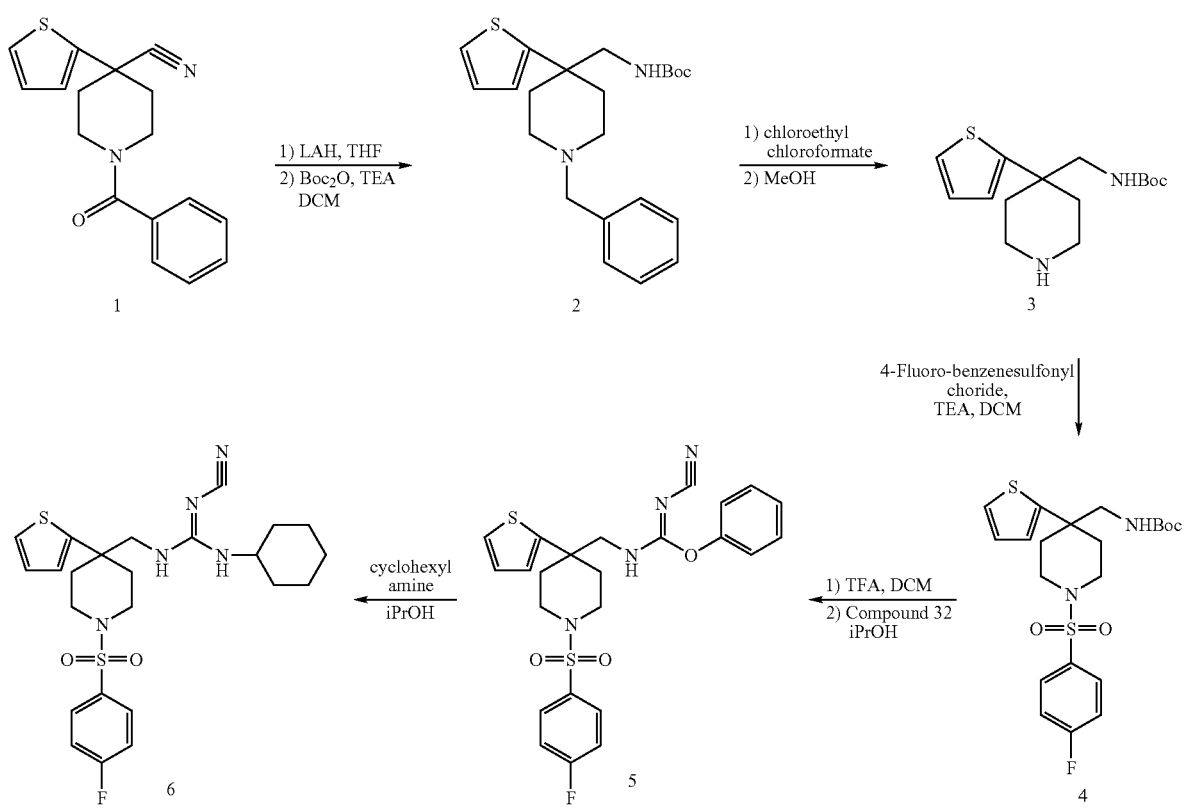

quenched with water (9.2 mL), 1N NaOH (5.8 mL) and water (9.2 mL). The quenched reaction mixture was stirred at ambient temperature for 0.5 h. The slurry was filtered through a celite pad and the filtrate was concentrated. The residue was diluted with EtOAc (200 mL), washed with saturated $NaHCO_3$ (2×100 mL), dried over $MgSO_4$, filtered and concentrated to give a brown oil. This residue was dissolved in dichloromethane (75 mL) and carbonic acid di-tert-butyl ester (2.9 g, 13 mmol) and TEA (1.8 mL, 13 mmol) were added subsequently. The reaction mixture was stirred at ambient temperature for 18 h and then concentrated. The product compound 2 was purified by flash silica gel chromatography elution with 2:1 hexane:ethylacetate (3.5g, 75% yield for two steps). HPLC Rt 2.44 min, Purity 100%, YMC S5 column 4.6×50 mm, 4 min gradient 0 to 100% MeOH (90% in water, 0.2% PPA) UV detection at 220 nm. LCMS Rt 1.39 min, [M+1] 387.24 Phenomenex S5 column 4.6×30 mm, 2 min gradient 0 to 100% MeOH (90% in water, 0.1% TFA) UV detection at 220 nm. NMR H ($CDCl_3$) 1.32 ppm, 9H, s; 1.80 ppm, 2H, m; 1.96 ppm, 2H, m; 2.22 ppm, 2H, m; 2.55-2.58 ppm, 2H, m; 3.21 ppm, 2H, d, J=6.3 Hz; 3.35 ppm, 2H, s; 4.30 ppm, 1H, m; 6.76 ppm, 1H, dd, J=0.8 Hz and 3.4 Hz; 6.90-6.91 ppm, 1H, m; 7.13-7.21 ppm, 6H, m.

Compound 3: Compound 2 (1.7 g, 4.5 mmol) was dissolved in dichloroethane (35 mL) and TEA (3.1 mL, 22.4

Compound 1: Compound 1 was prepared as described in Example 1.

Compound 2: To a solution of compound 1 (3.5 g, 12 mmol) in dry THF (70 mL) was added LAH (35 mL, 35 mmol, 1.0M solution in tetrahydrofuran). The reaction mixture was heated to reflux for 1.5 h then allowed to cool to ambient temperature. The solution was cooled to 0° C. and mmol) was added. At 0° C. chloroethyl chloroformate (0.97 mL, 8.9 mmol) in dichloroethane (17 mL) was added. The reaction mixture was stirred at ambient temperature for 1 h, then another 1.0 mL chloroethyl chloroformate and 3.0 mL TEA were added. The reaction mixture was stirred at ambient temperature for a further 2 h then concentrated and dried under high vacuum for 0.5 h. MeOH (20 mL) was added to the residue and was heated to reflux for 4 h. The reaction mixture was concentrated and the residue was taken directly to the next step.

Compound 4: Compound 3 was dissolved in dichloromethane (60 mL). At ambient temperature TEA (1.9 mL, 13.4 mmol) was added followed by the addition of 4-Fluorobenzenesulfonyl chloride (1.0 g, 5.4 mmol). The reaction mixture was stirred for 18 h and then concentrated. Compound 4 (1.44 g, 71% yield) was isolated as a white solid by column chromatography using 2:1 Hexane:EtOAc. HPLC Rt 3.56 min, Purity 100%, YMC S5 column 4.6×50 mm, 4 min gradient 0 to 100% MeOH (90% in water, 0.2% PPA) UV detection at 220 nm. LCMS Rt 1.82 min, [M+23] 477.13 YMC S5 column 4.6×30 mm, 2 min gradient 0 to 100% MeOH (90% in water, 0.1% TFA) UV detection at 220 nm. NMR H (CDCl$_3$) 1.32 ppm, 9H, s; 1.86-1.88 ppm, 2H, m; 2.03-2.06 ppm, 2H, m; 2.70-2.74 ppm, 2H, m; 3.13 ppm, 2H, d, J=6.6 Hz; 3.40-3.42 ppm, 2H, m; 4.30 ppm, 1H, m; 6.70 ppm, 1H, d, J=3.3 Hz; 6.87-6.89 ppm, 1H, m; 7.07-7.10 ppm, 1H, m; 7.13-7.14 ppm, 1H, m; 7.65-7.68 ppm, 2H, m.

Compound 5: Compound 4 (55 mg, 0.12 mmol) was dissolved in dichloromethane (1.3 mL). To this solution TFA (180 μL, 2.3 mmol) in dichloromethane (0.50 mL) was added and the reaction was stirred at ambient temperature till no starting material was detected according to LC-MS. The reaction mixture was concentrated and neutralized with TEA. To the concentrated residue was added diphenyl cyanocarbonimidate (32 mg, 0.13 mmol) and isopropyl alcohol (1.0 mL). The reaction mixture was heated to reflux for 18 h.

Title Compound: Cyclohexyl amine (19 mg, 0.19 mmol) was added to compound 5 and the reaction was heated at 95° C. for 24 h. The reaction mixture was concentrated and purified by Prep-HPLC YMC ODS S5 20×100 mm, 16 min gradient 40 to 100% MeOH (90% in water 0.1% TFA) at 20 mL/min UV detection at 220 nM to give the title compound as a yellow oil (23.8 mg, 39% yield). HPLC Rt 3.49 muin, Purity 100%, YMC S5 column 4.6×50 mm, 4 min gradient 0 to 100% MeOH (90% in water, 0.2% PPA) UV detection at 220 nm. LCMS Rt 1.81 min, [M+1] 504.24 YMC S5 column 4.6×30 mm, 2 min gradient 0 to 100% MeOH (90% in water, 0.1% TFA) UV detection at 220 nm. NMR H (CDCl$_3$) 1.01-1.24 ppm, 5H, m; 1.56-1.58 ppm, 1H, m; 1.66-1.77 ppm, 4H, m; 1.91-1.94 ppm, 2H, m; 2.15-2.18 ppm, 2H, m; 2.75-2.79 ppm, 2H, m; 2.98-3.01 ppm, 1H, m; 3.27 ppm, 2H, d, J=6.1 Hz; 3.45-3.47 ppm, 2H, m; 6.81 ppm, 1H, dd, J=3.9 Hz and 1.1 Hz; 6.98 ppm, 1H, dd, J=3.3 Hz and 4.9 Hz; 7.13-7.19 ppm, 2H, m; 7.25-7.29 ppm, 1H, m; 7.71-7.76 ppm, 2H, m.

Examples 60 to 63

Examples 60 to 63 were prepared as described in Example 59.

| Example | Structure | [M + 1] |
|---------|-----------|---------|
| 60 | 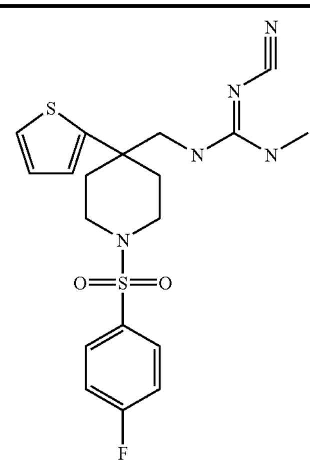 | 435 |
| 61 | 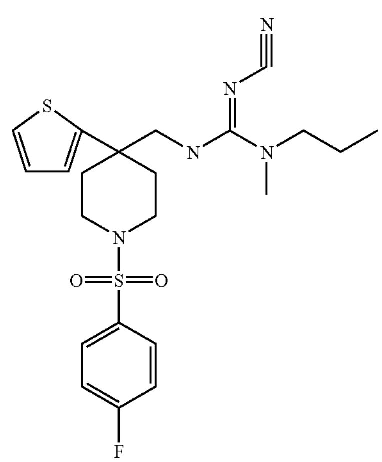 | 477 |

| Example | Structure | [M + 1] |
|---|---|---|
| 62 | 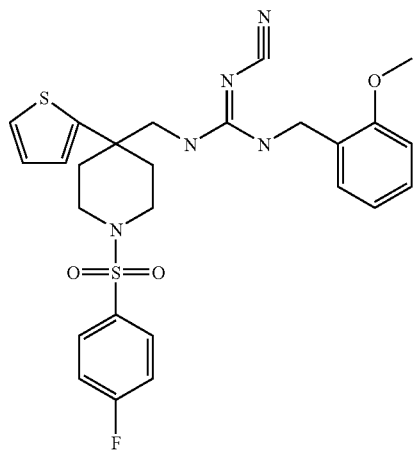 | 541 |
| 63 | 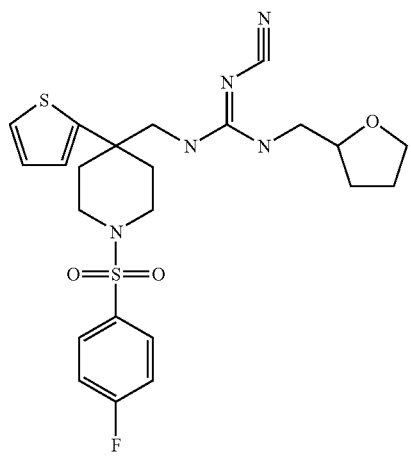 | 505 |
Example 64
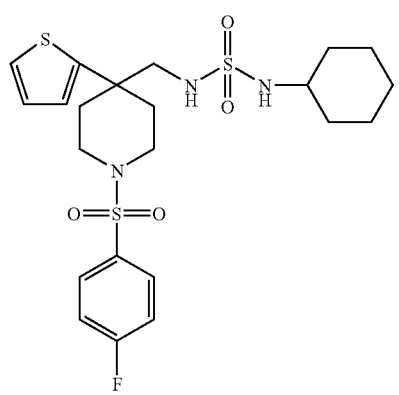
Synthesis
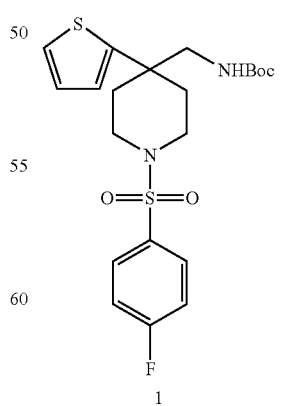
1) TFA, DCM
2) Chlorosulfonyl isocyanate, chloroethanol, TEA, DCM

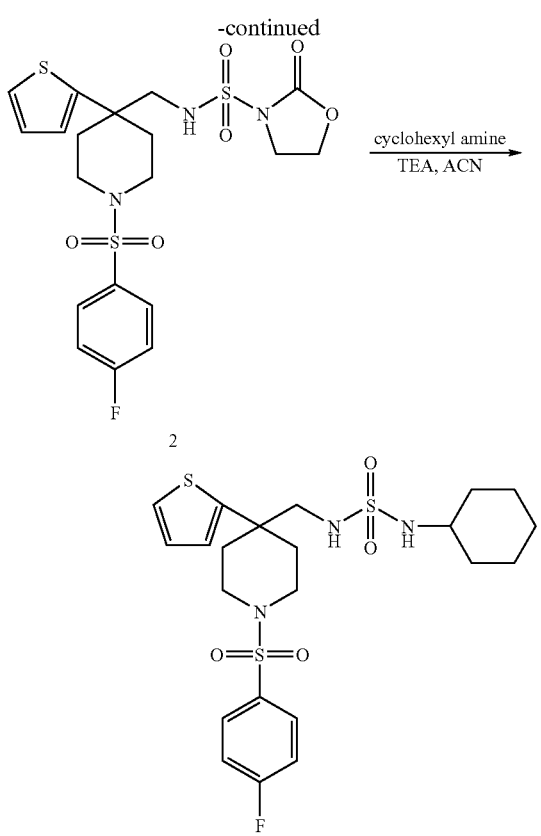

Compound 1: Compound I was prepared using methodology described in Example 59.

Compound 2: To the solution of compound 1 (500 mg, 1.1 mmol) in dichloromethane (5.0 mL) was added TFA (3.0 mL) in dichloromethane (12 mL) and the reaction was stirred for 1.5 h. Then the mixture was concentrated and neutralized with TEA. At 0° C. 2-chloroethanol (74 μL, 1.1 mmol) in dichlormethane (7.5 mL) was added to the solutions of chlorosulfonyl isocyanate (96 μL, 1.1 mmol) in dichloromethane (7.5 μL). The reaction mixture was stirred at 0° C. for 1 h. The crude amine in dichloromethane (5.0 mL) and TEA (460 μL, 3.3 mmol) were added. The reaction was stirred for 18 h and concentrated. Compound 2 (260 mg, 47% yield) was purified as a white solid by column chromatography using 1:1 Hexane:EtOAc. HPLC Rt 2.86 min, Purity 100%, YMC S5 column 4.6×50 mm, 4 min gradient 0 to 100% MeOH (90% in water, 0.2% PPA) UV detection at 220 nm. LCMS Rt 1.48 min, [M+1] 504.08 YMC S5 column 4.6×30 mm, 2 min gradient 0 to 100% MeOH (90% in water, 0.1% TFA) UV detection at 220 nm. NMR H (CDCl$_3$) 1.86-1.96 ppm, 2H, m; 2.14-2.17 ppm, 2H, m; 2.56-2.62 ppm, 2H, m; 3.07 ppm, 2H, d, J=6.9 Hz; 3.51-3.53 ppm, 2H, m; 3.90 ppm, 2H, t, J=7.8 Hz; 4.32 ppm, 2H, t, J=7.8 Hz; 5.17 ppm, 1H, t, J=6.9 Hz; 6.75 ppm, 1H, d, J=3.4 Hz; 6.88-6.90 ppm, 1H, m; 7.07-7.09 ppm, 2H, m; 7.11-7.18 ppm, 1H, m; 7.63-7.67 ppm, 2H, m.

Title Compound: Cyclohexyl amine (7.7 mg, 0.078 mmol), TEA (130 μL) and compound 2 (26 mg, 0.052 mmol) were dissolved in acetonitrile (1.0 mL). The reaction was heated at 85° C. for 18 h and concentrated. The title compound was purified as an orange oil (24.1 mg, 90% yield) by Prep-HPLC YMC ODS S5 20×100 mm, 16 min gradient 40 to 100% MeOH (90% in water 0.1% TFA) at 20 mL/min UV detection at 220 nM. HPLC Rt 3.51 min, Purity 100%, YMC S5 column 4.6×50 mm, 4 min gradient 0 to 100% MeOH (90% in water, 0.2% PPA) UV detection at 220 nm. LCMS Rt 1.82 min, [M+1] 516.16 YMC S5 column 4.6×30 mm, 2 min gradient 0 to 100% MeOH (90% in water, 0.1% TFA) UV detection at 220 nm. NMR H (CDCl$_3$) 1.05-1.11 ppm, 3H, m; 1.16-1.21 ppm, 2H, m; 1.49-1.51 ppm, 1H, m; 1.59-1.63 ppm, 2H, m; 1.77-1.80 ppm, 2H, m; 1.88-1.92 ppm, 2H, m; 2.15-2.18 ppm, 2H, m; 2.62-2.68 ppm, 2H, m; 2.94-2.98 ppm, 3H, m; 3.43-3.45 ppm, 2H, m; 3.84 ppm, 1H, m; 6.73-6.74 ppm, 1H, m; 6.88-6.89 ppm, 1H, m; 7.01-7.11 ppm, 2H, m; 7.17 ppm, 1H, dd, J=1.1 Hz and 5.5Hz; 7.65-7.67 ppm, 2H, m.

Examples 65 to 73

Examples 65 to 73 were prepared using methodology described in Example 64.

| Example | Structure | Name | [M + 1] |
|---|---|---|---|
| 65 | ![structure] | | 447 |

-continued

| Example | Structure | Name | [M + 1] |
|---|---|---|---|
| 66 | 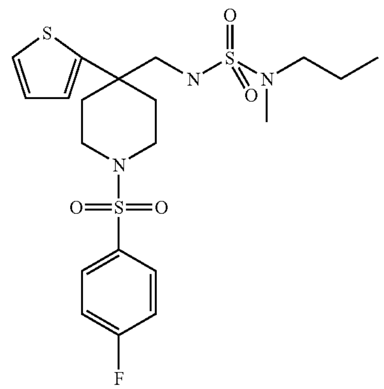 | | 489 |
| 67 | 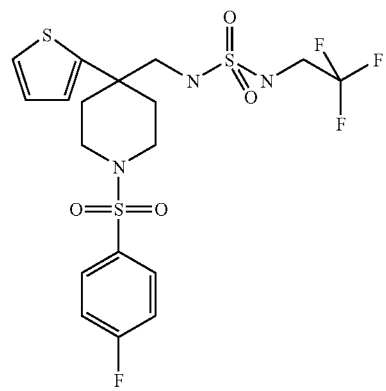 | | 515 |
| 68 | 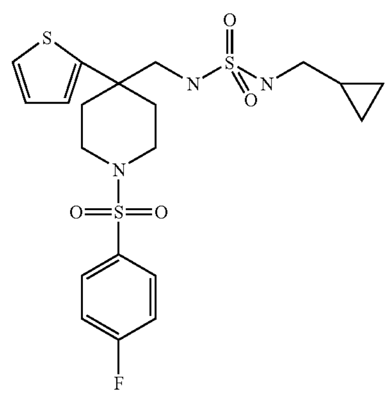 | | 487 |
| 69 | 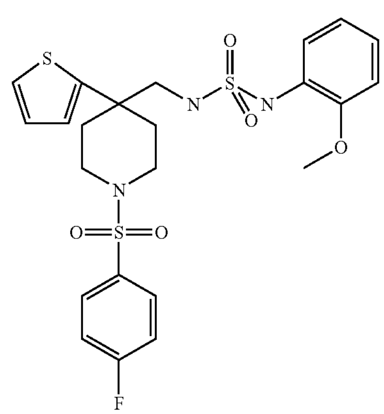 | | 539 |

-continued
| Example | Structure | Name | [M + 1] |
|---|---|---|---|
| 70 | 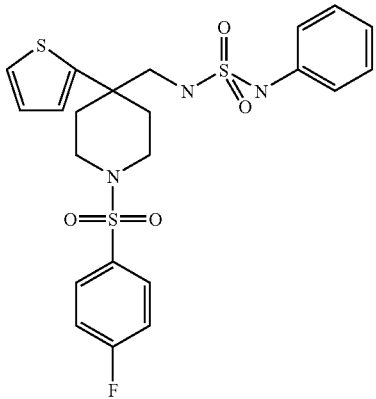 | | 509 |
| 71 | 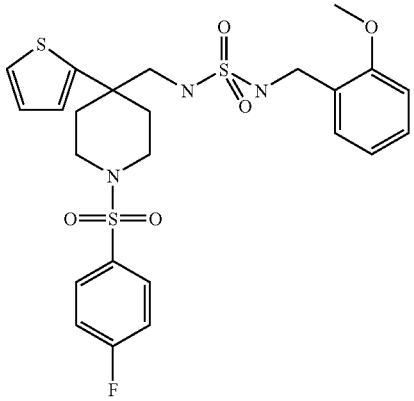 | | 553 |
| 72 | 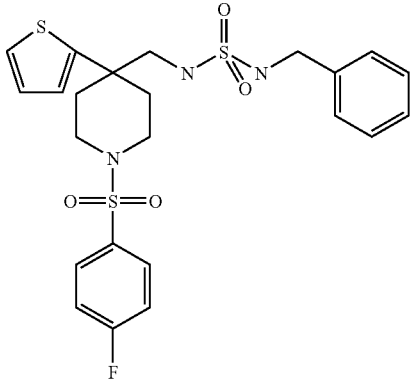 | | 523 |
| 73 | 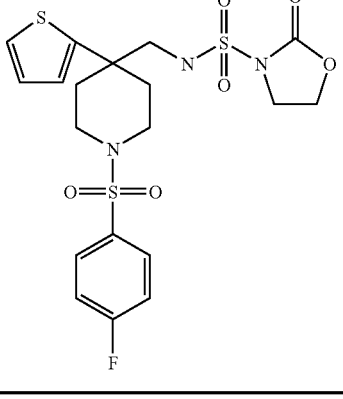 | | 503 |

Example 74

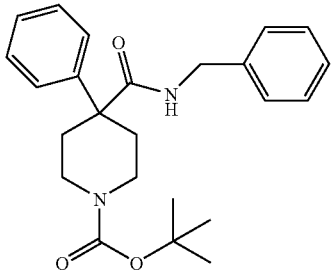

4-benzylcarbamoyl-4-phenyl-piperidine-1-carboxylic acid tert-butyl ester

Synthesis

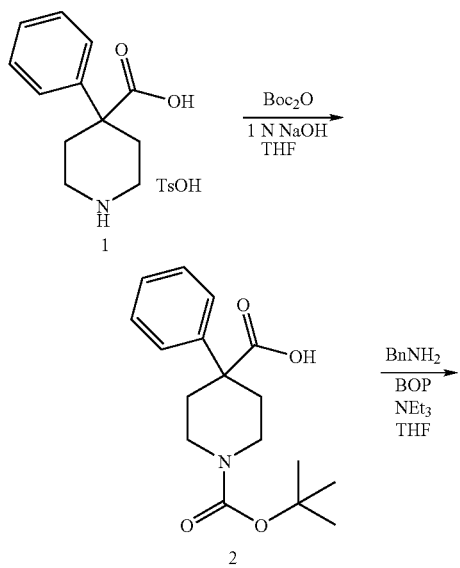

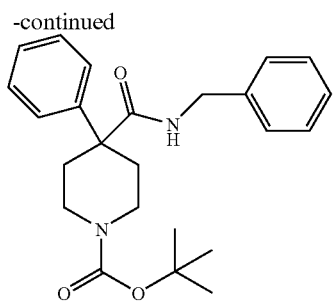

Compound 1: Compound 1 is commercially available.

Compound 2: A solution of compound 1 (12.6 g; 33.4 mmol) in 100 mL of 1 N sodium hydroxide and 25 mL of tetrahydrofuran was treated with di-tert-butyl dicarbonate (10.3 g; 47.2 mmol) at room temperature. After stirring for 20 h, 10% aqueous hydrochloric acid was slowly added to neutralize the reaction mixture to pH=7. Ethyl acetate (approximately 300 mL) was added and the organic layer was separated, washed with saturated aqueous sodium chloride, dried (anhydrous sodium sulfate), filtered and concentrated to give compound 2 as a white solid (10.2 g) that was used without further purification. LCMS m/z=306 (M+H)$^+$ Title Compound: A solution of compound 2 (0.92 g; 3.0 mmol) in tetrahydrofuran (30 mL) was treated with benzotriazol-1-yloxytris(dimethylamino)phosphonium hexafluorophosphate (1.77 g; 4.0 mmol) and triethylamine (0.63 mL; 4.5 mmol) at room temperature. The reaction mixture was allowed to stir for 0.5 h at which time benzyl amine (0.39 mL; 3.6 mmol) was added and the reaction mixture was heated to 45° C. for 2 h. The tetrahydrofuran was removed by evaporation and the residue was treated with ethyl acetate (approximately 150 mL) and 5% aqueous hydrochloric acid (approximately 100 mL). The organic layer was separated, washed with saturated aqueous sodium chloride, dried (sodium sulfate), filtered and concentrated. Column chromatography on silica gel using 7:3 hexane:ethyl acetate as the eluent gave 0.93 g of 4-benzylcarbamoyl-4-phenyl-piperidine-1-carboxylic acid tert-butyl ester as a white solid. LCMS m/z=396 (M+H)$^+$

Examples 75 to 84

Examples 75 to 84 were prepared as described in Example 74.

| Example | Structure | Name | [M + H] |
|---|---|---|---|
| 75 | 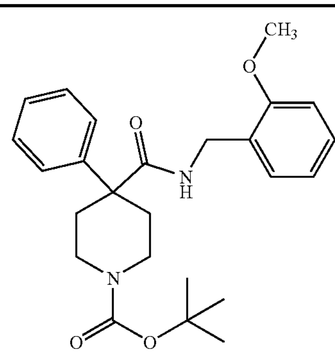 | 4-(2-Methoxy-benzylcarbamoyl)-4-phenyl-piperidine-1-carboxylic acid tert-butyl ester | 425 |

-continued

| Example | Structure | Name | [M + H] |
|---|---|---|---|
| 76 | 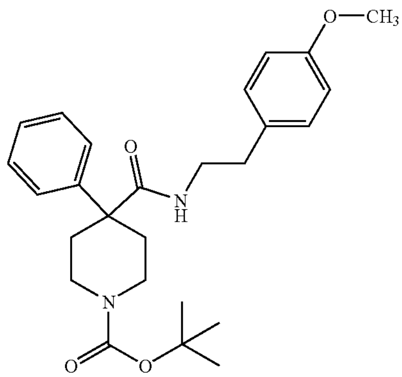 | 4-[2-(4-Methoxy-phenyl)-ethylcarbamoyl]-4-phenyl-piperidine-1-carboxylic acid tert-butyl ester | 439 |
| 77 | 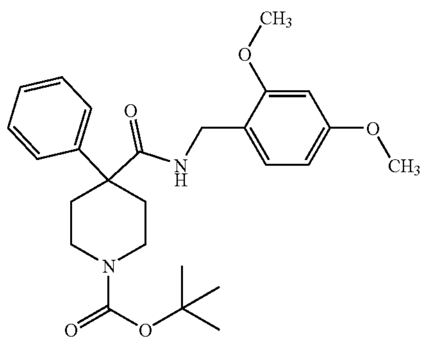 | 4-(2,4-Dimethoxy-benzylcarbamoyl)-4-phenyl-piperidine-1-carboxylic acid tert-butyl ester | 455 |
| 78 | 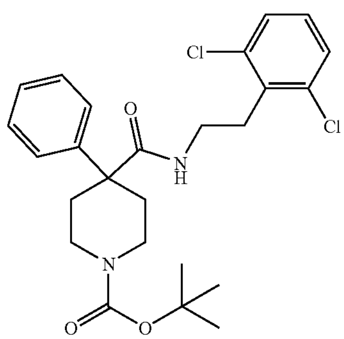 | 4-[2-(2,6-Dichloro-phenyl)-ethylcarbamoyl]-4-phenyl-piperidine-1-carboxylic acid tert-butyl ester | 478 |
| 79 | 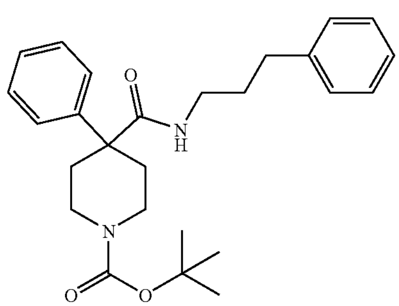 | 4-Phenyl-4-(3-phenyl-propylcarbamoyl)-piperidine-1-carboxylic acid tert-butyl ester | 423 |

| Example | Structure | Name | [M + H] |
|---------|-----------|------|---------|
| 80 | 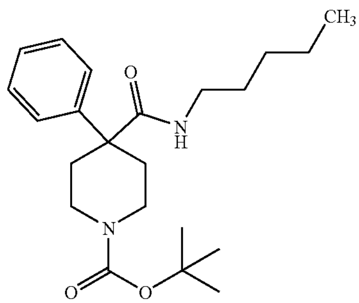 | 4-Pentylcarbamoyl-4-phenyl-piperidine-1-carboxylic acid tert-butyl ester | 375 |
| 81 | 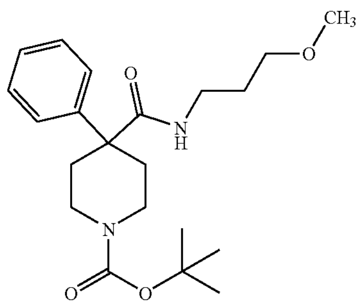 | 4-(3-Methoxy-propylcarbamoyl)-4-phenyl-piperidine-1-carboxylic acid tert-butyl ester | 377 |
| 82 | 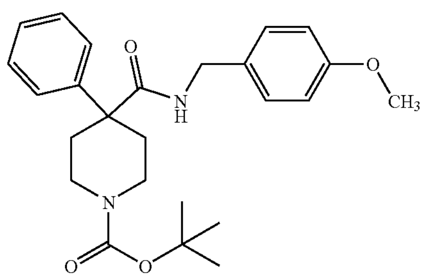 | 4-(4-Methoxy-benzylcarbamoyl)-4-phenyl-piperidine-1-carboxylic acid tert-butyl ester | 425 |
| 83 | 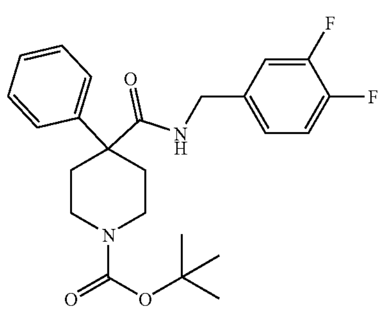 | 4-(3,4-Difluoro-benzylcarbamoyl)-4-phenyl-piperidine-1-carboxylic acid tert-butyl ester | 431 |
| 84 | 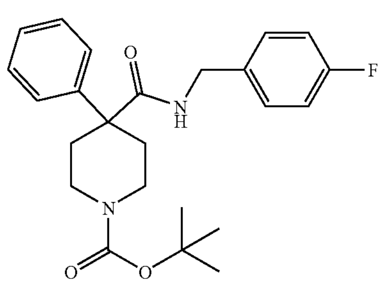 | 4-(4-Fluoro-benzylcarbamoyl)-4-phenyl-piperidine-1-carboxylic acid tert-butyl ester | 413 |

Example 85

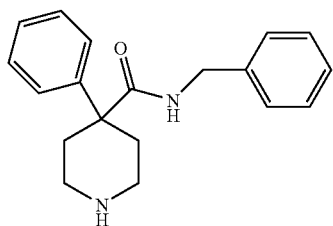

4-phenyl-piperidine-4-carboxylic acid benzylamide

Synthesis

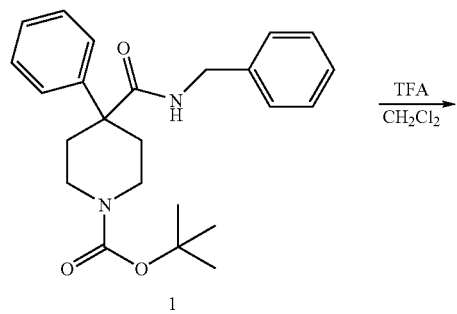

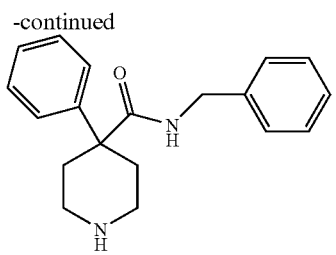

Compound 1: Compound 1 was prepared as described in Example 74.

Title Compound: A solution of compound 1 (0.93 g; 2.4 mmol) in 30 mL of dichloromethane was treated with 4 mL trifluroacetic acid at room temperature. After stirring for 20 h, an additional 100 mL of dichloromethane was added followed by 100 mL 1 N sodium hydroxide. The organic layer was separated, washed with water and saturated aqueous sodium chloride, dried (anhydrous sodium sulfate), filtered and concentrated to give 0.67 g of 4-phenyl-piperidine-4-carboxylic acid benzylamide as a colorless oil that was used without further purification. LCMS m/z=295 (M+H)$^+$

Examples 86 to 93

Examples 86 to 93 were prepared as described in Example 85.

| Example | Structure | Name | M + H |
|---|---|---|---|
| 86 | 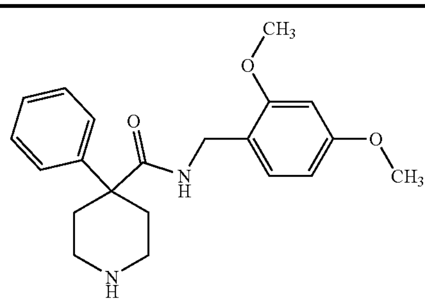 | 4-Phenyl-piperidine-4-carboxylic acid 2,4-dimethoxy-benzylamide | 355 |
| 87 | 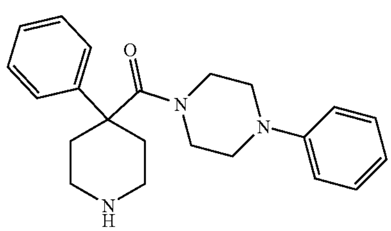 | (4-Phenyl-piperazin-1-yl)-(4-phenyl-piperidin-4-yl)-methanone | 350 |
| 88 | 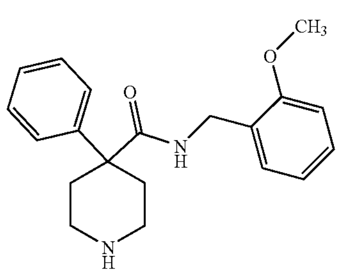 | 4-Phenyl-piperidine-4-carboxylic acid 2-methoxy-benzylamide | 325 |

-continued

| Example | Structure | Name | M + H |
|---------|-----------|------|-------|
| 89 | 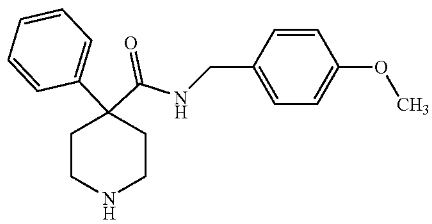 | 4-Phenyl-piperidine-4-carboxylic acid 4-methoxy-benzylamide | 325 |
| 90 | 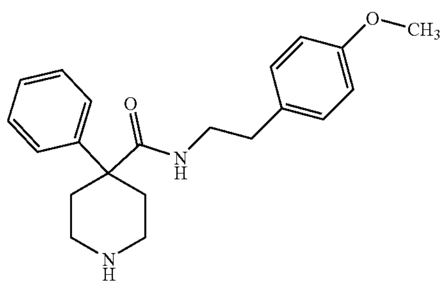 | 4-Phenyl-piperidine-4-carboxylic acid [2-(4-methoxy-phenyl)-ethyl]-amide | 339 |
| 91 | 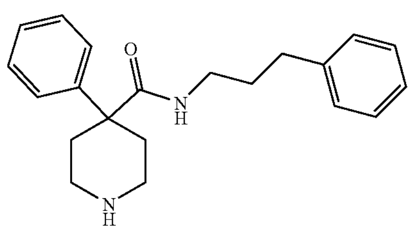 | 4-Phenyl-piperidine-4-carboxylic acid (3-phenyl-propyl)-amide | 323 |
| 92 | 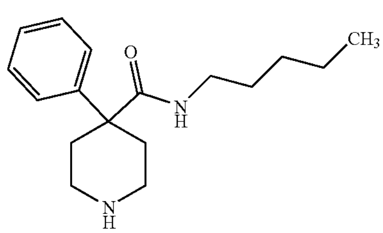 | 4-Phenyl-piperidine-4-carboxylic acid pentylamide | 275 |
| 93 | 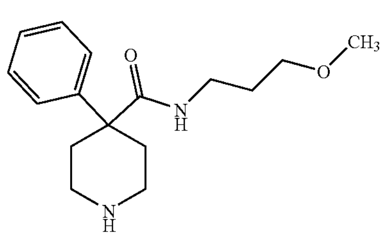 | 4-Phenyl-piperidine-4-carboxylic acid (3-methoxy-propyl)-amide | 277 |

Example 94

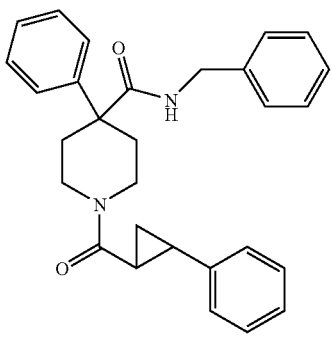

4-Phenyl-1-(2-phenyl-cyclopropanecarbonyl)-piperidine-4-carboxylic acid benzylamide Synthesis

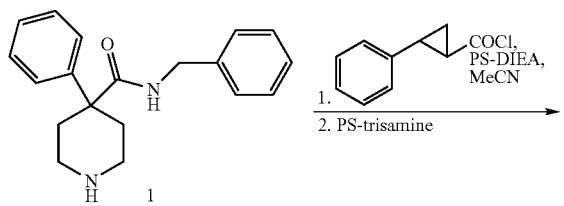

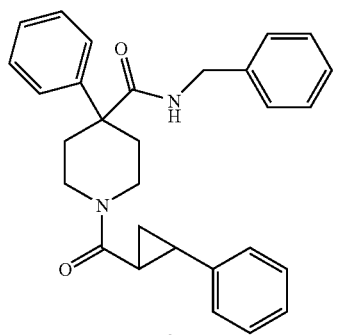

Compound 1: Compound 1 was prepared as described in Example 85.

Title Compound: Compound 1 (0.015 g; 0.05 mmol) was dissolved in 1 mL acetonitrile. Polystyrene-diisopropylethylamine (PS-DIEA) resin (0.1 g) was added and the resulting suspension was treated with trans-2-phenyl-cyclopropanecarbonyl chloride (0.02 g; 0.1 mmol) and shaken at room temperature. After 21 h, polystyrene-trisamine (PS-trisamine) resin (0.1 g) was added and the reaction mixture was allowed to shake an additional 24 h. The reaction mixture was filtered and concentrated to give 0.015 g of 4-phenyl-1-(2-phenyl-cyclopropanecarbonyl)-piperidine-4-carboxylic acid benzylamide as a colorless oil. LCMS m/z=440 (M+H)⁺.

Example 95

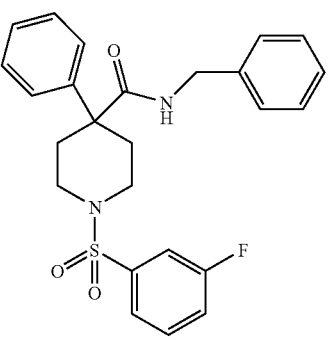

1-(3-Fluoro-benzenesulfonyl)-4-phenyl-piperidine-4-carboxylic acid benzylamide

Synthesis

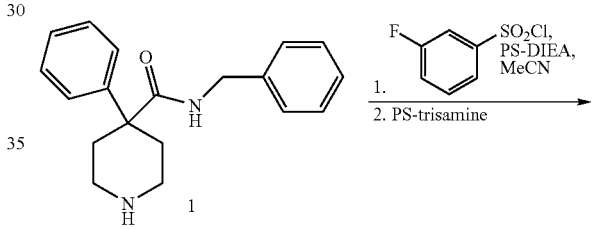

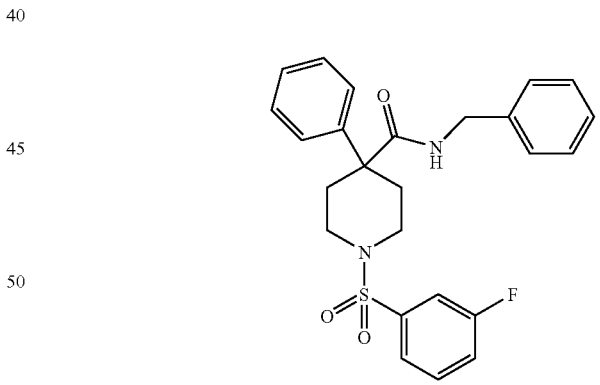

Compound 1: Compound 1 was prepared as described in Example 85.

Title Compound: Compound 1 (0.015 g; 0.05 mmol) was dissolved in 1 mL anhydrous acetonitrile. Polystyrene-diisopropylethylamine (PS-DIEA) resin (0.1 g) was added and the resulting suspension was treated 3-fluoro-benzenesulfonyl chloride (0.02 g; 0.1 mmol) and shaken at room temperature. After 21 h, polystyrene-trisamine (PS-trisamine) resin (0.1 g) was added and the reaction mixture was allowed to shake an additional 24 h. The reaction mixture was filtered and concentrated to give 0.012 g of 1-(3-fluoro-benzenesulfonyl)-4- phenyl-piperidine-4-carboxylic acid benzylamide as a colorless oil. LCMS m/z=454 (M+H)$^+$ Example 96

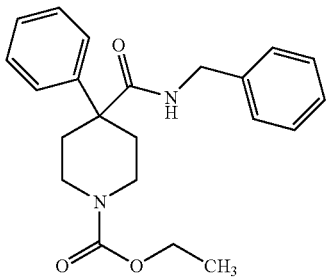

4-Benzylcarbamoyl-4-phenyl-piperidine-1-carboxylic acid ethyl ester

Synthesis

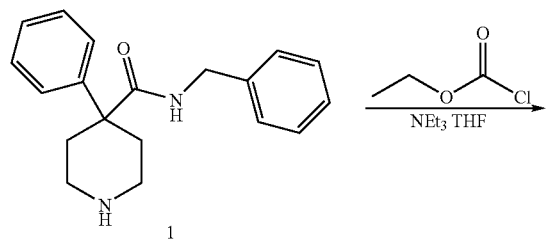

-continued

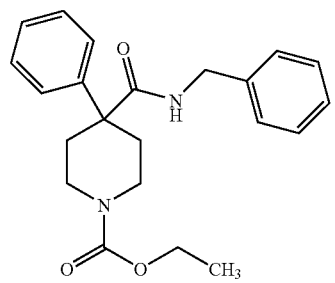

Compound 1: Compound 1 was prepared as described in Example 85.

Title Compound: 4-Benzylcarbamoyl-4-phenyl-piperidine-1-carboxylic acid ethyl ester was prepared using methodology described in Example 2. LCMS m/z=367 (M+H)$^+$ Examples 97 to 269

Examples 97 to 269 were synthesized using methodology described in Example 94, Example 95 and Example 96.

| Example | Structure | Name | M + H |
|---|---|---|---|
| 97 | 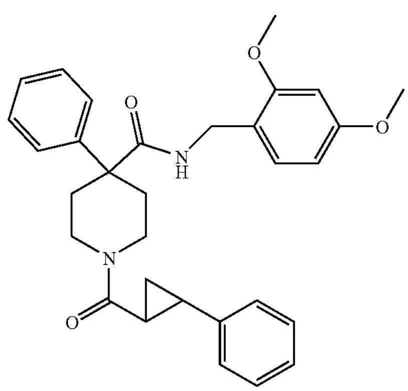 | 4-phenyl-1-(2-phenyl-cyclopropanecarbonyl)-piperidine-4-carboxylic acid 2,4-dimethoxy-benzylamide | 500 |

-continued

| Example | Structure | Name | M + H |
|---|---|---|---|
| 98 | 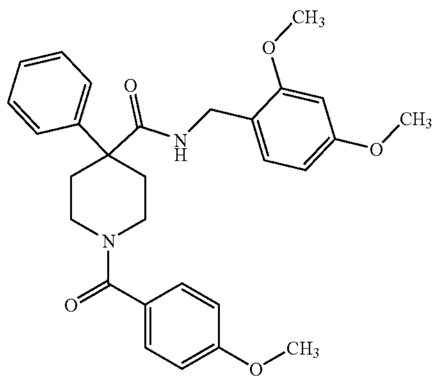 | 1-(4-Methoxy-benzoyl)-4-phenyl-piperidine-4-carboxylic acid 2,4-dimethoxy-benzylamide | 490 |
| 99 | 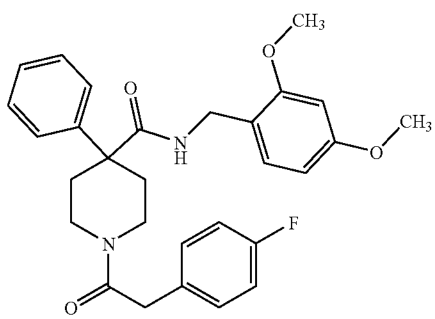 | 1-[2-(4-Fluoro-phenyl)-acetyl]-4-phenyl-piperidine-4-carboxylic acid, 2,4-dimethoxy-benzylamide | 492 |
| 100 | 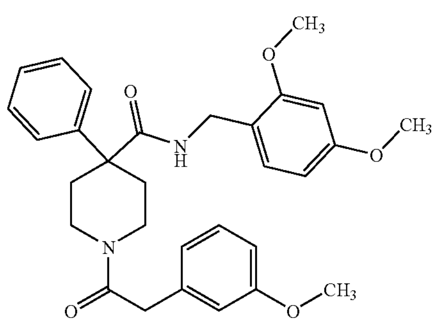 | 1-[2-(3-Methoxy-phenyl)-acetyl]-4-phenyl-piperidine-4-carboxylic acid 2,4-dimethoxy-benzylamide | 504 |
| 101 | 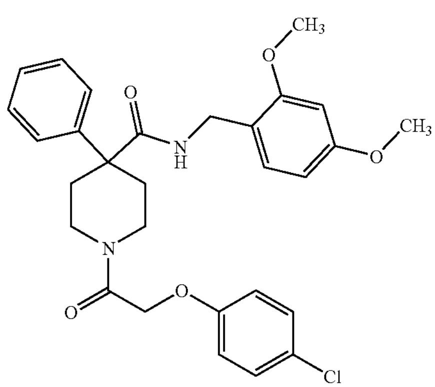 | 1-[2-(4-Chloro-phenoxy)-acetyl]-4-phenyl-piperidine-4-carboxylic acid 2,4-dimethoxy-benzylamide | 524 |

-continued

| Example | Structure | Name | M + H |
|---|---|---|---|
| 102 | 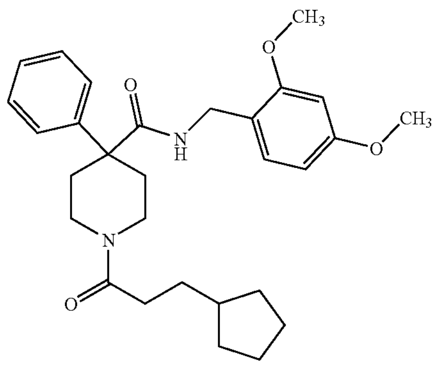 | 1-(3-Cyclopentyl-propionyl)-4-phenyl-piperidine-4-carboxylic acid 2,4-dimethoxy-benzylamide | 480 |
| 103 | 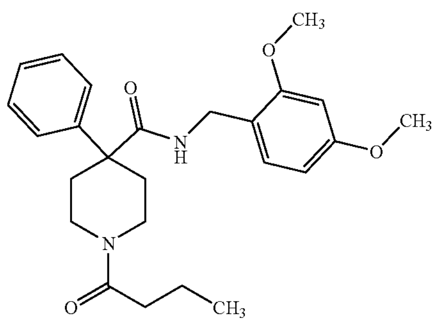 | 1-Butyryl-4-phenyl-piperidine-4-carboxylic acid 2,4-dimethoxy-benzylamide | 426 |
| 104 | 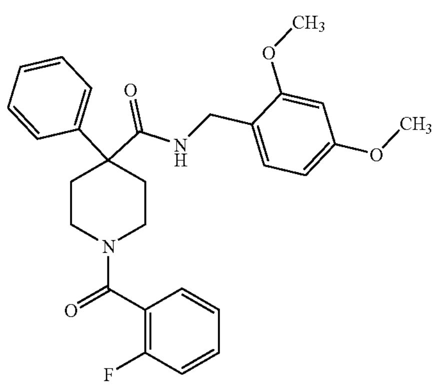 | 1-(2-Fluoro-benzoyl)-4-phenyl-piperidine-4-carboxylic acid 2,4-dimethoxy-benzylamide | 479 |
| 105 | 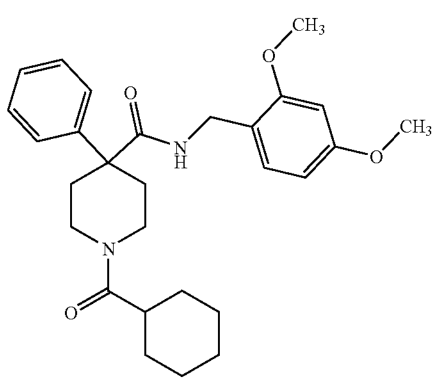 | 1-Cyclohexanecarbonyl-4-phenyl-piperidine-4-carboxylic acid 2,4-dimethoxy-benzylamide | 466 |

-continued

| Example | Structure | Name | M + H |
|---|---|---|---|
| 106 | 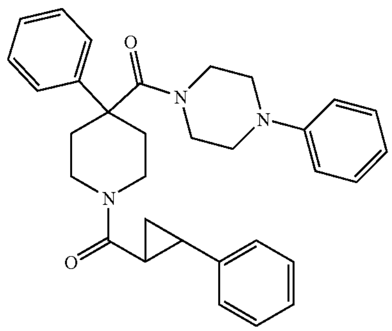 | (2-Phenyl-cyclopropyl)-[4-phenyl-4-(4-phenyl-piperazine-1-carbonyl)-piperidin-1-yl]-methanone | 495 |
| 107 | 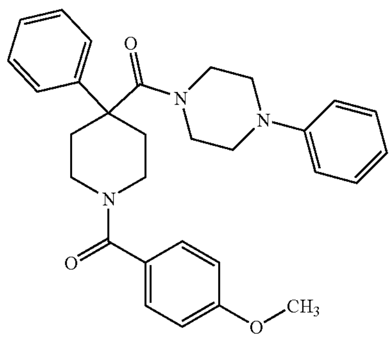 | [1-(4-Methoxy-benzoyl)-4-phenyl-piperidin-4-yl]-(4-phenyl-piperazin-1-yl)-methanone | 485 |
| 108 | 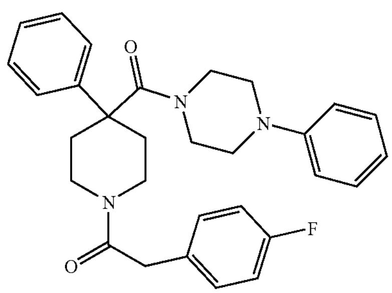 | 2-(4-Fluoro-phenyl)-1-[4-phenyl-4-(4-phenyl-piperazine-1-carbonyl)-piperidin-1-yl]-ethanone | 487 |
| 109 | 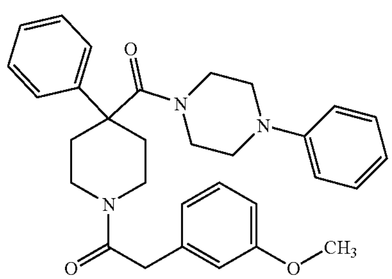 | 2-(3-Methoxy-phenyl)-1-[4-phenyl-4-(4-phenyl-piperazine-1-carbonyl)-piperidin-1-yl]-ethanone | 499 |
| 110 | 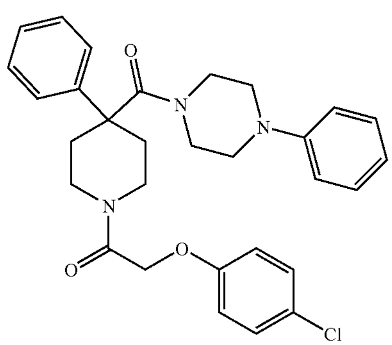 | 2-(4-Chloro-phenoxy)-1-[4-phenyl-4-(4-phenyl-piperazine-1-carbonyl)-piperidin-1-yl]-ethanone | 519 |

-continued

| Example | Structure | Name | M + H |
|---|---|---|---|
| 111 | 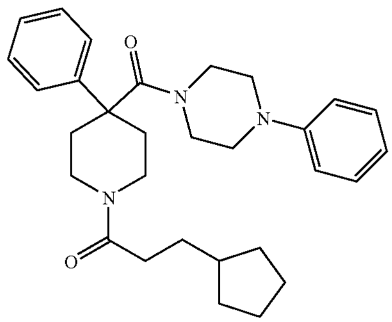 | 3-Cyclopentyl-1-[4-phenyl-4-(4-phenyl-piperazine-1-carbonyl)-piperidin-1-yl]-propan-1-one | 475 |
| 112 | 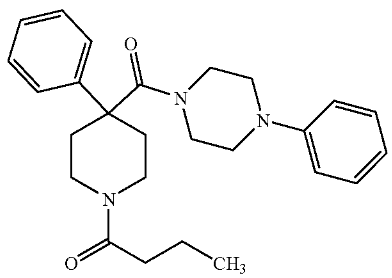 | 1-[4-Phenyl-4-(4-phenyl-piperazine-1-carbonyl)-piperidin-1-yl]-butan-1-one | 421 |
| 113 | 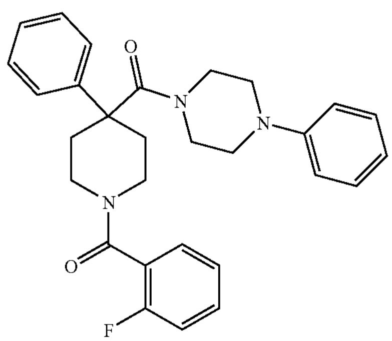 | (2-Fluoro-phenyl)-[4-phenyl-4-(4-phenyl-piperazine-1-carbonyl)-piperidin-1-yl]-methanone | 473 |
| 114 | 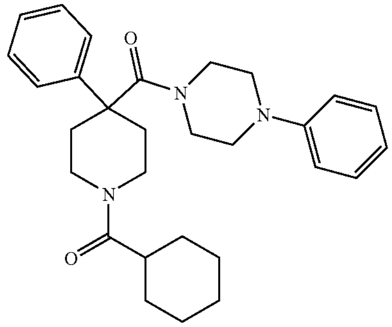 | (1-Cyclohexanecarbonyl-4-phenyl-piperidin-4-yl)-(4-phenyl-piperazin-1-yl)-methanone | 461 |

| Example | Structure | Name | M + H |
|---|---|---|---|
| 115 | 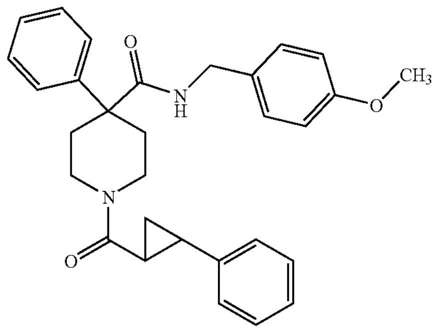 | 4-Phenyl-1-(2-phenyl-cyclopropanecarbonyl)-piperidine-4-carboxylic acid 4-methoxy-benzylamide | 470 |
| 116 | 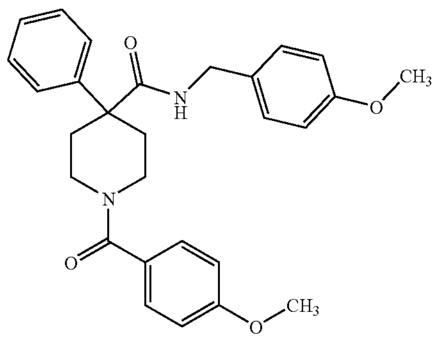 | 1-(4-Methoxy-benzoyl)-4-phenyl-piperidine-4-carboxylic acid 4-methoxy-benzylamide | 460 |
| 117 | 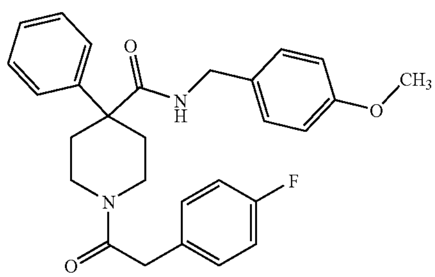 | 1-[2-(4-Fluoro-phenyl)-acetyl]-4-phenyl-piperidine-4-carboxylic acid 4-methoxy-benzylamide | 462 |
| 118 | 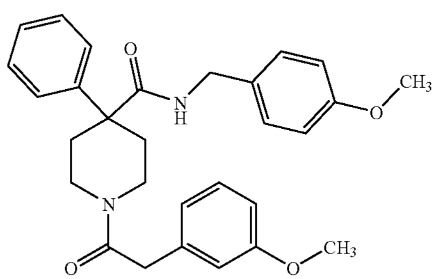 | 1-[2-(3-Methoxy-phenyl)-acetyl]-4-phenyl-piperidine-4-carboxylic acid 4-methoxy-benzylamide | 474 |
| 119 | 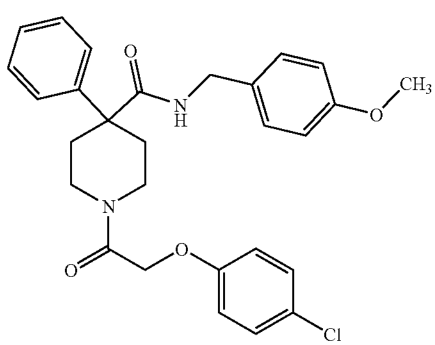 | 1-[2-(4-Chloro-phenoxy)-acetyl]-4-phenyl-piperidine-4-carboxylic acid 4-methoxy-benzylamide | 494 |

| Example | Structure | Name | M + H |
|---|---|---|---|
| 120 | 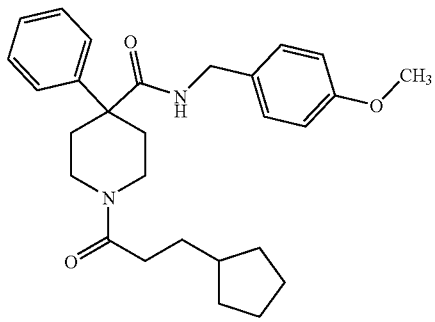 | 1-(3-Cyclopentyl-propionyl)-4-phenyl-piperidine-4-carboxylic acid 4-methoxy-benzylamide | 450 |
| 121 | 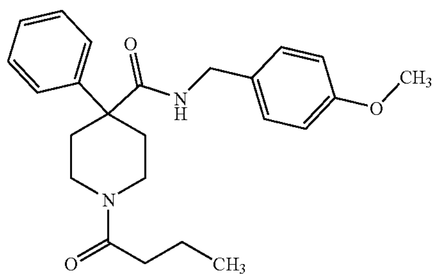 | 1-Butyryl-4-phenyl-piperidine-4-carboxylic acid 4-methoxy-benzylamide | 396 |
| 122 | 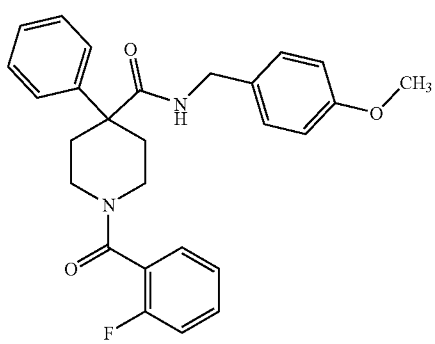 | 1-(2-Fluoro-benzoyl)-4-phenyl-piperidine-4-carboxylic acid 4-methoxy-benzylamide | 448 |
| 123 | 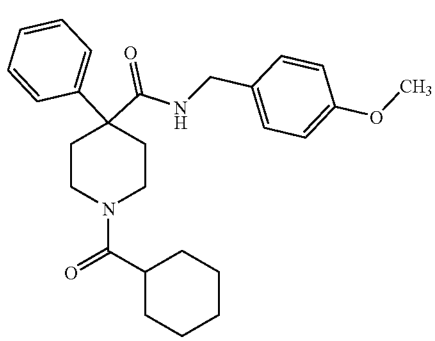 | 1-Cyclohexanecarbonyl-4-phenyl-piperidine-4-carboxylic acid 4-methoxy-benzylamide | 436 |

| Example | Structure | Name | M + H |
|---|---|---|---|
| 124 | 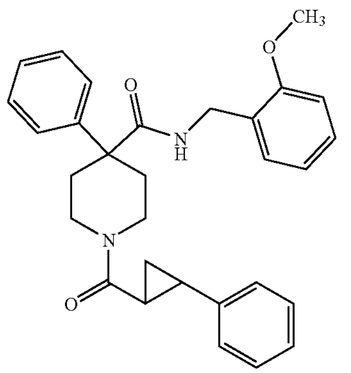 | 4-Phenyl-1-(2-phenyl-cyclopropanecarbonyl)-piperidine-4-carboxylic acid 2-methoxy-benzylamide | 470 |
| 125 | 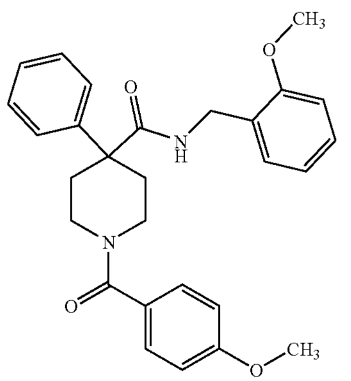 | 1-(4-Methoxy-benzoyl)-4-phenyl-piperidine-4-carboxylic acid 2-methoxy-benzylamide | 460 |
| 126 | 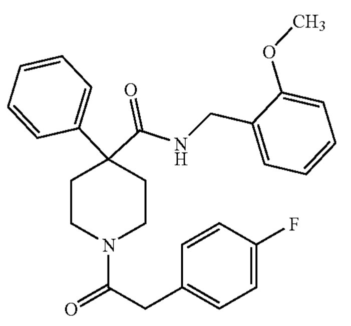 | 1-[2-(4-Fluoro-phenyl)-acetyl]-4-phenyl-piperidine-4-carboxylic acid 2-methoxy-benzylamide | 462 |
| 127 | 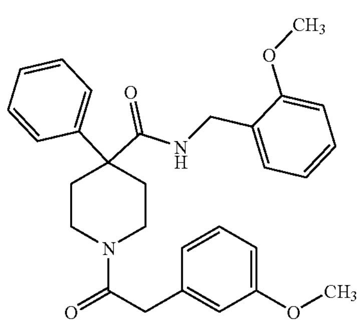 | 1-[2-(3-Methoxy-phenyl)-acetyl]-4-phenyl-piperidine-4-carboxylic acid 2-methoxy-benzylamide | 474 |

-continued

| Example | Structure | Name | M + H |
|---|---|---|---|
| 128 | 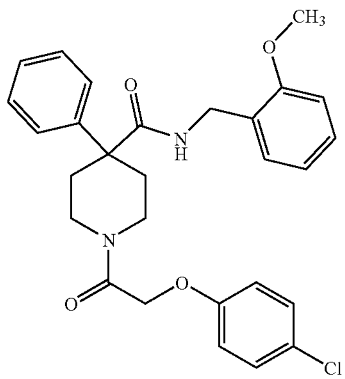 | 1-[2-(4-Chloro-phenoxy)-acetyl]-4-phenyl-piperidine-4-carboxylic acid 2-methoxy-benzylamide | 494 |
| 129 | 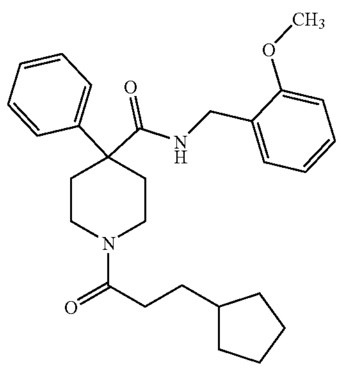 | 1-(3-Cyclopentyl-propionyl)-4-phenyl-piperidine-4-carboxylic acid 2-methoxy-benzylamide | 450 |
| 130 | 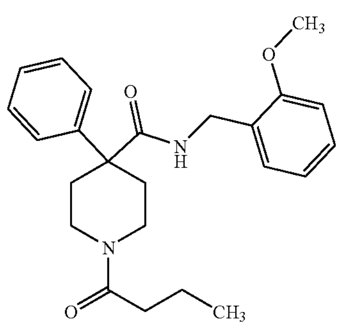 | 1-Butyryl-4-phenyl-piperidine-4-carboxylic acid 2-methoxy-benzylamide | 396 |
| 131 | 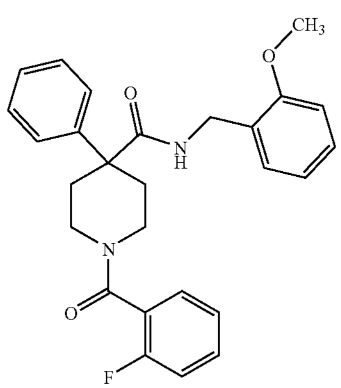 | 1-(2-Fluoro-benzyl)-4-phenyl-piperidine-4-carboxylic acid 2-methoxy-benzylamide | 448 |

-continued

| Example | Structure | Name | M + H |
|---|---|---|---|
| 132 | 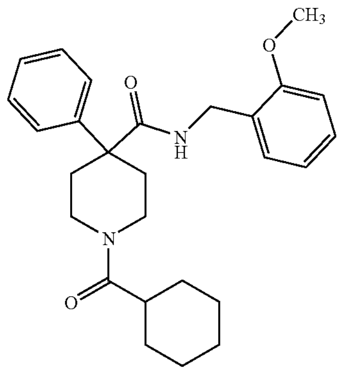 | 1-Cyclohexanecarbonyl-4-phenyl-piperidine-4-carboxylic acid 2-methoxy-benzylamide | 436 |
| 133 | 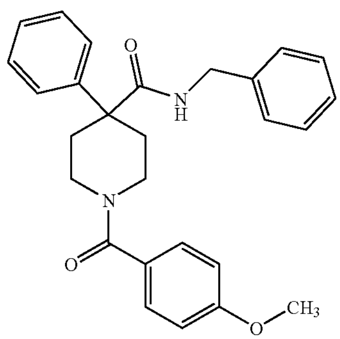 | 1-(4-Methoxy-benzoyl)-4-phenyl-piperidine-4-carboxylic acid benzylamide | 440 |
| 134 | 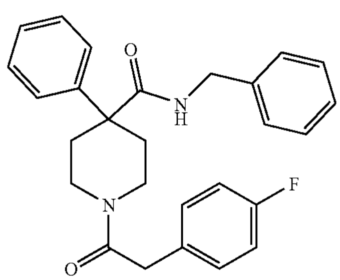 | 1-[2-(4-Fluoro-phenyl)-acetyl]-4-phenyl-piperidine-4-carboxylic acid benzylamide | 430 |
| 135 | 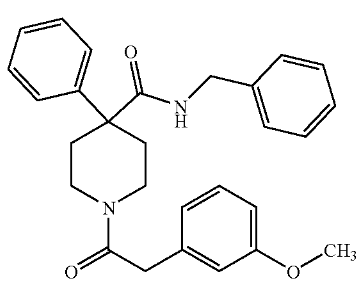 | 1-[2-(3-Methoxy-phenyl)-acetyl]-4-phenyl-piperidine-4-carboxylic acid benzylamide | 444 |

| Example | Structure | Name | M + H |
|---|---|---|---|
| 136 | 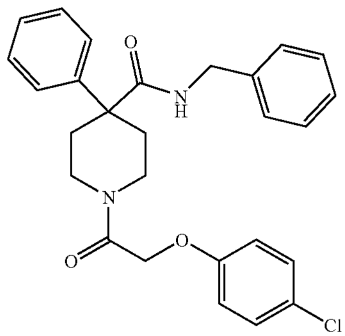 | 1-[2-(4-Chloro-phenoxy)-acetyl]-4-phenyl-piperidine-4-carboxylic acid benzylamide | 464 |
| 137 | 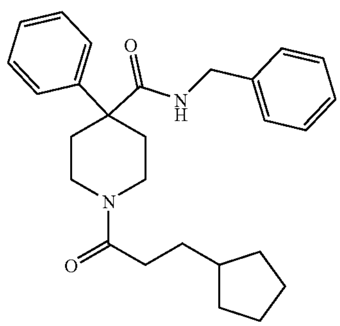 | 1-(3-Cyclopentyl-propionyl)-4-phenyl-piperidine-4-carboxylic acid benzylamide | 420 |
| 138 | 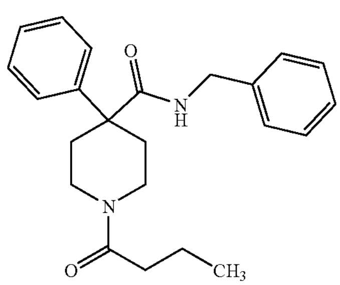 | 1-Butyryl-4-phenyl-piperidine-4-carboxylic acid benzylamide | 365 |
| 139 | 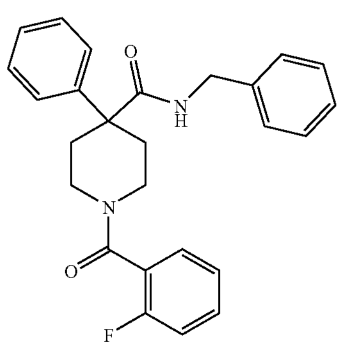 | 1-(2-Fluoro-benzoyl)-4-phenyl-piperidine-4-carboxylic acid benzylamide | 417 |

| Example | Structure | Name | M + H |
|---|---|---|---|
| 140 | 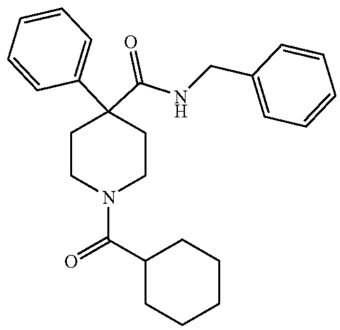 | 1-Cyclohexanecarbonyl-4-phenyl-piperidine-4-carboxylic acid benzylamide | 406 |
| 141 | 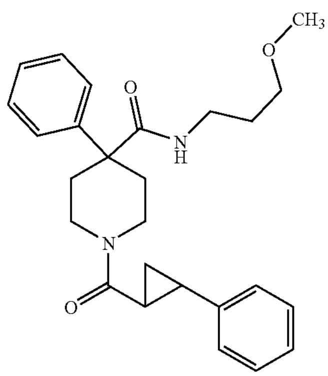 | 4-Phenyl-1-(2-phenyl-cyclopropanecarbonyl)-piperidine-4-carboxylic acid (3-methoxy-propyl)-amide | 422 |
| 142 | 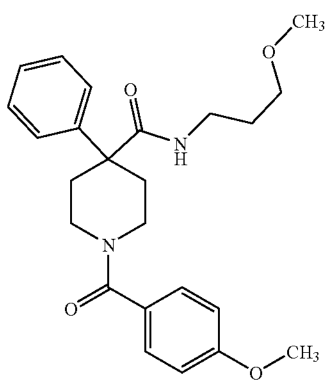 | 1-(4-Methoxy-benzoyl)-4-phenyl-piperidine-4-carboxylic acid (3-methoxy-propyl)-amide | 412 |
| 143 | 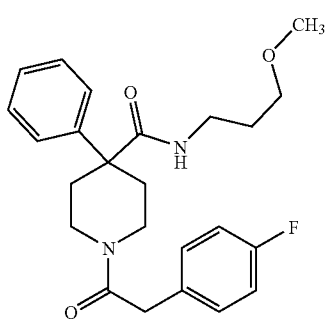 | 1-[2-(4-Fluoro-phenyl)-acetyl]-4-phenyl-piperidine-4-carboxylic acid (3-methoxy-propyl)-amide | 414 |

-continued

| Example | Structure | Name | M + H |
|---|---|---|---|
| 144 | 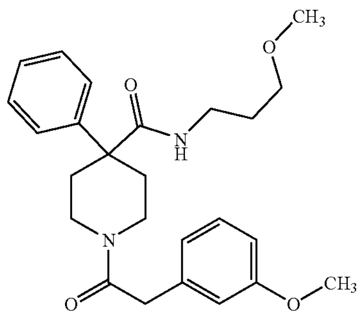 | 1-[2-(3-Methoxy-phenyl)-acetyl]-4-phenyl-piperidine-4-carboxylic acid (3-methoxy-propyl)-amide | 426 |
| 145 | 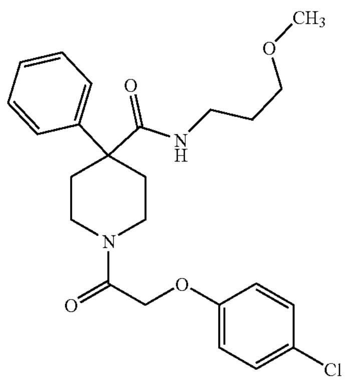 | 1-[2-(4-Chloro-phenoxy)-acetyl]-4-phenyl-piperidine-4-carboxylic acid (3-methoxy-propyl)-amide | 446 |
| 146 | 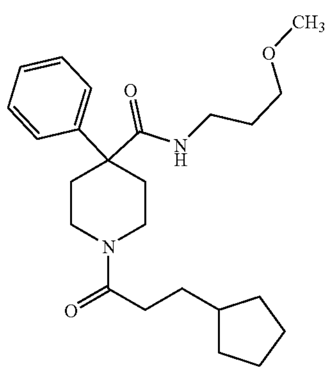 | 1-(3-Cyclopenyl-propionyl)-4-phenyl-piperidine-4-carboxylic acid (3-methoxy-propyl)-amide | 402 |
| 147 | 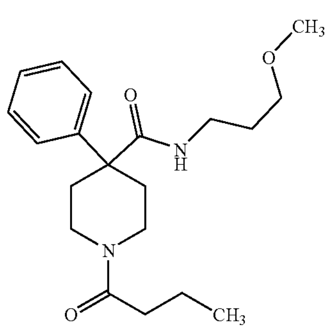 | 1-Butyryl-4-phenyl-piperidine-4-carboxylic acid (3-methoxy-propyl)-amide | 347 |

-continued

| Example | Structure | Name | M + H |
|---|---|---|---|
| 148 | 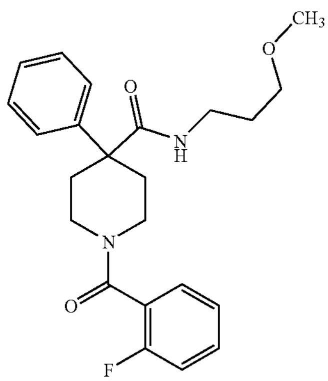 | 1-(2-Fluoro-benzoyl)-4-phenyl-piperidine-4-carboxylic acid (3-methoxy-propyl)-amide | 399 |
| 149 | 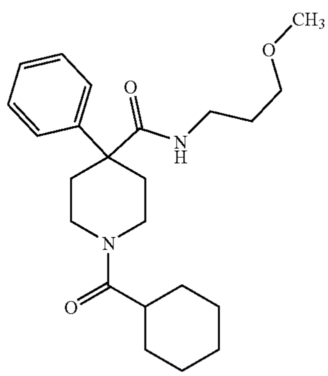 | 1-Cyclohexanecarbonyl-4-phenyl-piperidine-4-carboxylic acid (3-methoxy-propyl)-amide | 388 |
| 150 | 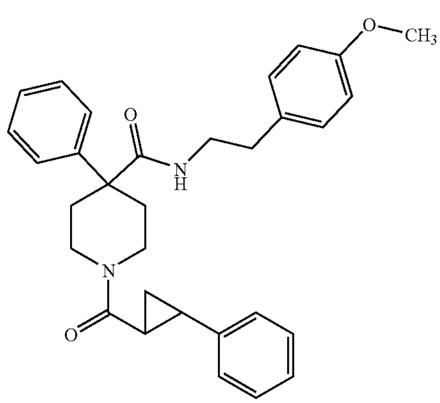 | 4-Phenyl-1-(2-phenyl-cyclopropanecarbonyl)-piperidine-4-carboxylic acid [2-(4-methoxy-phenyl)-ethyl]-amide | 484 |
| 151 | 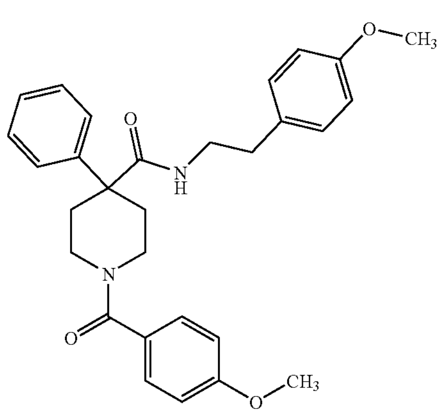 | 1-(4-Methoxy-benzoyl)-4-phenyl-piperidine-4-carboxylic acid [2-(4-methoxy-phenyl)-ethyl]-amide | 474 |

-continued

| Example | Structure | Name | M + H |
|---|---|---|---|
| 152 | 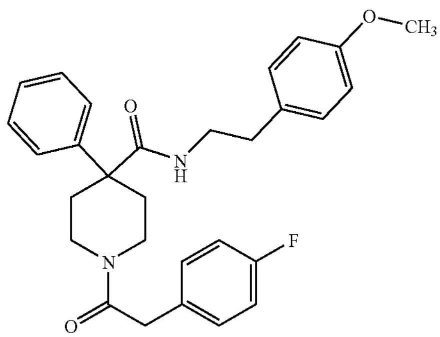 | 1-[2-(4-Fluoro-phenyl)-acetyl]-4-phenyl-piperidine-4-carboxylic acid [2-(4-methoxy-phenyl)-ethyl]-amide | 476 |
| 153 | 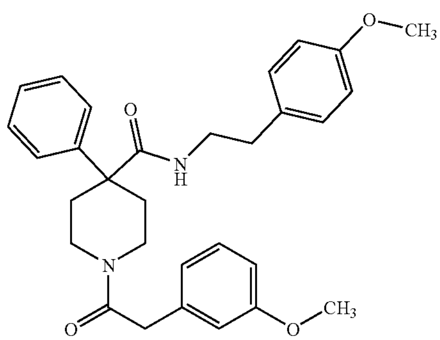 | 1-[2-(3-Methoxy-phenyl)-acetyl]-4-phenyl-piperidine-4-carboxylic acid [2-(4-methoxy-phenyl)-ethyl]-amide | 488 |
| 154 | 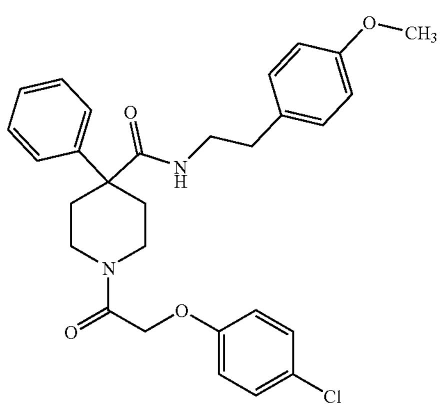 | 1-[2-(4-Chloro-phenoxy)-acetyl]-4-phenyl-piperidine-4-carboxylic acid [2-(4-methoxy-phenyl)-ethyl]-amide | 508 |
| 155 | 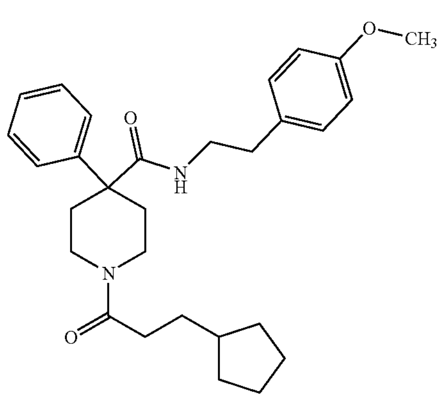 | 1-(3-Cyclopentyl-propionyl)-4-phenyl-piperidine-4-carboxylic acid [2-(4-methoxy-phenyl)-ethyl]-amide | 464 |

-continued

| Example | Structure | Name | M + H |
|---|---|---|---|
| 156 | 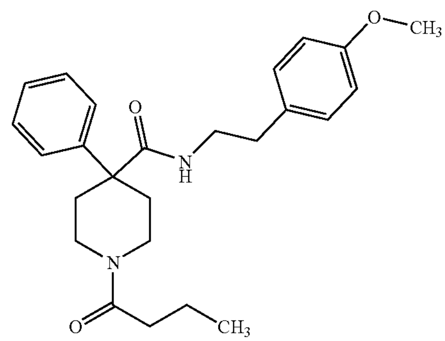 | 1-Butyryl-4-phenyl-piperidine-4-carboxylic acid [2-(4-methoxy-phenyl)-ethyl]-amide | 410 |
| 157 | 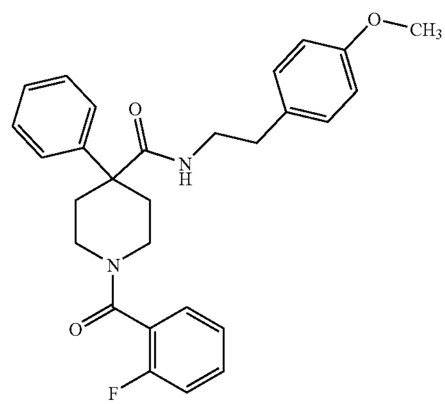 | 1-(2-Fluoro-benzoyl)-4-phenyl-piperidine-4-carboxylic acid [2-(4-methoxy-phenyl)-ethyl]-amide | 462 |
| 158 | 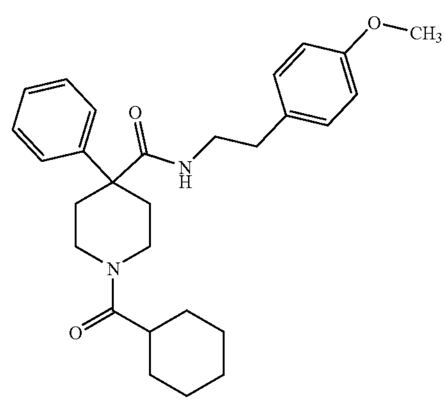 | 1-Cyclohexanecarbonyl-4-phenyl-piperidine-4-carboxylic acid [2-(4-methoxy-phenyl)-ethyl]-amide | 450 |
| 159 | 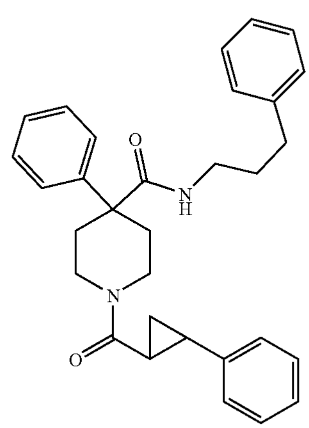 | 4-Phenyl-1-(2-phenyl-cyclopropanecarbonyl)-piperidine-4-carboxylic acid (3-phenyl-propyl)-amide | 468 |

-continued

| Example | Structure | Name | M + H |
|---|---|---|---|
| 160 | 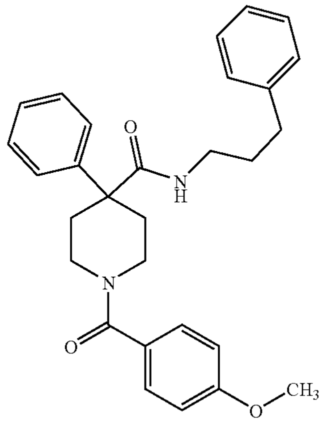 | 1-(4-Methoxy-benzoyl)-4-phenyl-piperidine-4-carboxylic acid (3-phenyl-propyl)-amide | 458 |
| 161 | 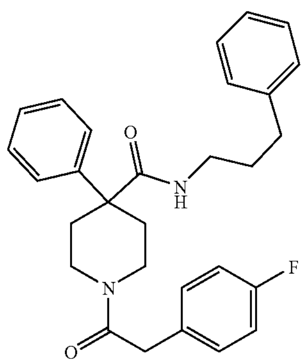 | 1-[2-(4-Fluoro-phenyl)-acetyl]-4-phenyl-piperidine-4-carboxylic acid (3-phenyl-propyl)-amide | 460 |
| 162 | 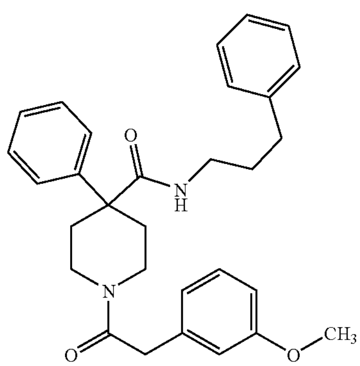 | 1-[2-(3-Methoxy-phenyl)-acetyl]-4-phenyl-piperidine-4-carboxylic acid (3-phenyl-propyl)-amide | 472 |
| 163 | 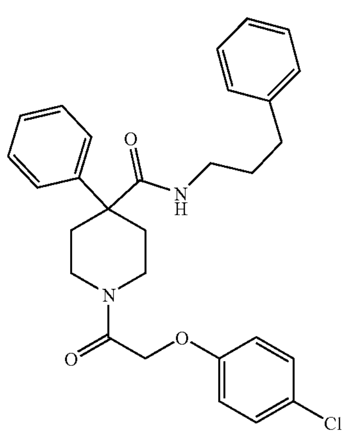 | 1-[2-(4-Chloro-phenoxy)-acetyl]-4-phenyl-piperidine-4-carboxylic acid (3-phenyl-propyl)-amide | 492 |

-continued

| Example | Structure | Name | M + H |
|---|---|---|---|
| 164 | 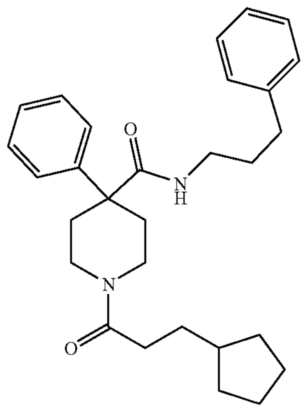 | 1-(3-Cyclopentyl-propionyl)-4-phenyl-piperidine-4-carboxylic acid (3-phenyl-propyl)-amide | 448 |
| 165 | 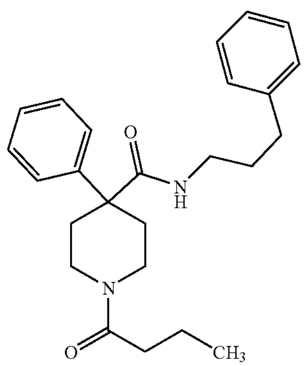 | 1-Butyryl-4-phenyl-piperidine-4-carboxylic acid (3-phenyl-propyl)-amide | 394 |
| 166 | 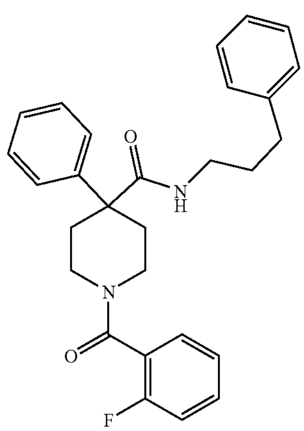 | 1-(2-Fluoro-benzoyl)-4-phenyl-piperidine-4-carboxylic acid (3-phenyl-propyl)-amide | 446 |

| Example | Structure | Name | M + H |
|---|---|---|---|
| 167 | 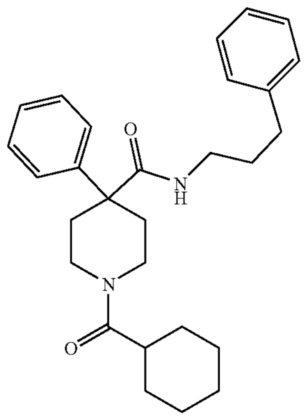 | 1-Cyclohexanecarbonyl-4-phenyl-piperidine-4-carboxylic acid (3-phenyl-propyl)-amide | 434 |
| 168 | 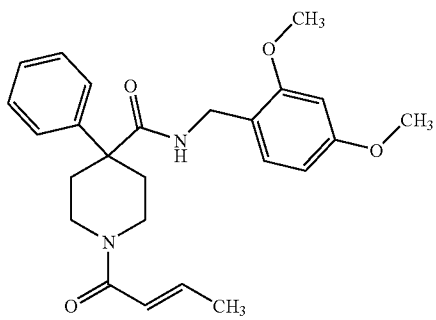 | 1-But-2-enoyl-4-phenyl-piperidine-4-carboxylic acid 2,4-dimethoxy-benzylamide | 424 |
| 169 | 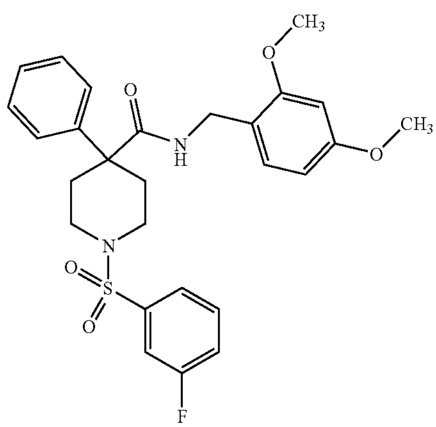 | 1-(3-Fluoro-benzenesulfonyl)-4-phenyl-piperidine-4-carboxylic acid 2,4-dimethoxy-benzylamide | 514 |
| 170 | 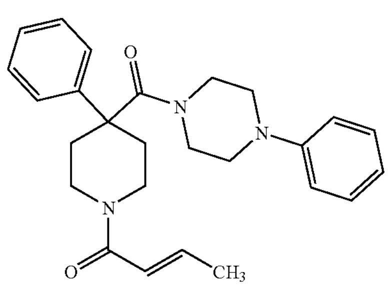 | 1-[4-Phenyl-4-(4-phenyl-piperazine-1-carbonyl)-piperidin-1-yl]-but-2-en-1-one | 419 |

-continued

| Example | Structure | Name | M + H |
|---|---|---|---|
| 171 | 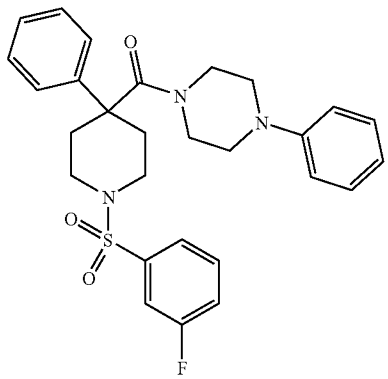 | [1-(3-Fluoro-benzenesulfonyl)-4-phenyl-piperidin-4-yl]-(4-phenyl-piperazin-1-yl)-methanone | 509 |
| 172 | 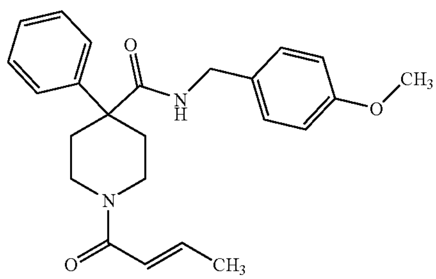 | 1-But-2-enoyl-4-phenyl-piperidine-4-carboxylic acid 4-methoxy-benzylamide | 394 |
| 173 | 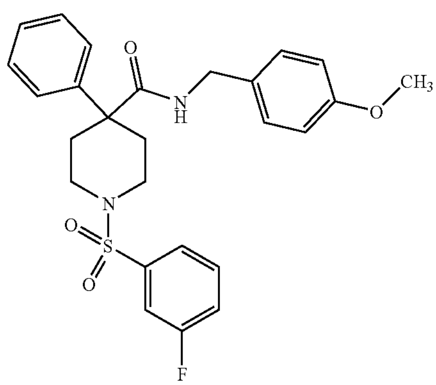 | 1-(3-Fluoro-benzenesulfonyl)-4-phenyl-piperidine-4-carboxylic acid 4-methoxy-benzylamide | 484 |
| 174 | 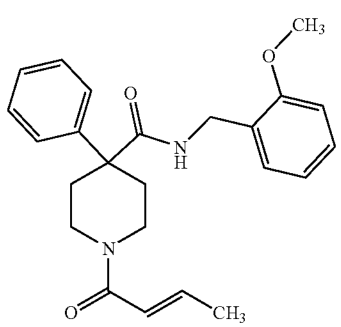 | 1-But-2-enoyl-4-phenyl-piperidine-4-carboxylic acid 2-methoxy-benzylamide | 394 |

-continued

| Example | Structure | Name | M + H |
|---|---|---|---|
| 175 | 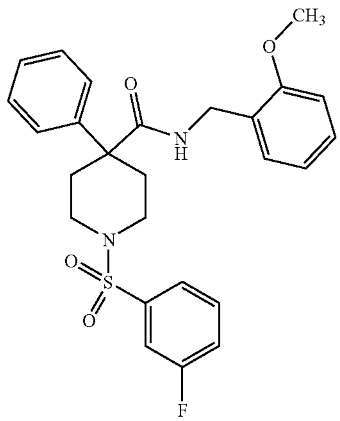 | 1-(3-Fluoro-benzenesulfonyl)-4-phenyl-piperidine-4-carboxylic acid 2-methoxy-benzylamide | 484 |
| 176 | 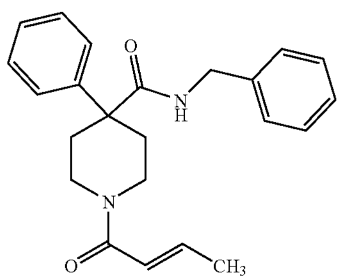 | 1-But-2-enoyl-4-phenyl-piperidine-4-carboxylic acid benzylamide | 363 |
| 177 | 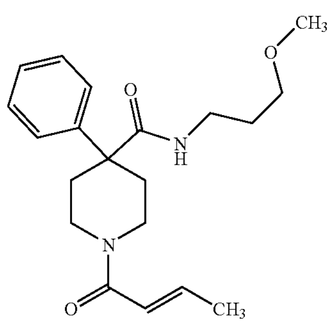 | 1-But-2-enoyl-4-phenyl-piperidine-4-carboxylic acid (3-methoxy-propyl)-amide | 345 |
| 178 | 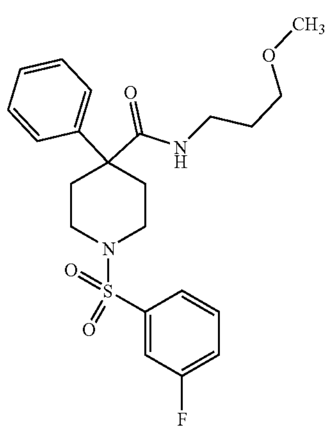 | 1-(3-Fluoro-benzenesulfonyl)-4-phenyl-piperidine-4-carboxylic acid (3-methoxy-propyl)-amide | 436 |

-continued

| Example | Structure | Name | M + H |
|---|---|---|---|
| 179 | 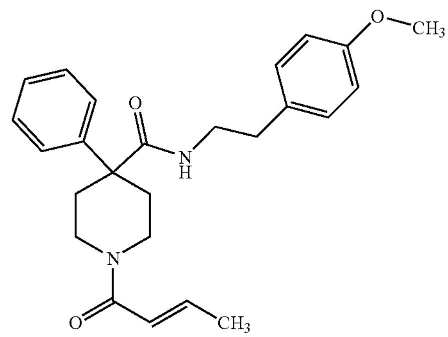 | 1-But-2-enoyl-4-phenyl-piperidine-4-carboxylic acid [2-(4-methoxy-phenyl)-ethyl]-amide | 408 |
| 180 | 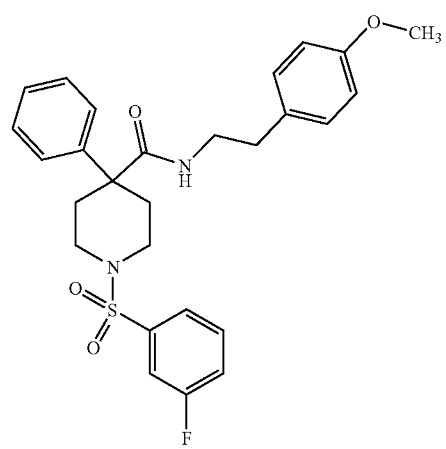 | 1-(3-Fluoro-benzenesulfonyl)-4-phenyl-piperidine-4-carboxylic acid [2-(4-methoxy-phenyl)-ethyl]-amide | 498 |
| 181 | 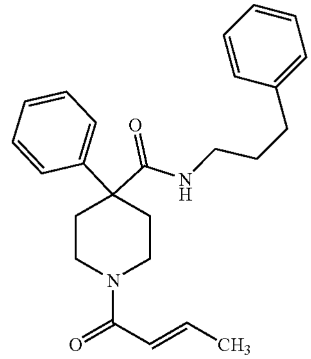 | 1-But-2-enoyl-4-phenyl-piperidine-4-carboxylic acid (3-phenyl-propyl)-amide | 392 |

-continued

| Example | Structure | Name | M + H |
|---|---|---|---|
| 182 | 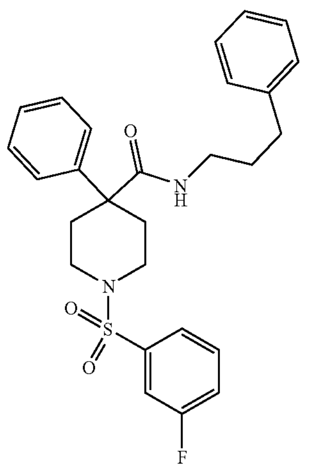 | 1-(3-Fluoro-benzenesulfonyl)-4-phenyl-piperidine-4-carboxylic acid (3-phenyl-propyl)-amide | 482 |
| 183 | 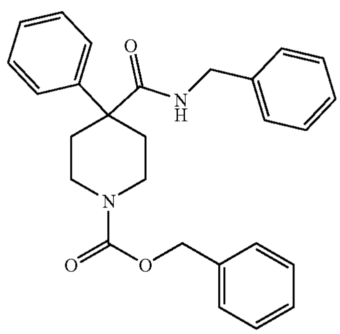 | 4-Benzylcarbamoyl-4-phenyl-piperidine-1-carboxylic acid benzyl ester | 430 |
| 184 | 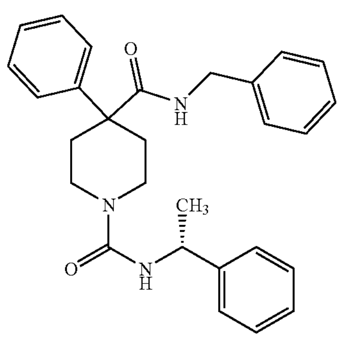 | 4-Phenyl-piperidine-1,4-dicarboxylic acid 4-benzylamide 1-[(1-phenyl-ethyl)-amide] | 443 |
| 185 | 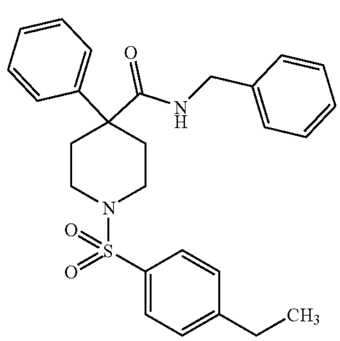 | 1-(4-Ethyl-benzenesulfonyl)-4-phenyl-piperidine-4-carboxylic acid benzylamide | 464 |

| Example | Structure | Name | M + H |
|---|---|---|---|
| 186 | 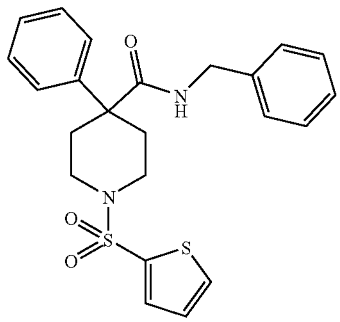 | 4-Phenyl-1-(thiophene-2-sulfonyl)-piperidine-4-carboxylic acid benzylamide | 442 |
| 187 | 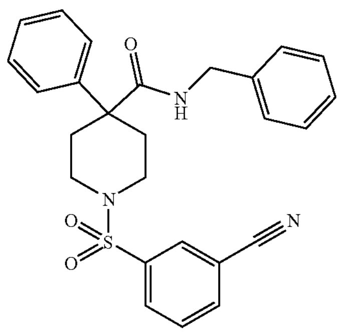 | 1-(3-Cyano-benzenesulfonyl)-4-phenyl-piperidine-4-carboxylic acid benzylamide | 461 |
| 188 | 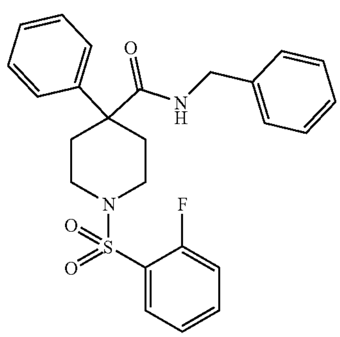 | 1-(2-Fluoro-benzenesulfonyl)-4-phenyl-piperidine-4-carboxylic acid benzylamide | 454 |
| 189 | 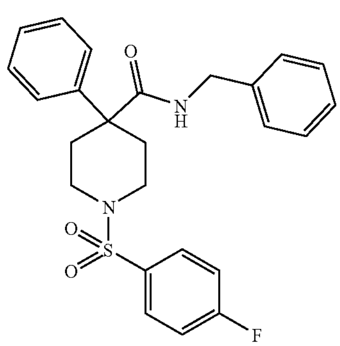 | 1-(4-Fluoro-benzenesulfonyl)-4-phenyl-piperidine-4-carboxylic acid benzylamide | 454 |

-continued

| Example | Structure | Name | M + H |
|---|---|---|---|
| 190 | 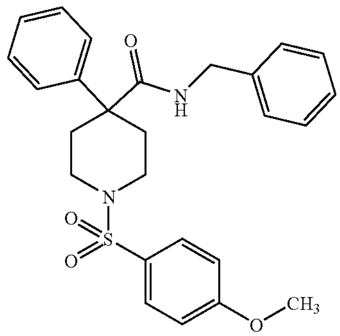 | 1-(4-Methoxy-benzenesulfonyl)-4-phenyl-piperidine-4-carboxylic acid benzylamide | 466 |
| 191 | 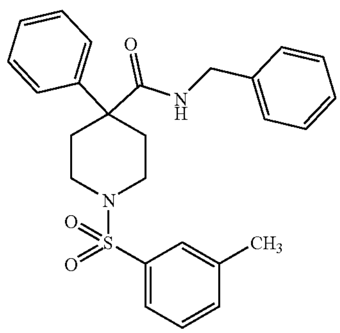 | 4-Phenyl-1-(toluene-3-sulfonyl)-piperidine-4-carboxylic acid benzylamide | 450 |
| 192 | 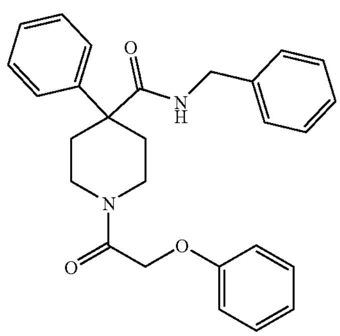 | 1-(2-Phenoxy-acetyl)-4-phenyl-piperidine-4-carboxylic acid benzylamide | 430 |
| 193 | 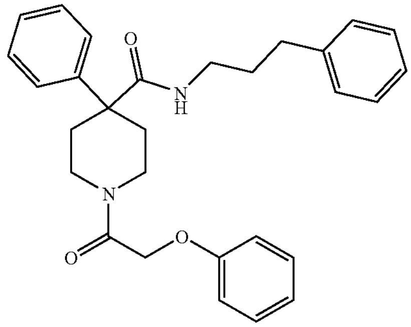 | 1-(2-Phenoxy-acetyl)-4-phenyl-piperidine-4-carboxylic acid (3-phenyl-propyl)-amide | 458 |

| Example | Structure | Name | M + H |
|---|---|---|---|
| 194 | 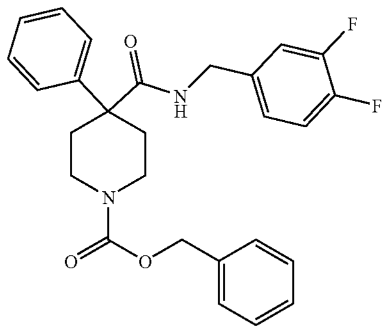 | 4-(3,4-Difluoro-benzylcarbamoyl)-4-phenyl-piperidine-1-carboxylic acid benzyl ester | 466 |
| 195 | 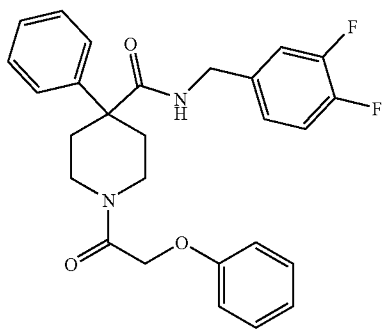 | 1-(2-Phenoxy-acetyl)-4-phenyl-piperidine-4-carboxylic acid 3,4-difluoro-benzylamide | 466 |
| 196 | 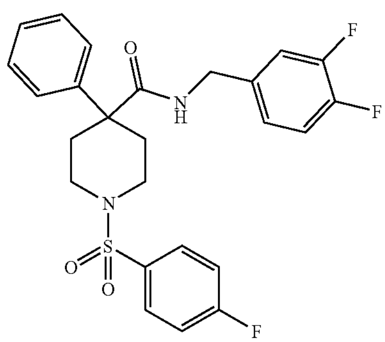 | 1-(4-Fluoro-benzenesulfonyl)-4-phenyl-piperidine-4-carboxylic acid 3,4-difluoro-benzylamide | 490 |
| 197 | 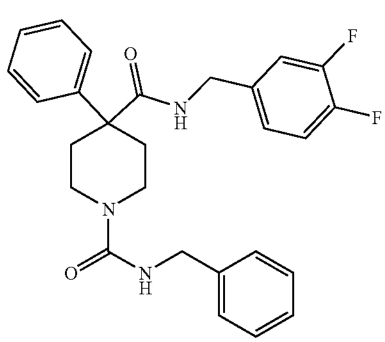 | 4-Phenyl-piperidine-1,4-dicarboxylic acid 1-benzylamide 4-(3,4-difluoro-benzylamide) | 465 |

-continued

| Example | Name | M + H |
|---|---|---|
| 198 | 4-Phenyl-1-(3-phenyl-acryloyl)-piperidine-4-carboxylic acid 3,4-difluoro-benzylamide | 462 |
| 199 | 4-Phenyl-1-phenylacetyl-piperidine-4-carboxylic acid 3,4-difluoro-benzylamide | 450 |
| 200 | 1-Benzoyl-4-phenyl-piperidine-4-carboxylic acid 3,4-difluoro-benzylamide | 435 |
| 201 | 4-Phenyl-1-propionyl-piperidine-4-carboxylic acid 3,4-difluoro-benzylamide | 387 |
| 202 | 1-(2-Benzyloxy-acetyl)-4-phenyl-piperidine-4-carboxylic acid 3,4-difluoro-benzylamide | 480 |

| Example | Structure | Name | M + H |
|---|---|---|---|
| 203 | 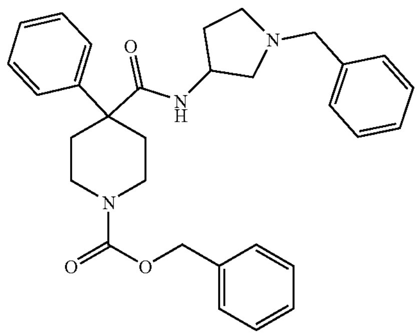 | 4-(1-Benzyl-pyrrolidin-3-ylcarbamoyl)-4-phenyl-piperidine-1-carboxylic acid benzyl ester | 499 |
| 204 | 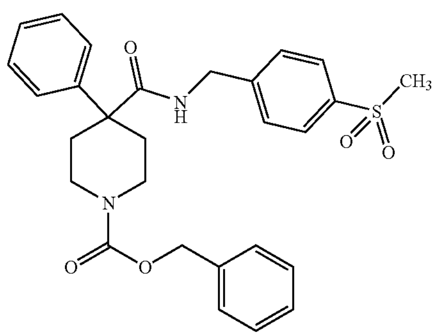 | 4-(4-Methanesulfonyl-benzylcarbamoyl)-4-phenyl-piperidine-1-carboxylic acid benzyl ester | 508 |
| 205 | 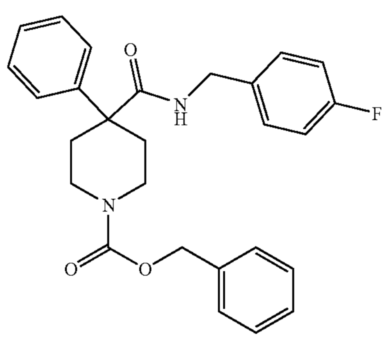 | 4-(4-Fluoro-benzylcarbamoyl)-4-phenyl-piperidine-1-carboxylic acid benzyl ester | 448 |
| 206 | 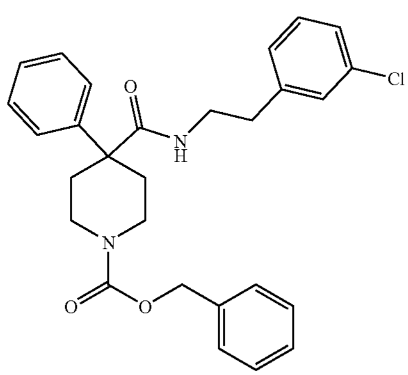 | 4-[2-(3-Chloro-phenyl)-ethylcarbamoyl]-4-phenyl-piperidine-1-carboxylic acid benzyl ester | 478 |

-continued

| Example | Structure | Name | M + H |
|---|---|---|---|
| 207 | 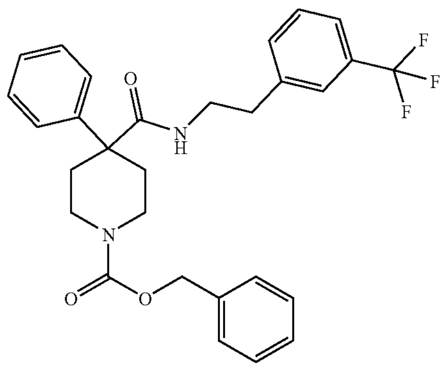 | 4-Phenyl-4-[2-(3-trifluoromethyl-phenyl)-ethylcarbamoyl]-piperidine-1-carboxylic acid benzyl ester | 512 |
| 208 | 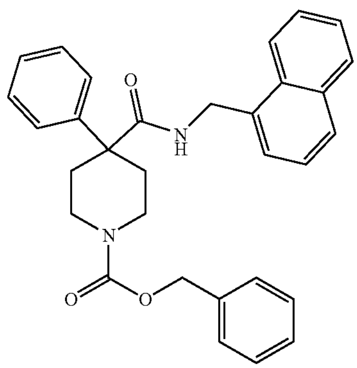 | 4-[(Naphthalen-1-ylmethyl)-carbamoyl]-4-phenyl-piperidine-1-carboxylic acid benzyl ester | 480 |
| 209 | 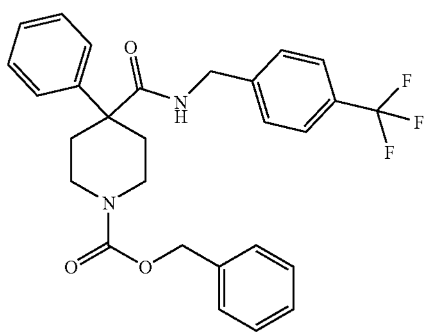 | 4-Phenyl-4-(4-trifluoromethyl-benzylcarbamoyl)-piperidine-1-carboxylic acid benzyl ester | 498 |
| 210 | 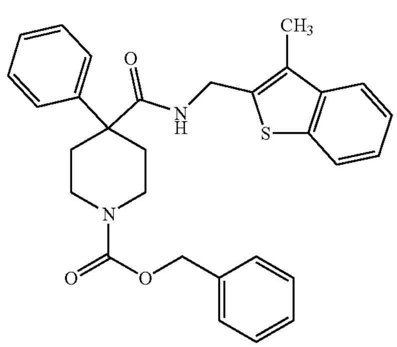 | 4-[(3-Methyl-benzo[b]thiophen-2-ylmethyl)-carbamoyl]-4-phenyl-piperidine-1-carboxylic acid benzyl ester | 500 |

-continued

| Example | Structure | Name | M + H |
|---|---|---|---|
| 211 | 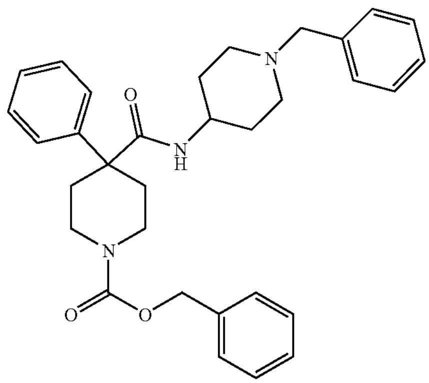 | 4-(1-Benzyl-piperidin-4-ylcarbamoyl)-4-phenyl-piperidine-1-carboxylic acid benzyl ester | 513 |
| 212 | 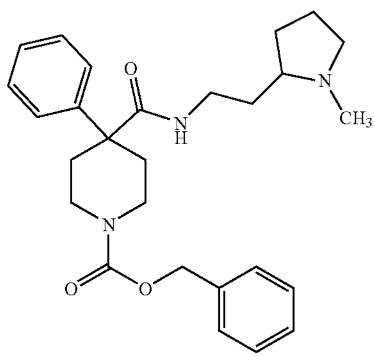 | 4-[2-(1-Methyl-pyrrolidin-2-yl)-ethylcarbamoyl]-4-phenyl-piperidine-1-carboxylic acid benzyl ester | 451 |
| 213 | 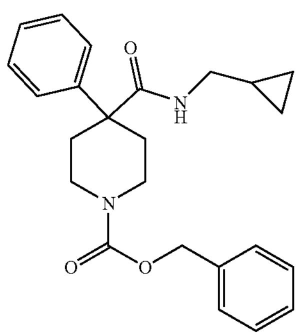 | 4-(Cyclopropylmethyl-carbamoyl)-4-phenyl-piperidine-1-carboxylic acid benzyl ester | 394 |
| 214 | 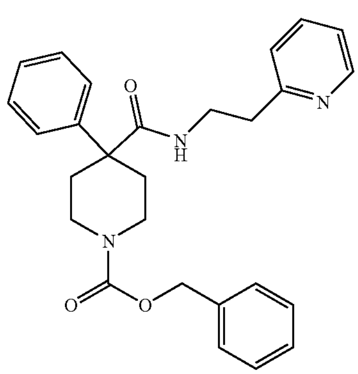 | 4-Phenyl-4-(2-pyridin-2-yl-ethylcarbamoyl)-piperidine-1-carboxylic acid benzyl ester | 445 |

-continued

| Example | Structure | Name | M + H |
|---|---|---|---|
| 215 | 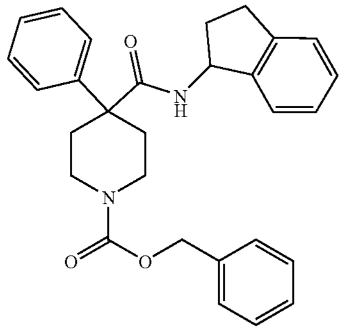 | 4-(Indan-1-ylcarbamoyl)-4-phenyl-piperidine-1-carboxylic acid benzyl ester | 456 |
| 216 | 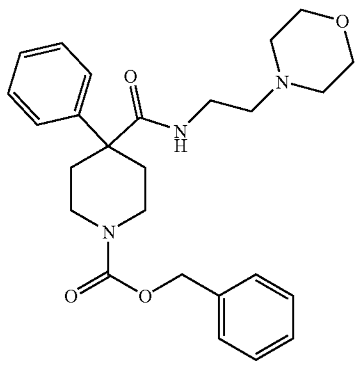 | 4-(2-Morpholin-4-yl-ethylcarbamoyl)-4-phenyl-piperidine-1-carboxylic acid benzyl ester | 453 |
| 217 | 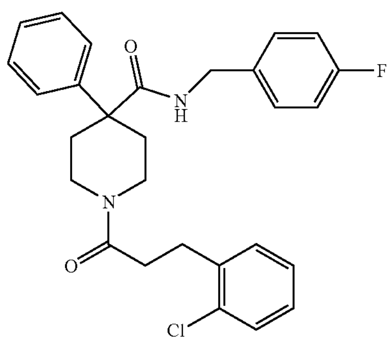 | 1-[3-(2-Chloro-phenyl)-propionyl]-4-phenyl-piperidine-4-carboxylic acid 4-fluoro-benzylamide | 480 |
| 218 | 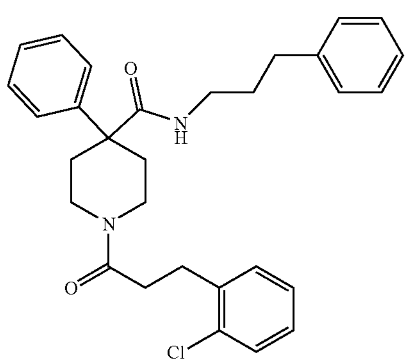 | 1-[3-(2-Chloro-phenyl)-propionyl]-4-phenyl-piperidin-4-carboxylic acid (3-phenyl-propyl)-amide | 490 |

-continued

| Example | Structure | Name | M + H |
|---|---|---|---|
| 219 | 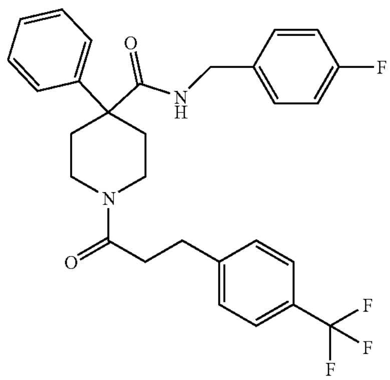 | 4-Phenyl-1-[3-(4-trifluoromethyl-phenyl)-propionyl]-piperidine-4-carboxylic acid 4-fluoro-benzylamide | 514 |
| 220 | 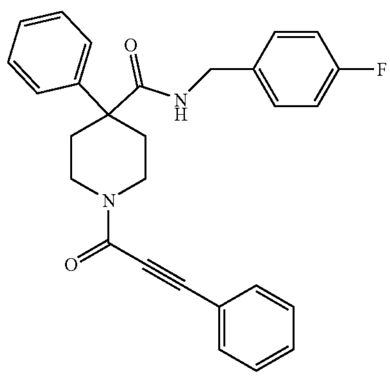 | 4-Phenyl-1-(3-phenyl-propynoyl)-piperidine-4-carboxylic acid 4-fluoro-benzylamide | 458 |
| 221 | 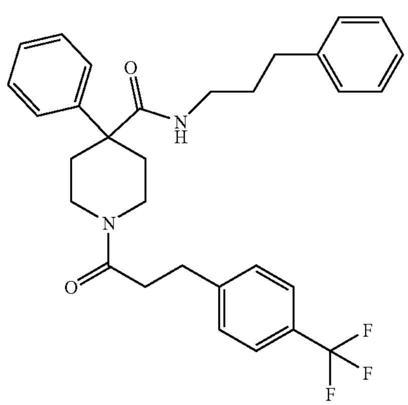 | 4-Phenyl-1-[3-(4-trifluoromethyl-phenyl)-propionyl]-piperidine-4-carboxylic acid (3-phenyl-propyl)-amide | 524 |
| 222 | 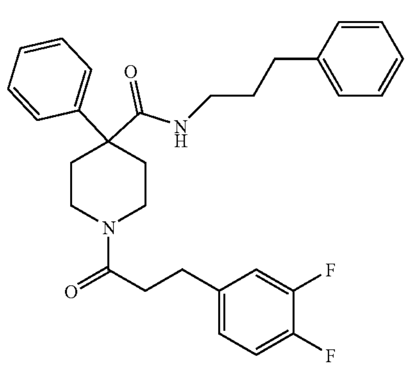 | 1-[3-(3,4-Difluoro-phenyl)-propionyl]-4-phenyl-piperidine-4-carboxylic acid (3-phenyl-propyl)-amide | 492 |

-continued

| Example | Structure | Name | M + H |
|---|---|---|---|
| 223 | 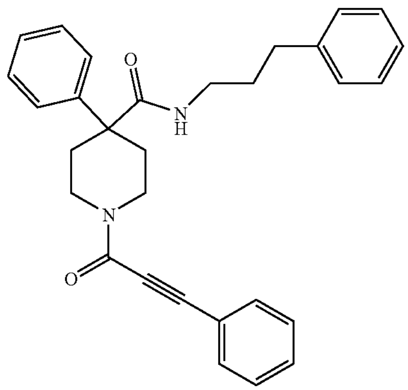 | 4-Phenyl-1-(3-phenyl-propynoyl)-piperidine-4-carboxylic acid (3-phenyl-propyl)-amide | 452 |
| 224 | 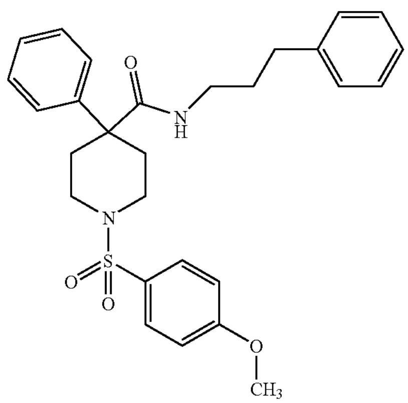 | 1-(4-Methoxy-benzenesulfonyl)-4-phenyl-piperidine-4-carboxylic acid (3-phenyl-propyl)-amide | 494 |
| 225 | 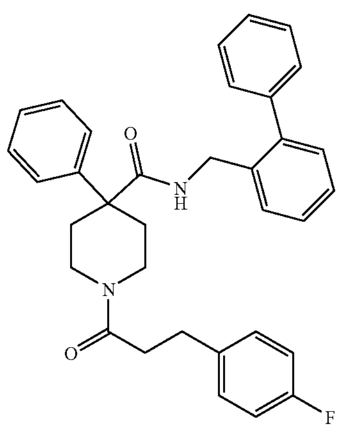 | 1-[3-(4-Fluoro-phenyl)-propionyl]-4-phenyl-piperidine-4-carboxylic acid (biphenyl-2-ylmethyl)-amide | 522 |
| 226 | 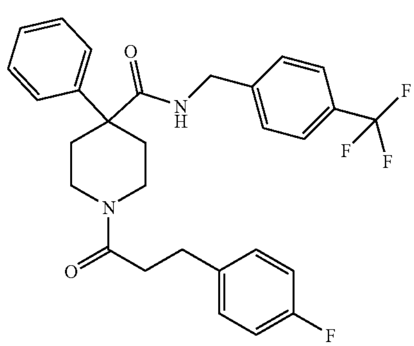 | 1-[3-(4-Fluoro-phenyl)-propionyl]-4-phenyl-piperidine-4-carboxylic acid 4-trifluoromethyl-benzylamide | 514 |

-continued

| Example | Structure | Name | M + H |
|---|---|---|---|
| 227 | 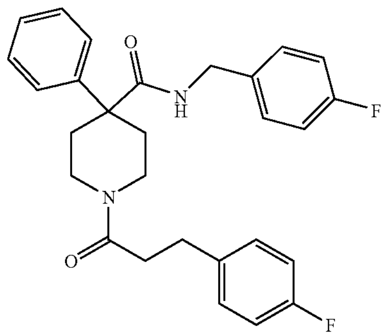 | 1-[3-(4-Fluoro-phenyl)-propionyl]-4-phenyl-piperidine-4-carboxylic acid 4-fluoro-benzylamide | 464 |
| 228 | 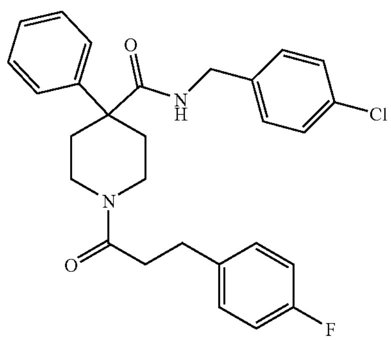 | 1-[3-(4-Fluoro-phenyl)-propionyl]-4-phenyl-piperidine-4-carboxylic acid 4-chloro-benzylamide | 480 |
| 229 | 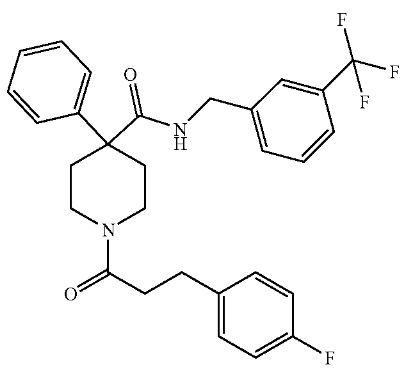 | 1-[3-(4-Fluoro-phenyl)-propionyl]-4-phenyl-piperidine-4-carboxylic acid 3-trifluoromethyl-benzylamide | 514 |
| 230 | 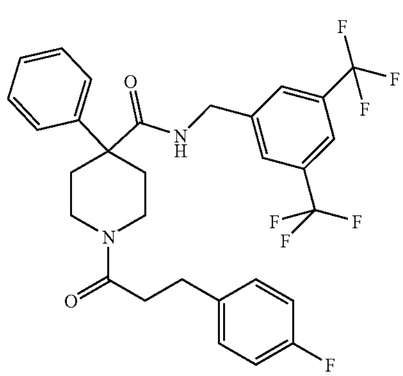 | 1-[3-(4-Fluoro-phenyl)-propionyl]-4-phenyl-piperidine-4-carboxylic acid 3,5-bis-trifluoromethyl-benzylamide | 582 |

| Example | Structure | Name | M + H |
|---|---|---|---|
| 231 | 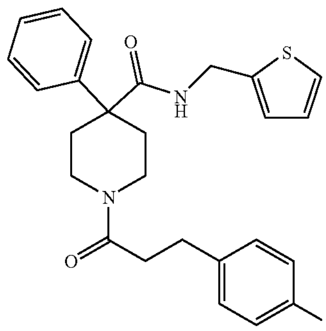 | 1-[3-(4-Fluoro-phenyl)-propionyl]-4-phenyl-piperidine-4-carboxylic acid (thiophen-2-ylmethyl)-amide | 452 |
| 232 | 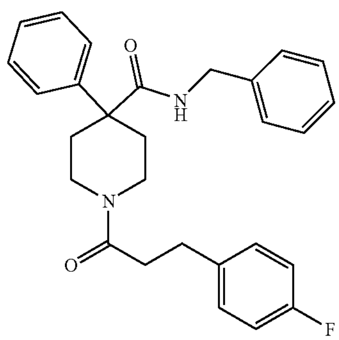 | 1-[3-(4-Fluoro-phenyl)-propionyl]-4-phenyl-piperidine-4-carboxylic acid benzylamide | 446 |
| 233 | 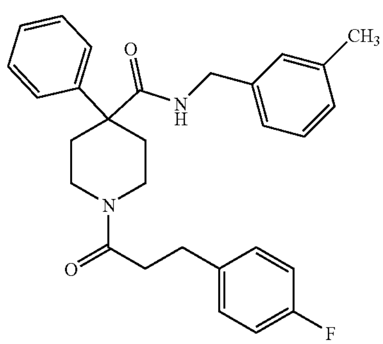 | 1-[3-(4-Fluoro-phenyl)-propionyl]-4-phenyl-piperidine-4-carboxylic acid 3-methyl-benzylamide | 460 |
| 234 | 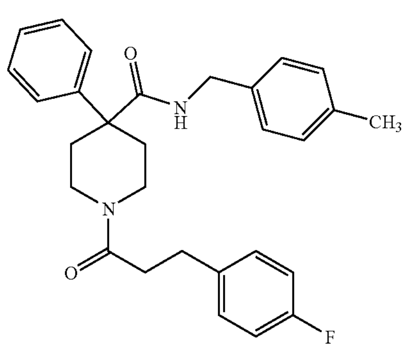 | 1-[3-(4-Fluoro-phenyl)-propionyl]-4-phenyl-piperidine-4-carboxylic acid 4-methyl-benzylamide | 460 |

-continued

| Example | Structure | Name | M + H |
|---|---|---|---|
| 235 | 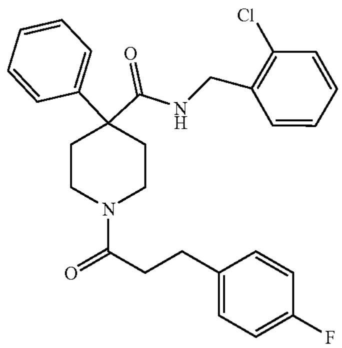 | 1-[3-(4-Fluoro-phenyl)-propionyl]-4-phenyl-piperidine-4-carboxylic acid 2-chloro-benzylamide | 480 |
| 236 | 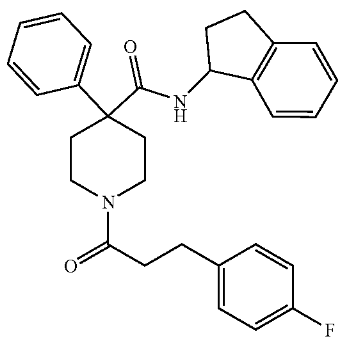 | 1-[3-(4-Fluoro-phenyl)-propionyl]-4-phenyl-piperidine-4-carboxylic acid indan-1-ylamide | 472 |
| 237 | 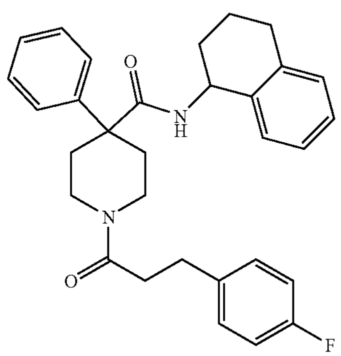 | 1-[3-(4-Fluoro-phenyl)-propionyl]-4-phenyl-piperidine-4-carboxylic acid (1,2,3,4-tetrahydro-naphthalen-1-yl)-amide | 486 |
| 238 | 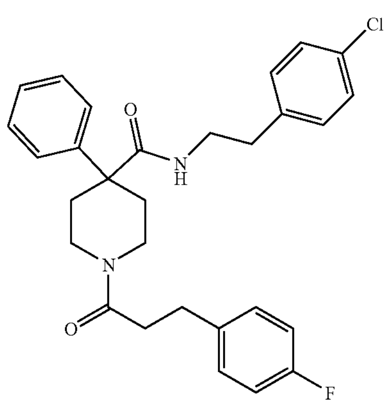 | 1-[3-(4-Fluoro-phenyl)-propionyl]-4-phenyl-piperidine-4-carboxylic acid [2-(4-chloro-phenyl)-ethyl]-amide | 494 |

-continued

| Example | Structure | Name | M + H |
|---|---|---|---|
| 239 | 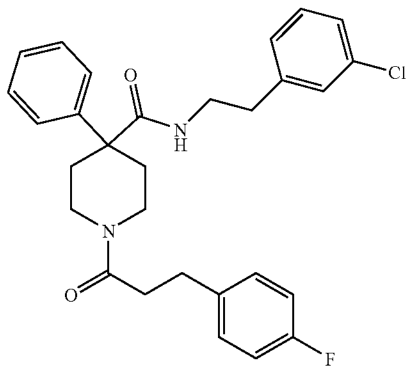 | 1-[3-(4-Fluoro-phenyl)-propionyl]-4-phenyl-piperidine-4-carboxylic acid [2-(3-chloro-phenyl)-ethyl]-amide | 494 |
| 240 | 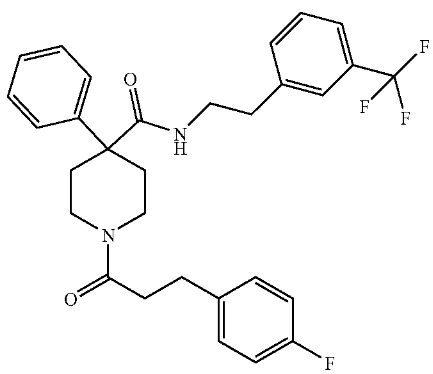 | 1-[3-(4-Fluoro-phenyl)-propionyl]-4-phenyl-piperidine-4-carboxylic acid [2-(3-trifluoromethyl-phenyl)-ethyl]-amide | 528 |
| 241 | 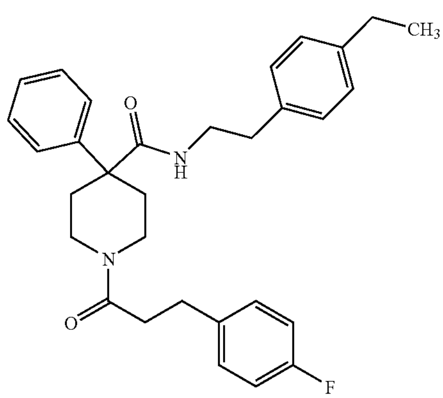 | 1-[3-(4-Fluoro-phenyl)-propionyl]-4-phenyl-piperidine-4-carboxylic acid [2-(4-ethyl-phenyl)-ethyl]-amide | 488 |
| 242 | 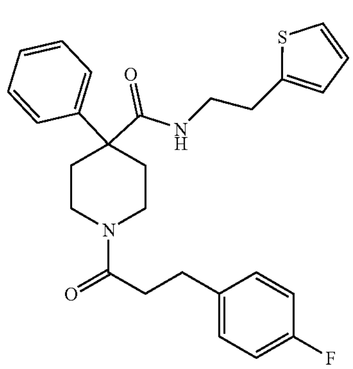 | 1-[3-(4-Fluoro-phenyl)-propionyl]-4-phenyl-piperidine-4-carboxylic acid (2-thiophen-2-yl-ethyl)-amide | 466 |

-continued

| Example | Structure | Name | M + H |
|---|---|---|---|
| 243 | 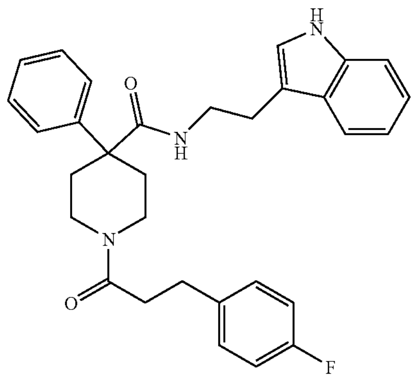 | 1-[3-(4-Fluoro-phenyl)-propionyl]-4-phenyl-piperidine-4-carboxylic acid [2-(1H-indol-3-yl)-ethyl]-amide | 499 |
| 244 | 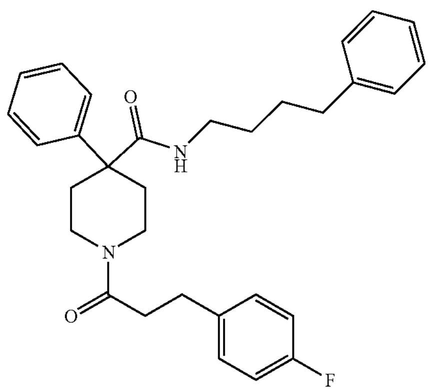 | 1-[3-(4-Fluoro-phenyl)-propionyl]-4-phenyl-piperidine-4-carboxylic acid (4-phenyl-butyl)-amide | 488 |
| 245 | 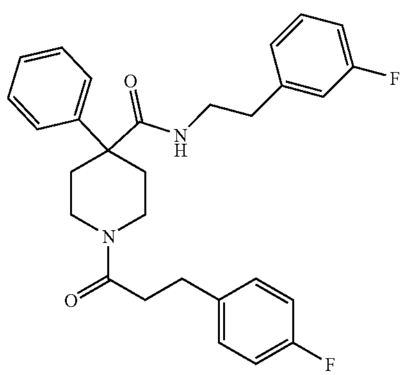 | 1-[3-(4-Fluoro-phenyl)-propionyl]-4-phenyl-piperidine-4-carboxylic acid [2-(3-Fluoro-phenyl)-ethyl]-amide | 478 |
| 246 | 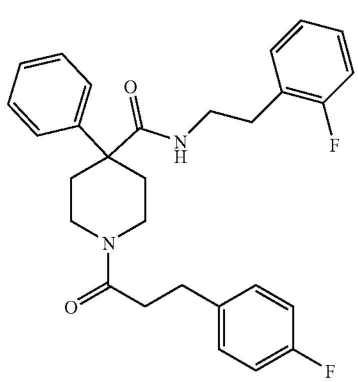 | 1-[3-(4-Fluoro-phenyl)-propionyl]-4-phenyl-piperidine-4-carboxylic acid [2-(2-fluoro-phenyl)-ethyl]-amide | 478 |

-continued

| Example | Structure | Name | M + H |
|---|---|---|---|
| 247 | 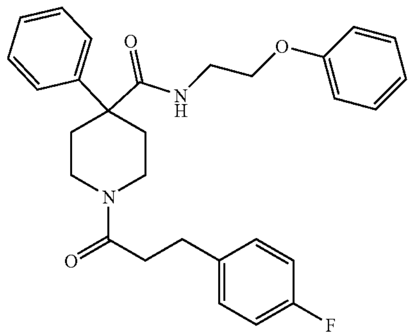 | 1-[3-(4-Fluoro-phenyl)-propionyl]-4-phenyl-piperidine-4-carboxylic acid (2-phenoxy-ethyl)-amide | 476 |
| 248 | 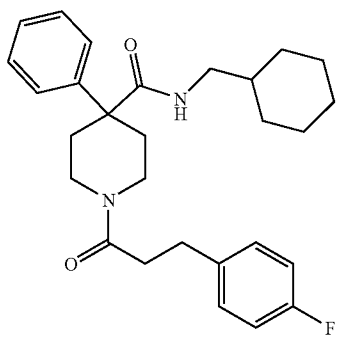 | 1-[3-(4-Fluoro-phenyl)-propionyl]-4-phenyl-piperidine-4-carboxylic acid cyclohexylmethyl-amide | 452 |
| 249 | 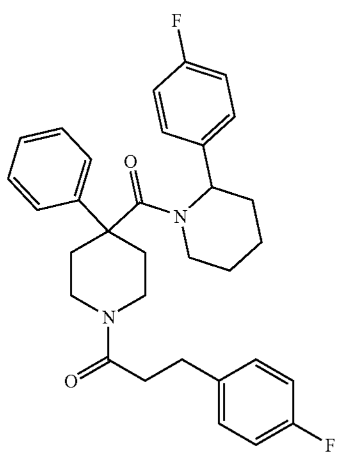 | 3-(4-Fluoro-phenyl)-1-{4-[2-(4-fluoro-phenyl)-piperidine-1-carbonyl]-4-phenyl-piperidin-1-yl}-propan-1-one | 518 |
| 250 | 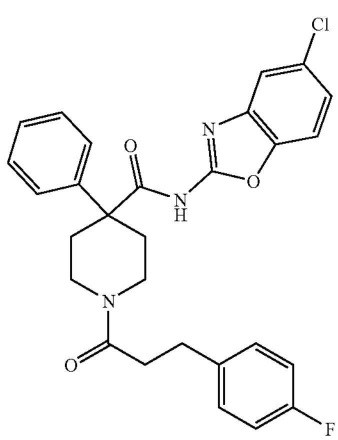 | 1-[3-(4-Fluoro-phenyl)-propionyl]-4-phenyl-piperidine-4-carboxylic acid (5-chloro-benzooxazol-2-yl)-amide | 507 |

-continued

| Example | Structure | Name | M + H |
|---|---|---|---|
| 251 | 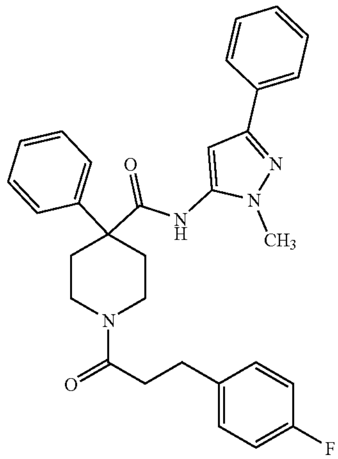 | 1-[3-(4-Fluoro-phenyl)-propionyl]-4-phenyl-piperidine-4-carboxylic acid (2-methyl-5-phenyl-2H-pyrazol-3-yl)-amide | 512 |
| 252 | 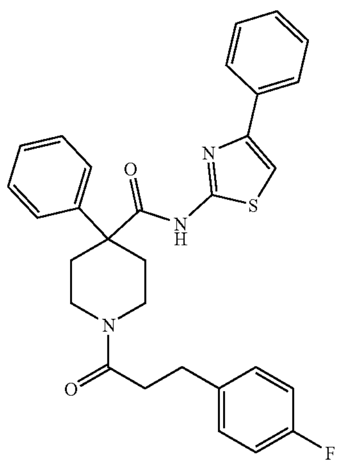 | 1-[3-(4-Fluoro-phenyl)-propionyl]-4-phenyl-piperidine-4-carboxylic acid (4-phenyl-thiazol-2-yl)-amide | 515 |
| 253 | 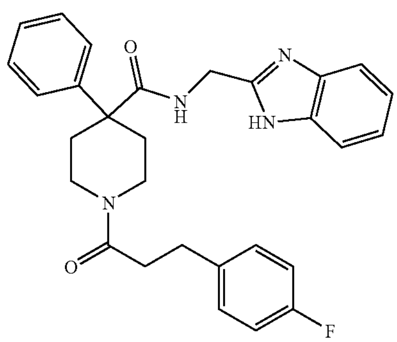 | 1-[3-(4-Fluoro-phenyl)-propionyl]-4-phenyl-piperidine-4-carboxylic acid (1H-benzoimidazol-2-ylmethyl)-amide | 486 |
| 254 | 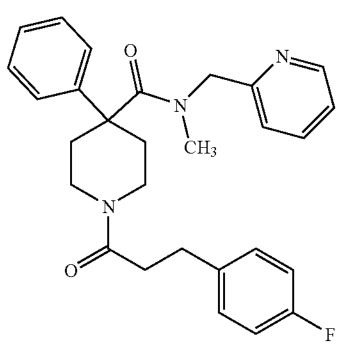 | 1-[3-(4-Fluoro-phenyl)-propionyl]-4-phenyl-piperidine-4-carboxylic acid methyl-pyridin-2-ylmethyl-amide | 461 |

-continued

| Example | Structure | Name | M + H |
|---|---|---|---|
| 255 | 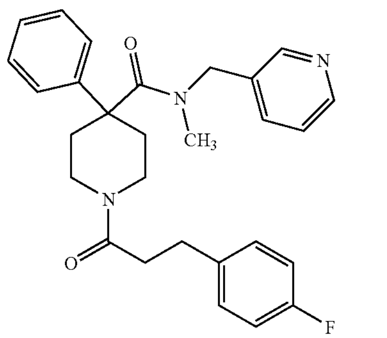 | 1-[3-(4-Fluoro-phenyl)-propionyl]-4-phenyl-piperidine-4-carboxylic acid methyl-pyridin-3-ylmethyl-amide | 461 |
| 256 | 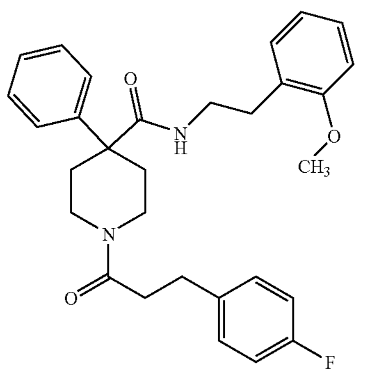 | 1-[3-(4-Fluoro-phenyl)-propionyl]-4-phenyl-piperidine-4-carboxylic acid [2-(2-methoxy-phenyl)-ethyl]-amide | 490 |
| 257 | 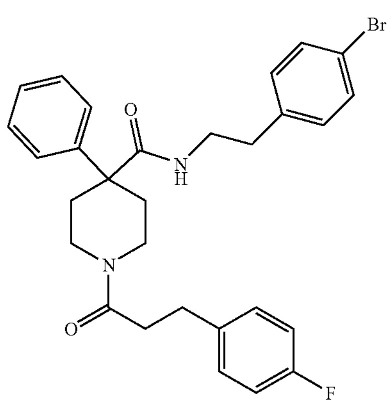 | 1-[3-(4-Fluoro-phenyl)-propionyl]-4-phenyl-piperidine-4-carboxylic acid [2-(4-bromo-phenyl)-ethyl]-amide | 538 |
| 258 | 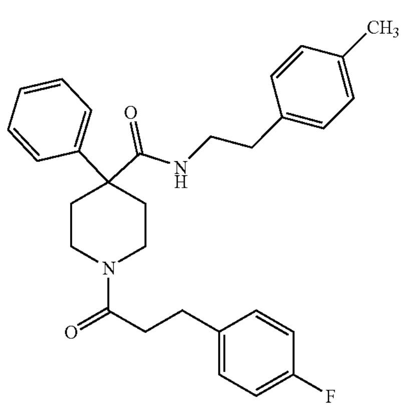 | 1-[3-(4-Fluoro-phenyl)-propionyl]-4-phenyl-piperidine-4-carboxylic acid (2-p-tolyl-ethyl)-amide | 474 |

-continued

| Example | Structure | Name | M + H |
|---|---|---|---|
| 259 | 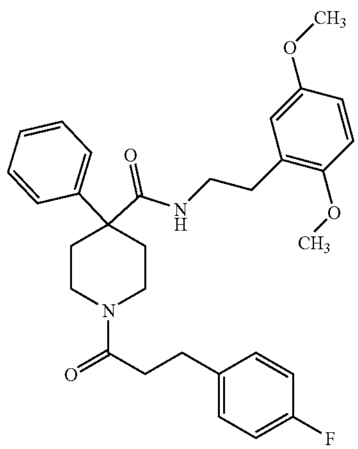 | 1-[3-(4-Fluoro-phenyl)-propionyl]-4-phenyl-piperidine-4-carboxylic acid [2-(2,5-dimethoxy-phenyl)-ethyl]-amide | 520 |
| 260 | 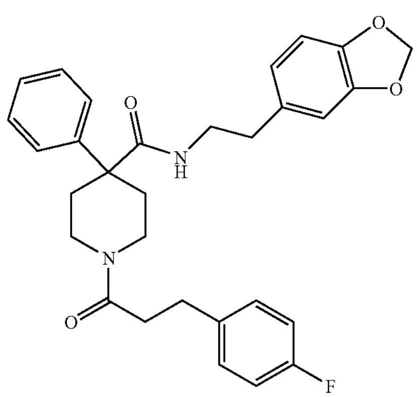 | 1-[3-(4-Fluoro-phenyl)-propionyl]-4-phenyl-piperidine-4-carboxylic acid (2-benzo[1,3]dioxo-5-yl-ethyl)-amide | 504 |
| 261 | 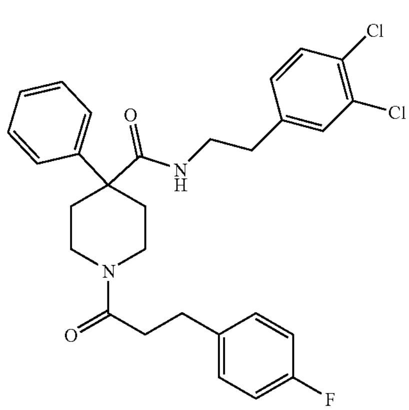 | 1-[3-(4-Fluoro-phenyl)-propionyl]-4-phenyl-piperidine-4-carboxylic acid [2-(3,4-dichloro-phenyl)-ethyl]-amide | 528 |

-continued

| Example | Structure | Name | M + H |
|---|---|---|---|
| 262 | 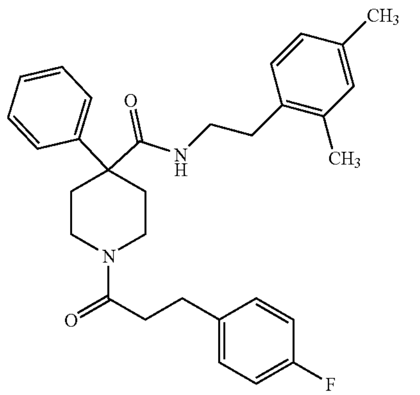 | 1-[3-(4-Fluoro-phenyl)-propionyl]-4-phenyl-piperidine-4-carboxylic acid [2-(2,4-dimethyl-phenyl)-ethyl]-amide | 488 |
| 263 | 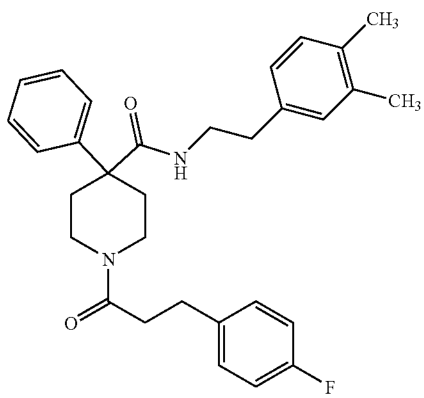 | 1-[3-(4-Fluoro-phenyl)-propionyl]-4-phenyl-piperidine-4-carboxylic acid [2-(3,4-dimethyl-phenyl)-ethyl]-amide | 488 |
| 264 | 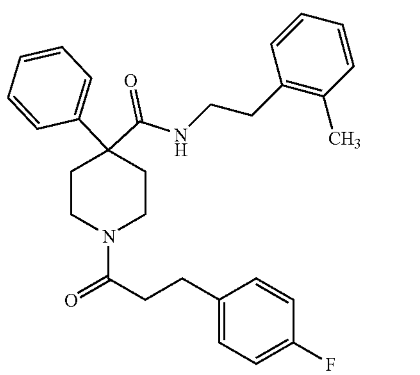 | 1-[3-(4-Fluoro-phenyl)-propionyl]-4-phenyl-piperidine-4-carboxylic acid (2-o-tolyl-ethyl)-amide | 474 |
| 265 | 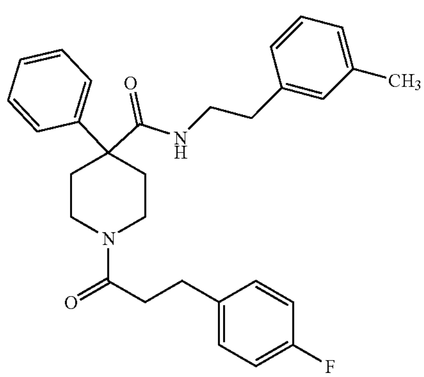 | 1-[3-(4-Fluoro-phenyl)-propionyl]-4-phenyl-piperidine-4-carboxylic acid (2-m-tolyl-ethyl)-amide | 474 |

-continued

| Example | Structure | Name | M + H |
|---|---|---|---|
| 266 | 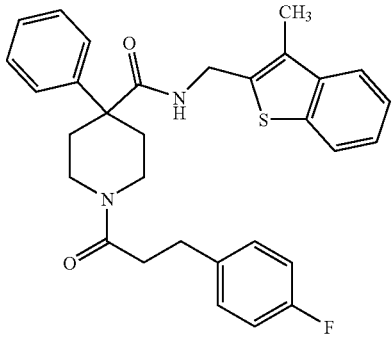 | 1-[3-(4-Fluoro-phenyl)-propionyl]-4-phenyl-piperidine-4-carboxylic acid (3-methyl-benzo[b]thiophen-2-ylmethyl)-amide | 516 |
| 267 | 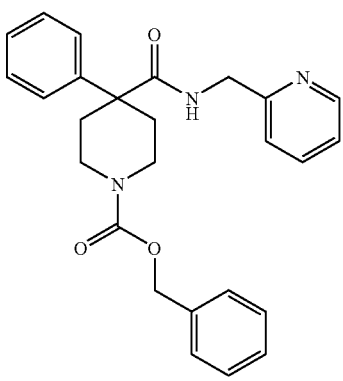 | 4-Phenyl-4-[(pyridin-2-ylmethyl)-carbamoyl]-piperidine-1-carboxylic acid benzyl ester | 431 |
| 268 | 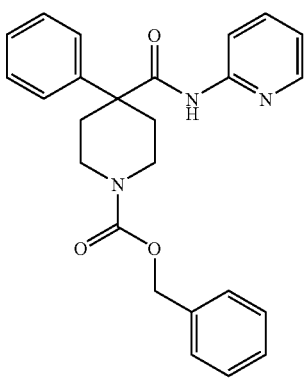 | 4-Phenyl-4-(pyridin-2-ylcarbamoyl)-piperidine-1-carboxylic acid benzyl ester | 516 |
| 269 | 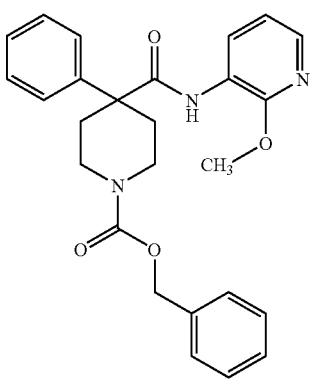 | 4-(2-Methoxy-pyridin-3-ylcarbamoyl)-4-phenyl-piperidine-1-carboxylic acid benzyl ester | 447 |

Example 270

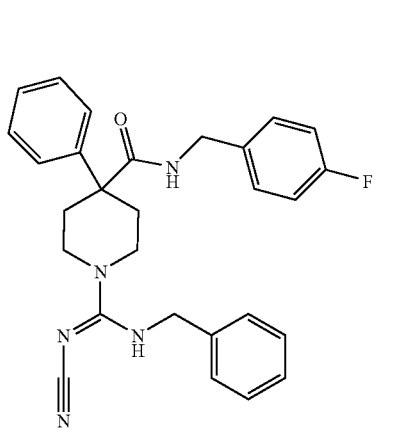

Synthesis

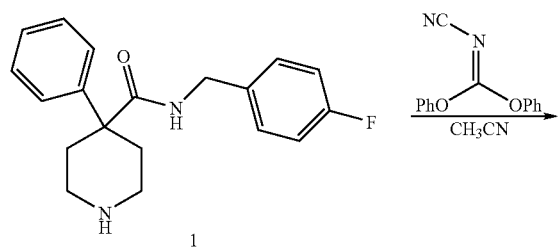

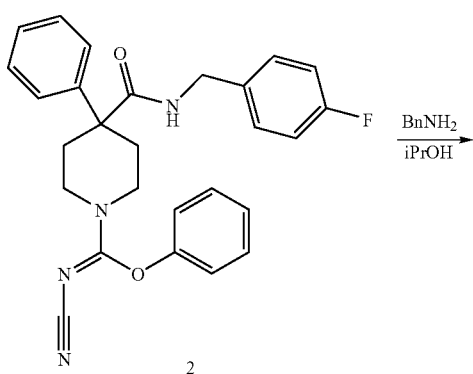

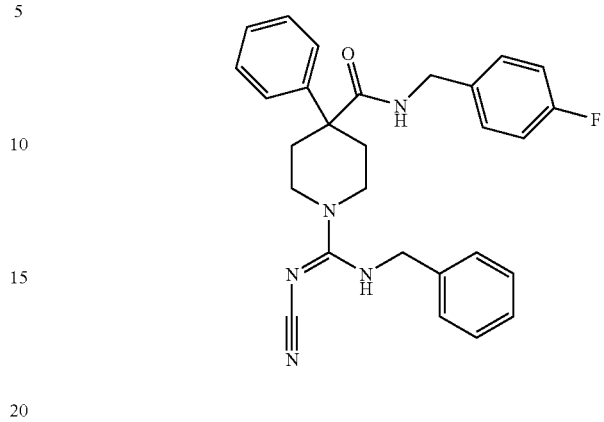

Compound 1: Compound 1 were prepared using methodology described in Example 85.

Compound 2: A solution of compound 1 (1.26 g; 4.03 mmol) in anhydrous acetonitrile (25 mL) was treated with diphenyl N-cyanocarbonimidate (1.0 g; 4.2 mmol) and heated at 85° C. for 1.5 h. The acetonitrile was removed by evaporation and the crude residue was purified by column chromatography on silica gel using a 7:3 hexane:ethyl acetate to 1:1 hexane:ethyl acetate gradient as the eluent to give 0.51 g of compound 2 as a white solid. LCMS m/z=338 (M+H)$^+$ Title Compound: A solution of compound 2 (0.081 g; 0.18 mol) in isopropanol (5 mL) was treated with benzyl amine (0.04 mL; 0.37 mmol) and heated at 90° C. for 15 h. The isopropanol was removed by evaporation and the crude residue was purified by recrystallization from ethyl acetate/hexane to give 0.061 g of the title compound as white crystals. LCMS m/z=471 (M+H)$^+$ Examples 271 to 274

Examples 271 to 274 were prepared using methodology described in Example 270.

| Example | Structure | Name | M + H |
|---|---|---|---|
| 271 | 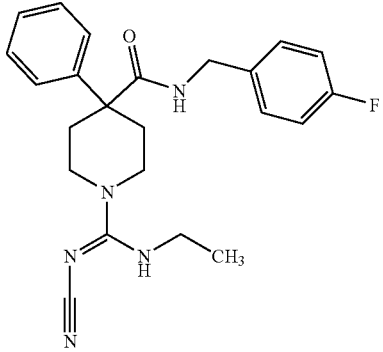 | | 408 |
| 272 | 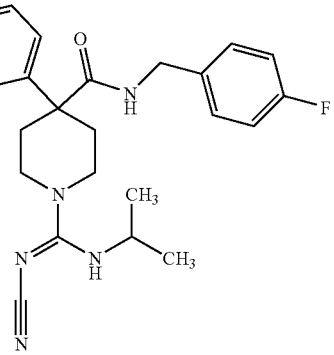 | | 423 |
| 273 | 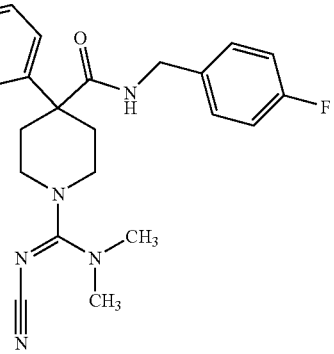 | | 408 |
| 274 | 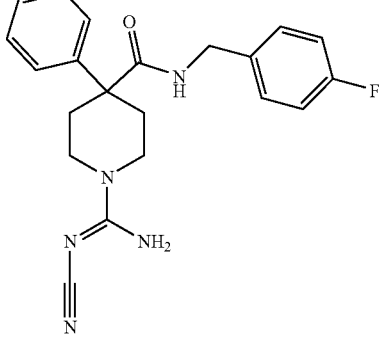 | | 380 |

Example 275

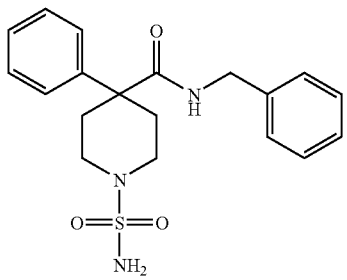

4-Phenyl-1-sulfamoyl-piperidine-4-carboxylic acid benzylamide

Synthesis

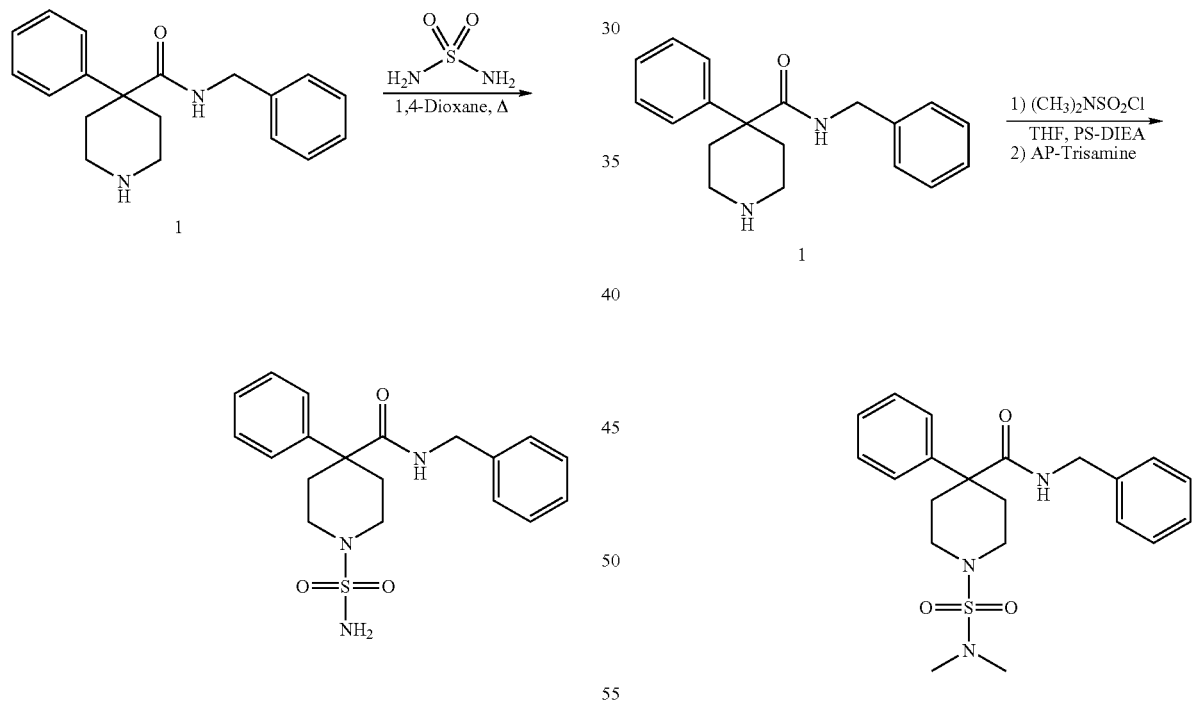

Compound 1: Compound 1 was prepared as described in Example 85.

Title Compound: 4-Phenyl-1-sulfamoyl-piperidine-4-carboxylic acid benzylamide was prepared using methodology described in Example 15. $^1$H NMR (CDCl$_3$, rt): δ ppm 2.15-2.24 (2H, m), 2.50-2.55 (2H, m), 3.21-3.27 (2H, m), 3.42-3.49 (2H, m), 4.28 (2H, s), 4.36 (2H, d, J=5.9 Hz), 5.47 (1H, bs), 7.02 (2H, d, J=7.5 Hz), 7.23 (2H, d, J=1.9 Hz), 7.30-7.41 (6H, m). LCMS Rt 1.45 min, [M+1]374.0.

Example 276

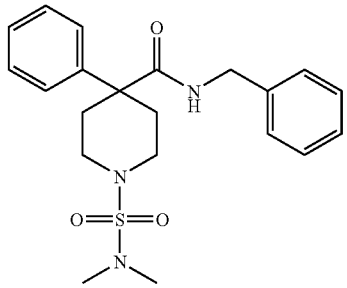

1-Dimethylsulfamoyl-4-phenyl-piperidine-4-carboxylic acid benzylamide

Scheme

Compound 1: Compound 1 was prepared as described in Example 85.

Title Compound: 1-Dimethylsulfamoyl-4-phenyl-piperidine-4-carboxylic acid benzylamide was prepared using methodology described in Example 16. $^1$H NMR (CDCl$_3$, rt): δ ppm 2.13-2.22 (2H, m), 2.42-2.49 (2H, m), 2.80 (6H, s), 3.31-3.45 (4H, m), 4.34 (2H, d, J=5.7 Hz), 4.28 (2H, s), 5.47

(1H, bs), 7.02 (2H, t, J=5.0, Hz), 7.21-7.25 (2H, m), 7.27-7.41 (6H, m). LCMS Rt 1.59 min, [M+1]402.0.

Example 277

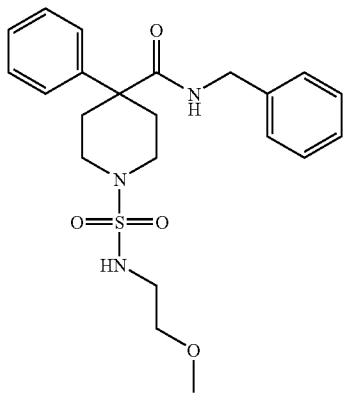

1-(2-Methoxy-ethylsulfamoyl)-4-phenyl-piperidine-4-carboxylic acid benzylamide

Scheme

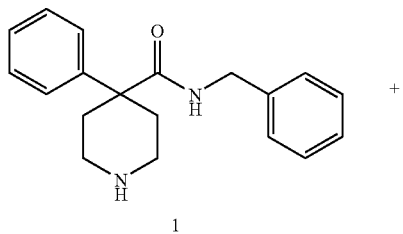

1

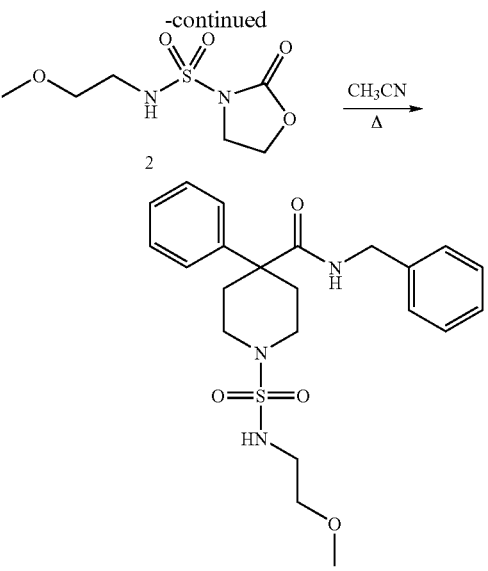

2

Compound 1: Compound 1 was prepared as described in Example 85.

Compound 2: Compound 2 was prepared as described in Example 17.

Title Compound: 1-(2-Methoxy-ethylsulfamoyl)-4-phenyl-piperidine-4-carboxylic acid benzylamide was prepared using methodology described in Example 17. $^1$H NMR (CDCl$_3$, rt): δ ppm) 2.15-2.24 (2H, m), 2.44-2.51 (2H, m), 3.11-3.25 (2H, m), 3.30-3.43 (6H, m), 3.48 (2H, t, J=5.2 Hz), 4.34 (2H, d, J=5.7 Hz), 4.51 (1H, bs), 5.46 (1H, s), 7.01-7.25 (4H, m), 7.29-7.41 (7H, m). LCMS Rt 1.47 min, [M+1]432.3.

Examples 278 to 285

Example 278 to 285 were prepared using methodology described in Example 277.

| Example | Structure | Name | M + H |
|---|---|---|---|
| 278 | 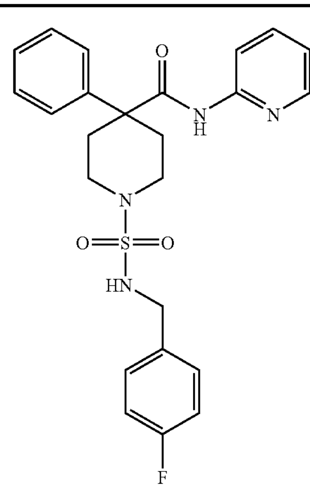 | 1-(4-Fluoro-benzylsulfamoyl)-4-phenyl-piperidine-4-carboxylic acid pyridin-2-ylamide | 470 |

-continued

| Example | Structure | Name | M + H |
|---|---|---|---|
| 279 | 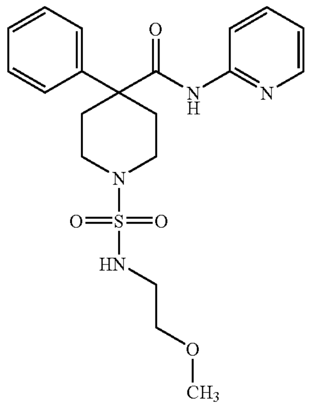 | 1-(2-Methoxy-ethylsulfamoyl)-4-phenyl-piperidine-4-carboxylic acid pyridin-2-ylamide | 420 |
| 280 | 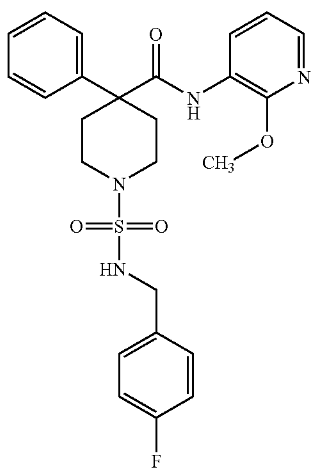 | 1-(4-Fluoro-benzylsulfamoyl)-4-phenyl-piperidine-4-carboxylic acid (2-methoxy-pyridin-3-yl)-amide | 500 |
| 281 | 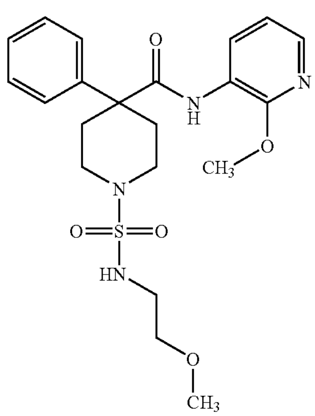 | 1-(2-Methoxy-ethylsulfamoyl)-4-phenyl-piperidine-4-carboxylic acid (2-methoxy-pyridin-3-yl)-amide | 450 |

-continued

| Example | Structure | Name | M + H |
|---------|-----------|------|-------|
| 282 | 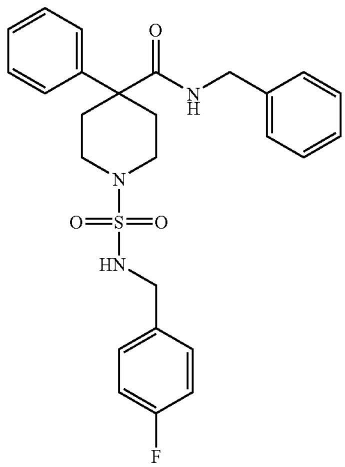 | N-[1-(4-Fluoro-benzylsulfamoyl)-4-phenyl-piperidin-4-ylmethyl]-2-methoxy-benzamide | 482 |
| 283 | 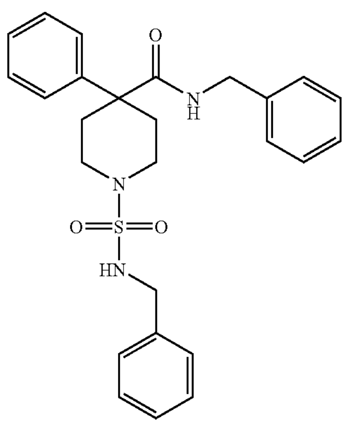 | N-(1-Benzylsulfamoyl-4-phenyl-piperidin-4-ylmethyl)-2-methoxy-benzamide | 464 |
| 284 | 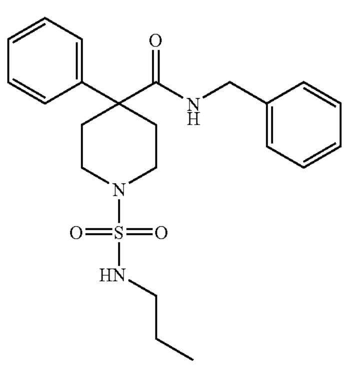 | 2-Methoxy-N-(4-phenyl-1-propylsulfamoyl-piperidin-4-ylmethyl)-benzamide | 416 |

| Example | Structure | Name | M + H |
|---|---|---|---|
| 285 | 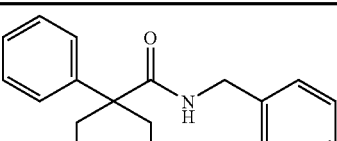 | N-(1-Dimethylsulfamoyl-4-phenyl-piperidin-4-ylmethyl)-2-methoxy-benzamide | 432 |
Example 286
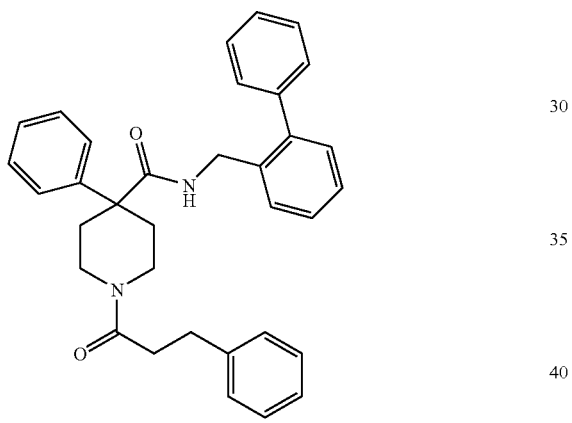
4-phenyl-1-(3-phenyl-propionyl)-piperidine-4-carboxylic acid (biphenyl-3-ylmethyl)-amide
Synthesis
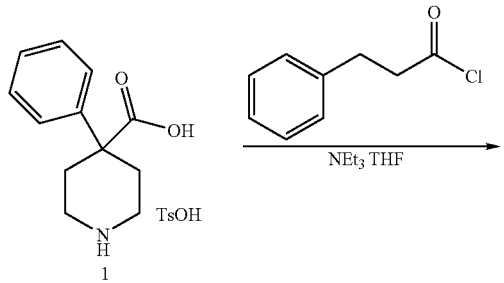
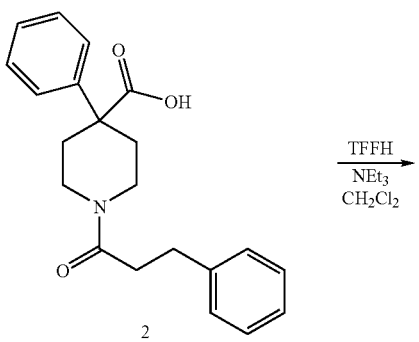
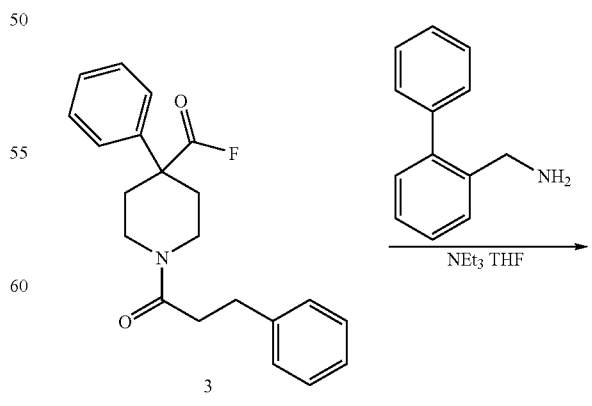

-continued

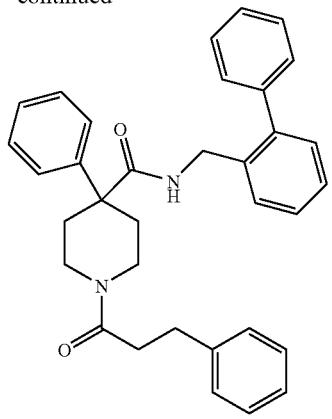

Compound 1: Compound 1 is commercially available.

Compound 2: A suspension of compound 1 (3.53 g; 9.35 mmol) in 50 mL of tetrahydrofuran was treated with triethylamine (2.9 mL; 20.8 mmol) and the reaction mixture was cooled to 0° C. Hydrocinnamoyl chloride (1.92 g; 11.4 mmol) was added as a solution in 5 mL of tetrahydrofuran. The reaction mixture was allowed to slowly warm to room temperature and stirred for 18 h. The tetrahydrofuran was removed by evaporation and the residue was treated with ethyl acetate (approximately 150 mL) and 10% aqueous hydrochloric acid (approximately 100 mL). The organic layer was separated, washed with saturated aqueous sodium chloride, dried (sodium sulfate), filtered and concentrated. The crude product was purified by recrystallization from ethanol to give 1.02 g of compound 2 as a white solid. LCMS m/z=338 (M+H)$^+$ Compound 3: A suspension of compound 2 (0.23 g; 0.67 mmol) in 12 mL of dichloromethane was treated with triethylamine (0.14 mL; 1.0 mmol) followed by fluoro-N,N,N',-tetramethylformamidinium hexafluorophosphate (0.22 g; 0.83 mmol) at room temperature. After stirring for 1 h, the dichloromethane was removed by evaporation to give 0.23 g of compound 3 that was used in the next step without further purification. LCMS m/z=340 (M+H)$^+$ Title Compound: A solution of compound 3 (0.13 g; 0.39 mmol) in 15 mL of dichloromethane was treated with triethylamine (0.071 mL; 0.51 mmol) followed by 2-phenylbenzyl amine (0.074 mL; 0.043 mmol) at room temperature. After stirring for 8 h, an additional 50 mL of dichloromethane an 40 mL of 10% aqueous hydrochloric acid was added. The organic layer was separated, washed with saturated aqueous sodium chloride, dried (sodium sulfate), filtered and concentrated. Column chromatography on silica gel using 1:1 hexane:ethyl acetate as the eluent gave 0.16 g of 4-phenyl-1-(3-phenyl-propionyl)-piperidine-4-carboxylic acid (biphenyl-3-ylmethyl)-amide as a white solid. m/z=504 (M+H)$^+$.

Example 287

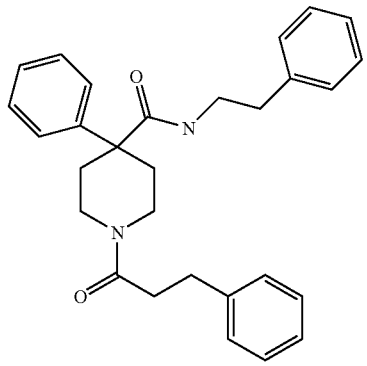

4-Phenyl-1-(3-phenyl-propionyl)-piperidine-4-carboxylic acid methyl-phenethyl-amide Synthesis

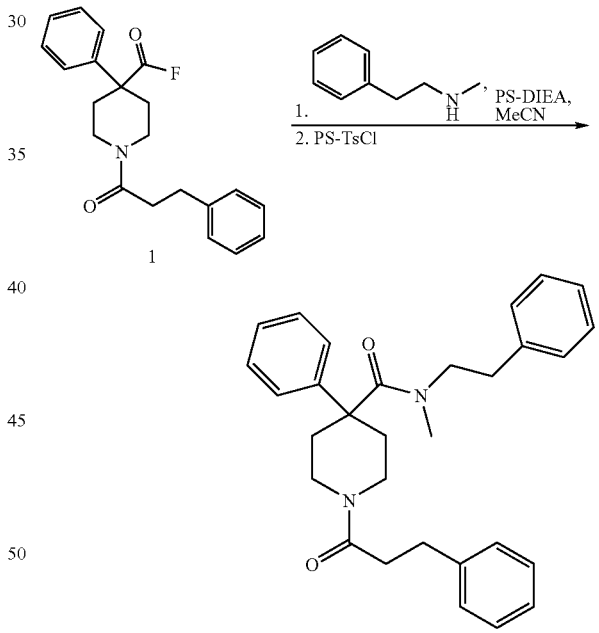

Compound 1: Compound 1 was prepared as described in Example 286.

Title Compound: Compound 1 (0.015 g; 0.05 mmol) was dissolved in 1 mL acetonitrile. Polystyrene-diisopropylethylamine (PS-DIEA) resin (0.1 g) was added and the resulting suspension was treated with N-methylphenethylamine 0.02 g; 0.1 mmol) and shaken at room temperature. After 24 h, polystyrene-tosyl chloride, high loading (PS-TsCl) resin (0.2 g) was added and the reaction mixture was allowed to shake additional 24 h. The reaction mixture was filtered and concentrated to give 0.010 g of 4-Phenyl-1-(3-phenyl-propionyl)-piperidine-4-carboxylic acid methyl-phenethyl-amide as a colorless oil. LCMS m/z=456 (M+H)$^+$ Examples 288 to 322

Examples 288 to 322 were prepared using methodology described in Example 287.

| Example | Structure | Name | M + H |
|---|---|---|---|
| 288 | 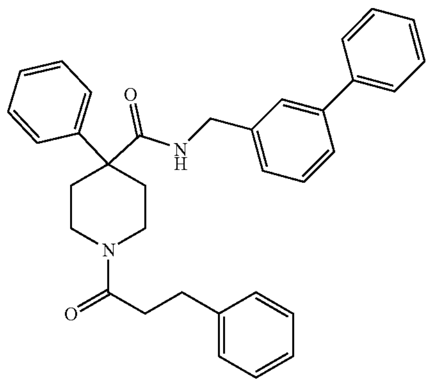 | 4-Phenyl-1-(3-phenyl-propionyl)-piperidine-4-carboxylic acid (biphenyl-3-ylmethyl)-amide | 504 |
| 289 | 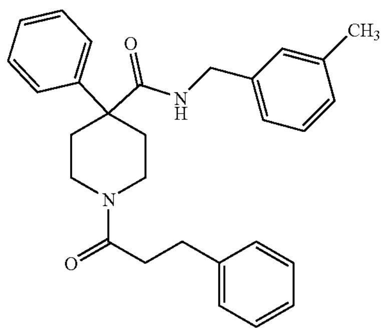 | 4-Phenyl-1-(3-phenyl-propionyl)-piperidine-4-carboxylic acid 3-methyl-benzylamide | 442 |
| 290 | 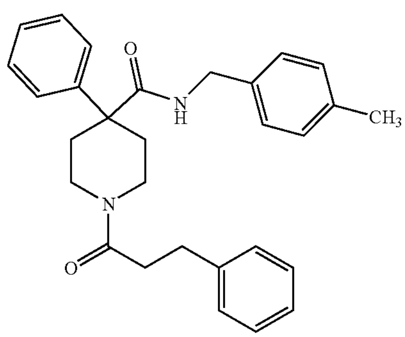 | 4-Phenyl-1-(3-phenyl-propionyl)-piperidine-4-carboxylic acid 4-chloro-benzylamide | 462 |
| 291 | 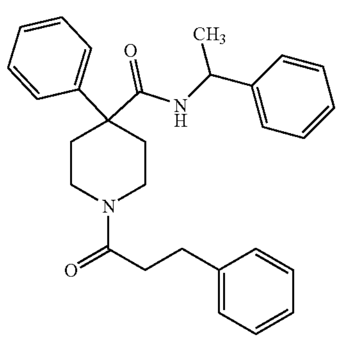 | 4-Phenyl-1-(3-phenyl-propionyl)-piperidine-4-carboxylic acid (1-phenyl-ethyl)-amide | 442 |

-continued

| Example | Structure | Name | M + H |
|---|---|---|---|
| 292 | 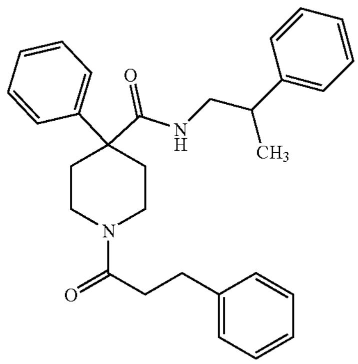 | 4-Phenyl-1-(3-phenyl-propionyl)-piperidine-4-carboxylic acid (2-phenyl-propyl)-amide | 456 |
| 293 | 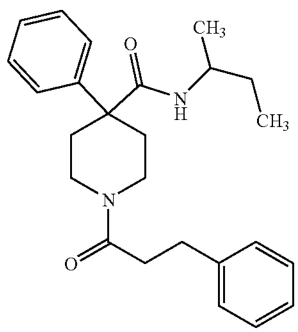 | 4-Phenyl-1-(3-phenyl-propionyl)-piperidine-4-carboxylic acid sec-butylamide | 394 |
| 294 | 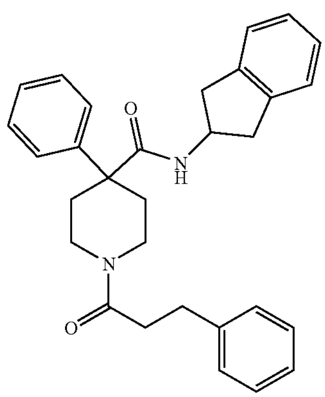 | 4-Phenyl-1-(3-phenyl-propionyl)-piperidine-4-carboxylic acid indan-2-ylamide | 454 |
| 295 | 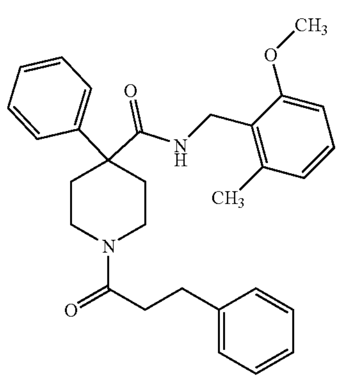 | 4-Phenyl-1-(3-phenyl-propionyl)-piperidine-4-carboxylic acid 2,6-dimethoxy-benzylamide | 488 |

| Example | Structure | Name | M + H |
|---|---|---|---|
| 296 | 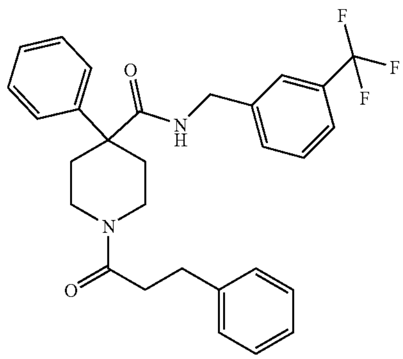 | 4-Phenyl-1-(3-phenyl-propionyl)-piperidine-4-carboxylic acid 3-trifluoromethyl-benzylamide | 496 |
| 297 | 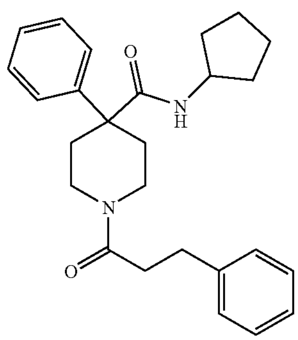 | 4-Phenyl-1-(3-phenyl-propionyl)-piperidine-4-carboxylic acid cyclopentylamide | 406 |
| 298 | 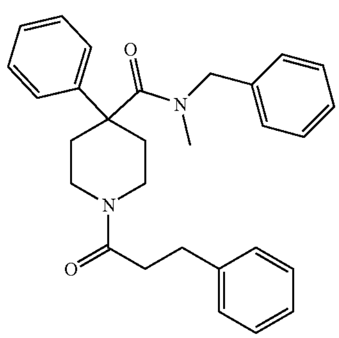 | 4-Phenyl-1-(3-phenyl-propionyl)-piperidine-4-carboxylic acid benzyl-methyl-amide | 442 |
| 299 | 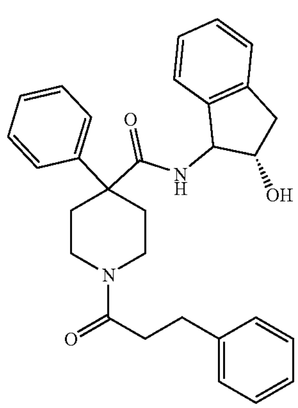 | 4-Phenyl-1-(3-phenyl-propionyl)-piperidine-4-carboxylic acid (2-hydroxy-indan-1-yl)-amide | 470 |

-continued

| Example | Structure | Name | M + H |
|---------|-----------|------|-------|
| 300 | 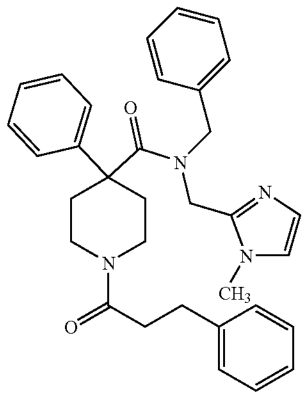 | 4-Phenyl-1-(3-phenyl-propionyl)-piperidine-4-carboxylic acid benzyl-(1-methyl-1H-imidazol-2-ylmethyl)-amide | 522 |
| 301 | 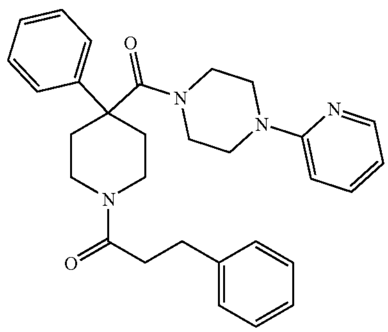 | 3-Phenyl-1-[4-phenyl-4-(4-pyridin-2-yl-piperazine-1-carbonyl)-piperidin-1-yl]-propan-1-one | 484 |
| 302 | 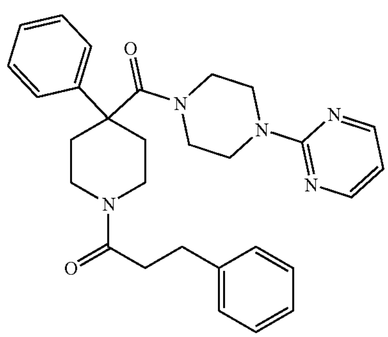 | 3-Phenyl-1-[4-phenyl-4-(4-pyrimidin-2-yl-piperazine-1-carbonyl)-piperidin-1-yl]-propan-1-one | 485 |
| 303 | 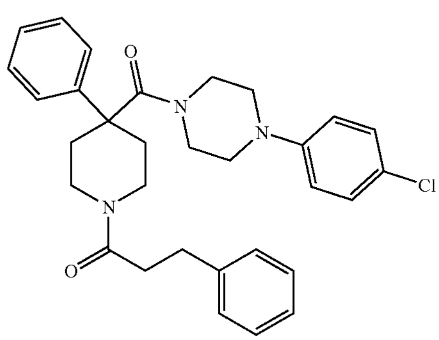 | 1-{4-[4-(4-Chloro-phenyl)-piperazine-1-carbonyl]-4-phenyl-piperidin-1-yl}-3-phenyl-propan-1-one | 517 |

| Example | Structure | Name | M + H |
|---|---|---|---|
| 304 | 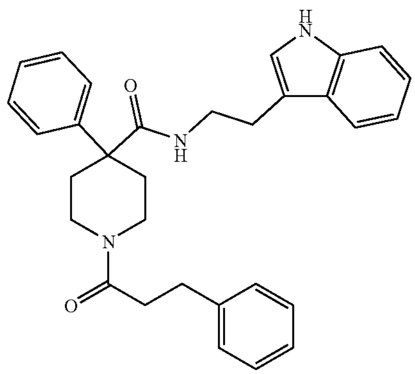 | 4-Phenyl-1-(3-phenyl-propionyl)-piperidine-4-carboxylic acid [2-(1H-indol-3-yl)-ethyl]-amide | 481 |
| 305 | 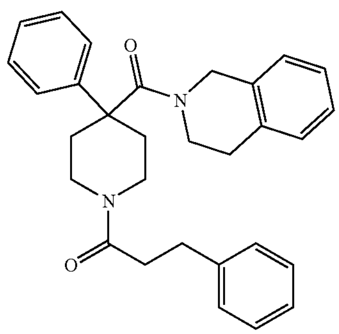 | 1-[4-(3,4-Dihydro-1H-isoquinoline-2-carbonyl)-4-phenyl-piperidin-1-yl]-3-phenyl-propan-1-one | 454 |
| 306 | 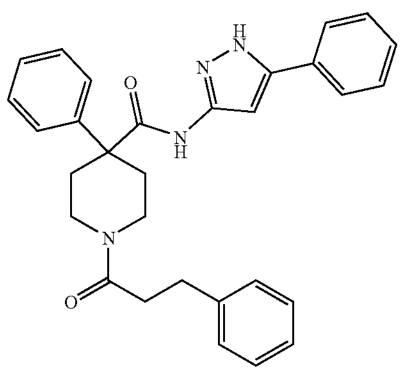 | 4-Phenyl-1-(3-phenyl-propionyl)-piperidine-4-carboxylic acid (5-phenyl-1H-pyrazol-3-yl)-amide | 480 |
| 307 | 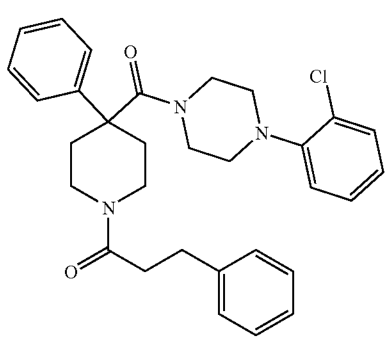 | 1-{4-[4-(2-Chloro-phenyl)-piperazine-1-carbonyl]-4-phenyl-piperidin-1-yl}-3-phenyl-propan-1-one | 517 |

-continued

| Example | Structure | Name | M + H |
|---|---|---|---|
| 308 | 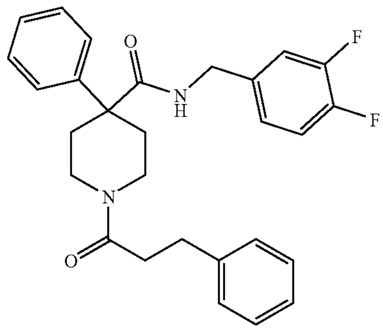 | 4-Phenyl-1-(3-phenyl-propionyl)-piperidine-1-carboxylic acid 3,4-difluoro-benzylamide | 464 |
| 309 | 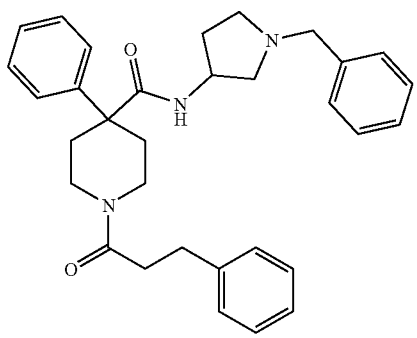 | 4-Phenyl-1-(3-phenyl-propionyl)-piperidine-4-carboxylic acid (1-benzyl-pyrrolidin-3-yl)-amide | 497 |
| 310 | 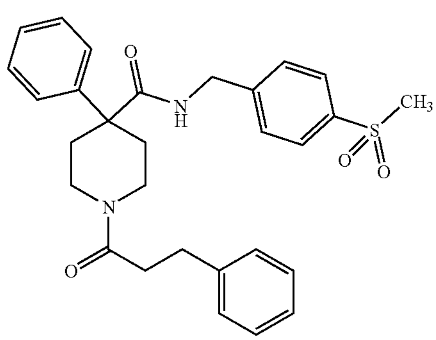 | 4-Phenyl-1-(3-phenyl-propionyl)-piperidine-4-carboxylic acid 4-methanesulfonyl-benzylamide | 506 |
| 311 | 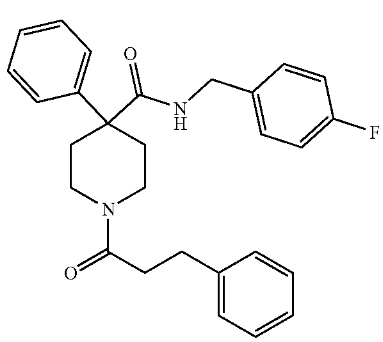 | 4-Phenyl-1-(3-phenyl-propionyl)-piperidine-4-carboxylic acid 4-fluoro-benzylamide | 446 |

| Example | Structure | Name | M + H |
|---|---|---|---|
| 312 | 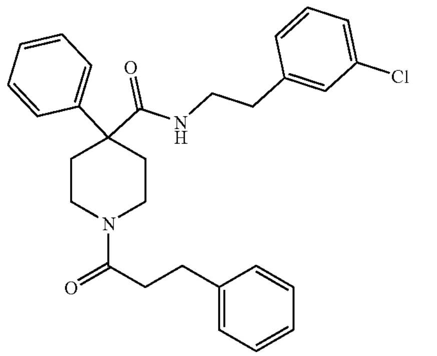 | 4-Phenyl-1-(3-phenyl-propionyl)-piperidine-4-carboxylic acid [2-(3-chloro-phenyl)-ethyl]-amide | 476 |
| 313 | 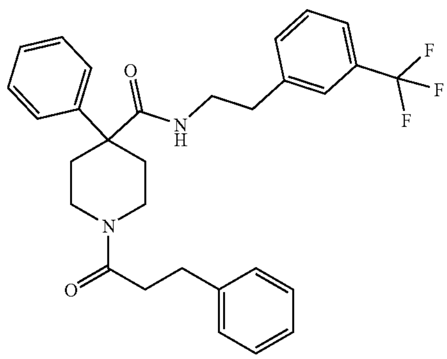 | 4-Phenyl-1-(3-phenyl-propionyl)-piperidine-4-carboxylic acid [2-(3-trifluoromethyl-phenyl)-ethyl]-amide | 510 |
| 314 | 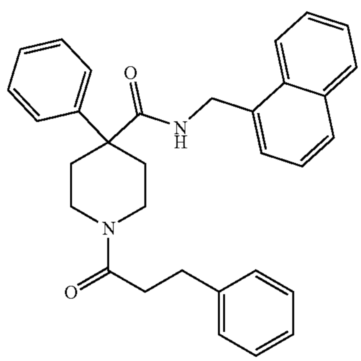 | 4-Phenyl-1-(3-phenyl-propionyl)-piperidine-4-carboxylic acid (naphthalen-1-ylmethyl)-amide | 478 |
| 315 | 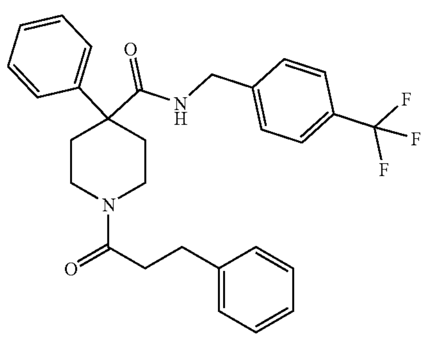 | 4-Phenyl-1-(3-phenyl-propionyl)-piperidine-4-carboxylic acid 4-trifluoromethyl-benzylamide | 496 |

-continued

| Example | Structure | Name | M + H |
|---|---|---|---|
| 316 | 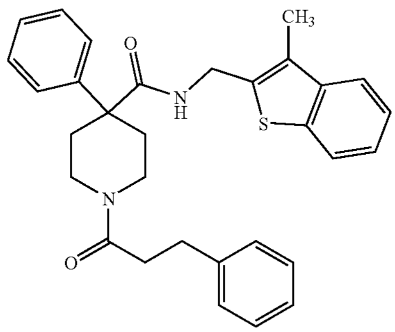 | 4-Phenyl-1-(3-phenyl-propionyl)-piperidine-4-carboxylic acid (3-methyl-benzol[b]thiophen-2-ylmethyl)-amide | 498 |
| 317 | 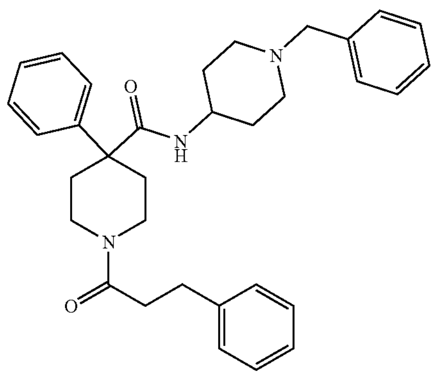 | 4-Phenyl-1-(3-phenyl-propionyl)-piperidine-4-carboxylic acid (1-benzyl-piperidin-4-yl)-amide | 511 |
| 318 | 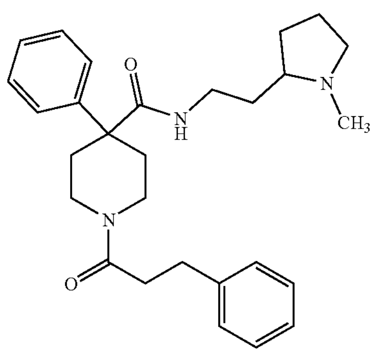 | 4-Phenyl-1-(3-phenyl-propionyl)-piperidine-4-carboxylic acid [2-(1-methyl-pyrrolidin-2-yl)-ethyl]-amide | 449 |
| 319 | 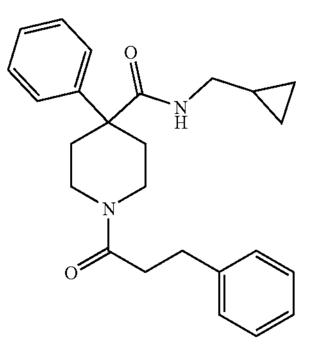 | 4-Phenyl-1-(3-phenyl-propionyl)-piperidine-4-carboxylic acid cyclopropylmethyl-amide | 392 |

-continued
| Example | Structure | Name | M + H |
|---|---|---|---|
| 320 | 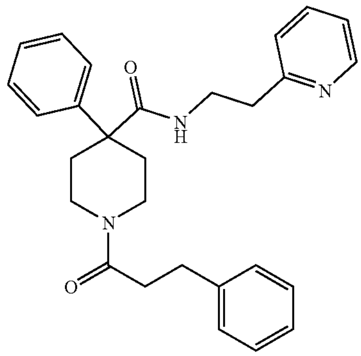 | 4-Phenyl-1-(3-phenyl-propionyl)-piperidine-4-carboxylic acid (2-pyridin-2-yl-ethyl)-amide | 443 |
| 321 | 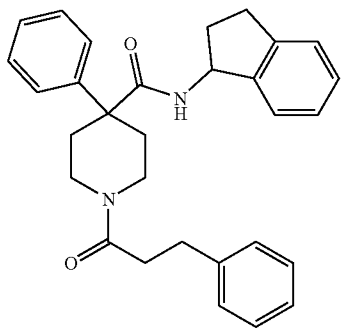 | 4-Phenyl-1-(3-phenyl-propionyl)-piperidine-4-carboxylic acid indan-1-ylamide | 454 |
| 322 | 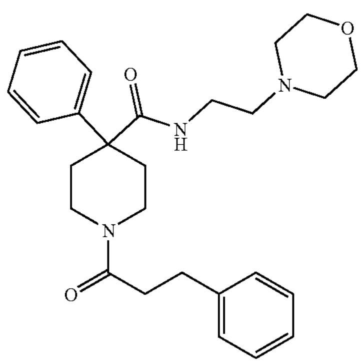 | 4-Phenyl-1-(3-phenyl-propionyl)-piperidine-4-carboxylic acid (2-morpholin-4-yl-ethyl)-amide | 451 |
Example 323
4-(Benzylcarbamoyl-methyl)-4-phenyl-piperidine-1-carboxylic acid benzyl ester
Synthesis
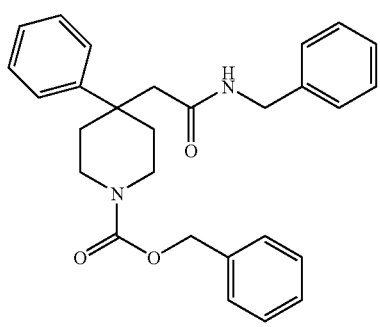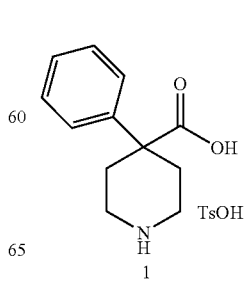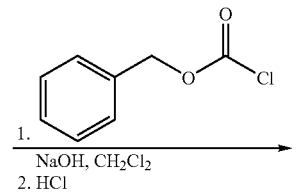

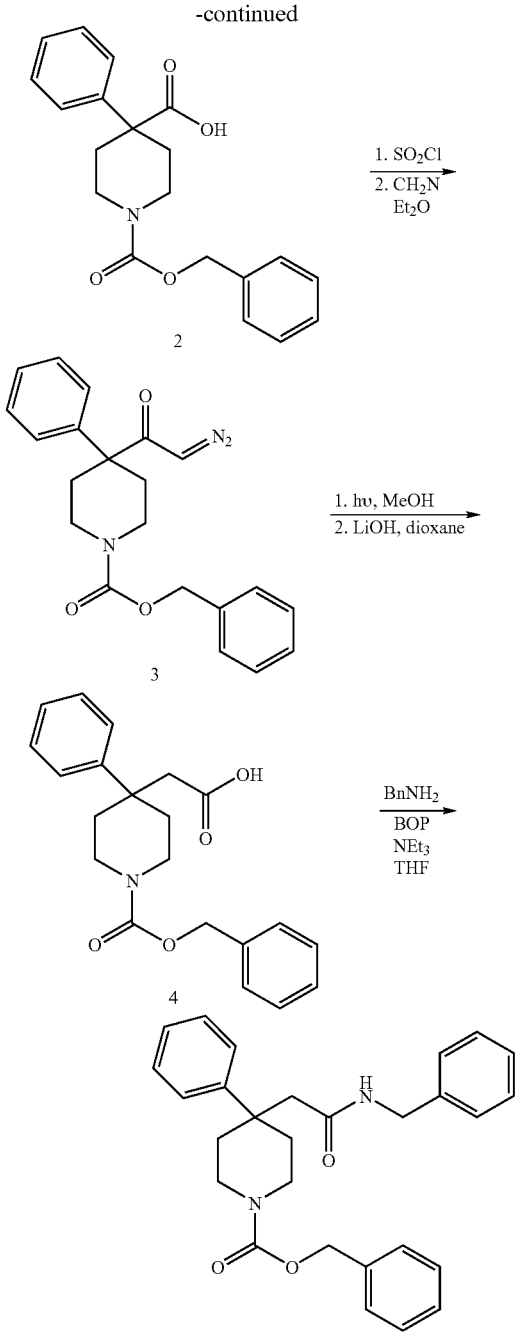

monobenzyl ester (2.00 g, 5.89 mmol) and heated to reflux for 2 hours. The reaction mixture was concentrated under reduced pressure, taken up in ethyl ether (25 mL), cooled to 0° C. and diazomethane in ethyl ether was (30.0 mmole, 100 mL) added. After completion of the reaction, as monitored by thin layer chromatography, the excess diazomethane was quenched with acetic acid (5 mL). The reaction mixture was concentrated under reduced pressure and crude product purified by column chromatography to give 1.27 g of 4-(2-diazo-acetyl)-4-phenyl-piperidine-1-carboxylic acid benzyl ester.

Compound 4: 4-(2-Diazo-acetyl)-4-phenyl-piperidine-1-carboxylic acid benzyl ester (1.50 g, 4.12 mmol) in methanol (40 mL) was irradiated under UV($\lambda$=365 nM) for 36 hours. The reaction mixture was concentrated under reduced pressure, crude product taken up in 3M lithium hydroxide (20 mL)/dioxane (20 mL) and heated to 60° C. for 1 hour. The reaction mixture was concentrated under reduced pressure to remove dioxane, made acidic with 6M hydrochloric acid, and extracted with ethyl acetate (6×50 mL). Organic layers were collected, concentrated and crude product purified by column chromatography to give 1.16 g of 4-carboxymethyl-4-phenyl-piperidine-1-carboxylic acid benzyl ester. $^1$H NMR (CD$_3$Cl$_3$, 300 MHz) $\delta$ 7.32 (m, 10H), 5.10 (s, 2H), 3.76(d, 2H, J=13.4 Hz), 3.20(t, 2H, J=10.7 Hz ), 2.56 (s, 2H), 2.31(d, 2H, J=13.6 Hz), 1.91(t, 2H, J=13.0 Hz).

Title Compound: Benzotriazol-1-yloxytris(dimethylamino)phosphonium hexafluorophosphate (0.120 g, 0.271 mmol) was added to a solution of benzyl amine (0.030 mL, 0.271 mmol), 4-carboxymethyl-4-phenyl-piperidine-1-carboxylic acid benzyl ester (0.100 g, 0.247 mmol), triethylamine (0.103 mL, 0.741 mmol) in tetrahydrofuran (5 mL). After 1 hour the mixture was diluted with ethyl ether (20 mL), washed with saturated aqueous sodium bicarbonate (20 mL) followed by water (2×10 mL). Organic layer collected, concentrated under reduced pressure and crude product purified by column chromatography to give 0.099 g of 4-(benzylcarbamoyl-methyl)-4-phenyl-piperidine-1-carboxylic acid benzyl ester. LRMS m/z 443.2 (M+H)$^+$.

Example 324

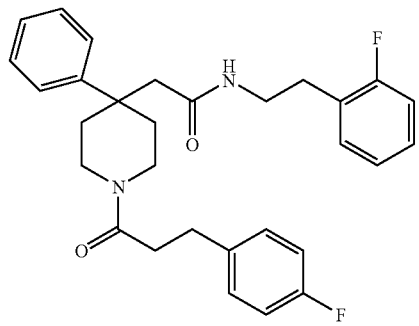

Compound 1: Compound 1 is commercially available.

Compound 2: Benzyl chloroformate (4.75 mL, 33.1 mmol) was added dropwise to a solution of 4-phenyl-4-piperidinecarboxylic acid p-methylbenzenesulfonate (10.0 g, 26.5 mmol) in 1M sodium hydroxide (200 mL)/dichloromethane (100 mL). After 2 hours the reaction mixture was made acidic with 1M hydrochloric acid (pH=3), the organic layer was separated and the aqueous layer extracted with ethyl acetate (3×100 mL). The organic layers were collected, concentrated and crude product washed with water (3×50 mL) to give 8.52 g of 4-phenyl-piperidine-1,4-dicarboxylic acid monobenzyl ester. LRMS m/z 340.2 (M+H)$^+$.

Compound 3: Thionyl chloride (4.29 mL, 58.9 mmol) was added to 4-Phenyl-piperidine-1,4-dicarboxylic acid

227

N-[2-(2-Fluoro-phenyl)-ethyl]-2-{1-[3-(4-fluoro-phenyl)-propionyl]-4-phenyl-piperidin-4-yl}-acetamide Synthesis

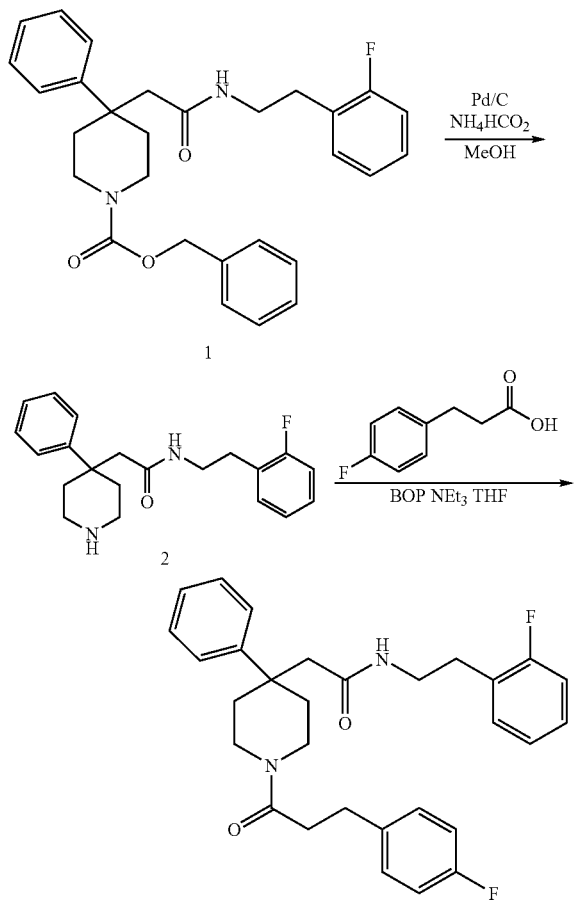

Compound 1: Compound 1 were prepared using methodology described in Example 323.

Compound 2: Ammonium formate (1.00 g) was added to a solution of 4-{[2-(2-fluoro-phenyl)-ethylcarbamoyl]-methyl}-4-phenyl-piperidine-1-carboxylic acid benzyl ester (0.520 g, 1.10 mmol) in methanol (50 mL) containing 10% palladium/carbon (0.500 g) and stirred for 4 h. The reaction mixture was filtered through celite and concentrated under reduced pressure. The crude product was taken up in 1M sodium hydroxide (100 mL) and extracted with ethyl acetate (3×50 mL). The organic layers were collected and concentrated under reduced pressure to give 0.328 g (87%) of N-[2-(2-fluoro-phenyl)-ethyl]-2-(4-phenyl-piperidin-4-yl)-acetamide. LRMS m/z 341.1 (M+H)$^+$.

Title Compound: Benzotriazol-1-yloxytris(dimethylamino)phosphonium hexafluorophosphate (0.311 g, 0.704 mmol) was added to a solution of N-[2-(2-fluoro-phenyl)-ethyl]-2-(4-phenyl-piperidin-4-yl)-acetamide (0.200 g, 0.587 mmol), 3-(4-Fluoro-phenyl)-propionic acid (0.118 g, 0.704 mmol) and triethylamine (0.245 mL, 1.76 mmol) in tetrahydrofuran (5 mL). After 1 hour the mixture was diluted with ethyl ether (20 mL) and washed with saturated aqueous sodium bicarbonate (20 mL) followed by water (2×10 mL). The organic layer was collected, concentrated under reduced pressure and crude product purified by column chromatography on silica gel to give 0.098 g (34 %) of N-[2-(2-fluoro-phenyl)-ethyl]-2-{1-[3-(4-fluoro-phenyl)-propionyl]-4-phenyl-piperidin-4-yl}-acetamide. LRMS m/z 491.1 (M+H)$^+$.

Examples 325 to 380

Examples 325 to 380 were synthesized using methodology described in Example 324.

| Example | Structure | Name | M + H |
|---|---|---|---|
| 325 | 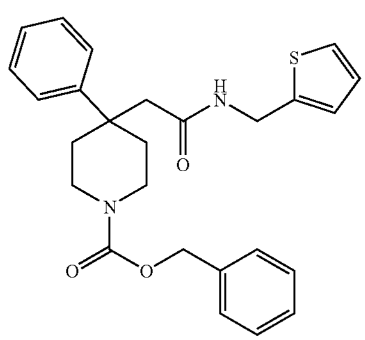 | 4-Phenyl-4-{[(thiophen-2-ylmethyl)-carbamoyl]-methyl}-piperidine-1-carboxylic acid benzyl acid | 450 |

-continued

| Example | Structure | Name | M + H |
|---|---|---|---|
| 326 | 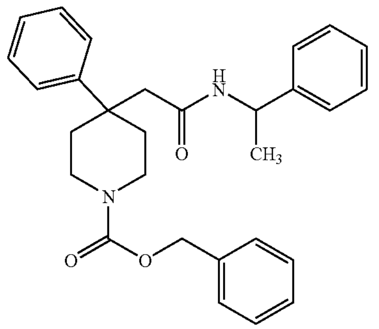 | 4-Phenyl-4-[(1-phenyl-ethylcarbamoyl)-methyl]-piperidine-1-carboxylic acid benzyl ester | 458 |
| 327 | 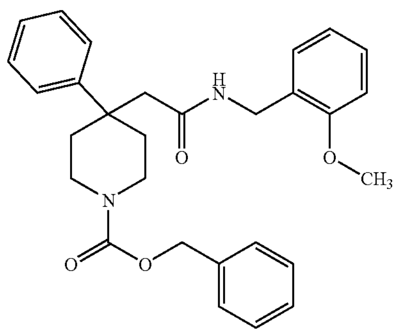 | 4-[(2-Methoxy-benzylcarbamoyl)-methyl]-4-phenyl-piperidine-1-carboxylic acid benzyl ester | 474 |
| 328 | 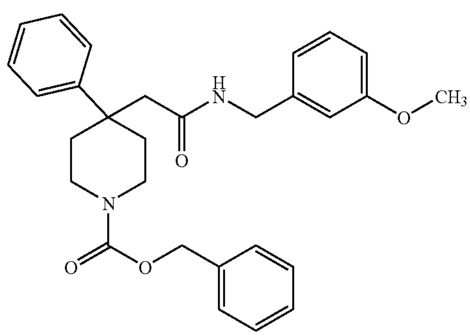 | 4-[(3-Methoxy-benzylcarbamoyl)-methyl]-4-phenyl-piperidine-1-carboxylic acid benzyl ester | 474 |
| 329 | 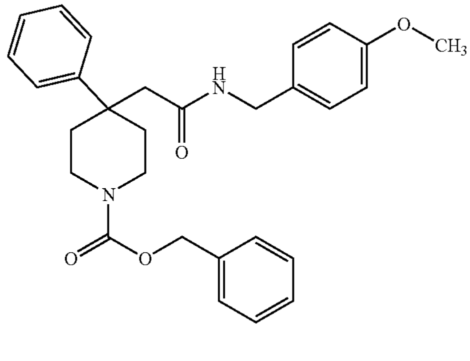 | 4-[(4-Methoxy-benzylcarbamoyl)-methyl]-4-phenyl-piperidine-1-carboxylic acid benzyl ester | 474 |

-continued

| Example | Structure | Name | M + H |
|---|---|---|---|
| 330 | 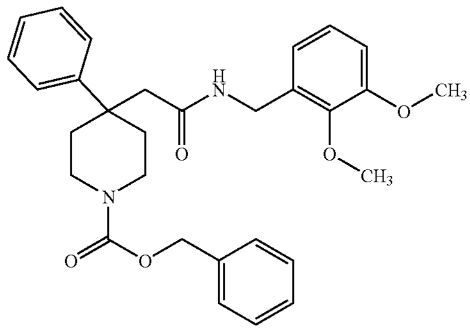 | 4-[(2,3-Dimethoxy-benzylcarbamoyl)-methyl]-4-phenyl-piperidine-1-carboxylic acid benzyl ester | 504 |
| 331 | 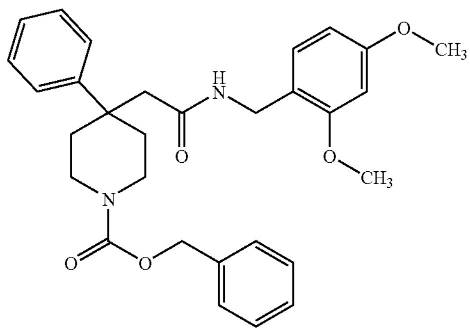 | 4-[(2,4-Dimethoxy-benzylcarbamoyl)-methyl]-4-phenyl-piperidine-1-carboxylic acid benzyl ester | 504 |
| 332 | 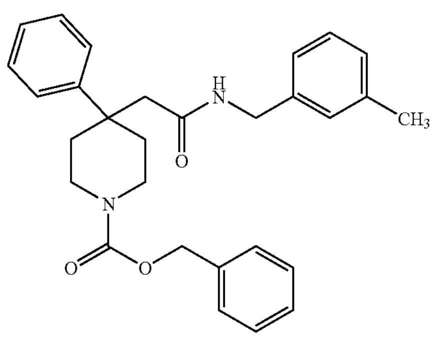 | 4-[(3-Methyl-benzylcarbamoyl)-methyl]-4-phenyl-piperidine-1-carboxylic acid benzyl ester | 458 |
| 333 | 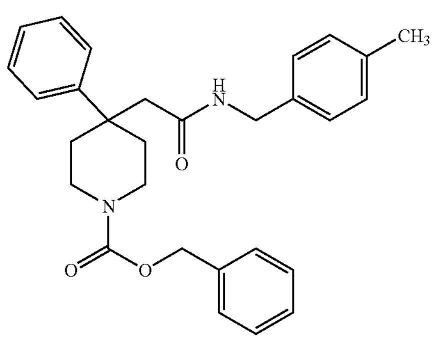 | 4-[(4-Methyl-benzylcarbamoyl)-methyl]-4-phenyl-piperidine-1-carboxylic acid benzyl ester | 458 |

-continued

| Example | Structure | Name | M + H |
|---|---|---|---|
| 334 | 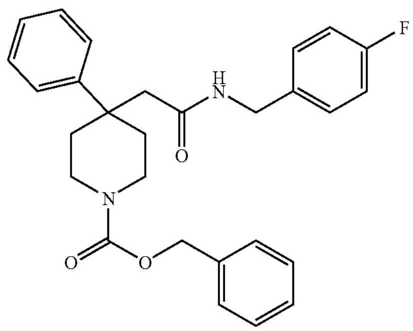 | 4-[(4-Fluoro-benzylcarbamoyl)-methyl]-4-phenyl-piperidine-1-carboxylic acid benzyl ester | 462 |
| 335 | 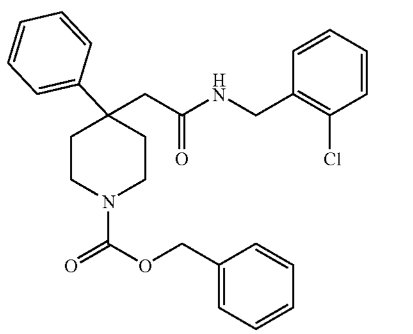 | 4-[(2-Chloro-benzylcarbamoyl)-methyl]-4-phenyl-piperidine-1-carboxylic acid benzyl ester | 478 |
| 336 | 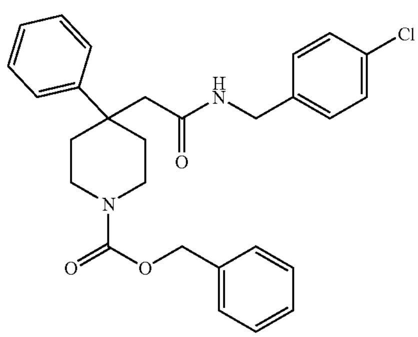 | 4-[(4-Chloro-benzylcarbamoyl)-methyl]-4-phenyl-piperidine-1-carboxylic acid benzyl ester | 478 |
| 337 | 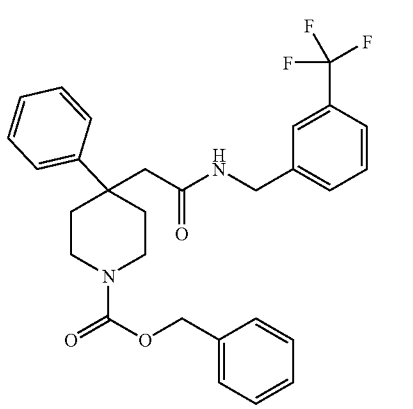 | 4-Phenyl-4-[(3-trifluoromethyl-benzylcarbamoyl)-methyl]-piperidine-1-carboxylic acid benzyl ester | 512 |

| Example | Structure | Name | M + H |
|---|---|---|---|
| 338 | 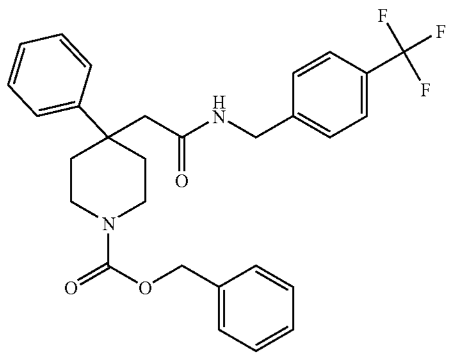 | 4-Phenyl-4-[(4-trifluoromethyl-benzylcarbamoyl)-methyl]-piperidine-1-carboxylic acid benzyl ester | 512 |
| 339 | 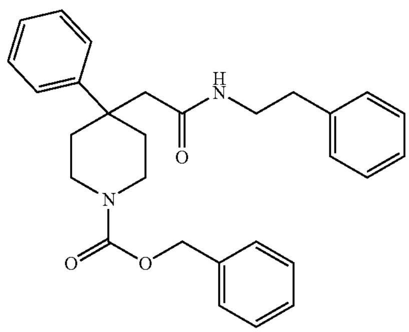 | 4-(Phenylethylcarbamoyl-methyl)-4-phenyl-piperidine-1-carboxylic acid benzyl ester | 458 |
| 340 | 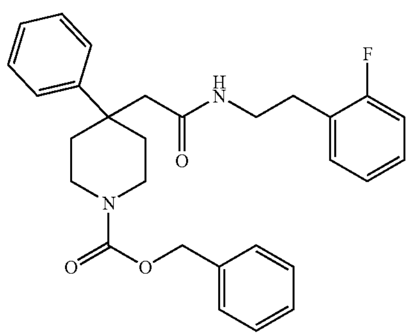 | 4-{[2-(2-Fluoro-phenyl)-ethylcarbamoyl]-methyl}-4-phenyl-piperidine-1-carboxylic acid benzyl ester | 476 |
| 341 | 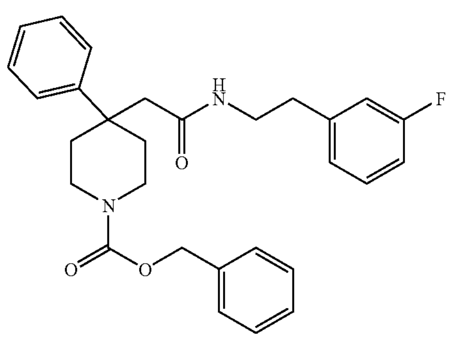 | 4-{[2-(3-Fluoro-phenyl)-ethylcarbamoyl]-methyl}-4-phenyl-piperidine-1-carboxylic acid benzyl ester | 476 |

-continued

| Example | Structure | Name | M + H |
|---|---|---|---|
| 342 | 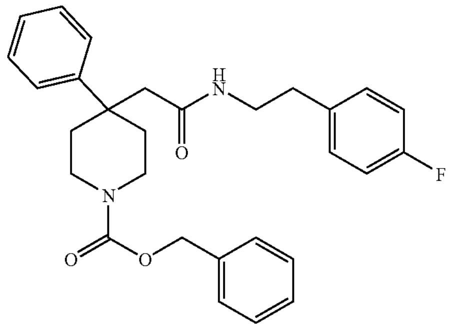 | 4-{[2-(4-Fluoro-phenyl)-ethylcarbamoyl]-methyl}-4-phenyl-piperidine-1-carboxylic acid benzyl ester | 476 |
| 343 | 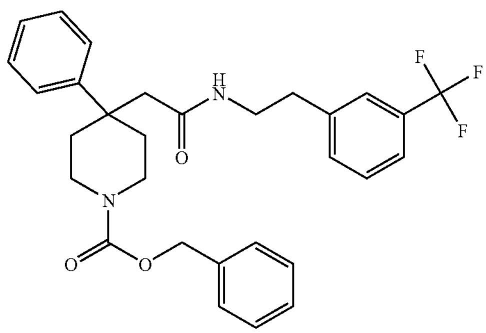 | 4-Phenyl-4-{[2-(3-trifluoromethyl-phenyl)-ethylcarbamoyl]-methyl}-piperidine-1-carboxylic acid benzyl ester | 526 |
| 344 | 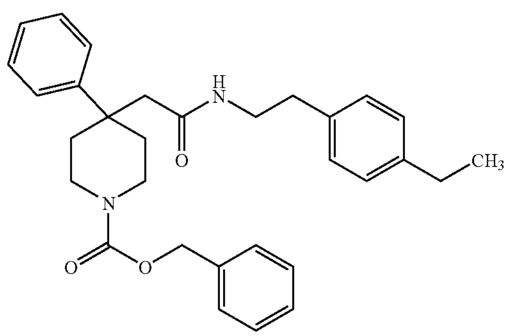 | 4-{[2-(4-Ethyl-phenyl)-ethylcarbamoyl]-methyl}-4-phenyl-piperidine-1-carboxylic acid benzyl ester | 486 |
| 345 | 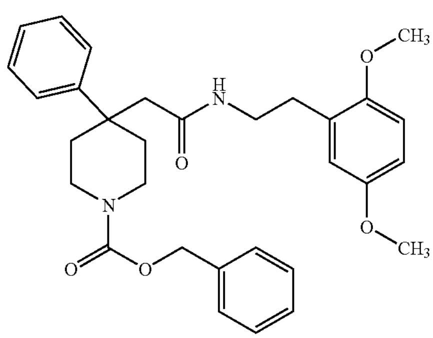 | 4-{[2-(2,5-Dimethoxy-phenyl)-ethylcarbamoyl]-methyl}-4-phenyl-piperidine-1-carboxylic acid benzyl ester | 518 |

-continued

| Example | Structure | Name | M + H |
|---|---|---|---|
| 346 | 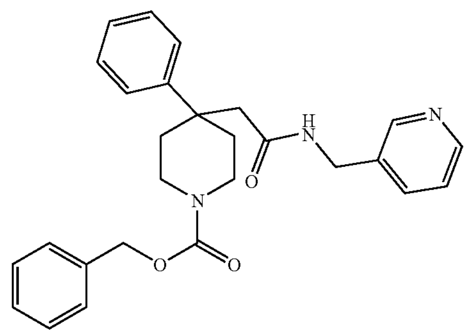 | 4-Phenyl-4-{[(pyridin-3-ylmethyl)-carbamoyl]-methyl}-piperidine-1-carboxylic acid benzyl ester | 445 |
| 347 | 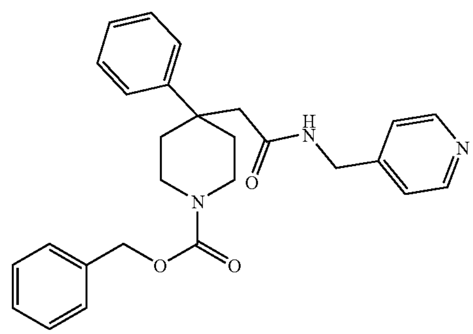 | 4-Phenyl-4-{[(pyridin-4-ylmethyl)-carbamoyl]-methyl}-piperidine-1-carboxylic acid benzyl ester | 445 |
| 348 | 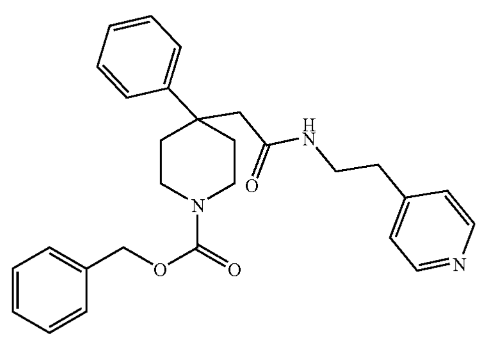 | 4-Phenyl-4-[(2-pyridin-4-yl-ethylcarbamoyl)-methyl]-piperidine-1-carboxylic acid benzyl ester | 459 |
| 349 | 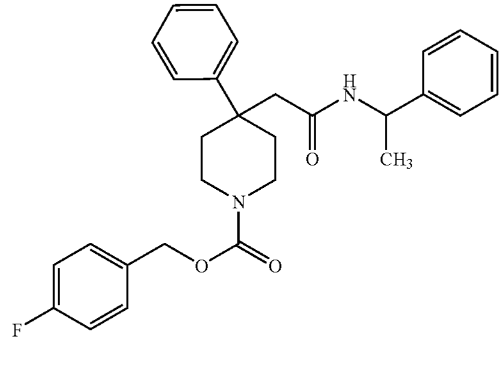 | 2-{1-[3-(4-Fluoro-phenyl)-propionyl]-4-phenyl-piperidin-4-yl}-N-(1-phenyl-ethyl)-acetamide | 474 |

-continued

| Example | Structure | Name | M + H |
|---|---|---|---|
| 350 | 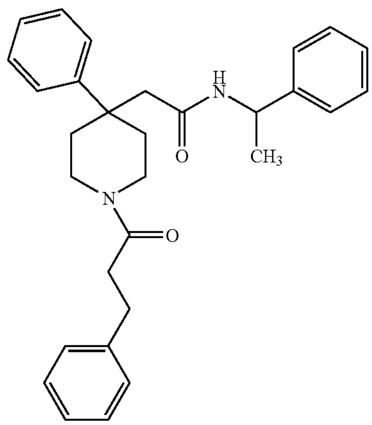 | N-(1-Phenyl-ethyl)-2-[4-phenyl-1-(3-phenyl-propionyl)-piperidin-4-yl]-acetamide | 456 |
| 351 | 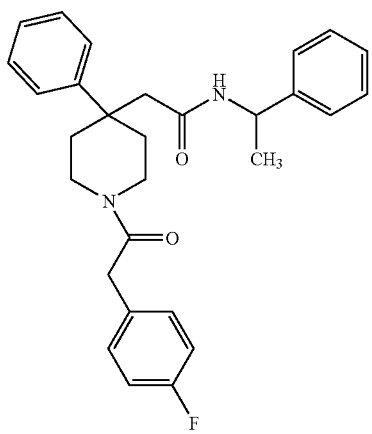 | 2-{1-[2-(4-Fluoro-phenyl)-acetyl]-4-phenyl-piperidin-4-yl}-N-(1-phenyl-ethyl)-acetamide | 460 |
| 352 | 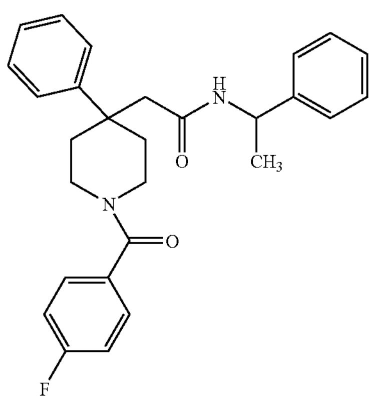 | 2-[1-(4-Fluoro-benzoyl)-4-phenyl-piperidin-4-yl]-N-(1-phenyl-ethyl)-acetamide | 446 |
| 353 | 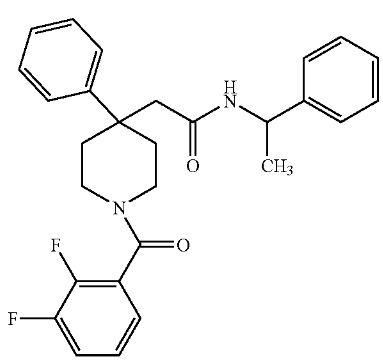 | 2-[1-(2,3-Difluoro-benzoyl)-4-phenyl-piperidin-4-yl]-N-(1-phenyl-ethyl)-acetamide | 464 |

-continued

| Example | Structure | Name | M + H |
|---|---|---|---|
| 354 | 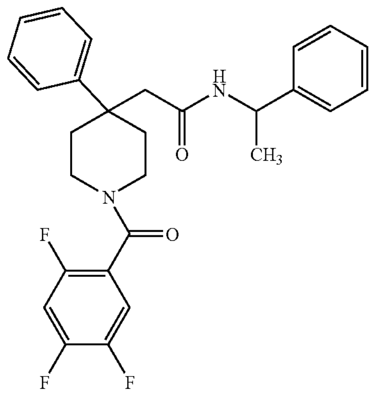 | N-(1-Phenyl-ethyl)-2-[4-phenyl-1-(2,4,5-trifluoro-benzoyl)-piperidin-4-yl]-acetamide | 482 |
| 355 | 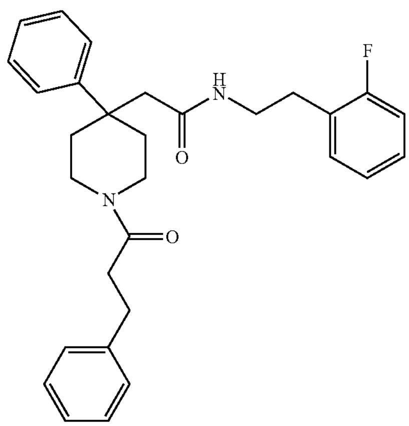 | N-[2-(2-Fluoro-phenyl)-ethyl]-2-[4-phenyl-1-(3-phenyl-propionyl)-piperidin-4-yl]-acetamide | 474 |
| 356 | 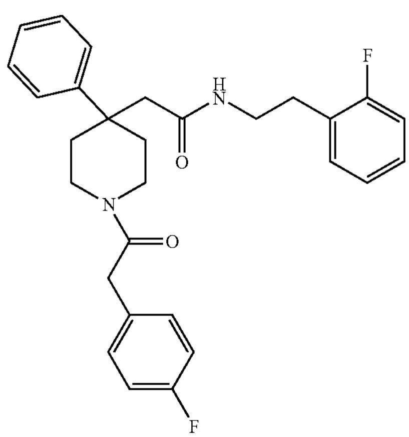 | 2-{1-[2-(4-Fluoro-phenyl)-acetyl]-4-phenyl-piperidin-4-yl}-N-[2-(2-fluoro-phenyl)-ethyl]-acetamide | 478 |

-continued

| Example | Name | M + H |
|---|---|---|
| 357 | 2-[1-(4-Fluoro-benzoyl)-4-phenyl-piperidin-4-yl]-N-[2-(2-fluoro-phenyl)-ethyl]-acetamide | 464 |
| 358 | 2-[1-(2,4-Difluoro-benzoyl)-4-phenyl-piperidin-4-yl]-N-[2-(2-fluoro-phenyl)-ethyl]-acetamide | 482 |
| 359 | N-[2-(2-Fluoro-phenyl)-ethyl]-2-[4-phenyl-1-(2,4,5-trifluoro-benzoyl)-piperidin-4-yl]-acetamide | 500 |
| 360 | 4-[(2-Methoxy-phenylcarbamoyl)-methyl]-4-phenyl-piperidine-1-carboxylic acid benzyl ester | 460 |

-continued

| Example | Structure | Name | M + H |
|---|---|---|---|
| 361 | 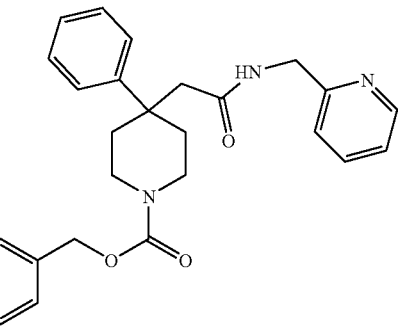 | 4-Phenyl-4-{[(pyridin-2-ylmethyl)-carbamoyl]-methyl}-piperidine-1-carboxylic acid benzyl ester | 445 |
| 362 | 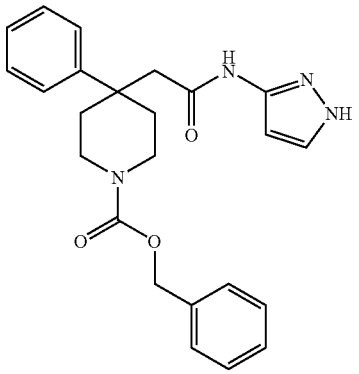 | 4-Phenyl-4-[(1H-pyrazol-3-ylcarbamoyl)-methyl]-piperidine-1-carboxylic acid benzyl ester | 419 |
| 363 | 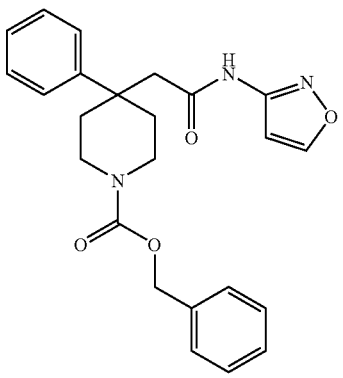 | 4-(Isoxazol-3-ylcarbamoylmethyl)-4-phenyl-piperidine-1-carboxylic acid benzyl ester | 420 |
| 364 | 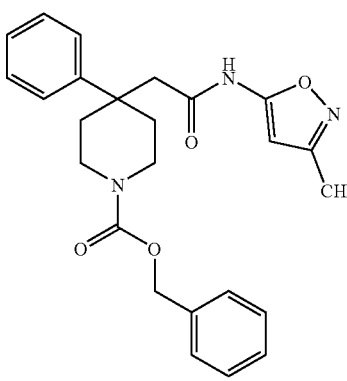 | 4-[(3-Methyl-isoxazol-5-ylcarbamoyl)-methyl]-4-phenyl-piperidine-1-carboxylic acid benzyl ester | 435 |

-continued

| Example | Structure | Name | M + H |
|---|---|---|---|
| 365 | 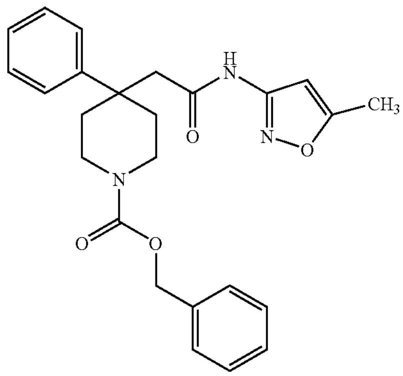 | 4-[(5-Methyl-isoxazol-3-ylcarbamoyl)-methyl]-4-phenyl-piperidine-1-carboxylic acid benzyl ester | 435 |
| 366 | 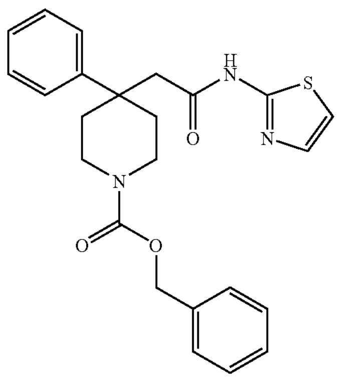 | 4-Phenyl-4-(thiazol-2-ylcarbamoylmethyl)-piperidine-1-carboxylic acid benzyl ester | 437 |
| 367 | 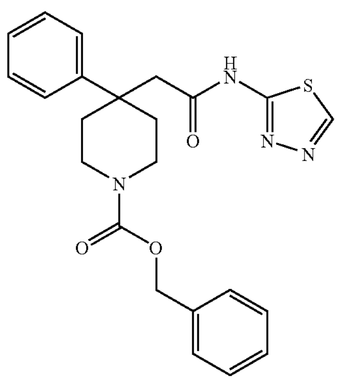 | 4-Phenyl-4-([1,3,4]thiadiazol-2-ylcarbamoylmethyl)-piperidine-1-carboxylic acid benzyl ester | 438 |
| 368 | 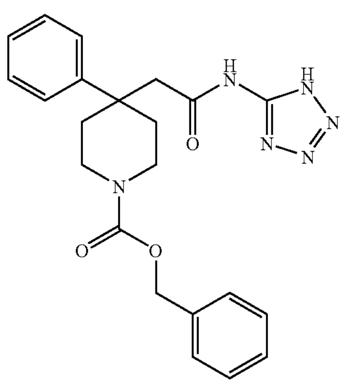 | 4-Phenyl-4-[(1H-tetraol-4-ylcarbamoyl)-methyl]-piperidine-1-carboxylic acid benzyl ester | 421 |

-continued

| Example | Structure | Name | M + H |
|---|---|---|---|
| 369 | 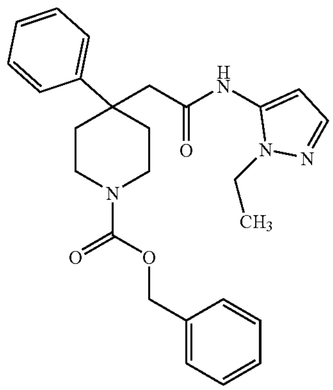 | 4-[(2-Ethyl-2H-pyrazol-3-ylcarbamoyl)-methyl]-4-phenyl-piperidine-1-carboxylic acid benzyl ester | 448 |
| 370 | 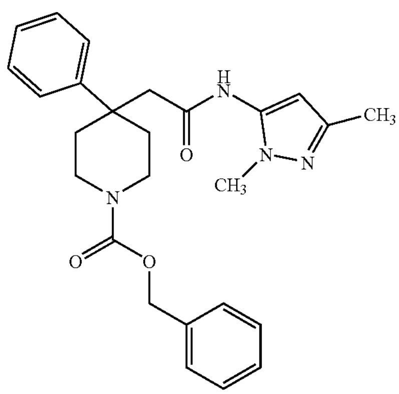 | 4-[(2,5-Dimethyl-2H-pyrazol-3-ylcarbamoyl)-methyl]-4-phenyl-piperidine-1-carboxylic acid benzyl ester | 448 |
| 371 | 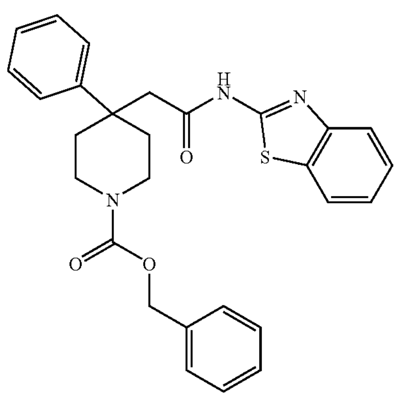 | 4-(Benzothiazol-2-ylcarbamoylmethyl)-4-phenyl-piperidine-1-carboxylic acid benzyl ester | 487 |
| 372 | 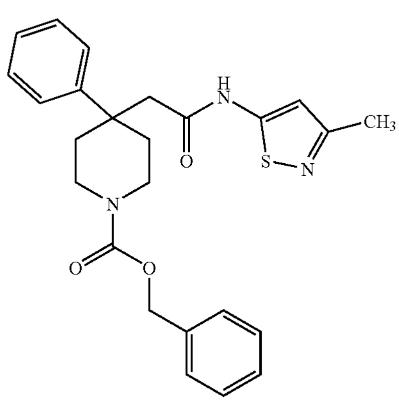 | 4-[(3-Methyl-isothiazol-5-ylcarbamoyl)-methyl]-4-phenyl-piperidine-1-carboxylic acid benzyl ester | 451 |

-continued

| Example | Structure | Name | M + H |
|---|---|---|---|
| 373 | 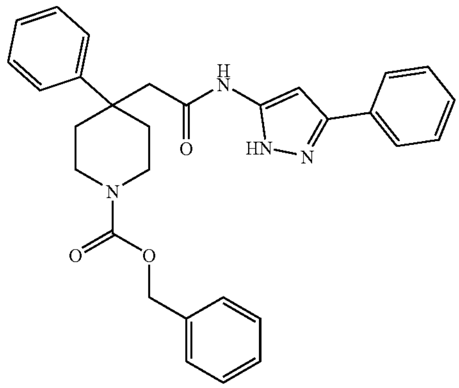 | 4-Phenyl-4-[(5-phenyl-2H-pyrazol-3-ylcarbamoyl)-methyl]-piperidine-1-carboxylic acid benzyl ester | 496 |
| 374 | 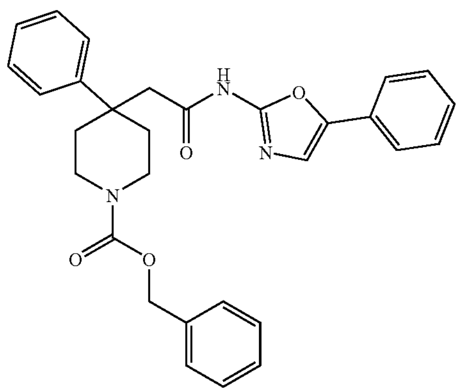 | 4-Phenyl-4-[(5-phenyl-oxazol-2-ylcarbamoyl)-methyl]-piperidine-1-carboxylic acid benzyl ester | 497 |
| 375 | 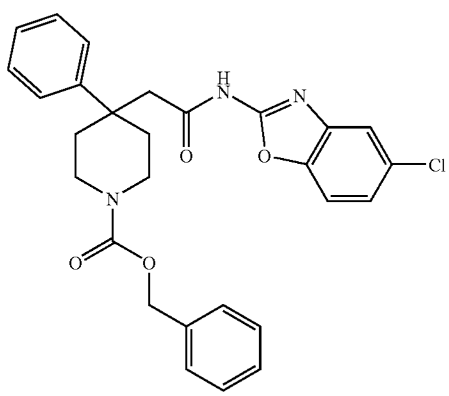 | 4-[(5-Chloro-benzooxazol-2-ylcarbamoyl)-methyl]-4-phenyl-piperidine-1-carboxylic acid benzyl ester | 505 |
| 376 | 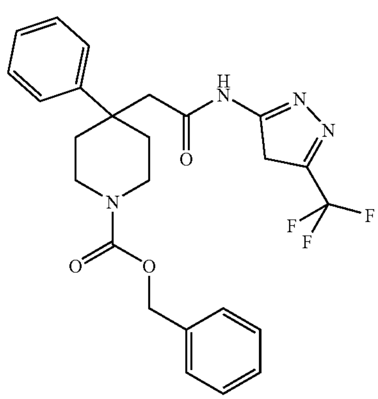 | 4-Phenyl-4-[(5-trifluoromethyl-[1,3,4]thiadiazol-2-ylcarbamoyl)-methyl]-piperidine-1-carboxylic acid benzyl ester | 506 |

-continued

| Example | Structure | Name | M + H |
|---|---|---|---|
| 377 | 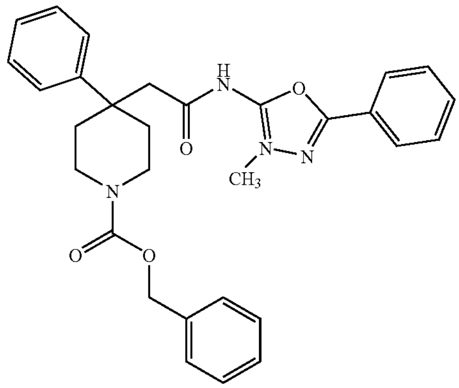 | 4-[(2-Methyl-5-phenyl-2H-pyrazol-3-ylcarbamoyl)-methyl]-4-phenyl-piperidine-1-carboxylic acid benzyl ester | 510 |
| 378 | 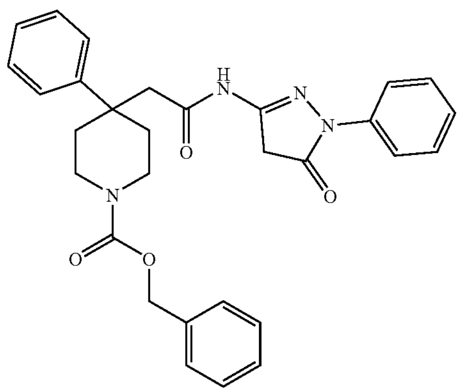 | 4-[(5-Oxo-1-phenyl-4,5-dihydro-1H-pyrazol-3-ylcarbamoyl)-methyl]-4-phenyl-piperidine-1-carboxylic acid benzyl ester | 512 |
| 379 | 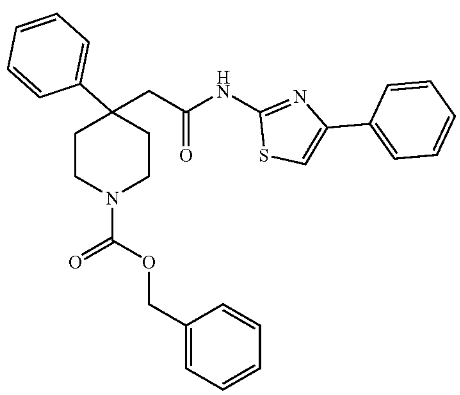 | 4-Phenyl-4-[(4-phenyl-thiazol-2-ylcarbamoyl)-methyl]-piperidine-1-carboxylic acid benzyl ester | 513 |
| 380 | 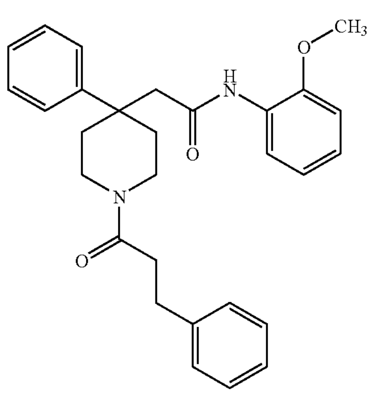 | N-(2-methoxy-phenyl)-2-[4-phenyl-1-(3-phenyl-propionyl)-piperidin-4-yl]-acetamide | 458 |

Example 381

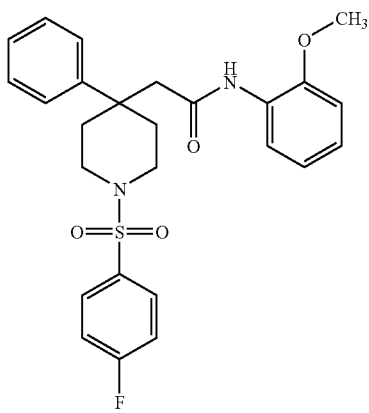

2-[1-(4-Fluoro-benzenesulfonyl)-4-phenyl-piperidin-4-yl]-N-(2-methoxy-phenyl)-acetamide Synthesis Title compound: 2-[1-(4-Fluoro-benzenesulfonyl)-4-phenyl-piperidin-4-yl]-N-(2-methoxy-phenyl)-acetamide was prepared using methodology described in Example 95. LRMS m/z 484 (M+H)$^+$.

Example 382

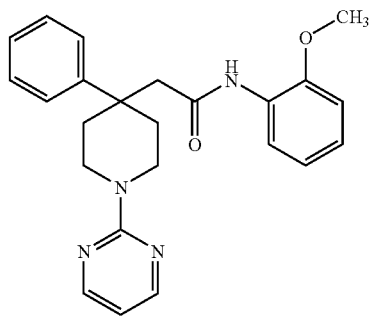

N-(2-Methoxy-phenyl)-2-(4-phenyl-1-pyrimidin-2-yl-piperidin-4-yl)-acetamide

Synthesis

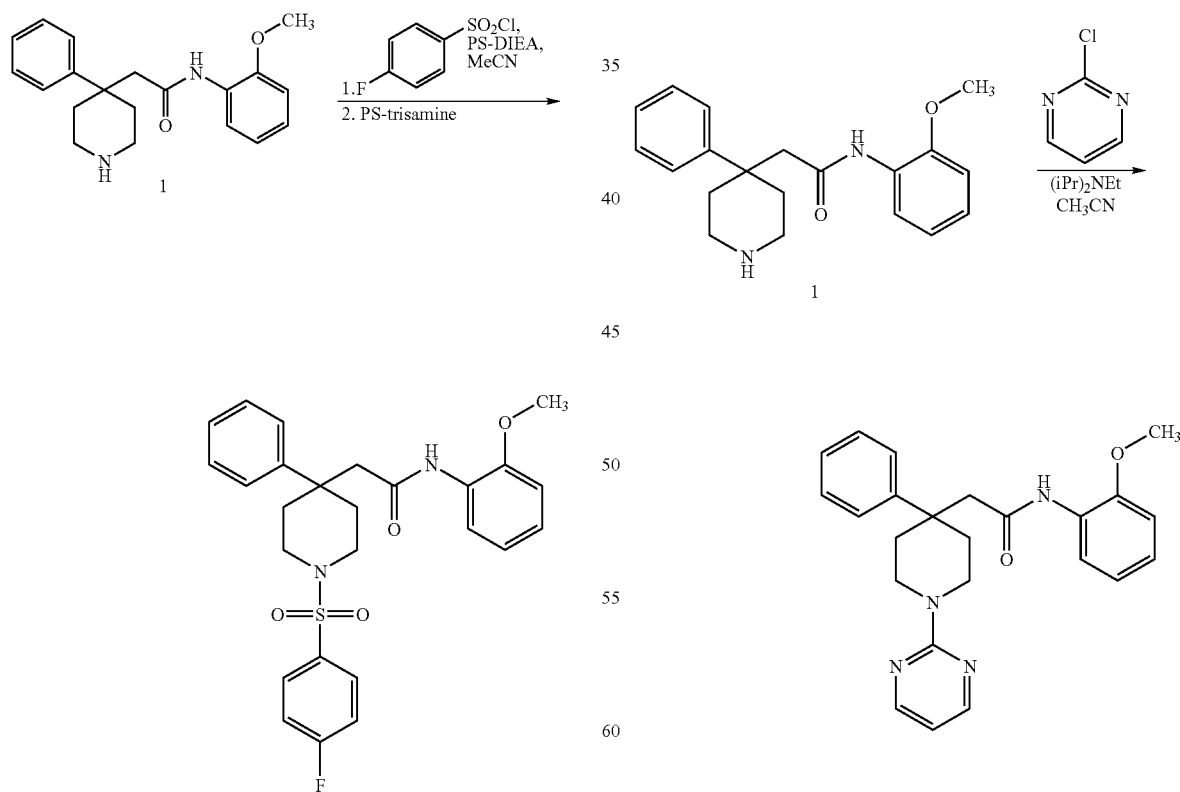

Compound 1: Compound 1 was prepared using methodology described in Example 324. LRMS m/z 325 (M+H)$^+$.

Compound 1: Compound 1 was prepared using methodology described in Example 324. LRMS m/z 325 (M+H)$^+$.

Title Compound: N-(2-Methoxy-phenyl)-2-(4-phenyl-1-pyrimidin-2-yl-piperidin-4-yl)-acetamide was prepared using methodology described in Example 521. LRMS m/z 403 (M+H)$^+$.

Example 383

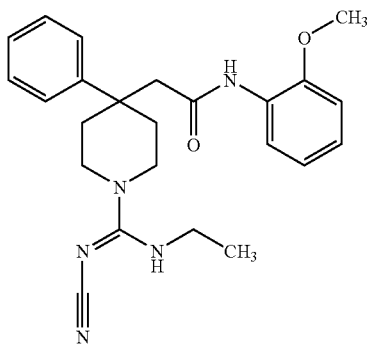

Synthesis

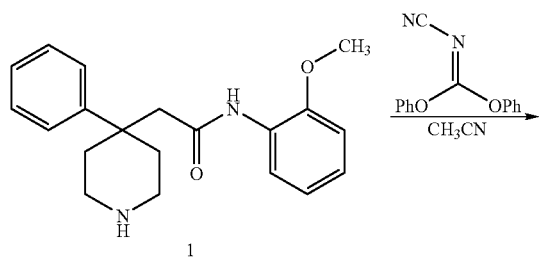

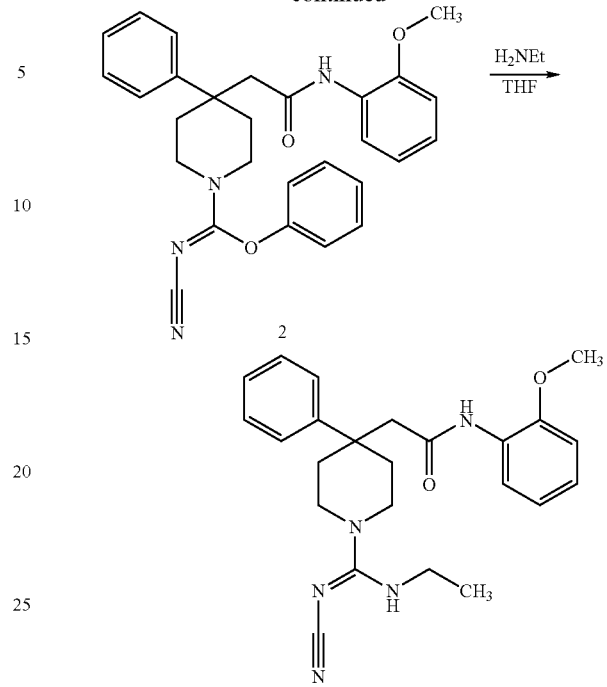

Compound 1: Compound 1 was prepared using methodology described in Example 324. LRMS m/z 325 (M+H)$^+$.

Compound 2: Compound 2 was prepared using methodology described in Example 25. LRMS m/z 470 (M+H)$^+$.

Title Compound: The title compound was prepared using methodology described in Example 25. LRMS m/z 421 (M+H)$^+$.

Examples 384 and 385

Examples 384 and 385 was prepared using methodology described in Example 383.

| Example | Structure | Name | (M + H) |
|---|---|---|---|
| 384 | 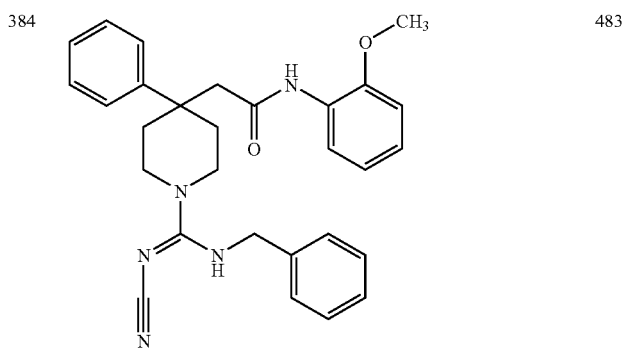 | | 483 |

| Example | Structure | Name | (M + H) |
|---|---|---|---|
| 385 | 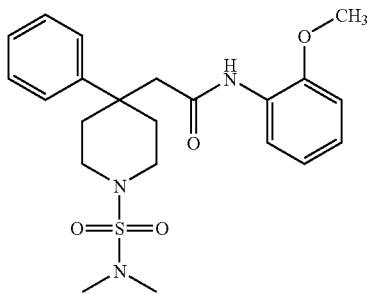 | | 497 |

Example 386

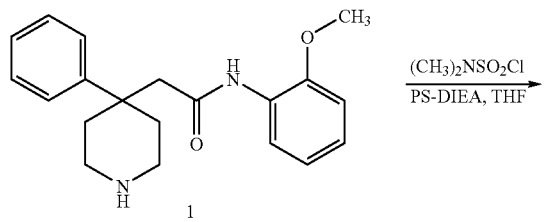

2-(1-Dimethylsulfamoyl-4-phenyl-piperidin-4-yl)-N-(2-methoxy-phenyl)-acetamide

Synthesis

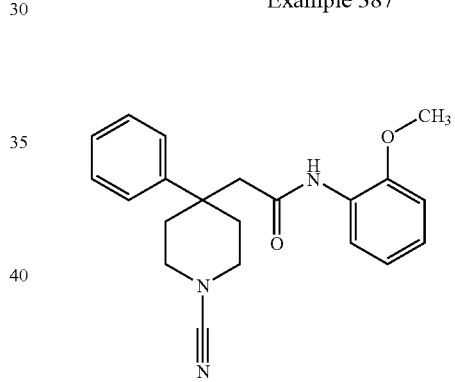

Compound 1: Compound 1 was prepared using methodology described in Example 324. LRMS m/z 325 (M+H)$^+$.

Title Compound: 2-(1-Dimethylsulfamoyl-4-phenyl-piperidin-4-yl)-N-(2-methoxy-phenyl)-acetamide was prepared using methodology described in Example 16. LRMS m/z 432 (M+H)$^+$.

Example 387

2-(1-Cyano-4-phenyl-piperidin-4-yl)-N-(2-methoxy-phenyl)-acetamide

Synthesis

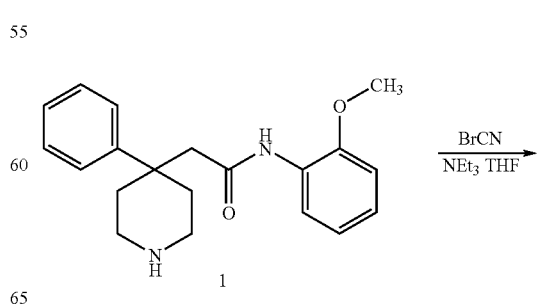

263

-continued

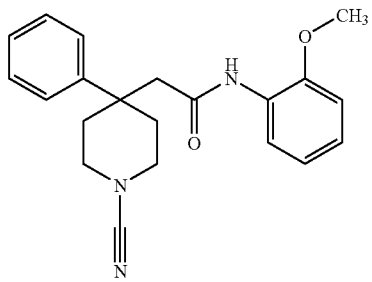

Compound 1: Compound 1 was prepared using methodology described in Example 324. LRMS m/z 325 (M+H)+.

Title Compound: 2-(1-Cyano-4-phenyl-piperidin-4-yl)-N-(2-methoxy-phenyl)-acetamide may prepared using methodology described in Example 521 using cyanogen bromide instead of 2-chloropyrimidine. LRMS m/z 350 (M+H)+.

Example 388

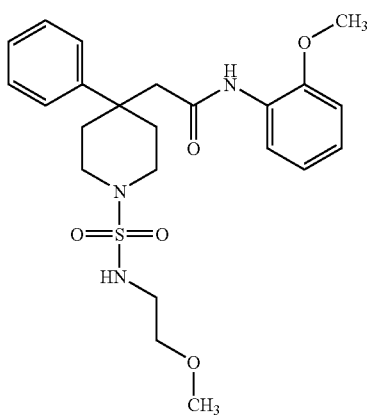

264

2-[1-(2-Methoxy-ethylsulfamoyl)-4-phenyl-piperidin-4-yl]-N-(2-methoxy-phenyl)-acetamide Synthesis

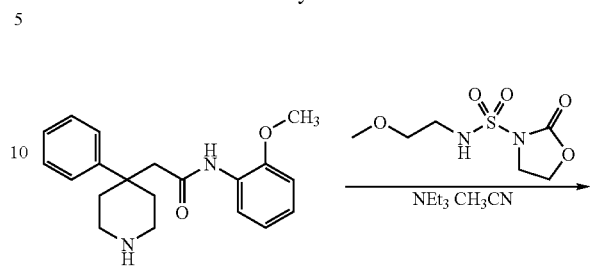

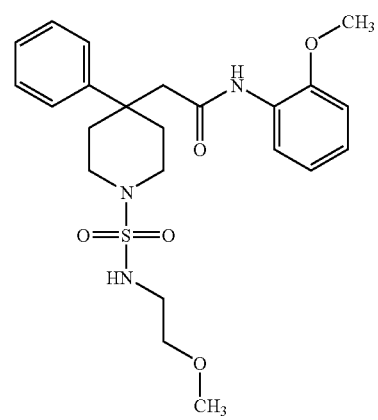

Compound 1: Compound 1 was prepared using methodology described in Example 324. LRMS m/z 325 (M+H)+.

Title Compound: 2-[1-(2-Methoxy-ethylsulfamoyl)-4-phenyl-piperidin-4-yl]-N-(2-methoxy-phenyl)-acetamide was prepared using methodology described in Example 17. LRMS m/z 462 (M+H)+.

Example 389

Example 389 was prepared using methodology described in Example 388.

| Example | Structure | Name | [M + H] |
|---|---|---|---|
| 389 | 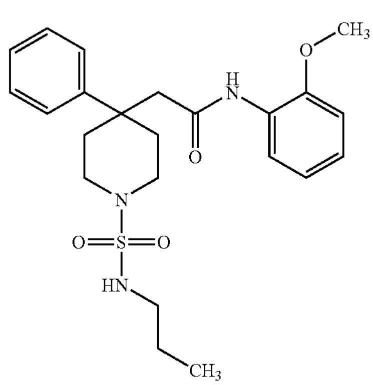 | N-(2-Methoxy-phenyl)-2-(4-phenyl-1-propylsulfamoyl-piperidin-4-yl)-acetamide | 447 |

Example 390

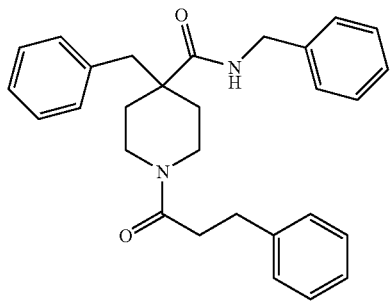

4-benzyl-1-(3-phenyl-propionyl)-piperidine-4-carboxylic acid benzylamide

Synthesis

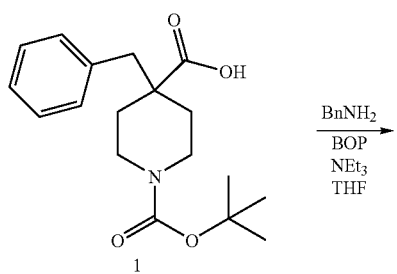

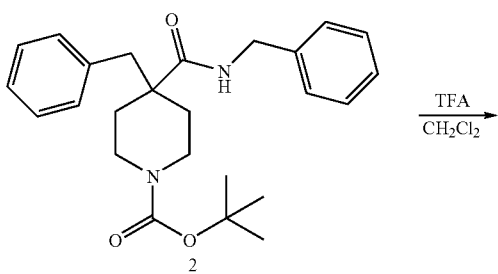

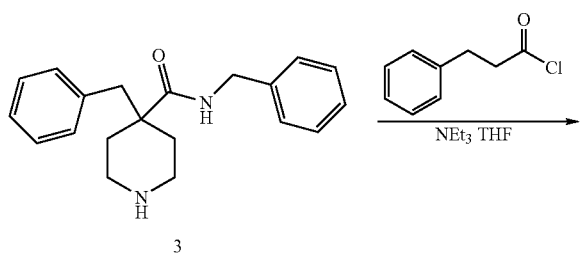

-continued

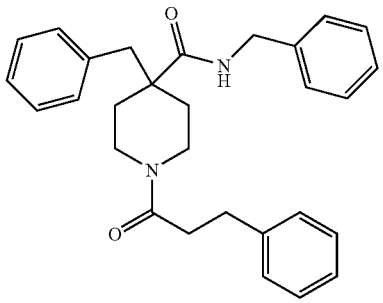

Compound 1: Compound 1 is commercially available.

Compound 2: A solution of compound 1 (0.86 g; 2.7 mmol) in tetrahydrofuran (25 mL) was treated with triethylamine (0.49 mL; 3.7 mmol) and benzotriazol-1-yloxytris(dimethylamino)phosphonium hexafluorophosphate (1.3 g; 2.9 mmol). After 0.5 h benzylamine (0.33 mL; 3.0 mmol) was added and the reaction mixture was heated to 50° C. for 15 h. The tetrahydrofuran was removed by evaporation and the residue was portioned between ethyl acetate and 5% aqueous hydrochloric acid. The organic layer was separated, washed with saturated aqueous sodium chloride, dried (anhydrous sodium sulfate), filtered and concentrated. Column chromatography on silica gel using 1:1 hexane:ethyl acetate as the eluent gave 0.81 g of compound 2 as a colorless oil. LRMS m/z 410 (M+H)$^+$ Compound 3: A solution of compound 2 (0.41 g; 1.0 mmol) in dichloromethane (15 mL) was treated with trifluoroacetic acid (2 mL) at room temperature. After 24 h additional dichloromethane (50 mL) and 1 N sodium hydroxide (40 mL) was added. The organic layer was separated, washed with saturated aqueous sodium chloride, dried (anhydrous sodium sulfate), filtered and concentrated to give compound 3 that was used in the next step without additional purification. LRMS m/z 309 (M+H)$^+$ Title Compound: A solution of compound 3 (0.16 g; 0.52 mmol) in tetrahydrofuran (20 mL) was treated with triethylamine (0.09 mL; 0.65 mmol) and hydrocinnamoyl chloride (0.1 g; 0.59 mmol) at room temperature. After 16 h the tetrahydrofuran was removed by evaporation and the residue was portioned between ethyl acetate and 5% aqueous hydrochloric acid. The organic layer was separated, washed with saturated sodium chloride, dried (anhydrous sodium sulfate) and concentrated. Column chromatography on silica gel using 1:1 hexane:ethyl acetate as the eluent gave 0.15 g of 4-benzyl-1-(3-phenyl-propionyl)-piperidine-4-carboxylic acid benzylamide as a white solid. LRMS m/z 442 (M+H)$^+$.

Example 391

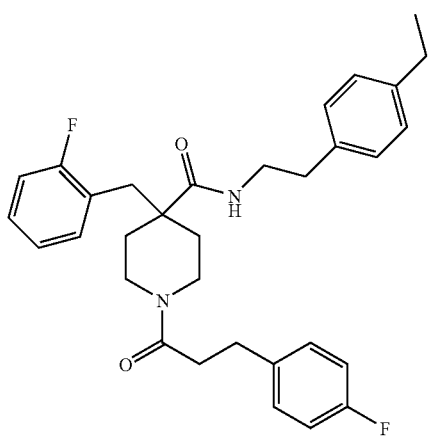

4-(2-Fluoro-benzyl)-1-[3-(4-fluoro-phenyl)-propionyl]-piperidine-4-carboxylic acid [2-(4-ethyl-phenyl)-ethyl]-amide Synthesis

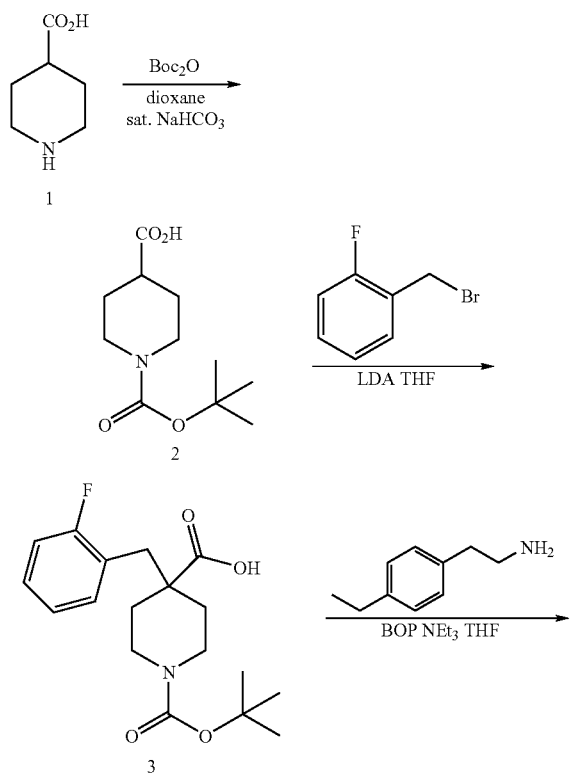

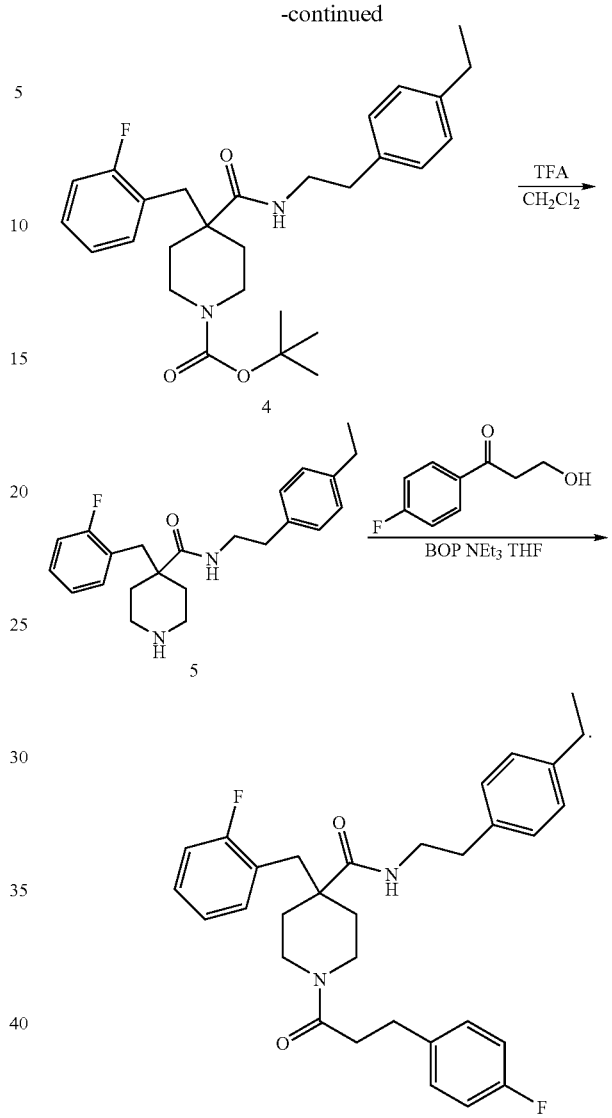

Compound 1: Compound 1 is commercially available.

Compound 2: Di-tert-butyl dicarbonate (12.66 g, 58.0 mmol) was added to a solution of piperidine-4-carboxylic acid (5.00 g, 38.7 mmol) in dioxane (100 mL) and saturated aqueous sodium bicarbonate (100 mL) and stirred at room temperature for 48 h. The reaction mixture was concentrated to 100 mL under reduced pressure and ethyl acetate (200 mL) was added. The solution was made acidic with 6M hydrochloric acid (pH=3), the organic layer collected and concentrated under reduced pressure to give 7.22 g of piperidine-1,4-dicarboxylic acid mono-tert-butyl ester. LRMS m/z 228.1 (M−H)$^−$.

Compound 3: Lithium diisopropylamide (10.9 mmol, 2M tetrahydrofuran) was added to a solution of piperidine-1,4-dicarboxylic acid mono-tert-butyl ester (1.00 g, 4.36 mmol) in tetrahydrofuran (25 mL) at 0° C. After 1.5 h 2-fluorobenzyl bromide (0.788 mL, 6.54 mmol) was added, the reaction mixture was allowed to warm to room temperature and stirred overnight. The reaction was quenched with the addition of water (10 mL) followed by 1M hydrochloric acid (10 mL). The aqueous layer was extracted with ethyl acetate (3×50 mL), the organic layers collected, concentrated under reduced pressure and crude product purified by column chromatography to give 0.330 g, (22 %) of 4-(2-fluoro-benzyl)-piperidine-1,4-dicarboxylic acid mono-tert-butyl ester. $^1$H-NMR (CD$_3$Cl$_3$, 300 MHz) δ 7.11-7.00 (m, 5H), 4.00 (br., 2H), 2.92 (s, 2H), 2.90 (br., 2H), 2.05 (br., 2H), 1.46 (br., 2H), 1.44 (s, 9H).

Compound 4: Benzotriazol-1-yloxytris(dimethylamino)phosphonium hexafluorophosphate (0.650 g, 1.47 mmol) was added to a solution of 2-(4-ethyl-phenyl)-ethylamine (0.235 mL, 1.47 mmol), 4-(2-fluoro-benzyl)-piperidine-1,4-dicarboxylic acid mono-tert-butyl ester (0.330 g, 0.978 mmol) and triethylamine (0.409 mL, 2.93 mmol) in tetrahydrofuran (5 mL). After 1 hour the mixture was diluted with ethyl ether (20 mL) and washed with saturated aqueous sodium bicarbonate (20 mL) followed by water (2×10 mL). The organic layer was collected, concentrated under reduced pressure and crude product purified by column chromatography to give 0.301 g (65 %) of 4-[2-(4-ethyl-phenyl)-ethylcarbamoyl]-4-(2-fluoro-benzyl)-piperidine-1-carboxylic acid tert-butyl ester. LRMS m/z 469.1 (M+H)$^+$.

Compound 5: Trifluoroacetic acid (20 mL) was added to a solution 4-[2-(4-ethyl-phenyl)-ethylcarbamoyl]-4-(2-fluoro-benzyl)-piperidine-1-carboxylic acid tert-butyl ester (0.300 g, 0.64 mmol) in dichloromethane (50 mL). After 1 h the reaction mixture was concentrated under reduced pressure, the crude product taken up in 1M sodium hydroxide (50 mL) and extracted with ethyl acetate (3×50 mL). The organic layers were collected, concentrated under reduced pressure and crude product purified by column chromatography to give 0.188 g (80 %) of 4-(2-fluoro-benzyl)-piperidine-4-carboxylic acid [2-(4-ethyl-phenyl)-ethyl]-amide LRMS m/z 369.1 (M+H)$^+$.

Title Compound: Benzotriazol-1-yloxytris(dimethylamino)phosphonium hexafluorophosphate (0.266 g, 0.602 mmol) was added to a solution of 4-(2-fluoro-benzyl)-piperidine-4-carboxylic acid [2-(4-ethyl-phenyl)-ethyl]-amide (0.185 g, 0.502 mmol), 3-(4-fluoro-phenyl)-propionic acid (0.101 g, 0.602 mmol) and triethylamine (0.210 mL, 1.51 mmol) in tetrahydrofuran (5 mL). After 1 h the mixture was diluted with ethyl ether (20 mL), washed with saturated aqueous sodium bicarbonate (20 mL) followed by water (2×10 mL). The organic layer was collected, concentrated under reduced pressure and the crude product purified by column chromatography to give 0.105 g (40 %) of 4-(2-fluoro-benzyl)-1-[3-(4-fluoro-phenyl)-propionyl]-piperidine-4-carboxylic acid [2-(4-ethyl-phenyl)-ethyl]-amide LRMS m/z 519.2 (M+H)$^+$.

Example 392

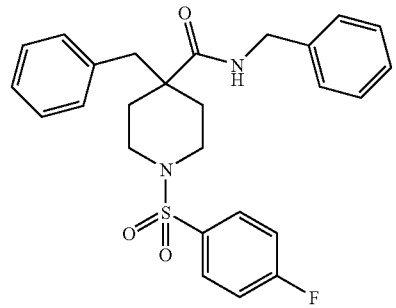

4-Benzyl-1-(4-fluoro-benzenesulfonyl)-piperidine-4-carboxylic acid benzylamide

Synthesis

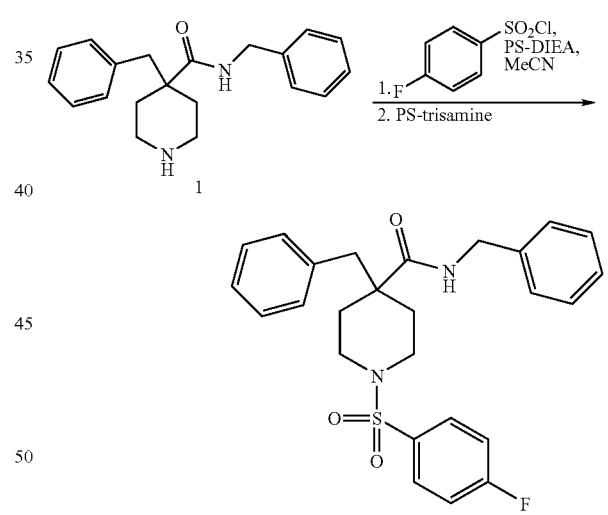

Compound 1: Compound 1 was prepared as described in Example 390.

Title Compound: 4-Benzyl-1-(4-fluoro-benzenesulfonyl)-piperidine-4-carboxylic acid benzylamide was prepared using methodology described in Example 95. LMRS m/z 467 (M+H)$^+$.

Examples 393 to 520

Examples 393 to 530 were synthesized using methodology described in Example 391 and Example 392.

| Example | Structure | Name | M + H |
|---|---|---|---|
| 393 | 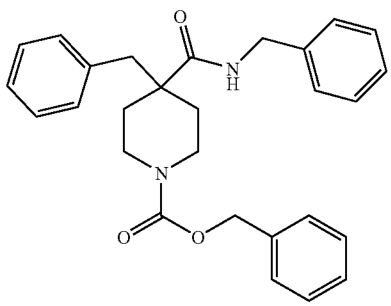 | 4-Benzyl-4-benzylcarbamoyl-piperidine-1-carboxylic acid benzyl ester | 444 |
| 394 | 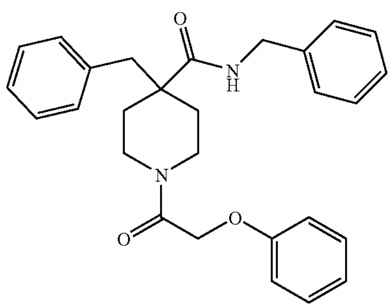 | 4-Benzyl-1-(2-phenoxy-acetyl)-piperidine-4-carboxylic acid benzylamide | 444 |
| 395 | 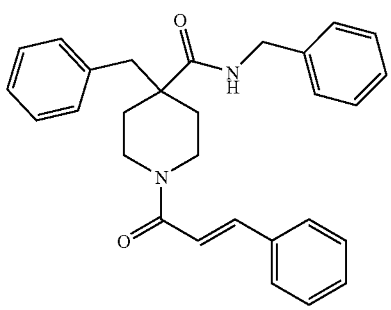 | 4-Benzyl-1-(3-phenyl-acryloyl)-piperidine-4-carboxylic acid benzylamide | 440 |
| 396 | 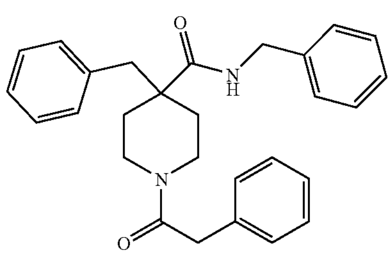 | 4-Benzyl-1-phenylacetyl-piperidine-4-carboxylic acid benzylamide | 428 |
| 397 | 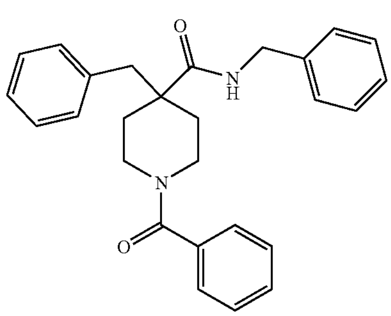 | 1-Benzoyl-4-benzyl-piperidine-4-carboxylic acid benzylamide | 414 |

-continued

| Example | Structure | Name | M + H |
|---|---|---|---|
| 398 | 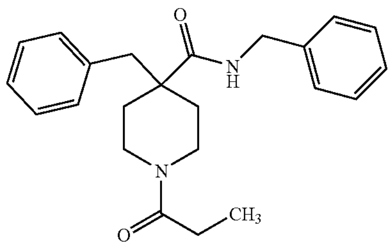 | 4-Benzyl-1-propionyl-piperidine-4-carboxylic acid benzylamide | 365 |
| 399 | 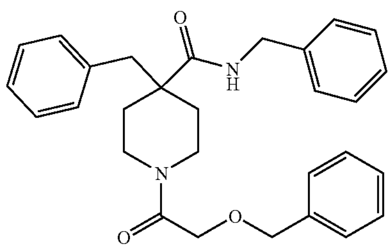 | 4-Benzyl-1-(2-benzyloxy-acetyl)-piperidine-4-carboxylic acid benzylamide | 458 |
| 400 | 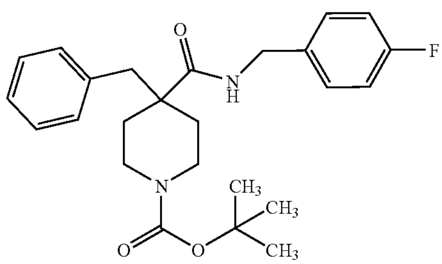 | 4-Benzyl-4-(4-fluoro-benzylcarbamoyl)-piperidine-1-carboxylic acid tert-butyl ester | 428 |
| 401 | 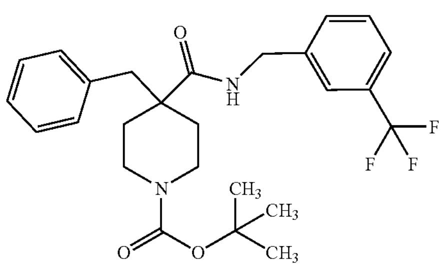 | 4-Benzyl-4-(3-trifluoromethyl-benzylcarbamoyl)-piperidine-1-carboxylic acid tert-butyl ester | 478 |
| 402 | 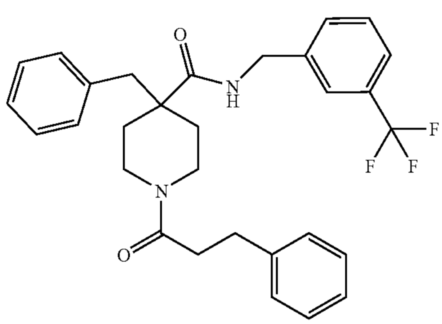 | 4-Benzyl-1-(3-phenyl-propionyl)-piperidine-4-carboxylic acid 3-trifluoromethyl-benzylamide | 510 |

-continued

| Example | Structure | Name | M + H |
|---|---|---|---|
| 403 | 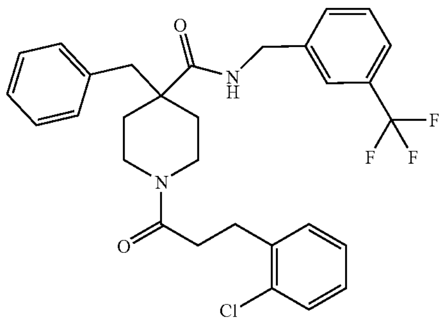 | 4-Benzyl-1-[3-(2-chloro-phenyl)-propionyl]-piperidine-4-carboxylic acid 3-trifluoromethyl-benzylamide | 544 |
| 404 | 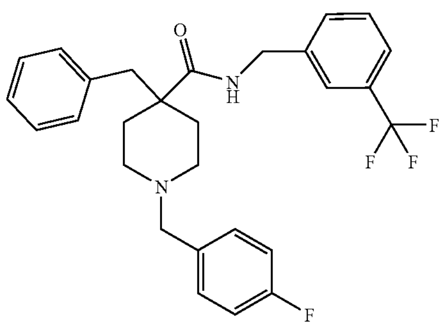 | 4-Benzyl-1-(4-Fluoro-benzyl)-piperidine-4-carboxylic acid 3-trifluoromethyl-benzylamide | 486 |
| 405 | 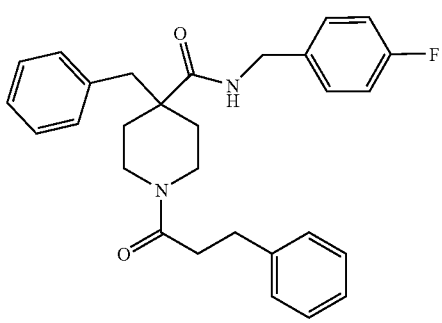 | 4-Benzyl-1-(3-phenyl-propionyl)-piperidine-4-carboxylic acid 4-fluoro-benzylamide | 460 |
| 406 | 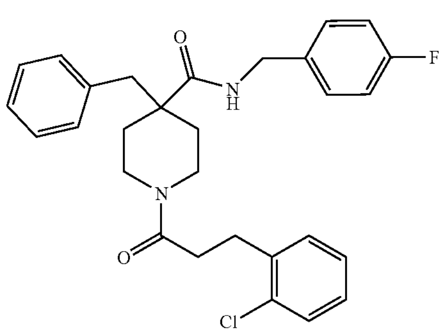 | 4-Benzyl-1-[3-(2-chloro-phenyl)-propionyl]-piperidine-4-carboxylic acid 4-fluoro-benzylamide | 494 |

-continued

| Example | Structure | Name | M + H |
|---|---|---|---|
| 407 | 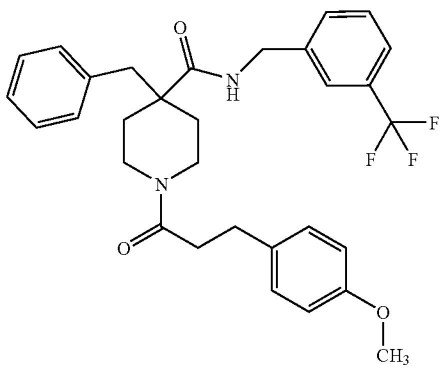 | 4-Benzyl-1-[3-(4-methoxy-phenyl)-propionyl]-piperidine-4-carboxylic acid 3-trifluoromethyl-benzylamide | 540 |
| 408 | 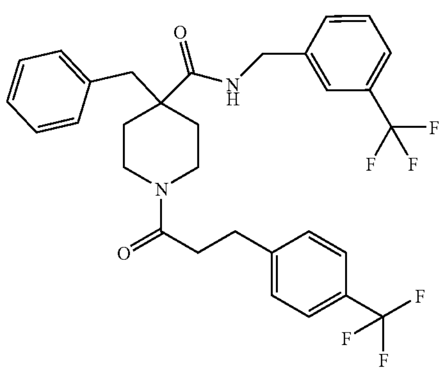 | 4-Benzyl-1-[3-(4-trifluoromethyl-phenyl)-propionyl]-piperidine-4-carboxylic acid 3-trifluoromethyl-benzylamide | 578 |
| 409 | 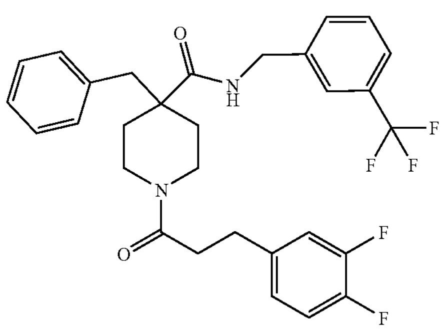 | 4-Benzyl-1-[3-(3,4-difluoro-phenyl)-propionyl]-piperidine-4-carboxylic acid 3-trifluoromethyl-benzylamide | 546 |
| 410 | 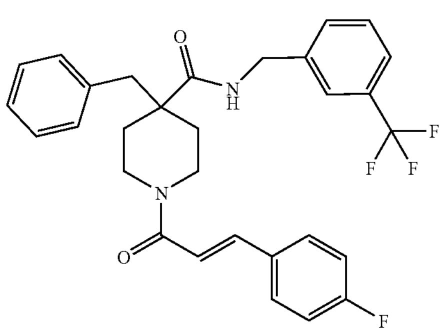 | 4-Benzyl-1-[3-(4-fluoro-phenyl)-acryloxyl]-piperidine-4-carboxylic acid 3-trifluoromethyl-benzylamide | 526 |

-continued

| Example | Structure | Name | M + H |
|---|---|---|---|
| 411 | 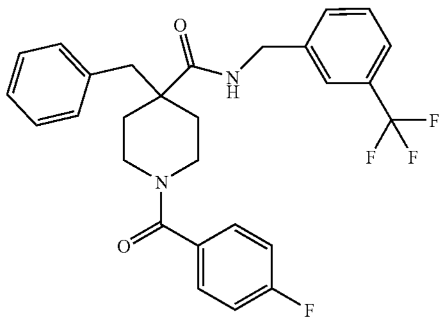 | 4-Benzyl-1-(4-fluoro-benzoyl)-piperidine-4-carboxylic acid 3-trifluoromethyl-benzylamide | 500 |
| 412 | 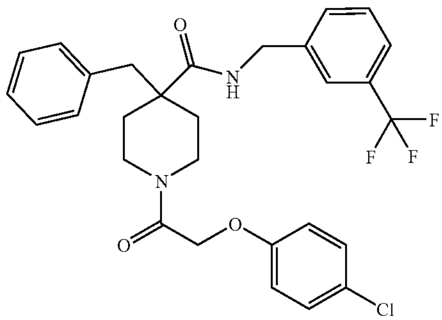 | 4-Benzyl-1-[2-(4-chloro-phenoxy)-acetyl]-piperidine-4-carboxylic acid 3-trifluoromethyl-benzylamide | 546 |
| 413 | 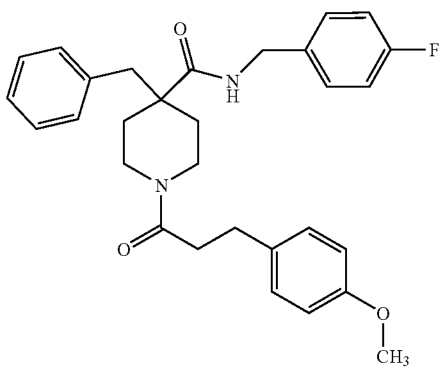 | 4-Benzyl-1-[3-(4-methoxy-phenyl)-propionyl]-piperidine-4-carboxylic acid 4-fluoro-benzylamide | 490 |
| 414 | 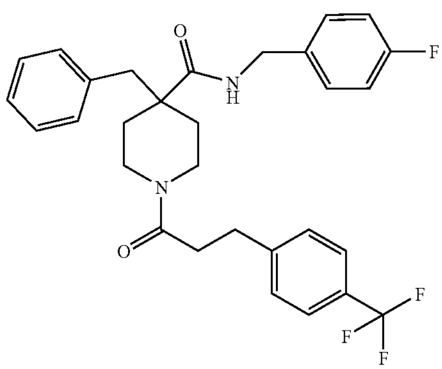 | 4-Benzyl-1-[3-(4-trifluoromethyl-phenyl)-propionyl]-piperidine-4-carboxylic acid 4-fluoro-benzylamide | 528 |

| Example | Structure | Name | M + H |
|---|---|---|---|
| 415 | 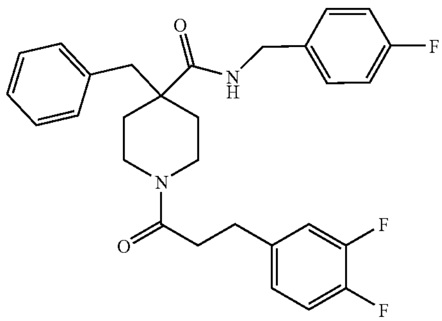 | 4-Benzyl-1-[3-(3,4-difluoro-phenyl)-propionyl]-piperidine-4-carboxylic acid 4-fluoro-benzylamide | 496 |
| 416 | 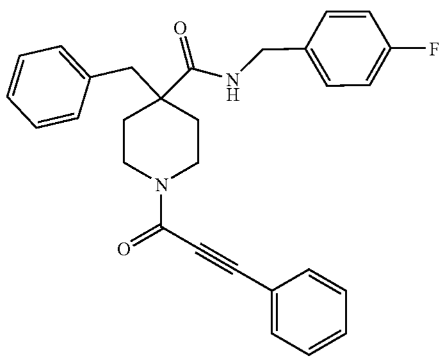 | 4-Benzyl-1-(3-phenyl-propynoyl)-piperidine-4-carboxylic acid 4-fluoro-benzylamide | 456 |
| 417 | 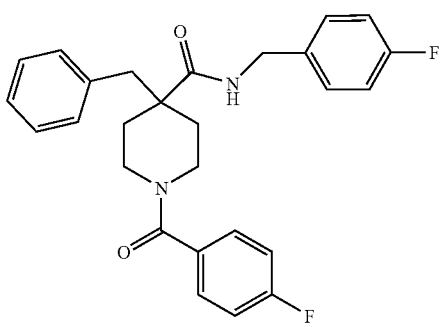 | 4-Benzyl-1-(4-fluoro-benzoyl)-piperidine-4-carboxylic acid 4-fluoro-benzylamide | 450 |
| 418 | 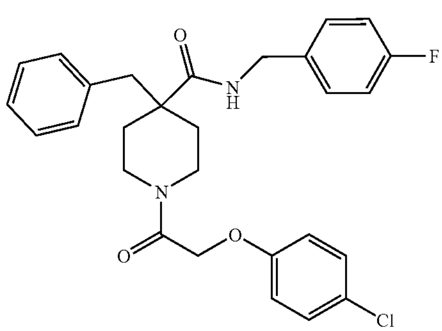 | 4-Benzyl-1-[2-(4-chloro-phenoxy)-acetyl]-piperidine-4-carboxylic acid 4-fluoro-benzylamide | 496 |

-continued

| Example | Structure | Name | M + H |
|---|---|---|---|
| 419 | 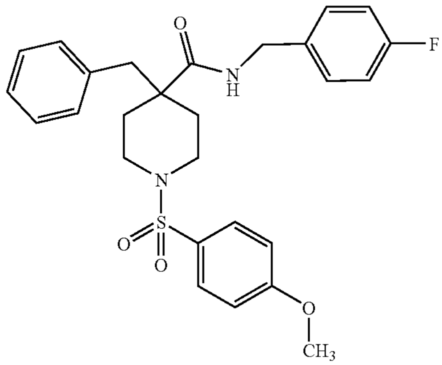 | 4-Benzyl-1-(4-methoxy-benzenesulfonyl)-piperidine-4-carboxylic acid 4-fluoro-benzylamide | 498 |
| 420 | 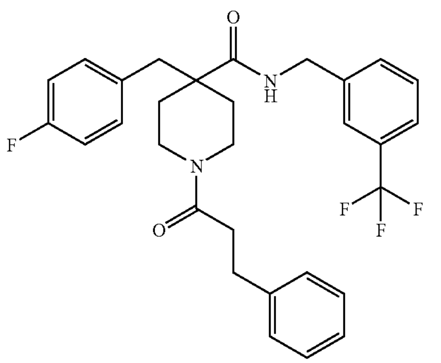 | 4-(4-Fluoro-benzyl)-1-(3-phenyl-propionyl)-piperidine-4-carboxylic acid 3-trifluoromethyl-benzylamide | 528 |
| 421 | 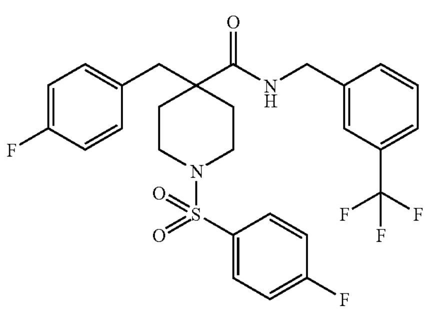 | 1-(4-fluoro-benzenesulfonyl)-4-(4-fluoro-benzyl)-piperidine-4-carboxylic acid 3-trifluoromethyl-benzylamide | 554 |
| 422 | 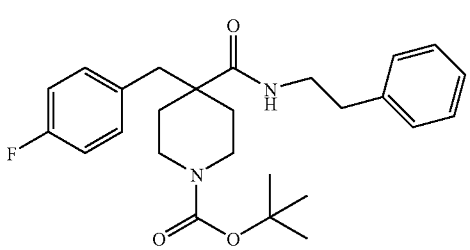 | 4-(4-Fluoro-benzyl)-4-phenylethylcarbamoyl-piperidine-1-carboxylic acid tert-butyl ester | 442 |
| 423 | 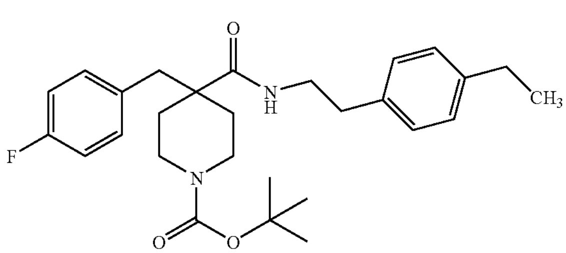 | 4-[2-(4-Ethyl-phenyl)-ethylcarbamoyl]-4-(4-fluoro-benzyl)-piperidine-1-carboxylic acid tert-butyl ester | 470 |

-continued

| Example | Structure | Name | M + H |
|---|---|---|---|
| 424 | 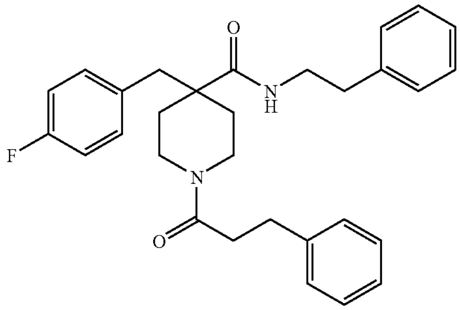 | 4-(4-Fluoro-benzyl)-1-(3-phenyl-propionyl)-piperidine-4-carboxylic acid phenethyl-amide | 474 |
| 425 | 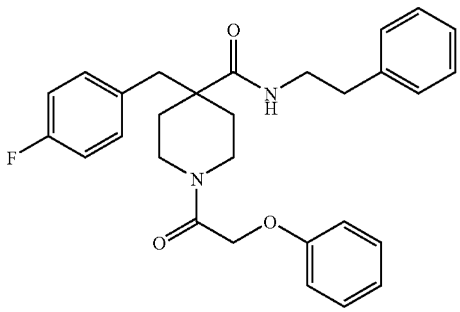 | 4-(4-Fluoro-benzyl)-1-(2-phenoxy-acetyl)-piperidine-4-carboxylic acid phenethyl-amide | 476 |
| 426 | 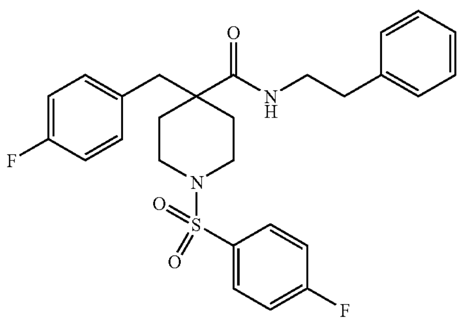 | 1-(4-Fluoro-benzenesulfonyl)-4-(4-fluoro-benzyl)-piperidine-4-carboxylic acid phenethyl-amide | 500 |
| 427 | 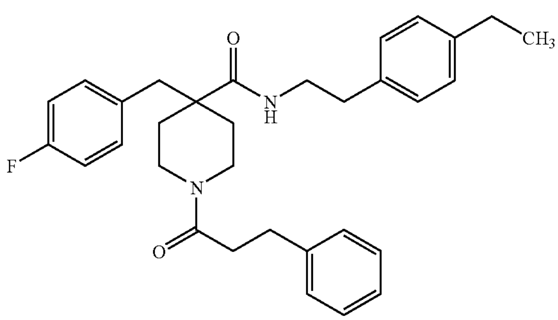 | 4-(4-Fluoro-benzyl)-1-(3-phenyl-propionyl)-piperidine-4-carboxylic acid [2-(4-ethyl-phenyl)-ethyl]-amide | 502 |
| 428 | 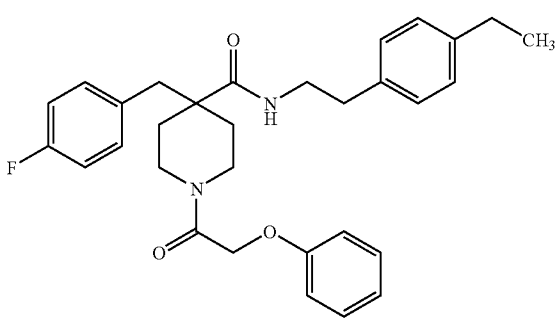 | 4-(4-Fluoro-benzyl)-1-(2-phenoxy-acetyl)-piperidine-4-carboxylic acid [2-(4-ethyl-phenyl)-ethyl]-amide | 504 |

-continued

| Example | Structure | Name | M + H |
|---|---|---|---|
| 429 | 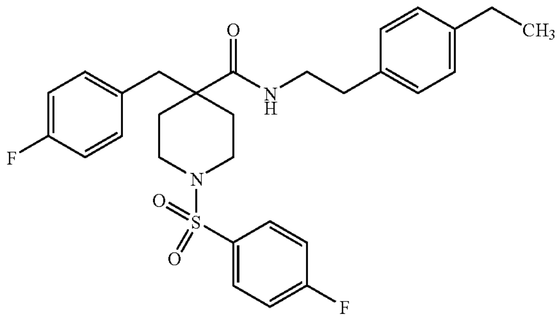 | 1-(4-Fluoro-benzenesulfonyl)-4-(4-fluoro-benzyl)-piperidine-4-carboxylic acid [2-(4-ethyl-phenyl)-ethyl]-amide | 528 |
| 430 | 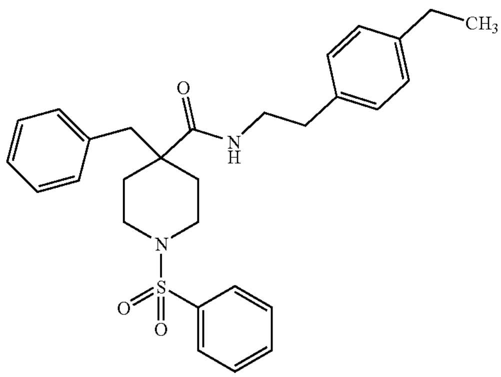 | 1-Benzenesulfonyl-4-benzyl-piperidine-4-carboxylic acid [2-(4-ethyl-phenyl)-ethyl]-amide | 492 |
| 431 | 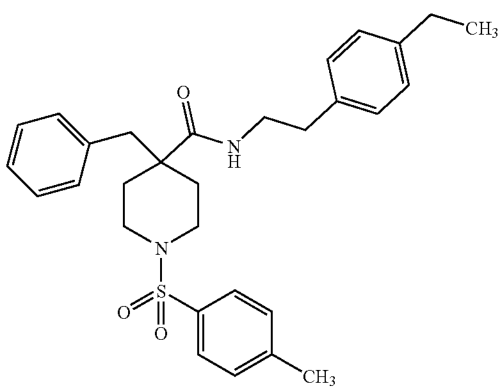 | 4-Benzyl-1-(toluene-4-sulfonyl)-piperidine-4-carboxylic acid [2-(4-ethyl-phenyl)-ethyl]-amide | 506 |
| 432 | 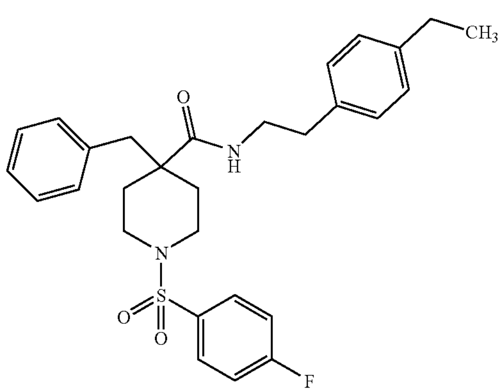 | 4-Benzyl-1-(4-fluoro-benzenesulfonyl)-piperidine-4-carboxylic acid [2-(4-ethyl-phenyl)-ethyl]-amide | 510 |

-continued

| Example | Structure | Name | M + H |
|---|---|---|---|
| 433 | 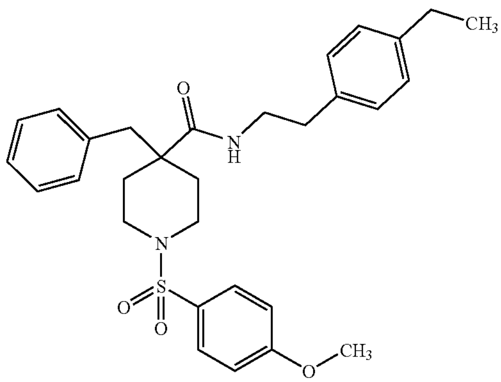 | 4-Benzyl-1-(4-methoxy-benzenesulfonyl)-piperidine-4-carboxylic acid [2-(4-ethyl-phenyl)-ethyl]-amide | 522 |
| 434 | 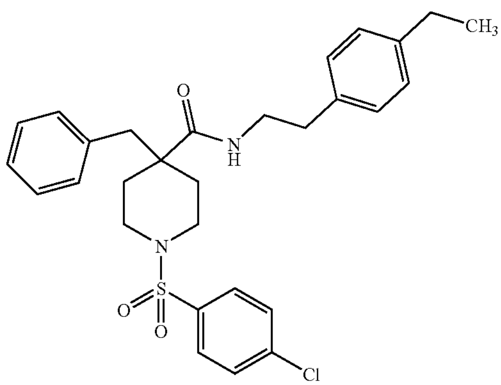 | 4-Benzyl-1-(4-chloro-benzenesulfonyl)-piperidine-4-carboxylic acid [2-(4-ethyl-phenyl)-ethyl]-amide | 526 |
| 435 | 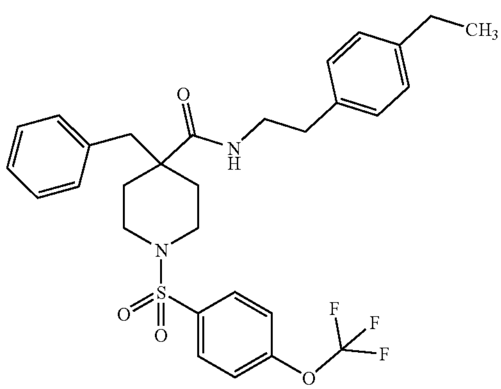 | 4-Benzyl-1-(4-trifluoromethoxy-benzenesulfonyl)-piperidine-4-carboxylic acid [2-(4-ethyl-phenyl)-ethyl]-amide | 576 |
| 436 | 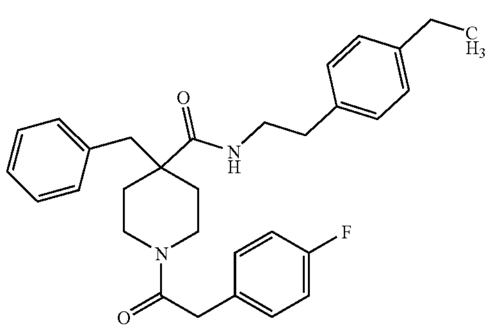 | 4-Benzyl-1-[2-(4-fluoro-phenyl)-acetyl]-piperidine-4-carboxylic acid [2-(4-ethyl-phenyl)-ethyl]-amide | 488 |

-continued

| Example | Structure | Name | M + H |
|---|---|---|---|
| 437 | 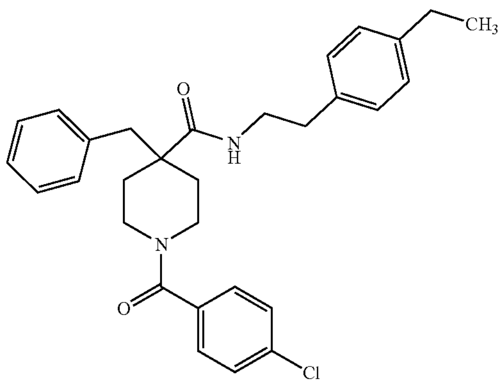 | 4-Benzyl-1-(4-chloro-benzoyl)-piperidine-4-carboxylic acid [2-(4-ethyl-phenyl)-ethyl]-amide | 490 |
| 438 | 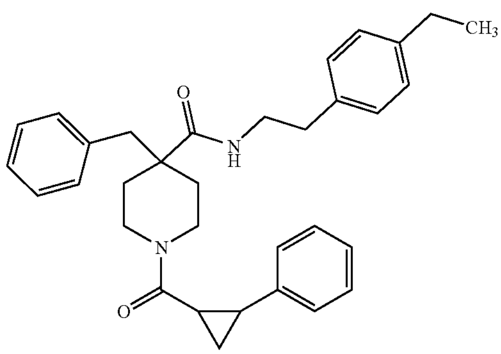 | 4-Benzyl-1-(2-phenyl-cyclopropanecarbonyl)-piperidine-4-carboxylic acid [2-(4-ethyl-phenyl)-ethyl]-amide | 496 |
| 439 | 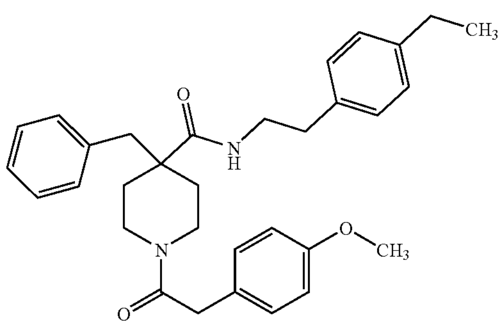 | 4-Benzyl-1-[2-(4-methoxy-phenyl)-acetyl]-piperidine-4-carboxylic acid [2-(4-ethyl-phenyl)-ethyl]-amide | 500 |
| 440 | 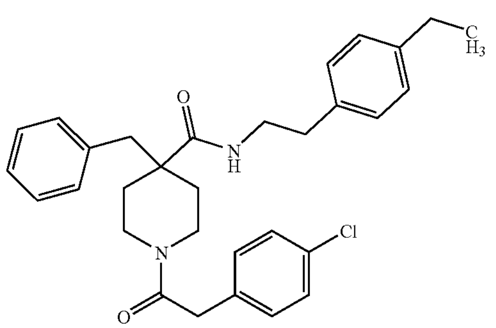 | 4-Benzyl-1-[2-(4-chloro-phenyl)-acetyl]-piperidine-4-carboxylic acid [2-(4-ethyl-phenyl)-ethyl]-amide | 504 |

-continued

| Example | Structure | Name | M + H |
|---|---|---|---|
| 441 | 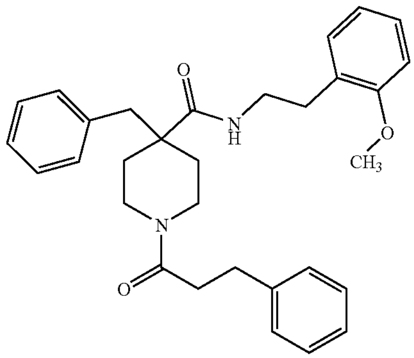 | 4-Benzyl-1-(3-phenyl-propionyl)-piperidine-4-carboxylic acid [2-(2-methoxy-phenyl)-ethyl]-amide | 486 |
| 442 | 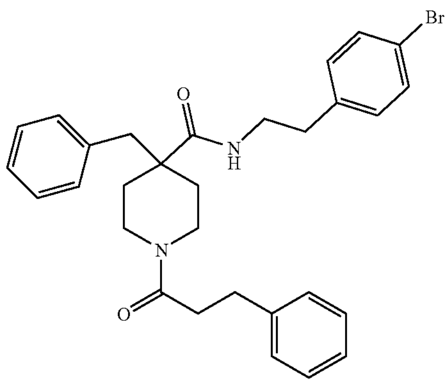 | 4-Benzyl-1-(3-phenyl-propionyl)-piperidine-4-carboxylic acid [2-(4-bromo-phenyl)-ethyl]-amide | 535 |
| 443 | 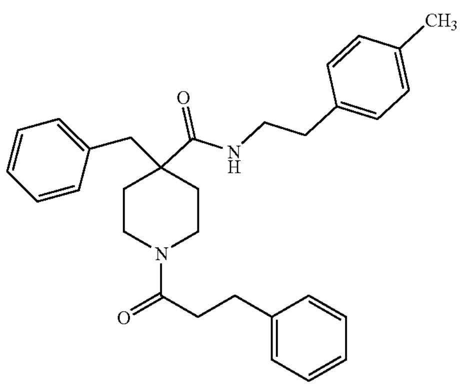 | 4-Benzyl-1-(3-phenyl-propionyl)-piperidine-4-carboxylic acid (2-p-tolyl-ethyl)-amide | 470 |
| 444 | 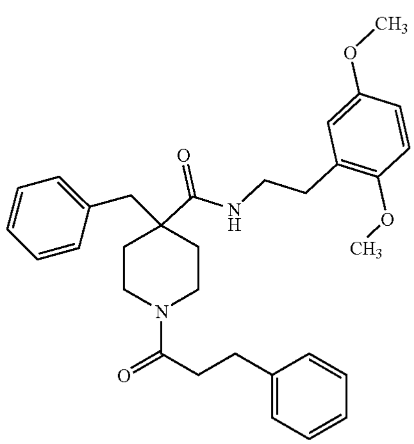 | 4-Benzyl-1-(3-phenyl-propionyl)-piperidine-4-carboxylic acid [2-(2,5-dimethoxy-phenyl)-ethyl]-amide | 516 |

-continued

| Example | Structure | Name | M + H |
|---|---|---|---|
| 445 | 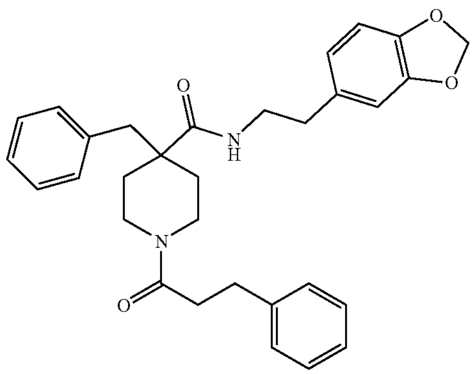 | 4-Benzyl-1-(3-phenyl-propionyl)-piperidine-4-carboxylic acid (2-benzo[1,3]dioxol-5-yl-ethyl)-amide | 500 |
| 446 | 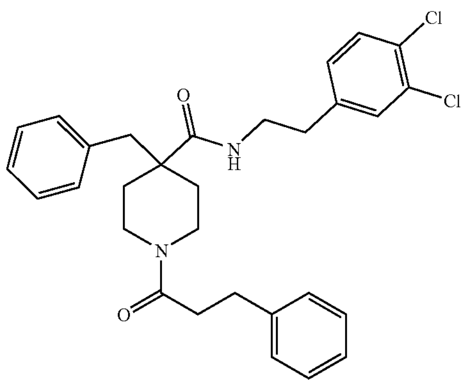 | 4-Benzyl-1-(3-phenyl-propionyl)-piperidine-4-carboxylic acid [2-(3,4-dichloro-phenyl)-ethyl]-amide | 525 |
| 447 | 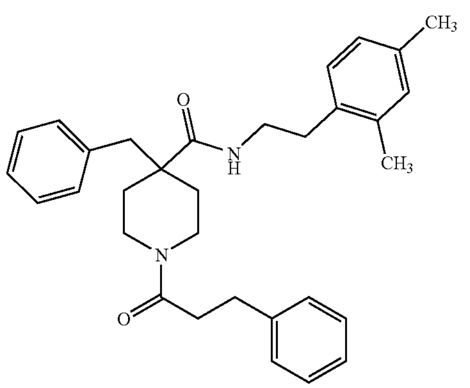 | 4-Benzyl-1-(3-phenyl-propionyl)-piperidine-4-carboxylic acid [2-(2,4-dimethyl-phenyl)-ethyl]-amide | 484 |
| 448 | 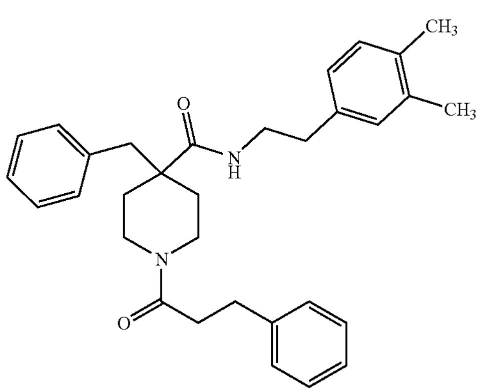 | 4-Benzyl-1-(3-phenyl-propionyl)-piperidine-4-carboxylic acid [2-(3,4-dimethyl-phenyl)-ethyl]-amide | 484 |

-continued

| Example | Structure | Name | M + H |
|---|---|---|---|
| 449 | 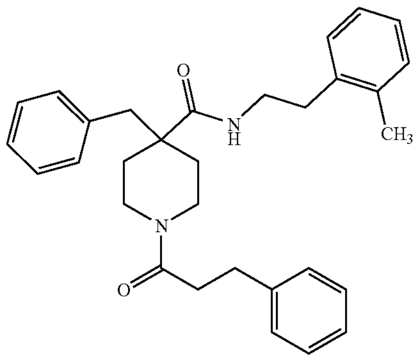 | 4-Benzyl-1-(3-phenyl-propionyl)-piperidine-4-carboxylic acid (2-o-tolyl-ethyl)-amide | 470 |
| 450 | 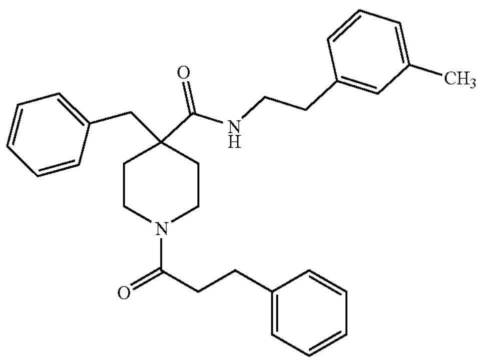 | 4-Benzyl-1-(3-phenyl-propionyl)-piperidine-4-carboxylic acid (2-m-tolyl-ethyl)-amide | 470 |
| 451 | 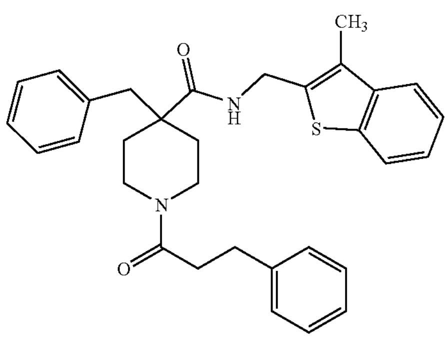 | 4-Benzyl-1-(3-phenyl-propionyl)-piperidine-4-carboxylic acid (3-methyl-benzo[b]thiophen-2-ylmethyl)-amide | 512 |
| 452 | 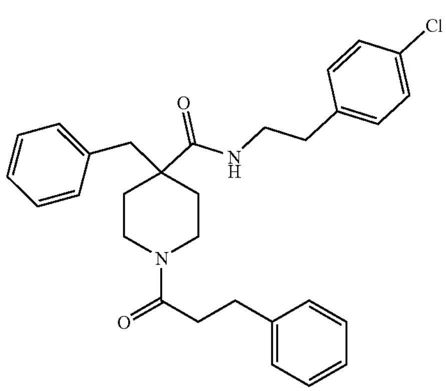 | 4-Benzyl-1-(3-phenyl-propionyl)-piperidine-4-carboxylic acid [2-(4-chloro-phenyl)-ethyl]-amide | 490 |

-continued
| Example | Structure | Name | M + H |
|---|---|---|---|
| 453 | 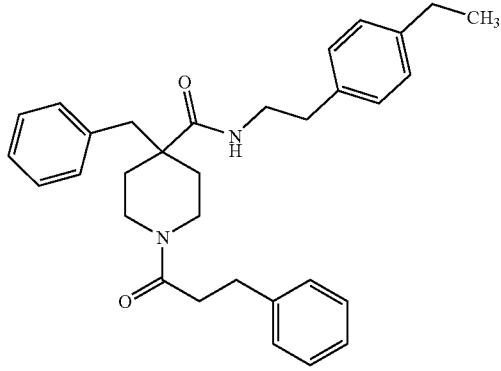 | 4-Benzyl-1-(3-phenyl-propionyl)-piperidine-4-carboxylic acid [2-(4-ethyl-phenyl)-ethyl]-amide | 484 |
| 454 | 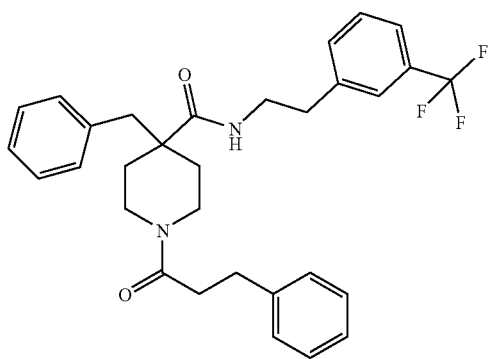 | 4-Benzyl-1-(3-phenyl-propionyl)-piperidine-4-carboxylic acid [2-(3-trifluoromethyl-phenyl)-ethyl]-amide | 524 |
| 455 | 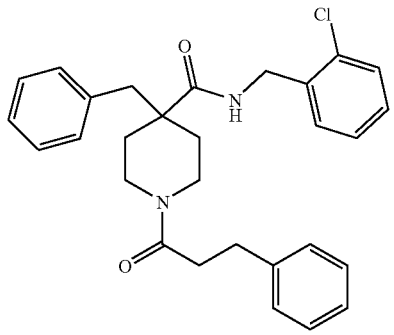 | 4-Benzyl-1-(3-phenyl-propionyl)-piperidine-4-carboxylic acid 2-chloro-benzylamide | 476 |
| 456 | 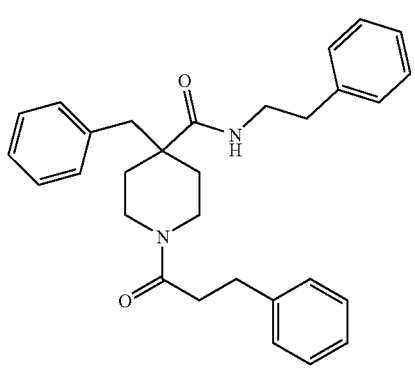 | 4-Benzyl-1-(3-phenyl-propionyl)-piperidine-4-carboxylic acid phenethyl-amide | 456 |

-continued

| Example | Structure | Name | M + H |
|---|---|---|---|
| 457 | 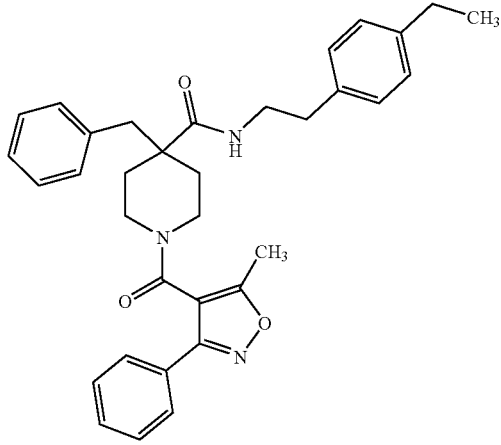 | 4-Benzyl-1-(5-methyl-3-phenyl-isoxazole-4-carbonyl)-piperidine-4-carboxylic acid [2-(4-ethyl-phenyl)-ethyl]-amide | 537 |
| 458 | 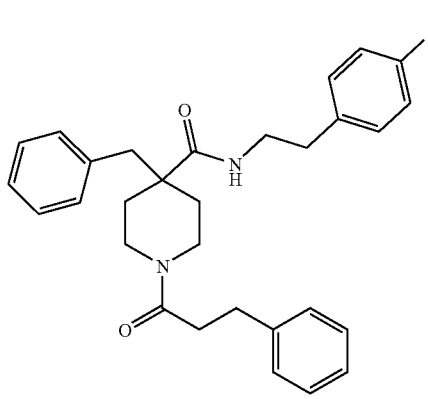 | 4-Benzyl-1-(3-phenyl-propionyl)-piperidine-4-carboxylic acid [2-(4-fluoro-phenyl)-ethyl]-amide | 474 |
| 459 | 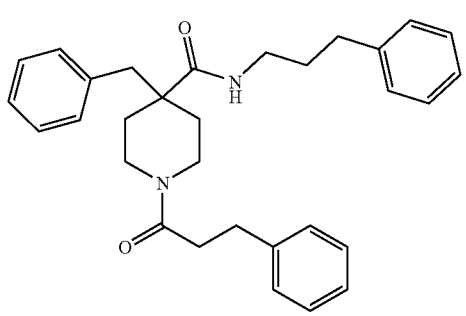 | 4-Benzyl-1-(3-phenyl-propionyl)-piperidine-4-carboxylic acid (3-phenyl-propyl)-amide | 470 |
| 460 | 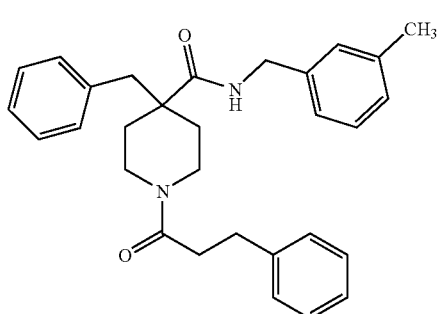 | 4-Benzyl-1-(3-phenyl-propionyl)-piperidine-4-carboxylic acid 3-methyl-benzylamide | 456 |

-continued

| Example | Structure | Name | M + H |
|---|---|---|---|
| 461 | 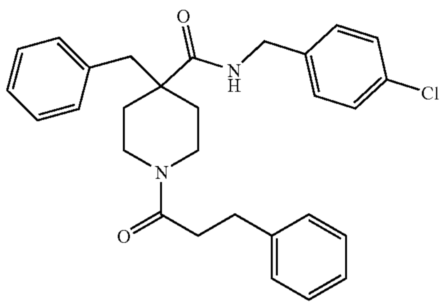 | 4-Benzyl-1-(3-phenyl-propionyl)-piperidine-4-carboxylic acid 4-chloro-benzylamide | 476 |
| 462 | 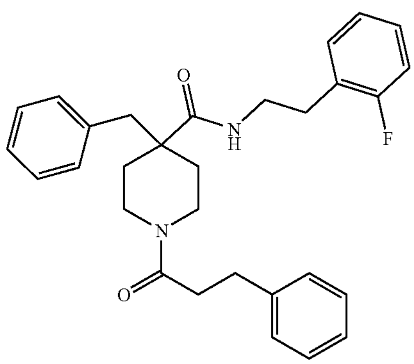 | 4-Benzyl-1-(3-phenyl-propionyl)-piperidine-4-carboxylic acid [2-(2-fluoro-phenyl)-ethyl]-amide | 474 |
| 463 | 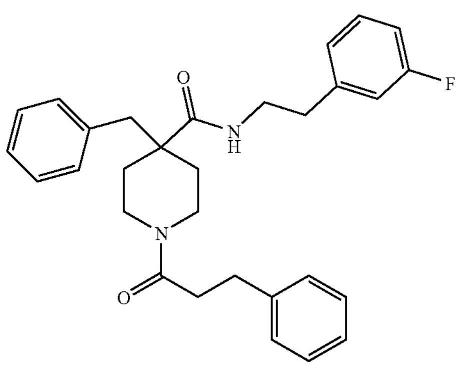 | 4-Benzyl-1-(3-phenyl-propionyl)-piperidine-4-carboxylic acid [2-(3-fluoro-phenyl)-ethyl]-amide | 474 |
| 464 | 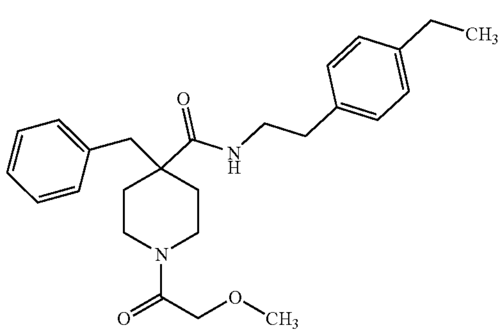 | 4-Benzyl-1-(2-methoxy-acetyl)-piperidine-4-carboxylic acid [2-(4-ethyl-phenyl)-ethyl]-amide | 424 |

-continued

| Example | Structure | Name | M + H |
|---|---|---|---|
| 465 | 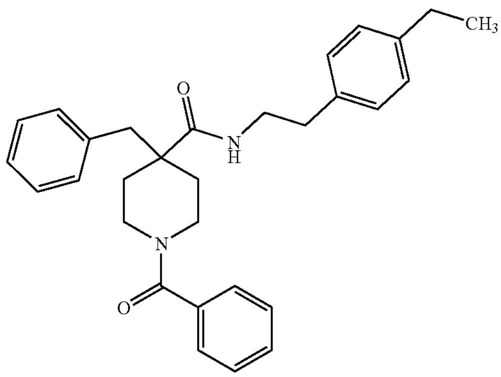 | 1-Benzoyl-4-benzyl-piperidine-4-carboxylic acid [2-(4-ethyl-phenyl)-ethyl]-amide | 456 |
| 466 | 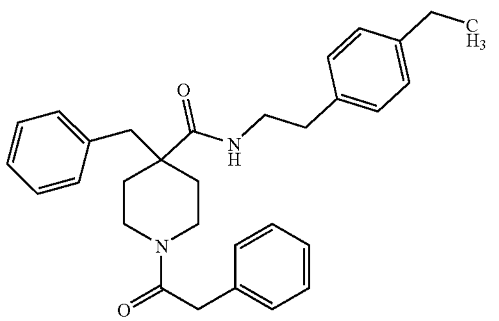 | 4-Benzyl-1-phenylacetyl-piperidine-4-carboxylic acid [2-(4-ethyl-phenyl)-ethyl]-amide | 470 |
| 467 | 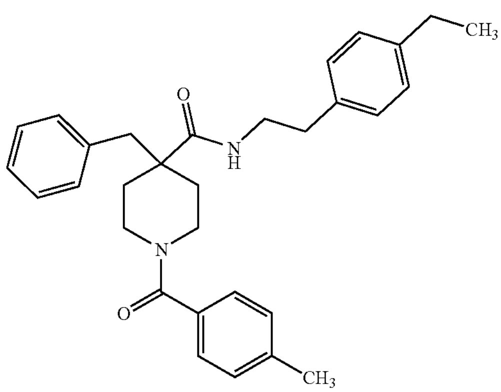 | 4-Benzyl-1-(4-methyl-benzoyl)-piperidine-4-carboxylic acid [2-(4-ethyl-phenyl)-ethyl]-amide | 470 |
| 468 | 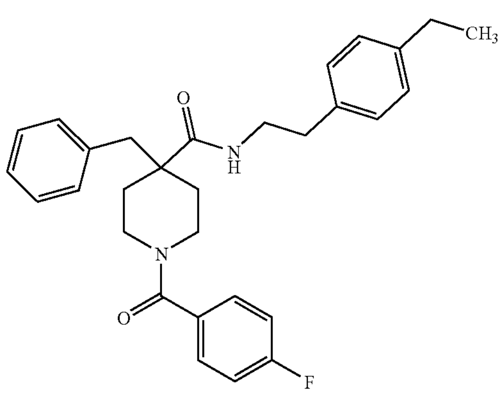 | 4-Benzyl-1-(4-fluoro-benzoyl)-piperidine-4-carboxylic acid [2-(4-ethyl-phenyl)-ethyl]-amide | 474 |

-continued

| Example | Structure | Name | M + H |
|---|---|---|---|
| 469 | 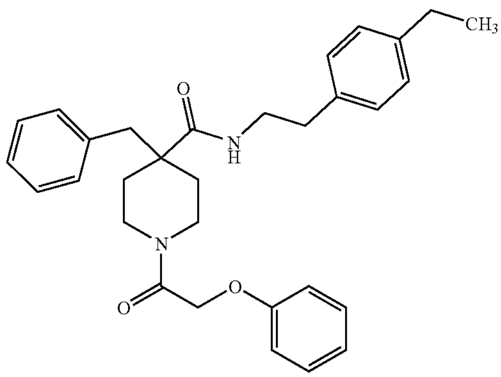 | 4-Benzyl-1-(2-phenoxy-acetyl)-piperidine-4-carboxylic acid [2-(4-ethyl-phenyl)-ethyl]-amide | 486 |
| 470 | 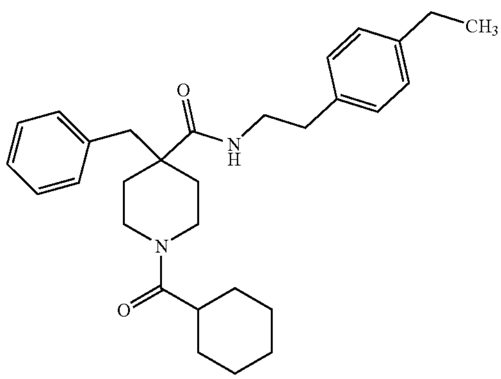 | 4-Benzyl-1-cyclohexanecarbonyl-piperidine-4-carboxylic acid [2-(4-ethyl-phenyl)-ethyl]-amide | 462 |
| 471 | 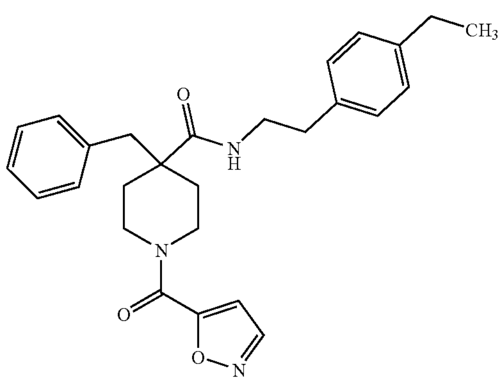 | 4-Benzyl-1-(isoxazole-5-carbonyl)-piperidine-4-carboxylic acid [2-(4-ethyl-phenyl)-ethyl]-amide | 447 |
| 472 | 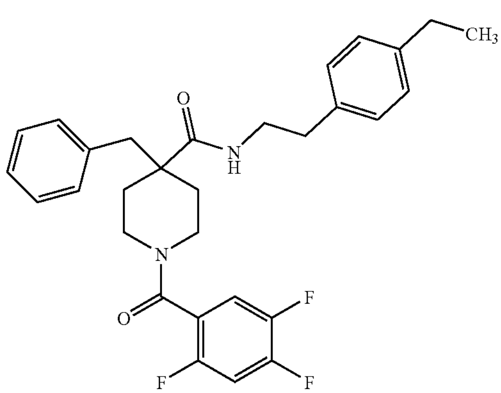 | 4-Benzyl-1-(2,4,5-trifluoro-benzoyl)-piperidine-4-carboxylic acid [2-(4-ethyl-phenyl)-ethyl]-amide | 510 |

-continued
| Example | Structure | Name | M + H |
|---|---|---|---|
| 473 | 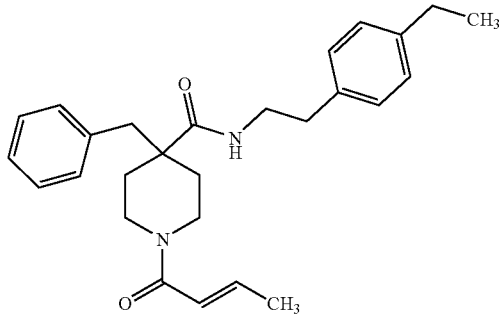 | 4-Benzyl-1-but-2-enoyl-piperidine-4-carboxylic acid [2-(4-ethyl-phenyl)-ethyl]-amide | 420 |
| 474 | 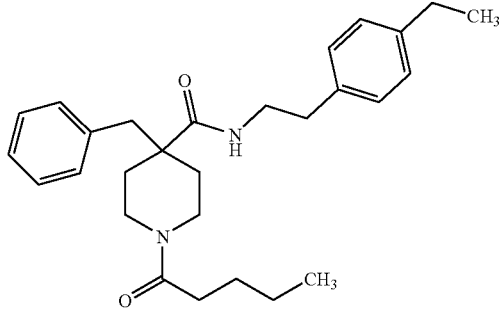 | 4-Benzyl-1-pentanoyl-piperidine-4-carboxylic acid [2-(4-ethyl-phenyl)-ethyl]-amide | 436 |
| 475 | 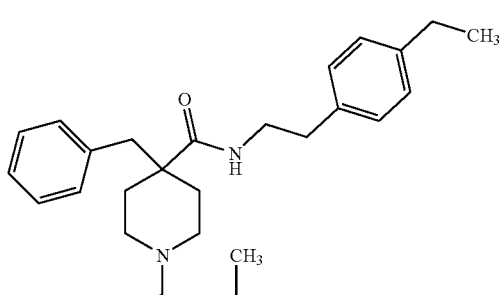 | 4-Benzyl-1-(3-methyl-butyryl)-piperidine-4-carboxylic acid [2-(4-ethyl-phenyl)-ethyl]-amide | 436 |
| 476 | 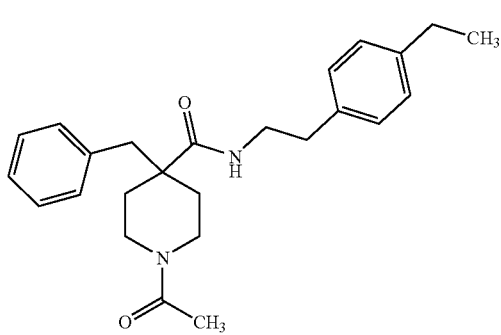 | 1-Acetyl-4-benzyl-piperidine-4-carboxylic acid [2-(4-ethyl-phenyl)-ethyl]-amide | 394 |

-continued

| Example | Structure | Name | M + H |
|---|---|---|---|
| 477 | 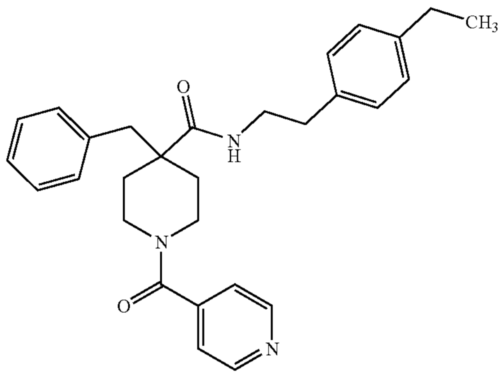 | 4-Benzyl-1-(pyridine-4-carbonyl)-piperidine-4-carboxylic acid [2-(4-ethyl-phenyl)-ethyl]-amide | 457 |
| 478 | 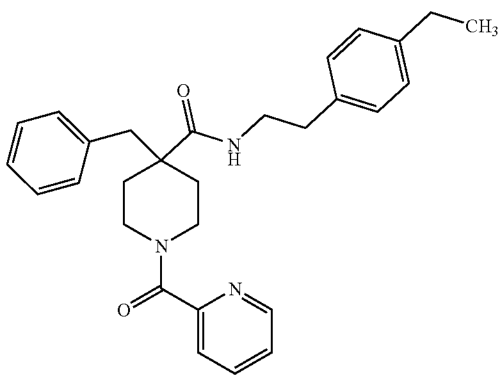 | 4-Benzyl-1-(pyridine-2-carbonyl)-piperidine-4-carboxylic acid [2-(4-ethyl-phenyl)-ethyl]-amide | 457 |
| 479 | 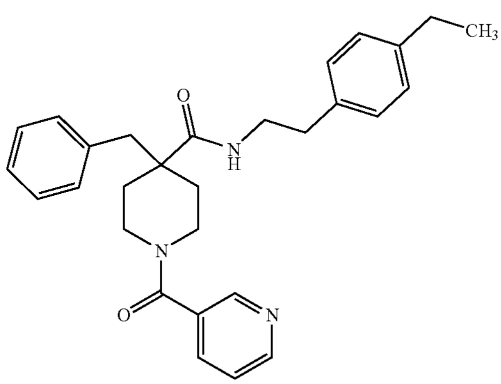 | 4-Benzyl-1-(pyridine-3-carbonyl)-piperidine-4-carboxylic acid [2-(4-ethyl-phenyl)-ethyl]-amide | 457 |
| 480 | 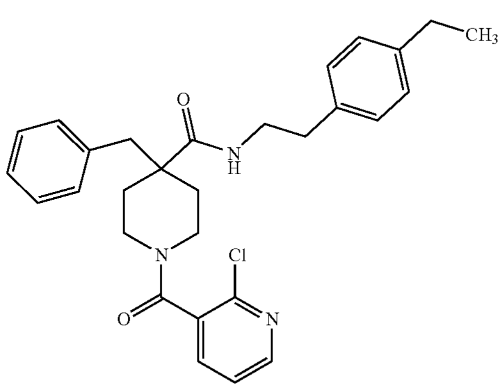 | 4-Benzyl-1-(2-chloro-pyridine-3-carbonyl)-piperidine-4-carboxylic acid [2-(4-ethyl-phenyl)-ethyl]-amide | 491 |

-continued

| Example | Structure | Name | M + H |
|---|---|---|---|
| 481 | 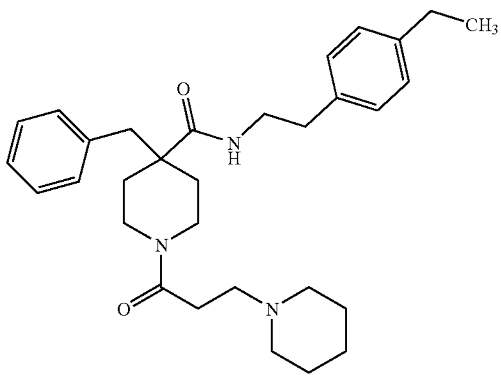 | 4-Benzyl-1-(3-piperidin-1-yl-propionyl)-piperidine-4-carboxylic acid [2-(4-ethyl-phenyl)-ethyl]-amide | 491 |
| 482 | 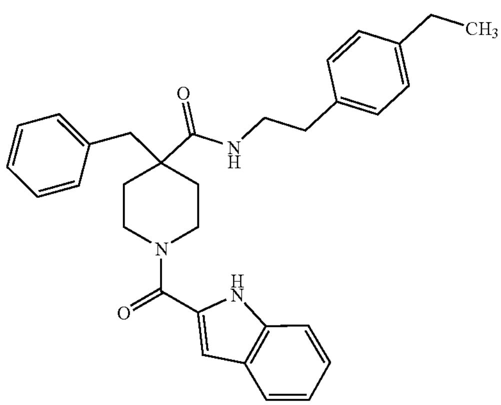 | 4-Benzyl-1-(1H-indole-2-carbonyl)-piperidine-4-carboxylic acid [2-(4-ethyl-phenyl)-ethyl]-amide | 495 |
| 483 | 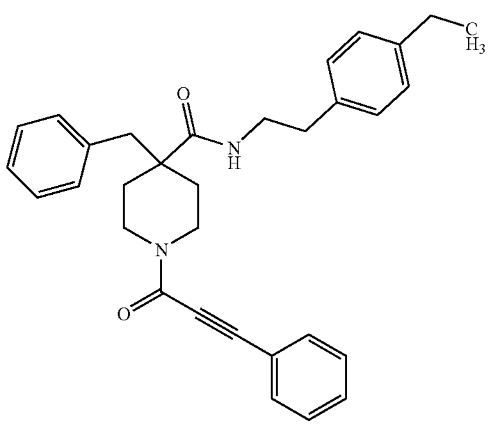 | 4-Benzyl-1-(3-phenyl-propynoyl)-piperidine-4-carboxylic acid [2-(4-ethyl-phenyl)-ethyl]-amide | 480 |
| 484 | 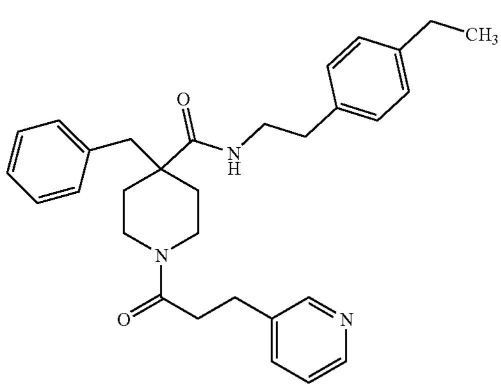 | 4-Benzyl-1-(3-pyridin-3-yl-propionyl)-piperidine-4-carboxylic acid [2-(4-ethyl-phenyl)-ethyl]-amide | 485 |

-continued

| Example | Structure | Name | M + H |
|---|---|---|---|
| 485 | 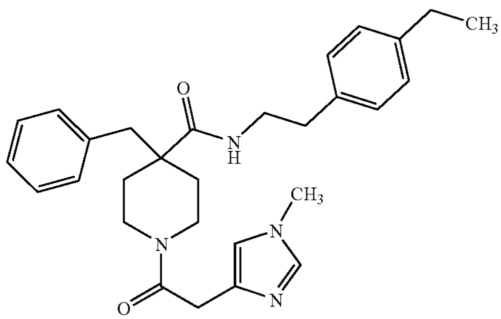 | 4-Benzyl-1-[2-(1-methyl-1H-imidazol-4-yl)-acetyl]-piperidine-4-carboxylic acid [2-(4-ethyl-phenyl)-ethyl]-amide | 474 |
| 486 | 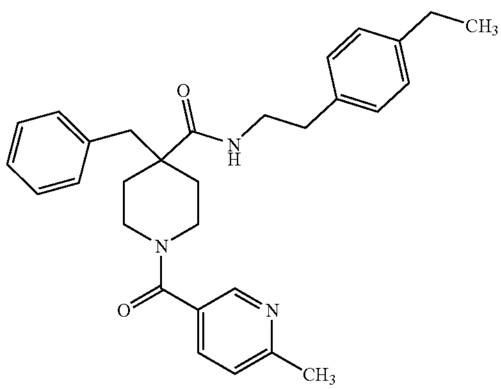 | 4-Benzyl-1-(6-methyl-pyridine-4-carbonyl)-piperidine-4-carboxylic acid [2-(4-ethyl-phenyl)-ethyl]-amide | 471 |
| 487 | 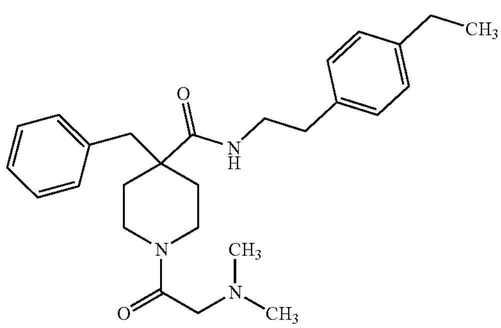 | 4-Benzyl-1-(2-dimethylamino-acetyl)-piperidine-4-carboxylic acid [2-(4-ethyl-phenyl)-ethyl]-amide | 437 |
| 488 | 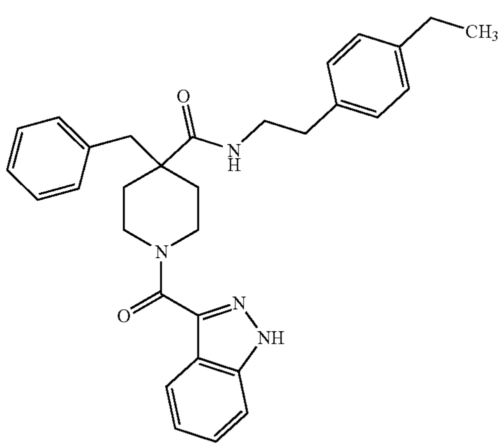 | 4-Benzyl-1-(1H-indazole-3-carbonyl)-piperidine-4-carboxylic acid [2-(4-ethyl-phenyl)-ethyl]-amide | 496 |

-continued

| Example | Structure | Name | M + H |
|---|---|---|---|
| 489 | 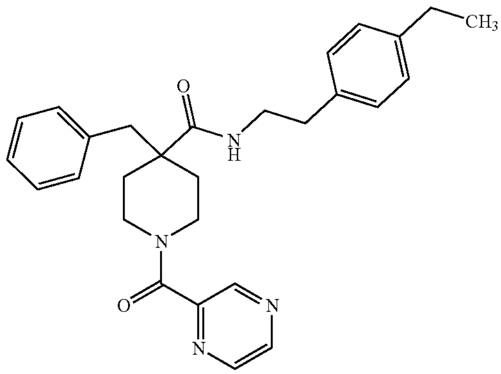 | 4-Benzyl-1-(pyrazine-2-carbonyl)-piperidine-4-carboxylic acid [2-(4-ethyl-phenyl)-ethyl]-amide | 458 |
| 490 | 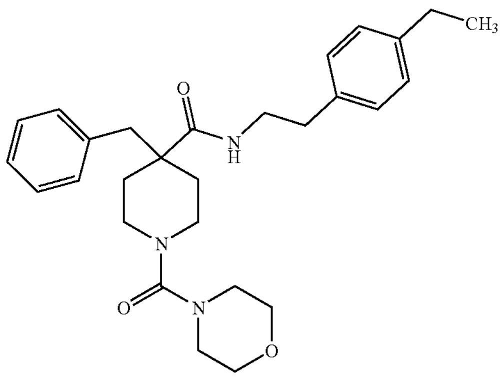 | 4-Benzyl-1-(morpholine-4-carbonyl)-piperidine-4-carboxylic acid [2-(4-ethyl-phenyl)-ethyl]-amide | 465 |
| 491 | 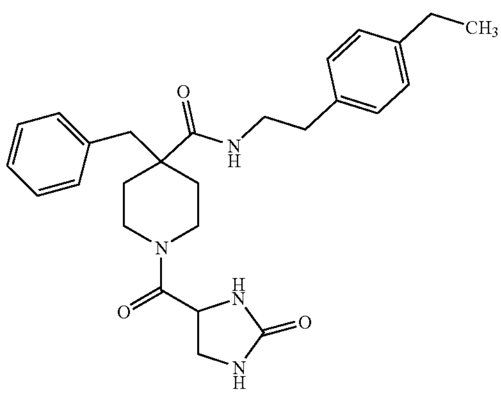 | 4-Benzyl-1-(2-oxo-imidazolidine-4-carbonyl)-piperidine-4-carboxylic acid [2-(4-ethyl-phenyl)-ethyl]-amide | 464 |
| 492 | 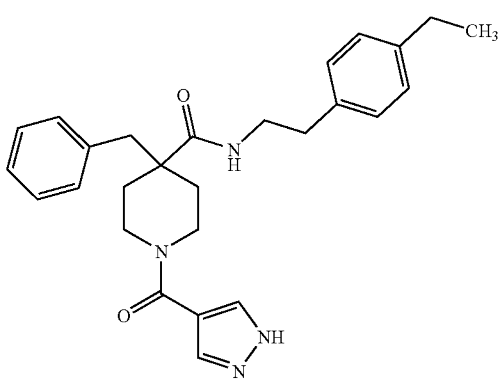 | 4-Benzyl-1-(1H-pyrazole-4-carbonyl)-piperidine-4-carboxylic acid [2-(4-ethyl-phenyl)-ethyl]-amide | 446 |

-continued

| Example | Structure | Name | M + H |
|---|---|---|---|
| 493 | 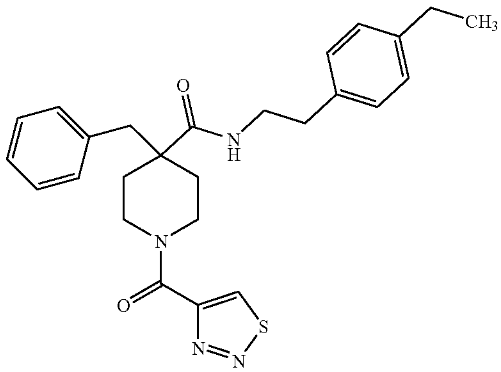 | 4-Benzyl-1-([1,2,3]thiadiazole-4-carbonyl)-piperidine-4-carboxylic acid [2-(4-ethyl-phenyl)-ethyl]-amide | 464 |
| 494 | 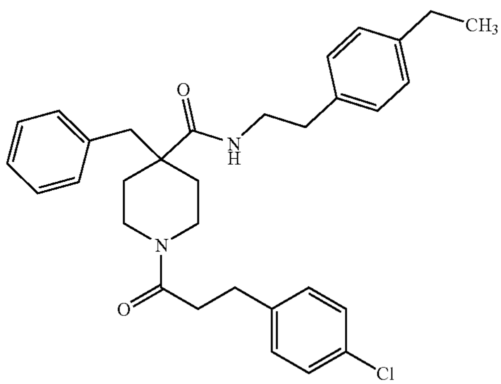 | 4-Benzyl-1-[3-(4-chloro-phenyl)-propionyl]-piperidine-4-carboxylic acid [2-(4-ethyl-phenyl)-ethyl]-amide | 518 |
| 495 | 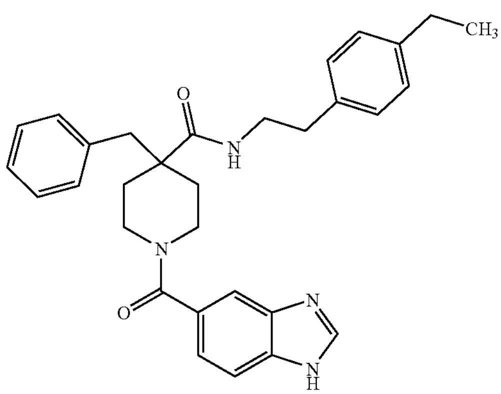 | 1-(1H-Benzoimidazole-5-carbonyl)-4-benzyl-piperidine-4-carboxylic acid [2-(4-ethyl-phenyl)-ethyl]-amide | 496 |
| 496 | 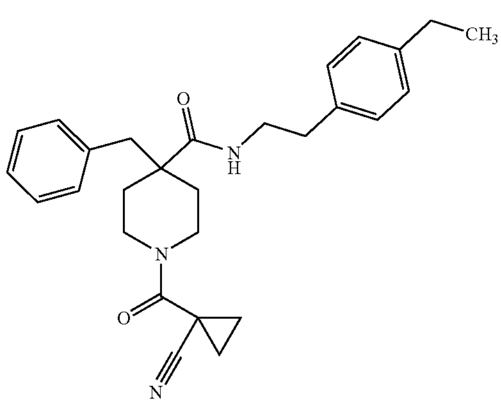 | 4-Benzyl-1-(1-cyano-cyclopropanecarbonyl)-piperidine-4-carboxylic acid [2-(4-ethyl-phenyl)-ethyl]-amide | 445 |

-continued

| Example | Structure | Name | M + H |
| --- | --- | --- | --- |
| 497 | 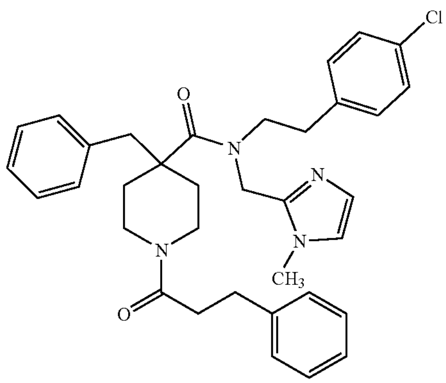 | 4-Benzyl-1-(3-phenyl-propionyl)-piperidine-4-carboxylic acid [2-(4-chloro-phenyl)-ethyl]-(1-methyl-1H-imidazol-2-ylmethyl)-amide | 584 |
| 498 | 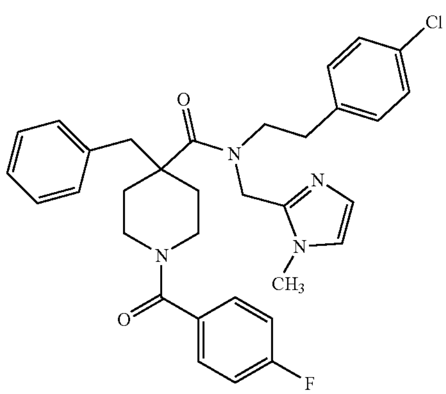 | 4-Benzyl-1-(4-fluoro-benzoyl)-piperidine-4-carboxylic acid [2-(4-chloro-phenyl)-ethyl]-(1-methyl-1H-imidazol-2-ylmethyl)-amide | 574 |
| 499 | 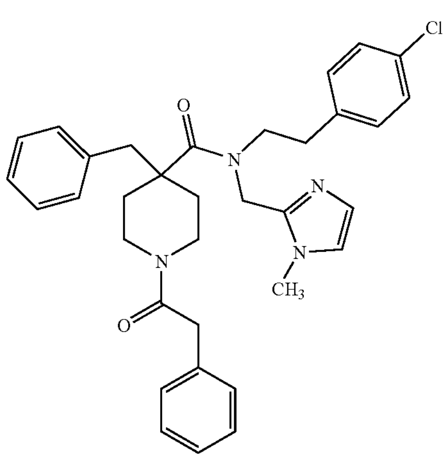 | 4-Benzyl-1-phenylacetyl-piperidine-4-carboxylic acid [2-(4-chloro-phenyl)-ethyl]-(1-methyl-1H-imidazol-2-ylmethyl)-amide | 570 |

-continued

| Example | Structure | Name | M + H |
|---|---|---|---|
| 500 | 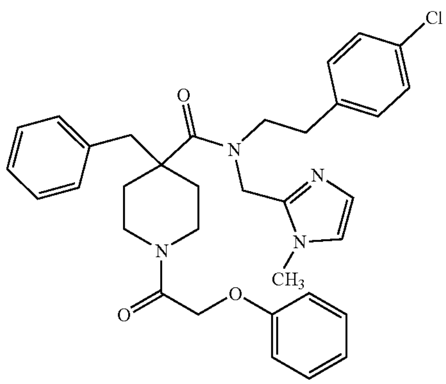 | 4-Benzyl-1-(2-phenoxy-acetyl)-piperidine-4-carboxylic acid [2-(4-chloro-phenyl)-ethyl]-(1-methyl-1H-imidazol-2-ylmethyl)-amide | 586 |
| 501 | 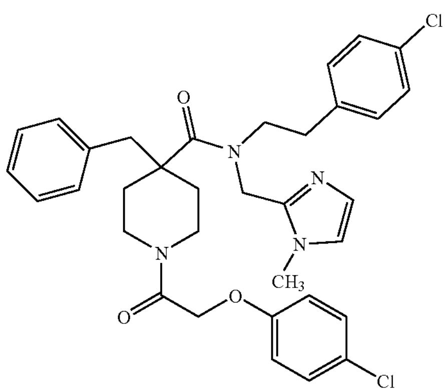 | 4-Benzyl-1-[2-(4-chloro-phenoxy)-acetyl]-piperidine-4-carboxylic acid [2-(4-chloro-phenyl)-ethyl]-(1-methyl-1H-imidazol-2-ylmethyl)-amide | 621 |
| 502 | 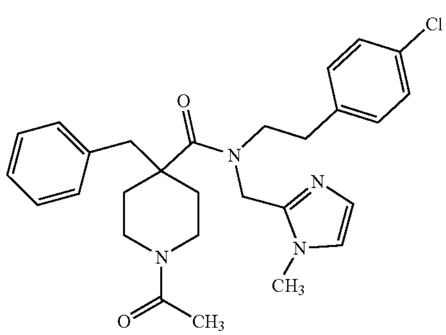 | 1-Acetyl-4-benzyl-piperidine-4-carboxylic acid [2-(4-chloro-phenyl)-ethyl]-(1-methyl-1H-imidazol-2-ylmethyl)-amide | 494 |
| 503 | 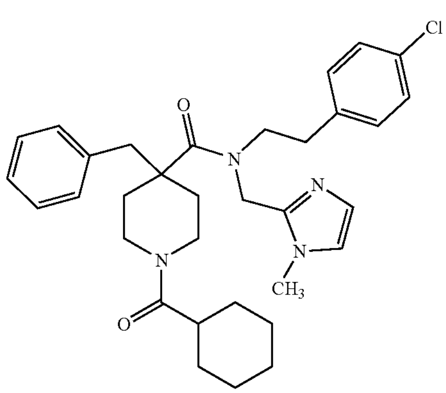 | 4-Benzyl-1-cyclohexanecarbonyl-piperidine-4-carboxylic acid [2-(4-chloro-phenyl)-ethyl]-(1-methyl-1H-imidazol-2-ylmethyl)-amide | 562 |

-continued

| Example | Structure | Name | M + H |
|---------|-----------|------|-------|
| 504 | 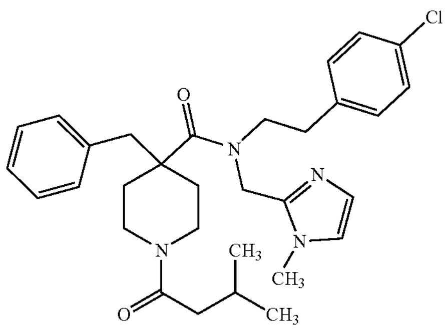 | 4-Benzyl-1-(3-methyl-butyryl)-piperidine-4-carboxylic acid [2-(4-chloro-phenyl)-ethyl]-(1-methyl-1H-imidazol-2-ylmethyl)-amide | 536 |
| 505 | 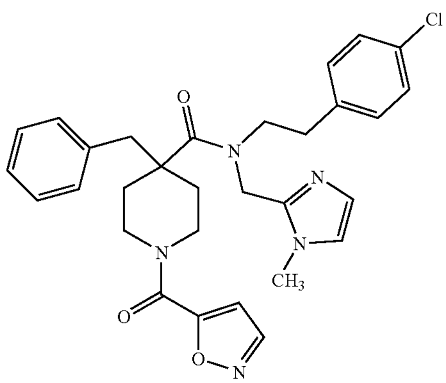 | 4-Benzyl-1-(isoxazole-5-carbonyl)-piperidine-4-carboxylic acid [2-(4-chloro-phenyl)-ethyl]-(1-methyl-1H-imidazol-2-ylmethyl)-amide | 547 |
| 506 | 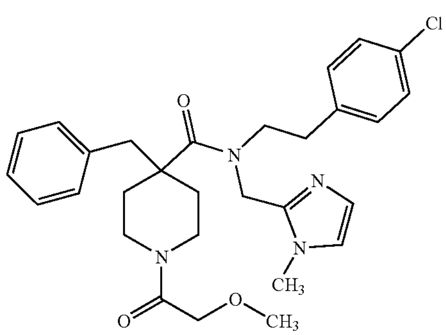 | 4-Benzyl-1-(2-methoxy-acetyl)-piperidine-4-carboxylic acid [2-(4-chloro-phenyl)-ethyl]-(1-methyl-1H-imidazol-2-ylmethyl)-amide | 524 |
| 507 | 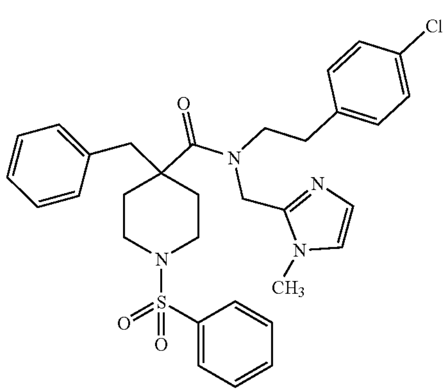 | 1-Benzenesulfonyl-4-benzyl-piperidine-4-carboxylic acid [2-(4-chloro-phenyl)-ethyl]-(1-methyl-1H-imidazol-2-ylmethyl)-amide | 592 |

-continued

| Example | Structure | Name | M + H |
|---|---|---|---|
| 508 | 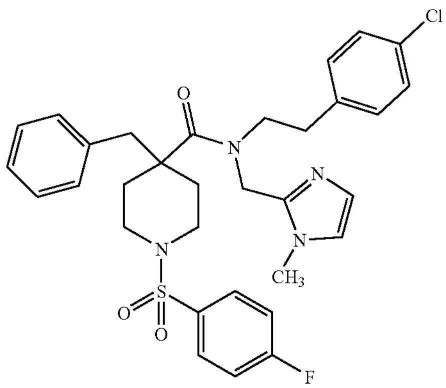 | 4-Benzyl-1-(4-fluoro-benzenesulfonyl)-piperidine-4-carboxylic acid [2-(4-chloro-phenyl)-ethyl]-(1-methyl-1H-imidazol-2-ylmethyl)-amide | 610 |
| 509 | 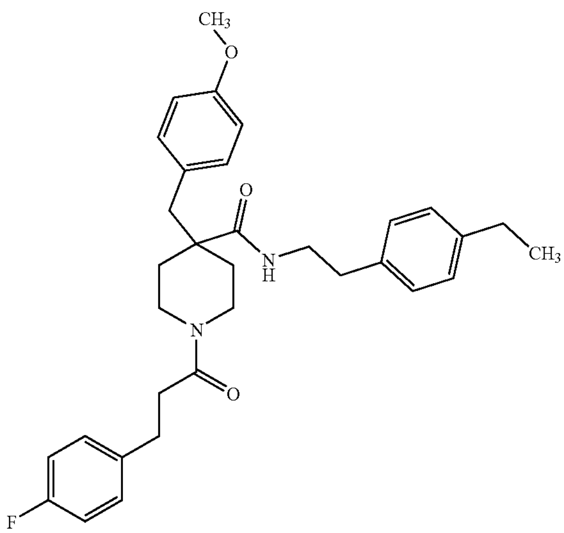 | 1-[3-(4-Fluoro-phenyl)-propionyl]-4-(4-methoxy-benzyl)-piperidine-4-carboxylic acid [2-(4-ethyl-phenyl)-ethyl]-amide | 532 |
| 510 | 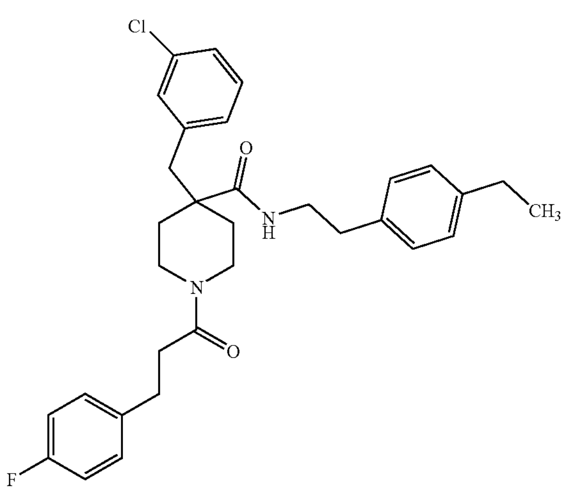 | 4-(3-Chloro-benzyl)-1-[3-(4-fluoro-phenyl)-propionyl]-piperidine-4-carboxylic acid [2-(4-ethyl-phenyl)-ethyl]-amide | 536 |

Example 521

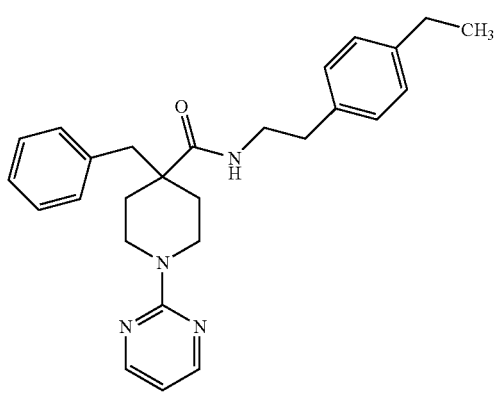

4-Benzyl-1-pyrimidin-2-yl-piperidine-4-carboxylic acid [2-(4-ethyl-phenyl)-ethyl]-amide

Synthesis

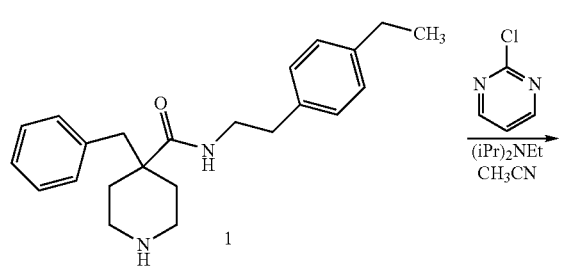

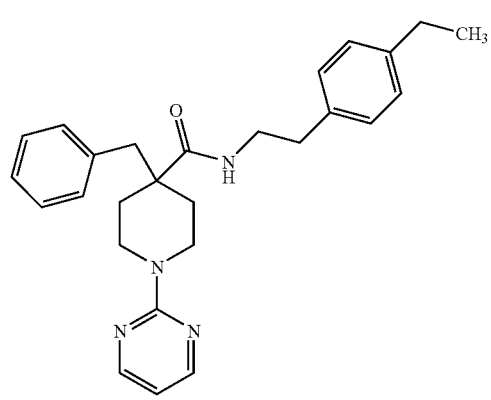

Compound 1: Compound 1 was prepared using methodlogy described in Example 390. LRMS m/z 352 (M+H)⁺.

Title Compound: A solution of compound 1 (0.05 g; 0.14 mmol) in anhydrous acetonitrile (1 mL) was treated with 2-chloropyrimidine (0.024 g; 0.21 mmol) and diisopropyl ethylamine (0.036 mL; 0.21 mmol) and heated at 90° C. for 1 h. The acetonitrile was removed by evaporation and the crude residue was purified by preparative HPLC to give 4-benzyl-1-pyrimidin-2-yl-piperidine-4-carboxylic acid [2-(4-ethyl-phenyl)-ethyl]-amide as a white solid. LRMS m/z 430 (M+H)⁺.

Example 522

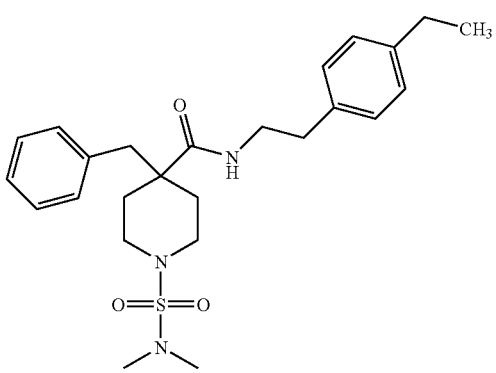

4-Benzyl-1-dimethylsulfamoyl-piperidine-4-carboxylic acid [2-(4-ethyl-phenyl)-ethyl]-amide

Synthesis

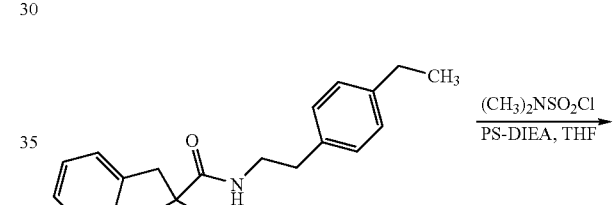

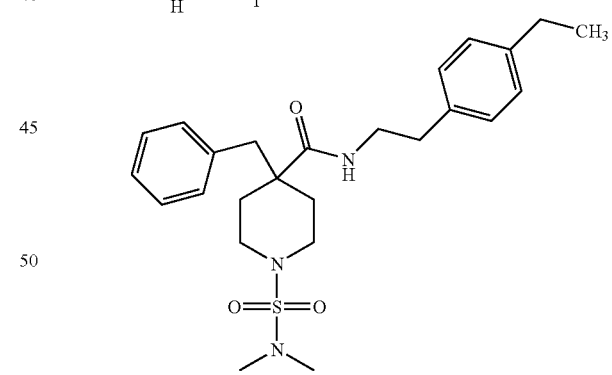

Compound 1: Compound 1 was prepared using methodology described in Example 390. LRMS m/z 352 (M+H)⁺.

Title Compound: 4-Benzyl-1-dimethylsulfamoyl-piperidine-4-carboxylic acid [2-(4-ethyl-phenyl)-ethyl]-amide was prepared using methodology described in Example 16. LRMS m/z 458 (M+H)⁺.

Example 523

Example 523 was prepared using methodology described in Example 522.

| Example | Structure | Name | M + H |
|---|---|---|---|
| 523 | 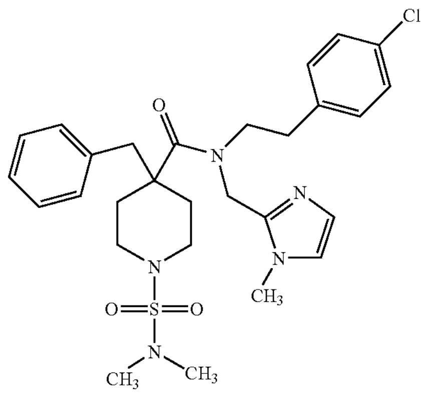 | 4-Benzyl-1-dimethylsulfamoyl-piperidine-4-carboxylic acid [2-(4-chloro-phenyl)-ethyl]-(1-methyl-1H-imidazol-2-ylmethyl)-amide | 559 |
Example 524
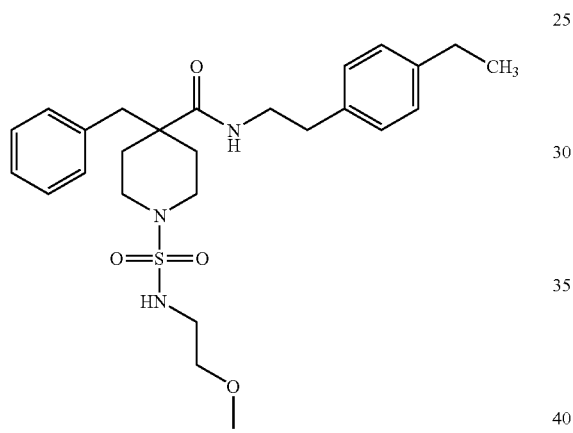
4-Benzyl-1-(2-methoxy-ethylsulfamoyl)-piperidine-4-carboxylic acid [2-(4-ethyl-phenyl)-ethyl]-amide
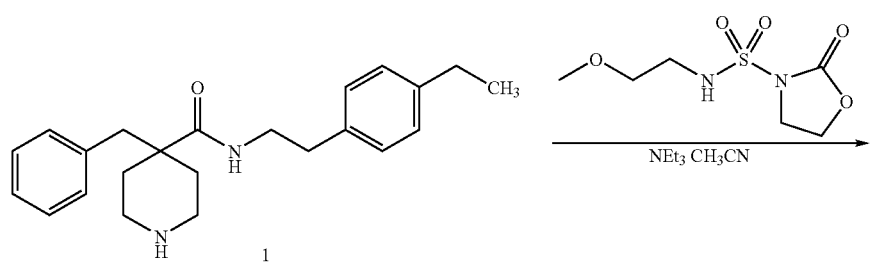

-continued

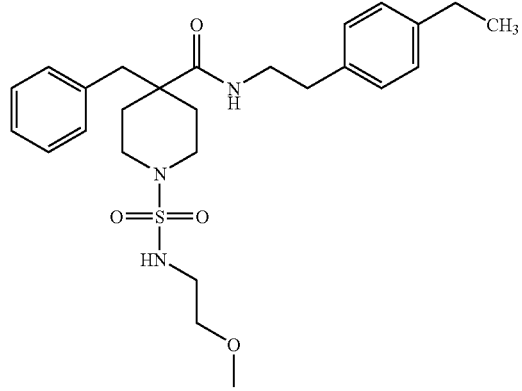

Compound 1: Compound 1 was prepared using methodology described in Example 390. LRMS m/z 352 (M+H)+.

Title Compound: 4-Benzyl-1-(2-methoxy-ethylsulfamoyl)-piperidine-4-carboxylic acid [2-(4-ethyl-phenyl)-ethyl]-amide was prepared using methodology described in Example 17. LRMS m/z 488 (M+H)+.

Examples 525 to 526

Examples 525 to 526 were prepared using methodology described in Example 524.

| Example | Structure | Name | M + H |
|---|---|---|---|
| 525 | 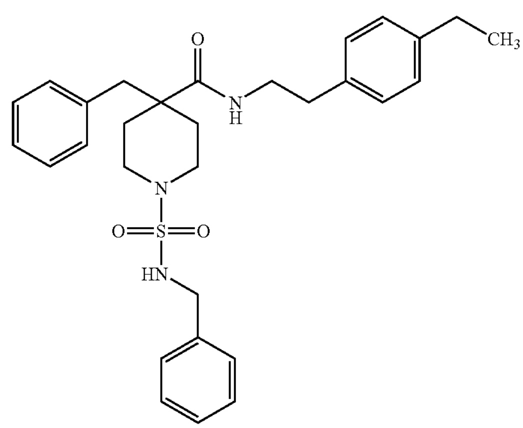 | 4-Benzyl-1-benzylsulfamoyl-piperidine-4-carboxylic acid [2-(4-ethyl-phenyl)-ethyl]-amide | 521 |
| 526 | 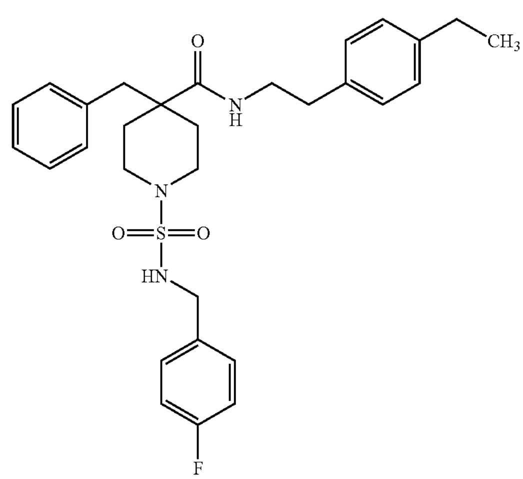 | 4-Benzyl-1-(4-fluoro-benzylsulfamoyl)-piperidine-4-carboxylic acid [2-(4-ethyl-phenyl)-ethyl]-amide | 539 |

Example 527

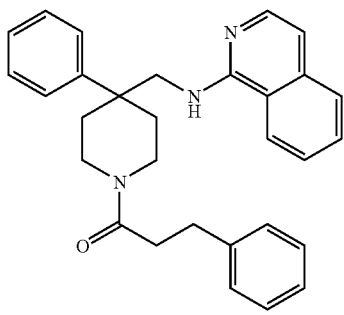

1-[4-(isoquinolin-1-ylaminomethyl)-4-phenyl-piperidin-1-yl]-3-phenyl-propan-1-one Synthesis

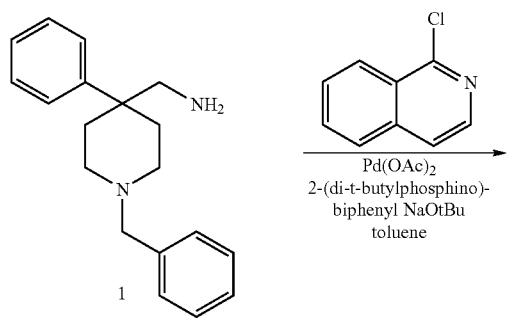

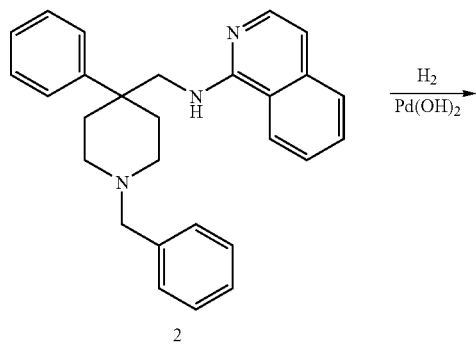

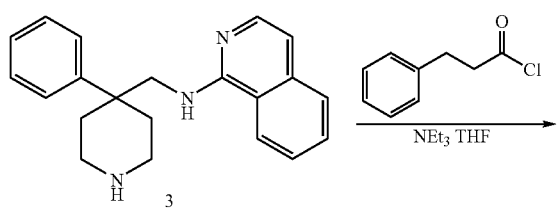

-continued

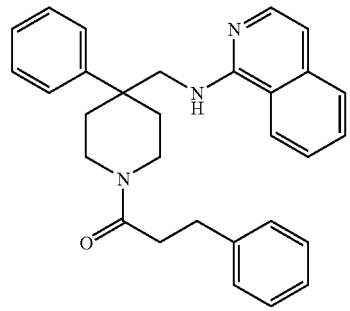

Compound 1: A suspension of 1-benzyl-4-phenyl-piperidine-4-carbonitrile (6.24 g; 20 mmol) in tetrahydrofuran was cooled to 0° C. and treated with lithium aluminum hydride (3.04 g; 80 mmol). The reaction mixture was allowed slowly warm to room temperature overnight. The reaction was cooled in an ice-acetone bath and quenched with water (12 mL) and 15% aqueous sodium hydroxide (3 mL). The resulting slurry was filtered through celite eluting with ethyl ether and evaporated to give 4.51 g of compound 1 as a colorless oil that was used in the next step without additional purification. LRMS m/z 281 (M+H)$^+$.

Compound 2: Pd(OAc)$_2$ (4.5 mg, 0.02 mmol), 2-(di-t-butylphosphino)biphenyl (11.9 mg, 0.04 mmol) and sodium t-butoxide (0.54 g, 5.6 mmol) were added to toluene (8 mL) and the mixture was sparged with argon. 1-Chloroisoquinoline (0.65 g, 4 mmol) and compound 1 (1.35 g, 4.8 mmol) were added and the reaction was heated at reflux under an argon atmosphere. After 48 hours a second portion of Pd(OAc)$_2$ (4.5 mg, 0.02 mmol) and -(di-t-butylphosphino)biphenyl (11.9 mg, 0.04 mmol) was added. The reaction was allowed to reflux another 24 hours then diluted with water (8 mL). The mixture was filtered through celite pad and portioned between ethyl acetate and water. The organic phase was separated, dried (anhydrous magnesium sulfate), filtered and concentrated. Column chromatography on silica gel using a dichloromethane to ethyl acetate gradient as the eluent gave 0.29 g compound 2. LRMS m/z 408 (M+H)$^+$.

Compound 3: A solution of compound 2 (0.250 g) in methanol (20 mL) was treated with Pd(OH)$_2$ (50 mg), placed under at atmosphere of hydrogen (60 psi) and heated to 40° C. until no starting material remained as judged by LCMS. The reaction mixture was filtered through celite using ethyl acetate as the eluent and evaporated to give 0.19 g compound 3 that was used in the next step without further purification. LRMS m/z 318 (M+H)$^+$.

Title Compound: 1-[4-(isoquinolin-1-ylaminomethyl)-4-phenyl-piperidin-1-yl]-3-phenyl-propan-1-one was prepared using methodology described in Example 390. LRMS m/z 451 (M+H)+.

Example 528

[1-(4-Fluoro-benzenesulfonyl)-4-phenyl-piperidin-4-ylmethyl]-isoquinolin-1-yl-amine

Synthesis

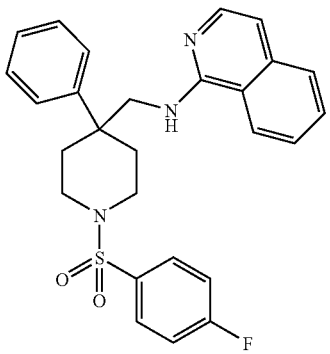

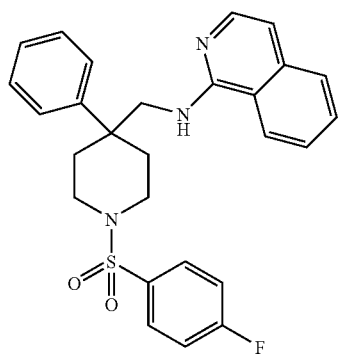

Compound 1: Compound 1 was prepared as described in Example 527.

Title Compound: [1-(4-Fluoro-benzenesulfonyl)-4-phenyl-piperidin-4-ylmethyl]-isoquinolin-1-yl-amine was prepared using methodology described in Example 95. LRMS m/z 477 (M+H)+.

Example 529

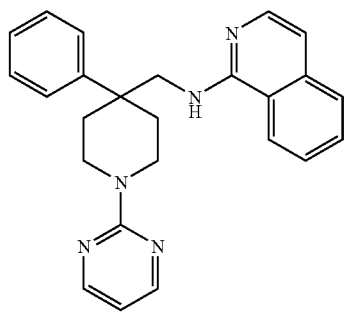

Isoquinolin-1-yl-(4-phenyl-1-pyrimidin-2-yl-piperidin-4-ylmethyl)-amine

Synthesis

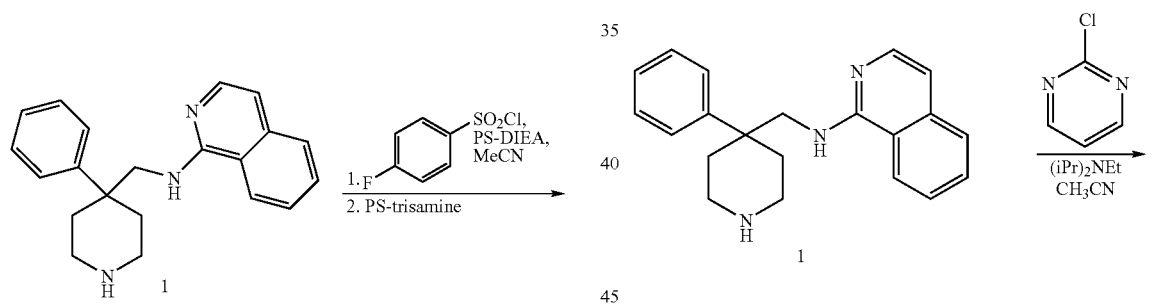

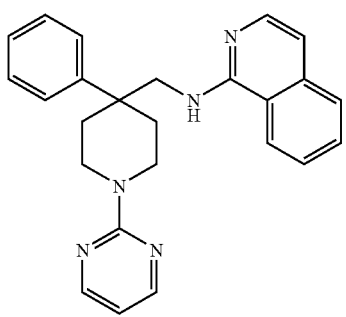

Compound 1: Compound 1 was prepared as described in Example 527.

Title Compound: Isoquinolin-1-yl-(4-phenyl-1-pyrimidin-2-yl-piperidin-4-ylmethyl)-amine was prepared using methodology described in Example 521. LRMS m/z 396 (M+H)+.

Example 530

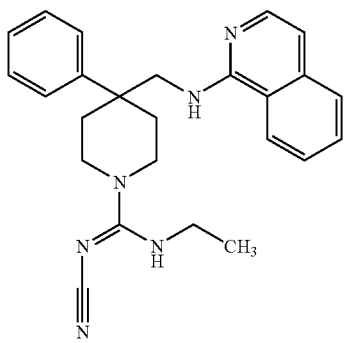

Synthesis

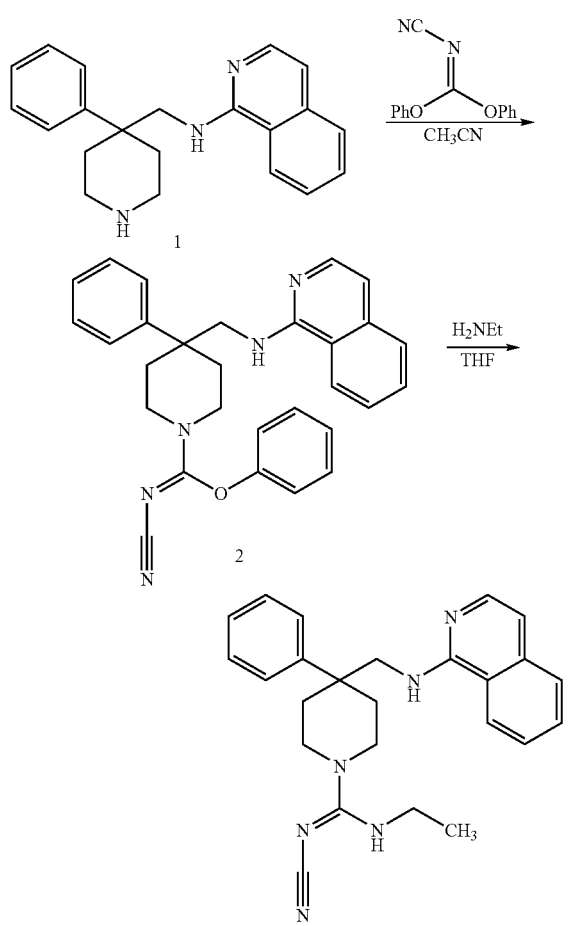

Compound 1: Compound 1 was prepared as described in Example 527.

Compound 2: Compound 2 was prepared using methodology described in Example 25. LRMS m/z 463 (M+H)+.

Title Compound: The title compound was prepared using methodology described in Example 25. LRMS m/z 413 (M+H)+.

Example 531

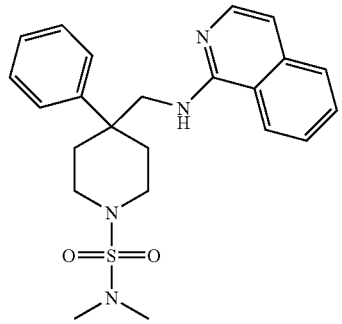

4-(Isoquinolin-1-ylaminomethyl)-4-phenyl-piperidine-1-sulfonic acid dimethylamide Synthesis

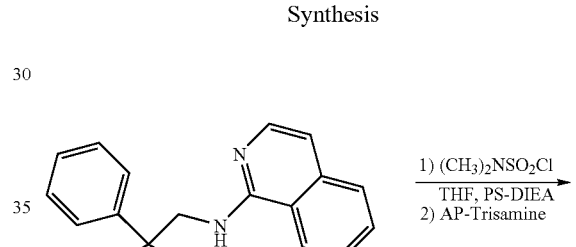

Compound 1: Compound 1 was prepared as described in Example 527.

Title Compound: 4-(Isoquinolin-1-ylaminomethyl)-4-phenyl-piperidine-1-sulfonic acid dimethylamide was prepared using methodology described in Example 16. LRMS m/z 426 (M+H)+.

Example 532

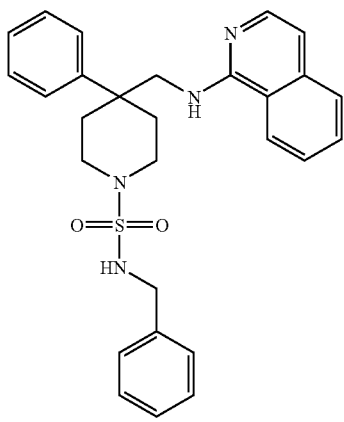

4-(Isoquinolin-1-ylaminomethyl)-4-phenyl-piperidine-1-sulfonic acid benzylamide

Synthesis

Title Compound: 4-(Isoquinolin-1-ylaminomethyl)-4-phenyl-piperidine-1-sulfonic acid benzylamide was prepared using methodology described in Example 17. LRMS m/z 488 (M+H)+.

Example 533

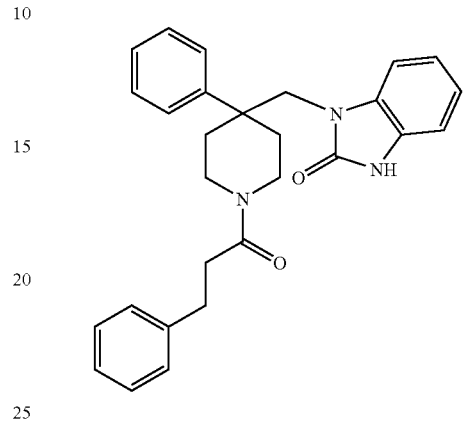

1-[4-phenyl-1-(3-phenyl-propionyl)-piperidin-4-ylmethyl]-1,3-dihydro-benzoimidazol-2-one Synthesis

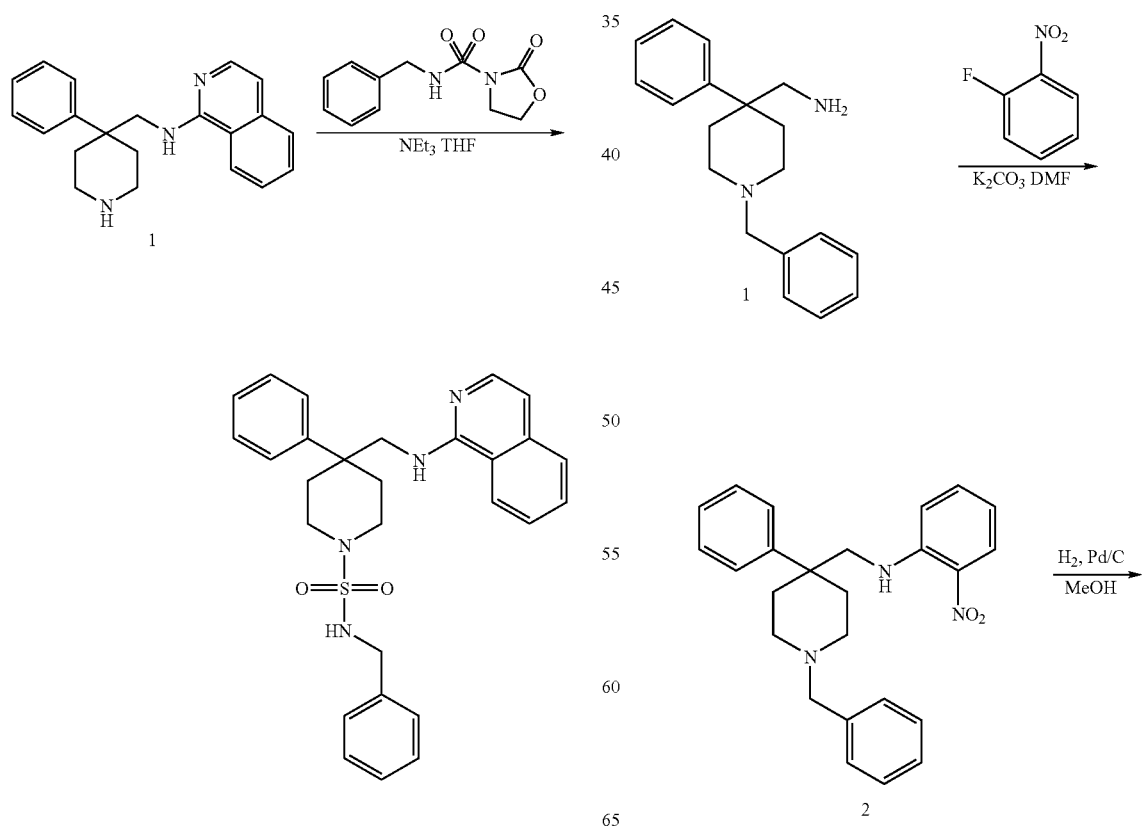

Compound 1: Compound 1 was prepared as described in Example 527.

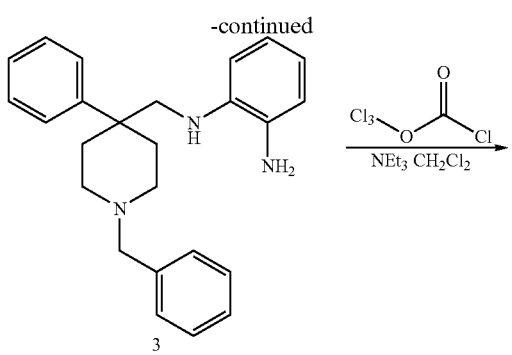

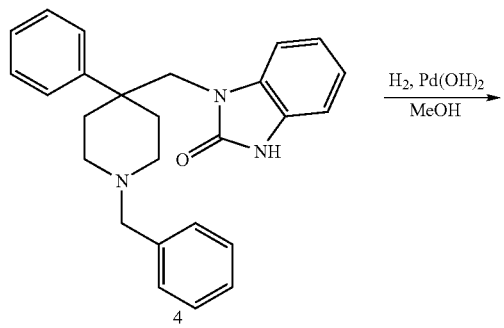

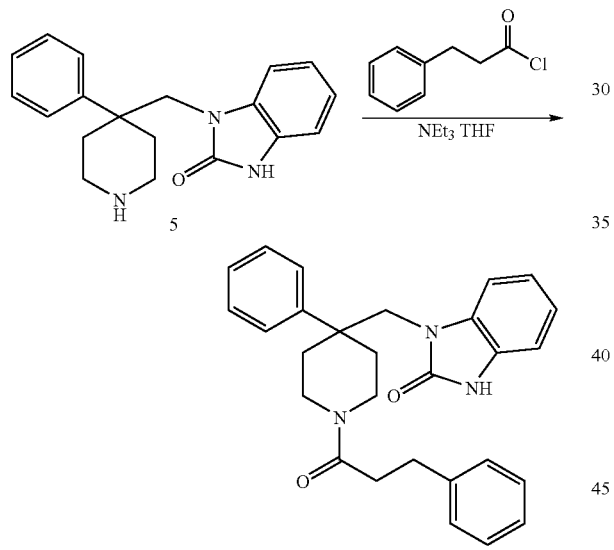

Compound 1: Compound 1 was prepared as described in Example 527.

Compound 2: A mixture of compound 1 (0.60 g, 2.14 mmol), 2-fluronitrobenzene (0.25 mL, 2.35 mmol) and potassium carbonate (excess) in N,N-dimethylformamide, was stirred overnight at 70° C. The reaction was diluted with water (4 mL) then extracted with ethyl ether (4×15 mL). The combined extracts were evaporated and the residue was purified by column chromatography on silica gel using a dichloromethane to 1:1 dichloromethane/ethyl acetate gradient. Product fractions were combined and evaporated to give 0.75 g (87%) compound 2. LRMS m/z 403 (M+H)$^+$.

Compound 3: Compound 2 (0.75 g, 1.87 mmol) was dissolved in methanol and a catalytic amount of 10% palladium/carbon was added. The mixture was stirred under H$_2$ (balloon pressure) until the color disappeared. The reaction was filtered through a celite pad and evaporated to give 0.58 g (84%) of compound 3. LRMS m/z 373 (M+H)$^+$.

Compound 4: A solution of compound 3 (76.3 mg, 0.206 mmol) in dichloromethane (4 mL) was treated with triethylamine (63 µL, 0.45 mmol) and a solution of diphosgene (13.7 µL, 0.113 mmol) in dichloromethane (2 mL). After stirring overnight, the reaction was quenched with saturated aqueous sodium bicarbonate and separated. The organic phase was dried (anhydrous magnesium sulfate), filtered and concentrated. Column chromatography on silica gel using dichloromethane as the eluent gave 0.077 g of compound 4. LRMS m/z 399 (M+H)$^+$.

Compound 5: Compound 4 (63.1 mg, 0.159 mmol) was dissolved in methanol and Pd(OH)$_2$/C (wet) was added. The mixture was hydrogenated at 60 psi and 50° C. overnight. The reaction was purified directly by column chromatography on silica gel using 59:40:1 methanol:chloroform:ammonium hydroxideas the eluent to give 10 mg (20%) of compound 5. LRMS m/z 508 (M+H)$^+$.

Title Compound: 1-[4-phenyl-1-(3-phenyl-propionyl)-piperidin-4-ylmethyl]-1,3-dihydro-benzoimidazol-2-one was prepared using methodology described in Example 390. LRMS m/z 441 (M+H)$^+$.

Example 534

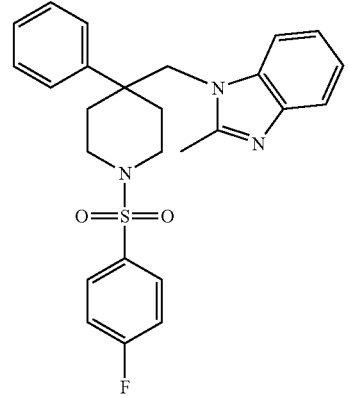

1-[1-(4-Fluoro-benzenesulfonyl)-4-phenyl-piperidin-4-ylmethyl]-2-methyl-1H-benzoimidazole Synthesis

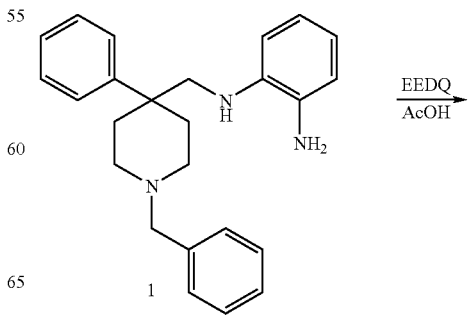

-continued

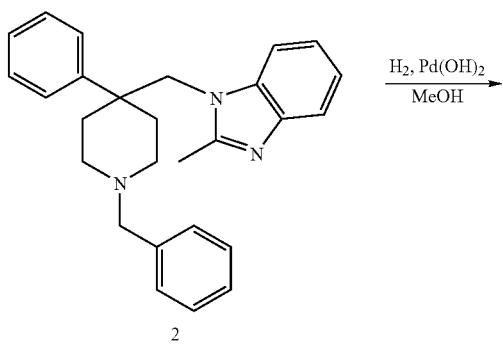
2

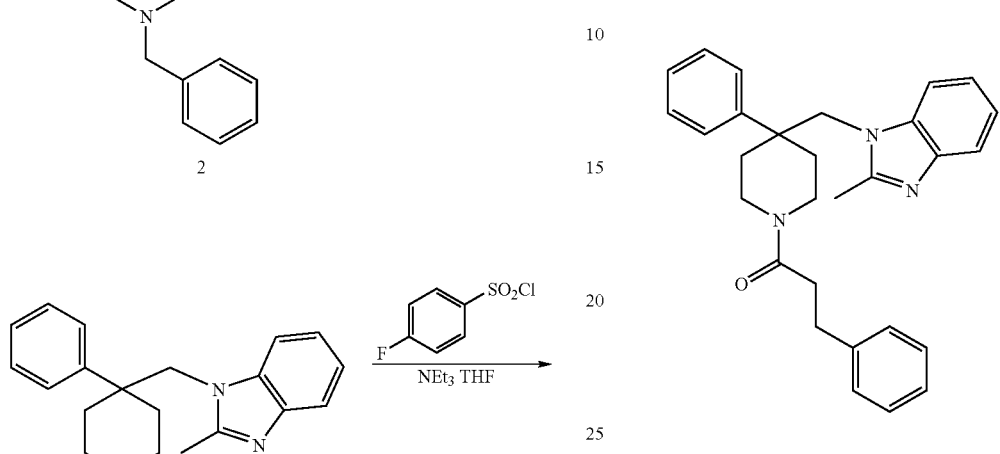
3

Compound 1: Compound 1 was prepared as described in Example 533.

Compound 2: A solution of compound 1 (0.2508 g, 0.676 mmol) in acetic acid (2 mL) was treated with EEDQ (0.170 g, 0.678 mmol) and heated to 120° C. After 12 h, the reaction mixture was evaporated to dryness and the residue was portioned between ethyl acetate (4 mL) and saturated aqueous sodium bicarbonate (3 mL). The aqueous layers was separated and washed with dichloromethane (2×4 mL). The combined organic layers were combined, dried (anhydrous magnesium sulfate), filtered and concentrated. Column chromatography on silica gel using an ethyl acetate to 10% methanol:ethyl acetate gradient as the eluent gave 0.21 g of compound 2. LRMS m/z 397 (M+H)+

Compound 3: Compound 3 was prepared using methodology described in Example 533. LRMS m/z 306 (M+H)+

Title Compound: 1-[1-(4-Fluoro-benzenesulfonyl)-4-phenyl-piperidin-4-ylmethyl]-2-methyl-1H-benzoimidazole was prepared using methodology described in Example 95. LRMS m/z 464 (M+H)+

Example 535

1-[4-(2-Methyl-benzoimidazol-1-ylmethyl)-4-phenyl-piperidin-1-yl]-3-phenyl-propan-1-one Synthesis

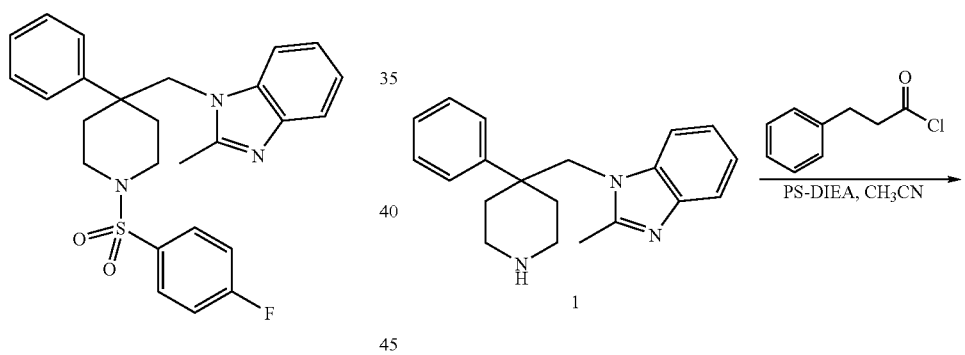

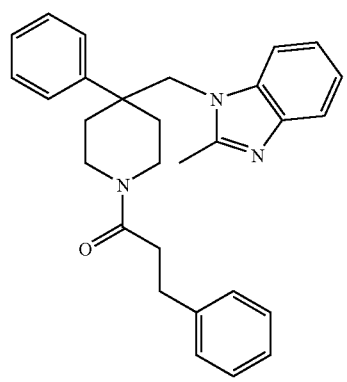

Compound 1: Compound 1 was prepared as described in Example 534.

Title Compound: 1-[4-(2-Methyl-benzoimidazol-1-ylmethyl)-4-phenyl-piperidin-1-yl]-3-phenyl-propan-1-one was prepared using methodology described in Example 94. LRMS m/z 439 (M+H)$^+$.

Example 536

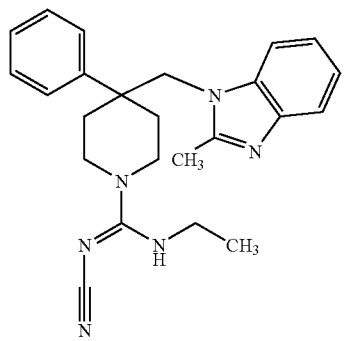

Synthesis

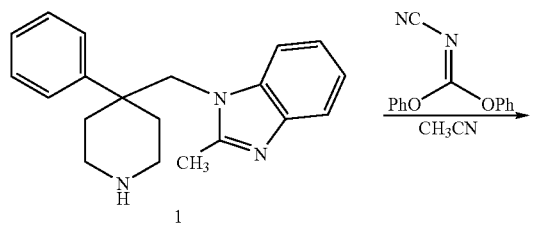

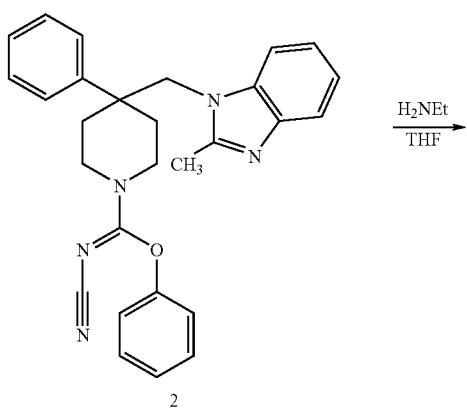

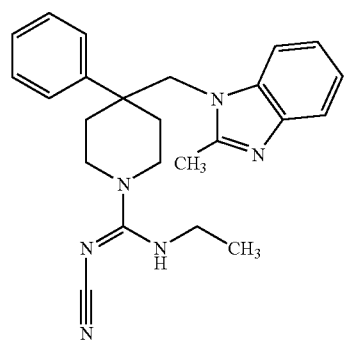

Compound 1: Compound 1 was prepared as described in Example 534.

Compound 2: Compound 2 was prepared using methodology described in Example 25. LRMS m/z 451 (M+H)$^+$.

Title Compound: The title compound was prepared using methodology described in Example 25. LRMS m/z 402 (M+H)$^+$.

Example 537

Example 537 was prepared using methodology described in Example 536.

| Example | Structure | Name | M + H |
|---------|-----------|------|-------|
| 537 | 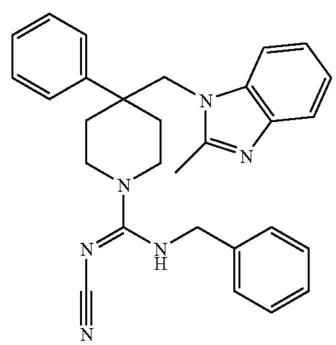 |  | 464 |

Example 538

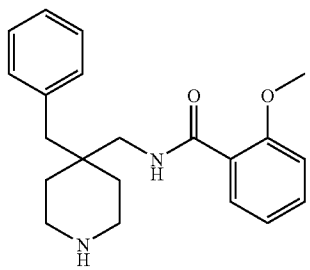

N-(4-Benzyl-piperidin-4-ylmethyl)-2-methoxy-benzamide

Synthesis

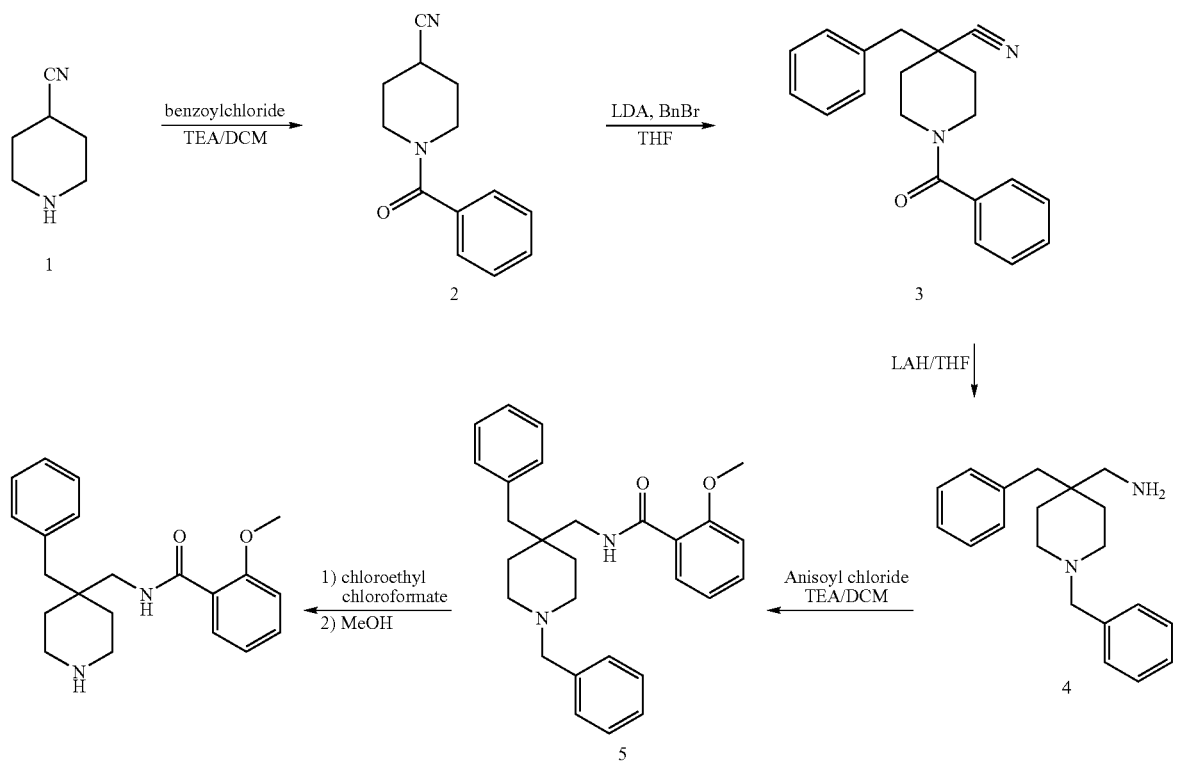

Compound 1: Compound 1 is commercially available.

Compound 2: To compound 1 (1.0 g, 9.08 mmol) in dichloromethane (30 mL) at 0° C. was added triethylamine (1.5 mL, 10.7 mmol) followed by benzoylchloride (1.1 mL, 9.08 mmol). The reaction mixture was stirred at room temperature for 3 h, diluted with ethyl ether (100 mL), washed with saturated 1 N HCl, 1 N NaOH, water and dried over anhydrous sodium sulfate, filtered and concentrated. The residue was purified by silica gel chromotography using Hexanes/EtOAc (2/1) as eluent to give a white solid compound 2, 1.41 g (73% yield). LCMS Rt 1.06 min, [M+1]215.2.

Compound 3: To a solution of diisopropylamine (0.35 mL, 2.52 mmol) in dry tetrahydrofuran (2.5 mL) at 0° C. was added 1.58 mL (2.52 mmol) of 1.6 M n-BuLi in hexanes. After 30 minutes, the reaction mixture was cooled to −78° C. Compound 2 (360 mg, 1.68 mmol) in dry tetrahydrofuran (2.5 mL) was added dropwise. After 1 h, BnBr (0.22 mL, 1.85 mmol) was added. After stirring from −78° C. to room temperature over 2 h the reaction mixture was quenched with water and diluted with Et$_2$O (30 mL). The organic phase was washed with 1 N HCl, water and brine. The aqueous phase was extracted with CH$_2$Cl$_2$. The combined organic phase was dried over Anhydrous sodium sulfate, filtered and concentrated. The residue was purified by silica gel chromotography using Hexanes/EtOAc (1/4) as eluent to give a white solid compound 3, 0.472 g (92% yield). NMR $^1$H (CDCl$_3$) δ (ppm) 1.40-2.05 (4H, m), 2.89 (2H, s), 3.00-3.42 (2H, m), 3.70-3.90 (1H, bs), 4.70-4.90 (1H, bs), 7.26-7.43 (10 H, m).

Compound 4: To compound 3 in dry tetrahydrofuran (5 mL) was added 231 mg (mmol) of LAH then stirred at 65° C. for 20 h. The solution was cooled to 0° C. and quenched with water (0.23 mL), 15% NaOH (0.69 mL) and water (0.23 mL). The quenched reaction mixture was stirred at ambient temperature for 0.5 h. The solid was filtered and washed with Et$_2$O. The organic solution was dried over Na$_2$SO$_4$, filtered and concentrated to give a colorless oil compound 4 sufficiently pure to be taken on to the next step. LCMS [M+1] 295.2.

Compound 5: To compound 4 (1.52 mmol) in dichloromethane (5 mL) at 0° C. was added 0.43 mL (3.06 mmol) of Et$_3$N followed by 0.25 mL (1.68 mmol) of o-anisoyl chloride. After stirring 2 hours from 0° C. to room temperature, the reaction mixture was diluted with Et$_2$O (30 mL), washed with 1N NaOH, water, sat. sodium chloride, dried over anh. sodium sulfate and concentrated. The residue was purified by silica gel chromatography using EtOAc as eluent to give a light yellow syrup compound 5, 0.551 g (85% yield). NMR $^1$H (CDCl$_3$) δ (ppm) 1.45-2.0 (4H, m), 2.02-2.70 (4H, m), 2.69 (2H, s), 3.40 (2H, d, J=5.9 Hz), 3.55 (2H, s), 4.00 (2H, s), 7.00 (1H, d, J=8.2 Hz), 7.08-7.40 (12H, m), 7.45 (1H, dt, J=1.7, 11.1 Hz), 8.05 (1H, bs), 8.23 (1H, dd, J=1.8, 7.8 Hz). LCMS Rt 1.72 min, [M+1]429.2.

Title Compound: N-(4-Benzyl-piperidin-4-ylmethyl)-2-methoxy-benzamide was prepared using methodology described in Example 1. LCMS [M+1]339.1.

Example 539

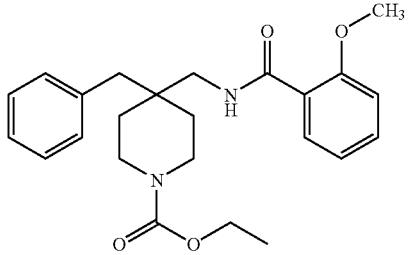

4-Benzyl-4-[(2-methoxy-benzoylamino)-methyl]-piperidine-1-carboxylic acid ethyl ester Synthesis

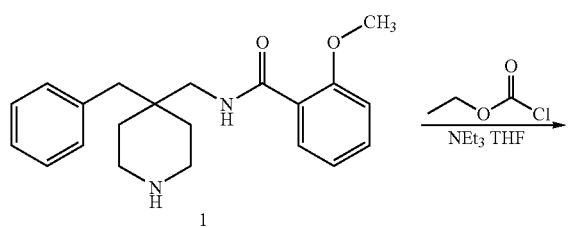

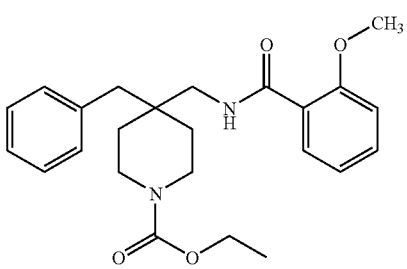

Compound 1: Compound 1 was prepared as described in Example 538.

Title Compound: 4-Benzyl-4-[(2-methoxy-benzoylamino)-methyl]-piperidine-1-carboxylic acid ethyl ester was prepared using methodology described in Example 2. NMR $^1$H (CDCl$_3$) δ (ppm) 1.24 (3H, t, J=7.1 Hz), 1.47-1.51-(4H, m), 2.70 (2H, s), 3.41-3.50 (4H, m), 3.65-3.72 (2H, m), 4.01 (3H, s), 4.11 (2H, q, J=7.1 Hz), 7.02 (1H, d, J=8.2 Hz), 7.09-7.33 (6H, m), 8.06 (1H, bs), 7.48 (1H, td, J=1.7, 7.5 Hz), 8.22 (1H, dd, J=2.2, 7.8 Hz). LCMS Rt 1.72 min, [M+1] 411.1.

Example 540

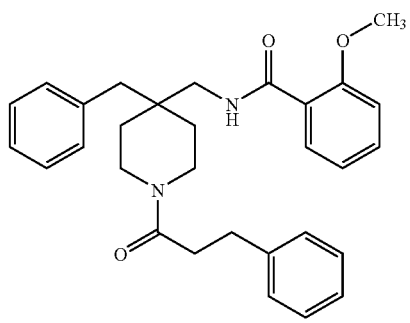

N-[4-Benzyl-1-(3-phenyl-propionyl)-piperidin-4-ylmethyl]-2-methoxy-benzamide

Synthesis

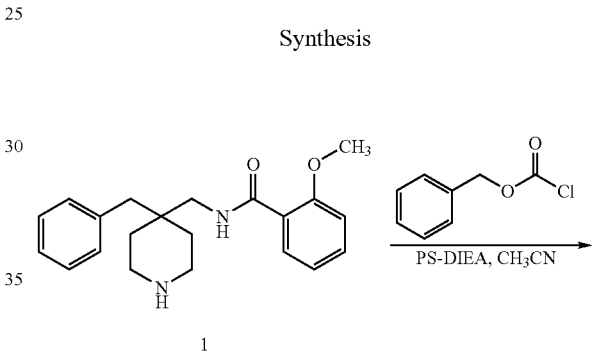

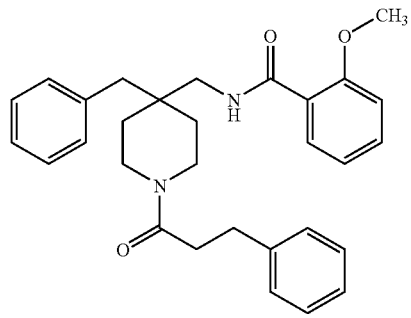

Compound 1: Compound 1 was prepared as described in Example 538.

Title Compound: N-[4-Benzyl-1-(3-phenyl-propionyl)-piperidin-4-ylmethyl]-2-methoxy-benzamide was prepared using methodology described in Example 94. NMR $^1$H (CDCl$_3$) δ (ppm) 1.26-1.38 (2H, m), 1.43-1.50 (2H, m), 2.59-2.64 (2H, m), 2.65 (2H, s), 2.93-2.98 (2H, m), 3.23-3.62 (5H, m), 3.95-4.05 (1H, m), 4.01 (3H, s), 7.02 (11H, d, J=8.2 Hz), 7.09-7.34 (11H, m), 7.45-7.55 (1H, m), 8.07 (1H, t, J=5.8 Hz), 8.21 (1H, dd, J=1.8, 7.8 Hz). LCMS Rt 1.77 min, [M+1] 471.1.

Example 541

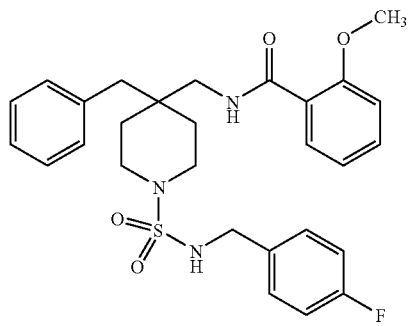

N-[4-Benzyl-1-(4-fluoro-benzylsulfamoyl)-piperidin-4-ylmethyl]-2-methoxy-benzamide Synthesis

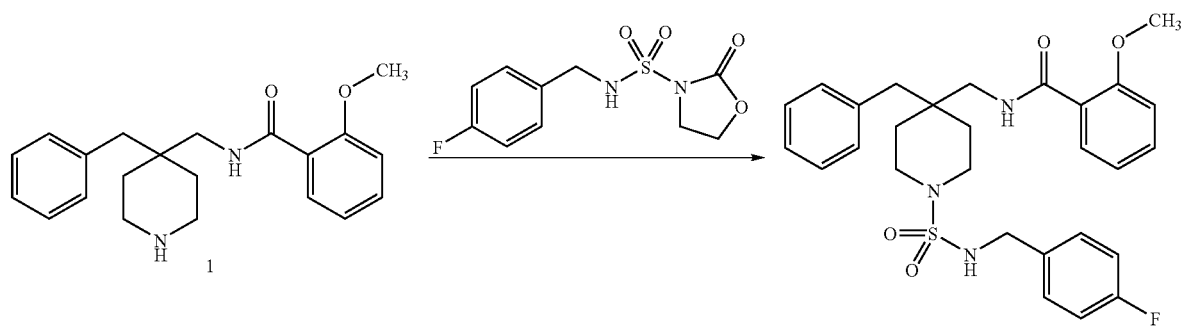

Compound 1: Compound 1 was prepared as described in Example 538.

Title Compound: N-[4-Benzyl-1-(4-fluoro-benzylsulfamoyl)-piperidin-4-ylmethyl]-2-methoxy-benzamide was prepared using methodology described in Example 17. NMR $^1$H (CDCl$_3$) δ (ppm) 1.50-1-70 (4H, m), 2.66 (2H, s), 3.20-3.50 (6H, m), 4.02 (3H, s), 4.19 (2H, d, J=5.0 Hz), 4.58 (1H, bs), 6.99-7.33 (10 H, m), 7.48 (1H, td, J=1.7, 8.0 Hz), 8.08 (1H, bt, J=5.7 Hz), 8.20 (1H, dd, J=1.8, 7.8 Hz).

Example 542

Example 542 was prepared using methodology described in Example 541.

| Example | Structure | Name | (M + 1)+ |
|---|---|---|---|
| 542 | 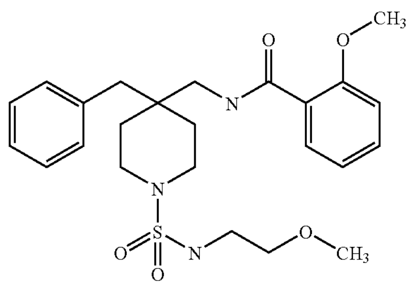 | N-[4-Benzyl-1-(2-methoxy-ethylsulfamoyl)-piperidin-4-ylmethyl]-2-methoxy-benzamide | 476.2 |

Example 543

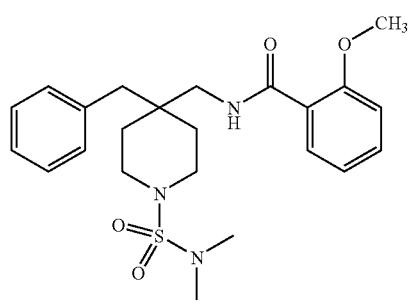

N-(4-Benzyl-1-dimethylsulfamoyl-piperidin-4-ylmethyl)-2-methoxy-benzamide

Synthesis

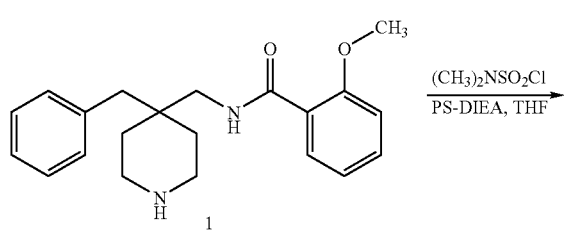

-continued

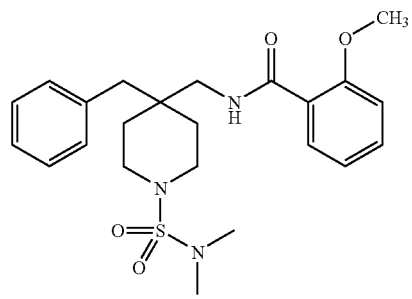

Compound 1: Compound 1 was prepared as described in Example 538.

Title Compound: N-(4-Benzyl-1-dimethylsulfamoyl-piperidin-4-ylmethyl)-2-methoxy-benzamide was prepared using methodology described in Example 16. LRMS m/z 446 (M+H)+.

Examples 544 and 545

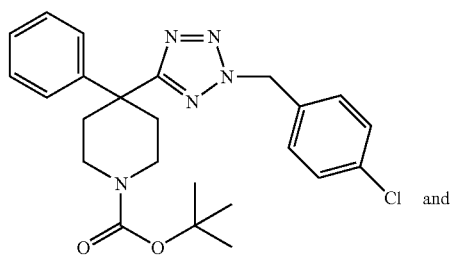
and

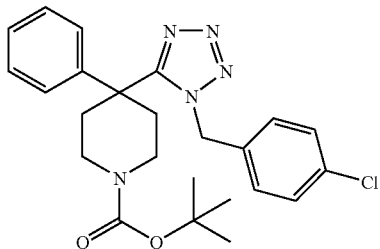

4-[2-(4-Chloro-benzyl)-2H-tetrazol-5-yl]-4-phenyl-piperidine-1-carboxylic acid tert-butyl ester and 4-[1-(4-Chloro-benzyl)-1H-tetrazol-5-yl]-4-phenyl-piperidine-1-carboxylic acid tert-butyl ester Synthesis

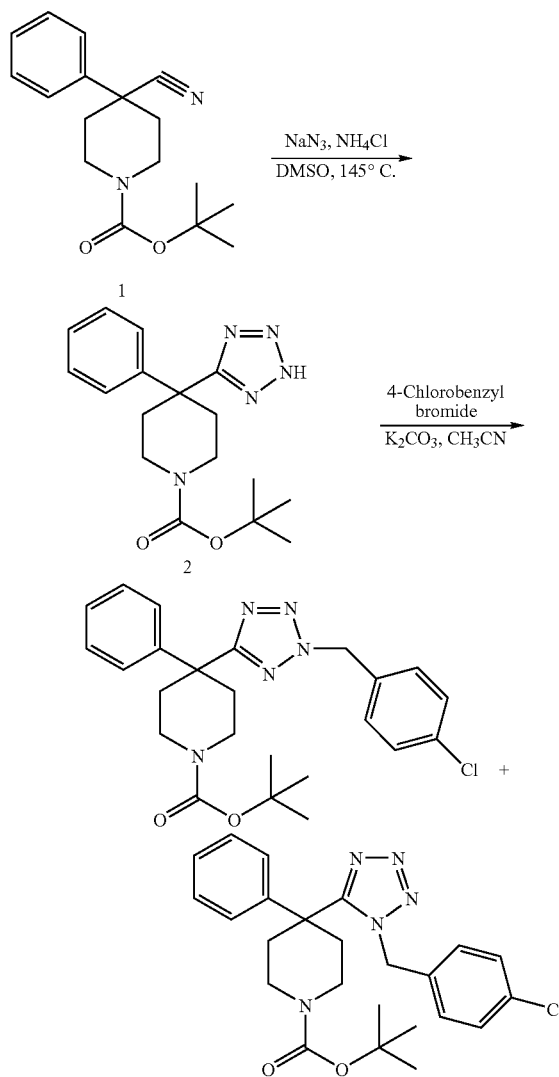

Compound 1: Compound 1 was prepared using methodology described in Example 74. LRMS m/z 287 (M+H)+.

Compound 2: Compound 1 (286 mg, 1.0 mmol), sodium azide (325 mg, 5.0 mmol) and ammonium chloride (268 mg, 5.0 mmol) in DMF (1.5 mL) was heated at 145° C. for 24 hours. After cooling to room temperature the reaction mixture was diluted with water (15 mL) and extracted with ethyl acetate (3×10 mL). The combined organic fractions were washed with water, saturated sodium chloride, dried over anhydrous sodium sulfate, filtered and concentrated. The residue was purified by silica gel chromotography using $CHCl_3$/MeOH (95:5) as eluent to give a white solid compound 2, 250 mg (76% yield). NMR $^1$H (CDCl$_3$) δ (ppm) 1.42 (9H, s), 2.05-2.20 (2H, m), 2.60-3.30 (4H, m), 3.90 (2H, bd, J=13.6 Hz), 7.15-7.30 (5H, m).

Title Compounds: Compound 2 (240 mg, 0.73 mmol), $K_2CO_3$ (111 mg, 0.8 mmol), 4-chlorobenzyl bromide (164 mg, 0.8 mmol) in acetonitrile (6 mL) was heated at 70° C. for 2 hours. The reaction mixture was cooled to room temperature, diluted with ethyl acetate (30 mL), washed with water, saturated sodium chloride, dried over anhydrous sodium chloride, filtered and concentrated. The residue was purified by silica gel chromotography using Hexanes/Ethyl acetate (3:1) as eluent to give a white solid 4-[2-(4-chloro-benzyl)-2H-tetrazol-5-yl]-4-phenyl-piperidine-1-carboxylic acid tert-butyl ester, 244 mg (74% yield) NMR $^1$H (CDCl$_3$) δ (ppm) 1.44 (9H, s), 2.10-2.25 (2H, m), 2.75-2.90 (4H, m), 3.95 (2H, bs), 5.68 (2H, s), 7.16-7.35 (9H, m). LCMS Rt 1.38 min, [M+1]454.0 and white solid 4-[1-(4-chloro-benzyl)-1H-tetrazol-5-yl]-4-phenyl-piperidine-1-carboxylic acid tert-butyl ester, 38 mg (11% yield) NMR $^1$H (CDCl$_3$) δ (ppm) 1.43 (9H, s), 2.00-2.55 (4H, m), 2.75-2.90 (2H, m), 3.00 (1H, bs), 3.35 (1H, bs), 3.82 (2H, bs), 5.92 (2H, bs), 6.71 (2H, d, J=8.6 Hz), 7.09 (2H, d, J=1.4 Hz), 7.11 (1H, d, J=1.9 Hz), 7.22-7.38 (4H, m). LCMS Rt 1.38 min, [M+1]454.2

Example 546

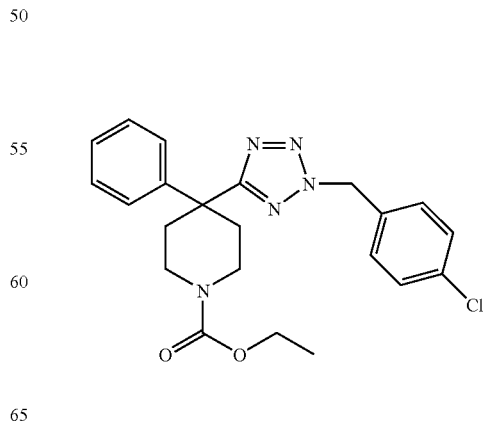

4-[2-(4-Chloro-benzyl)-2H-tetrazol-5-yl]-4-phenyl-piperidine-1-carboxylic acid ethyl ester Synthesis

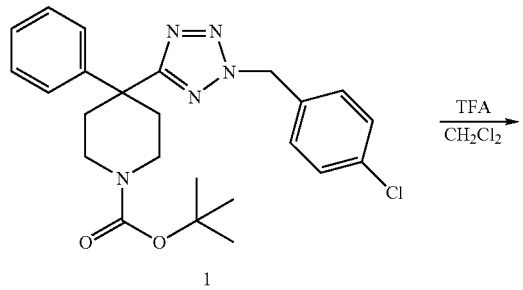

1

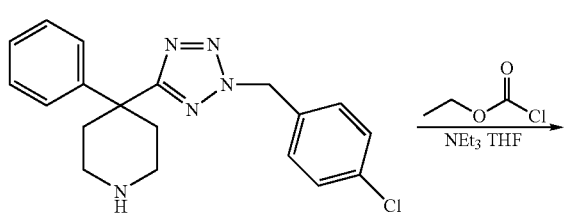

2

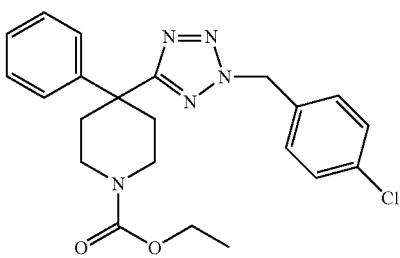

Compound 1: Compound 1 was prepared as described in Example 544.

Compound 2: Compound 1 (236 mg, 0.52 mmol) in dichloromethane (3 mL) and TFA (1 mL) was stirred at room temperature for 1 hour then concentrated. The residue was dissolved in ethyl acetate (20 mL), washed with 1N NaOH (2×5 mL), water, saturated aqueous sodium chloride, dried over anhydrous sodium sulfate and concentrated to give an oil compound 2, 181 mg (98%). NMR H (CDCl$_3$) δ (ppm) 1.24 (3H, t, J=7.0 Hz), 2.11 (2H, bs), 2.43 (2H, bs), 3.05 (1H, bs), 3.35 (1H, bs), 3.85-3.95 (2H, bs), 4.11 (2H, q, J=7.0 Hz), 4.91 (2H, s), 6.72 (2H, d, J=8.4 Hz), 7.21 (2H, d, J=8.4 Hz), 7.10 (2H, d, J=6.1 Hz), 7.29-7.38 (3H, m). [M+1]426.0

Title Compound: 4-[2-(4-Chloro-benzyl)-2H-tetrazol-5-yl]-4-phenyl-piperidine-1-carboxylic acid ethyl ester was prepared using methodology described in Example 2. LRMS m/z 455 (M+H)$^+$.

Example 547

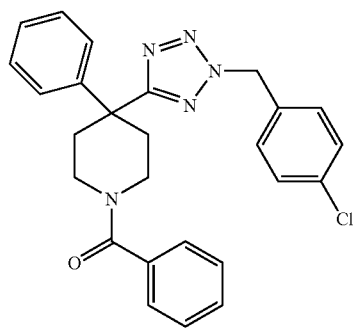

{4-[2-(4-Chloro-benzyl)-2H-tetrazol-5-yl]-4-phenyl-piperidin-1-yl}-phenyl-methanone Synthesis

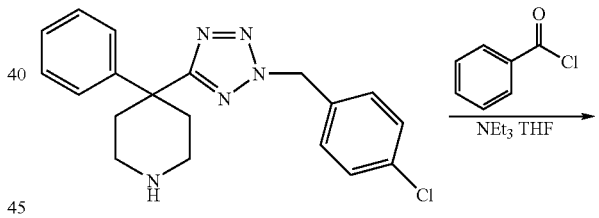

1

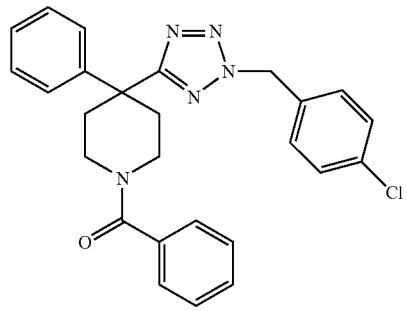

Compound 1: Compound 1 was prepared as described in Example 544.

Title Compound: {4-[2-(4-Chloro-benzyl)-2H-tetrazol-5-yl]-4-phenyl-piperidin-1-yl}-phenyl-methanone was prepared using methodology described in Example 94. LRMS m/z 459 (M+H)+.

Example 548

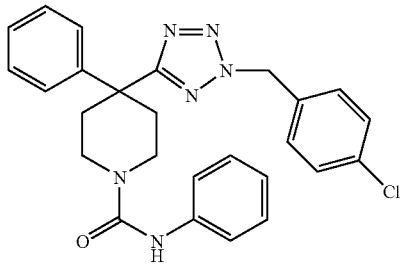

4-[2-(4-Chloro-benzyl)-2H-tetrazol-5-yl]-4-phenyl-piperidine-1-carboxylic acid phenylamide Synthesis

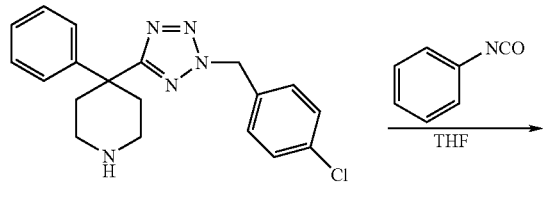

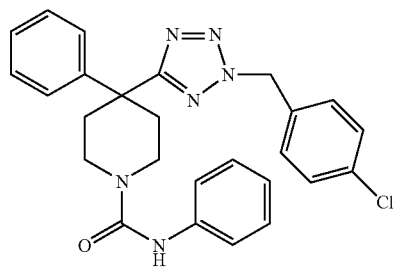

Compound 1: Compound 1 was prepared as described in Example 544.

Title Compound: 4-[2-(4-Chloro-benzyl)-2H-tetrazol-5-yl]-4-phenyl-piperidine-1-carboxylic acid phenylamide was prepared using methodology as described in Example 390. LRMS m/z 474 (M+H)+.

Examples 549 to 598

Examples 549 to 598 were prepared using methodology described in Example 546, Example 547 and Example 548.

| Example | Structure | Name | (M + 1)+ |
|---|---|---|---|
| 549 | 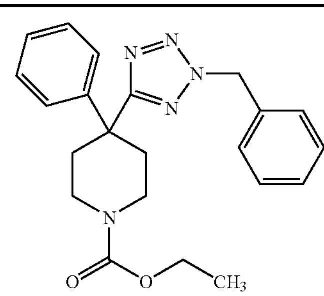 | 4-(2-Benzyl-2H-tetrazol-5-yl)-4-phenyl-piperidine-1-carboxylic acid ethyl ester | 392.2 |
| 550 | 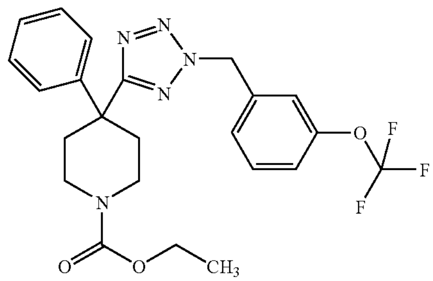 | 4-Phenyl-4-[2-(3-trifluoromethoxy-benzyl)-2H-tetrazol-5-yl]-piperidine-1-carboxylic acid ethyl ester | 476.2 |

-continued

| Example | Name | (M + 1)+ |
|---|---|---|
| 551 | 4-[2-(3-Methyl-benzyl)-2H-tetrazol-5-yl]-4-phenyl-piperidine-1-carboxylic acid ethyl ester | 406.2 |
| 552 | 4-[2-(3-Bromo-benzyl)-2H-tetrazol-5-yl]-4-phenyl-piperidine-1-carboxylic acid ethyl ester | 470.1 |
| 553 | 4-{2-[2-(3-Methyl-benzyl)-2-oxo-ethyl]-2H-tetrazol-5-yl}-4-phenyl-piperidine-1-carboxylic acid ethyl ester | 450.2 |
| 554 | 4-[2-(3,4-Dichloro-benzyl)-2H-tetrazol-5-yl]-4-phenyl-piperidine-1-carboxylic acid ethyl ester | 460.1 |
| 555 | 4-[2-(4-Fluoro-3-trifluoromethyl-benzyl)-2H-tetrazol-5-yl]-4-phenyl-piperidine-1-carboxylic acid ethyl ester | 478.2 |

-continued

| Example | Name | (M + 1)+ |
|---|---|---|
| 556 | 4-[2-(4-Methyl-benzyl)-2H-tetrazol-5-yl]-4-phenyl-piperidine-1-carboxylic acid ethyl ester | 406.2 |
| 557 | 4-[2-(2-Oxo-2-phenyl-ethyl)-2H-tetrazol-5-yl]-4-phenyl-piperidine-1-carboxylic acid ethyl ester | 420.2 |
| 558 | 4-[2-(4-tert-Butyl-benzyl)-2H-tetrazol-5-yl]-4-phenyl-piperidine-1-carboxylic acid ethyl ester | 448.2 |
| 559 | 4-Phenyl-4-[2-(4-trifluoromethoxy-benzyl)-2H-tetrazol-5-yl]-piperidine-1-carboxylic acid ethyl ester | 476.2 |
| 560 | 4-(2-Naphthalen-2-ylmethyl-2H-tetrazol-5-yl)-4-phenyl-piperidine-1-carboxylic acid ethyl ester | 442.2 |

-continued

| Example | Structure | Name | (M + 1)+ |
|---|---|---|---|
| 561 | 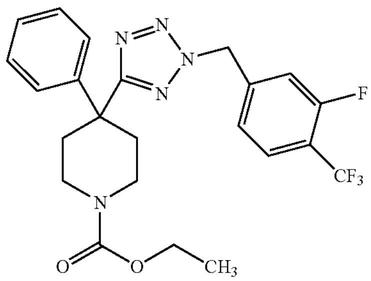 | 4-[2-(3-Fluoro-4-trifluoromethyl-benzyl)-2H-tetrazol-5-yl]-4-phenyl-piperidine-1-carboxylic acid ethyl ester | 478.2 |
| 562 | 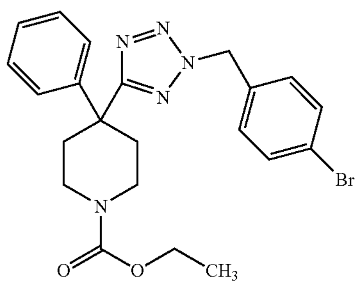 | 4-[2-(4-Bromo-benzyl)-2H-tetrazol-5-yl]-4-phenyl-piperidine-1-carboxylic acid ethyl ester | 470.1 |
| 563 | 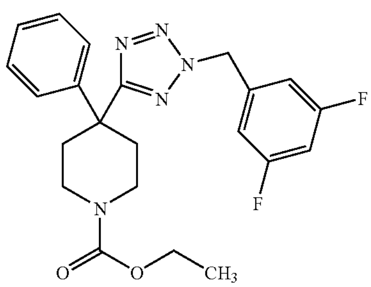 | 4-[2-(3,5-Difluoro-benzyl)-2H-tetrazol-5-yl]-4-phenyl-piperidine-1-carboxylic acid ethyl ester | 428.2 |
| 564 | 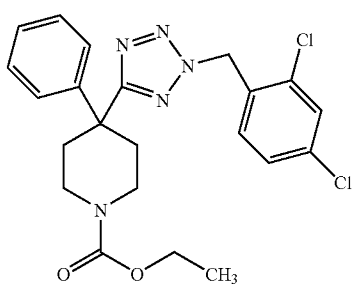 | 4-[2-(2,4-Dichloro-benzyl)-2H-tetrazol-5-yl]-4-phenyl-piperidine-1-carboxylic acid ethyl ester | 460.1 |
| 565 | 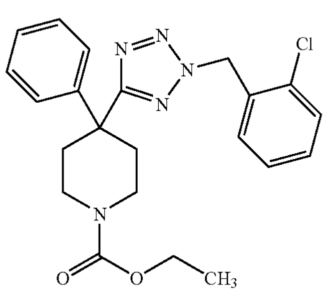 | 4-[2-(2-Chloro-benzyl)-2H-tetrazol-5-yl]-4-phenyl-piperidine-1-carboxylic acid ethyl ester | 426.1 |

-continued

| Example | Structure | Name | (M + 1)+ |
|---|---|---|---|
| 566 | 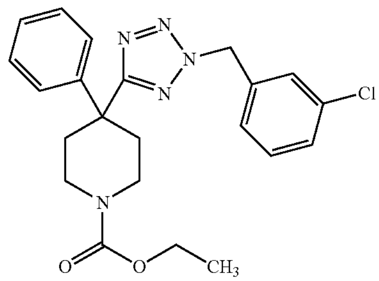 | 4-[2-(3-Chloro-benzyl)-2H-tetrazol-5-yl]-4-phenyl-piperidine-1-carboxylic acid ethyl ester | 426.1 |
| 567 | 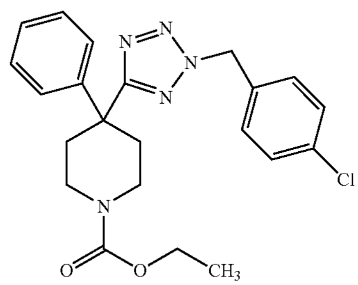 | 4-[2-(4-Chloro-benzyl)-2H-tetrazol-5-yl]-4-phenyl-piperidine-1-carboxylic acid ethyl ester | 426.1 |
| 568 | 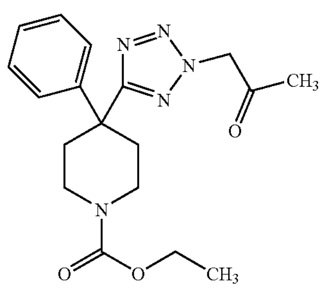 | 4-[2-(2-Oxo-propyl)-2H-tetrazol-5-yl]-4-phenyl-piperidine-1-carboxylic acid ethyl ester | 358.2 |
| 569 | 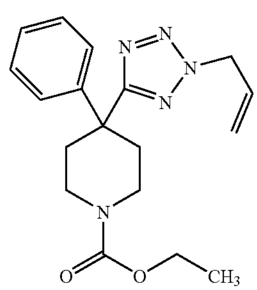 | 4-(2-Allyl-2H-tetrazol-5-yl)-4-phenyl-piperidine-1-carboxylic acid ethyl ester | 342.2 |
| 570 | 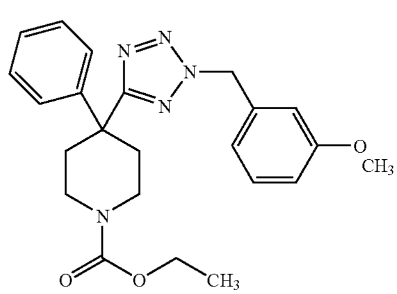 | 4-[2-(3-Methoxy-benzyl)-2H-tetrazol-5-yl]-4-phenyl-piperidine-1-carboxylic acid ethyl ester | 422.2 |

-continued

| Example | Structure | Name | (M + 1)+ |
|---|---|---|---|
| 571 | 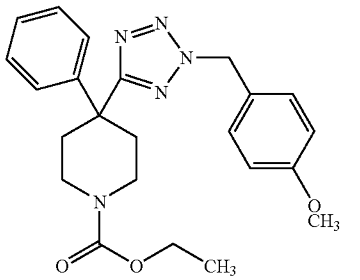 | 4-[2-(4-Methoxy-benzyl)-2H-tetrazol-5-yl]-4-phenyl-piperidine-1-carboxylic acid ethyl ester | 422.2 |
| 572 | 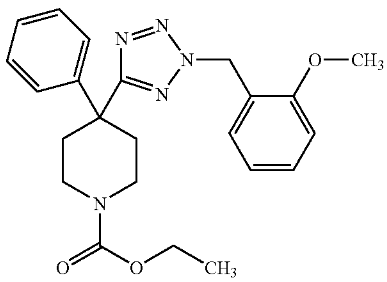 | 4-[2-(2-Methoxy-benzyl)-2H-tetrazol-5-yl]-4-phenyl-piperidine-1-carboxylic acid ethyl ester | 422.2 |
| 573 | 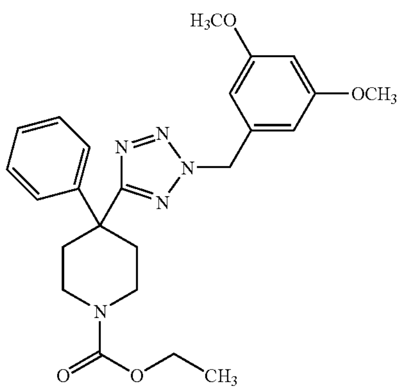 | 4-[2-(3,5-Dimethoxy-benzyl)-2H-tetrazol-5-yl]-4-phenyl-piperidine-1-carboxylic acid ethyl ester | 452.2 |
| 574 | 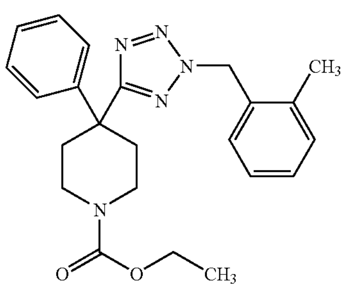 | 4-[2-(2-Methyl-benzyl)-2H-tetrazol-5-yl]-4-phenyl-piperidine-1-carboxylic acid ethyl ester | 406.2 |
| 575 | 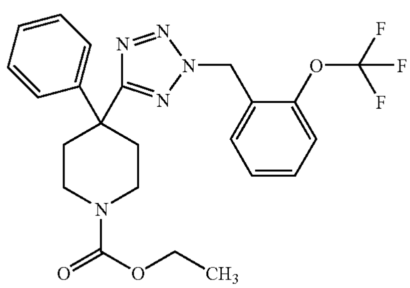 | 4-Phenyl-4-[2-(2-trifluoromethoxy-benzyl)-2H-tetrazol-5-yl]-piperidine-1-carboxylic acid ethyl ester | 476.1 |

-continued

| Example | Name | (M + 1)+ |
|---------|------|----------|
| 576 | 4-[2-(4-Chloro-benzyl)-2H-tetrazol-5-yl]-4-phenyl-piperidine-1-carboxylic acid ethyl ester | 454.2 |
| 577 | 4-[2-(2-Fluoro-benzyl)-2H-tetrazol-5-yl]-4-phenyl-piperidine-1-carboxylic acid ethyl ester | 410.2 |
| 578 | 4-[2-(3-Fluoro-benzyl)-2H-tetrazol-5-yl]-4-phenyl-piperidine-1-carboxylic acid ethyl ester | 410.2 |
| 579 | 4-[2-(4-Fluoro-benzyl)-2H-tetrazol-5-yl]-4-phenyl-piperidine-1-carboxylic acid ethyl ester | 410.2 |
| 580 | 4-Phenyl-4-[2-(2-trifluoromethyl-benzyl)-2H-tetrazol-5-yl]-piperidine-1-carboxylic acid ethyl ester | 460.2 |

-continued

| Example | Structure | Name | (M + 1)+ |
|---|---|---|---|
| 581 | 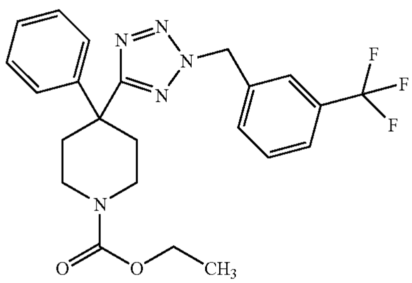 | 4-Phenyl-4-[2-(3-trifluoromethyl-benzyl)-2H-tetrazol-5-yl]-piperidine-1-carboxylic acid ethyl ester | 460.2 |
| 582 | 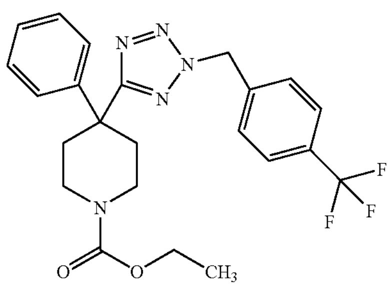 | 4-Phenyl-4-[2-(4-trifluoromethyl-benzyl)-2H-tetrazol-5-yl]-piperidine-1-carboxylic acid ethyl ester | 460.2 |
| 583 | 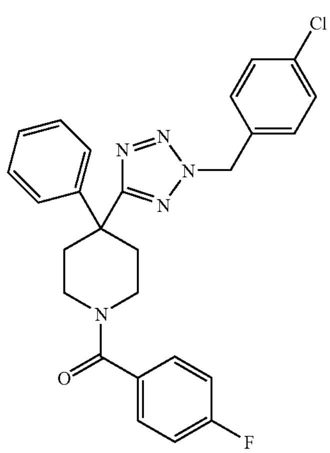 | {4-[2-(4-Chloro-benzyl)-2H-tetrazol-5-yl]-4-phenyl-piperidine-1-yl}-(4-fluoro-phenyl)-methanone | 476.1 |
| 584 | 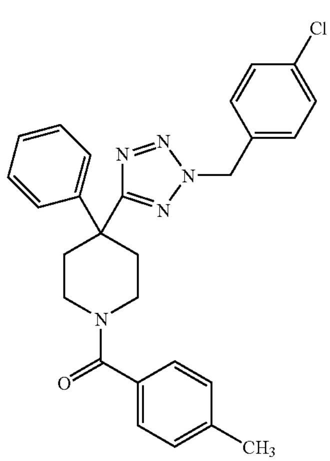 | {4-[2-(4-Chloro-benzyl)-2H-tetrazol-5-yl]-4-phenyl-piperidine-1-yl}-p-tolyl-methanone | 472.2 |

-continued

| Example | Structure | Name | (M + 1)+ |
| --- | --- | --- | --- |
| 585 | 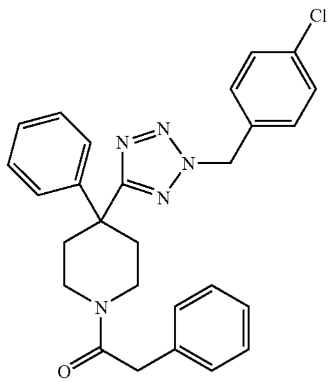 | 1-{4-[2-(4-Chloro-benzyl)-2H-tetrazol-5-yl]-4-phenyl-piperidine-1-yl}-2-phenyl-ethanone | 472.2 |
| 586 | 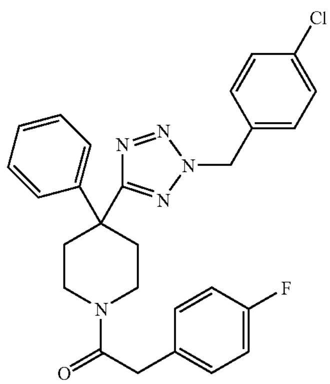 | 1-{4-[2-(4-Chloro-benzyl)-2H-tetrazol-5-yl]-4-phenyl-piperidine-1-yl}-2-(4-fluoro-phenyl)-ethanone | 490.2 |
| 587 | 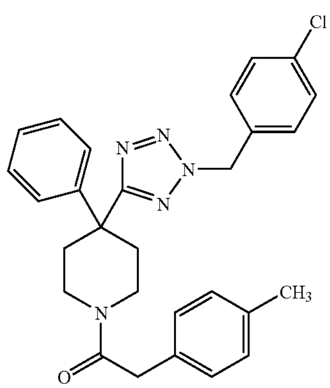 | 1-{4-[2-(4-Chloro-benzyl)-2H-tetrazol-5-yl]-4-phenyl-piperidine-1-yl}-2-p-tolyl-ethanone | 486.2 |
| 588 | 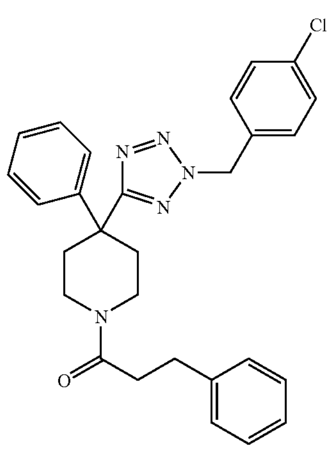 | 1-{4-[2-(4-Chloro-benzyl)-2H-tetrazol-5-yl]-4-phenyl-piperidine-1-yl}-2-phenyl-propan-1-one | 486.2 |

-continued

| Example | Structure | Name | (M + 1)+ |
|---|---|---|---|
| 589 | 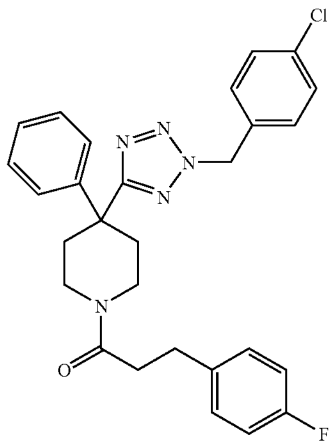 | 1-{4-[2-(4-Chloro-benzyl)-2H-tetrazol-5-yl]-4-phenyl-piperidin-1-yl}-3-(4-fluoro-phenyl)-propan-1-one | 504.2 |
| 590 | 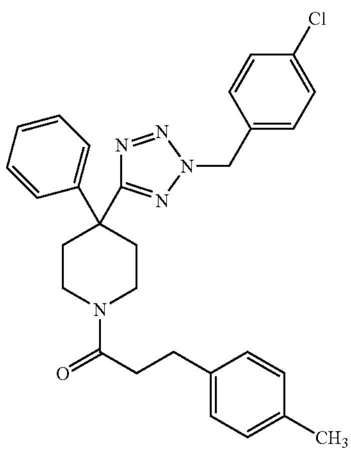 | 1-{4-[2-(4-Chloro-benzyl)-2H-tetrazol-5-yl]-4-phenyl-piperidin-1-yl}-3-p-tolyl-propan-1-one | 500.2 |
| 591 | 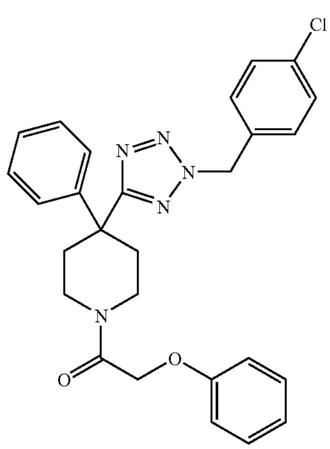 | 1-{4-[2-(4-Chloro-benzyl)-2H-tetrazol-5-yl]-4-phenyl-piperidine-1-yl}-2-phenoxy-ethanone | 488.1 |

-continued

| Example | Structure | Name | (M + 1)+ |
| --- | --- | --- | --- |
| 592 | 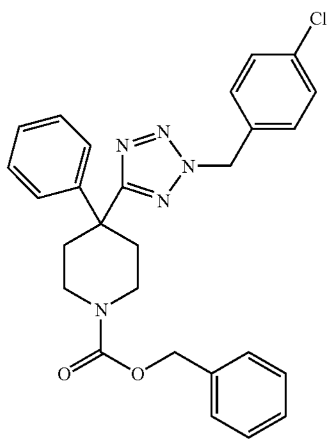 | 4-[2-(4-Chloro-benzyl)-2H-tetrazol-5-yl]-4-phenyl-piperidine-1-carboxylic acid ethyl ester | 488.1 |
| 593 | 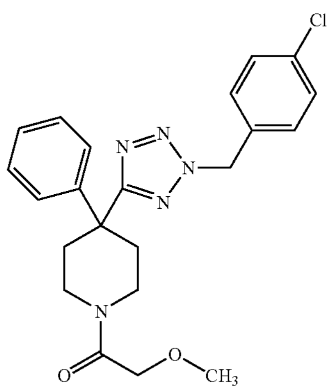 | 1-{4-[2-(4-Chloro-benzyl)-2H-tetrazol-5-yl]-4-phenyl-piperidine-1-yl}-2-phenoxy-ethanone | 426.2 |
| 594 | 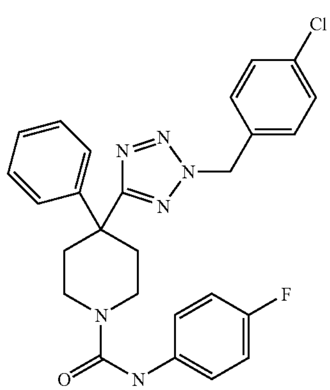 | 4-[2-(4-Chloro-benzyl)-2H-tetrazol-5-yl]-4-phenyl-piperidine-1-carboxylic acid (4-fluoro-phenyl)-amide | 491.2 |
| 595 | 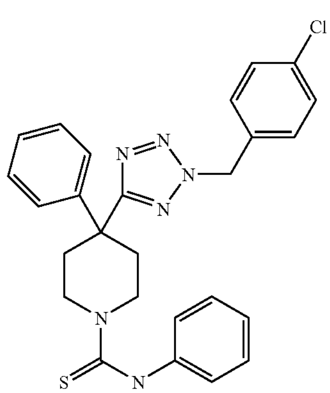 | 4-[2-(4-Chloro-benzyl)-2H-tetrazol-5-yl]-4-phenyl-piperidine-1-carbothioic acid phenylamide | 489.1 |

-continued

| Example | Structure | Name | (M + 1)+ |
|---|---|---|---|
| 596 | 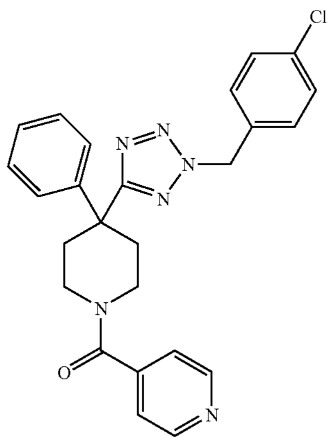 | {4-[2-(4-Chloro-benzyl)-2H-tetrazol-5-yl]-4-phenyl-piperidine-1-yl}-pyridin-4-yl-methanone | 459.2 |
| 597 | 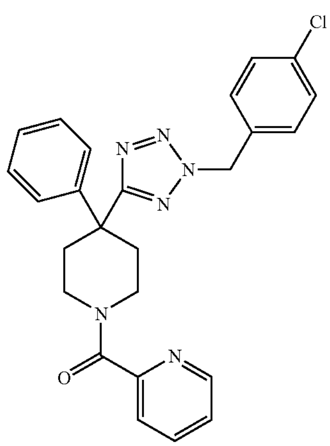 | {4-[2-(4-Chloro-benzyl)-2H-tetrazol-5-yl]-4-phenyl-piperidine-1-yl}-pyridin-4-yl-methanone | 459.2 |
| 598 | 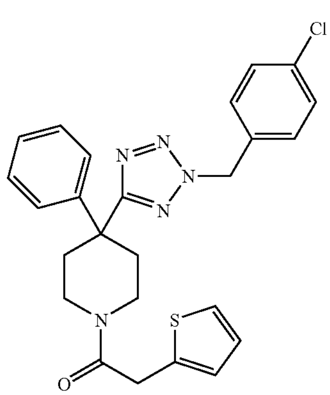 | 1-{4-[2-(4-Chloro-benzyl)-2H-tetrazol-5-yl]-4-phenyl-piperidine-1-yl}-2-thiophen-2-yl-ethanone | 478.1 |

Example 599

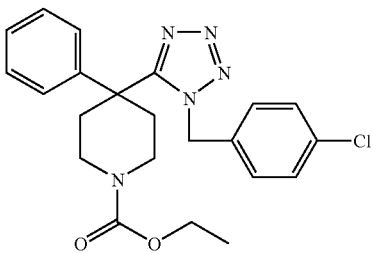

4-[1-(4-Chloro-benzyl)-1H-tetrazol-5-yl]-4-phenyl-piperidine-1-carboxylic acid ethyl ester

Synthesis

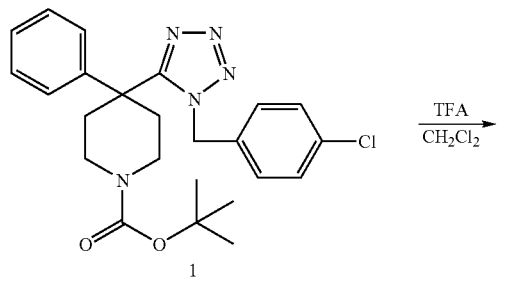

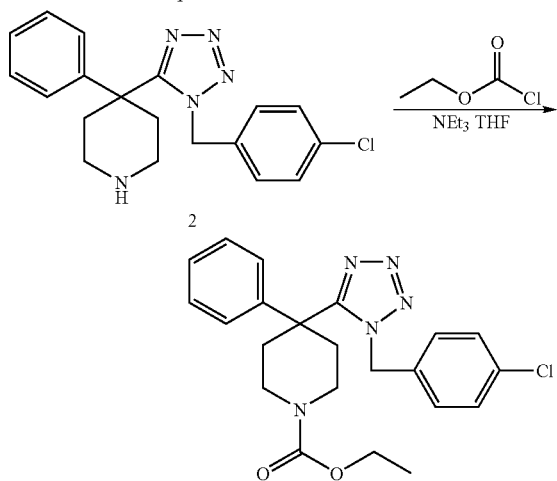

Compound 1: Compound 1 was prepared as described in Example 545.

Compound 2: Compound 1 (31 mg, 0.068 mmol) in dichloromethane (0.75 mL) and TFA (0.25 mL) was stirred at room temperature for 1.5 hour then concentrated. The residue was dissolved in ethyl acetate (10 mL), washed with 1N NaOH (2×5 mL), water, saturated sodium chloride, dried over anhydrous sodium sulfate and concentrated to give an oil compound 6, 20 mg (83%). NMR H (CDCl$_3$) δ (ppm) 1.72 (1H, bs), 2.12-2.21 (2H, m), 2.46 (2H, bd, J=13.7 Hz), 2.94 (4H, bs), 4.92(2H, s), 6.71 (2H, d, J=8.4 Hz), 7.12(2H, d, J=6.4 Hz), 7.16 (2H, d, J=11.3 Hz), 7.21-7.36 (3H, m).

Title Compound: 4-[1-(4-Chloro-benzyl)-1H-tetrazol-5-yl]-4-phenyl-piperidine-1-carboxylic acid ethyl ester was prepared using methodology described in Example 2. NMR H (CDCl$_3$) δ (ppm) 1.24 (3H, t, J=7.0 Hz), 2.11 (2H, bs), 2.43 (2H, bs), 3.05 (1H, bs), 3.35 (1H, bs), 3.85-3.95 (2H, bs), 4.11 (2H, q, J=7.0 Hz), 4.91 (2H, s), 6.72 (2H, d, J=8.4 Hz), 7.21 (2H, d, J=8.4 Hz), 7.10 (2H, d, J=6.1 Hz), 7.29-7.38 (3H, m). [M+1] 426.0

Example 600

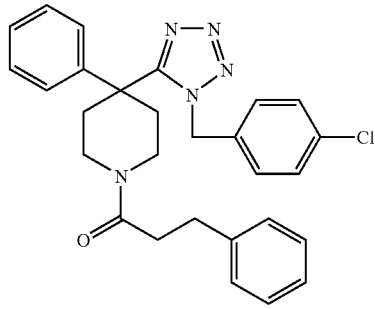

1-{4-[1-(4-Chloro-benzyl)-1H-tetrazol-5-yl]-4-phenyl-piperidin-1-yl}-3-phenyl-propan-1-one

Synthesis

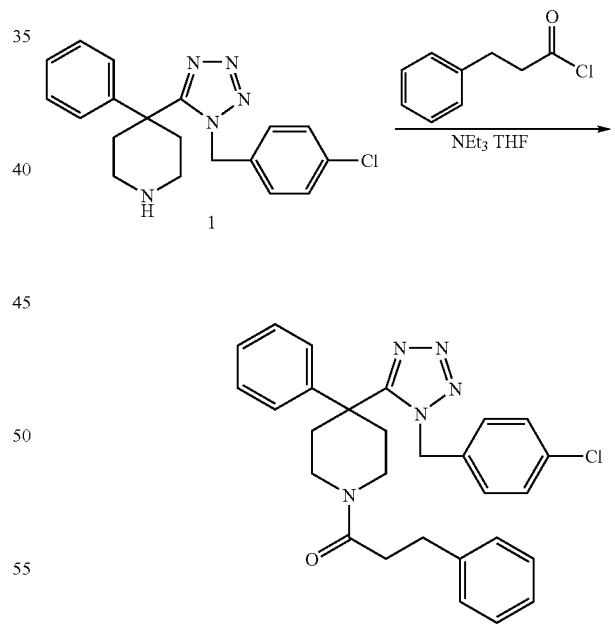

Compound 1: Compound 1 was prepared as described in Example 599.

Title Compound: 1-{4-[1-(4-Chloro-benzyl)-1H-tetrazol-5-yl]-4-phenyl-piperidin-1-yl}-3-phenyl-propan-1-one was prepared using methodology described in Example 390. NMR H (CDCl$_3$) δ (ppm) 1.72-1.77 (1H, m), 2.09-2.27 (2H, m), 2.48-2.62 (3H, m), 2.69-2.77 (1H, m), 2.92-2.96 (2H, m), 3.63 (2H, dd, J=3.0, 8.0 Hz), 4.31-4.35 (1H, m), 4.81 (1H, d, J=15.8 Hz), 4.98 (1H, d, J=15.8 Hz), 6.71 (2H, d, J=8.5 Hz), 6.71 (2H, d, J=8.5 Hz), 7.06-7.38 (8H, m). [M+1] 486.3

Example 601

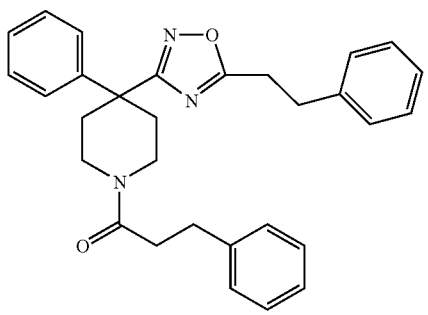

1-[4-(5-Phenethyl-[1,2,4]oxadiazol-3-yl)-4-phenyl-piperidin-1-yl]-3-phenyl-propan-1-one Synthesis

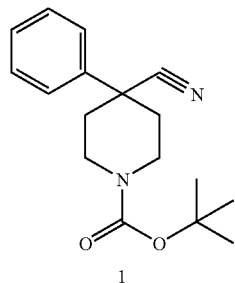

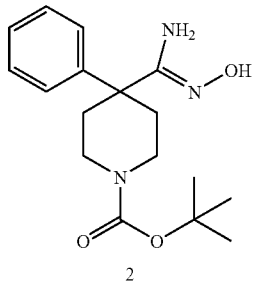

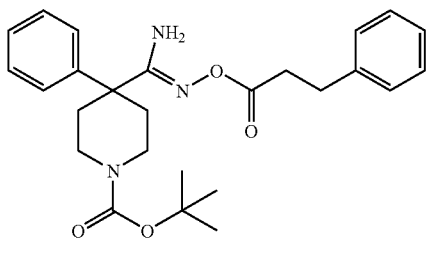

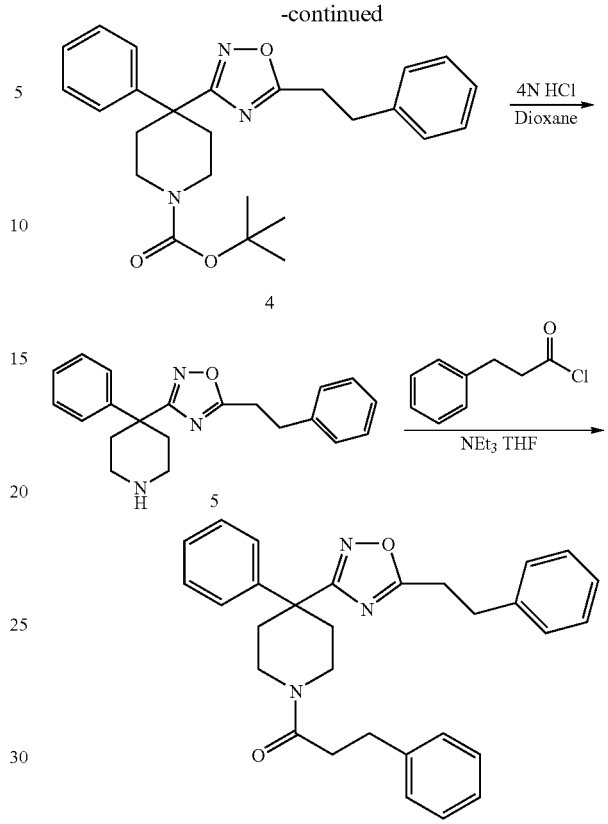

Compound 1: Compound 1 was prepared as described in Example 74.

Compound 2: To hydroxylamine hydrochloride (4.25 g, 61.2 mmol) and sodium methoxide (3.30 g, 61.2 mmol) in PrOH (100 mL) was added compound 1 (5.8 g, 20.4 mmol). The reaction mixture was heated at reflux overnight, diluted with Ethyl acetate (200 mL), washed with water, sat. sodium chloride, dried over anhydrous sodium sulfate and concentrated to give a white solid compound 2, 4.60 g (72% yield). LCMS Rt 1.06 min, [M+1] 320.2.

Compound 3: Compound 2 (31 mg, 0.10 mmol), Et$_3$N (15 mg, 0.15 mmol) and hydrocinnamoyl chloride (19 mg, 0.11 mmol) in tetrahydrofuran (0.5 mL) was stirred overnight. The reaction mixture was diluted with ethyl acetate (5 mL), washed with saturated sodium bicarbonate, water, brine, dried over anhydrous sodium sulfate, filtered and concentrated to give a white solid compound 3, 0.03 g (66% yield).

Compound 4: To compound 3 (30 mg, 0.066 mmol) in dry tetrahydrofuran (0.5 mL) was added 0.13 mL (0.132 mmol) of tetrabutyl ammonium fluoride. After stirring for two hours at room temperature the reaction mixture was diluted with Ethyl acetate (5 mL), washed with water, brine, dried over anhydrous sodium sulfate, filtered and concentrated to give a white solid compound 4 sufficiently pure to be taken on to the next step.

Compound 5: Compound 5 were prepared using methodology described in Example 85 using hydrochloric acid instead of trifluoroacetic acid to accomplish nitrogen deprotection. LRMS m/z 334 (M+H)$^+$.

Title Compound: 1-[4-(5-Phenethyl-[1,2,4]oxadiazol-3-yl)-4-phenyl-piperidin-1-yl]-3-phenyl-propan-1-one was prepared using methodology described in Example 94. LRMS m/z 466 (M+H)$^+$.

Examples 602 to 626

Examples 602 to 626 were prepared as described in Example 601.

| Example | Structure | Name | (M + H)+ |
|---|---|---|---|
| 602 | 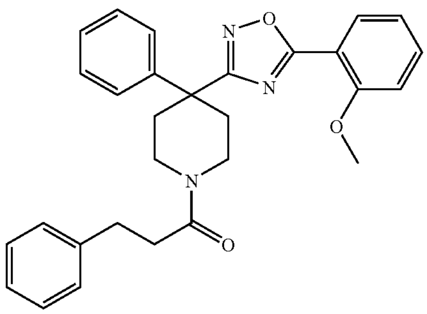 | 1-{4-[5-(2-Methoxy-phenyl)-[1,2,4]oxadiazol-3-yl]-4-phenyl-piperidin-1-yl}-3-phenyl-propan-1-one | 468.2 |
| 603 | 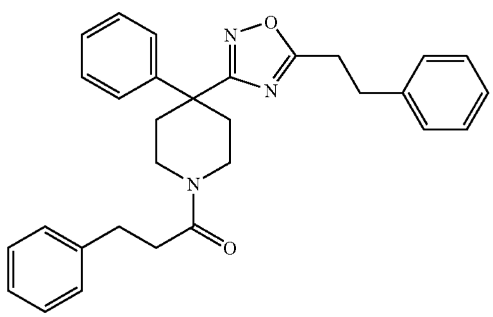 | 1-[4-(5-Phenethyl-[1,2,4]oxadiazol-3-yl)-4-phenyl-piperidin-1-yl}-3-phenyl-ethanone | 452.2 |
| 604 | 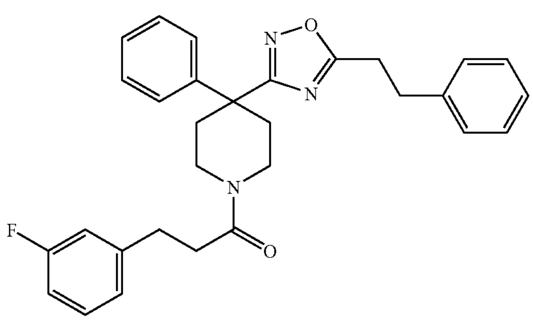 | 2-(4-Fluoro-phenyl)-1-[4-(5-phenethyl-[1,2,4]oxadiazol-3-yl)-4-phenyl-piperidin-1-yl]-ethanone | 470.2 |
| 605 | 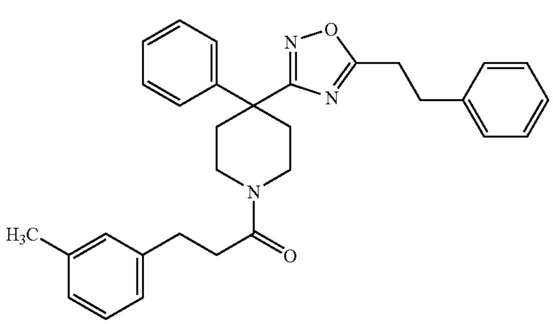 | 1-[4-(5-Phenethyl-[1,2,4]oxadiazol-3-yl)-4-phenyl-piperidin-1-yl}-2-p-tolyl-ethanone | 466.2 |

-continued

| Example | Name | (M + H)+ |
|---|---|---|
| 606 | 3-(4-Fluoro-phenyl)-1-[4-(5-phenethyl-[1,2,4]oxadiazol-3-yl)-4-phenyl-piperidin-1-yl]-propan-1-one | 484.2 |
| 607 | 1-[4-(5-Phenethyl-[1,2,4]oxadiazol-3-yl)-4-phenyl-piperidin-1-yl}-3-p-tolyl-propan-1-one | 480.3 |
| 608 | 1-{4-[5-(4-Chloro-benzyl)-[1,2,4]oxadiazol-3-yl]-4-phenyl-piperidin-1-yl}-2-phenyl-ethanone | 472.2 |
| 609 | 1-{4-[5-(4-Chloro-benzyl)-[1,2,4]oxadiazol-3-yl]-4-phenyl-piperidin-1-yl}-2-(4-fluoro-phenyl)-ethanone | 490.2 |
| 610 | 1-{4-[5-(4-Chloro-benzyl)-[1,2,4]oxadiazol-3-yl]-4-phenyl-piperidin-1-yl}-2-p-tolyl-ethanone | 486.2 |

-continued

| Example | Structure | Name | (M + H)+ |
|---|---|---|---|
| 611 | 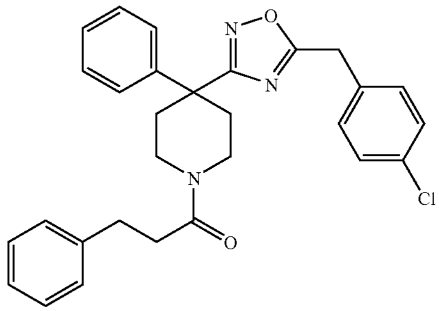 | 1-{4-[5-(4-Chloro-benzyl)-[1,2,4]oxadiazol-3-yl]-4-phenyl-piperidin-1-yl}-3-phenyl-propan-1-one | 486.2 |
| 612 | 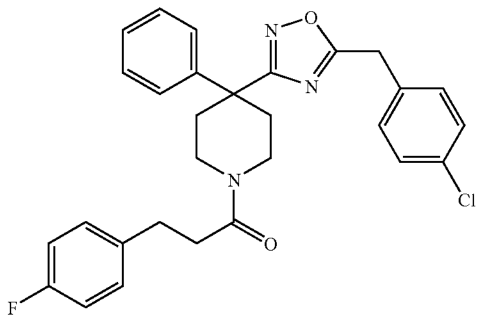 | 1-{4-[5-(4-Chloro-benzyl)-[1,2,4]oxadiazol-3-yl]-4-phenyl-piperidin-1-yl}-3-(4-fluoro-phenyl)-propan-1-one | 504.2 |
| 613 | 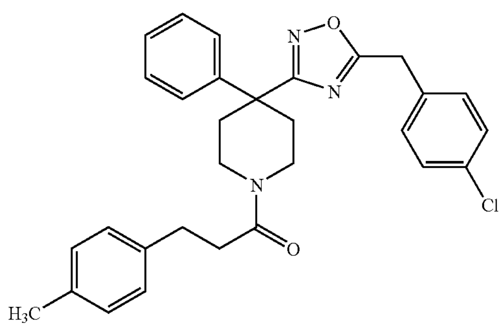 | 1-{4-[5-(4-Chloro-benzyl)-[1,2,4]oxadiazol-3-yl]-4-phenyl-piperidin-1-yl}-3-p-tolyl-propan-1-one | 500.2 |
| 614 | 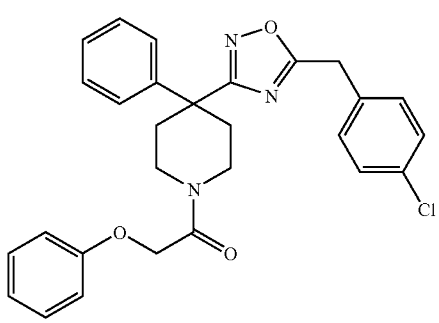 | 1-{4-[5-(4-Chloro-benzyl)-[1,2,4]oxadiazol-3-yl]-4-phenyl-piperidin-1-yl}-2-phenoxy-ethanone | 488.2 |

-continued

| Example | Name | (M + H)⁺ |
|---------|------|----------|
| 615 | [4-(5-Benzyl-[1,2,4]oxadiazol-3-yl)-4-phenyl-piperidin-1-yl]-(4-fluoro-phenyl)-methanone | 442.2 |
| 616 | 1-[4-(5-Benzyl-[1,2,4]oxadiazol-3-yl)-4-phenyl-piperidin-1-yl]-2-phenyl-ethanone | 438.2 |
| 617 | 1-[4-(5-Benzyl-[1,2,4]oxadiazol-3-yl)-4-phenyl-piperidin-1-yl]-2-(4-fluoro-phenyl)-ethanone | 456.2 |
| 618 | 1-[4-(5-Benzyl-[1,2,4]oxadiazol-3-yl)-4-phenyl-piperidin-1-yl]-2-p-tolyl-ethanone | 452.2 |
| 619 | 1-{4-(5-Benzyl-[1,2,4]oxadiazol-3-yl)-4-phenyl-piperidin-1-yl]-3-phenyl-propan-1-one | 452.2 |

-continued

| Example | Structure | Name | (M + H)+ |
|---|---|---|---|
| 620 | 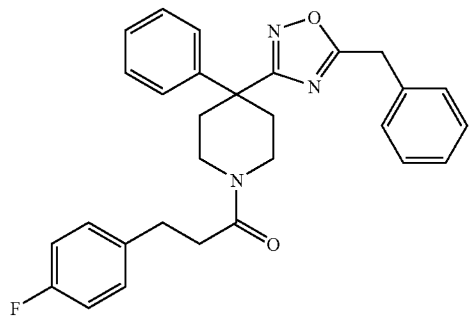 | 1-[4-(5-Benzyl-[1,2,4]oxadiazol-3-yl)-4-phenyl-piperidin-1-yl]-3-(4-fluoro-phenyl)-propan-1-one | 470.2 |
| 621 | 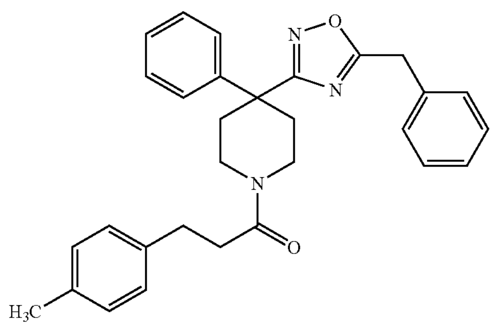 | 1-{4-(5-Phenethyl-[1,2,4]-oxadiazol-3-yl)-4-phenyl-piperidin-1-yl]-2-thiophen-2-yl-ethanone | 458.2 |
| 622 | 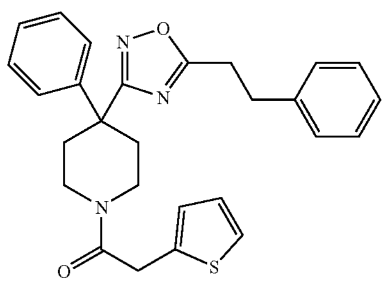 | 1-[4-(5-Phenethyl-[1,2,4]-oxadiazol-3-yl)-4-phenyl-piperidin-1-yl]-2-thiophen-2-yl-ethanone | 458.2 |
| 623 | 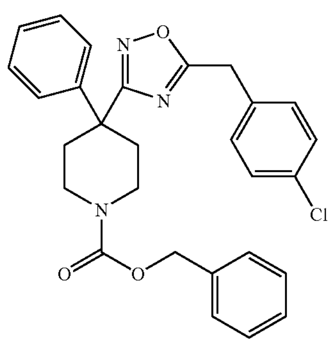 | 4-[5-(4-Chloro-benzyl)-[1,2,4]oxadiazol-3-yl]-4-phenyl-piperidine-1-carboxylic acid benzyl ester | 488.2 |
| 624 | 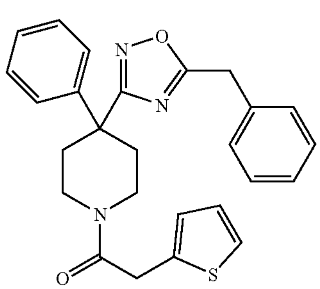 | 1-[4-(5-Benzyl-[1,2,4]-oxadiazol-3-yl)-4-phenyl-piperidin-1-yl]-2-thiophen-2-yl-ethanone | 444.2 |

| Example | Structure | Name | (M + H)+ |
|---|---|---|---|
| 625 | 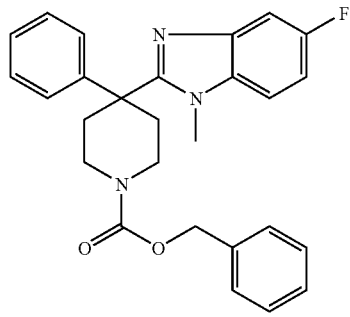 | 1-{4-[5-(4-Methoxy-benzyl)-[1,2,4]oxadiazol-3-yl]-4-phenyl-piperidin-1-yl}-3-phenyl-propan-1-one | 482.2 |
| 626 | 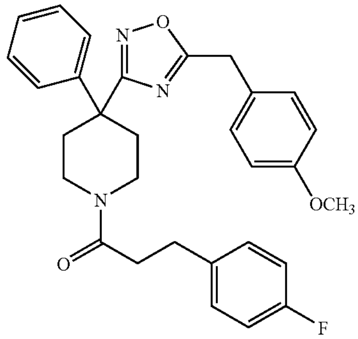 | 3-(4-Fluoro-phenyl)-1-{4-[5-(4-methoxy-benzyl)-[1,2,4]-oxadiazol-3-yl]-4-phenyl-piperidin-1-yl}-propan-1-one | 500.2 |
Example 627
4-(5-Fluoro-1-methyl-1H-benzoimidazol-2-yl)-4-phenyl-piperidine-1-carboxylic acid benzyl ester
Synthesis
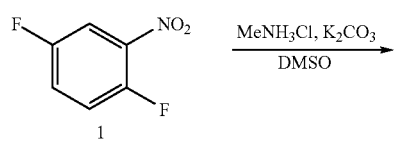
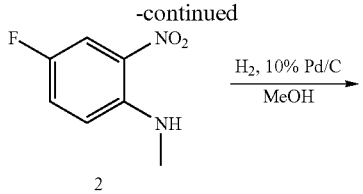
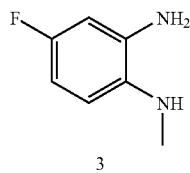
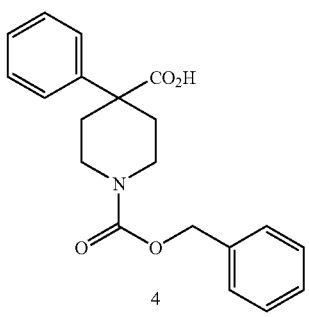

401

-continued

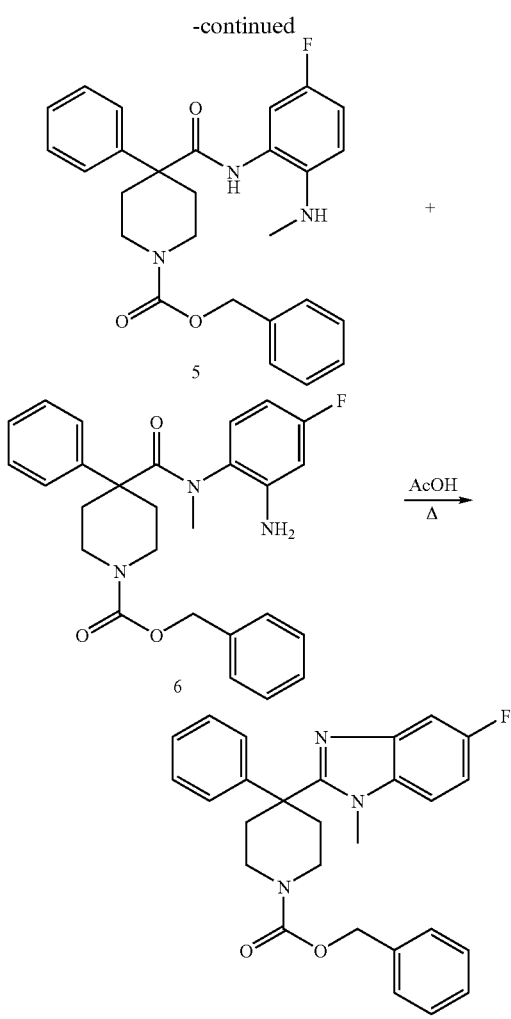

Compound 1: Compound 1 is commercially available.
Compound 2: 2,5-Difluoronitrobenzene (1.0 g, 6.29 mmol), methylamine hydrochloride (2.12 g, 31.43 mmol) and potassium carbonate (4.34 g, 31.43 mmol) in DMSO (10 mL) was stirred for 24 hours, diluted with Et2O (200 mL), washed with water (3 times), brine, dried over anhydrous sodium sulfate and concentrated to give compound 2 as an orange solid 1.1 g (100%).

Compound 3: Compound 2 (1.1 g, 6.29 mmol) and 10% Pd on charcoal (300 mg) in methanol (20 mL) was stirred under hydrogen for 24 hours, filtered over celite and concentrated. The residue was purified by silica gel chromotography using Hexanes/Ethyl acetate (2:1) as eluent to give a white solid compound 3, 672 mg (74% yield). NMR $^1$H (CDCl$_3$) δ (ppm) 2.83 (3H, s), 3.28 (3H, bs), 6.40-6.60 (3H, m).

Compound 4: Compound 4 was prepared as described in Example 323.

Compounds 5 and 6: Compound 4 (700 mg, 2.06 mmol) in thionyl chloride was heated at reflux for 2 hours then concentrated. The residue was dissolved in CH$_2$Cl$_2$ (3.5 mL) and cooled to 0° C. Compound 3 (289 mg, 2.06 mmol) in CH$_2$Cl$_2$ (3.5 mL) followed by Et$_3$N (1.44 mL, 10.3 mmol) were added. After 1 hour the reaction mixture was diluted with Ethyl acetate (30 mL), washed with 1N NaOH, water, brine, dried over anh. sodium sulfate and concentrated. The residue was purified by silica gel chromotography using Hexanes/Ethyl acetate (2:1) as eluent to give a white solid compound 5 and compound 6 521 mg (55% yield) as an inseparable mixture. LCMS Rt 1.42 min and 1.52, [M+1] 462.2.

Title Compound: The mixture of compound 5 and compound 6 (521 mg, 1.12 mmol) in glacial acetic acid (5 mL) was heated at reflux for 2 hours then concentrated. The residue was purified by silica gel chromotography using Hexanes/Ethyl acetate (2:1) as eluent to give a white solid 4-(5-fluoro-1-methyl-1H-benzoimidazol-2-yl)-4-phenyl-piperidine-1-carboxylic acid benzyl ester, 365 mg (73% yield). NMR $^1$H (CDCl$_3$) δ (ppm) 2.05-2.40 (2H, m), 2.55-2.75 (2H, m), 3.22 (3H, s), 3.25-3.40 (1H, m), 3.50-3.70 (1H, m), 5.14 (2H, s), 7.01 (1H, dt, J=2.4, 9.1 Hz), 7.09-7.35 (13H, m), 7.48 (1H, dd, J=2.2, 9.4 Hz). LCMS Rt 1.41 min, [M+1] 442.2.

Examples 628 to 646

Examples 628 to 646 were prepared as described in Example 627.

| Example | Structure | Name | (M + 1)+ |
|---|---|---|---|
| 628 | 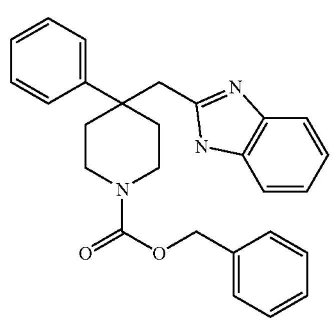 | 4-(1H-Benzoimidazol-2-ylmethyl)-4-phenyl-piperidine-1-carboxylic acid benzyl ester | 426.2 |

-continued

| Example | Structure | Name | (M + 1)+ |
|---|---|---|---|
| 629 | 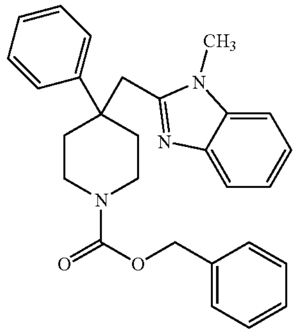 | 4-(1-Methyl-1H-benzoimidazol-2-ylmethyl)-4-phenyl-piperidine-1-carboxylic acid benzyl ester | 440.2 |
| 630 | 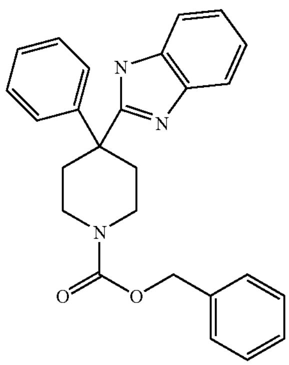 | 4-(1H-Benzoimidazol-2-yl)-4-phenyl-piperidine-1-carboxylic acid benzyl ester | 412.2 |
| 631 | 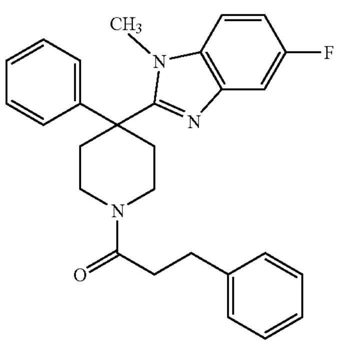 | 1-[4-(5-Fluoro-1-methyl-1H-benzoimidazol-2-yl)-4-phenyl-piperidine-1-yl]-3-phenyl-propan-1-one | 442.2 |
| 632 | 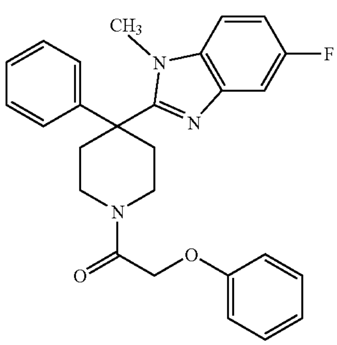 | 1-[4-(5-Fluoro-1-methyl-1H-benzoimidazol-2-yl)-4-phenyl-piperidin-1-yl]-2-phenoxy-ethanone | 444.2 |

-continued

| Example | Structure | Name | (M + 1)+ |
| --- | --- | --- | --- |
| 633 | 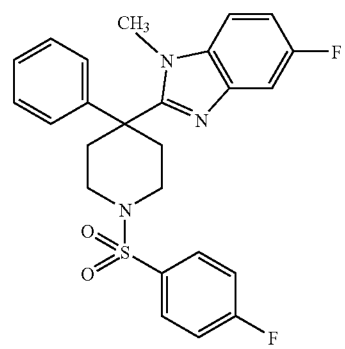 | 5-Fluoro-2-[1-(4-fluoro-benzenesulfonyl)-4-phenyl-piperidin-4-yl]-1-methyl-1H-benzoimidazole | 468.2 |
| 634 | 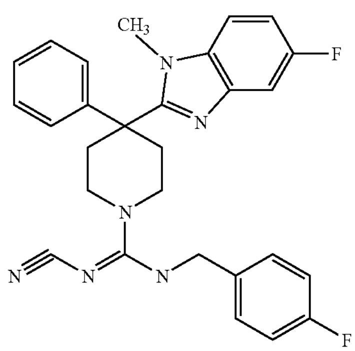 | | 485.2 |
| 635 | 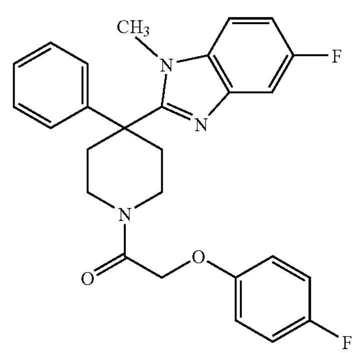 | 1-[4-(5-Fluoro-1-methyl-1H-benzoimidazol-2-yl)-4-phenyl-piperidin-1-yl]-2-(4-fluoro-phenoxy)-ethanone | 462.2 |
| 636 | 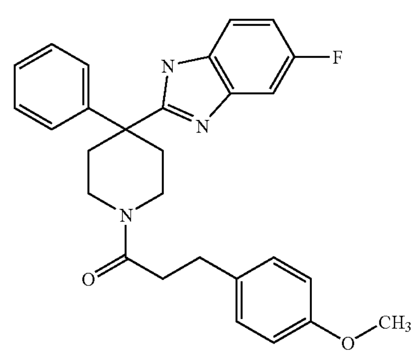 | 1-[4-(5-Fluoro-1H-benzoimidazol-2-yl)-4-phenyl-piperidin-1-yl]-3-(4-methoxy-phenyl)-propan-1-one | 458.2 |

| Example | Structure | Name | (M + 1)+ |
|---|---|---|---|
| 637 | 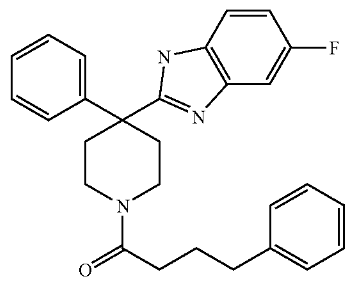 | 1-[4-(5-Fluoro-1H-benzoimidazol-2-yl)-4-phenyl-piperidin-1-yl]-4-phenyl-butan-1-one | 442.2 |
| 638 | 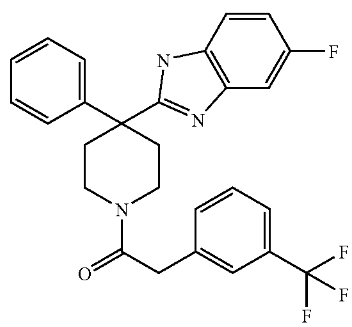 | 1-[4-(5-Fluoro-1H-benzoimidazol-2-yl)-4-phenyl-piperidin-1-yl]-2-(3-trifluoromethyl-phenyl)-ethanone | 482.2 |
| 639 | 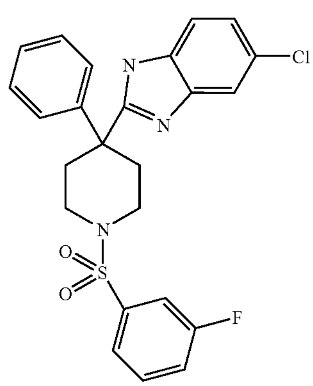 | 5-Chloro-2-[1-(3-fluoro-benzenesulfonyl)-4-phenyl-piperidin-4-yl]-1H-benzoimidazole | 470.1 |
| 640 | 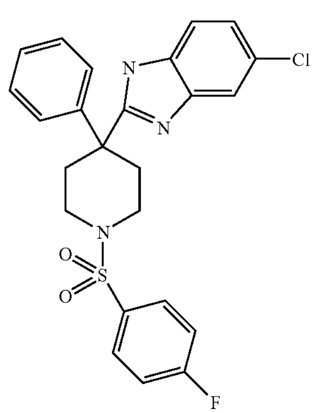 | 5-Chloro-2-[1-(4-fluoro-benzenesulfonyl)-4-phenyl-piperidin-4-yl]-1H-benzoimidazole | 470.1 |

-continued

| Example | Structure | Name | (M + 1)+ |
|---|---|---|---|
| 641 | 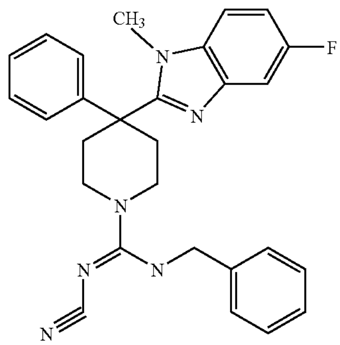 | | 467.2 |
| 642 | 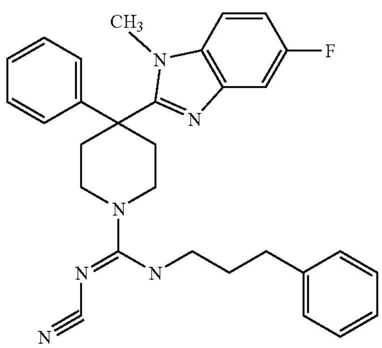 | | 495.2 |
| 643 | 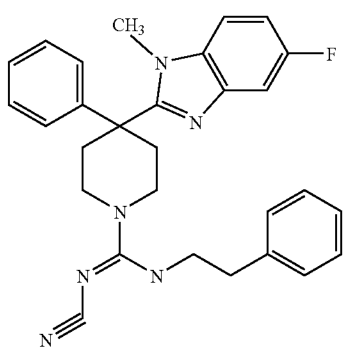 | | 481.2 |
| 644 | 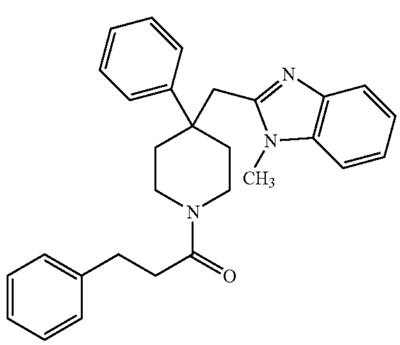 | 1-[4-(1-Methyl-1H-benzoimidazol-2-ylmethyl)-4-phenyl-piperidin-1-yl]-3-phenyl-propan-1-one | 438.3 |

| Example | Structure | Name | (M + 1)+ |
|---|---|---|---|
| 645 | 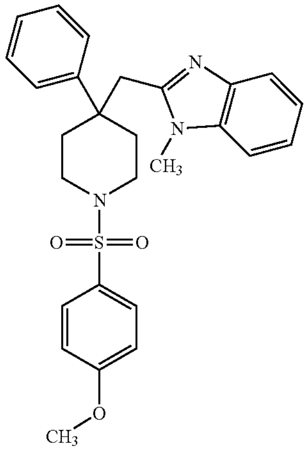 | 2-[1-(4-Methoxy-benzenesulfonyl)-4-phenyl-piperidin-4-ylmethyl]-1-methyl-1H-benzoimidazole | 476.2 |
| 646 | 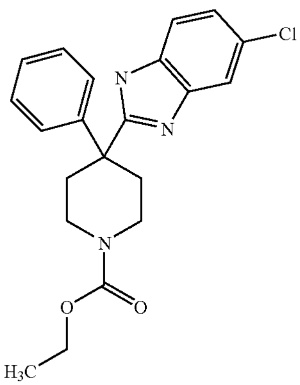 | 4-(5-Chloro-1H-benzoimidazol-2-yl)-4-phenyl-piperidine-1-carboxylic acid ethyl ester | 384.1 |
Example 647
4-tert-Butoxycarbonylamino-4-phenyl-piperidine-1-carboxylic acid benzyl ester
Synthesis
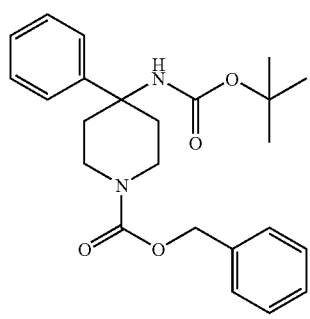
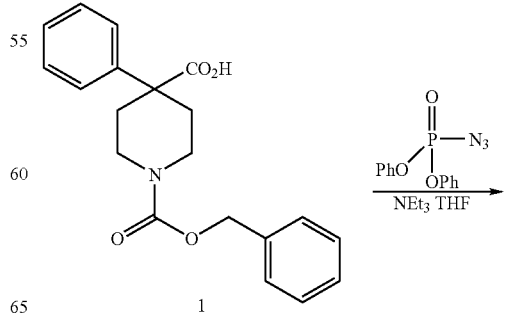
1

-continued

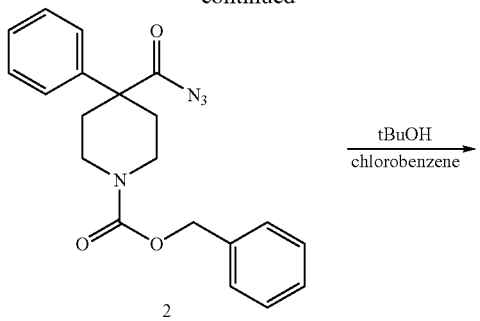

2

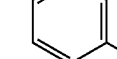

3

Compound 1: Compound 1 was prepared as described in Example 323.

Compound 2: A solution of compound 1 (0.62 g; 1.8 mmol) in tetrahydrofuran (40 mL) was cooled to 0° C. and treated with triethylamine (0.38 mL; 2.7 mmol) and diphenylphosphoryl azide (0.44 mL; 2.0 mmol). The cooling bath was removed and the reaction mixture was allowed to stir at room temperature 18 h. The tetrahydrofuran was removed by evaporation and the crude residue was purified by column chromatography on silica gel using 8:2 hexane:ethyl acetate as the eluent to give 0.67 g of compound 2. LRMS m/z 365 (M+H)$^+$.

Title Compound: A solution of compound 2 (0.67 g; 1.8 mmol) in chlorobenzene (15 mL) was treated with t-butanol (25 mL) and heated at 115° C. for 20 h. The chlorobenzene was removed by evaporation and the residue was subjected to column chromatography on silica gel using an 8:2 hexane:ethyl acetate to 1:1 hexane:ethyl acetate gradient as the eluent to give 0.05 g of 4-tert-butoxycarbonylamino-4-phenyl-piperidine-1-carboxylic acid benzyl ester as a colorless oil LRMS m/z 411 (M+H)$^+$ and 0.2 g compound 3 as a colorless oil LRMS m/z 337 (M+H)$^+$.

Example 648

4-(2-Methoxy-benzoylamino)-4-phenyl-piperidine-1-carboxylic acid benzyl ester

Synthesis

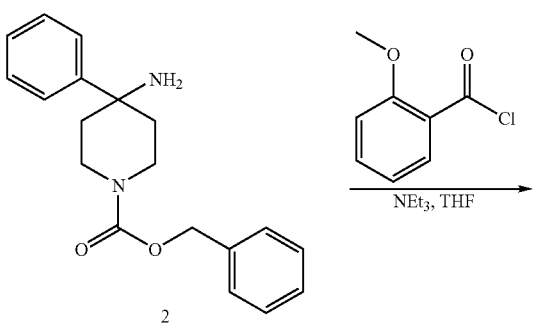

415

-continued

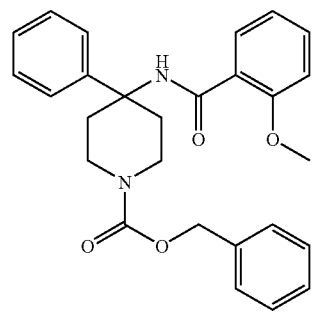

Compound 1: Compound 1 was prepared as described in Example 626.

Compound 2: A solution of compound 1 (0.05 g; 0.1 mmol) in dichloromethane (2 mL) was treated with trifluoroaceric acid (1 mL) and allowed to stir at room temperature for 1 h at which time LCMS indicated complete consumption of compound 1. Additional dichloromethane (20 mL) and 1 N sodium hydroxide (20 mL) were added. The organic layer was separated, washed with saturated aqueous sodium chloride, dried (anhydrous sodium sulfate), filtered and concentrated to give 0.03 g of compound 2 that was used in the next step without additional purification. LCMS m/z=311 (M+H)$^+$ Title Compound: A solution of compound 2 (0.03 g; 0.009 mmol) in tetrahydrofuran (2 mL) was treated with triethylamine (0.1 mL; 0.7 mmol) and o-anisoyl chloride (0.05 g; 0.3 mmol) at room temperature. After stirring 15 h the tetrahydrofuran was removed by evaporation and the residue was purified by prep LC to give 0.011 g of compound 4-(2-methoxy-benzoylamino)-4-phenyl-piperidine-1-carboxylic acid benzyl ester as a white solid. LCMS m/z=461 (M+H)$^+$

Example 649

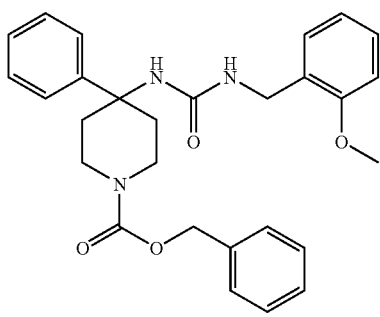

416

4-[3-(2-Methoxy-benzyl)-ureido]-4-phenyl-piperidine-1-carboxylic acid benzyl ester Synthesis

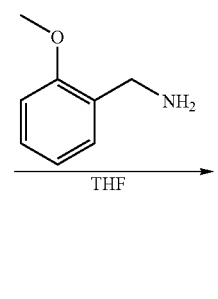

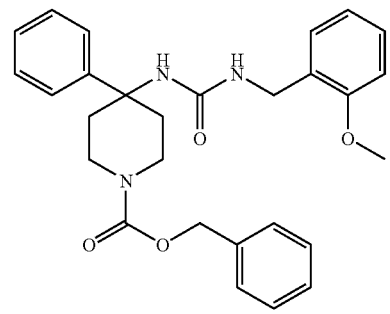

Compound 1: Compound 1 was prepared as described in Example 626.

Title Compound: A solution of compound 1 (0.05 g; 0.15 mmol) in anyhydrous tetrahydrofuran (2 mL) was treated with 2-methoxybenzyl amine (0.041 g; 0.30 mmol) at room temperature. After stirring 2 h the tetrahydrofuran was removed by evaporation and the residue was purified by prep LC to give 0.015 g of 4-[3-(2-methoxy-benzyl)-ureido]-4-phenyl-piperidine-1-carboxylic acid benzyl ester as a white solid. LCMS m/z=475 (M+H)$^+$.

Examples 650 to 652

Examples 650 to 652 were prepared as described in Example 649.

| Example | Structure | Name | M + H |
|---|---|---|---|
| 650 | 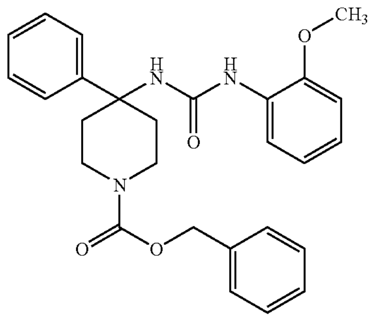 | 4-[3-(2-Methoxy-phenyl)-ureido]-4-phenyl-piperidine-1-carboxylic acid benzyl ester | 461 |
| 651 | 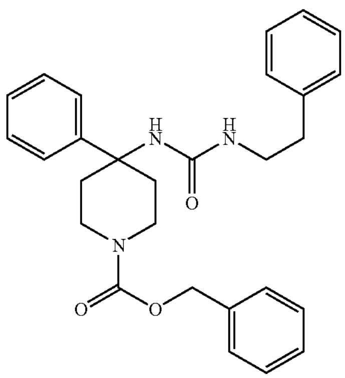 | 4-(3-Phenethyl-ureido)-4-phenyl-piperidine-1-carboxylic acid benzyl ester | 459 |
| 652 | 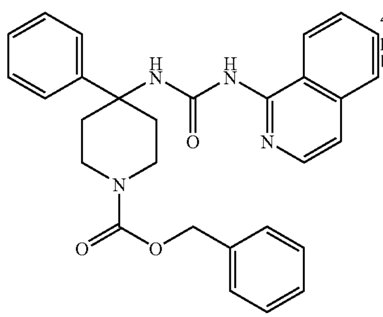 | 4-(3-Isoquinolin-1-yl-ureido)-4-phenyl-piperidine-1-carboxylic acid benzyl ester | 482 |
Example 653      3-Amino-pyrazine-2-carboxylic acid (4-phenyl-piperidin-4-ylmethyl)-amide
Synthesis
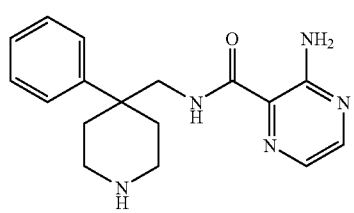
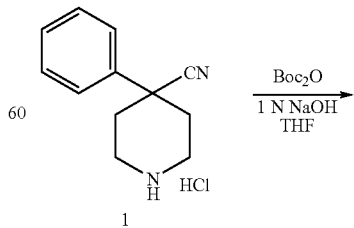

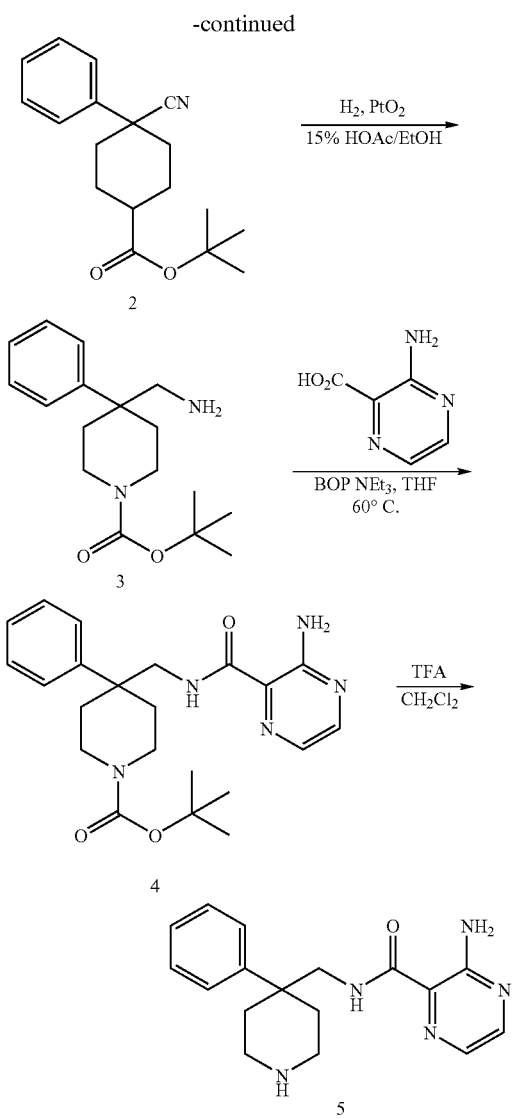

Compound 1: Compound 1 is commercially available.

Compound 2: A solution of compound 1 (20 g; 90 mmol) in 1 N sodium hydroxide (200 mL) and tetrahydrofuran (50 mL) was treated with di-tert-butyl dicarbonate (19.7 g; 90.3 mmol) at room temperature. After stirring 24 h the reaction mixture was adjusted to pH=7 by the addition of 1 N hydrochloric acid and washed with ethyl acetate (2×100 mL). The organic layers were combined, washed with saturated aqueous sodium chloride, dried (sodium sulfate), filtered and concentrated. The crude product was recyrstallized from the minimum amount of ethanol to give 20 g compound 2 as a white solid. LRMS m/z=287 (M+H)$^+$ Compound 3: A solution of compound 2 (4.5 g; 15.7 mmol) in ethanol (42.5 mL) and acetic acid (7.5 mL) was treated with platinum oxide (250 mg) and hydrogenated at 60 psi for 12 h. Analysis by thin layer chromatography indicated the reaction was not complete. Additional platinum oxide (124 mg) was added and the reaction mixture hydrogenated at 60 psi for another 12 h. The reaction mixture was filtered through celite and concentrated to give 4.6 g of compound 3 as a colorless oil that was used without additional purification. LRMS m/z=291 (M+H)$^+$ Compound 4: A suspension of 3-amino-pyrazine-2-carboxylic acid (2.9 g; 20.8 mmol) in tetrahydrofuran (30 mL) was treated with triethylamine (7 mL; 50 mmol) followed by benzotriazole-1-yl-oxy-tris-(dimethylamino)-phosphonium-hexafluorophosphate (8.8 g; 19.9 mmol) at room temperature. After 15 minutes of stirring the reaction mixture became homogeneous and compound 3 (4.6 g; 15.8 mmol) was added as a solution in tetrahydrofuran (20 mL). The reaction was heated at 60° C. for 12 h. The solvent was removed by rotary evaporation and the crude product was purified directly by column chromatography on silica gel using 1:1 ethyl acetate: hexane as the eluent to give 2.0 g of compound 4 as a white foam. LRMS m/z=412 (M+H)$^+$ Title Compound: A solution of compound 4 (1.9 g; 4.6 mmol) in anhydrous dichloromethane (50 mL) was treated with trifluoroacetic acid (50 mL) at room temperature. After stirring for 19 h the reaction mixture was made basic (pH=12) with 6 N NaOH and additional dichloromethane (100 mL) was added. The organic layer was separated, washed with saturated aqueous sodium chloride, dried (sodium sulfate), filtered and concentrated to give 1.4 g of the title compound as a white foam that was used without additional purification. LRMS m/z=312 (M+H)$^+$ Example 654

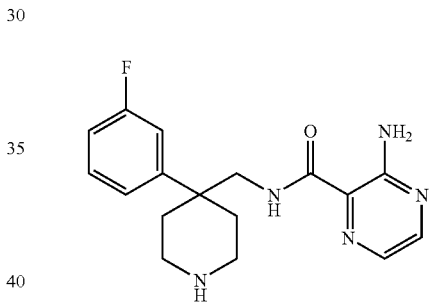

3-Amino-pyrazine-2-carboxylic acid [4-(3-fluoro-phenyl)-piperidin-4-ylmethyl]-amide Synthesis

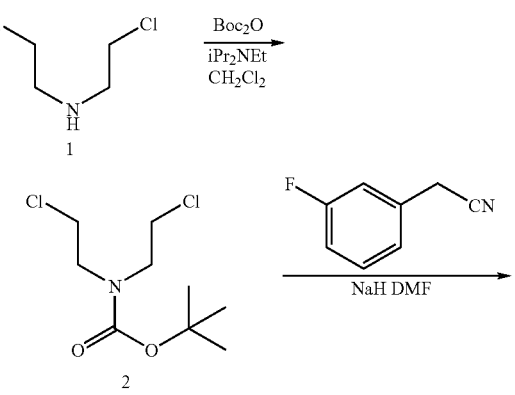

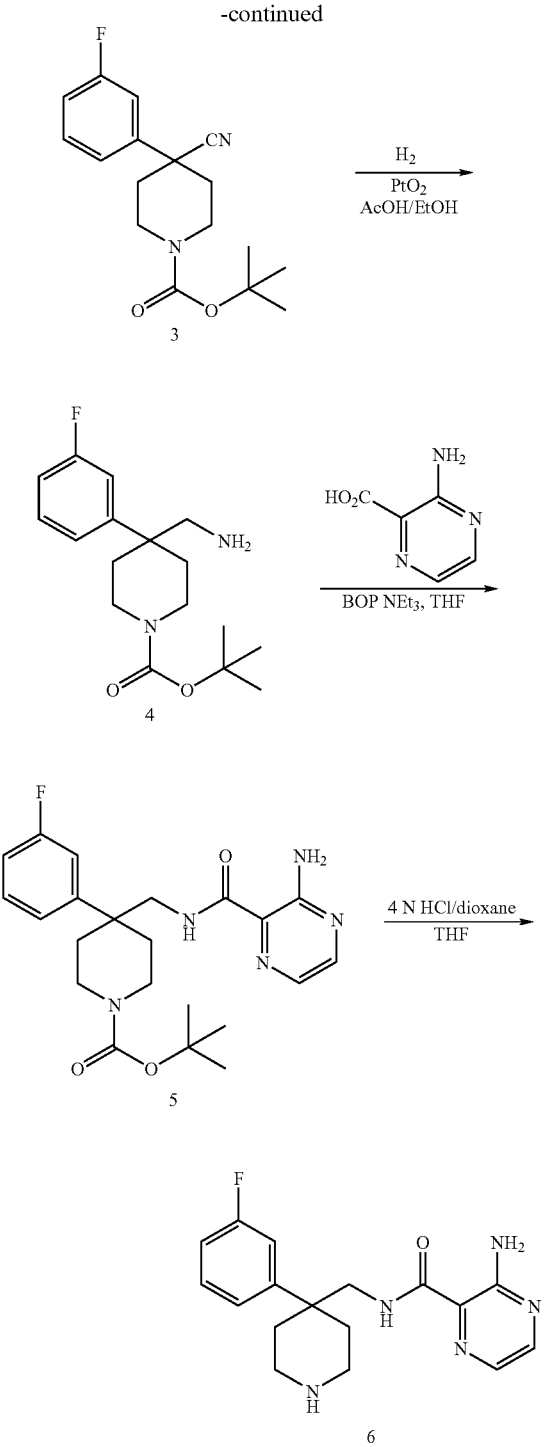

Compound 1: Compound 1 is commercially available.

Compound 2: Compound 1 (5.0 g, 28.0 mmol) was suspended in 100 mL of dichloromethane. Di-tert-butyl dicarbonate (6.1 g, 28.0 mmol) and diisopropylethylamine (10.7 mL, 61.6 mmol) was added and the reaction mixture was stirred at room temperature overnight. The reaction mixture was diluted with diethyl ether (300 mL), washed with 1N hydrochloric acid (2×100 mL), saturated sodium bicarbonate (100 mL), water (100 mL) and saturated aqueous sodium chloride (100 mL). The organic layer was dried (sodium sulfate) and concentrated. The crude residue was purified by silica gel chromatography using 9:1 hexane:diethyl ether as eluent to give 3.46 g of compound 2 as a colorless oil.

Compound 3: Sodium hydride (1.9 g, 79.0 mmol) was suspended in dimethylformamide (30 mL) and cooled to 0° C. 3-Fluorophenylacetonitrile (2.61 g, 19.3 mmol) was slowly added followed by the addition of compound 2 (3.68 g, 15.2 mmol) as a solution in dimethylformamide (30 mL). The reaction was stirred at 0° C. for 0.5 hours and was allowed to warm to room temperature and stirred overnight. The reaction mixture was poured into ice and extracted with ethyl acetate (200 mL). The aqueous layer was extracted with ethyl acetate (2×200 mL). The organic layers were combined and washed with 10% lithium chloride (2×100 mL), dried (sodium sulfate), filtered and concentrated. The crude residue was purified by flash chromatography on silica gel using 9:1 hexane:ethyl acetate as the eluent to give 4.04 g of compound 3 as a yellow oil. $^1$H NMR (CDCl$_3$) δ1.48 (9H, s), 1.92 (2H, td, J=4.3, 13.1), 2.05 (2H, t, J=10.2), 3.19 (2H, t, J=12.4), 4.29 (2H, d, J=13.7), 7.01-7.45 (4H, m). LRMS m/z 305 (M+H)$^+$.

Compound 4: Compound 3 (4.04 g, 13.27 mmol) in 50 mL of 15% acetic acid in ethanol was treated with platinum (IV) oxide (0.210 g, 0.925 mmol) and hydrogenated at 60 psi (Parr Apparatus) for 48 h. The reaction mixture was filtered through a thick pad of celite and concentrated. To the concentrate was added 200 mL of diethyl ether and the organic solution was washed with 1N sodium hydroxide (2×50 mL) and dried (sodium sulfate), filtered and concentrated to give 4.07 g of compound 4. LRMS m/z 309 (M+H)$^+$.

Compound 5: To compound 4 (0.562 g, 1.94 mmol) in 15 mL of tetrahydrofuran was added 3-aminopyrazine-2-carboxylic acid (0.270 g, 1.94 mmol), benzotriazole-1-yl-oxy-tris-(dimethylamino)-phosphoniumhexafluorophosphate (0.858 g, 1.94 mmol) and triethylamine (0.271 mL, 1.94 mmol). The reaction mixture was stirred for 2 hours at room temperature then diluted with diethyl ether (50 mL), washed with water (3×50 mL), saturated sodium chloride (50 mL) and dried over sodium sulfate. After filtration, the solvent was removed by rotary evaporation and the crude residue was purified using flash chromatography (1:1 hexane/diethyl ether) to give 0.69 g of compound 5. LRMS m/z 430 (M+H)$^+$.

Title Compound: Compound 5 (0.691 g, 1.61 mmol) was suspended in tetrahydrofuran (5 mL) and 4 N hydrochloric acid in 1,4-dioxane (5 mL) and the reaction mixture was stirred overnight at room temperature. The reaction mixture was concentrated, dissolved in water (15 mL) and the aqueous layer was washed with diethyl ether (2×15 mL). 6 N Sodium hydroxide was added to basify the aqueous layer that was then extracted with dichloromethane (3×20 mL). The organic layers were combined, dried (sodium sulfate), filtered and concentrated to give 0.47 g of the title compound as a yellow solid which was used without additional purification. LRMS m/z 330 (M+H)$^+$.

Examples 655 to 695

Examples 655-695 were synthesized using methodology described in Example 1 and Example 654.

| Example | Structure | Name | M + H |
|---|---|---|---|
| 655 | 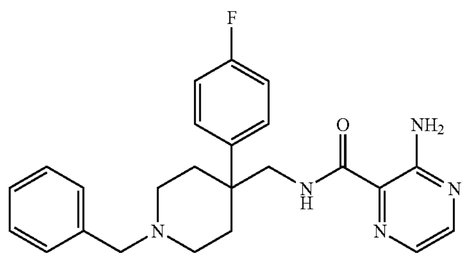 | 3-Amino-pyrazine-2-carboxylic acid [1-benzyl-4-(4-fluoro-phenyl)-piperidin-4-ylmethyl]-amide | 422 |
| 656 | 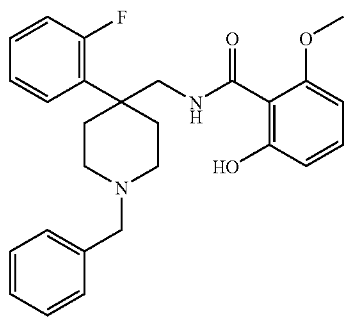 | N-[1-Benzyl-4-(2-fluoro-phenyl)-piperidin-4-ylmethyl]-2-hydroxy-6-methoxy-benzamide | 450 |
| 657 | 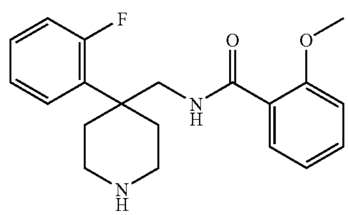 | N-[4-(2-Fluoro-phenyl)-piperidin-4-ylmethyl]-2-methoxy-benzamide | 343 |
| 658 | 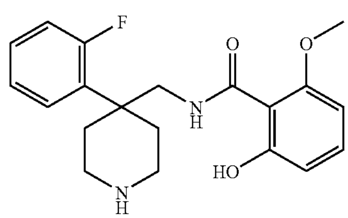 | N-[4-(2-Fluoro-phenyl)-piperidin-4-ylmethyl]-2-hydroxy-6-methoxy-benzamide | 359 |
| 659 | 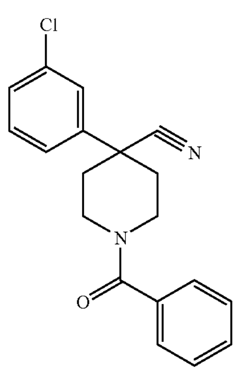 | 1-Benzoyl-4-(3-chloro-phenyl)-piperidine-4-carbonitrile | 326 |

| Example | Structure | Name | M + H |
|---------|-----------|------|-------|
| 660 | 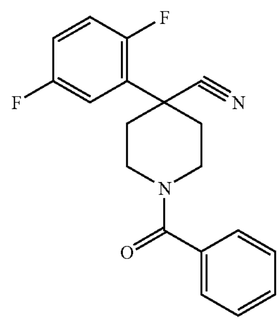 | 1-Benzoyl-4-(2,5-difluoro-phenyl)-piperidine-4-carbonitrile | 327 |
| 661 | 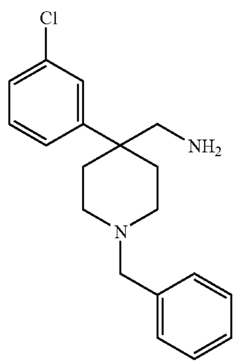 | C-[1-Benzyl-4-(3-chloro-phenyl)-piperidin-4-yl]-methylamine | 316 |
| 662 | 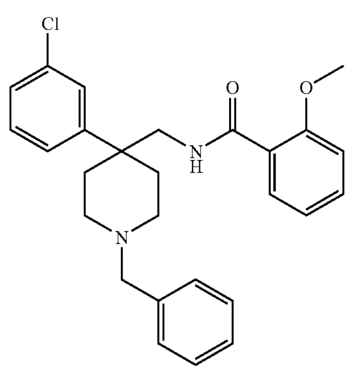 | N-[1-Benzyl-4-(3-chloro-phenyl)-piperidin-4-ylmethyl]-2-methoxy-benzamide | 450 |
| 663 | 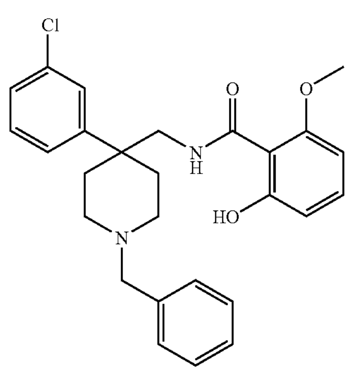 | N-[1-Benzyl-4-(3-chloro-phenyl)-piperidin-4-ylmethyl]-2-hydroxy-6-methoxy-benzamide | 466 |

| Example | Structure | Name | M + H |
|---|---|---|---|
| 664 | 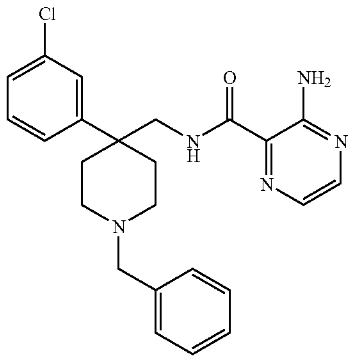 | 3-Amino-pyrazine-2-carboxylic acid [1-benzyl-4-(3-chloro-phenyl)-piperidin-4-yl-methyl]-amide | 437 |
| 665 | 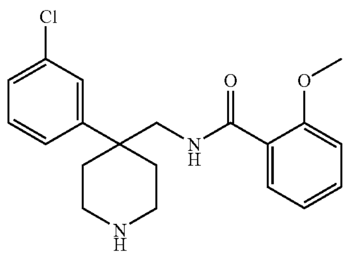 | N-[4-(3-Chloro-phenyl)-piperidin-4-ylmethyl]-2-methoxy-benzamide | 360 |
| 666 | 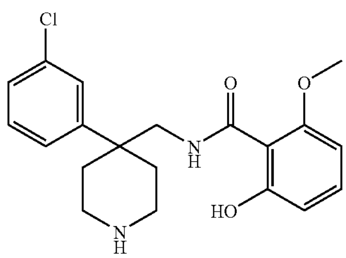 | N-[4-(3-Chloro-phenyl)-piperidin-4-ylmethyl]-2-hydroxy-6-methoxy-benzamide | 376 |
| 667 | 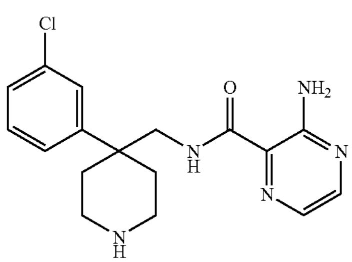 | 3-Amino-pyrazine-2-carboxylic acid [4-(3-chloro-phenyl)-piperidin-4-ylmethyl]-amide | 347 |
| 668 | 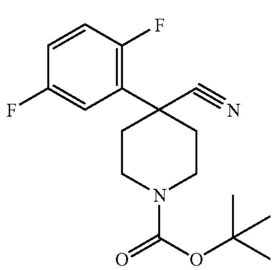 | 4-Cyano-4-(2,5-difluoro-phenyl)-piperidine-1-carboxylic acid tert-butyl ester | 323 |

| Example | Structure | Name | M + H |
|---|---|---|---|
| 669 | 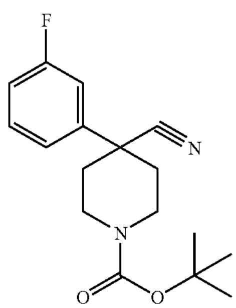 | 4-Cyano-4-(3-fluoro-phenyl)-piperidine-1-carboxylic acid tert-butyl ester | 305 |
| 670 | 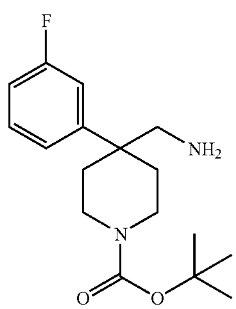 | 4-Aminomethyl-4-(3-fluoro-phenyl)-piperidine-1-carboxylic acid tert-butyl ester | 309 |
| 671 | 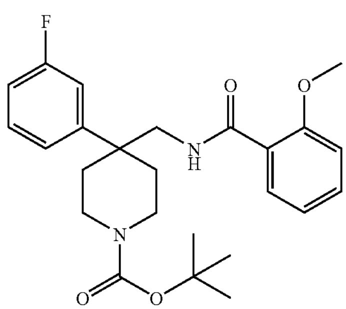 | 4-(3-Fluoro-phenyl)-4-[(2-methoxy-benzoylamino)-methyl]-piperidine-1-carboxylic acid tert-butyl ester | 444 |
| 672 | 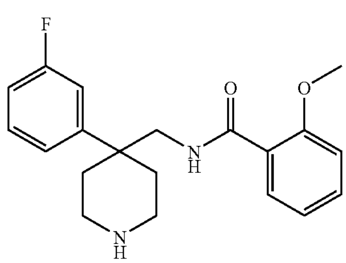 | N-[4-(3-Fluoro-phenyl)-piperidin-4-ylmethyl]-2-methoxy-benzamide | 343 |
| 673 | 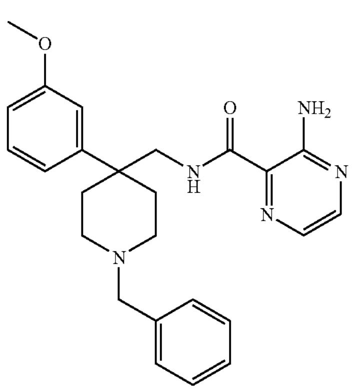 | 3-Amino-pyrazine-2-carboxylic acid [1-benzyl-4-(3-methoxy-phenyl)-piperidin-4-ylmethyl]-amide | 433 |

| Example | Structure | Name | M + H |
|---|---|---|---|
| 674 | 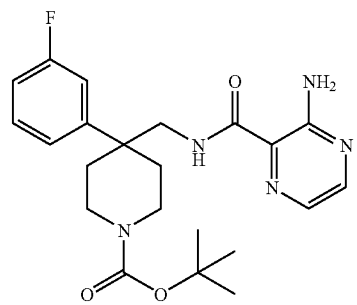 | 4-{[(3-Amino-pyrazine-2-carbonyl)-amino]-methyl}-4-(3-fluoro-phenyl)-piperidine-1-carboxylic acid tert-butyl ester | 430 |
| 675 | 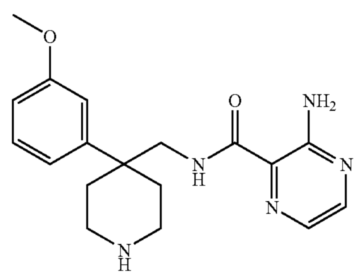 | 3-Amino-pyrazine-2-carboxylic acid [4-(3-methoxy-phenyl)-piperidin-4-ylmethyl]-amide | 342 |
| 676 | 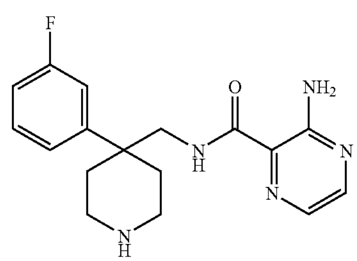 | 3-Amino-pyrazine-2-carboxylic acid [4-(3-fluoro-phenyl)-piperidin-4-ylmethyl]-amide | 330 |
| 677 | 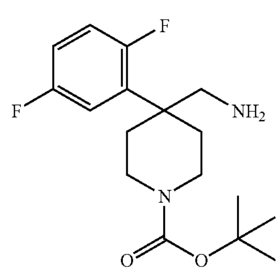 | 4-Aminomethyl-4-(2,5-difluoro-phenyl)-piperidine-1-carboxylic acid tert-butyl ester | 327 |
| 678 | 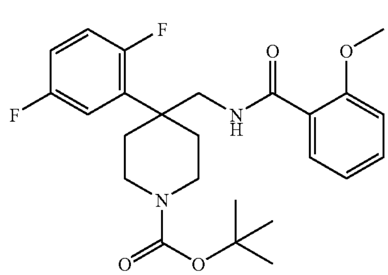 | 4-(2,5-Difluoro-phenyl)-4-[(2-methoxy-benzoylamino)-methyl]-piperidine-1-carboxylic acid tert-butyl ester | 462 |

| Example | Structure | Name | M + H |
|---|---|---|---|
| 679 | 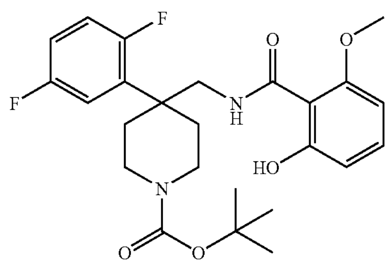 | 4-(2,5-Difluoro-phenyl)-4-[(2-hydroxy-6-methoxy-benzoylamino)-methyl]-piperidine-1-carboxylic acid tert-butyl ester | 478 |
| 680 | 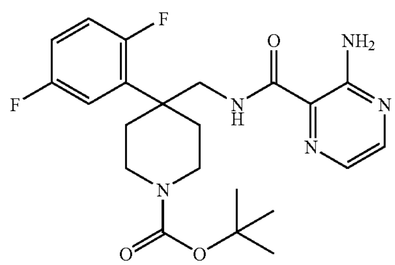 | 4-{[(3-Amino-pyrazine-2-carbonyl)-amino]-methyl}-4-(2,5-difluoro-phenyl)-piperidine-1-carboxylic acid tert-butyl ester | 448 |
| 681 | 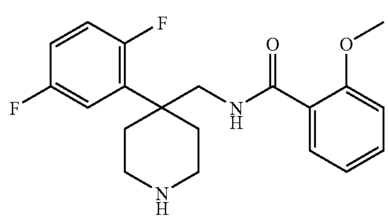 | N-[4-(2,5-Difluoro-phenyl)-piperidin-4-ylmethyl]-2-methoxy-benzamide | 361 |
| 682 | 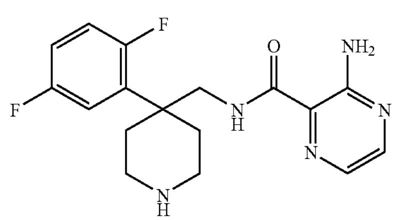 | 3-Amino-pyrazine-2-carboxylic acid [4-(2,5-difluoro-phenyl)-piperidin-4-ylmethyl]-amide | 348 |
| 683 | 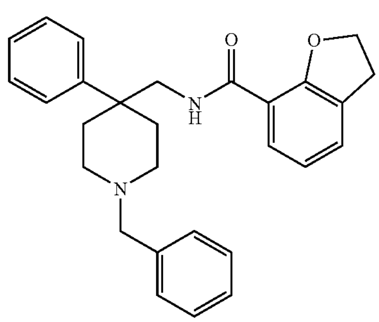 | 2,3-Dihydro-benzofuran-7-carboxylic acid (1-benzyl-4-phenyl-piperidin-4-ylmethyl)-amide | 428 |

-continued
| Example | Structure | Name | M + H |
|---|---|---|---|
| 684 | 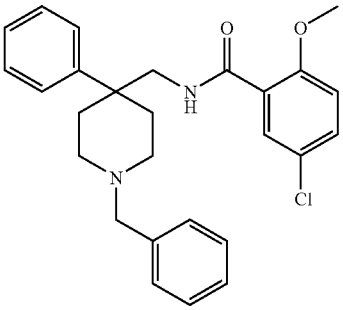 | N-(1-Benzyl-4-phenyl-piperidin-4-ylmethyl)-5-chloro-2-methoxy-benzamide | 450 |
| 685 | 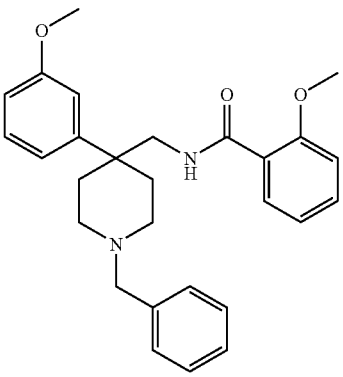 | N-[1-Benzyl-4-(3-methoxy-phenyl)-piperidin-4-ylmethyl]-2-methoxy-benzamide | 446 |
| 686 | 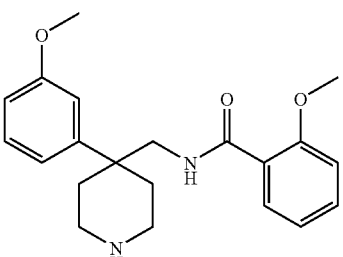 | 2-Methoxy-N-[4-(3-methoxy-phenyl)-piperidin-4-ylmethyl]-benzamide | 355 |
| 687 | 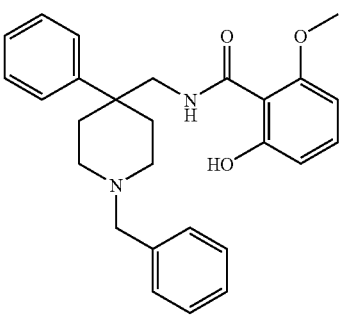 | N-(1-Benzyl-4-phenyl-piperidin-4-ylmethyl)-2-hydroxy-6-methoxy-benzamide | 432 |
| 688 | 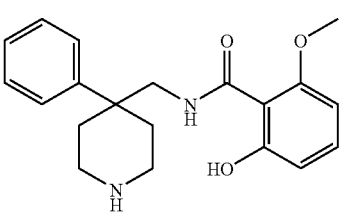 | 2-Hydroxy-6-methoxy-N-(4-phenyl-piperidin-4-ylmethyl)-benzamide | 341 |

| Example | Structure | Name | M + H |
|---|---|---|---|
| 689 | 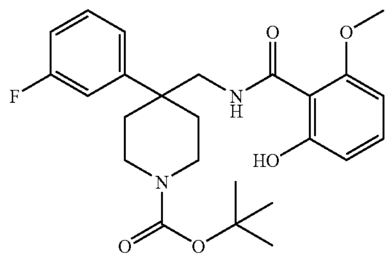 | 4-(3-Fluoro-phenyl)-4-[(2-hydroxy-6-methoxy-benzoylamino)-methyl]-piperidine-1-carboxylic acid tert-butyl ester | 460 |
| 690 | 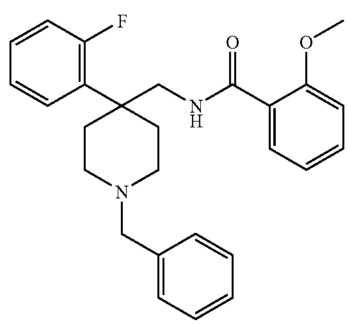 | N-[1-Benzyl-4-(2-fluoro-phenyl)-piperidin-4-ylmethyl]-2-methoxy-benzamide | 434 |
| 691 | 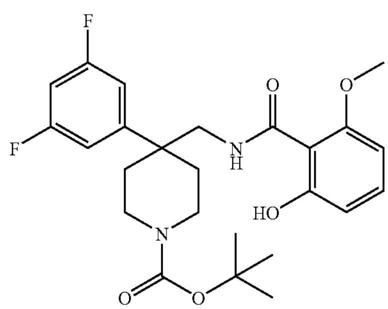 | 4-(3,5-Difluoro-phenyl)-4-[(2-hydroxy-6-methoxy-benzoylamino)-methyl]-piperidine-1-carboxylic acid tert-butyl ester | 478 |
| 692 | 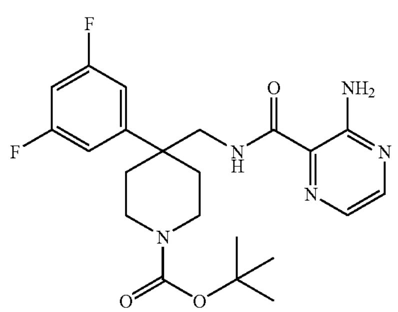 | 4-{[(3-Amino-pyrazine-2-carbonyl)-amino]-methyl}-4-(3,5-difluoro-phenyl)-piperidine-1-carboxylic acid tert-butyl ester | 448 |
| 693 | 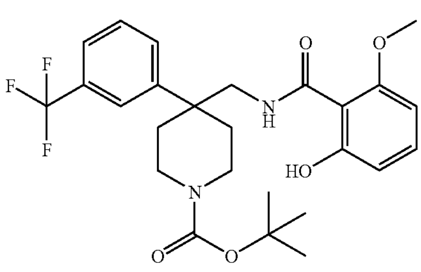 | 4-[(2-Hydroxy-6-methoxy-benzoylamino)-methyl]-4-(3-trifluoromethyl-phenyl)-piperidine-1-carboxylic acid tert-butyl ester | 510 |

-continued
| Example | Structure | Name | M + H |
|---|---|---|---|
| 694 | 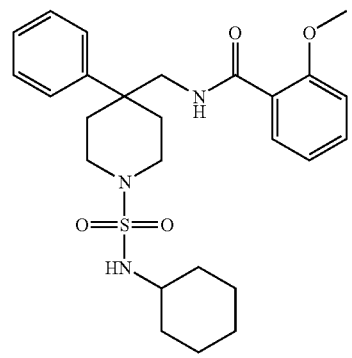 | 4-{[(3-Amino-pyrazine-2-carbonyl)-amino]-methyl}-4-(3-trifluoromethyl-phenyl)-piperidine-1-carboxylic acid tert-butyl ester | 481 |
| 695 | 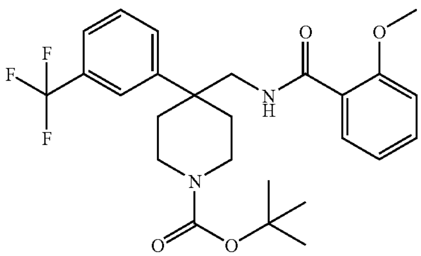 | 4-[(2-Methoxy-benzoylamino)-methyl]-4-(3-trifluoromethyl-phenyl)-piperidine-1-carboxylic acid tert-butyl ester | 494 |
Example 696
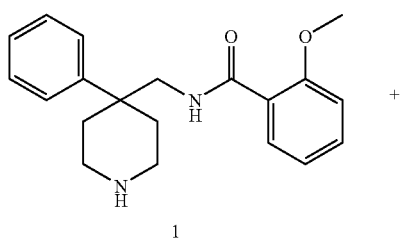
N-(1-Cyclohexylsulfamoyl-4-phenyl-piperidin-4-ylmethyl)-2-methoxy-benzamide
Synthesis
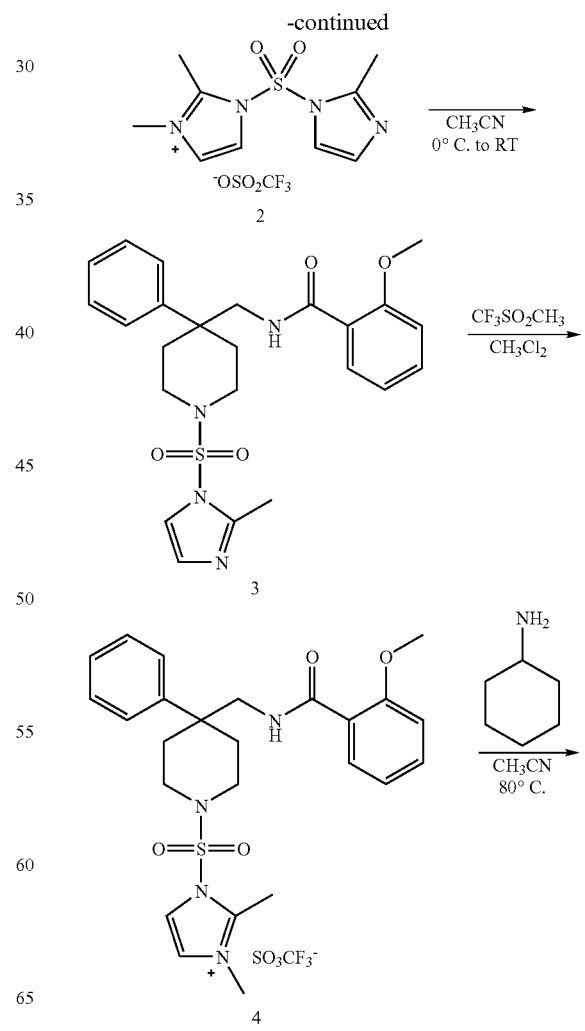

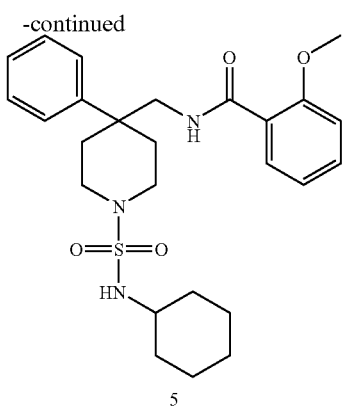

Compound 1: Compound 1 was prepared as described in Example 15.

Compound 2: Compound 2 was prepared as described in *J. Org. Chem.* 2003, 68, 115-119.

Compound 3: Compound 2 (3.34 g, 8.6 mmol) was suspended in 15 mL of acetonitrile and cooled to 0° C. Compound 1 (2.14 g, 6.6 mmol) was slowly added. The reaction was allowed to warm to room temperature overnight. The reaction mixture was concentrated and purified directly by flash chromatography on silica gel using 3:1 ethylacetate/hexane as the eluent to give 1.92 g of compound 3. LRMS m/z 469 (M+H)+.

Compound 4: Compound 3 (1.9 g, 4.05 mmol) was suspended in 16 mL of dichloromethane and cooled to 0° C. A solution of methyl triflate (0.505 mL, 4.46 mmol) in dichloromethane (16 mL) was slowly added. The reaction was allowed to warm to room temperature, stirred for 2 h and concentrated. Compound 4 was used in the next step without further purification. LRMS m/z 483 (M+H)+.

Title Compound: To compound 4 (0.075 g, 0.118 mmol) and cyclohexylamine (0.016 mL, 0.142 mmol) was added 0.695 mL of acetonitrile. The reaction mixture was heated to 80° C. for 4 h and concentrated. The crude material was purified using preparative reverse phase HPLC to give 0.026 g of the title compound as a white solid. LRMS m/z 488 (M+H)+.

Examples 697 to 843

Examples 697 to 843 were prepared using methodology described in Example 15 Example 16, Example 17 and Example 696.

| Example | Structure | Name | M + H |
|---------|-----------|------|-------|
| 697 | 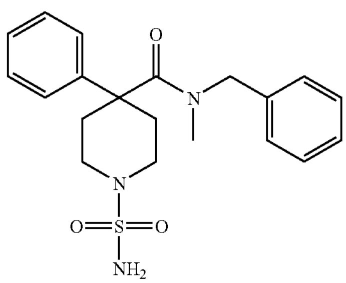 | 4-Phenyl-1-sulfamoyl-piperidine-4-carboxylic acid benzyl-methyl-amide | 390 |
| 698 | 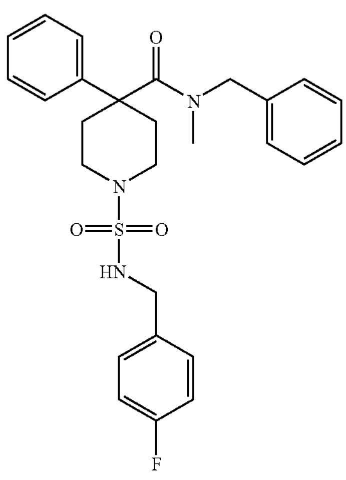 | 1-(4-Fluoro-benzyl-sulfamoyl)-4-phenyl-piperidine-4-carboxylic acid benzyl-methyl-amide | 498 |

| Example | Structure | Name | M + H |
| --- | --- | --- | --- |
| 699 | 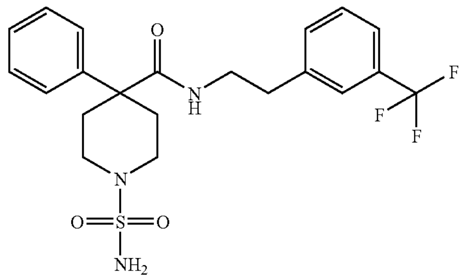 | 4-Phenyl-1-sulfamoyl-piperidine-4-carboxylic acid [2-(3-trifluoromethyl-phenyl)-ethyl]-amide | 457 |
| 700 | 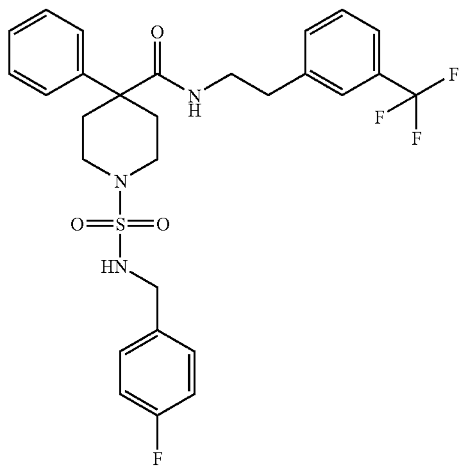 | 1-(4-Fluoro-benzyl-sulfamoyl)-4-phenyl-piperidine-4-carboxylic acid [2-(3-trifluoromethyl-phenyl)-ethyl]-amide | 566 |
| 701 | 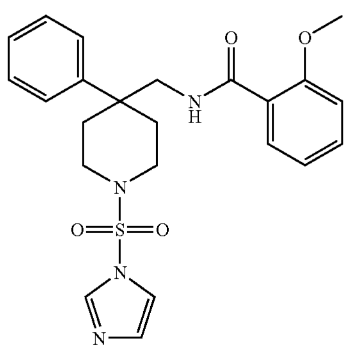 | N-[1-(Imidazole-1-sulfonyl)-4-phenyl)-piperidin-4-yl-methyl]-2-methoxy-benzamide | 457 |
| 702 | 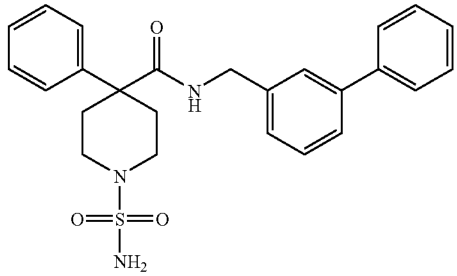 | 4-Phenyl-1-sulfamoyl-piperidine-4-carboxylic acid (biphenyl-3-ylmethyl)-amide | 452 |

-continued
| Example | Structure | Name | M + H |
|---|---|---|---|
| 703 | 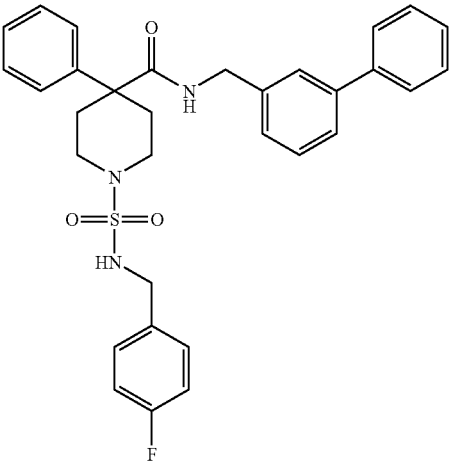 | 1-(4-Fluoro-benzyl-sulfamoyl)-4-phenyl-piperidine-4-carboxylic acid (biphenyl-3-ylmethyl)-amide | 560 |
| 704 | 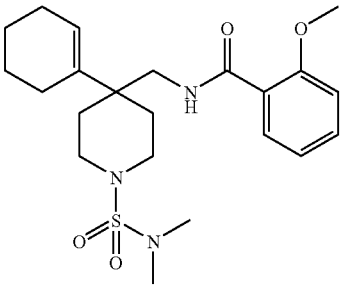 | N-(4-Cyclohex-1-enyl-1-dimethylsulfamoyl-piperidin-4-ylmethyl)-2-methoxy-benzamide | 438 |
| 705 | 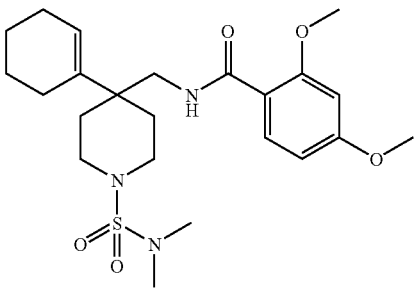 | N-(4-Cyclohex-1-enyl-1-dimethylsulfamoyl-piperidin-4-ylmethyl)-2,4-dimethoxy-benzamide | 468 |
| 706 | 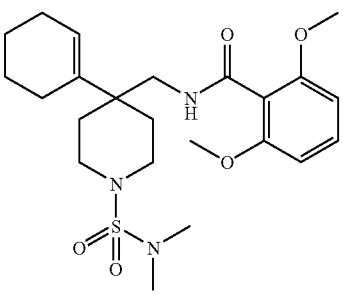 | N-(4-Cyclohex-1-enyl-1-dimethylsulfamoyl-piperidin-4-ylmethyl)-2,6-dimethoxy-benzamide | 468 |

| Example | Structure | Name | M + H |
|---|---|---|---|
| 707 | 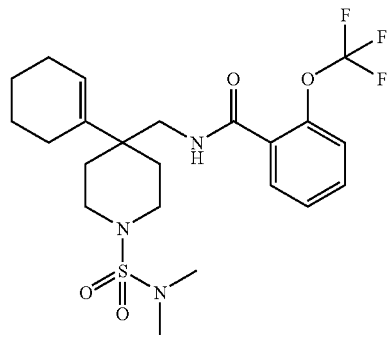 | N-(4-Cyclohex-1-enyl-1-dimethylsulfamoyl-piperidin-4-ylmethyl)-2-trifluoromethoxy-benzamide | 492 |
| 708 | 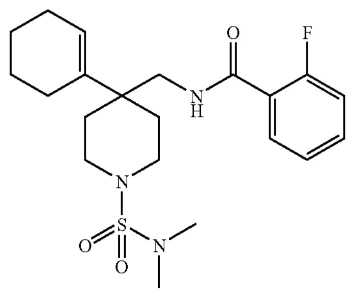 | N-(4-Cyclohex-1-enyl-1-dimethylsulfamoyl-piperidin-4-ylmethyl)-2-fluoro-benzamide | 426 |
| 709 | 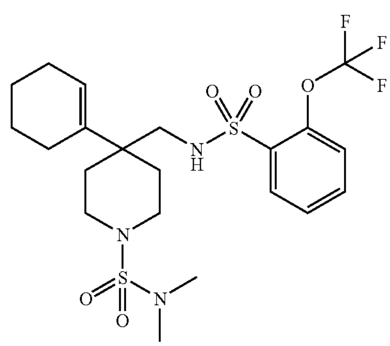 | 4-Cyclohex-1-enyl-4-[(2-trifluoromethoxy-benzenesulfonylamino)-methyl]-piperidine-1-sulfonic acid dimethylamide | 528 |
| 710 | 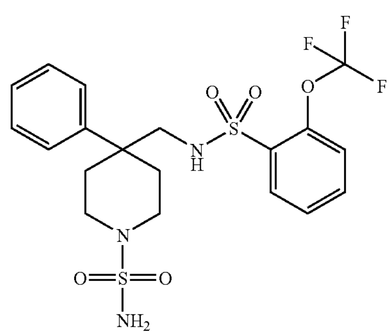 | 4-Phenyl-4-[(2-trifluoromethoxy-benzenesulfonylamino)-methyl]-piperidine-1-sulfonic acid amide | 496 |

| Example | Structure | Name | M + H |
|---|---|---|---|
| 711 | 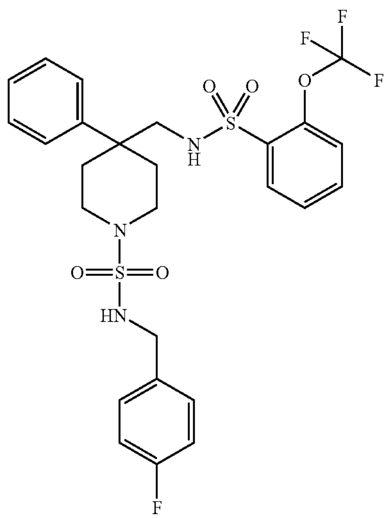 | 4-Phenyl-4-[(2-tri-fluoromethoxy-benzene-sulfonylamino)-methyl]-piperidine-1-sulfonic acid 4-fluoro-benzyl-amide | 604 |
| 712 | 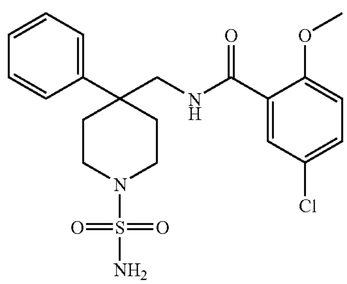 | 5-Chloro-2-methoxy-N-(4-phenyl-1-sulfamoyl-piperidine-4-ylmethyl)-benzamide | 440 |
| 713 | 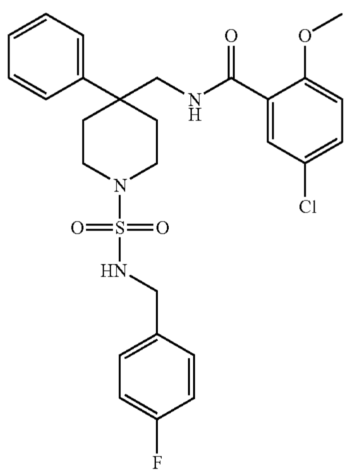 | 5-Chloro-N-[1-(4-fluoro-benzyl-sulfamoyl)-4-phenyl-piperidin-4-ylmethyl]-2-methoxy-benzamide | 548 |
| 714 | 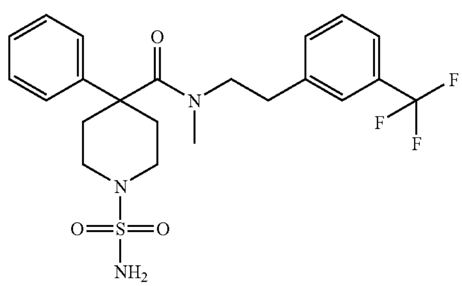 | 4-Phenyl-1-sulfamoyl-piperidine-4-carboxylic acid methyl-[2-(3-trifluoromethyl-phenyl)-ethyl]-amide | 472 |

-continued

| Example | Structure | Name | M + H |
|---|---|---|---|
| 715 | 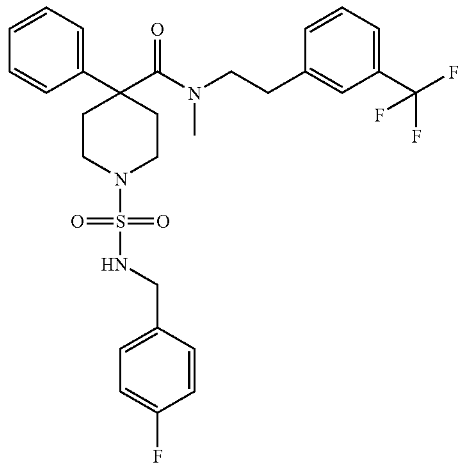 | 1-(4-Fluoro-benzyl-sulfamoyl)-4-phenyl-piperidine-4-carboxylic acid methyl-[2-(3-trifluoromethyl-phenyl)-ethyl]-amide | 580 |
| 716 | 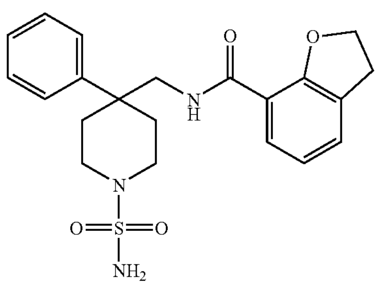 | 2,3-Dihydro-benzofuran-7-carboxylic acid(4-phenyl-1-sulfamoyl-piperidin-4-yl-methyl)-amide | 418 |
| 717 | 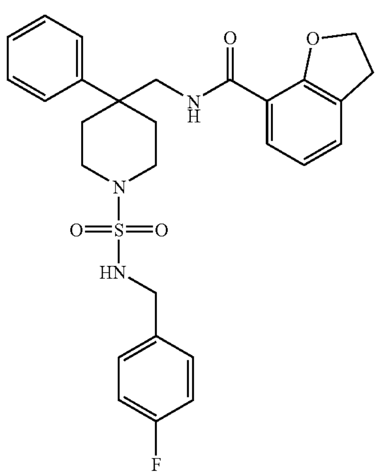 | 2,3-Dihydro-benzofuran-7-carboxylic acid[1-(4-fluoro-benzyl-sulfamoyl)-4-phenyl-piperidin-4-ylmethyl]-amide | 526 |
| 718 | 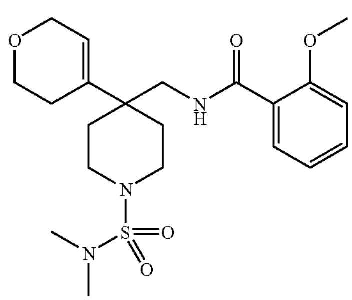 | N-[4-(3,6-Dihydro-2H-pyran-4-yl)-1-dimethylsulfamoyl-piperidin-4-ylmethyl]-2-methoxy-benzamide | 440 |

| Example | Structure | Name | M + H |
|---|---|---|---|
| 719 | 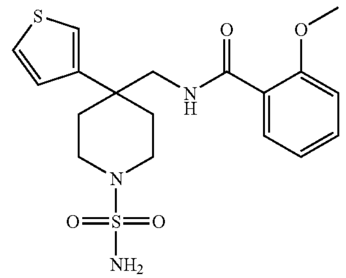 | 2-Methoxy-N-(1-sulfamoyl-4-thiophen-3-yl-piperidin-4-yl-methyl)-benzamide | 412 |
| 720 | 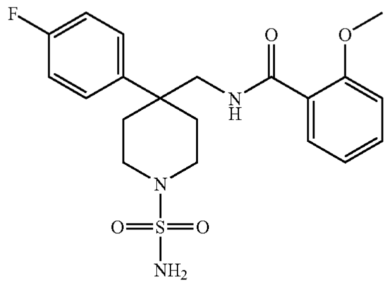 | N-[4-(4-Fluoro-phenyl)-1-sulfamoyl-piperidin-4-yl-methyl]-2-methoxy-benzamide | 423 |
| 721 | 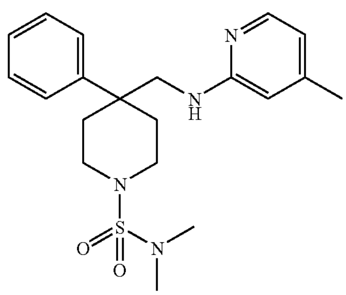 | 4-[(4-Methyl-pyridin-2-yl-amino)-methyl]-4-phenyl-piperidine-1-sulfonic acid dimethylamide | 391 |
| 722 | 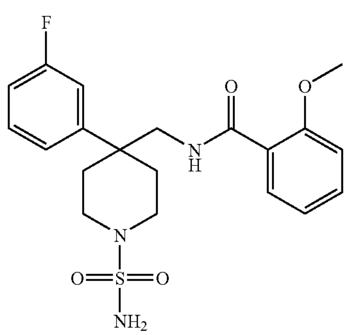 | N-[4-(3-Fluoro-phenyl)-1-sulfamoyl-piperidin-4-yl-methyl]-2-methoxy-benzamide | 423 |
| 723 | 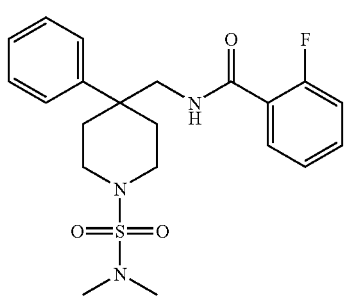 | N-(1-Dimethylsulfamoyl-4-phenyl-piperidin-4-yl-methyl)-2-fluoro-benzamide | 422 |

-continued

| Example | Structure | Name | M + H |
|---|---|---|---|
| 724 | 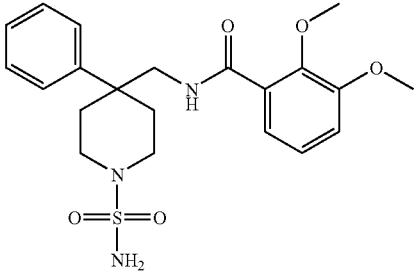 | 2,3-Dimethoxy-N-(4-phenyl-1-sulfamoyl-piperidin-4-yl-methyl)-benzamide | 436 |
| 725 | 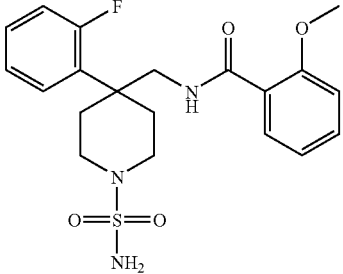 | N-[4-(2-Fluoro-phenyl)-1-sulfamoyl-piperidin-4-yl-methyl]-2-methoxy-benzamide | 423 |
| 726 | 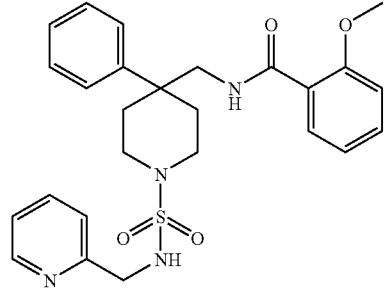 | 2-Methoxy-N-{4-phenyl-1-[(pyridin-2-ylmethyl)-sulfamoyl]-piperidin-4-yl-methyl}-benzamide | 497 |
| 727 | 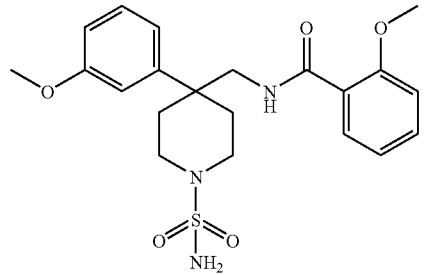 | 2-Methoxy-N-[4-(3-methoxy-phenyl)-1-sulfamoyl-piperidin-4-yl-methyl]-benzamide | 436 |
| 728 | 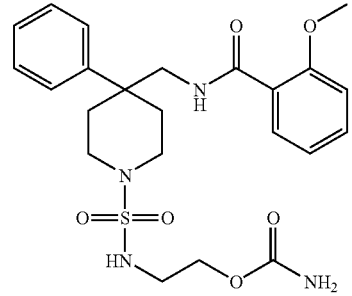 | Carbamic acid 2-{4-[(2-methoxy-benzoylamino)-methyl]-4-phenyl-piperidine-1-sulfonylamino}-ethyl ester | 493 |

| Example | Structure | Name | M + H |
|---|---|---|---|
| 729 | 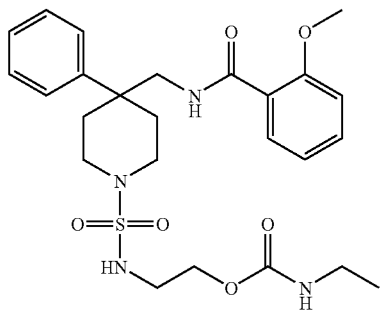 | Ethyl-carbamic acid 2-{4-[(2-methoxy-benzoylamino)-methyl]-4-phenyl-piperidine-1-sulfonylamino}-ethyl ester | 521 |
| 730 | 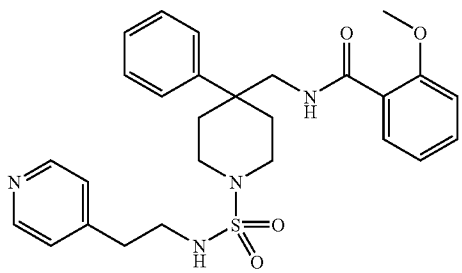 | 2-Methoxy-N-[4-phenyl-1-(2-pyriidn-4-yl-ethyl-sulfamoyl)-piperidin-4-ylmethyl]-benzamide | 511 |
| 731 | 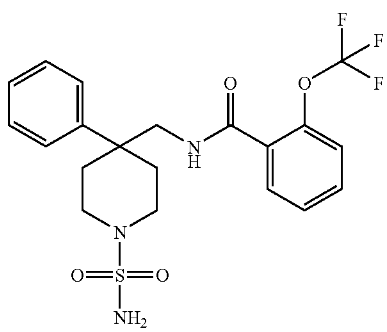 | N-(4-Phenyl-1-sulfamoyl-piperidin-4-ylmethyl)-2-trifluoromethoxy-benzamide | 459 |
| 732 | 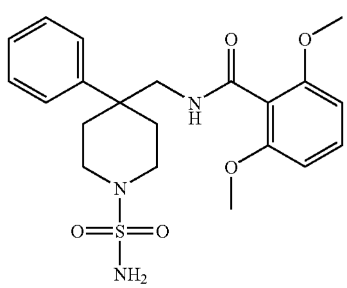 | 2,6-Dimethoxy-N-(4-phenyl-1-sulfamoyl-piperidin-4-ylmethyl)-benzamide | 436 |
| 733 | 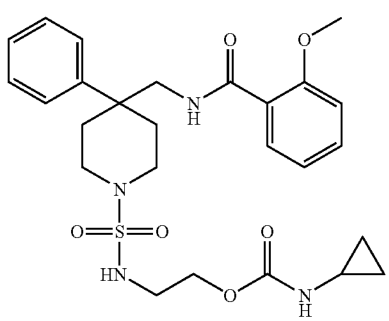 | Cyclopropyl-carbamic acid 2-{4-[(2-methoxy-benzoylamino)-methyl]-4-phenyl-piperidine-1-sulfonylamino}-ethyl ester | 533 |

-continued

| Example | Structure | Name | M + H |
|---|---|---|---|
| 734 | 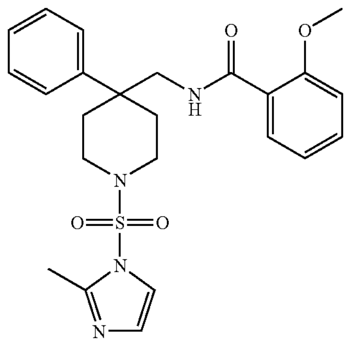 | 2-Methoxy-N-[1-(2-methyl-imidazole-1-sulfonyl)-4-phenyl-piperidin-4-yl-methyl]-benzamide | 471 |
| 735 | 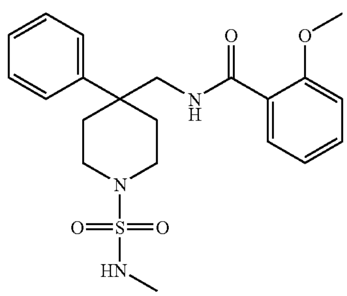 | 2-Methoxy-N-(1-methylsulfamoyl-4-phenyl-piperidin-4-ylmethyl)-benzamide | 420 |
| 736 | 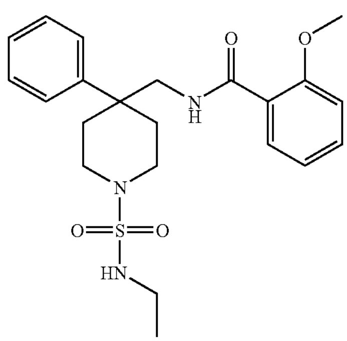 | N-(1-Ethylsulfamoyl-4-phenyl-piperidin-4-yl-methyl)-2-methoxy-benzamide | 434 |
| 737 | 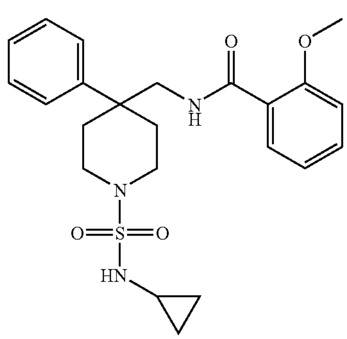 | N-(1-Cyclopropylsulfamoyl-4-phenyl-piperidin-4-yl-methyl)-2-methoxy-benzamide | 446 |

| Example | Structure | Name | M + H |
|---------|-----------|------|-------|
| 738 | 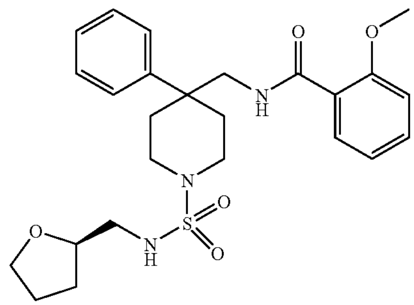 | 2-Methoxy-N-{4-phenyl-1-[(tetra-hydro-furan-2-yl-methyl)-sulfamoyl]-piperidin-4-ylmethyl}-benzamide | 490 |
| 739 | 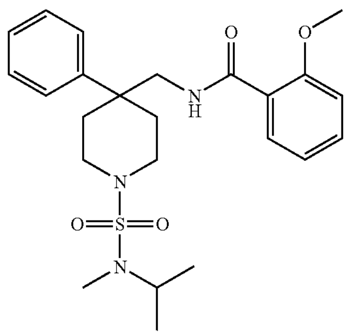 | N-[1-(Isopropyl-methyl-sulfamoyl)-4-phenyl-piperidin-4-ylmethyl]-2-methoxy-benzamide | 462 |
| 740 | 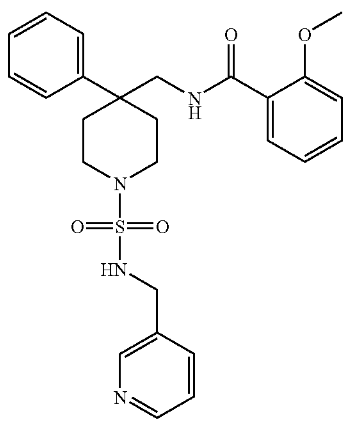 | 2-Methoxy-N-{4-phenyl-1-[(pyridin-3-ylmethyl)-sulfamoyl]-piperidin-4-ylmethyl}-benzamide | 497 |
| 741 | 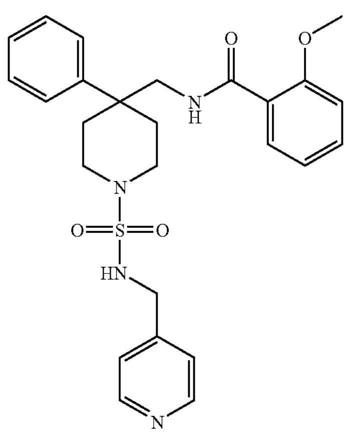 | 2-Methoxy-N-{4-phenyl-1-[(pyridin-4-ylmethyl)-sulfamoyl]-piperidin-4-ylmethyl}-benzamide | 497 |

-continued

| Example | Structure | Name | M + H |
|---|---|---|---|
| 742 | 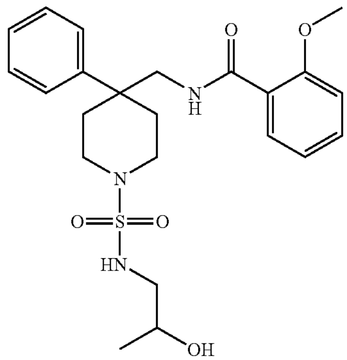 | N-[1-(2-Hydroxy-propyl-sulfamoyl)-4-phenyl-piperidin-4-ylmethyl]-2-methoxy-benzamide | 464 |
| 743 | 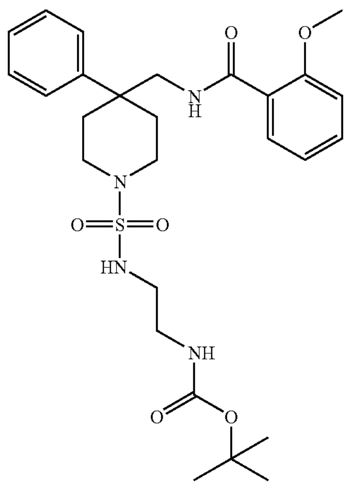 | (2-{4-[(2-Methoxy-benzoyl-amino)-methyl]-4-phenyl-piperidine-1-sulfonyl-amino}-ethyl)-carbamic acid tert-butyl ester | 549 |
| 744 | 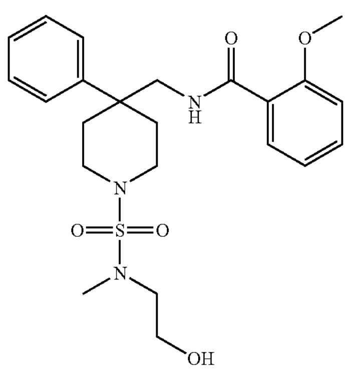 | N-{1-[(2-Hydroxy-ethyl)-methyl-sulfamoyl]-4-phenyl-piperidin-4-ylmethyl}-2-methoxy-benzamide | 464 |
| 745 | 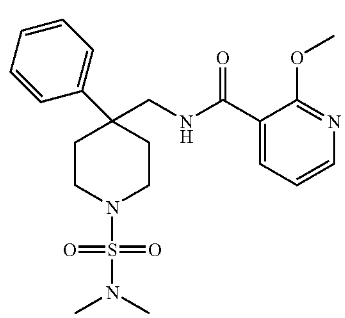 | N-(1-Dimethylsulfamoyl-4-phenyl-piperidin-4-yl-methyl)-2-methoxy-nicotinamide | 435 |

-continued
| Example | Structure | Name | M + H |
|---|---|---|---|
| 746 | 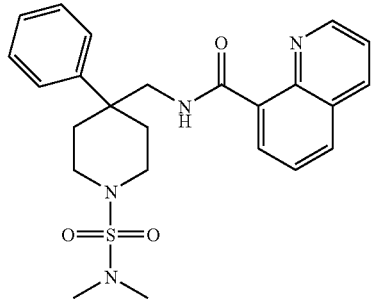 | Quinoline-8-carboxylic acid (1-dimethylsulfamoyl-4-phenyl-piperidin-4-yl-methyl)-amide | 455 |
| 747 | 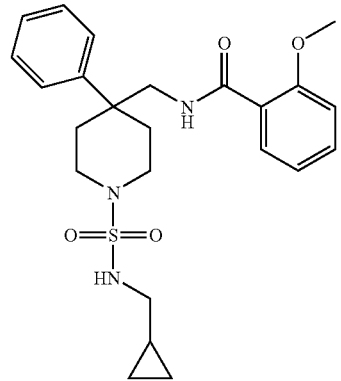 | N-[1-(Cyclopropylmethyl-sulfamoyl)-4-phenyl-piperidin-4-ylmethyl]-2-methoxy-benzamide | 460 |
| 748 | 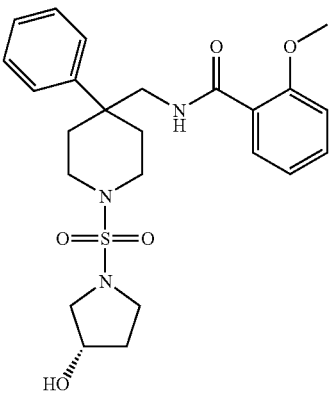 | N-[1-(3-Hydroxy-pyrrolidine-1-sulfonyl)-4-phenyl-piperidin-4-yl-methyl]-2-methoxy-benzamide | 476 |
| 749 | 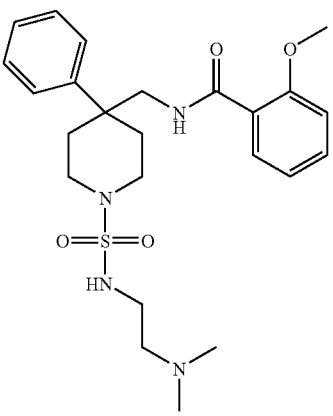 | N-[1-(2-Dimethylamino-ethylsulfamoyl)-4-phenyl-piperidin-4-ylmethyl]-2-methoxy-benzamide | 477 |

-continued

| Example | Structure | Name | M + H |
|---|---|---|---|
| 750 | 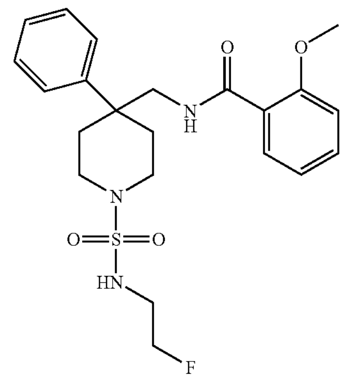 | N-[1-(2-Fluoro-ethyl-sulfamoyl)-4-phenyl-piperidin-4-ylmethyl]-2-methoxy-benzamide | 452 |
| 751 | 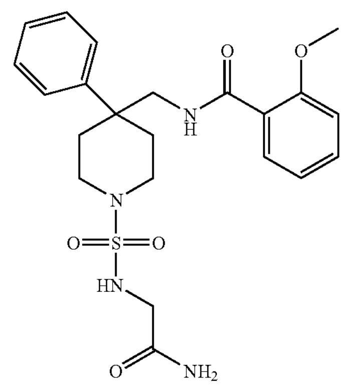 | N-[1-(Carbamoylmethyl-sulfamoyl)-4-phenyl-piperidin-4-ylmethyl]-2-methoxy-benzamide | 463 |
| 752 | 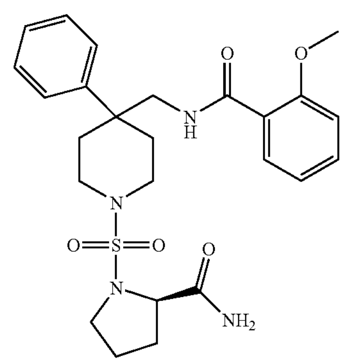 | 1-{4-[(2-Methoxy-benzoyl-amino)-methyl]-4-phenyl-piperidine-1-sulfonyl}-pyrrolidine-2-carboxylic acid amide | 503 |
| 753 | 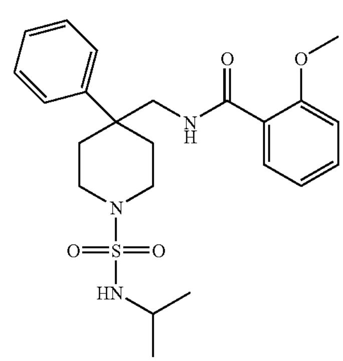 | N-(1-Isopropylsulfamoyl-4-phenyl-piperidin-4-yl-methyl)-2-methoxy-benzamide | 448 |

| Example | Structure | Name | M + H |
|---|---|---|---|
| 754 | 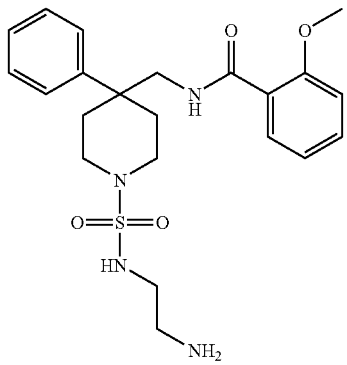 | N-[1-(2-Amino-ethyl-sulfamoyl)-4-phenyl-piperidin-4-ylmethyl]-2-methoxy-benzamide | 449 |
| 755 | 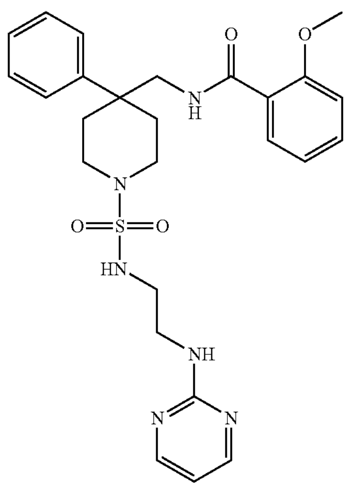 | 2-Methoxy-N-{4-phenyl-1-[2-(pyrimidin-2-ylamino)-ethyl-sulfamoyl]-piperidin-4-ylmethyl}-benzamide | 527 |
| 756 | 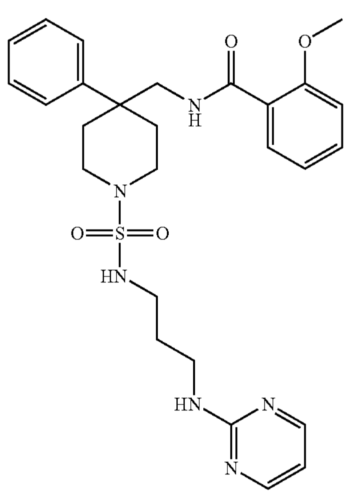 | 2-Methoxy-N-{4-phenyl-1-[3-(pyrimidin-2-ylamino)-propyl-sulfamoyl]-piperidin-4-ylmethyl}-benzamide | 541 |

-continued

| Example | Structure | Name | M + H |
|---|---|---|---|
| 757 | 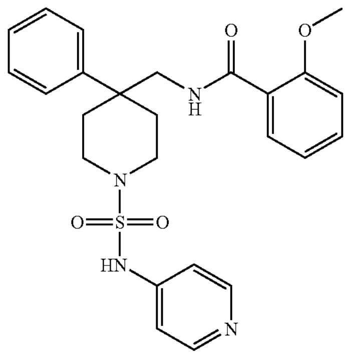 | 2-Methoxy-N-[4-phenyl-1-(pyridin-4-ylsulfamoyl)-piperidin-4-yl-ylmethyl]-benzamide | 483 |
| 758 | 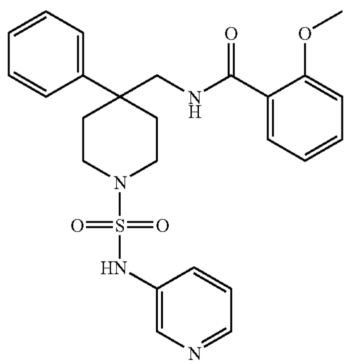 | 2-Methoxy-N-[4-phenyl-1-(pyridin-3-ylsulfamoyl)-piperidin-4-ylmethyl]-benzamide | 483 |
| 759 | 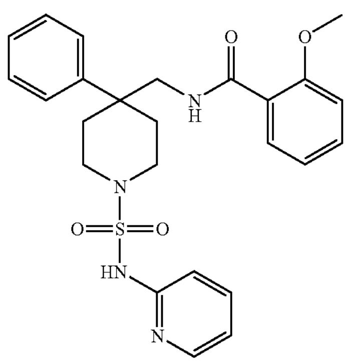 | 2-Methoxy-N-[4-phenyl-1-(pyridin-2-ylsulfamoyl)-piperidin-4-ylmethyl]-benzamide | 483 |
| 760 | 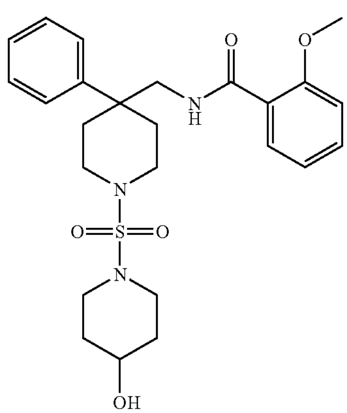 | N-[1-(4-Hydroxy-piperidine-1-sulfonyl)-4-phenyl-piperidin-4-ylmethyl]-2-methoxy-benzamide | 490 |

-continued

| Example | Structure | Name | M + H |
|---|---|---|---|
| 761 | 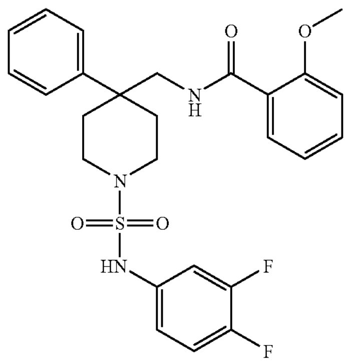 | N-[1-(3,4-Difluoro-phenyl-sulfamoyl)-4-phenyl-piperidin-4-ylmethyl]-2-methoxy-benzamide | 518 |
| 762 | 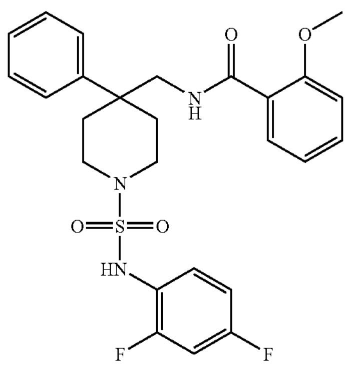 | N-[1-(2,4-Difluoro-phenyl-sulfamoyl)-4-phenyl-piperidin-4-ylmethyl]-2-methoxy-benzamide | 518 |
| 763 | 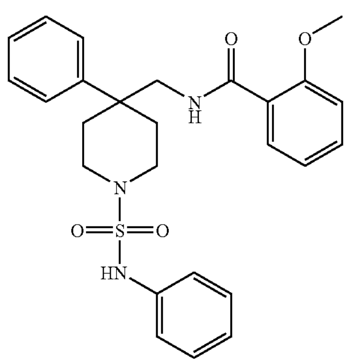 | 2-Methoxy-N-(4-phenyl-1-phenyl-sulfamoyl-piperidin-4-ylmethyl)-benzamide | 482 |
| 764 | 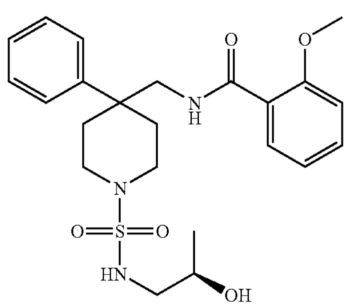 | N-[1-(2-Hydroxy-propyl-sulfamoyl)-4-phenyl-piperidin-4-ylmethyl]-2-methoxy-benzamide | 464 |

-continued

| Example | Structure | Name | M + H |
|---|---|---|---|
| 765 | 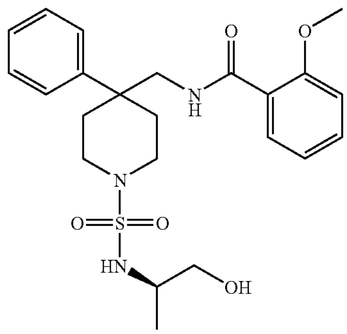 | N-[1-(2-Hydroxy-1-methyl-ethyl-sulfamoyl)-4-phenyl-piperidin-4-ylmethyl]-2-methoxy-benzamide | 464 |
| 766 | 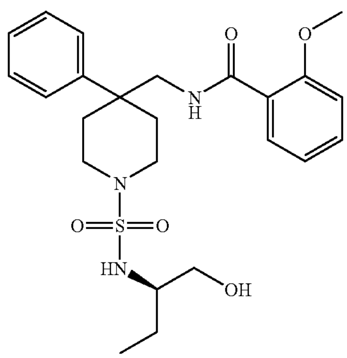 | N-[1-(1-Hydroxymethyl-propyl-sulfamoyl)-4-phenyl-piperidin-4-ylmethyl]-2-methoxy-benzamide | 478 |
| 767 | 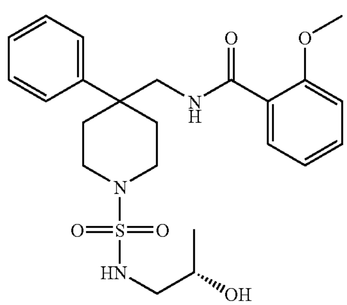 | N-[1-(2-Hydroxy-propyl-sulfamoyl)-4-phenyl-piperidin-4-ylmethyl]-2-methoxy-benzamide | 464 |
| 768 | 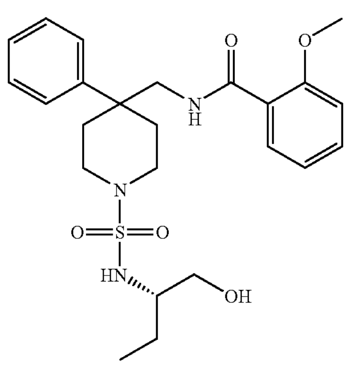 | N-[1-(1-Hydroxymethyl-propyl-sulfamoyl)-4-phenyl-piperidin-4-ylmethyl]-2-methoxy-benzamide | 478 |

-continued

| Example | Structure | Name | M + H |
|---|---|---|---|
| 769 | 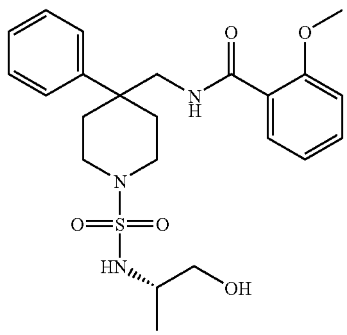 | N-[1-(2-Hydroxy-1-methyl-ethyl-sulfamoyl)-4-phenyl-piperidin-4-ylmethyl]-2-methoxy-benzamide | 464 |
| 770 | 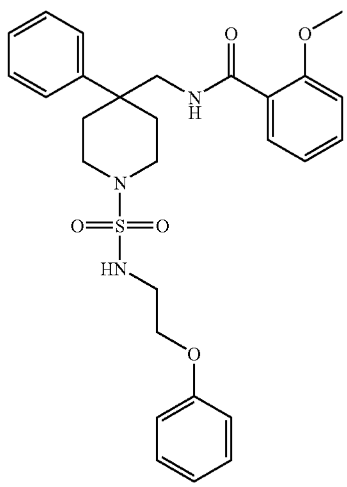 | 2-Methoxy-N-[1-(2-phenoxy-ethylsulfamoyl)-4-phenyl-piperidin-4-ylmethyl]-benzamide | 526 |
| 771 | 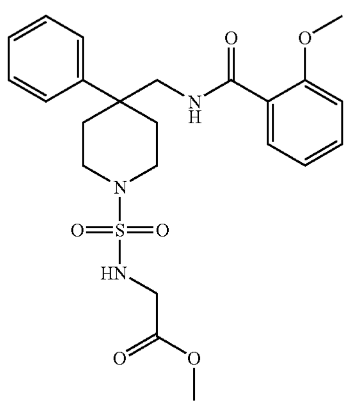 | {4-[(2-Methoxy-benzoyl-amino)-methyl]-4-phenyl-piperidine-1-sulfonylamino}-acetic acid methyl ester | 478 |
| 772 | 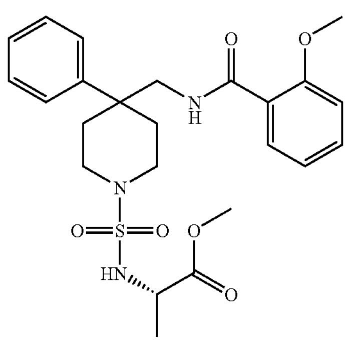 | 2-{4-[(2-Methoxy-benzoyl-amino)-methyl]-4-phenyl-piperidine-1-sulfonylamino}-propionic acid methyl ester | 492 |

-continued

| Example | Structure | Name | M + H |
|---|---|---|---|
| 773 | 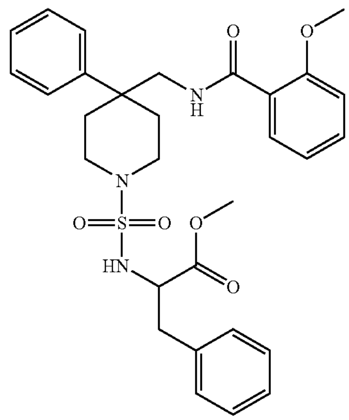 | 2-{4-[(2-Methoxy-benzoyl-amino)-methyl]-4-phenyl-piperidine-1-sulfonylamino}-3-phenyl-propionic acid methyl ester | 568 |
| 774 | 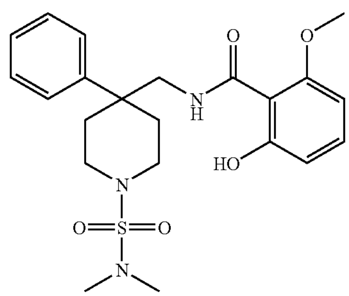 | N-(1-Dimethylsulfamoyl-4-phenyl-piperidin-4-yl-methyl)-2-hydroxy-6-methoxy-benzamide | 450 |
| 775 | 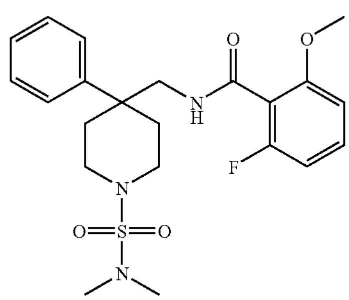 | N-(1-Dimethylsulfamoyl-4-phenyl-piperidin-4-yl-methyl)-2-fluoro-6-methoxy-benzamide | 452 |
| 776 | 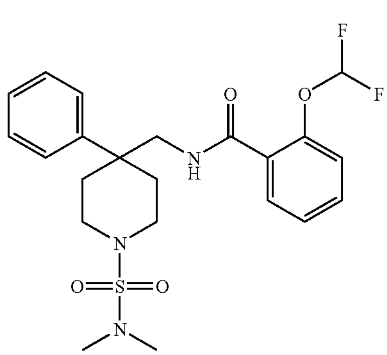 | 2-Difluoromethoxy-N-(1-dimethylsulfamoyl-4-phenyl-piperidin-4-ylmethyl)-benzamide | 470 |

-continued

| Example | Structure | Name | M + H |
|---|---|---|---|
| 777 | 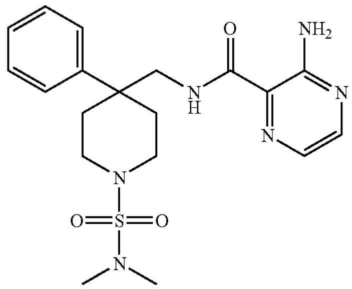 | 3-Amino-pyrazine-2-carboxylic acid(1-dimethylsulfamoyl-4-phenyl-piperidin-4-ylmethyl)-amide | 421 |
| 778 | 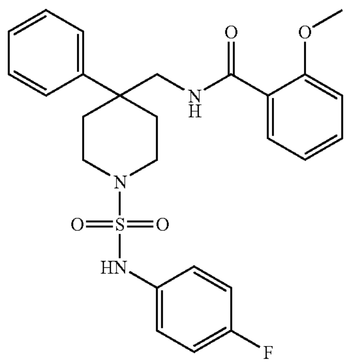 | N-[1-(4-Fluoro-phenylsulfamoyl)-4-phenyl-piperidin-4-ylmethyl]-2-methoxy-benzamide | 500 |
| 779 | 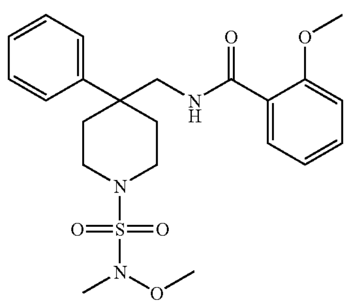 | 2-Methoxy-N-[1-(methoxy-methyl-sulfamoyl)-4-phenyl-piperidin-4-ylmethyl]-benzamide | 450 |
| 780 | 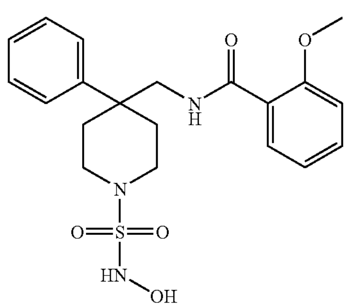 | N-(1-Hydroxysulfamoyl-4-phenyl-piperidin-4-yl-methyl)-2-methoxy-benzamide | 422 |

-continued

| Example | Structure | Name | M + H |
|---|---|---|---|
| 781 | 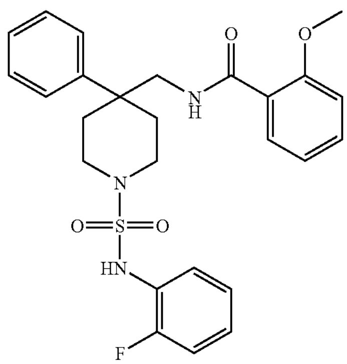 | N-[1-(2-Fluoro-phenyl-sulfamoyl)-4-phenyl-piperidin-4-ylmethyl]-2-methoxy-benzamide | 500 |
| 782 | 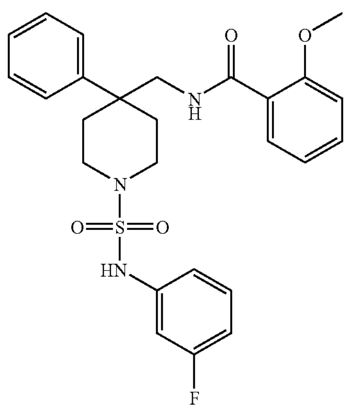 | N-[1-(3-Fluoro-phenyl-sulfamoyl)-4-phenyl-piperidin-4-ylmethyl]-2-methoxy-benzamide | 500 |
| 783 | 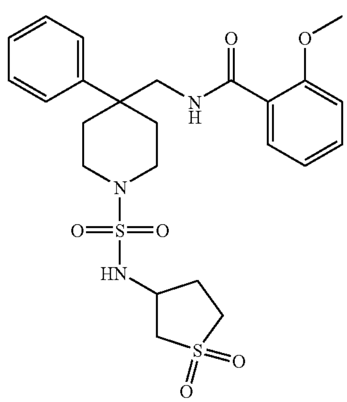 | N-[1-(1,1-Dioxo-tetrahydro-1lambda*6*-thiophen-3-yl-sulfamoyl)-4-phenyl-piperidin-4-ylmethyl]-2-methoxy-benzamide | 524 |
| 784 | 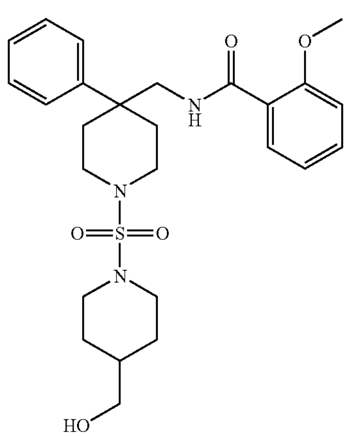 | N-[1-(4-Hydroxymethyl-piperidine-1-sulfonyl)-4-phenyl-piperidin-4-ylmethyl]-2-methoxy-benzamide | 504 |

| Example | Structure | Name | M + H |
|---|---|---|---|
| 785 | 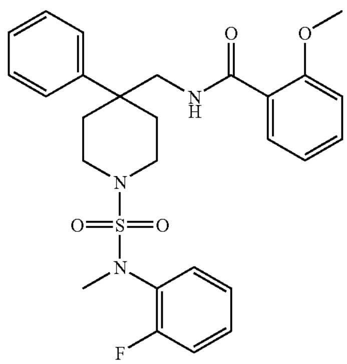 | N-{1-[(2-Fluoro-phenyl)-methyl-sulfamoyl]-4-phenyl-piperidin-4-ylmethyl}-2-methoxy-benzamide | 514 |
| 786 | 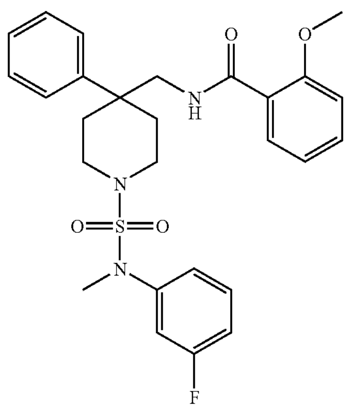 | N-{1-[(3-Fluoro-phenyl)-methyl-sulfamoyl]-4-phenyl-piperidin-4-ylmethyl}-2-methoxy-benzamide | 514 |
| 787 | 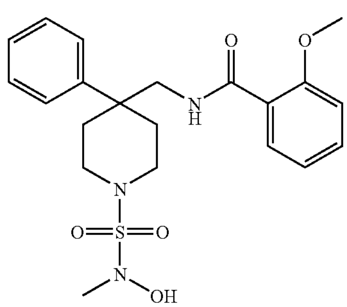 | N-[1-(Hydroxy-methyl-sulfamoyl)-4-phenyl-piperidin-4-ylmethyl]-2-methoxy-benzamide | 436 |
| 788 | 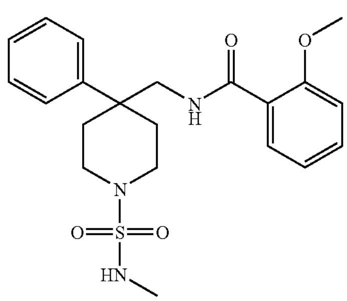 | 2-Methoxy-N-(1-methylsulfamoyl-4-phenyl-piperidin-4-ylmethyl)-benzamide | 419 |

| Example | Structure | Name | M + H |
|---|---|---|---|
| 789 | 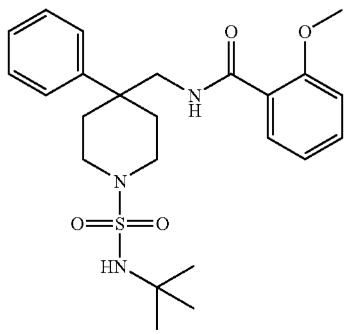 | N-(1-tert-Butylsulfamoyl-4-phenyl-piperidin-4-yl-methyl)-2-methoxy-benzamide | 462 |
| 790 | 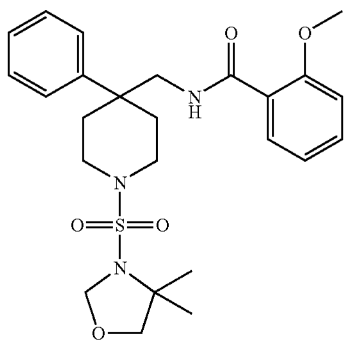 | N-[1-(4,4-Dimethyl-oxazolidine-3-sulfonyl)-4-phenyl-piperidin-4-yl-methyl]-2-methoxy-benzamide | 490 |
| 791 | 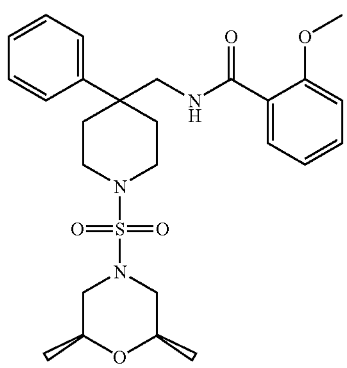 | N-[1-(2,6-Dimethyl-morpholine-4-sulfonyl)-4-phenyl-piperidin-4-yl-methyl]-2-methoxy-benzamide | 504 |
| 792 | 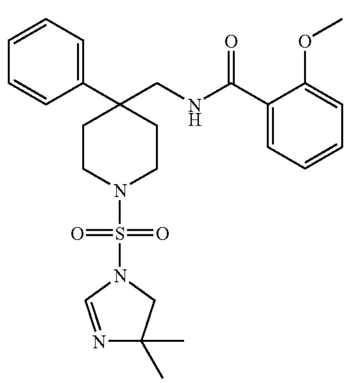 | N-[1-(4,4-Dimethyl-4,5-dihydro-imidazole-1-sulfonyl)-4-phenyl-piperidin-4-ylmethyl]-2-methoxy-benzamide | 487 |

-continued

| Example | Structure | Name | M + H |
|---|---|---|---|
| 793 | 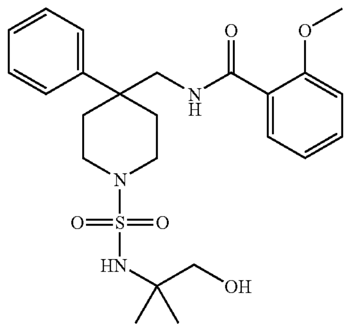 | N-[1-(2-Hydroxy-1,1-dimethyl-ethylsulfamoyl)-4-phenyl-piperidin-4-yl-methyl]-2-methoxy-benzamide | 478 |
| 794 | 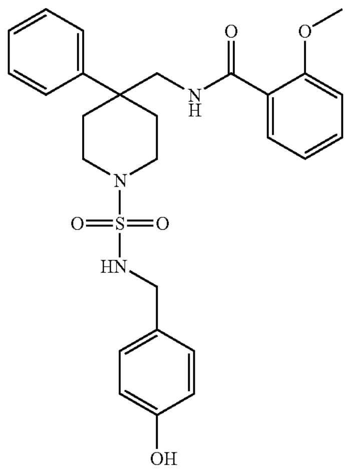 | N-[1-(4-Hydroxy-benzyl-sulfamoyl)-4-phenyl-piperidin-4-ylmethyl]-2-methoxy-benzamide | 512 |
| 795 | 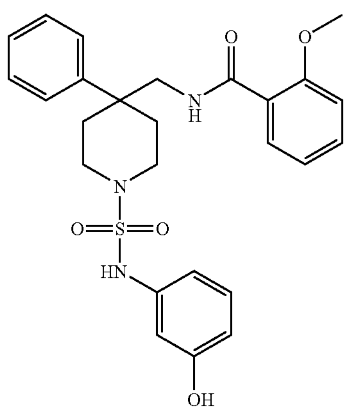 | N-[1-(3-Hydroxy-phenyl-sulfamoyl)-4-phenyl-piperidin-4-ylmethyl]-2-methoxy-benzamide | 498 |
| 796 | 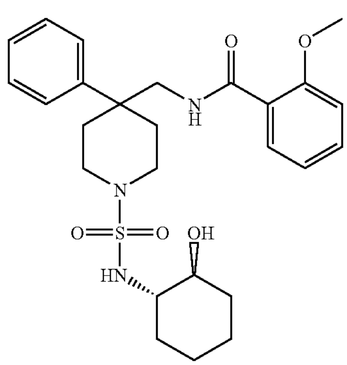 | N-[1-(2-Hydroxy-cyclohexylsulfamoyl)-4-phenyl-piperidin-4-ylmethyl]-2-methoxy-benzamide | 504 |

| Example | Structure | Name | M + H |
|---------|-----------|------|-------|
| 797 | 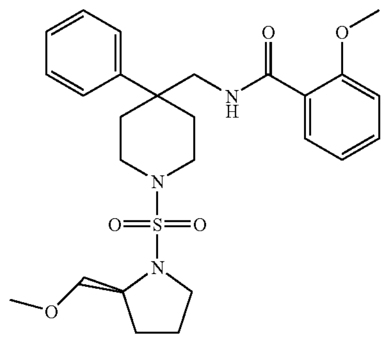 | 2-Methoxy-N-[1-(2-methoxymethyl-pyrrolidine-1-sulfonyl)-4-phenyl-piperidin-4-ylmethyl]-benzamide | 504 |
| 798 | 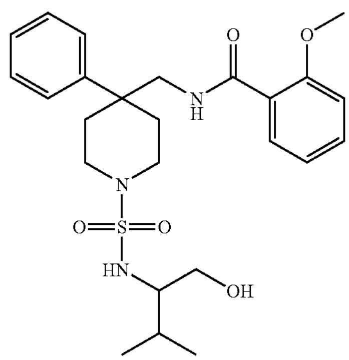 | N-[1-(1-Hydroxymethyl-2-methyl-propylsulfamoyl)-4-phenyl-piperidin-4-ylmethyl]-2-methoxy-benzamide | 492 |
| 799 | 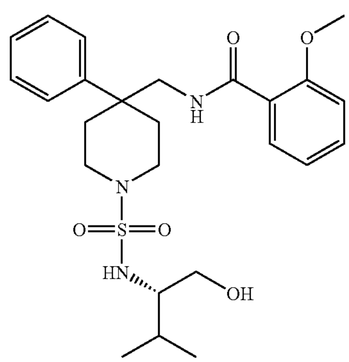 | N-[1-(1-Hydroxymethyl-2-methyl-propylsulfamoyl)-4-phenyl-piperidin-4-ylmethyl]-2-methoxy-benzamide | 492 |
| 800 | 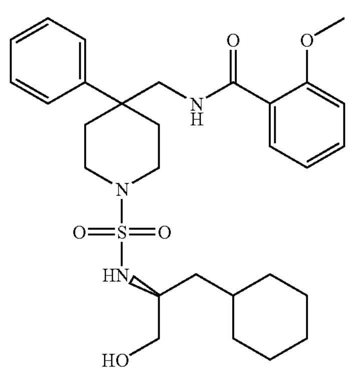 | N-[1-(2-Cyclohexyl-1-hydroxymethyl-ethylsulfamoyl)-4-phenyl-piperidin-4-ylmethyl]-2-methoxy-benzamide | 546 |

-continued

| Example | Structure | Name | M + H |
|---|---|---|---|
| 801 | 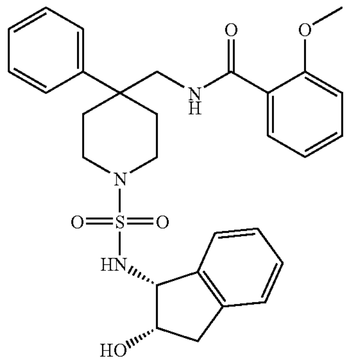 | N-[1-(2-Hydroxy-indan-1-yl-sulfamoyl)-4-phenyl-piperidin-4-ylmethyl]-2-methoxy-benzamide | 538 |
| 802 | 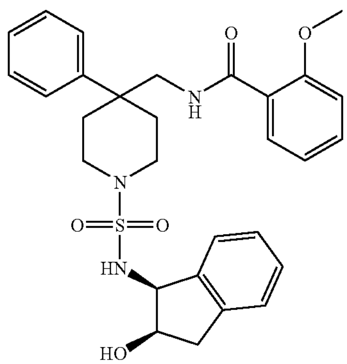 | N-[1-(2-Hydroxy-indan-1-yl-sulfamoyl)-4-phenyl-piperidin-4-ylmethyl]-2-methoxy-benzamide | 538 |
| 803 | 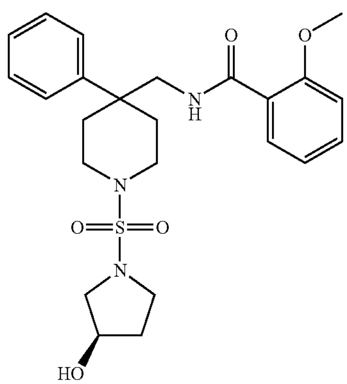 | N-[1-(3-Hydroxy-pyrrolidine-1-sulfonyl)-4-phenyl-piperidin-4-ylmethyl]-2-methoxy-benzamide | 476 |
| 804 | 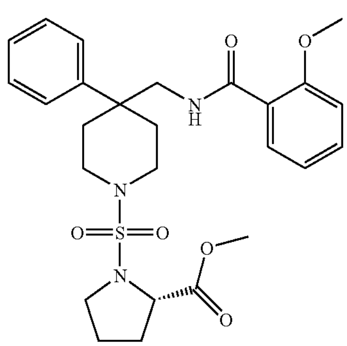 | 1-{4-[(2-Methoxy-benzoyl-amino)-methyl]-4-phenyl-piperidine-1-sulfonyl}-pyrrolidine-2-carboxylic acid methyl ester | 518 |

-continued

| Example | Structure | Name | M + H |
|---|---|---|---|
| 805 | 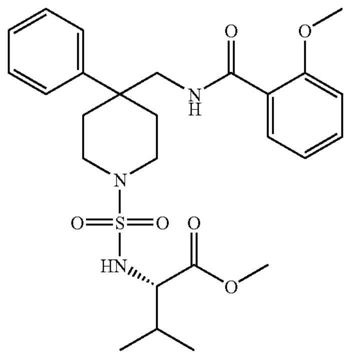 | 2-{4-[(2-Methoxy-benzoyl-amino)-methyl]-4-phenyl-piperidine-1-sulfonylamino}-3-methyl-butyric acid methyl ester | 520 |
| 806 | 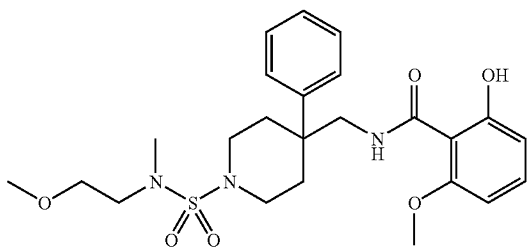 | 2-Hydroxy-6-methoxy-N-{1-[(2-methoxy-ethyl)-methyl-sulfamoyl]-4-phenyl-piperidin-4-ylmethyl}-benzamide | 494 |
| 807 | 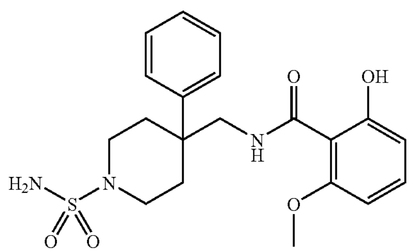 | 2-Hydroxy-6-methoxy-N-(4-phenyl-1-sulfamoyl-piperidin-4-ylmethyl)-benzamide | 422 |
| 808 | 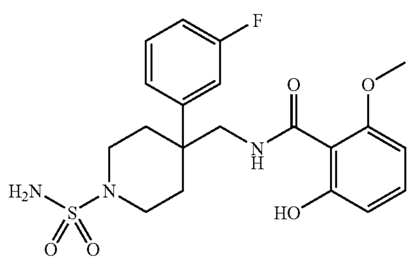 | N-[4-(3-Fluoro-phenyl)-1-sulfamoyl-piperidin-4-yl-methyl]-2-hydroxy-6-methoxy-benzamide | 439 |
| 809 | 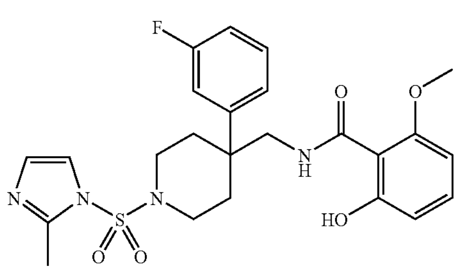 | N-[4-(3-Fluoro-phenyl)-1-(2-methyl-imidazole-1-sulfonyl)-piperidin-4-yl-methyl]-2-hydroxy-6-methoxy-benzamide | 505 |

| Example | Structure | Name | M + H |
|---|---|---|---|
| 810 | 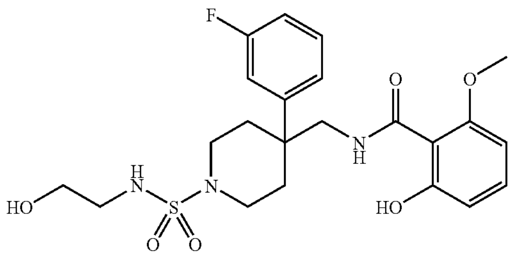 | N-[4-(3-Fluoro-phenyl)-1-(2-hydroxy-ethylsulfamoyl)-piperidin-4-ylmethyl]-2-hydroxy-6-methoxy-benzamide | 484 |
| 811 | 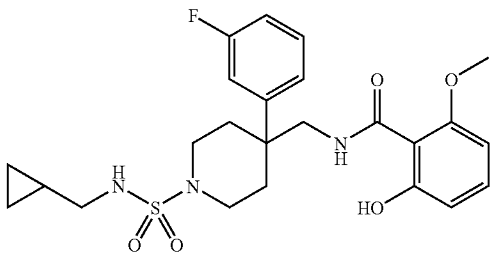 | N-[1-(Cyclopropylmethyl-sulfamoyl)-4-(3-fluoro-phenyl)-piperidin-4-ylmethyl]-2-hydroxy-6-methoxy-benzamide | 494 |
| 812 | 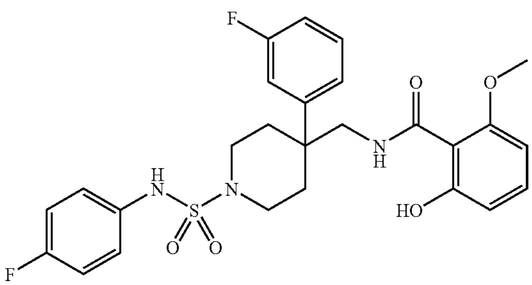 | N-[4-(3-Fluoro-phenyl)-1-(4-fluoro-phenylsulfamoyl)-piperidin-4-ylmethyl]-2-hydroxy-6-methoxy-benzamide | 534 |
| 813 | 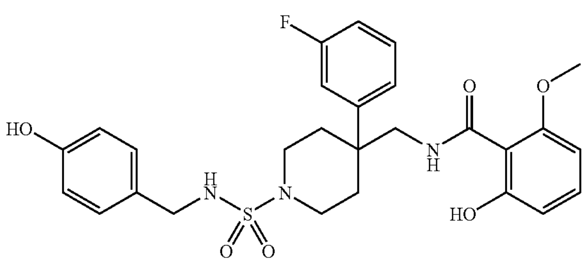 | N-[4-(3-Fluoro-phenyl)-1-(4-hydroxy-benzyl-sulfamoyl)-piperidin-4-ylmethyl]-2-hydroxy-6-methoxy-benzamide | 546 |
| 814 | 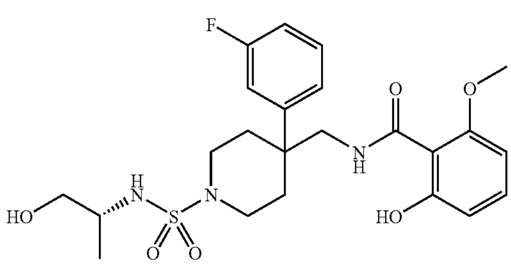 | N-[4-(3-Fluoro-phenyl)-1-(2-hydroxy-1-methyl-ethyl-sulfamoyl)-piperidin-4-ylmethyl]-2-hydroxy-6-methoxy-benzamide | 498 |

-continued

| Example | Structure | Name | M + H |
|---|---|---|---|
| 815 | 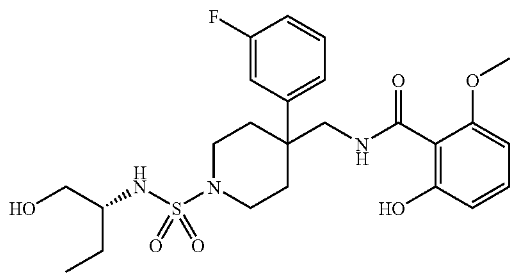 | N-[4-(3-Fluoro-phenyl)-1-(1-hydroxymethyl-propyl-sulfamoyl)-piperidin-4-yl-methyl]-2-hydroxy-6-methoxy-benzamide | 512 |
| 816 | 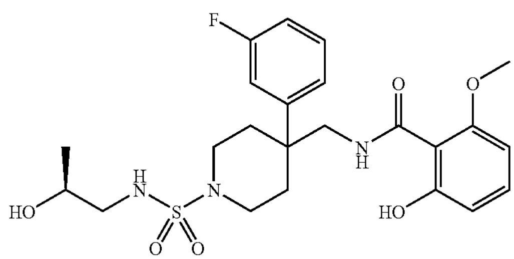 | N-[4-(3-Fluoro-phenyl)-1-(2-hydroxy-propyl-sulfamoyl)-piperidin-4-yl-methyl]-2-hydroxy-6-methoxy-benzamide | 498 |
| 817 | 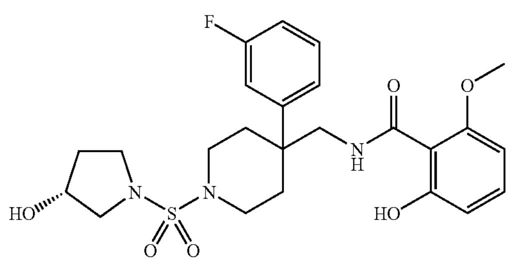 | N-[4-(3-Fluoro-phenyl)-1-(3-hydroxy-pyrrolidine-1-sulfonyl)-piperidin-4-yl-methyl]-2-hydroxy-6-methoxy-benzamide | 510 |
| 818 | 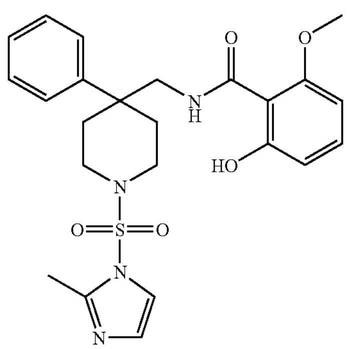 | 2-Hydroxy-6-methoxy-N-[1-(2-methyl-imidazole-1-sulfonyl)-4-phenyl-piperidin-4-ylmethyl]-benzamide | 487 |
| 819 | 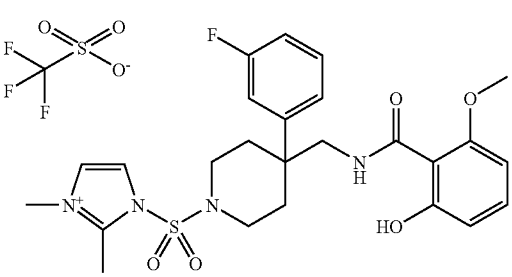 | Trifluoro-methane-sulfonate3-{4-(3-fluoro-phenyl)-4-[(2-hydroxy-6-methoxy-benzoyl-amino)-methyl]-piperidine-1-sulfonyl}-1,2-dimethyl-3H-imidazol-1-ium; | 669 |

-continued

| Example | Structure | Name | M + H |
|---|---|---|---|
| 820 | 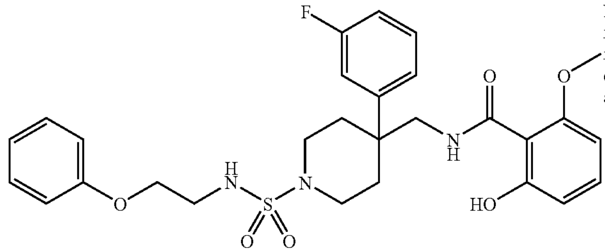 | N-[4-(3-Fluoro-phenyl)-1-(2-phenoxy-ethylsulfamoyl)-piperidin-4-ylmethyl]-2-hydroxy-6-methoxy-benzamide | 560 |
| 821 | 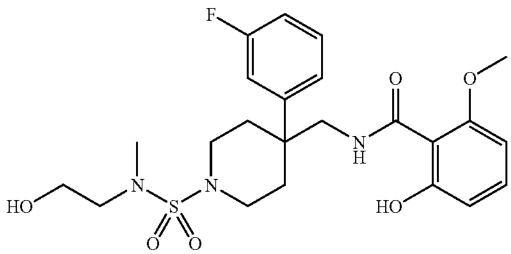 | N-{4-(3-Fluoro-phenyl)-1-[(2-hydroxy-ethyl)-methyl-sulfamoyl]-piperidin-4-ylmethyl}-2-hydroxy-6-methoxy-benzamide | 498 |
| 822 | 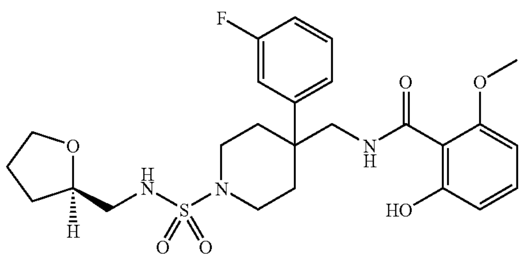 | N-{4-(3-Fluoro-phenyl)-1-[(tetrahydro-furan-2-yl-methyl)-sulfamoyl]-piperidin-4-ylmethyl}-2-hydroxy-6-methoxy-benzamide | 524 |
| 823 | 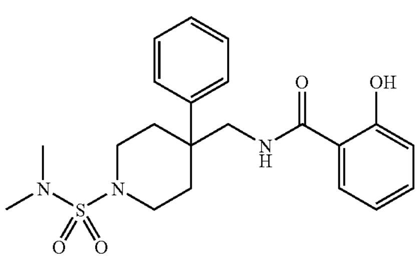 | N-(1-Dimethylsulfamoyl-4-phenyl-piperidin-4-ylmethyl)-2-hydroxy-benzamide | 420 |
| 824 | 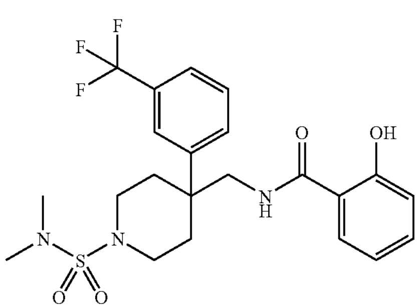 | N-[1-Dimethylsulfamoyl-4-(3-trifluoromethyl-phenyl)-piperidin-4-ylmethyl]-2-hydroxy-benzamide | 488 |

-continued

| Example | Structure | Name | M + H |
|---|---|---|---|
| 825 | 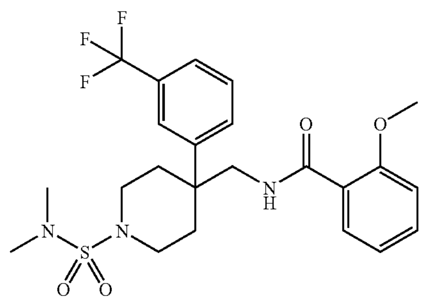 | N-[1-Dimethylsulfamoyl-4-(3-trifluoromethyl-phenyl)-piperidin-4-ylmethyl]-2-methoxy-benzamide | 502 |
| 826 | 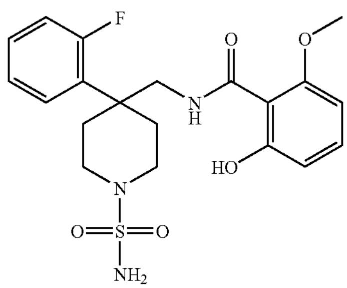 | N-[4-(2-Fluoro-phenyl)-1-sulfamoyl-piperidin-4-yl-methyl]-2-hydroxy-6-methoxy-benzamide | 439 |
| 827 | 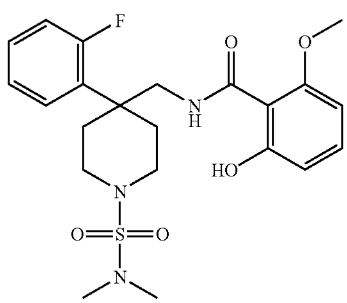 | N-[1-Dimethylsulfamoyl-4-(2-fluoro-phenyl)-piperidin-4-yl-methyl]-2-hydroxy-6-methoxy-benzamide | 468 |
| 828 | 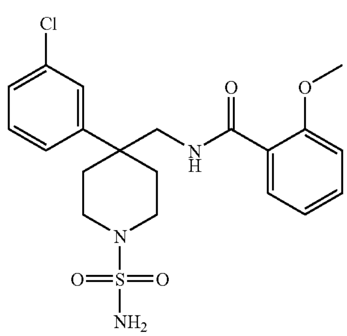 | N-[4-(3-Chloro-phenyl)-1-sulfamoyl-piperidin-4-yl-methyl]-2-methoxy-benzamide | 440 |
| 829 | 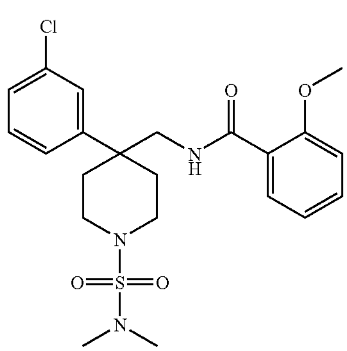 | N-[4-(3-Chloro-phenyl)-1-dimethylsulfamoyl-piperidin-4-ylmethyl]-2-methoxy-benzamide | 468 |

-continued

| Example | Structure | Name | M + H |
|---|---|---|---|
| 830 | 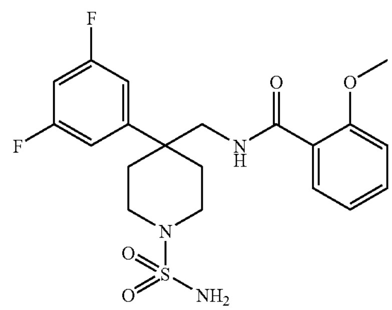 | N-[4-(3,5-Difluoro-phenyl)-1-sulfa-moyl-piperidin-4-yl-methyl]-2-methoxy-benz-amide | 441 |
| 831 | 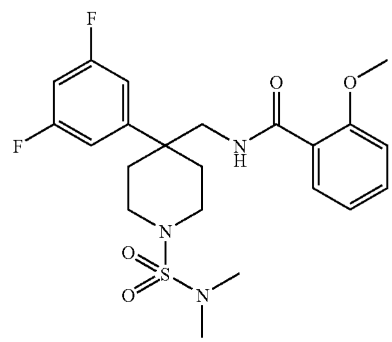 | N-[4-(3,5-Difluoro-phenyl)-1-di-methylsulfamoyl-pipe-ridin-4-ylmethyl]-2-meth-oxy-benzamide | 470 |
| 832 | 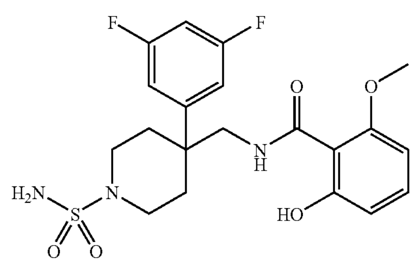 | N-[4-(3,5-Difluoro-phenyl)-1-sul-famoyl-piperidin-4-yl-methyl]-2-hydroxy-6-meth-oxy-benzamide | 457 |
| 833 | 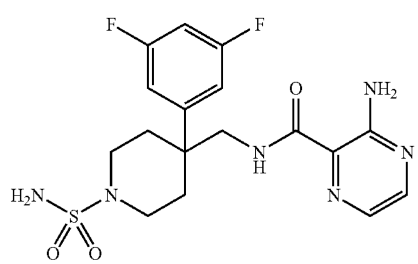 | 3-Amino-pyrazine-2-car-boxylic acid[4-(3,5-di-fluoro-phenyl)-1-sul-famoyl-piperidin-4-yl-methyl]-amide | 428 |
| 834 | 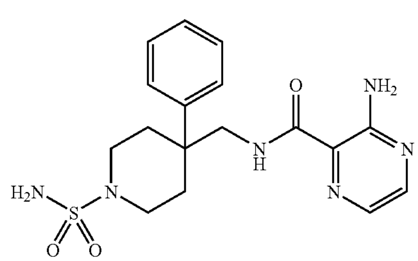 | 3-Amino-pyrazine-2-car-boxylic acid(4-phenyl-1-sul-famoyl-piperidin-4-yl-methyl)-amide | 392 |

| Example | Structure | Name | M + H |
|---|---|---|---|
| 835 | 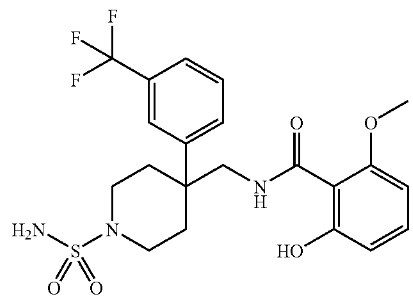 | 2-Hydroxy-6-methoxy-N-[1-sulfamoyl-4-(3-trifluoromethyl-phenyl)-piperidin-4-ylmethyl]-benzamide | 489 |
| 836 | 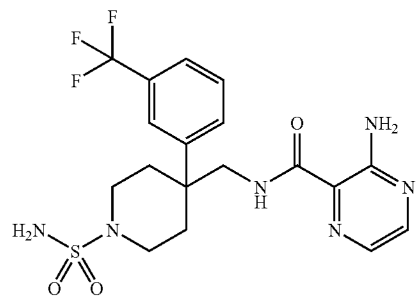 | 3-Amino-pyrazine-2-carboxylic acid[1-sulfamoyl-4-(3-trifluoromethyl-phenyl)-piperidin-4-ylmethyl]-amide | 460 |
| 837 | 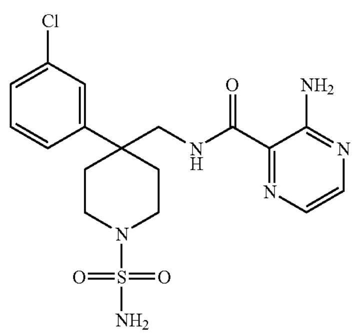 | 3-Amino-pyrazine-2-carboxylic acid[4-(3-chloro-phenyl)-1-sulfamoyl-piperidin-4-ylmethyl]-amide | 427 |
| 838 | 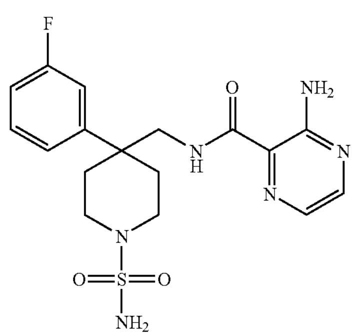 | 3-Amino-pyrazine-2-carboxylic acid[4-(3-fluoro-phenyl)-1-sulfamoyl-piperidin-4-ylmethyl]-amide | 410 |
| 839 | 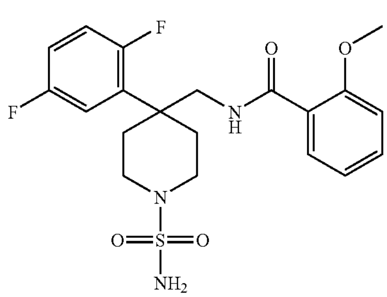 | N-[4-(2,5-Difluoro-phenyl)-1-sulfamoyl-piperidin-4-ylmethyl]-2-methoxy-benzamide | 441 |

-continued

| Example | Structure | Name | M + H |
|---------|-----------|------|-------|
| 840 | 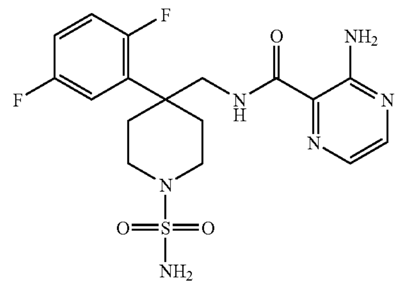 | 3-Amino-pyrazine-2-carboxylic acid[4-(2,5-difluoro-phenyl)-1-sulfamoyl-piperidin-4-yl-methyl]-amide | 428 |
| 841 | 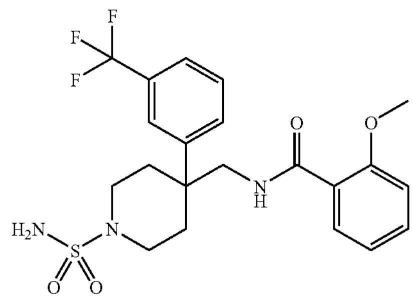 | 2-Methoxy-N-[1-sulfamoyl-4-(3-trifluoromethyl-phenyl)-piperidin-4-yl-methyl]-benzamide | 472 |
| 842 | 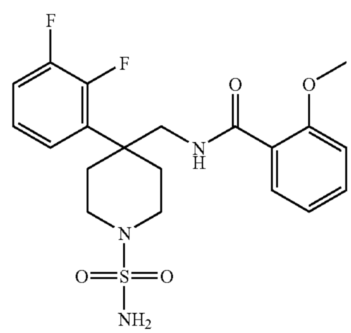 | N-[4-(2,3-Difluoro-phenyl)-1-sulfamoyl-piperidin-4-yl-methyl]-2-methoxy-benzamide | 440 |
| 843 | 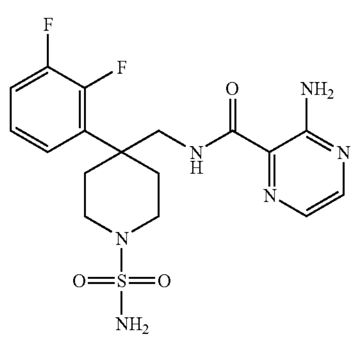 | 3-Amino-pyrazine-2-carboxylic acid[4-(2,3-difluoro-phenyl)-1-sulfamoyl-piperidin-4-yl-methyl]-amide | 427 |

Example 844

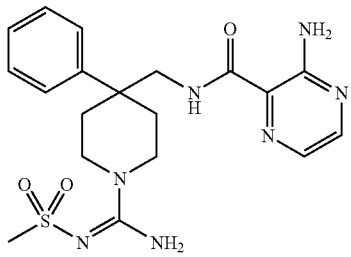

3-Amino-pyrazine-2-carboxylic acid [1-(amino-methanesulfonylimino-methyl)-4-phenyl-piperidin-4-ylmethyl]-amide Synthesis

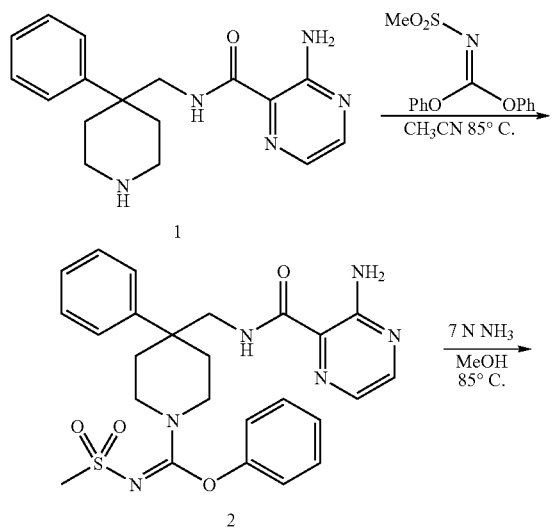

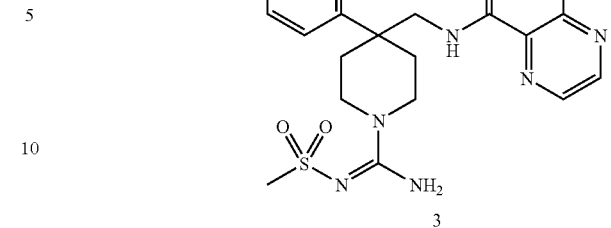

Compound 1: Compound 1 was prepared as described in Example 653.

Compound 2: A solution of compound 1 (0.15 g; 0.47 mmol) in anhydrous acetonitrile (8 mL) at room temperature was treated with N-diphenoxymethylene-methanesulfonamide (for preparation see U.S. Pat. No. 4,871,765) (0.17 g; 0.5 mmol). The reaction mixture was heated to 85° C. for 2 h. The solvent was removed by rotary evaporation and the crude residue was purified directly by column chromatography on silica gel using 9:1 ethyl acetate:hexane as the eluent to give 0.2 g of compound 2 as a white solid. LRMS m/z=510 $(M+H)^+$ Title Compound: Compound 2 (0.060 g; 0.12 mmol) was treated with 7 N ammonia in methanol (2 mL) and heated to 85° C. for 15 minutes in a sealed tube. The solvent was removed by rotary evaporation and the crude residue was purified directly by column chromatography on silica gel using 10:1 chloroform:methanol as the eluent to give 0.024 g of the title compound as a white solid. LRMS m/z=433 $(M+H)^+$

Examples 845 to 852

Examples 845 to 852 were prepared using methodology described in Example 844.

| Example | Structure | Name | M + H |
|---------|-----------|------|-------|
| 845 | 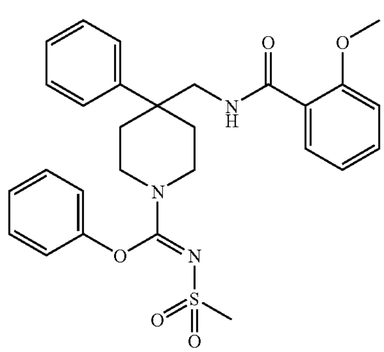 | N-[1-(Methanesulfonylimino-phenoxy-methyl)-4-phenyl-piperidin-4-ylmethyl]-2-methoxy-benzamide | 523 |

-continued

| Example | Structure | Name | M + H |
|---------|-----------|------|-------|
| 846 | 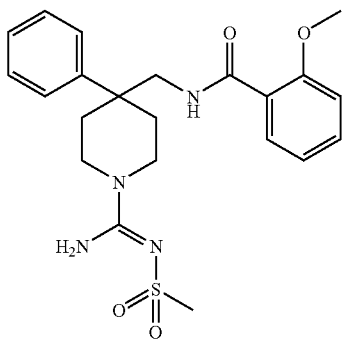 | N-[1-(Amino-methanesulfonylimino-methyl)-4-phenyl-piperidin-4-ylmethyl]-2-methoxy-benzamide | 446 |
| 847 | 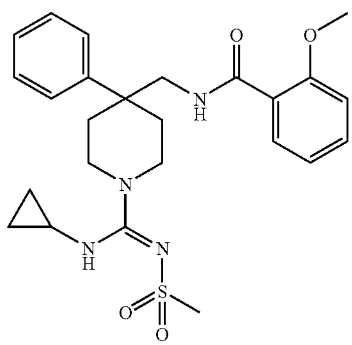 | N-[1-(Cyclopropylamino-methanesulfonylimino-methyl)-4-phenyl-piperidin-4-ylmethyl]-2-methoxy-benzamide | 486 |
| 848 | 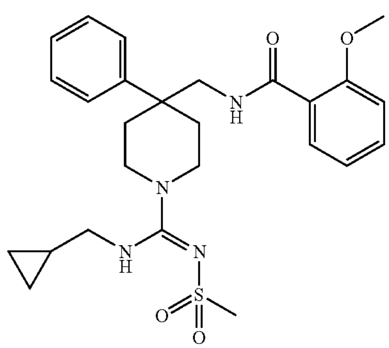 | N-{1-[(Cyclopropylmethyl-amino)-methanesulfonylimino-methyl]-4-phenyl-piperidin-4-ylmethyl}-2-methoxy-benzamide | 500 |
| 849 | 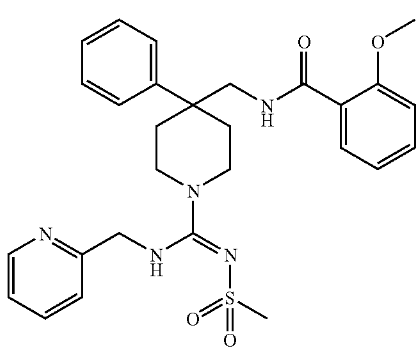 | N-(1-{Methanesulfonylimino-[(pyridin-2-ylmethyl)-amino]-methyl}-4-phenyl-piperidin-4-ylmethyl)-2-methoxy-benzamide | 537 |

| Example | Structure | Name | M + H |
|---|---|---|---|
| 850 | 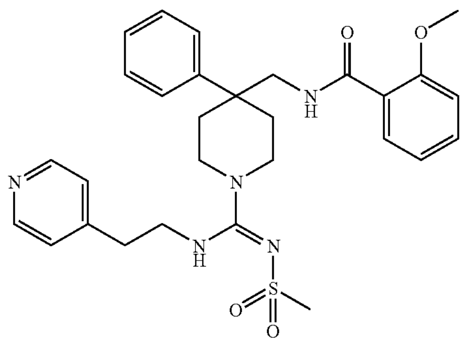 | N-{1-[Methanesulfonylimino-(2-pyridin-4-yl-ethylamino)-methyl]-4-phenyl-piperidin-4-ylmethyl}-2-methoxy-benzamide | 551 |
| 851 | 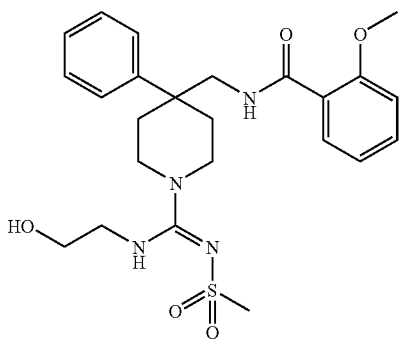 | N-{1-[(2-Hydroxy-ethylamino)-methanesulfonylimino-methyl]-4-phenyl-piperidin-4-ylmethyl}-2-methoxy-benzamide | 490 |
| 852 | 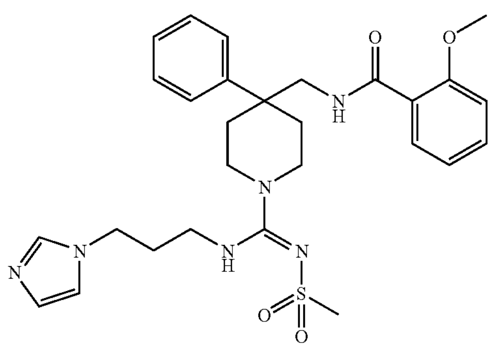 | N-{1-[(3-Imidazol-1-yl-propylamino)-methanesulfonylimino-methyl]-4-phenyl-piperidin-4-ylmethyl}-2-methoxy-benzamide | 554 |
Example 853
Synthesis
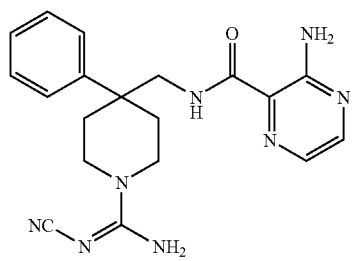
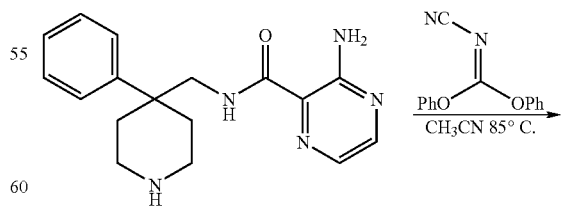

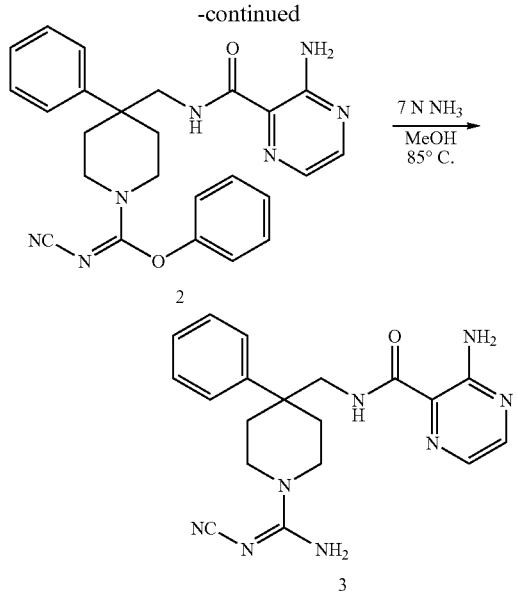

Compound 1: Compound 1 was prepared as described in Example 653.

Compound 2: A solution of compound 1 (0.211 mg; 0.68 mmol) in anhydrous acetonitrile (5 mL) was treated with dipenyl N-cyanocarbonimide (0.180 mg; 0.76 mmol) and heated to 85° C. for 1 h. The solvent was removed by rotary evaporation and the crude residue was purified directly by column chromatography on silica gel using 7:3 ethyl acetate:hexane as the eluent to give 0.273 g of compound 2 as a white foam. LRMS m/z=457 (M+H)$^+$ Title Compound: Compound 2 (0.061 g; 0.13 mmol) was treated with 7 N ammonia in methanol (2 mL) and heated to 60° C. for 1 h in a sealed tube. The solvent was removed by rotary evaporation and the crude residue was purified by preparative reverse phase HPLC to give 0.030 g of the title compound as a white solid. LRMS m/z=379 (M+H)$^+$ Examples 854 to 915

Examples 854 to 915 were prepared using methodology described in Example 25 and Example 853.

| Example | Structure | M + H |
|---------|-----------|-------|
| 854 | 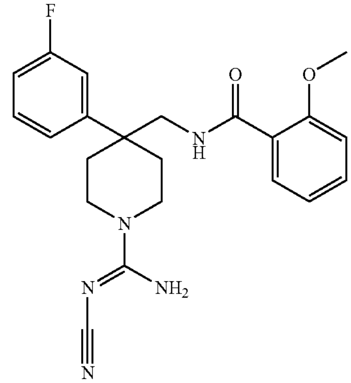 | 411 |
| 855 | 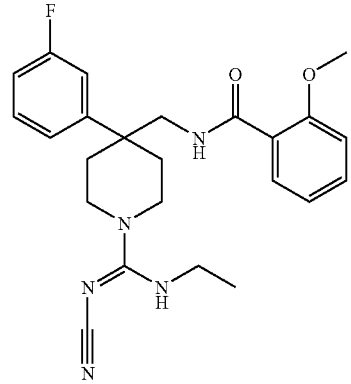 | 440 |

-continued
| Example | Structure | M + H |
|---------|-----------|-------|
| 856 | 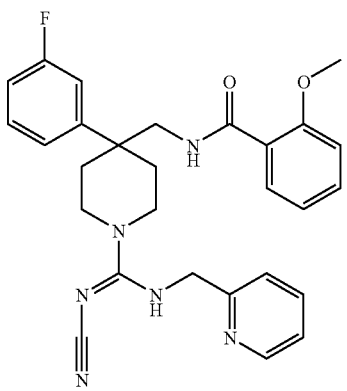 | 503 |
| 857 | 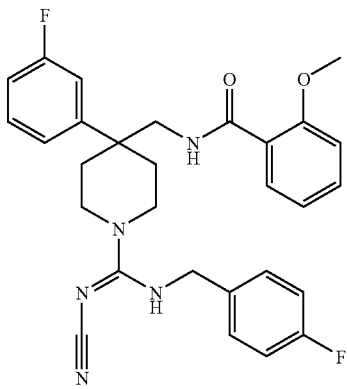 | 520 |
| 858 | 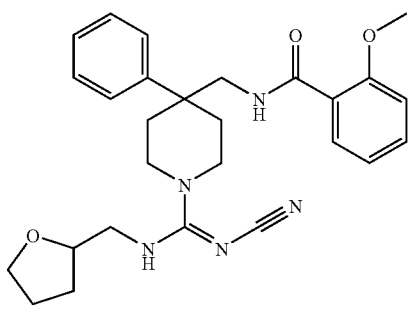 | 478 |
| 859 | 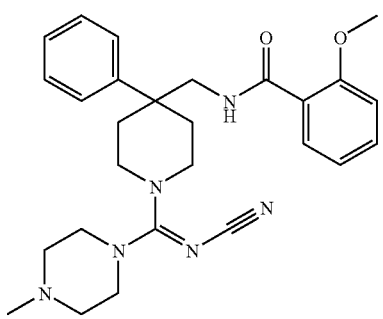 | 477 |

-continued

| Example | Structure | M + H |
|---------|-----------|-------|
| 860 | 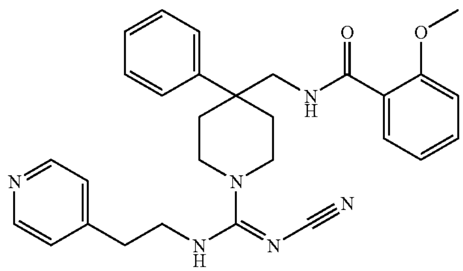 | 499 |
| 861 | 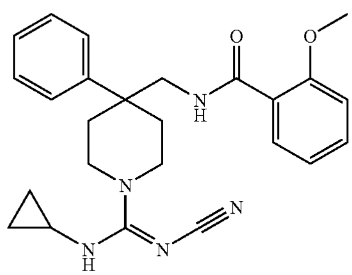 | 434 |
| 862 | 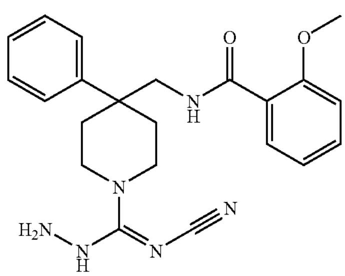 | 408 |
| 863 | 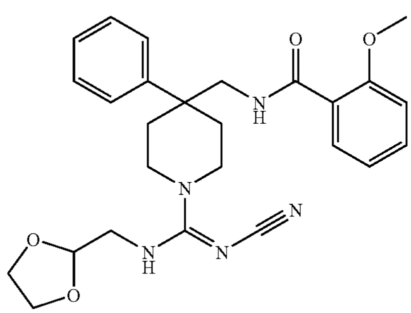 | 480 |
| 864 | 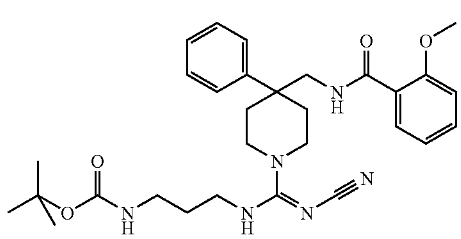 | 551 |

| Example | Structure | M + H |
|---|---|---|
| 865 | 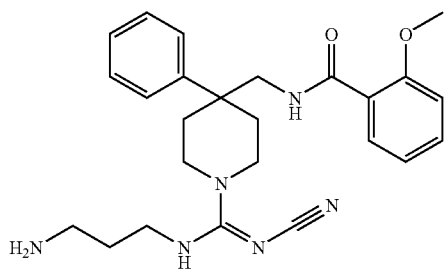 | 451 |
| 866 | 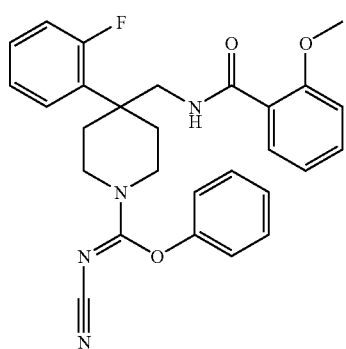 | 489 |
| 867 | 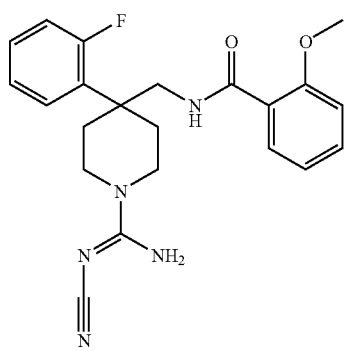 | 411 |
| 868 | 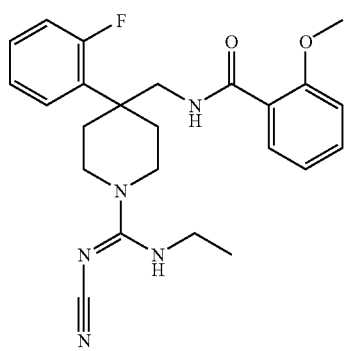 | 440 |

| Example | Structure | M + H |
|---|---|---|
| 869 | 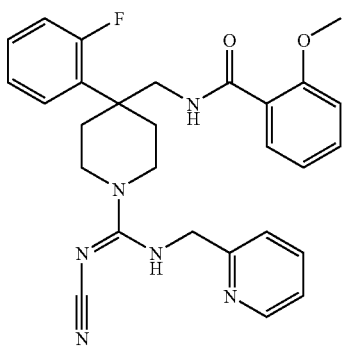 | 503 |
| 870 | 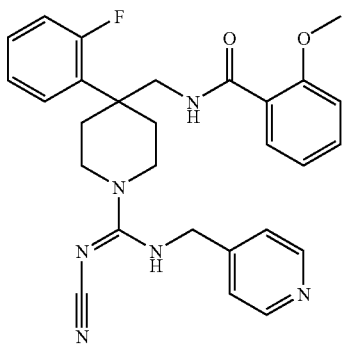 | 503 |
| 871 | 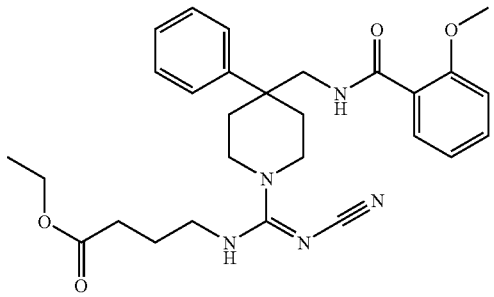 | 508 |
| 872 | 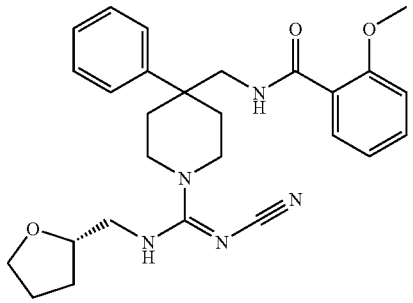 | 478 |

-continued
| Example | Structure | M + H |
|---------|-----------|-------|
| 873 | 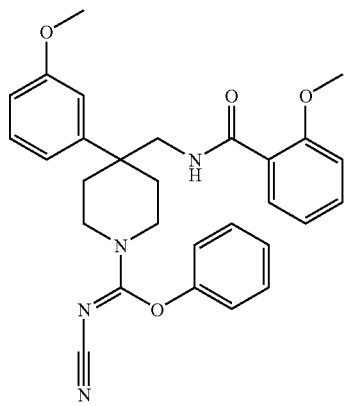 | 501 |
| 874 | 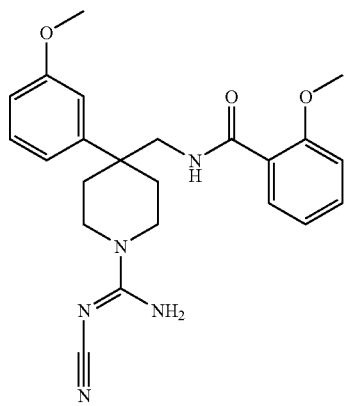 | 423 |
| 875 | 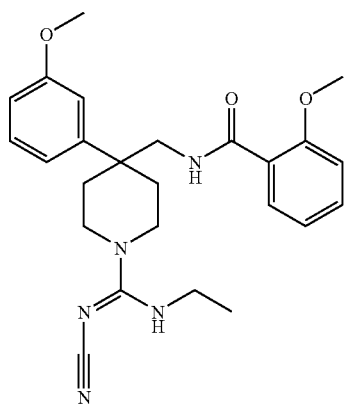 | 452 |

-continued
| Example | Structure | M + H |
|---|---|---|
| 876 | 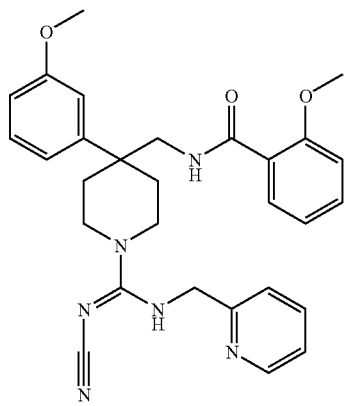 | 515 |
| 877 | 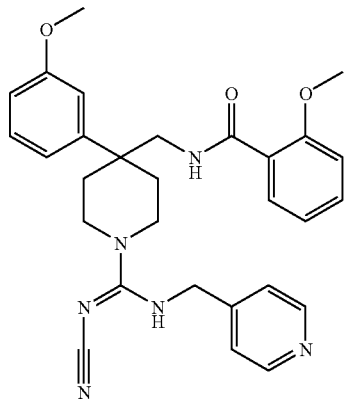 | 515 |
| 878 | 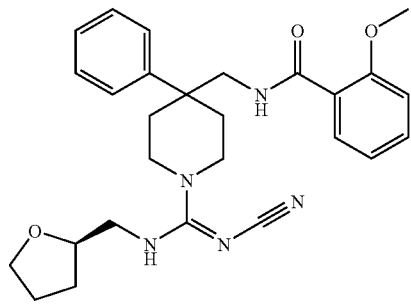 | 478 |
| 879 | 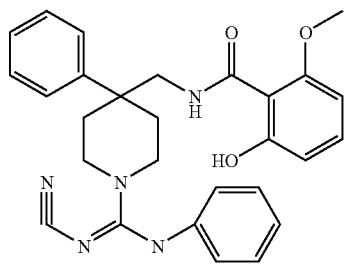 | 487 |

-continued

| Example | Structure | M + H |
|---------|-----------|-------|
| 880 | 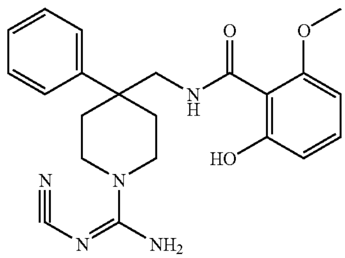 | 409 |
| 881 | 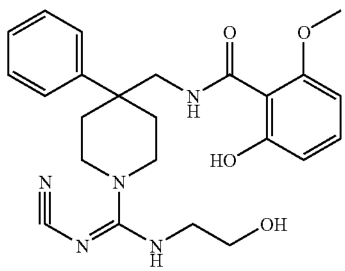 | 454 |
| 882 | 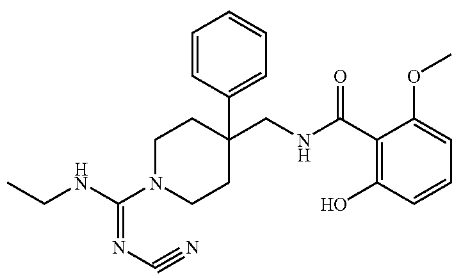 | 438 |
| 883 | 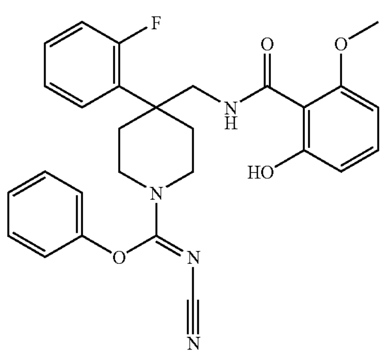 | 505 |
| 884 | 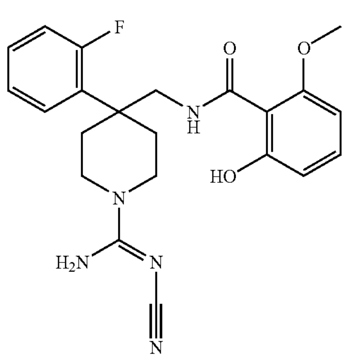 | 427 |

-continued

| Example | Structure | M + H |
|---------|-----------|-------|
| 885 | 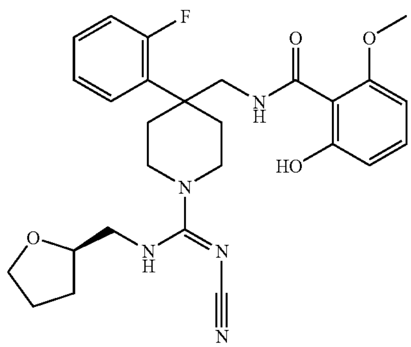 | 512 |
| 886 | 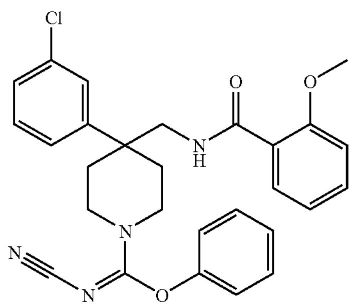 | 505 |
| 887 | 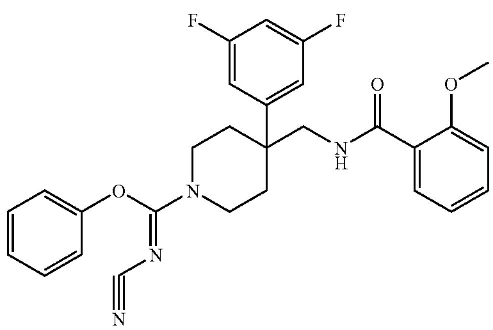 | 507 |
| 888 | 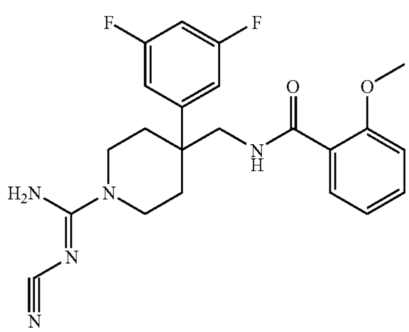 | 429 |
| 889 | 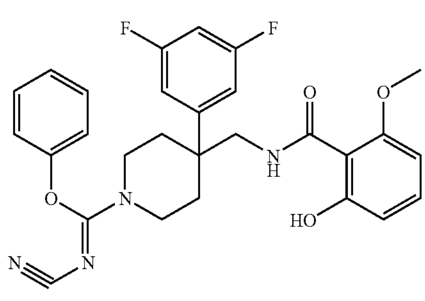 | 523 |

-continued
| Example | Structure | M + H |
|---|---|---|
| 890 | 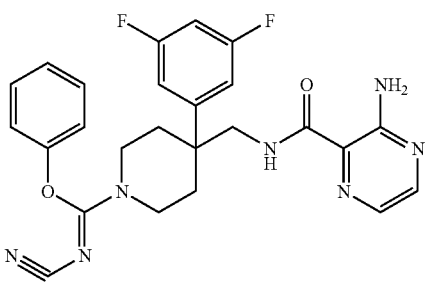 | 494 |
| 891 | 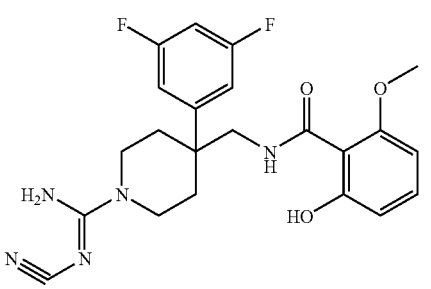 | 445 |
| 892 | 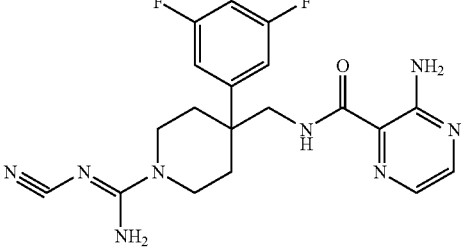 | 416 |
| 893 | 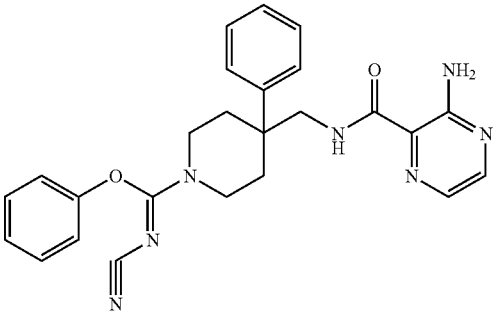 | 458 |
| 894 | 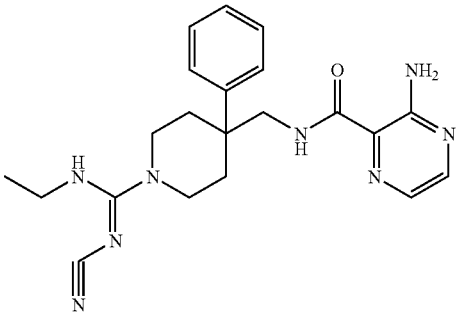 | 408 |

-continued

| Example | Structure | M + H |
|---------|-----------|-------|
| 895 | 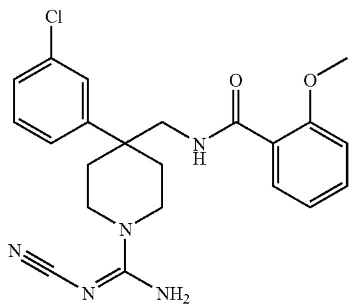 | 428 |
| 896 | 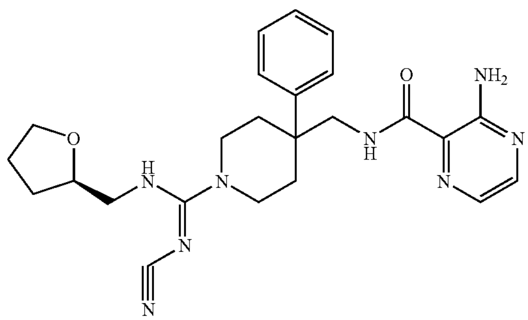 | 465 |
| 897 | 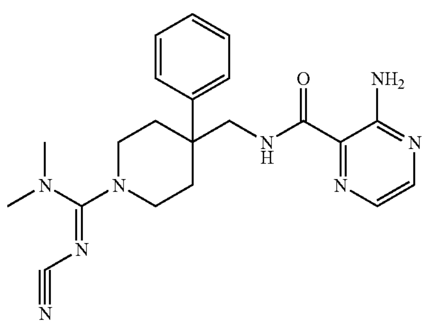 | 408 |
| 898 | 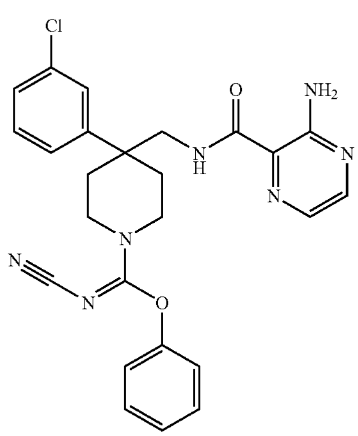 | 492 |

-continued
| Example | Structure | M + H |
|---------|-----------|-------|
| 899 | 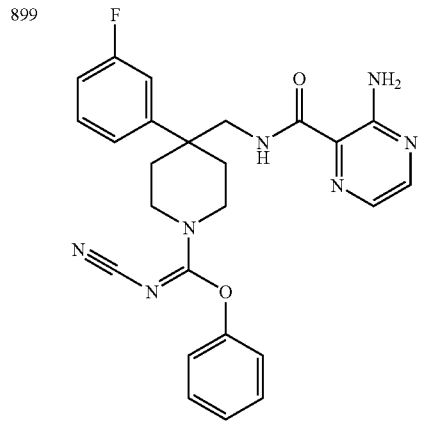 | 476 |
| 900 | 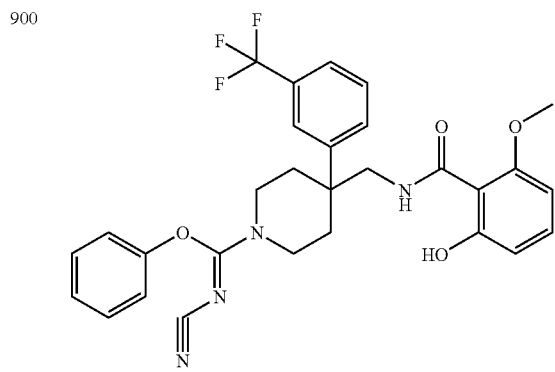 | 555 |
| 901 | 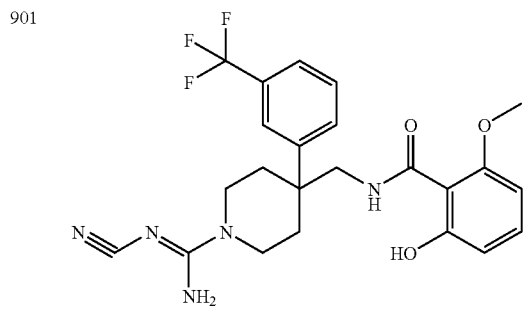 | 477 |
| 902 | 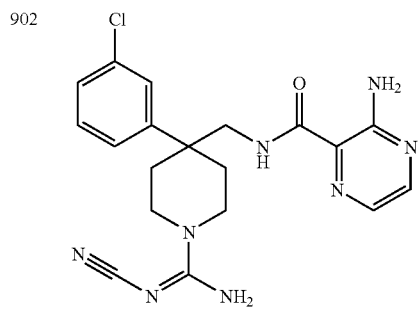 | 415 |

-continued
| Example | Structure | M + H |
|---------|-----------|-------|
| 903 | 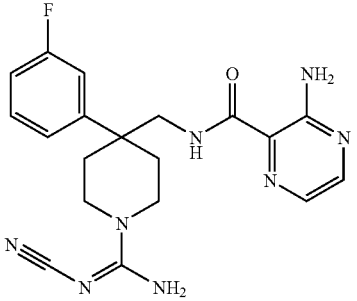 | 398 |
| 904 | 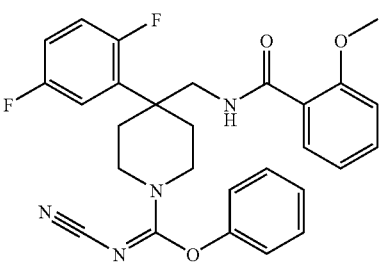 | 507 |
| 905 | 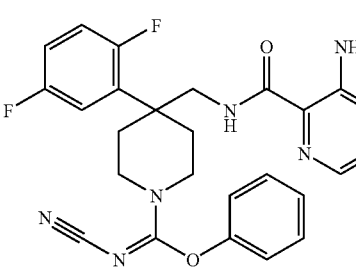 | 494 |
| 906 | 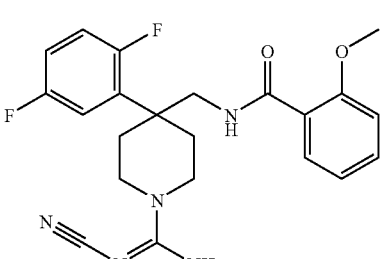 | 428 |
| 907 | 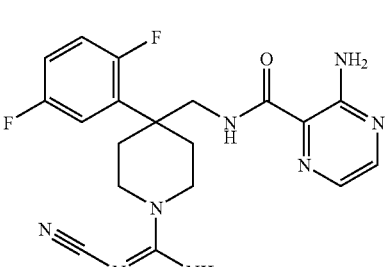 | 415 |

| Example | Structure | M + H |
|---|---|---|
| 908 | 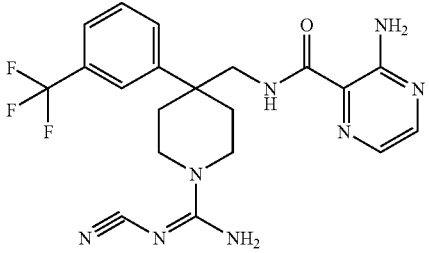 | 447 |
| 909 | 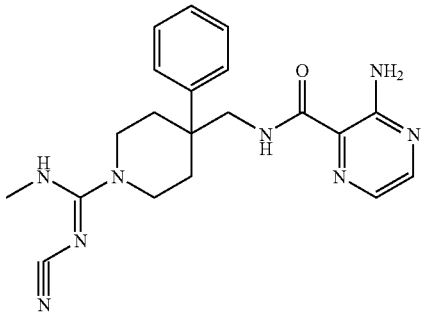 | 393 |
| 910 | 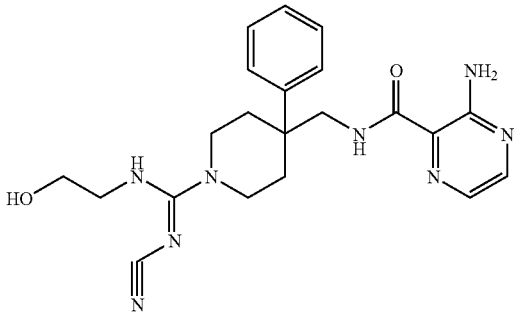 | 423 |
| 911 | 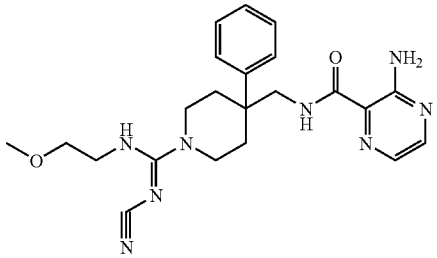 | 438 |
| 912 | 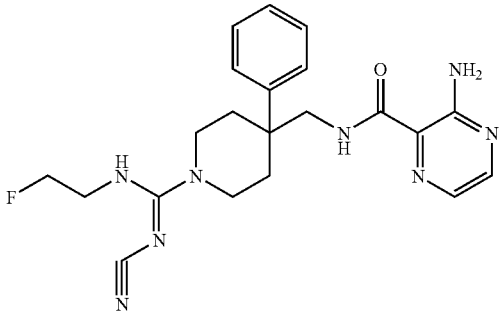 | 425 |

-continued
| Example | Structure | M + H |
|---|---|---|
| 913 | 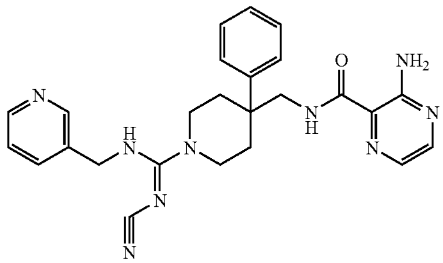 | 471 |
| 914 | 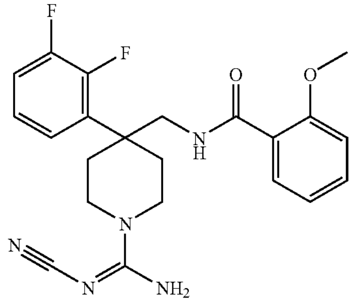 | 428 |
| 915 | 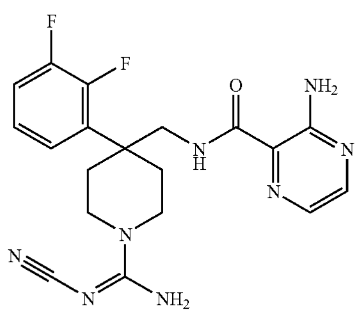 | 415 |
Example 916
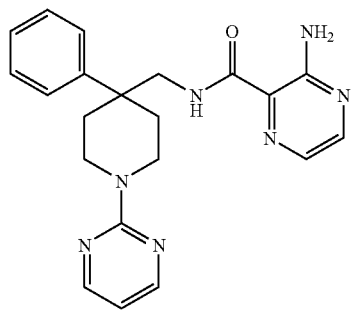
3-Amino-pyrazine-2-carboxylic acid (4-phenyl-1-pyrimidin-2-yl-piperidin-4-ylmethyl)-amide
Synthesis
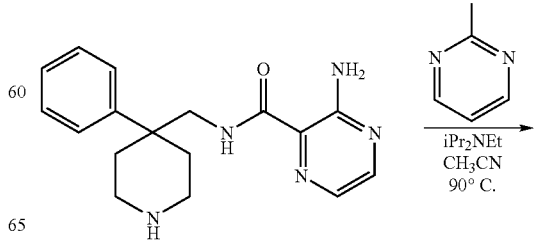

-continued

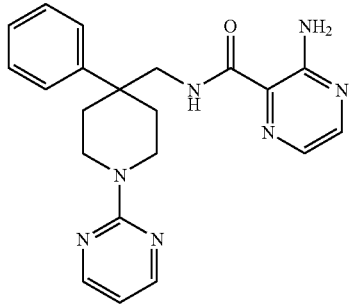

2

Compound 1: Compound 1 was prepared using methodology described in Example 653.

Title Compound: The title compound was prepared using methodology described in Example 521 and purified by preparative reverse phase HPLC to give a white solid. LRMS m/z 390 (M+H)$^+$.

Examples 917 to 924

Examples 917 to 924 were prepared using methodology described in Example 916.

| Example | Structure | Name | M + H |
|---|---|---|---|
| 917 | 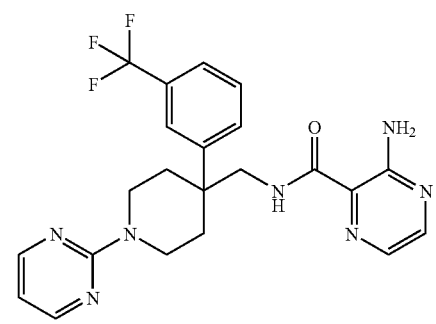 | 3-Amino-pyrazine-2-carboxylic acid [1-pyrimidin-2-yl-4-(3-trifluoromethyl-phenyl)-piperidin-4-ylmethyl]-amide | 459 |
| 918 | 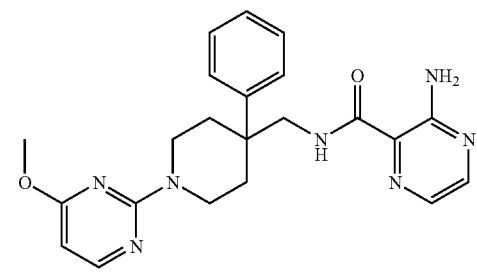 | 3-Amino-pyrazine-2-carboxylic acid [1-(4-methoxy-pyrimidin-2-yl)-4-phenyl-piperidin-4-ylmethyl]-amide | 421 |
| 919 | 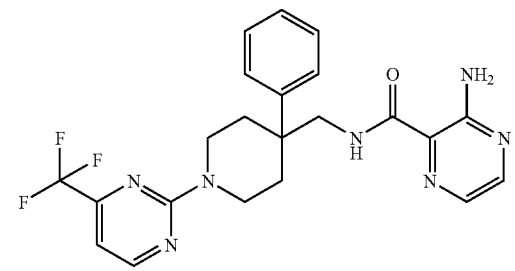 | 3-Amino-pyrazine-2-carboxylic acid [4-phenyl-1-(4-trifluoromethyl-pyrimidin-2-yl)-piperidin-4-ylmethyl]-amide | 459 |

-continued

| Example | Structure | Name | M + H |
|---|---|---|---|
| 920 | 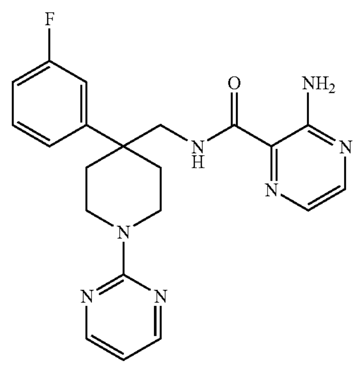 | 3-Amino-pyrazine-2-carboxylic acid [4-(3-fluoro-phenyl)-1-pyrimidin-2-yl-piperidin-4-ylmethyl]-amide | 409 |
| 921 | 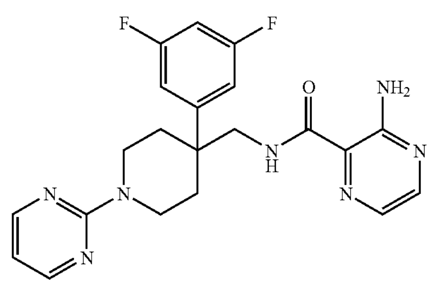 | 3-Amino-pyrazine-2-carboxylic acid [4-(3,5-difluoro-phenyl)-1-pyrimidin-2-ylpiperidin-4-ylmethyl]-amide | 410 |
| 922 | 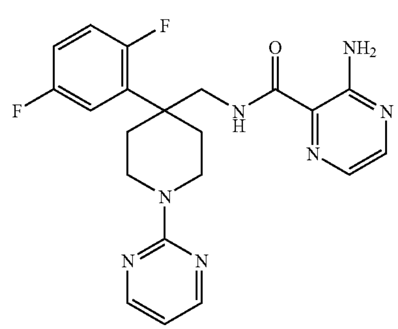 | 3-Amino-pyrazine-2-carboxylic acid [4-(2,5-difluoro-phenyl)-1-pyrimidin-2-yl-piperidin-4-ylmethyl]-amide | 427 |
| 923 | 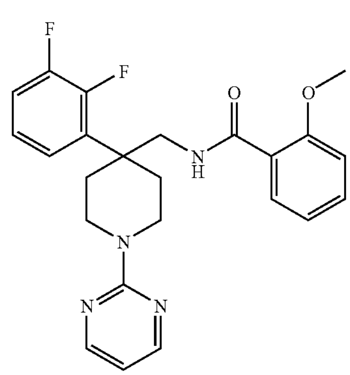 | N-[4-(2,3-Difluoro-phenyl)-1-pyrimidin-2-yl-piperidin-4-ylmethyl]-2-methoxy-benzamide | 439 |

| Example | Structure | Name | M + H |
|---|---|---|---|
| 924 | 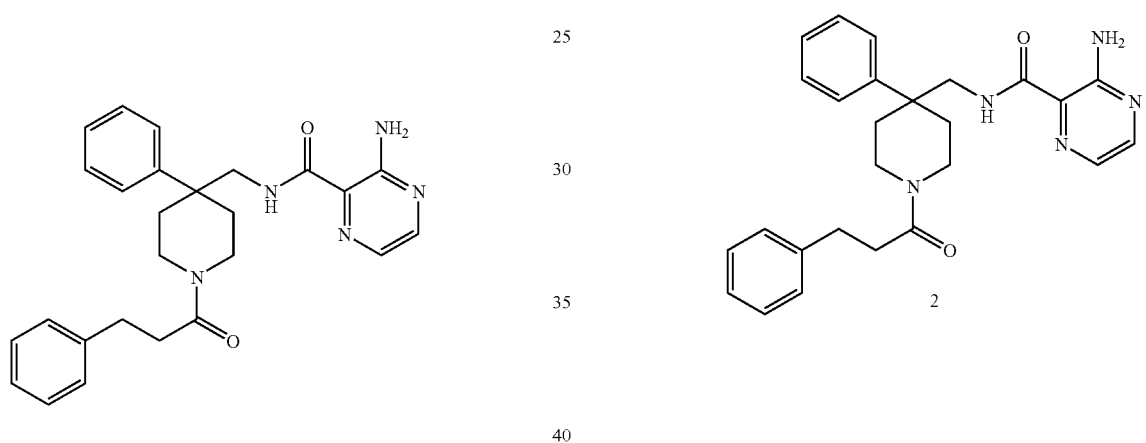 | 3-Amino-pyrazine-2-carboxylic acid [4-(2,3-difluoro-phenyl)-1-pyrimidin-2-yl-piperidin-4-ylmethyl]-amide | 426 |

Example 925

3-Amino-pyrazine-2-carboxylic acid (4-phenyl-1-pyrimidin-2-yl-piperidin-4-ylmethyl)-amide Synthesis

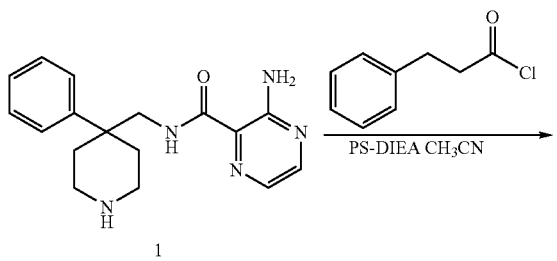

Compound 1: Compound 1 was prepared as described in Example 653.

Title Compound: A solution of compound 1 (0.072 g; 0.23 mmol) in anhydrous acetonitrile (2 mL) was treated with polystyrene-diisopropylethylamine (300 mg) and hydrocinnamoyl chloride (0.045 g; 0.27 mmol) at room temperature. The reaction was shaken for 24 h, filtered and concentrated by rotary evaporation. The crude residue was purified by preparative reverse phase HPLC to give 0.054 g of the title compound as white solid. LRMS m/z=444 (M+H)$^+$

Examples 926 to 929

Examples 926 to 929 were prepared using methodology described in Example 925.

| Example | Structure | Name | M + H |
|---|---|---|---|
| 926 | 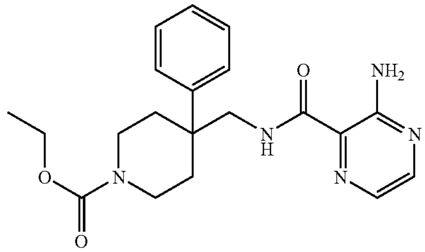 | 4-{[(3-Amino-pyrazine-2-carbonyl)-amino]-methyl}-4-phenyl-piperidine-1-carboxylic acid ethyl ester | 385 |
| 927 | 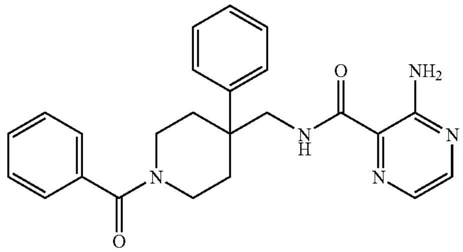 | 3-Amino-pyrazine-2-carboxylic acid (1-benzoyl-4-phenyl-piperidin-4-ylmethyl)-amide | 417 |
| 928 | 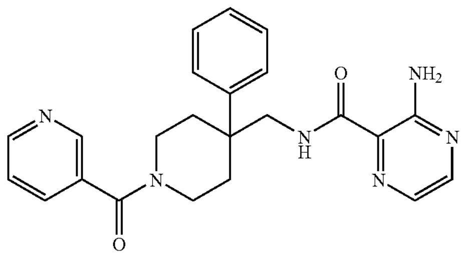 | 3-Amino-pyrazine-2-carboxylic acid [4-phenyl-1-(pyridine-3-carbonyl)-piperidin-4-ylmethyl]-amide | 418 |
| 929 | 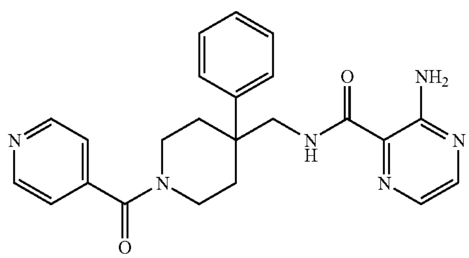 | 3-Amino-pyrazine-2-carboxylic acid [4-phenyl-1-(pyridine-4-carbonyl)-piperidin-4-ylmethyl]-amide | 418 |

Example 930

3-Amino-pyrazine-2-carboxylic acid [1-(1-amino-2-nitro-vinyl)-4-phenyl-piperidin-4-ylmethyl]-amide

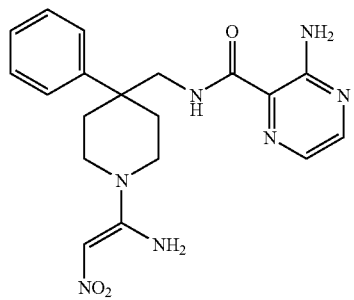

Synthesis

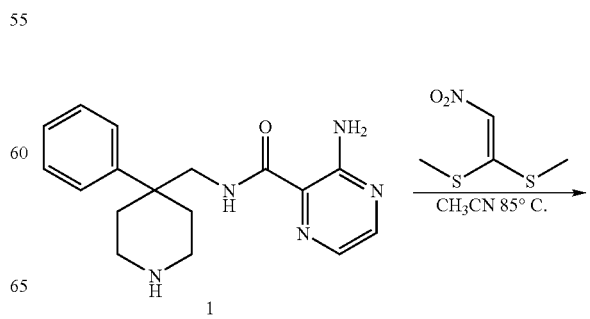

Compound 1: Compound 1 was prepared as described in Example 653.

Compound 2: A solution of compound 1 (0.065 g; 0.21 mmol) in anhydrous acetonitrile (3 mL) was treated with 1,1-bis(methylthio)-2-nitroethylene (0.058 g; 0.35 mmol) and heated at 85° C. for 3 h. The solvent was removed by rotary evaporation and the crude residue was purified by recyrstallization from ethyl acetate to give 0.068 g of compound 2 as a bright yellow solid. LRMS m/z=430 (M+H)$^+$ Title Compound: Compound 2 (0.042 g; 0.098 mmol) was treated with 7 N ammonia in methanol (1 mL) and heated at 85° C. for 15 min in a sealed tube. The solvent was removed by rotary evaporation and the crude residue was purified directly by column chromatography on silica gel using 9:1 ethyl acetate:hexane as the eluent to give 0.018 g of the title compound as a white solid. LRMS m/z=398 (m+H)$^+$ Example 931

3-Amino-pyrazine-2-carboxylic acid [1-(3,5-dimethyl-isoxazole-4-sulfonyl)-4-phenyl-piperidin-4-ylmethyl]-amide Synthesis Compound 1: Compound 1 was prepared using methodology described in Example 653.

Title Compound: A solution of compound 1 (0.043 mg; 0.14 mmol) in anhydrous acetonitrile (1 mL) was treated with triethylamine (0.1 mL; 0.7 mmol) and 3,5-dimethyl-isoxazole-4-sulfonyl chloride (0.040 mg; 0.2 mmol) and allowed to stir at room temperature for 0.5 h. The solvent was removed by rotary evaporation and the crude residue was purified directly by column chromatography on silica gel using 1:1 ethyl acetate:hexane as the eluent to give 0.012 g of the title compound as a white solid. LRMS m/z=472 (m+H)$^+$ Examples 932 to 936

Examples 932 to 936 were prepared using methodology described in Example 931.

| Example | Structure | Name | M + H |
|---|---|---|---|
| 932 | 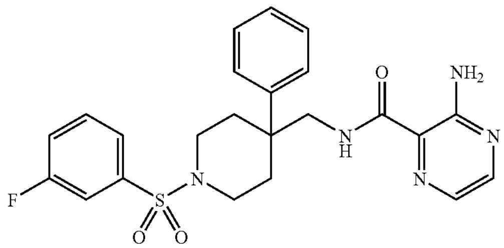 | 3-Amino-pyrazine-2-carboxylic acid [1-(3-fluoro-benzenesulfonyl)-4-phenyl-piperidin-4-ylmethyl]-amide | 471 |
| 933 | 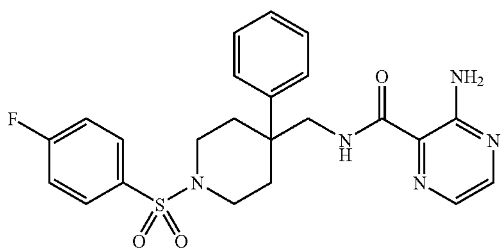 | 3-Amino-pyrazine-2-carboxylic acid [1-(4-fluoro-benzenesulfonyl)-4-phenyl-piperidin-4-ylmethyl]-amide | 471 |
| 934 | 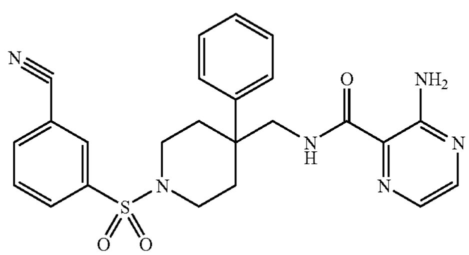 | 3-Amino-pyrazine-2-carboxylic acid [1-(3-cyano-benzenesulfonyl)-4-phenyl-piperidin-4-ylmethyl]-amide | 478 |
| 935 | 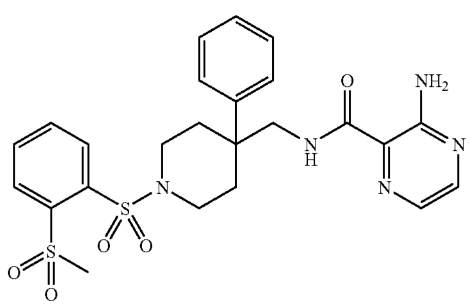 | 3-Amino-pyrazine-2-carboxylic acid [1-(2-methanesulfonyl-benzenesulfonyl)-4-phenyl-piperidin-4-ylmethyl]-amide | 531 |
| 936 | 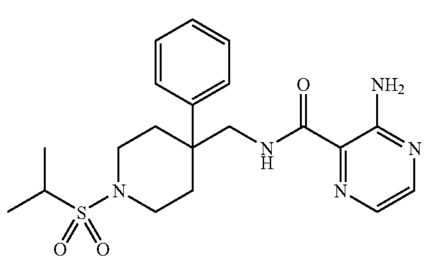 | 3-Amino-pyrazine-2-carboxylic acid [4-phenyl-1-(propane-2-sulfonyl)-piperidin-4-ylmethyl]-amide | 419 |

Example 937

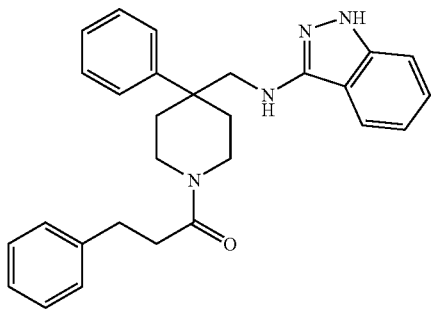

1-{4-[(1H-Indazol-3-ylamino)-methyl]-4-phenyl-piperidin-1-yl}-3-phenyl-propan-1-one Synthesis

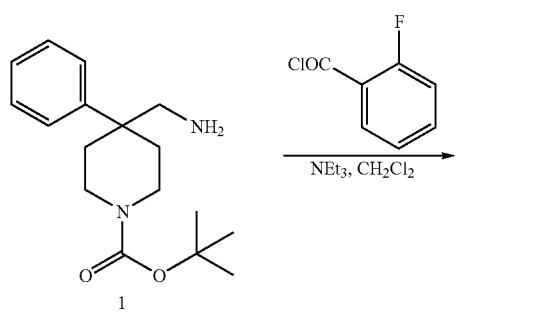

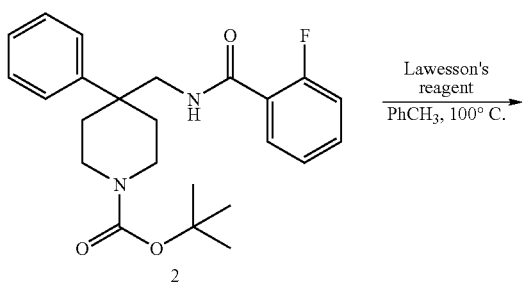

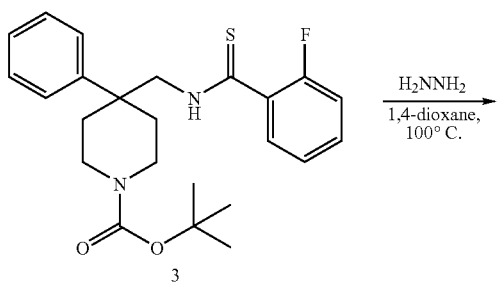

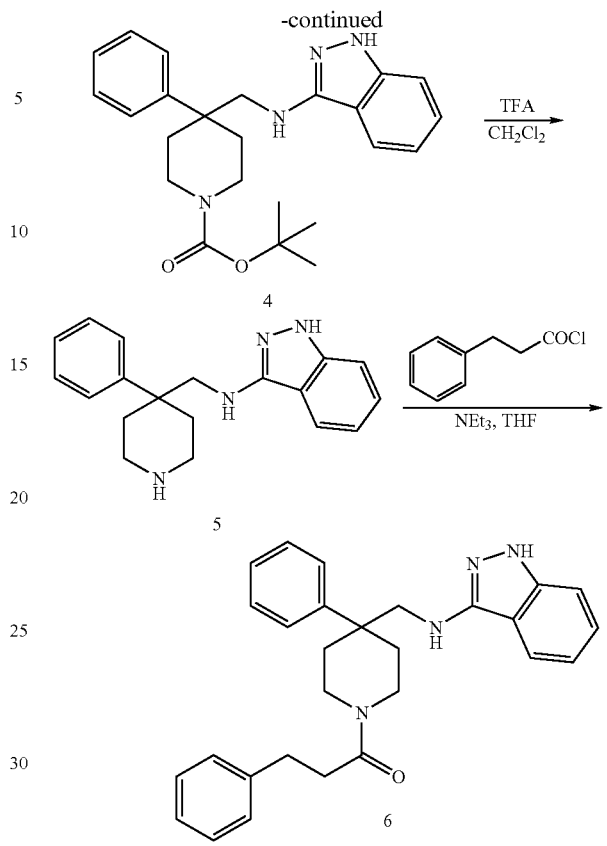

Compound 1: Compound 1 was prepared as described in Example 653.

Compound 2: To compound 1 (0.89 g, 3.06 mmol) and triethylamine (0.95 g, 9.36 mmol) in dichloromethane (5 mL) was added 2-fluorobenzoyl chloride (0.53 g, 3.37 mmol). After 1 h, the reaction mixture was diluted with diethyl ether (20 mL) then washed with 1 N sodium hydroxide, water and saturated aqueous sodium chloride. The organic layer was separated, dried (sodium sulfate), filtered and concentrated. Purification by silica gel chromatography using 2:1 hexanes: ethyl acetate as the eluent gave compound 2 (344 mg, 27%) as a colorless oil. $^1$H NMR (CDCl$_3$, 300 MHz) δ1.43 (9H, s), 1.82-1.91 (2H, m), 2.15-2.20 (2H, m), 3.18-3.26 (2H, m), 3.68-3.74 (4H, m), 6.32-6.36 (1H, m), 7.03 (1H, dd, J=6.1, 12.0 Hz), 7.20-7.46 (7H, m), 8.03 (1H, td, J=1.8, 7.9 Hz). LRMS m/z 357 (M+H)$^+$.

Compound 3: Compound 2 (340 mg, 0.82 mmol) and Lawesson's reagent (433 mg, 1.07 mmol) in toluene (3 mL) was heated at 100° C. for 3 h then cooled to room temperature. Water (1 mL), saturated aqueous sodium bicarbonate (3 mL) and ethyl acetate (3 mL) were added. After stirring for 20 min, the reaction mixture was diluted with ethyl acetate then washed with water and saturated aqueous sodium chloride. The organic layer was separated, dried (sodium sulfate), filtered and concentrated. Purification by silica gel chromatography using 3:1 hexanes:ethyl acetate as the eluent gave compound 3 (255 mg, 72%) as a yellow solid. $^1$H NMR (CDCl$_3$, 300 MHz) δ1.44 (9H, s), 1.94-1.98 (2H, m), 2.17-2.25 (2H, m), 3.27-3.34 (2H, m), 3.67-3.75 (2H, m), 4.15 (2H, d, J=5.0 Hz), 6.95-7.01 (1H, m), 7.15 (1H, td, J=1.0, 7.4 Hz), 7.27-7.63 (7H, m), 8.07 (1H, td, J=1.9, 8.0 Hz). LRMS m/z 429 (M+H)$^+$.

Compound 4: Compound 3 (250 mg, 0.58 mmol) and hydrazine (187 mg, 5.80 mmol) in 1,4-dioxane (3 mL) was heated at 100° C. for 3 days then cooled to room temperature. The reaction mixture was diluted with ethyl acetate (10 mL) then washed with saturated aqueous sodium bicarbonate, water and saturated aqueous sodium chloride. The organic layer was separated, dried (sodium sulfate), filtered and concentrated. Purification by silica gel chromatography using 3:1 hexanes:ethyl acetate as the eluent gave compound 4 (149 mg, 63%) as a white solid. $^1$H NMR (CDCl$_3$, 300 MHz) δ1.43 (9H, s), 1.90-1.97 (2H, m), 2.20-2.25 (2H, m), 3.16-3.25 (2H, m), 3.64 (2H, s), 3.64-3.69 (3H, m), 6.98 (1H, td, J=1.5, 7.9 Hz), 7.29-7.35 (5H, m), 7.42 (4H, d, J=4.4 Hz). LRMS m/z 407 (M+H)$^+$.

Compound 5: Compound 4 (143 mg, 0.35 mmol) in dichloromethane (0.75 mL) and trifluoroacetic acid (0.25 mL) was stirred for 1.5 h then concentrated under reduced pressure. 1N Sodium hydroxide (5 mL) was added then extracted with dichloromethane (3×10 mL). The combined organic layers were dried (sodium sulfate), filtered and concentrated to give the compound 5 (107 mg, 100%) as a white solid. LRMS m/z 307 (M+H)$^+$.

Title Compound: The title compound was prepared using methodology described in Example 390. LRMS m/z 440 (M+H)$^+$.

Example 938

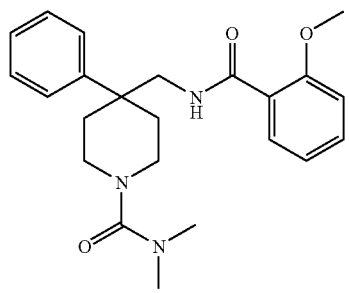

4-[(2-Methoxy-benzoylamino)-methyl]-4-phenyl-piperidine-1-carboxylic acid dimethylamide Synthesis

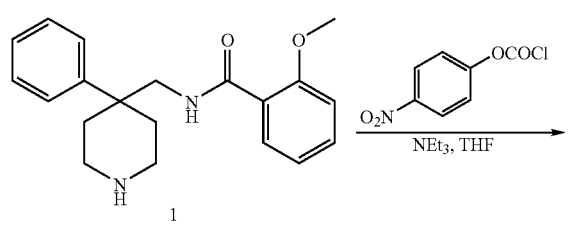

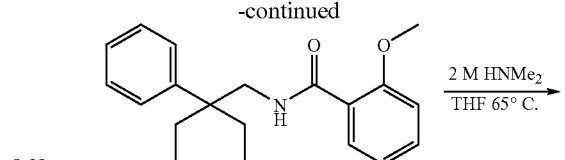

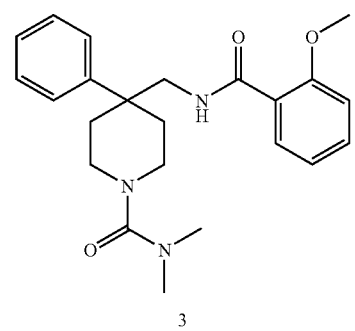

Compound 1: Compound 1 was prepared as described in Example 15.

Compound 2: A solution of compound 1 (0.63 g; 1.9 mmol) in tetrahydrofuran (25 mL) was treated with triethylamine (0.33 mL; 2.4 mmol) and 4-nitro phenyl chloroformate (0.47 g; 2.3 mmol) at room temperature. After 24 h the solvent was removed by rotary evaporation and the crude residue was purified directly by column chromatography on silica gel using 1:1 ethyl acetate:hexane as the eluent to give 0.53 g of compound 2 as a white foam. LRMS m/z 491 (M+H)$^+$.

Title Compound: Compound 2 (0.050 g; 0.10 mmol) was treated with 2 M dimethylamine in tetrahydrofuran (2 mL) and heated to 65° C. in a sealed tube for 12 h. The solvent was removed by rotary evaporation and the crude residue was purified by preparative reverse phase HPLC to give 0.018 g of the title compound as a white solid. LRMS m/z 396 (M+H)$^+$.

Examples 939 to 942

Examples 939 to 942 were prepared using methodology described in Example 938.

| Example | Structure | Name | + H |
|---|---|---|---|
| 939 | 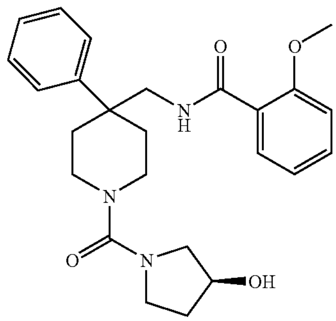 | N-[1-(3-Hydroxy-pyrrolidine-1-carbonyl)-4-phenyl-piperidin-4-ylmethyl]-2-methoxy-benzamide | 440 |
| 940 | 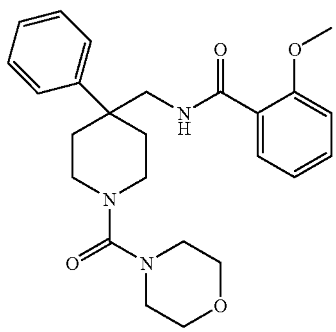 | 2-Methoxy-N-[1-(morpholine-4-carbonyl)-4-phenyl-piperidin-4-ylmethyl]-benzamide | 440 |
| 941 | 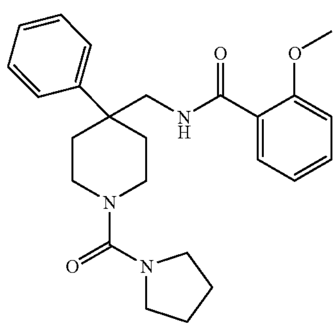 | 2-Methoxy-N-[4-phenyl-1-(pyrrolidine-1-carbonyl)-piperidin-4-ylmethyl]-benzamide | 424 |
| 942 | 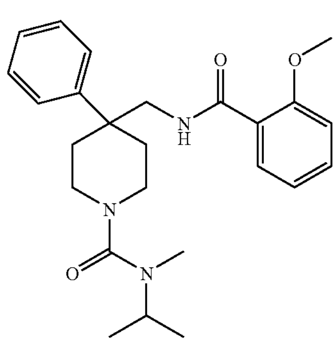 | 4-[(2-Methoxy-benzoylamino)-methyl]-4-phenyl-piperidine-1-carboxylic acid isopropyl-methyl-amide | 426 |

Example 943

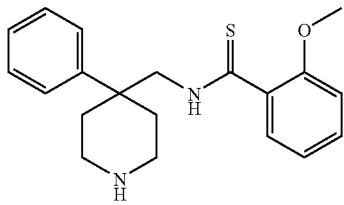

2-Methoxy-N-(4-phenyl-piperidin-4-ylmethyl)-thiobenzamide

Synthesis

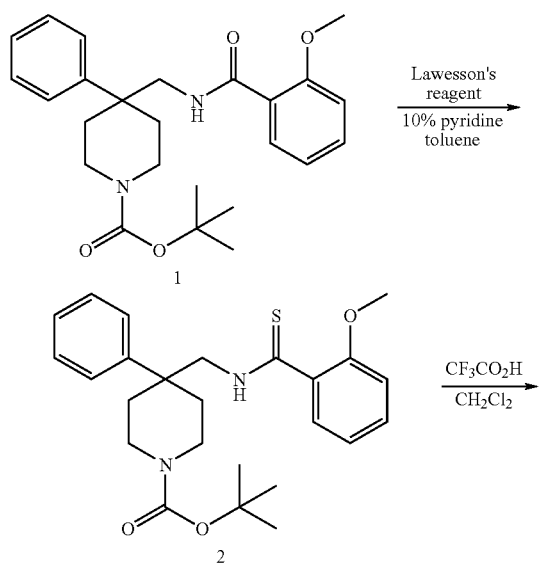

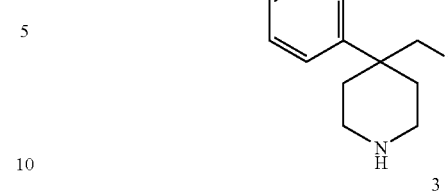

Compound 1: Compound 1 was prepared using methodology described in Example 653.

Compound 2: A solution of compound 1 (0.32 g; 0.76 mmol) and Lawesson's reagent (0.38 g; 0.95 mmol) in 10% pyridine in toluene (5 mL) was heated at reflux for 3 h. The reaction mixture was cooled to room temperature and diluted with ethyl acetate (5 mL), water (2 mL) and saturated aqueous sodium bicarbonate (5 mL) and stirred for 0.5 h. Additional ethyl acetate was added and the organic layer was separated, washed with water and saturated aqueous sodium chloride, dried (sodium sulfate), filtered and concentrated. The crude residue was purified by column chromatography on silica gel using 3:1 hexane:ethyl acetate as the eluent to give 0.24 g of compound 2 as a yellow solid. LRMS m/z 442 (M+H)$^+$.

Title Compound: Compound 2 (0.044 g; 0.10 mmol) was treated with 0.75 mL dichloromethane and 0.25 mL trifluoroacetic acid and the reaction mixture was stirred at room temperature for 0.5 h. The solvents were removed by rotary evaporation to give 0.040 g of the title compound as the trifluoroacetic acid salt as a white solid that was used without additional purification. LRMS m/z 341 (M+H)$^+$.

Examples 944 to 947

Examples 944 to 947 were prepared using methodologies described in Example 943 and Example 15, Example 16 or Example 25.

| Example | Structure | Name | M + H |
|---|---|---|---|
| 944 | 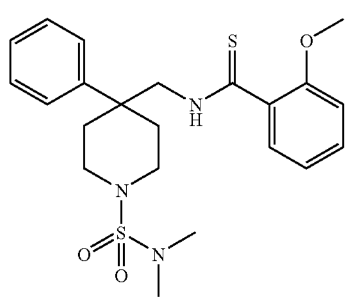 | N-(1-Dimethylsulfamoyl-4-phenyl-piperidin-4-ylmethyl)-2-methoxy-thiobenzamide | 450 |

-continued
| Example | Structure | Name | M + H |
|---|---|---|---|
| 945 | 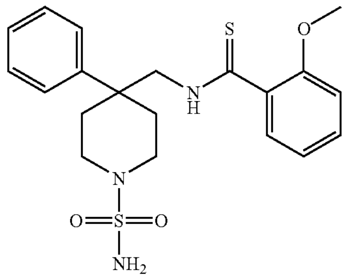 | 2-Methoxy-N-(4-phenyl-1-sulfamoyl-piperidin-4-ylmethyl)-thiobenzamide | 422 |
| 946 | 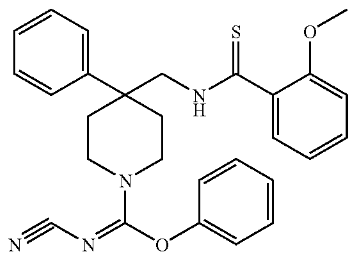 | | 487 |
| 947 | 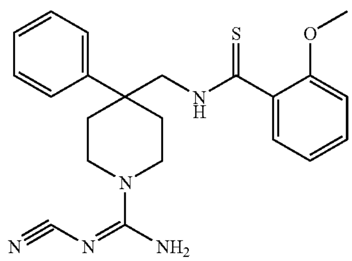 | | 410 |
Example 948
N-[1-(N-Ethylcarbamimidoyl)-4-phenyl-piperidin-4-ylmethyl]-2-methoxy-benzamide
Synthesis
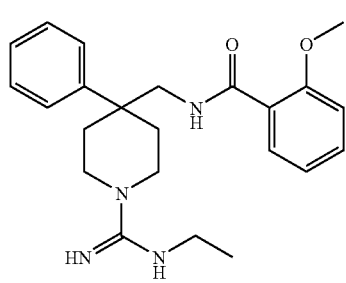
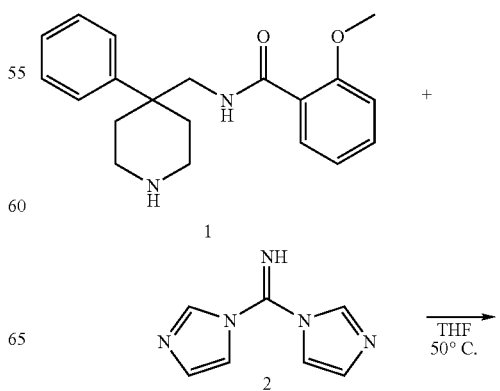

569

-continued

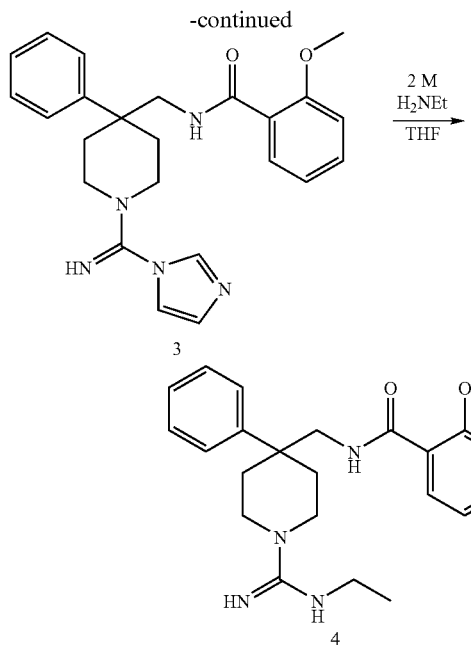

Compound 1: Compound 1 was prepared using methodology described in Example 15.

Compound 2: Compound 2 was prepared as described in *J. Org. Chem.* 2002, 67, 7553-7556.

Compound 3: A solution of compound 1 (0.63 g; 1.9 mmol) and compound 2 (0.45 g; 2.8 mmol) in tetrahydrofuran (15 mL) was heated at 50° C. for 24 h. The solvent was removed by rotary evaporation and the residue was treated with ethyl acetate (50 mL) and water (50 mL). The organic layer was separated, washed with water and saturated aqueous sodium chloride. The organic layer was separated, dried (sodium sulfate), filtered and concentrated to give 0.7 g of compound 3 as a light yellow foam that was used without additional purification. LRMS m/z 419 (M+H)$^+$.

Title Compound: Compound 3 (0.059 g; 0.14 mmol) was treated with 2 M ethylamine in tetrahydrofuran (2.5 mL) and heated to 60° C. in a sealed tube for 48 h. The solvent was removed by rotary evaporation and the crude residue was purified by preparative reverse phase HPLC to give 0.022 mg of the title compound as the trifluoroacetic acid salt as a white solid. LRMS m/z 396 (M+H)$^+$.

Example 949

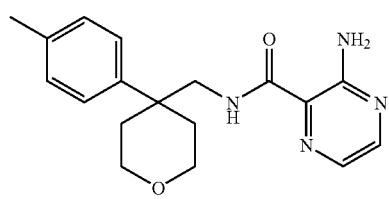

570

3-Amino-pyrazine-2-carboxylic acid (4-p-tolyl-tetrahydro-pyran-4-ylmethyl)-amide Synthesis

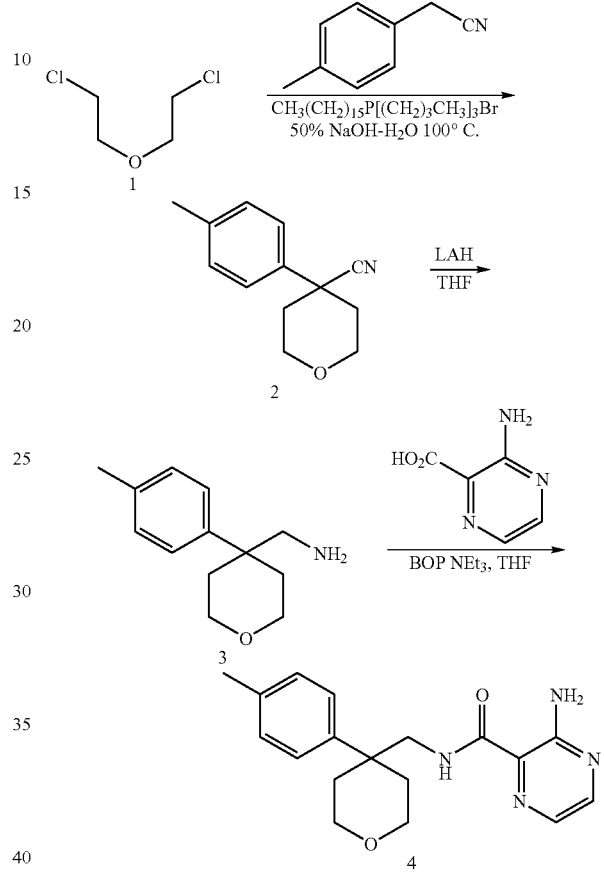

Compound 1: Compound 1 is commercially available.

Compound 2: A solution of compound 1 (0.71 g; 5 mmol), 4-methyl benzyl cyanide (0.66 g; 5 mmol) and hexadecyl tributyl phosphonium bromide (0.13 g; 0.25 mmol) in 50% NaOH in water (8 mL) was heated at 100° C. for 2 h. The reaction was cooled to room temperature, diluted with water (20 mL) and extracted with diethyl ether (3×10 mL). The combined organic layers were washed with water and saturated aqueous sodium chloride, dried (sodium sulfate), filtered and concentrated. The crude residue was purified by column chromatography on silica gel using 8.5:1.5 hexane: ethyl acetate as the eluent to give 0.776 g of compound 2 as a yellow oil. LRMS m/z 202 (M+H)$^+$.

Compound 3: Compound 3 was prepared using methodology described in Example 15. LRMS m/z 206 (M+H)$^+$.

Title Compound: The title compound was prepared using methodology described in Example 653. LRMS n/z 327 (M+H)$^+$.

Examples 950 to 955

Examples 950 to 955 were prepared using methodology described in Example 949.

| Example | Structure | Name | M + H |
|---|---|---|---|
| 950 | 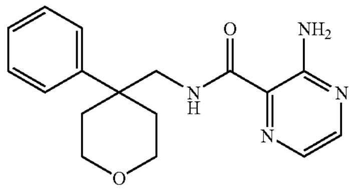 | 3-Amino-pyrazine-2-carboxylic acid (4-phenyl-tetrahydro-pyran-4-ylmethyl)-amide | 313 |
| 951 | 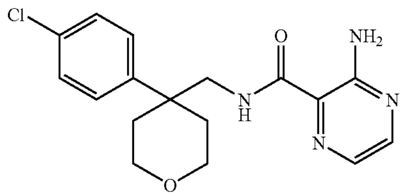 | 3-Amino-pyrazine-2-carboxylic acid [4-(4-chloro-phenyl)-tetrahydro-pyran-4-ylmethyl]-amide | 348 |
| 952 | 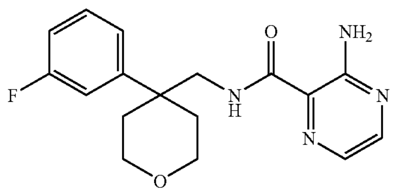 | 3-Amino-pyrazine-2-carboxylic acid [4-(3-fluoro-phenyl)-tetrahydro-pyran-4-ylmethyl]-amide | 331 |
| 953 | 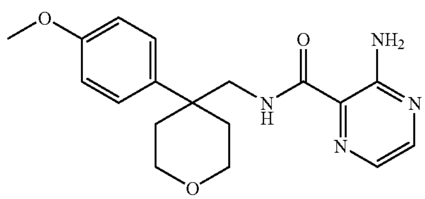 | 3-Amino-pyrazine-2-carboxylic acid [4-(4-methoxy-phenyl)-tetrahydro-pyran-4-ylmethyl]-amide | 343 |
| 954 | 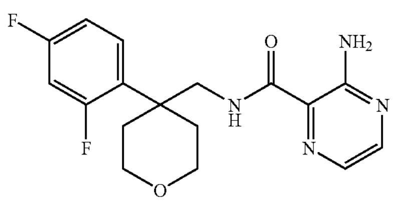 | 3-Amino-pyrazine-2-carboxylic acid [4-(2,4-difluoro-phenyl)-tetrahydro-pyran-4-ylmethyl]-amide | 349 |
| 955 | 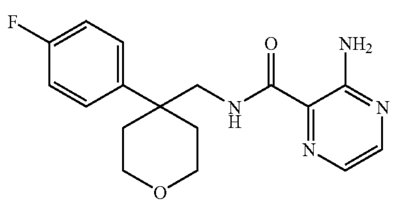 | 3-Amino-pyrazine-2-carboxylic acid [4-(4-fluoro-phenyl)-tetrahydro-pyran-4-ylmethyl]-amide | 331 |

Example 956

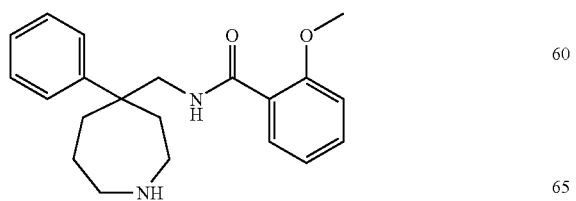

2-Methoxy-N-(4-phenyl-azepan-4-ylmethyl)-benzamide

Synthesis

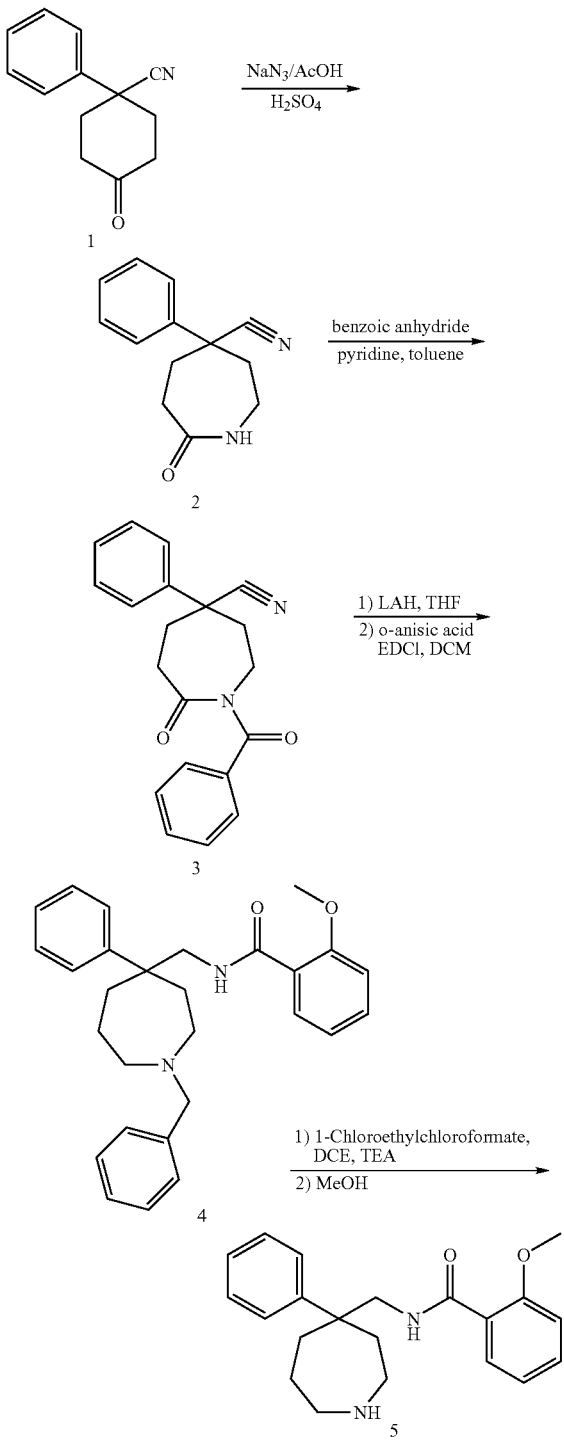

Compound 1: Compound 1 is commercially available

Compound 2: To a solution of ketone 1 (500 mg, 2.51 mmol) in glacial acetic acid (30 mL) was added concentrated sulfuric acid (0.3 mL) at room temperature. The solution was heated to 65° C. and sodium azide (0.50 g, 7.7 mmol) was added in 3 equal portions over 5 min at 65° C. After a further 5 min at 65° C., the reaction mixture was allowed to cool and stirred at ambient temperature for 16 h. The resulting slurry was poured cautiously into a saturated NaHCO$_3$ solution (ca. 100 mL), transferred to a separation funnel and the aqueous portion extracted with dichloromethane (3×50 mL). The combined organic portions were washed with NaHCO$_3$ (20 mL), dried over Na$_2$SO$_4$, decanted and concentrated yielding a pale yellow oil. Methanol (ca. 5 mL) was added to the oil and the white precipitate was collected and dried under high vacuum (153 mg). The methanol solution was purified by preparative HPLC. YMC ODS S5 30×50 mm, 10 min gradient, 0-100% MeOH (90% in water, 0.1% TFA) UV detection 220 nM, 50 mL/min flow rate. The product retention time was 5.23 min. The product was neutralized with saturated NaHCO$_3$ and extracted into dichloromethane. A further 119 mg of product was isolated and combined with the product isolated by precipitation, (combined mass 272 mg, yield 51%). HPLC Rt 2.17 min, Purity 98%, Phenomenex Luna S5 column 4.6×50 mm, 4 min gradient 0 to 100% MeOH (90% in water, 0.1% PPA) UV detection at 220 nm. LCMS Rt 1.12 min, [M+1] 215.42 Phenomenex S5 column 4.6×30 mm, 2 min gradient 0 to 100% MeOH (90% in water, 0.1% TFA) UV detection at 220 nm. NMR H (DMSO) 1.98 ppm, 1H, multiplet; 2.10 ppm, 1H, multiplet; 2.30 ppm, 1H, multiplet; 2.78 ppm, 1H, multiplet; 3.21 ppm, 1H, multiplet; 3.43 ppm, 1H, multiplet; 7.31 ppm, 1H, t, J=7.9 Hz; 7.42 ppm, 2H, dd, J=7.9 Hz and J=7.9 Hz; 7.55 ppm, 2H, d, J=8.4 Hz; 7.82 ppm, 1H, s.

Compound 3: Benzoic anhydride (4.22 g, 18.7 mmol) and pyridine (3.1 mL, 37 mmol) were added to a suspension of compound 2 (2.00 g, 9.33 mmol) in toluene (20 mL). After heating at 100° C. for 18 hours, the reaction mixture was concentrated and purified by ISCO hexane/EtOAc, 0% EtOAc—10% EtOAc over 10 minutes, 10% EtOAc—30% EtOAc over 10 minutes, 30% EtOAc for 20 minutes, 30% EtOAc—100% EtOAc over 2 minutes, 100% EtOAc for 5 minutes. Compound 3 eluted at a retention time of 12.8 min as a white solid (2.62 g, 88% yield). HPLC Rt 3.08 min, Purity 86%, Phenomenex Luna S5 column 4.6×50 mm, 4 min gradient 0 to 100% MeOH (90% in water, 0.1% PPA) UV detection at 220 nm. LCMS Rt 1.57 min, [M+1] 319.18 Phenomenex S5 column 4.6×30 mm, 2 min gradient 0 to 100% MeOH (90% in water, 0.1% TFA) UV detection at 220 nm. NMR H (CDCl$_3$) 2.23 ppm, 2H, multiplet; 2.37 ppm, 1H, multiplet; 2.47 ppm, 1H, multiplet; 2.76 ppm, 1H, multiplet; 3.34 ppm, 1H, multiplet; 3.91 ppm, 1H, dd, J=12.0 and 16.0 Hz; 4.66 ppm, 1H, dd, J=12.0 and 16.0 Hz; 7.44 ppm, 8H, multiplet; 7.57 ppm, 2H, multiplet.

Compound 4: To a solution of compound 3 (500 mg, 1.57 mmol) in CH$_2$Cl$_2$ (8 mL) and THF (4 mL) was added a 1.0 M solution of lithium aluminum hydride in THF (9.4 mL, 9.4 mmol) at 0° C. The reaction mixture was allowed to warm up to room temperature and stirred for 18 hours. The reaction was quenched with H$_2$O (1.7 mL), 1 N NaOH (1.0 mL) and H$_2$O (1.7 mL). After stirring at room temperature for 30 minutes, the reaction was filtered and the filtrate was concentrated. The resulting residue was dissolved in CH$_2$Cl$_2$ (75 mL). The organic layer was washed with brine (25 mL), dried over MgSO$_4$, filtered, concentrated, and the resulting residue was dissolved in CH$_2$Cl$_2$ (2.0 mL). The solution was added to a solution of O-anisic acid (215 mg, 1.42 mmol) and EDCI (296 mg, 1.54 mmol) in CH$_2$Cl$_2$ (2 mL). After 2 hours, the reaction mixture was concentrated and purified by ISCO Hexane/EtOAc; 0% EtOAc—30% EtOAc over 10 minutes, 30% EtOAc—50% EtOAc over 10 minutes, 50% EtOAc for 10 minutes, 50% EtOAc—100% EtOAc over 5 minutes, 100%

EtOAc for 5 minutes. Compound N+2 eluted at a retention time of 13.3 min as a white solid compound (211 mg, 31%). HPLC Rt 2.40 min, Purity 100%, Phenomenex Luna S5 column 4.6×50 mm, 4 min gradient 0 to 100% MeOH (90% in water, 0.1% PPA) UV detection at 220 nm. LCMS Rt 1.46 min, [M+1] 429.22 Phenomenex S5 column 4.6×30 mm, 2 min gradient 0 to 100% MeOH (90% in water, 0.1% TFA) UV detection at 220 nm. NMR H (CDCl$_3$) 1.63 ppm, 1H, multiplet; 1.75 ppm, 1H, multiplet; 1.89 ppm, 1H, multiplet; 1.99 ppm, 1H, multiplet; 2.22 ppm, 2H, multiplet; 2.61 ppm, 4H, multiplet; 2.92 ppm, 3H, s; 3.54 ppm, 2H, s; 3.64 ppm, 2H, d, J=4.0 Hz; 6.75 ppm, 1H, d, J=8.0 Hz; 6.96 ppm, 1H, t, J=6.0 Hz; 7.20 ppm, 6H, multiplet; 7.30 ppm, 5H, multiplet; 7.50 ppm, 1H, multiplet; 8.11 ppm, 1H, dd, J=4.0 and 8.0 Hz.

Title Compound: At 0° C. 1-chloroethyl chloroformate (159 μL, 1.48 mmol) was added to a solution of compound 4 (211 mg, 0.492 mmol) and TEA (341 μL, 2.45 mmol) in dichloroethane (5 mL). The reaction was allowed to warm up to room temperature and stirred for 3 hours. The reaction mixture was concentrated and dried on oil pump for 0.5 hours. The solution of the resulting residue in MeOH (5 mL) was heated under reflux for 5 hours and concentrated. Crude product was purified by preparative HPLC YMC ODS S5 30×100 mm Ballistic column 10-100% MeOH (90% in water, 0.1% TFA) gradient over 10 min with flow rate 40 mL/min and UV detection at 220 nm. Compound 5 eluted at a retention time of 6.6 mins and was isolated as a yellow oil (101.3 mg, yield 61%) NMR H (CDCl$_3$) 1.60 ppm, 1H, multiplet; 1.91 ppm, 3H, multiplet; 2.34 ppm, 2H, multiplet; 3.22 ppm, 2H, multiplet; 3.36 ppm, 1H, multiplet; 3.52 ppm, 1H, multiplet; 3.53 ppm, 3H, s; 3.62 ppm, 2H, multiplet; 6.76 ppm, 1H, d, J=1.8 Hz; 6.80 ppm, 1H, d, J=7.9 Hz; 6.98 ppm, 1H, t, J=7.7 Hz; 7.06 ppm, 1H, d, J=1.8 Hz; 7.22 ppm, 1H, multiplet; 7.34 ppm, 3H, multiplet; 7.56 ppm, 1H, t, J=5.7 Hz; 8.11 ppm, 1H, dd, J=1.8 and 7.5 Hz.

Example 957

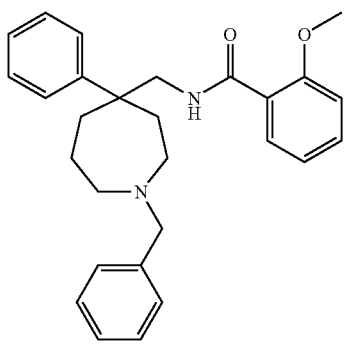

N-(1-Benzyl-4-phenyl-azepan-4-ylmethyl)-2-methoxy-benzamide

Synthesis

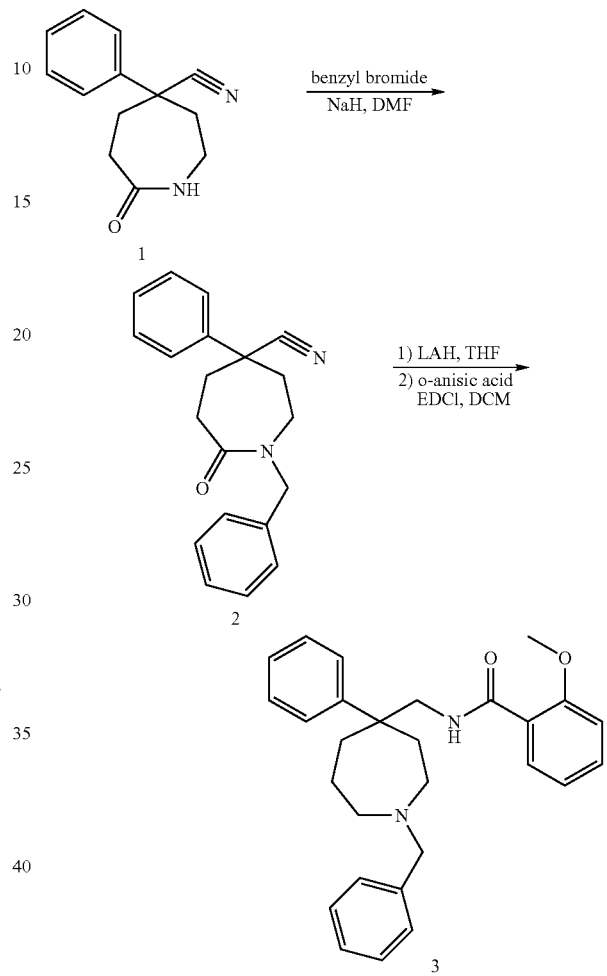

Compound 1: Compound 1 was synthesized as described in Example 956.

Compound 2: NaH (95%) (71 mg, 2.8 mmol) was added to the suspension of compound 1 (500 mg, 2.33 mmol) in DMF (10 mL). After 30 minutes benzylbromide (333 μL, 2.80 mmol) was added and the reaction was stirred for 18 hours. LiCl (10%, 50 mL) was added. The aqueous layer was extracted with EtOAc (3×25 mL). The combined organic layers were dried over MgSO$_4$, filtered, concentrated and purified by ISCO Hexane/EtOAc, 0% EtOAc to 10% EtOAc over 10 minutes, 10% EtOAc for 5 minutes, 10% EtOAc to 30% EtOAc over 10 minutes, 30% EtOAc for 10 minutes, 30% EtOAc to 100% EtOAc over 5 minutes. Compound N+1' eluted at 23 min as a clear oil (454.7 mg, 64% yield).

Title Compound: At room temperature a 1.0 M solution of Lithium aluminum hydride in THF (480 μL, 0.480 mmol) was added to a solution of compound 2 (48.5 mg, 0.160 mmol) in THF (1 mL). After 3 hours the reaction mixture was quenched with H$_2$O (60 μL), 1 N NaOH (36 μL) and H$_2$O (60 μL). The reaction was stirred at room temperature for 0.5 hours, dried over MgSO$_4$, filtered and concentrated. The solution of the resulting residue in CH$_2$Cl$_2$ (1 mL) was added to the mixture of o-anisic acid (27 mg, 0.18 mmol) and EDCI (37 mg, 0.19 mmol) in CH$_2$Cl$_2$ (1 mL). After 1 hours the reaction was concentrated and purified by preparative HPLC yielding compound N+2 as a yellow oil (17.5 mg, 26%).

Example 958

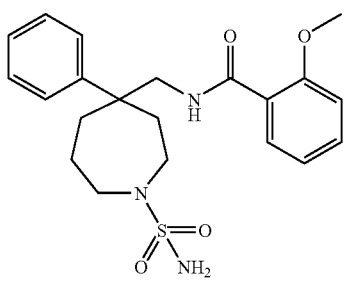

2-Methoxy-N-(4-phenyl-1-sulfamoyl-azepan-4-ylmethyl)-benzamide

Synthesis

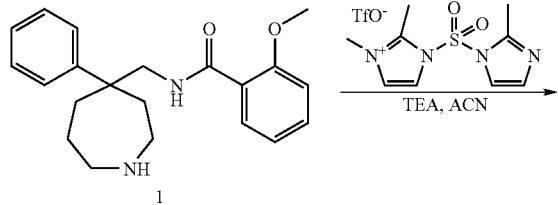

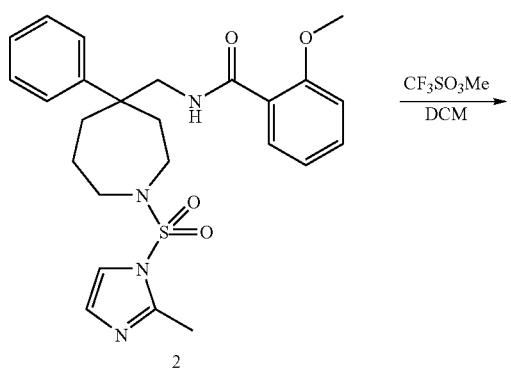

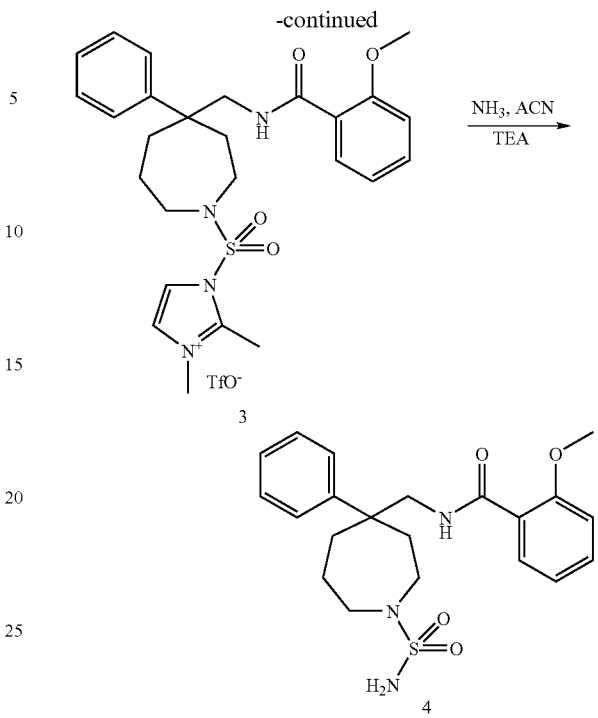

Compound 1: Compound 1 was synthesized as described in Example 956.

Compound 2: At 0° C. N,N'-sulfuryl bis-2-methylimidazole mono-methyl triflate salt (317 mg, 0.390 mmol) was added to a solution of compound 1 (101 mg, 0.300 mmol) in acetonitrile (10 mL) followed by the addition of TEA (100 µL). The reaction was allowed to warm up to room temperature and stirred for 18 hours. The mixture was concentrated and purified by ISCO hexane (0.1% TEA)/EtOAc, 0% EtOAc—50% EtOAc over 15 minutes, 50% EtOAc for 15 minutes, 50% EtOAc—100% EtOAc over 5 minutes, 100% EtOAc for 5 minutes. Compound 2 eluted at a retention time of 26 min as a yellow oil (78.8 mg, 54% yield) NMR H (CDCl$_3$) 1.58 ppm, 1H, multiplet; 1.89 ppm, 3H, multiplet; 2.35 ppm, 2H, multiplet; 2.45 ppm, 3H, s; 3.20 ppm, 2H, multiplet; 3.37 ppm, 1H, multiplet; 3.51 ppm, 1H, multiplet; 3.53 ppm, 3H, s; 3.62 ppm, 2H, multiplet; 6.76 ppm, 1H, d, J=1.8 Hz; 6.80 ppm, 2H, multiplet; 6.98 ppm, 1H, t, J=7.5 Hz; 7.06 ppm, 1H, d, J=1.8 Hz; 7.23 ppm, 2H, multiplet; 7.33 ppm, 3H, multiplet; 7.56 ppm, 1H, t, J=5.7 Hz; 8.10 ppm, 1H, dd, J=1.8 and 7.9 Hz Title Compound: A solution of compound 2 (34 mg, 0.070 mmol) in CH$_2$Cl$_2$ (1 mL) was added methyl trifluoromethanesulfonate (8 µL, 0.08 mmol) at 0° C. After 1.5 hours, the reaction was concentrated to give crude product of compound 3 as a white foam. This product was used directly to the next step without further purification. A 2.0 M solution of NH$_3$ in MeOH (170 µL, 0.35 mmol) was added to a solution of compound 4 and TEA (100 µL) in acetonitrile (1 mL). The reaction mixture was heated at 80° C. for 8 hours. The concentrated reaction mixture was purified by preparative HPLC YMC ODS S5 30×100 mm Ballistic column 10-100% MeOH (90% in water, 0.1% TFA) gradient over 12 min with flow rate 40 mL/min and UV detection at 220 nm. Compound 5 eluted at a retention time of 9.6 mins and was isolated as a clear oil (18.27 mg, 63% yield from compound 3). HPLC Rt 2.91 min, Purity 100%, Phenomenex Luna S5 column 4.6×50 mm, 4 min gradient 0 to 100% MeOH (90% in water, 0.1% PPA) UV detection at 220 nm. LCMS Rt 1.60 min, [M+1] 418.17 YMC-ODS S5 column 4.6×33 mm, 2 min gradient 0 to 100% MeOH (90% in water, 10 mM NH₄OAc) UV detection at 220 nm. NMR H (CDCl₃) 1.65 ppm, 1H, multiplet; 1.84 ppm, 2H, multiplet; 1.99 ppm, 2H, multiplet; 2.25 ppm, 1H, multiplet; 2.37 ppm, 2H, multiplet; 3.23 ppm, 2H, multiplet; 3.31 ppm, 1H, multiplet; 3.52 ppm, 3H, s; 3.57 ppm, 2H, s; 3.69 ppm, 1H, multiplet; 4.40 ppm, 2H, bs; 6.79 ppm, 1H, d, J=8.4 Hz; 6.97 ppm, 1H, t, J=7.5 Hz; 7.23 ppm, 1H, multiplet; 7.34 ppm, 5H, multiplet; 7.61 ppm, 1H, multiplet; 8.09 ppm, 1H, dd, J=1.7 and 7.9 Hz.

Examples 959 to 963

Compounds 959 to 963 were synthesized using methodology described in Example 958.

| Example | Structure | Name | [M + 1] |
|---|---|---|---|
| 959 | 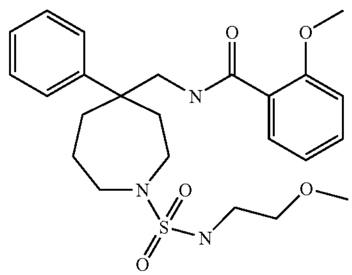 | 2-Methoxy-N-[1-(2-methoxy-ethylsulfamoyl)-4-phenyl-azepan-4-ylmethyl]-benzamide | 476 |
| 960 | 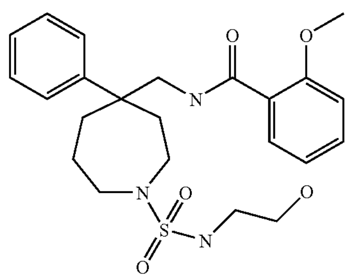 | N-[1-(2-Hydroxy-ethylsulfamoyl)-4-phenyl-azepan-4-ylmethyl]-2-methoxy-benzamide | 462 |
| 961 | 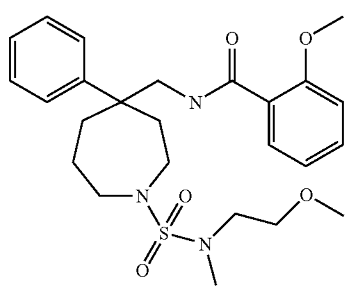 | 2-Methoxy-N-{1-[(2-methoxy-ethyl)-methyl-sulfamoyl]-4-phenyl-azepan-4-ylmethyl}-benzamide | 490 |
| 962 | 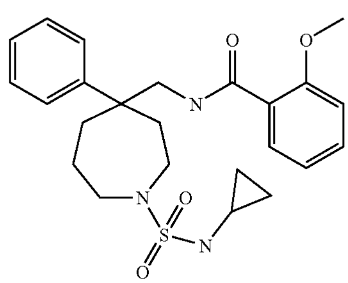 | N-(1-Cyclopropylsulfamoyl-4-phenyl-azepan-4-ylmethyl)-2-methoxy-benzamide | 458 |

| Example | Structure | Name | [M + 1] |
|---|---|---|---|
| 963 | 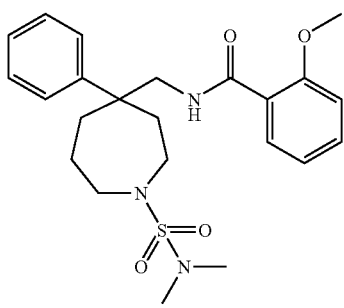 | 2-Methoxy-N-(1-methylsulfamoyl-4-phenyl-azepan-4-ylmethyl)-benzamide | 432 |

Example 964

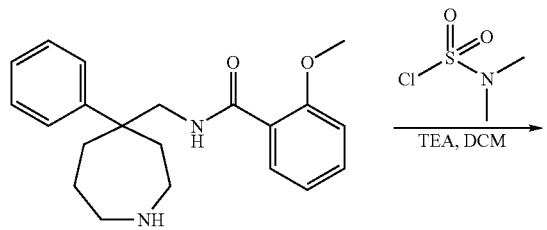

N-(1-Dimethylsulfamoyl-4-phenyl-azepan-4-ylm-ethyl)-2-methoxy-benzamide

Synthesis

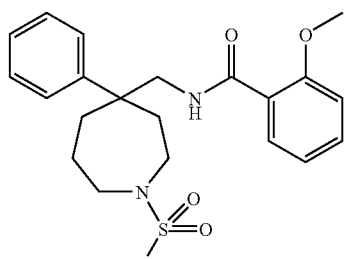

Compound 1: Compound 1 was synthesized as described in Example 956.

Title Compound: Dimethylsulfomoyl chloride (3.44 mg, 0.0240 mmol) was added to a solution of compound 1 (6.76 mg, 0.0200 mmol) in $CH_2Cl_2$ (0.5 mL). TEA (5 μL) was added and the reaction was stirred at room temperature for 2 hours. The concentrated reaction mixture was purified by preparative HPLC YMC ODS S5 30×100 mm Ballistic column 20-100% MeOH (90% in water, 0.1% TFA) gradient over 10 min with flow rate 40 mL/min and UV detection at 220 nm. Compound 2 eluted at a retention time of 9.0 min and was isolated as a clear oil (5.7 mg, 64% yield). HPLC Rt 3.30 min, Purity 100%, Phenomenex Luna S5 column 4.6×50 mm, 4 min gradient 0 to 100% MeOH (90% in water, 0.1% PPA) UV detection at 220 nm. LCMS Rt 1.68 min, [M+1] 446.21 Phenomenex S5 column 4.6×30 mm, 2 min gradient 0 to 100% MeOH (90% in water, 10 mM $NH_4OAc$) UV detection at 220 nm. NMR H ($CDCl_3$) 1.61 ppm, 1H, multiplet; 1.89 ppm, 3H, multiplet; 2.34 ppm, 2H, multiplet; 2.61 ppm, 6H, s; 3.18 ppm, 2H, multiplet; 3.26 ppm, 1H, multiplet; 3.54 ppm, 3H, s; 3.57 ppm, 3H, multiplet; 6.80 ppm, 1H, d, J=8.0 Hz; 6.98 ppm, 1H, t, J=8.0 Hz; 7.23 ppm, 1H, multiplet; 7.33 ppm, 5H, multiplet; 7.58 ppm, 1H, multiplet; 8.11 ppm, 1H, multiplet.

Example 965

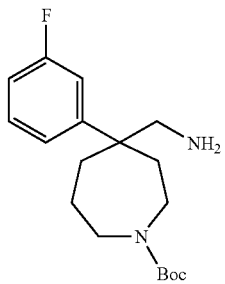

4-Aminomethyl-4-(3-fluoro-phenyl)-azepane-1-carboxylic acid tert-butyl ester

Synthesis

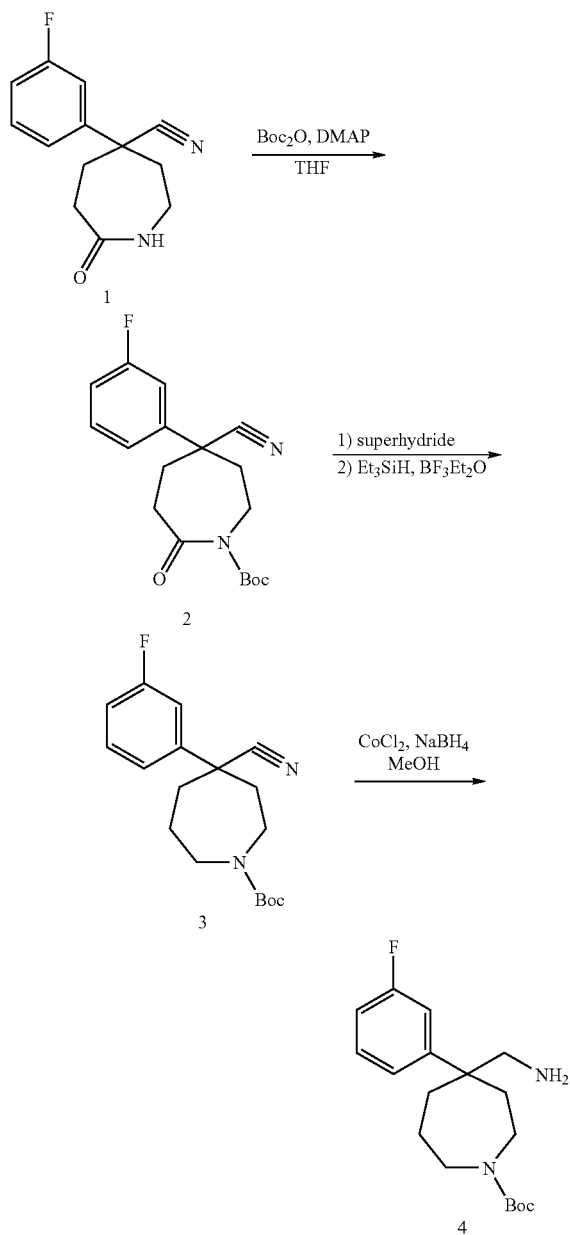

Compound 1: Compound 1 was synthesized via the intermediate cyclohexanone according to the procedures described in Journal of Medicinal Chemistry, 1998, 821. The intermediate cyclohexanone was converted to the lactam as described for Example 956.

Compound 2: To a suspension of the crude compound 1 in THF (20 mL) was added subsequently di-tert-butyl dicarbonate (2.33 mL, 10.1 mmol) and dimethylaminopyridine (1.24 g, 10.1 mmol). After 3 hours the reaction mixture was concentrated. The resulting residue was dissolved in Ethyl acetate (100 mL). The organic layer was washed with 1 N HCl (2×50 mL) and dried over $MgSO_4$. Evaporation and purification by ISCO (hexane/EtOAc, 0% EtOAc—10% EtOAc over 10 minutes, 10% EtOAc—30% EtOAc over 10 minutes, 30% EtOAc for 15 minutes, 30% EtOAc—100% EtOAc over 5 minutes, 100% EtOAc for 5 minutes) yielded compound 2 with a retention time of 16 min as a white solid (2.69 g, 88% from ketone) NMR H ($CDCl_3$) 2.03 ppm, 1H, multiplet; 2.28 ppm, 3H, multiplet; 2.76 ppm, 1H, dd, J=7.2 and 15.6 Hz; 3.21 ppm, 1H, multiplet; 3.75 ppm, 1H, dd, J=10.5 and 16.3 Hz; 4.44 ppm, 1H, dd, J=6.5 and 15.9 Hz; 7.05 ppm, 1H, multiplet; 7.16 ppm, 1H, multiplet; 7.26 ppm, 1H, multiplet; 7.38 ppm, 1H, multiplet.

Compound 3: At −78° C. a 1.0 M solution of lithium triethylborohydride in THF (4.87 mL, 4.87 mmol) was added to a solution of compound 2 (1.35 g, 4.06 mmol) in THF (25 mL). After 30 minutes the reaction was quenched with saturated $NaHCO_3$ (7.6 mL) and warmed to 0° C. At 0° C. $H_2O_2$ (12 drops) was added and the reaction was stirred for 20 minutes. THF was removed and the aqueous layer was extracted with $CH_2Cl_2$ (3×25 mL). The combined organic layers were dried over $MgSO_4$, filtered and concentrated. The resulting thick oil was dissolved in $CH_2Cl_2$ (50 mL). At −78° C. triethylsilane (648 µL, 4.06 mmol) was added followed by drop wise addition of boron trifluoride etherate (566 µL, 4.47 mmol). After 30 minutes another portion of triethylsilane (648 µL, 4.06 mmol) and boron trifluoride etherate (566 µL, 4.47 mmol) were added and the reaction was continued to stir for 2 hours at −78° C. The reaction was quenched with saturated $NaHCO_3$ (15 mL). The aqueous layer was extracted with $CH_2Cl_2$ (3×20 mL) and the combined organic layers were dried over $MgSO_4$, filtered and concentrated to give crude compound 3 (1.19 g) as an oil. This crude product was used to the next step directly without further purification.

Title Compound: To a solution of crude compound 3 (1.19 g, 3.73 mmol) in MeOH (35 mL) was added cobalt (II) chloride hexahydrate (1.41 g, 7.46 mmol). The resulted purple mixture was stirred at room temperature for 10 minutes. At 0° C. $NaBH_4$ (1.41 g, 37.3 mmol) was added in three portions over 25 minutes. The reaction mixture was stirred at room temperature for 2 hours, concentrated to give a black residue. The black residue was dissolved in 30% ammonium hydroxide solution (100 mL), extracted with ethyl acetate (3×50 mL). The combined organic layers were dried over $MgSO_4$, filtered and concentrated to give a crude pink solid of compound 4 (1.46 g). This crude solid was used directly to the following acylation reaction.

Example 966

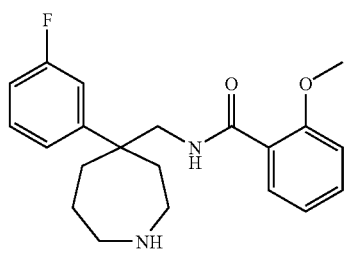

585
N-[4-(3-Fluoro-phenyl)-azepan-4-ylmethyl]-2-methoxy-benzamide

Synthesis

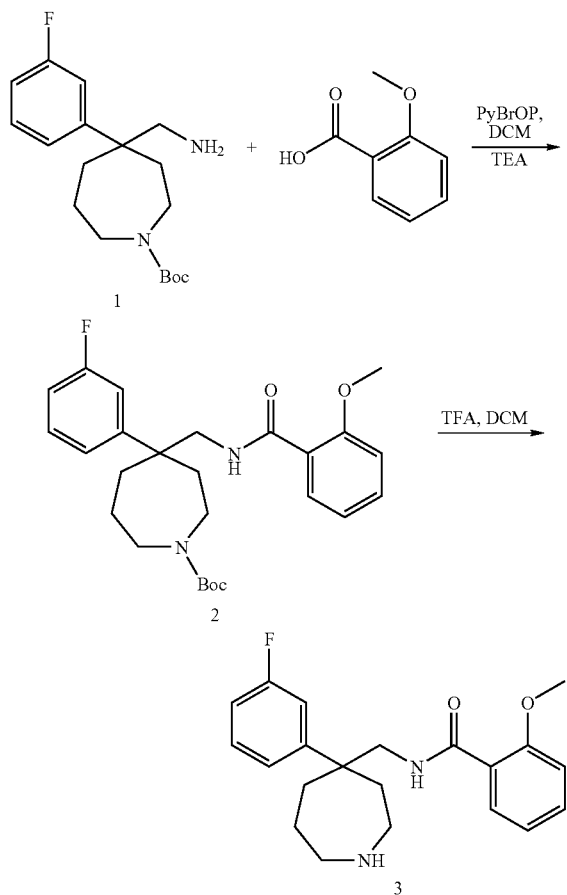

586

Compound 1: The synthesis of Compound 1 is described for Example 965.

Compound 2: To a solution of crude compound 1 (729 mg, 2.26 mmol), o-anisic acid (345 mg, 2.26 mmol) and TEA (314 µL, 2.26 mmol) in $CH_2Cl_2$ (10 mL) was added PyBrOP (1.05 g, 2.26 mmol) at room temperature. After 3 hours, the reaction was concentrated and purified by flash chromatography using Hexane/EtOAc (2/1) to yield compound 2 as a white solid (536.2 mg, 58% from compound N+13). HPLC Rt 3.79 min, Purity 100%, Phenomenex Luna S5 column 4.6×50 mm, 4 min gradient 0 to 100% MeOH (90% in water, 0.1% PPA) UV detection at 220 nm. LCMS Rt 2.04 min, [M+1] 357.43 Phenomenex S5 column 4.6×30 mm, 2 min gradient 0 to 100% MeOH (90% in water, 0.1% TFA) UV detection at 220 nm. NMR H ($CDCl_3$) 1.38 ppm, 9H, d, J=12.8 Hz; 1.64 ppm, 1H, multiplet; 1.78 ppm, 3H, multiplet; 2.32 ppm, 2H, multiplet; 3.31 ppm, 3H, multiplet; 3.65 ppm, 6H, multiplet; 6.89 ppm, 1H, d, J=8.4 Hz; 6.99 ppm, 1H, multiplet; 7.06 ppm, 2H, multiplet; 7.16 ppm, 1H, d, J=7.5 Hz; 7.40 ppm, 2H, multiplet; 7.62 ppm, 1H, multiplet; 8.20 ppm, 1H, d, J=7.5 Hz.

Title Compound: To a solution of compound 2 (526 mg, 1.24 mmol) in $CH_2Cl_2$ (5 mL) was added a solution of TFA (1 mL) in $CH_2Cl_2$ (4 mL) at room temperature. After 1.5 hours the reaction was diluted with $CH_2Cl_2$ (50 mL) and was with saturated $NaHCO_3$ (2×20 mL), dried over $MgSO_4$, filtered and concentrated to give a crude product of compound N+18 as a white solid (483 mg, quantitative yield). The crude product was used directly to the next step without further purification.

Examples 967 to 970

Compounds 967 to 970 were prepared using the methodology described for Example 966 and Example 958.

| Example | Structure | Name | [M + H] |
|---|---|---|---|
| 967 | (structure) | N-[4-(3-Fluoro-phenyl)-1-(2-methyl-imidazole-1-sulfonyl)-azepan-4-ylmethyl]-2-methoxy-benzamide | 501 |

-continued
| Example | Structure | Name | [M + H] |
|---|---|---|---|
| 968 | 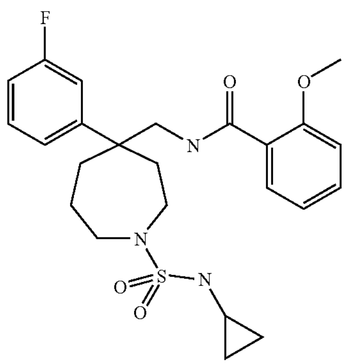 | N-[1-Cyclopropylsulfamoyl-4-(3-fluoro-phenyl)-azepan-4-ylmethyl]-2-methoxy-benzamide | 476 |
| 969 | 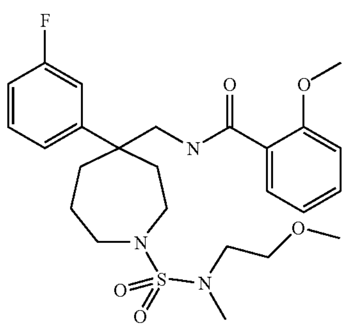 | N-{4-(3-Fluoro-phenyl)-1-[(2-methoxy-ethyl)-methyl-sulfamoyl]-azepan-4-ylmethyl }-2-methoxy-benzamide | 508 |
| 970 | 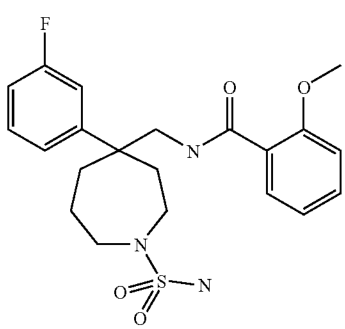 | N-[4-(3-Fluoro-phenyl)-1-sulfamoyl-azepan-4-ylmethyl]-2-methoxy-benzamide | 436 |
Example 971
Synthesis
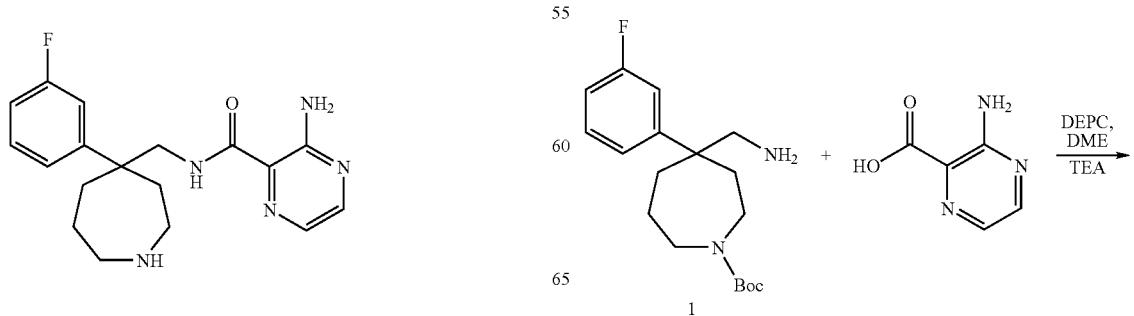

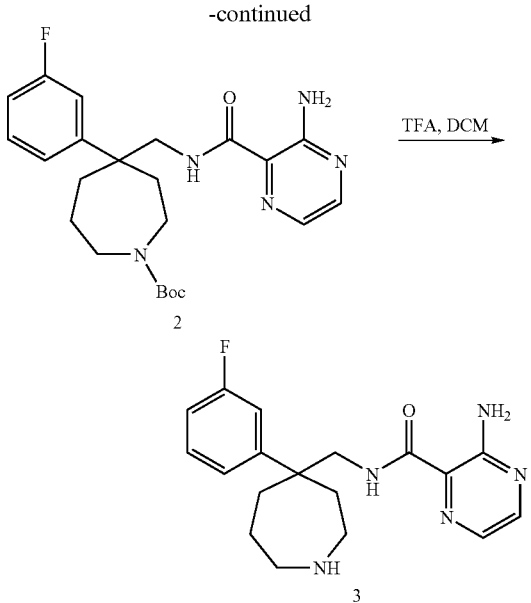

Compound 1: The synthesis of Compound 1 is described for Example 965.

Compound 2: To a solution of crude compound 1 (729 mg, 2.26 mmol) and 3-aminopyrazine-2-carboxylic acid (377 mg, 2.26 mmol) in ethylene glycol dimethyl ether (10 mL) was added drop wise diethyl phosphoryl cyanide (411 μL, 2.71 mmol) and TEA (630 μL, 4.52 mmol) respectively at 0° C. The reaction was stirred at 0° C. for 1 hour and at 40° C. for 1 hour under $N_2$. The mixture was diluted with EtOAc (100 mL) and washed with $H_2O$ (25 mL), saturated $NaHCO_3$ (25 mL) and $H_2O$ (25 mL) successively. The organic layer was dried over $MgSO_4$ and concentrated to afford the crude product, which was purified by ISCO Hexane/EtOAc; 0% EtOAc—50% EtOAc over 10 minutes, 50% EtOAc for 25 minutes, 50% EtOAc—100% EtOAc over 5 minutes, 100% EtOAc for 5 minutes. Compound 2 eluted at a retention time of 14 min as a yellow solid (432.7 mg, 51% from compound 1). HPLC Rt 3.67 min, Purity 100%, Phenomenex Luna S5 column 4.6×50 mm, 4 min gradient 0 to 100% MeOH (90% in water, 0.1% PPA) UV detection at 220 nm. LCMS Rt 1.90 min, [M+1] 344.45 Phenomenex S5 column 4.6×30 mm, 2 min gradient 0 to 100% MeOH (90% in water, 0.1% TFA) UV detection at 220 nm. NMR H ($CDCl_3$) 1.38 ppm, 9H, d, J=12.8 Hz; 1.62 ppm, 1H, multiplet; 1.71 ppm, 1H, mutiplet; 1.87 ppm, 2H, multiplet; 2.34 ppm, 2H, multiplet; 3.17 ppm, 2H, multiplet; 3.38 ppm, 1H, multiplet; 3.46 ppm, 2H, multiplet; 3.67 ppm, 1H, multiplet; 6.99 ppm, 2H, multiplet; 7.11 ppm, 1H, multiplet; 7.37 ppm, 1H, multiplet; 7.71 ppm, 2H, multiplet; 8.11 ppm, 1H, s.

Title Compound: To a solution of compound 2 (457 mg, 1.03 mmol) in $CH_2Cl_2$ (5 mL) was added a solution of TFA (1 mL) in $CH_2Cl_2$ (4 mL) at room temperature. After 1.5 hours the reaction was diluted with $CH_2Cl_2$ (50 mL) and was washed with saturated $NaHCO_3$ (2×20 mL), dried over $MgSO_4$, filtered and concentrated to give a crude product of compound 3 as a yellow solid (291 mg, 82% crude yield). The crude product was used directly to the next step without further purification.

Examples 972 to 974

Compounds 972 to 974 were prepared using the methodology described for Example 971 and Example 961.

| Example | Structure | Name | [M + 1] |
|---|---|---|---|
| 972 | 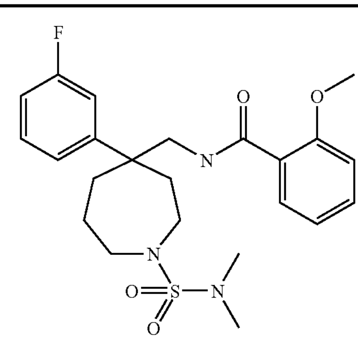 | N-[1-Dimethylsulfamoyl-4-(3-fluoro-phenyl)-azepan-4-ylmethyl]-2-methoxy-benzamide | 464 |
| 973 | 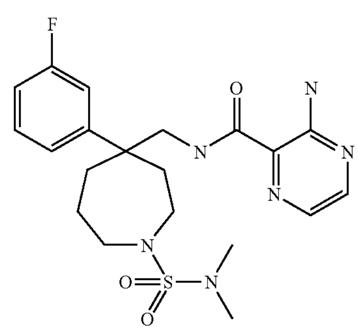 | 3-Amino-pyrazine-2-carboxylic acid [1-dimethylsulfamoyl-4-(3-fluoro-phenyl)-azepan-4-ylmethyl]-amide | 451 |

-continued

| Example | Structure | Name | [M + 1] |
|---|---|---|---|
| 974 | 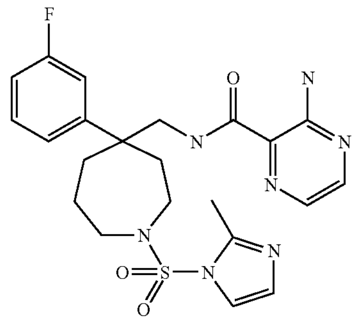 | 3-Amino-pyrazine-2-carboxylic acid [4-(3-fluoro-phenyl)-1-(2-methyl-imidazole-1-sulfonyl)-azepan-4-ylmethyl]-amide | 488 |

Example 975

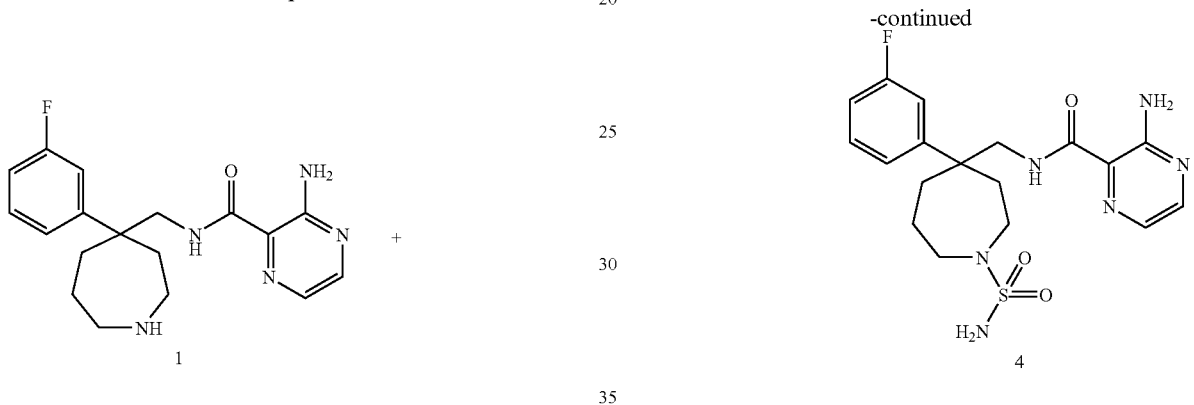

Compound 1: Compound 1 was prepared as described in Example 671.

Compound 3: N-(tert-Butoxycarbonyl)-N-[4-(dimethyla-zaniumylidene)-1,4-dihydropyridin-1-ylsulfonyl]azanide was made according to Organic Letters, 2001, Vol. 3., No. 14, 2241-2243. Compound 1 (19 mg, 0.058 mmol) was added to Compound 2 (20 mg, 0.064 mmol) in $CH_2Cl_2$ (1 mL) and was stirred at room temperature for 18 hours. The residue was concentrated and purified by preparative silica thin layer chromatography (25×25cm plate, 1 mm thickness silica with UV indicator) using Hexane/EtOAc (1/2) as eluent to yield compound 3 as a clear oil (26 mg, 87% yield) NMR H ($CDCl_3$) 1.44 ppm, 9H, s; 1.64 ppm, 1H, multiplet; 1.98 ppm, 3H, multiplet; 2.37 ppm, 2H, multiplet; 3.24 ppm, 2H, multiplet; 3.49 ppm, 3H, multiplet; 3.81 ppm, 1H, multiplet; 6.99 ppm, 2H, multiplet; 7.35 ppm, 1H, multiplet; 7.67 ppm, 1H, multiplet; 7.69 ppm, 1H, d, J=4.0 Hz; 8.00 ppm, 1H, s; 8.12 ppm, 1H, d, J=4.0 Hz.

Title Compound: At room temperature, a solution of TFA (0.25 mL) in $CH_2Cl_2$ (1 mL) was added to a solution of compound 3 (26 mg, 0.050 mmol). After 2 hours the reaction mixture was concentrated and purified by preparative HPLC YMC ODS S5 30×100 mm Ballistic column 20-100% MeOH (90% in water, 0.1% TFA) gradient over 10 min with flow rate 40 mL/min and UV detection at 220 nm. Compound 4 eluted at a retention time of 7.0 min and was isolated as a clear oil (20.2 mg, 95% yield). HPLC Rt 2.68 min, Purity 100%, Phenomenex Luna S5 column 4.6×50 mm, 4 min gradient 0 to 100% MeOH (90% in water, 0.1% PPA) UV detection at 220 nm. LCMS Rt 1.39 min, [M+1] 423.31 Phenomenex S5 column 4.6×30 mm, 2 min gradient 0 to 100% MeOH (90% in water, 10 mM NH$_4$OAc) UV detection at 220 nm. NMR H (CDCl$_3$) 1.66 ppm, 1H, multiplet; 1.90 ppm, 2H, multiplet; 2.00 ppm, 1H, multiplet; 2.30 ppm, 1H, multiplet; 2.41 ppm, 1H, multiplet; 3.16 ppm, 2H, multiplet; 3.41 ppm, 1H, multiplet; 3.51 ppm, 2H, multiplet; 3.66 ppm, 1H, multiplet; 7.00 ppm, 2H, multiplet; 7.10 ppm, 1H, d, J=8.0 Hz; 7.38 ppm, 1H, multiplet; 7.60 ppm, t, J=6.0 Hz; 7.81 ppm, 1H, d, J=4.0 Hz; 7.93 ppm, 1H, multiplet.

We claim:

1. A compound of formula I

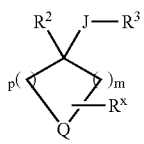

I enantiomers, diastereomers, and salts thereof wherein
m and p are independently 0, 1, or 2 provided that the sum of m and p is 2;
Q is NR$^1$;

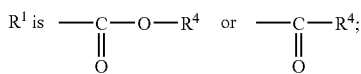

R$^2$ is aryl, which may be optionally independently substituted with one or more groups T$^1$, T$^2$ or T$^3$;
J is a bond or C$_{1-4}$ alkylene optionally independently substituted with one or more groups T$^{1a}$, T$^{2a}$ or T$^{3a}$;
R$^3$ is —R$^5$;
R$^4$ is alkyl or aryl, any of which may be optionally independently substituted with one or more groups T$^{1b}$, T$^{2b}$ or T$^{3b}$;
R$^5$ is —NR$^{6a}$R$^{7a}$;
R$^{6a}$ is indazolyl, which may be optionally independently substituted with one or more groups T$^{1d}$, T$^{2d}$ or T$^{3d}$;
R$^{7a}$ is H;
R$^X$ is one or more optional substituents, attached to any available ring carbon atom, independently selected from T$^{1g}$, T$^{2g}$ or T$^{3g}$;
T$^{1\text{-}1g}$, T$^{2\text{-}2g}$, and T$^{3\text{-}3g}$ are each independently hydrogen, alkyl, haloalkyl, aryl, —OH, —Oalkyl or halo.

2. A compound of claim 1 wherein
Q is NR$^1$

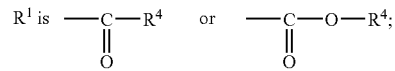

R$^2$ is aryl, which may be optionally independently substituted with one or more groups T$^1$, T$^2$ or T$^3$;
J is a bond or methylene; and
R$^3$ is R$^5$.

3. A compound of claim 2 wherein
Q is NR$^1$;
R$^4$ is alkyl which may be optionally independently substituted with one or more T$^{1b}$, T$^{2b}$ T$^{3b}$;
R$^5$ is —NR$^{6a}$R$^{7a}$;
R$^{6a}$ is indazolyl, which may be optionally substituted with one or more groups T$^{1d}$, T$^{2d}$ or T$^{3d}$; and
R$^{7a}$ is H.

4. A pharmaceutical composition comprising at least one compound of claim 1 together with a suitable vehicle or carrier therefor.

* * * * *